United States Patent
Alexander et al.

(10) Patent No.: US 8,242,116 B2
(45) Date of Patent: Aug. 14, 2012

(54) FUSED THIAZOLE DERIVATIVES AS KINASE INHIBITORS

(75) Inventors: Rikki Peter Alexander, Slough (GB); Pavandeep Singh Aujla, Slough (GB); Karen Viviane Lucile Crépy, Slough (GB); Anne Marie Foley, Slough (GB); Richard Jeremy Franklin, Slough (GB); Alan Findlay Haughan, Slough (GB); Helen Tracey Horsley, Slough (GB); William Mark Jones, Slough (GB); Bénédicte Irma Léonce Frédérique Lallemand, Brussels (BE); Stephen Robert Mack, Slough (GB); Trevor Morgan, Slough (GB); Patrick Marie Ghislain Pasau, Brussels (BE); David Jonathan Phillips, High Peak (GB); Verity Margaret Sabin, Slough (GB); George Martin Buckley, Slough (GB); Kerry Jenkins, Slough (GB); Benjamin Garfield Perry, Slough (GB)

(73) Assignee: UCB Pharma S.A., Brussels (BE)

( * ) Notice: Subject to any disclaimer, the term of this patent is extended or adjusted under 35 U.S.C. 154(b) by 588 days.

(21) Appl. No.: 12/306,151

(22) PCT Filed: Jun. 26, 2007

(86) PCT No.: PCT/GB2007/002390
§ 371 (c)(1),
(2), (4) Date: Sep. 3, 2009

(87) PCT Pub. No.: WO2008/001076
PCT Pub. Date: Jan. 3, 2008

(65) Prior Publication Data
US 2010/0137302 A1    Jun. 3, 2010

(30) Foreign Application Priority Data

Jun. 26, 2006  (GB) .................................. 0612644.5
Oct. 10, 2006  (GB) .................................. 0620062.0

(51) Int. Cl.
*A61K 31/535*  (2006.01)
*C07D 413/14*  (2006.01)

(52) U.S. Cl. ....................................... 514/234.2; 544/127
(58) Field of Classification Search .................. 544/127; 514/234.2
See application file for complete search history.

(56) References Cited

FOREIGN PATENT DOCUMENTS
WO    WO2006114606    11/2006

OTHER PUBLICATIONS

Byrn et al., Solid-State Chemistry of Drugs, 2nd Ed., SSCI, Inc., West Lafayette, IN, Ch. 11, pp. 233-247 (1999).*
Cancer and Metastasis Reviews (1998), 17(1), 91-106.*
Science (1999), vol. 286, 531-537.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/index.html>.*
Hahnemann C et al., on the Reaction of Thiazole-2, 4-diamines with Isothiocyanates—Preparation and Transformation of 2, 4-Diaminothiazole-5-carbothioamides, Helvetica Chimica ACTA, 2003, pp. 1949-1965, vol. 86.
Ried, Walter et al., Thiazoles from N-cyanomidates or 3-(cyano)isoureas and thioglycolic acid derivatives, Liebigs Ann. Chem., 1986, pp. 780-784.
International Search Report dated Nov. 22, 2007.

* cited by examiner

*Primary Examiner* — Rebecca Anderson
(74) *Attorney, Agent, or Firm* — McDonnell Boehnen Hulbert & Berghoff LLP

(57) ABSTRACT

A series of 6,7-dihydro[1,3]thiazolo[5,4-c]pyridin-4(5H)-one derivatives, and analogues thereof, which are substituted in the 2-position by an optionally substituted morpholin-4-yl moiety, being selective inhibitors of PI3 kinase enzymes, are accordingly of benefit in medicine, for example in the treatment of inflammatory, autoimmune, cardiovascular, neurodegenerative, metabolic, oncological, nociceptive or ophthalmic conditions.

7 Claims, No Drawings

FUSED THIAZOLE DERIVATIVES AS KINASE INHIBITORS

This is a National Stage of International Application No. PCT/GB2007/002390, filed Jun. 26, 2007.

The present invention relates to a class of fused thiazole derivatives, and to their use in therapy. More particularly, the invention provides a family of 6,7-dihydro-[1,3]thiazolo[5,4-c]pyridin-4(5H)-one derivatives, and analogues thereof, which are substituted in the 2-position by an optionally substituted morpholin-4-yl moiety. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymann et al., *Trends in Pharmacol. Sci.*, 2003, 24, 366-376). Aberrant upregulation of the PI3K pathway is implicated in a wide variety of human cancers (cf. S. Brader & S. A. Eccles, *Tumori*, 2004, 90, 2-8).

The compounds in accordance with the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds in accordance with the present invention may be beneficial as pharmacological standards for use in the development of new biological tests and in the search for new pharmacological agents. Thus, the compounds of this invention may be useful as radioligands in assays for detecting compounds capable of binding to human PI3K enzymes.

Various fused thiazole derivatives are disclosed in *Liebigs Annalen der Chemie*, 1986, 780-784; and in *Russian Journal of General Chemistry* (translation of *Zhurnal Obshchei Khimii*), 2000, 70[5], 784-787. However, none of the compounds disclosed in either of those publications corresponds to a compound of the present invention; and no therapeutic utility is ascribed to any of the compounds disclosed therein.

The compounds in accordance with the present invention are potent and selective PI3K inhibitors having a binding affinity ($IC_{50}$) for the human PI3Kα and/or PI3Kβ and/or PI3Kγ and/or PI3Kδ isoform of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human PI3Kα and/or PI3Krβ and/or PI3Kγ and/or PI3Kδ isoform relative to other human kinases.

The present invention provides a compound of formula (I), or a pharmaceutically acceptable salt or solvate thereof:

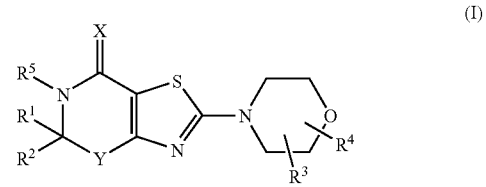

(I)

wherein

X represents oxygen or sulphur;

Y represents a group of formula $CR^6R^7$ or $NR^8$;

$R^1$ represents hydrogen or $C_{1-6}$ alkyl; and $R^2$ represents hydrogen; or $C_{1-6}$ alkyl, $C_{1-6}$ alkoxy, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; or $R^1$ and $R^2$, when taken together with the carbon atom to which they are both attached, represent $C_{3-7}$ cycloalkyl or $C_{3-7}$ heterocycloalkyl, either of which groups may be optionally substituted by one or more substituents;

$R^3$ and $R^4$ independently represent hydrogen; or $C_{1-6}$ alkyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)-alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^3$ and $R^4$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;

$R^5$ represents hydrogen or $C_{1-6}$ alkyl;

$R^6$ represents hydrogen; or $C_{1-6}$ alkyl, $C_{1-6}$ alkoxy, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; and $R^7$ represents hydrogen or $C_{1-6}$ alkyl; or $R^6$ and $R^7$, when taken together with the carbon atom to which they are both attached, represent $C_{3-7}$ cycloalkyl or $C_{3-7}$ heterocycloalkyl, either of which groups may be optionally substituted by one or more substituents; or $R^2$ and $R^6$, when taken together with the carbon atoms to which they are attached, represent $C_{5-7}$ cycloalkyl, phenyl or heteroaryl, any of which groups may be optionally benzo-fused and/or substituted by one or more substituents; and $R^8$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; or $R^2$ and $R^8$, when taken together with the carbon and nitrogen atoms to which they are respectively attached, represent $C_{5-7}$ heterocycloalkyl or heteroaryl, either of which groups may be optionally benzo-fused and/or substituted by one or more substituents.

Where any of the groups in the compounds of formula (I) above is stated to be optionally substituted, this group may be unsubstituted, or substituted by one or more substituents. Typically, such groups will be unsubstituted, or substituted by one or two substitutents. Suitably, such groups will be unsubstituted or monosubstituted.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

A specific $C_{2-6}$ alkynyl group is prop-2-yn-1-yl.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl. Suitable aryl($C_{1-6}$)alkyl groups include benzyl, phenylethyl, phenylpropyl and naphthylmethyl.

Specific aryl($C_{2-6}$)alkenyl groups include 2-phenylethenyl and 3-phenylprop-2-en-1-yl.

A specific aryl($C_{2-6}$)alkynyl group is 3-phenylprop-2-yn-1-yl.

Particular biaryl groups include biphenyl and naphthylphenyl.

Suitable heterocycloalkyl groups, which may comprise benzo-fused analogues thereof, include azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl and thiomorpholinyl.

Suitable heteroaryl groups include furyl, benzofuryl, dibenzofuryl, thienyl, benzothienyl, pyrrolyl, indolyl, pyrrolo[2,3-b]pyridinyl, pyrrolo[3,2-c]pyridinyl, pyrazolyl, pyrazolo[1,5-a]pyridinyl, indazolyl, oxazolyl, benzoxazolyl, isoxazolyl, thiazolyl, benzothiazolyl, isothiazolyl, imidazolyl, benzimidazolyl, imidazo[1,2-a]pyridinyl, imidazo[4,5-b]pyridinyl, imidazo[1,2-a]pyrimidinyl, imidazo[1,2-a]pyrazinyl, oxadiazolyl, thiadiazolyl, triazolyl, benzotriazolyl, tetrazolyl, pyridinyl, quinolinyl, isoquinolinyl, pyridazinyl, cinnolinyl, pyrimidinyl, pyrazinyl, quinoxalinyl and chromenyl groups.

The term "halogen" as used herein is intended to include fluorine, chlorine, bromine and iodine atoms, especially fluoro or chloro.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)-enol ($CH=CHOH$) tautomers. Formula (I) and the formulae depicted hereinafter are intended to represent all individual tautomers and all possible mixtures thereof, unless stated or shown otherwise.

Specific sub-classes of compounds in accordance with the present invention are represented by the compounds of formula (IA), (IB), (IC) and (ID):

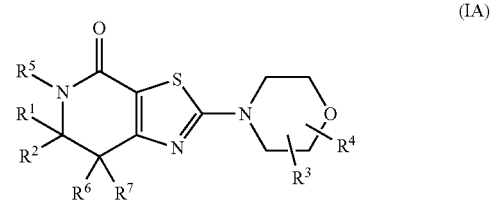

(IA)

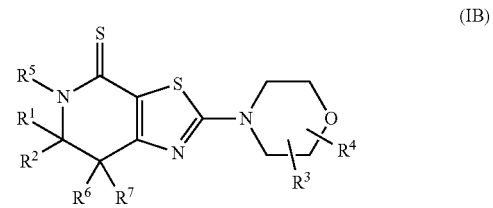

(IB)

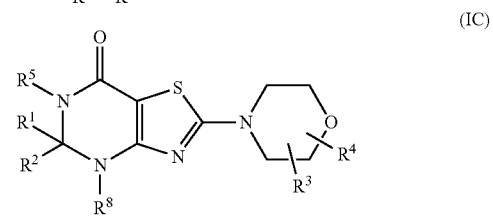

(IC)

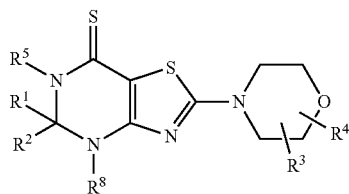

(ID)

wherein $R^1$, $R^2$, $R^3$, $R^4$, $R^5$, $R^6$, $R^7$ and $R^8$ are as defined above.

Representative sub-classes of compounds in accordance with the present invention are represented by the compounds of formula (IA), (IB) and (IC) as depicted above.

Particular sub-classes of compounds in accordance with the present invention are represented by the compounds of formula (IA) and (IC) as depicted above.

In a preferred embodiment, X represents oxygen. In another embodiment, X represents sulphur.

In one embodiment, Y represents $CR^6R^7$. In another embodiment, Y represents $NR^8$.

Typical values of $R^1$ include hydrogen, methyl and ethyl. In one embodiment, $R^1$ is hydrogen. In another embodiment, $R^1$ is $C_{1-6}$ alkyl. In one aspect of that embodiment, $R^1$ is methyl. In another aspect of that embodiment, $R^1$ is ethyl.

Suitably, $R^2$ represents hydrogen; or $C_{1-6}$ alkyl, $C_{1-6}$ alkoxy, $C_{3-7}$ cycloalkyl or aryl, any of which groups may be optionally substituted by one or more substituents.

Examples of typical substituents on $R^2$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)alkylaminosulphonyl; especially halogen, $C_{1-6}$ alkoxy or $C_{1-6}$ alkylthio.

Examples of particular substituents on $R^2$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, methoxy or methylthio.

Typical values of $R^2$ include hydrogen, methyl, ethoxy, n-propyl, isopropyl, isobutyl, cyclohexyl and phenyl. A particular value of $R^2$ is methyl.

Alternatively, $R^1$ and $R^2$ may together form an optionally substituted spiro linkage. Thus, $R^1$ and $R^2$, when taken together with the carbon atom to which they are both attached, may represent $C_{3-7}$ cycloalkyl or $C_{3-7}$ heterocycloalkyl, either of which groups may be unsubstituted, or substituted by one or more, typically by one or two, substituents. In this context, $R^1$ and $R^2$, when taken together with the carbon atom to which they are both attached, may suitably represent an optionally substituted cyclopentyl, cyclohexyl, pyrrolidine or piperidine ring.

Typically, $R^3$ represents hydrogen; or $C_{1-6}$ alkyl, aryl, aryl($C_{1-6}$)alkyl, aryl-($C_{2-6}$)alkynyl, biaryl($C_{1-6}$)alkyl, $C_{3-7}$ heterocycloalkyl($C_{1-6}$)alkyl, $C_{3-7}$ heterocycloalkylcarbonyl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

Generally, $R^3$ represents hydrogen; or $C_{2-6}$ alkynyl, aryl ($C_{1-6}$)alkyl or heteroaryl-($C_{1-6}$)alkyl, any of which groups may be optionally substituted by one or more substituents. More particularly, $R^3$ represents aryl($C_{1-6}$)alkyl or heteroaryl ($C_{1-6}$)alkyl, either of which groups may be optionally substituted by one or more substituents.

In one specific embodiment, $R^3$ represents hydrogen.

In a representative embodiment, $R^3$ represents $C_{1-6}$ alkyl, aryl($C_{1-6}$)alkyl, biaryl-($C_{1-6}$)alkyl, heteroaryl($C_{1-6}$)alkyl or heteroaryl-aryl($C_{1-6}$)alkyl, any of which groups may be optionally substituted by one or more substituents. Preferably, $R^3$ represents methyl, arylmethyl, biarylmethyl, heteroarylmethyl or heteroaryl-arylmethyl, any of which groups may be optionally substituted by one or more substituents. More particularly, $R^3$ represents arylmethyl or heteroarylmethyl, either of which groups may be optionally substituted by one or more substituents.

In a particular embodiment, $R^3$ represents substituted or unsubstituted indolyl-($C_{1-6}$)alkyl. Advantageously, $R^3$ represents substituted or unsubstituted indolylmethyl.

In a typical embodiment, $R^3$ represents substituted or unsubstituted phenyl-($C_{1-6}$)alkyl. Advantageously, $R^3$ represents substituted or unsubstituted benzyl.

In another embodiment, $R^3$ represents substituted or unsubstituted benzofuryl-($C_{1-6}$)alkyl. Advantageously, $R^3$ represents substituted or unsubstituted benzofurylmethyl.

In a further embodiment, $R^3$ represents substituted or unsubstituted pyrrolo[3,2-c]-pyridinyl($C_{1-6}$)alkyl. Advantageously, $R^3$ represents substituted or unsubstituted pyrrolo[3, 2-c]pyridinylmethyl.

Illustratively, $R^3$ represents hydrogen; or methyl, phenyl, benzyl, phenylethyl, naphthylmethyl, phenylpropynyl, biphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, pyrrolo[2,3-b]pyridinylmethyl, benzimidazolylmethyl, benzotriazolylmethyl, pyridinylmethyl, quinolinylmethyl, isoquinolinylmethyl, benzofurylbenzyl, thienylbenzyl, benzothienylbenzyl, indolylbenzyl, isoxazolylbenzyl, pyrazolylbenzyl, pyridinylbenzyl, pyrimidinylbenzyl or phenylpyridinylmethyl, any of which groups may be optionally substituted by one or more substituents. Additionally, $R^3$ may represent propynyl, benzofurylmethyl or pyrrolo[3,2-c]pyridinylmethyl, any of which groups may be optionally substituted by one or more substituents.

Suitably, $R^4$ represents hydrogen or optionally substituted $C_{1-6}$ alkyl.

Definitive examples of suitable substituents on $R^3$ and/or $R^4$ include halogen, cyano, nitro, $C_{1-6}$ alkyl, $C_{2-6}$ alkenyl, $C_{3-7}$ cycloalkyl, ($C_{1-6}$)alkylaryl, di($C_{1-6}$)alkylaryl, piperidinyl ($C_{1-6}$)alkylaryl, piperazinyl($C_{1-6}$)alkylaryl, ($C_{1-6}$)alkylpiperazinyl($C_{1-6}$)alkylaryl, morpholinyl($C_{1-6}$)alkylaryl, ($C_{1-6}$) alkoxyaryl, cyano($C_{1-6}$)alkoxyaryl, di($C_{1-6}$)alkylamino-($C_{1-6}$)alkylaryl, ($C_{1-6}$)alkylaminocarbonylaryl, aryl($C_{1-6}$) alkyl, oxazolinyl, azetidinyl, haloarylpyrrolidinyl, dioxopyrrolidinyl, aminopyrrolidinyl, di($C_{1-6}$)alkylaminopyrrolidinyl, indolinyl, oxoindolinyl, arylpiperidinyl, arylcarbonylpiperidinyl, di($C_{1-6}$)alkylaminocarbonylpiperidinyl, piperazinyl, ($C_{1-6}$)alkylpiperazinyl, haloarylpiperazinyl, pyridinylpiperazinyl, furoylpiperazinyl, homopiperazinyl, ($C_{1-6}$)alkylhomopiperazinyl, morpholinyl, ($C_{1-6}$)

alkylpiperazinyl($C_{1-6}$)alkyl, morpholinyl($C_{1-6}$)alkyl, benzofuryl, benzothienyl, pyrazolyl, ($C_{1-6}$)alkylpyrazolyl, di($C_{1-6}$)alkylpyrazolyl, tri($C_{1-6}$)alkylpyrazolyl, [di($C_{1-6}$)alkyl](trifluoromethyl)pyrazolyl, cyano($C_{1-6}$)alkylpyrazolyl, [cyano-($C_{1-6}$)alkyl][di($C_{1-6}$)alkyl]pyrazolyl, hydroxy($C_{1-6}$)alkylpyrazolyl, [hydroxy($C_{1-6}$)-alkyl][di($C_{1-6}$)alkyl]pyrazolyl, methoxy($C_{1-6}$)alkylpyrazolyl, [(hydroxy)(methoxy)($C_{1-6}$)-alkyl]pyrazolyl, amino($C_{1-6}$)alkylpyrazolyl, [($C_{1-6}$)alkyl][amino($C_{1-6}$)alkyl]pyrazolyl, [amino($C_{1-6}$)alkyl][di($C_{1-6}$)alkyl]pyrazolyl, di($C_{1-6}$)alkylamino($C_{1-6}$)alkylpyrazolyl, di($C_{1-6}$)alkoxyphosphono($C_{1-6}$)alkylpyrazolyl, ($C_{2-6}$)alkenylpyrazolyl, ($C_{3-7}$)cycloalkyl-($C_{1-6}$)alkylpyrazolyl, [($C_{3-7}$)cycloalkyl($C_{1-6}$)alkyl][di($C_{1-6}$)alkyl]pyrazolyl, [($C_{1-6}$)alkyl]-(aryl)pyrazolyl, (aryl)(trifluoromethyl)pyrazolyl, aryl($C_{1-6}$)alkylpyrazolyl, aminoaryl-($C_{1-6}$)alkylpyrazolyl, piperidinylpyrazolyl, tetrahydropyranyl($C_{1-6}$)alkylpyrazolyl, [di-($C_{1-6}$)alkyl][tetrahydropyranyl($C_{1-6}$)alkyl]pyrazolyl, pyrrolidinyl($C_{1-6}$)alkylpyrazolyl, piperidinyl($C_{1-6}$)alkylpyrazolyl, ($C_{1-6}$)alkylpiperidinyl($C_{1-6}$)alkylpyrazolyl, morpholinyl($C_{1-6}$)alkylpyrazolyl, pyridinyl($C_{1-6}$)alkylpyrazolyl, oxypyridinyl($C_{1-6}$)alkylpyrazolyl, [arylcarbonyl($C_{1-6}$)alkyl][di($C_{1-6}$)alkyl]pyrazolyl, [($C_{1-6}$)alkyl](piperazinylcarbonyl)pyrazolyl, [($C_{1-6}$)alkylaminocarbonyl][($C_{1-6}$)alkylaryl]pyrazolyl, [($C_{1-6}$)alkyl]-[amino($C_{1-6}$)alkylaminocarbonyl]pyrazolyl, aminocarbonyl($C_{1-6}$)alkylpyrazolyl, [aminocarbonyl($C_{1-6}$)alkyl][di($C_{1-6}$)alkyl]pyrazolyl, di($C_{1-6}$)alkylaminocarbonyl($C_{1-6}$)alkylpyrazolyl, pyrazolo[1,5-a]pyridinyl, di($C_{1-6}$)alkylisoxazolyl, (amino)[($C_{1-6}$)alkyl]-isoxazolyl, thiazolyl, di($C_{1-6}$)alkylthiazolyl, imidazolyl, ($C_{1-6}$)alkylimidazolyl, di($C_{1-6}$)-alkylimidazolyl, imidazo[1,2-a]pyridinyl, ($C_{1-6}$)alkylimidazo[1,2-a]pyridinyl, ($C_{1-6}$)-alkylimidazo[4,5-b]pyridinyl, imidazo[1,2-a]pyrimidinyl, imidazo[1,2-a]pyrazinyl, ($C_{1-6}$)-alkylthiadiazolyl, triazolyl, pyridinyl, halopyridinyl, ($C_{1-6}$)alkylpyridinyl, [($C_{1-6}$)alkyl]-(halo)pyridinyl, di($C_{1-6}$)alkylpyridinyl, ($C_{2-6}$)alkenylpyridinyl, ($C_{1-6}$)alkylpiperazinylpyridinyl, [($C_{1-6}$)alkyl](piperazinyl)pyridinyl, [($C_{1-6}$)alkoxycarbonylpiperazinyl][($C_{1-6}$)-alkyl]pyridinyl, piperidinyl($C_{1-6}$)alkylpyridinyl, [($C_{1-6}$)alkyl](oxy)pyridinyl, hydroxypyridinyl, hydroxy($C_{1-6}$)alkylpyridinyl, ($C_{1-6}$)alkoxypyridinyl, [($C_{1-6}$)alkoxy]-[($C_{1-6}$)alkyl]pyridinyl, [($C_{1-6}$)alkoxy][di($C_{1-6}$)alkyl]pyridinyl, ($C_{1-6}$)alkoxy($C_{1-6}$)alkylpyridinyl, aminopyridinyl, carboxy($C_{1-6}$)alkylpyridinyl, ($C_{1-6}$)alkoxycarbonyl($C_{1-6}$)alkylpyridinyl, pyridazinyl, ($C_{1-6}$)alkylpyridazinyl, piperidinylpyridazinyl, oxypyridazinyl, ($C_{1-6}$)alkoxypyridazinyl, aminopyridazinyl, hydroxy($C_{1-6}$)alkylaminopyridazinyl, di-($C_{1-6}$)alkylaminopyridazinyl, pyrimidinyl, ($C_{1-6}$)alkylpyrimidinyl, [($C_{1-6}$)alkyl](halo)-pyrimidinyl, di($C_{1-6}$)alkylpyrimidinyl, pyrrolidinylpyrimidinyl, ($C_{1-6}$)alkylpiperazinylpyrimidinyl, [($C_{1-6}$)alkyl](piperazinyl)pyrimidinyl, [($C_{1-6}$)alkoxycarbonyl][($C_{1-6}$)alkyl]-piperazinylpyrimidinyl, hydroxypyrimidinyl, [($C_{1-6}$)alkyl](hydroxy)pyrimidinyl, [($C_{1-6}$)-alkyl][hydroxy($C_{1-6}$)alkyl]pyrimidinyl, [($C_{1-6}$)alkyl][hydroxy($C_{2-6}$)alkynyl]pyrimidinyl, ($C_{1-6}$)alkoxypyrimidinyl, aminopyrimidinyl, di($C_{1-6}$)alkylaminopyrimidinyl, [di($C_{1-6}$)alkylamino](halo)pyrimidinyl, carboxypyrimidinyl, [($C_{1-6}$)alkoxycarbonyl($C_{1-6}$)alkyl][($C_{1-6}$)-alkyl]pyrimidinyl, aminocarbonylpyrimidinyl, pyrazinyl, ($C_{1-6}$)alkoxypyrazinyl, aminopyrazinyl, hydroxy, ($C_{1-6}$)alkoxy, difluoromethoxy, trifluoromethoxy, $C_{3-7}$ cycloalkoxy, $C_{3-7}$ cycloalkyl($C_{1-6}$)alkoxy, aryl($C_{1-6}$)alkoxycarbonylpiperidinyloxy, morpholinyl($C_{1-6}$)-alkoxy, aryloxy, haloaryloxy, di($C_{1-6}$)alkylpyrazolyloxy, halopyridinyloxy, pyrrolidinylpyridinyloxy, ($C_{1-6}$)alkylpiperazinylpyridinyloxy, ($C_{1-6}$)alkylpyrazolylpyridinyloxy, ($C_{1-6}$)alkylaminopyridinyloxy, carboxypyridinyloxy, aminocarbonylpyridinyloxy, ($C_{1-6}$)alkylpyridazinyloxy, pyrimidinyloxy, ($C_{1-6}$)alkylpyrimidinyloxy, [($C_{1-6}$)alkyl](halo)pyrimidinyloxy, hydroxy($C_{1-6}$)alkyl, dihydroxy($C_{1-6}$)alkyl, pyridinyloxy($C_{1-6}$)alkyl, amino, ($C_{1-6}$)alkylamino, dihydroxy($C_{1-6}$)alkylamino, ($C_{1-6}$)-alkoxy($C_{1-6}$)alkylamino, N—($C_{1-6}$)alkoxy($C_{1-6}$)alkyli-N—($C_{1-6}$)alkyl]amino, di($C_{1-6}$)-alkylamino($C_{1-6}$)alkylamino, N—[($C_{1-6}$)alkyl]-N-[di($C_{1-6}$)alkylamino($C_{1-6}$)alkyl]amino, N—[($C_{1-6}$)alkyl]-N—[($C_{3-7}$)cycloalkyl]amino, haloarylamino, N—[($C_{1-6}$)alkyl]-N-(haloaryl)amino, methylenedioxyphenylamino, morpholinyl($C_{1-6}$)alkylphenylamino, oxazolinylphenylamino, [($C_{1-6}$)alkyl](oxo)pyrazolylphenylamino, oxazolylphenylamino, isoxazolylphenylamino, thazolylphenylamino, ($C_{1-6}$)alkyltriazolylphenylamino, ($C_{1-6}$)alkylpyrimidinylphenylamino, pyrazolyl($C_{1-6}$)alkylphenylamino, triazolyl($C_{1-6}$)alkylphenylamino, $C_{1-6}$ alkylsulphonylaminophenylamino, morpholinylcarbonylphenylamino, $C_{1-6}$ alkylsulphonylphenylamino, morpholinylsulphonylphenylamino, N—[($C_{1-6}$)alkyl]-N-[aryl($C_{1-6}$)alkyl]amino, N-[di($C_{1-6}$)alkylamino($C_{1-6}$)alkyl]-N-[aryl($C_{1-6}$)alkyl]amino, cyanoaryl($C_{1-6}$)alkylamino, (cyano)(halo)aryl($C_{1-6}$)alkylamino, methylenedioxyaryl($C_{1-4}$-alkylamino, dihydrobenzofuranylamino, N—[($C_{1-6}$)alkyl]-N—[($C_{1-6}$)alkylpyrrolidinyl]amino, $C_{1-6}$ alkylsulphonylindolinylamino, chromanonylamino, piperidinylamino, N—[($C_{1-6}$)alkyl]-N-(piperidinyl)amino, N—[($C_{3-7}$)cycloalkyl($C_{1-6}$)alkyl]-N-(piperidinypamino, ($C_{1-6}$)alkylpiperidinylamino, N—[($C_{1-6}$)alkyl]-N—[($C_{1-6}$)alkylpiperidinyl]amino, N—[($C_{1-6}$)alkyl]-N—[($C_{3-7}$)cycloalkylpiperidinyl]amino, N—[($C_{1-6}$)alkyl]-N—[($C_{2-6}$)alkylcarbonylpiperidinyl]-amino, dihydroquinolinonylamino, benzoxazinonylamino, pyrrolidinyl($C_{1-6}$)alkylamino, N—[($C_{1-6}$)alkyl]-N-[pyrrolidinyl($C_{1-6}$)alkyl]amino, N—[($C_{1-6}$)alkyl]-N-[piperidinyl($C_{1-6}$)-alkyl]amino, benzothienylamino, indolylamino, dioxoindolylamino, ($C_{1-6}$)alkylpyrazolylamino, [($C_{1-6}$)alkyl](halo)pyrazolylamino, di($C_{1-6}$)alkylpyrazolylamino, tri($C_{1-6}$)alkylpyrazolylamino, N—[($C_{1-6}$)alkyl]-N—[($C_{1-6}$)alkylpyrazolyl]amino, ($C_{1-6}$)alkylindazolylamino, benzoxazolylamino, benzoxazolonylamino, di($C_{1-6}$)alkylisoxazolylamino, thiazolylamino, benzothiazolylamino, ($C_{1-6}$)alkylisothiazolylamino, imidazolylamino, [($C_{1-6}$)alkoxycarbonyl][($C_{1-6}$)alkyl]imidazolyl amino, ($C_{1-6}$)alkylbenzimidazolylamino, benzimidazolonylamino, di($C_{1-6}$)alkylbenzimidazolonylamino, ($C_{1-6}$)alkyloxadiazolylamino, furyloxadiazolylamino, ($C_{1-6}$)alkylthiadiazolylamino, pyridinylamino, halopyridinylamino, ($C_{1-6}$)alkylpyridinylamino, di($C_{1-6}$)alkylpyridinylamino, trifluoromethylpyridinylamino, hydroxypyridinylamino, hydroxy($C_{1-6}$)alkylpyridinylamino, dihydroxy($C_{1-6}$)alkylpyridinylamino, ($C_{1-6}$)alkoxypyridinylamino, dihydroxy($C_{1-6}$)alkoxypyridinylamino, di($C_{1-6}$)alkyldioxolanyl($C_{1-6}$)alkoxypyridinylamino, ($C_{1-6}$)alkoxy($C_{1-6}$)-alkylpyridinylamino, ($C_{1-6}$)alkoxy($C_{2-6}$)alkenylpyridinylamino, dihydroxy($C_{1-6}$)alkylaminopyridinylamino, di($C_{1-6}$)alkylaminopyridinylamino, ($C_{1-6}$)alkylamino($C_{1-6}$)alkylpyridinylamino, di($C_{1-6}$)alkylamino($C_{1-6}$)alkylpyridinylamino, oxopyridinylamino, carboxypyridinylamino, N—[($C_{1-6}$)alkyl]-N—[($C_{1-6}$)alkylpyridinyl]amino, bis[($C_{1-6}$)alkylpyridinyl]amino, bis(trifluoromethylpyridinyl)amino, isoquinolinylamino, ($C_{1-6}$)alkylpyridazinylamino, N—[($C_{1-6}$)alkyl]-N—[($C_{1-6}$)alkylpyridazinyl]amino, N-[aryl($C_{1-6}$)alkyl]-N—[($C_{1-6}$)alkylpyridazinyl]amino, di($C_{1-6}$)alkylpyridazinylamino, arylpyridazinylamino, piperidinylpyridazinylamino, ($C_{1-6}$)alkoxypyridazinylamino, [($C_{1-6}$)alkoxyl](halo)-pyridazinylamino, di($C_{1-6}$)alkylaminopyridazinylamino, bis[($C_{1-6}$)

alkylpyridazinyl]amino, $(C_{1-6})$alkylcinnolinylamino, oxopyrimidinylamino, thioxopyrimidinylamino, quinoxalinylamino, $(C_{1-6})$alkylchromenylamino, benzofuryl$(C_{1-6})$alkylamino, thienyl$(C_{1-6})$-alkylamino, indolyl$(C_{1-6})$alkylamino, $(C_{1-6})$alkylpyrazolyl$(C_{1-6})$alkylamino, [di$(C_{1-6})$alkyl]-(halo)pyrazolyl$(C_{1-6})$alkylamino, di$(C_{1-6})$alkylisoxazolyl$(C_{1-6})$alkylamino, thiazolyl$(C_{1-6})$-alkylamino, imidazolyl$(C_{1-6})$alkylamino, $(C_{1-6})$alkylimidazolyl$(C_{1-6})$alkylamino, pyridinyl$(C_{1-6})$alkylamino, $(C_{1-6})$alkylpyridinyl$(C_{1-6})$alkylamino, N—[$(C_{1-6})$alkyl]-N-[pyridinyl$(C_{1-6})$alkyl]amino, N-[dihydroxy$(C_{1-6})$alkyl]-N-[pyridinyl$(C_{1-6})$alkyl]amino, N—[$(C_{1-6})$alkylpyridinyl$(C_{1-6})$alkyl]-N-[dihydroxy$(C_{1-6})$alkyl]amino, amino$(C_{1-6})$alkyl, $(C_{1-6})$-alkylamino$(C_{1-6})$alkyl, di$(C_{1-6})$alkylamino$(C_{1-6})$alkyl, pyridinylamino$(C_{1-6})$alkyl, $C_{2-6}$ alkylcarbonylamino, N—[$(C_{2-6})$alkylcarbonyl]-N—[$(C_{1-6})$alkylpyridinyl$(C_{1-6})$alkyl]amino, di$(C_{1-6})$alkylamino$(C_{1-6})$alkylcarbonylamino, $C_{2-6}$ alkylcarbonylaminomethyl, $(C_{3-7})$-cycloalkylcarbonylamino, $(C_{1-6})$alkylpiperidinylcarbonylamino, $(C_{1-6})$alkylimidazolylcarbonylamino, $C_{2-6}$ alkoxycarbonylamino, [$(C_{2-6})$alkoxycarbonyl][$(C_{1-6})$alkyl]amino, $C_{1-6}$ alkylsulphonylamino, formyl, $C_{2-6}$ alkylcarbonyl, $C_{2-6}$ alkylcarbonyl oxime, $C_{2-6}$ alkylcarbonyl O-(methyl) oxime, trifluoromethylcarbonyl, carboxy, $C_{2-6}$ alkoxycarbonyl, aminocarbonyl, $C_{1-6}$ alkylaminocarbonyl, [hydroxy$(C_{1-6})$alkyl]aminocarbonyl, [di$(C_{1-6})$-alkylamino$(C_{1-6})$alkyl]aminocarbonyl, di$(C_{1-6})$alkylaminocarbonyl, [$(C_{1-6})$alkyl][cyano-$(C_{1-6})$alkyl]aminocarbonyl, [$(C_{1-6})$alkyl][hydroxy$(C_{1-6})$alkyl]aminocarbonyl, [$(C_{1-6})$alkoxy-$(C_{1-6})$alkyl][$(C_{1-6})$alkyl]aminocarbonyl, [di$(C_{1-6})$alkylamino$(C_{1-6})$alkyl][$(C_{1-6})$alkyl]aminocarbonyl, $C_{3-7}$ cycloalkyl$(C_{1-6})$alkylaminocarbonyl, aryl$(C_{1-6})$alkylaminocarbonyl, $(C_{1-6})$-alkylpiperidinylaminocarbonyl, N—[$(C_{1-6})$alkyl]-N—[$(C_{1-6})$-alkylpiperidinyl]aminocarbonyl, piperidinyl$(C_{1-6})$alkylaminocarbonyl, heteroarylaminocarbonyl, heteroaryl$(C_{1-6})$alkylaminocarbonyl, azetidinylcarbonyl, hydroxyazetidinylcarbonyl, aminoazetidinylcarbonyl, $C_{2-6}$ alkoxycarbonylaminoazetidinylcarbonyl, pyrrolidinylcarbonyl, $(C_{1-6})$alkylpyrrolidinylcarbonyl, $C_{1-6}$ alkoxy$(C_{1-6})$alkylpyrrolidinylcarbonyl, di$(C_{1-6})$alkylaminopyrrolidinylcarbonyl, thiazolidinylcarbonyl, oxothiazolidinylcarbonyl, piperidinylcarbonyl, $(C_{1-6})$alkylpiperazinylcarbonyl, morpholinylcarbonyl, $C_{1-6}$ alkylthio, $C_{1-6}$ alkylsulphinyl, $C_{1-6}$ alkylsulphonyl, $C_{1-6}$ alkylsulphonylmethyl, di$(C_{1-6})$alkylaminosulphonyl, $C_{2-6}$ alkoxycarbonyloxy, trimethylsilyl and tetra$(C_{1-6})$alkyldioxaborolanyl.

Examples of typical substituents on $R^3$ and/or $R^4$ include halogen, cyano, nitro, $C_{1-6}$ alkyl, hydroxy$(C_{1-6})$alkyl, trifluoromethyl, pyrazolyl, $(C_{1-6})$alkylpyrazolyl, di$(C_{1-6})$alkylpyrazolyl, aryl$(C_{1-6})$alkylpyrazolyl, morpholinyl$(C_{1-6})$alkylpyrazolyl, $(C_{1-6})$alkylimidazolyl, $(C_{1-6})$alkylpyridinyl, pyrimidinyl, aryl$(C_{1-6})$alkyl, hydroxy, $C_{1-6}$ alkoxy, difluoromethoxy, trifluoromethoxy, aryloxy, aryl$(C_{1-6})$alkoxy, pyridinyloxy$(C_{1-6})$alkyl, methylenedioxy, difluoromethylenedioxy, $C_{1-6}$ alkylthio, arylthio, $C_{1-6}$ alkylsulphinyl, arylsulphinyl, $C_{1-6}$ alkylsulphonyl, arylsulphonyl, $C_{1-6}$ alkylsulphonyloxy, amino, $C_{1-6}$ alkylamino, di$(C_{1-6})$alkylamino, phenylamino, [$(C_{1-6})$alkyl](phenyl)amino, pyridinylamino, halopyridinylamino, $(C_{1-6})$alkylpyridinylamino, di$(C_{1-6})$alkylpyridinylamino, $(C_{1-6})$alkoxypyridinylamino, pyrrolidinyl, morpholinyl, $C_{2-6}$ alkylcarbonylamino, benzofurylcarbonylamino, $C_{2-6}$ alkoxycarbonylamino, $C_{1-6}$ alkylsulphonylamino, arylsulphonylamino, amino$(C_{1-6})$alkyl, $(C_{1-6})$alkylamino$(C_{1-6})$alkyl, di$(C_{1-6})$alkylamino$(C_{1-6})$alkyl, pyridinylamino$(C_{1-6})$alkyl, $(C_{1-6})$alkylpiperazinyl$(C_{1-6})$alkyl, morpholinyl$(C_{1-6})$alkyl, formyl, $C_{2-6}$ alkylcarbonyl, carboxy, $C_{2-6}$ alkoxycarbonyl, aminocarbonyl, $C_{1-6}$ alkylaminocarbonyl, [hydroxy$(C_{1-6})$alkyl]aminocarbonyl, di$(C_{1-6})$alkylaminocarbonyl, [$(C_{1-6})$alkyl][hydroxy$(C_{1-6})$alkyl]aminocarbonyl, aryl$(C_{1-6})$alkylaminocarbonyl, benzothienylmethylaminocarbonyl, azetidinylcarbonyl, pyrrolidinylcarbonyl, piperidinylcarbonyl, $(C_{1-6})$alkylpiperazinylcarbonyl, morpholinylcarbonyl, aminosulphonyl, $C_{1-6}$ alkylaminosulphonyl, di$(C_{1-6})$alkylaminosulphonyl and $C_{2-6}$ alkoxycarbonyloxy.

Examples of suitable substituents on $R^3$ and/or $R^4$ include halogen, cyano, nitro, $C_{1-6}$ alkyl, hydroxy$(C_{1-6})$alkyl, trifluoromethyl, aryl$(C_{1-6})$alkyl, hydroxy, $C_{1-6}$ alkoxy, difluoromethoxy, trifluoromethoxy, aryloxy, aryl$(C_{1-6})$alkoxy, methylenedioxy, $C_{1-6}$ alkylthio, arylthio, $C_{1-6}$ alkylsulphinyl, arylsulphinyl, $C_{1-6}$ alkylsulphonyl, arylsulphonyl, $C_{1-6}$ alkylsulphonyloxy, amino, $C_{1-6}$ alkylamino, di$(C_{1-6})$alkylamino, phenylamino, [$C_{1-6}$alkyl](phenyl)amino, pyridinylamino, pyrrolidinyl, morpholinyl, $C_{2-6}$ alkylcarbonylamino, benzofurylcarbonylamino, $C_{2-6}$ alkoxycarbonylamino, $C_{1-6}$ alkylsulphonylamino, arylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di$(C_{1-6})$alkylaminocarbonyl, benzothienylmethylaminocarbonyl, aminosulphonyl, $C_{1-6}$ alkylaminosulphonyl and di$(C_{1-6})$alkylaminosulphonyl.

Selected examples of typical substituents on $R^3$ and/or $R^4$ include halogen, nitro, $C_{1-6}$ alkyl, hydroxy$(C_{1-6})$alkyl, pyrazolyl, $(C_{1-6})$alkylpyrazolyl, di$(C_{1-6})$alkylpyrazolyl, aryl$(C_{1-6})$alkylpyrazolyl, morpholinyl$(C_{1-6})$alkylpyrazolyl, $(C_{1-6})$alkylimidazolyl, $(C_{1-6})$alkylpyridinyl, pyrimidinyl, hydroxy, difluoromethoxy, trifluoromethoxy, pyridinyloxy$(C_{1-6})$alkyl, difluoromethylenedioxy, amino, pyridinylamino, halopyridinylamino, $(C_{1-6})$alkylpyridinylamino, di$(C_{1-6})$alkylpyridinylamino, $(C_{1-6})$alkoxypyridinylamino, di$(C_{1-6})$alkylamino$(C_{1-6})$alkyl, pyridinylamino$(C_{1-6})$alkyl, $(C_{1-6})$alkylpiperazinyl$(C_{1-6})$alkyl, morpholinyl$(C_{1-6})$alkyl, formyl, carboxy, $C_{2-6}$ alkoxycarbonyl, $C_{1-6}$ alkylaminocarbonyl, [hydroxy$(C_{1-6})$alkyl]aminocarbonyl, di$(C_{1-6})$alkylaminocarbonyl, [$(C_{1-6})$alkyl][hydroxy$(C_{1-6})$alkyl]aminocarbonyl, aryl$(C_{1-6})$alkylaminocarbonyl, azetidinylcarbonyl, piperidinylcarbonyl, $(C_{1-6})$alkylpiperazinylcarbonyl, morpholinylcarbonyl and $C_{2-6}$ alkoxycarbonyloxy.

Examples of illustrative substituents on $R^3$ and/or $R^4$ include fluoro, chloro, bromo, cyano, nitro, methyl, hydroxymethyl, trifluoromethyl, pyrazolyl, methylpyrazolyl, dimethylpyrazolyl, propylpyrazolyl, isobutylpyrazolyl, benzylpyrazolyl, morpholinylethylpyrazolyl, methylimidazolyl, methylpyridinyl, pyrimidinyl, benzyl, hydroxy, methoxy, ethoxy, difluoromethoxy, trifluoromethoxy, phenoxy, benzyloxy, pyridinyloxymethyl, methylenedioxy, difluoromethylenedioxy, methylthio, phenylthio, methylsulphinyl, phenylsulphinyl, methylsulphonyl, phenylsulphonyl, methylsulphonyloxy, amino, methylamino, dimethylamino, phenylamino, N-methyl-N-phenylamino, pyridinylamino, chloropyridinylamino, methylpyridinylamino, dimethylpyridinylamino, methoxypyridinylamino, pyrrolidinyl, morpholinyl, acetylamino, benzofurylcarbonylamino, methoxycarbonylamino, methylsulphonylamino, phenylsulphonylamino, aminomethyl, methylaminomethyl, dimethylaminomethyl, pyridinylaminomethyl, methylpiperazinylmethyl, morpholinylmethyl, formyl, acetyl, carboxy, methoxycarbonyl, aminocarbonyl, methylaminocarbonyl, (hydroxyethyl)aminocarbonyl, dimethylaminocarbonyl, N-(hydroxyethyl)-N-methylaminocarbonyl, benzylaminocarbonyl, benzothienylmethylaminocarbonyl, azetidinylcarbonyl, pyrrolidinylcarbonyl, piperidinylcarbonyl, methylpiperazinylcarbonyl, morpholinylcarbonyl, aminosulphonyl, methylaminosulphonyl, dimethylaminosulphonyl and tert-butoxycarbonyloxy.

Examples of representative substituents on $R^3$ and/or $R^4$ include fluoro, chloro, bromo, cyano, nitro, methyl, hydroxymethyl, trifluoromethyl, benzyl, hydroxy, methoxy, ethoxy, difluoromethoxy, trifluoromethoxy, phenoxy, benzyloxy, methylenedioxy, methylthio, phenylthio, methylsulphinyl, phenylsulphinyl, methylsulphonyl, phenylsulphonyl, methylsulphonyloxy, amino, methylamino, dimethylamino, phenylamino, N-methyl-N-phenylamino, pyridinylamino, pyrrolidinyl, morpholinyl, acetylamino, benzofurylcarbonylamino, methoxycarbonylamino, methylsulphonylamino, phenylsulphonylamino, formyl, acetyl, carboxy, methoxycarbonyl, aminocarbonyl, methylaminocarbonyl, dimethylaminocarbonyl, benzothienylmethylaminocarbonyl, aminosulphonyl, methylaminosulphonyl and dimethylaminosulphonyl.

Definitive examples of specific substituents on $R^3$ and/or $R^4$ include fluoro, chloro, bromo, cyano, nitro, methyl, n-propyl, isopropyl, allyl, cyclopropyl, methylphenyl, dimethylphenyl, piperidinylmethylphenyl, piperazinylmethyl-phenyl, methylpiperazinylmethylphenyl, morpholinylmethylphenyl, methoxyphenyl, cyanomethoxyphenyl, dimethylaminomethylphenyl, methylaminocarbonylphenyl, benzyl, oxazolinyl, azetidinyl, chlorophenylpyrrolidinyl, dioxopyrrolidinyl, aminopyrrolidinyl, dimethylaminopyrrolidinyl, indolinyl, oxoindolinyl, phenylpiperidinyl, benzoylpiperidinyl, diethylaminocarbonylpiperidinyl, piperazinyl, methylpiperazinyl, chlorophenylpiperazinyl, pyridinylpiperazinyl, furoylpiperazinyl, homopiperazinyl, methylhomopiperazinyl, morpholinyl, methylpiperazinylmethyl, methylpiperazinylethyl, morpholinylmethyl, benzofuryl, benzothienyl, pyrazolyl, methylpyrazolyl, ethylpyrazolyl, propylpyrazolyl, 2-methylpropylpyrazolyl, 3-methylbutylpyrazolyl, dimethylpyrazolyl, trimethylpyrazolyl, (dimethyl)(ethyl)pyrazolyl, (dimethyl)(isopropyl)pyrazolyl, (dimethyl)(2-methylpropyl)-pyrazolyl, (dimethyl)(3-methylbutyl)pyrazolyl, (dimethyl)(trifluoromethyl)pyrazolyl, cyanomethylpyrazolyl, (cyanomethyl)(dimethyl)pyrazolyl, hydroxyethylpyrazolyl, hydroxypropylpyrazolyl, 2-hydroxy-2-methylpropylpyrazolyl, (hydroxyethyl)(dimethyl)-pyrazolyl, (hydroxypropyl)(dimethyl)pyrazolyl, methoxypropylpyrazolyl, [(hydroxy)-(methoxy)propyl]pyrazolyl, aminoethylpyrazolyl, aminopropylpyrazolyl, (aminopropyl)-(methyl)pyrazolyl, (aminopropyl)(dimethyl)pyrazolyl, dimethylaminoethylpyrazolyl, dimethylaminopropylpyrazolyl, diethoxyphosphonopropylpyrazolyl, allylpyrazolyl, cyclopropylmethylpyrazolyl, (cyclopropylmethyl)(dimethyl)pyrazolyl, (methyl)(phenyl)-pyrazolyl, (phenyl)(trifluoromethyl)pyrazolyl, benzylpyrazolyl, aminobenzylpyrazolyl, piperidinylpyrazolyl, tetrahydropyranylmethylpyrazolyl, (dimethyl)(tetrahydropyranylmethyl)pyrazolyl, pyrrolidinylethylpyrazolyl, piperidinylethylpyrazolyl, methylpiperidinylethylpyrazolyl, morpholinylethylpyrazolyl, pyridinylmethylpyrazolyl, oxypyridinylmethylpyrazolyl, (dimethyl)(phenylcarbonylmethyl)pyrazolyl, (ethyl)(piperazinylcarbonyl)pyrazolyl, (methylaminocarbonyl)(methylphenyl)pyrazolyl, (aminoethylaminocarbonyl)(methyl)pyrazolyl, aminocarbonylmethylpyrazolyl, (aminocarbonylmethyl)(dimethyl]pyrazolyl, dimethylaminocarbonylmethylpyrazolyl, pyrazolo[1,5-a]pyridinyl, dimethylisoxazolyl, (amino)(methyl)isoxazolyl, thiazolyl, dimethylthiazolyl, imidazolyl, methylimidazolyl, dimethylimidazolyl, imidazo[1,2-a]pyridinyl, methylimidazo[1,2-a]pyridinyl, methylimidazo[4,5-b]pyridinyl, imidazo[1,2-a]pyrimidinyl, imidazo[1,2-a]pyrazinyl, methylthiadiazolyl, triazolyl, pyridinyl, fluoropyridinyl, methylpyridinyl, (fluoro)(methyl)pyridinyl, dimethylpyridinyl, vinylpyridinyl, (methylpiperazinyl)pyridinyl, (methyl)(piperazinyl)pyridinyl, (tertbutoxycarbonylpiperazinyl)(methyl)pyridinyl, piperidinylmethylpyridinyl, (methyl)(oxy)-pyridinyl, hydroxypyridinyl, hydroxymethylpyridinyl, hydroxyethylpyridinyl, methoxypyridinyl, (methoxy)(methyl)pyridinyl, (dimethyl)(methoxy)pyridinyl, methoxymethylpyridinyl, aminopyridinyl, carboxymethylpyridinyl, ethoxycarbonylmethylpyridinyl, pyridazinyl, methylpyridazinyl, piperidinylpyridazinyl, oxypyridazinyl, methoxypyridazinyl, aminopyridazinyl, hydroxyethylaminopyridazinyl, dimethylaminopyridazinyl, pyrimidinyl, methylpyrimidinyl, (chloro)(methyl)pyrimidinyl, dimethylpyrimidinyl, pyrrolidinylpyrimidinyl, methylpiperazinylpyrimidinyl, (methyl)-(piperazinyl)pyrimidinyl, (tert-butoxycarbonylpiperazinyl)(methyl)pyrimidinyl, hydroxypyrimidinyl, (hydroxy)(methyl)pyrimidinyl, (hydroxyethyl)(methyl)pyrimidinyl, (hydroxypropyl)(methyl)pyrimidinyl, (hydroxypropynyl)(methyl)pyrimidinyl, methoxypyrimidinyl, aminopyrimidinyl, dimethylaminopyrimidinyl, (dimethylamino)-(fluoro)pyrimidinyl, carboxypyrimidinyl, (methoxycarbonylmethyl)(methyl)pyrimidinyl, aminocarbonylpyrimidinyl, pyrazinyl, methoxypyrazinyl, aminopyrazinyl, hydroxy, methoxy, isopropoxy, difluoromethoxy, trifluoromethoxy, cyclobutyloxy, cyclopropylmethoxy, benzyloxycarbonylpiperidinyloxy, morpholinylethoxy, phenoxy, fluorophenoxy, dimethylpyrazolyloxy, bromopyridinyloxy, pyrrolidinylpyridinyloxy, methylpiperazinylpyridinyloxy, methylpyrazolylpyridinyloxy, isopropylaminopyridinyloxy, carboxypyridinyloxy, aminocarbonylpyridinyloxy, methylpyridazinyloxy, pyrimidinyloxy, methylpyrimidinyloxy, (chloro)(methyl)pyrimidinyloxy, hydroxymethyl, 1-hydroxy-1-methylethyl, dihydroxypropyl, pyridinyloxymethyl, amino, isopropylamino, dihydroxypropylamino, methoxyethylamino, methoxypropylamino, N-(methoxyethyl)-N-(methyl)amino, N-(methoxypropyl)-N-(methyl)amino, dimethylaminoethylamino, dimethylaminopropylamino, N-(dimethylaminoethyl)-N-(methyl)amino, N-(diethylaminoethyl)-N-(methyl)amino, N-(dimethylaminopropyl)-N-(methyl)amino, N-(dimethylaminoethyl)-N-(ethyl)amino, N-(dimethylaminopropyl)-N-(ethyl)amino, N-(cyclohexyl)-N-(methyl)amino, fluorophenylamino, N-fluorophenyl-N-methylamino, methylenedioxyphenylamino, morpholinylmethylphenylamino, oxazolinylphenylamino, (methyl)(oxo)pyrazolylphenylamino, oxazolylphenylamino, isoxazolylphenylamino, triazolylphenylamino, methyltriazolylphenylamino, methylpyrimidinylphenylamino, pyrazolylmethylphenylamino, triazolylmethylphenylamino, methylsulphonylaminophenylamino, morpholinylcarbonylphenylamino, methylsulphonylphenylamino, morpholinylsulphonylphenylamino, N-benzyl-N-methylamino, N-(benzyl)-N-(dimethylaminoethyl)amino, cyanobenzylamino, (cyano)(phenyl)ethylamino, (cyano)(fluoro)-benzylamino, methylenedioxybenzylamino, dihydrobenzofuranylamino, N-(methyl)-N-(methylpyrrolidinyl)amino, methylsulphonylindolinylamino, chromanonylamino, piperidinylamino, N-(methyl)-N-(piperidinyl)amino, N-(ethyl)-N-(piperidinyl)amino, N-(cyclopropylmethyl)-N-(piperidinyl)amino, methylpiperidinylamino, N-(methyl)-N-(methylpiperidinyl)amino, N-(methyl)-N-(2-methylpropylpiperidinyl)amino, N-(cyclopentylpiperidinyl)-N-(methyl)amino, N-(acetylpiperidinyl)-N-(methyl)amino, dihydroquinolinonylamino, benzoxazinonylamino, pyrrolidinylethylamino, pyrrolidinylpropylamino, N-(methyl)-N-(pyrrolidinylethyl)amino, N-(methyl)-N-(pyrrolidinylpropyl)amino, N-(methyl)-N-(piperidinylmethyl)amino, benzothienylamino, indolylamino, dioxoindolylamino, methylpyrazolylamino, (bromo)(methyl)pyrazolylamino, dimethylpyrazolylamino, trimethylpyrazolylamino, N-(ethyl)-N-(methylpyrazolyl)-amino, methylindazolylamino, benzoxazolylamino, benzoxazolonylamino, dimethylisoxazolylamino, thiazolylamino, benzothiazolylamino, methylisothiazolylamino, imidazolylamino, (ethoxycarbonyl)(methyl)imidazolylamino, methylbenzimidazolylamino, benzimidazolonylamino, dimethylbenzimidazolonylamino, methyloxadiazolylamino, furyloxadiazolylamino, methylthiadiazolylamino, pyridinylamino, chloropyridinylamino, bromopyridinylamino, methylpyridinylamino, dimethylpyridinylamino, trifluoromethylpyridinylamino, hydroxypyridinylamino, hydroxyethylpyridinylamino, dihydroxyethylpyridinylamino, methoxypyridinylamino, dihydroxypropoxypyridinylamino, dimethyldioxolanylmethoxypyridinylamino, methoxyethylpyridinylamino, methoxyvinylpyridinylamino, dihydroxypropylaminopyridinylamino, dimethylaminopyridinylamino, methylaminomethylpyridinylamino, dimethylaminomethylpyridinylamino, oxopyridinylamino, carboxypyridinylamino, N-(methyl)-N-(methylpyridinyl)-amino, N-(ethyl)-N-(methylpyridinyl)amino, bis(methylpyridinyl)amino, bis(trifluoromethylpyridinyl)amino, isoquinolinylamino, methylpyridazinylamino, N-(methyl)-N-(methylpyridazinyl)amino, N-(benzyl)-N-(methylpyridazinyl)amino, dimethylpyridazinylamino, phenylpyridazinylamino, piperidinylpyridazinylamino, methoxypyridazinylamino, (chloro)(methoxy)pyridazinylamino, dimethylaminopyridazinylamino, bis(methylpyridazinyl)amino, methylcinnolinylamino, oxopyrimidinylamino, thioxopyrimidinylamino, quinoxalinylamino, methylchromenylamino, benzofurylmethylamino, thienylmethylamino, indolylmethylamino, methylpyrazolylmethylamino, (chloro)(dimethyl)pyrazolylmethylamino, dimethylisoxazolylmethylamino, thiazolylmethylamino, imidazolylmethylamino, methylimidazolylmethylamino, pyridinylmethylamino, methylpyridinylmethylamino, N-(methyl)-N-(pyridinylethyl)-amino, N-(dihydroxypropyl)-N-(pyridinylmethyl)amino, N-(dihydroxypropyl)-N-(methylpyridinylmethyl)amino, aminomethyl, methylaminomethyl, dimethylaminomethyl, pyridinylaminomethyl, acetylamino, N-(acetyl)-N-(methylpyridinyl)amino, dimethylaminoethylcarbonylamino, acetylaminomethyl, cyclohexylcarbonylamino, methylpiperidinylcarbonylamino, methylimidazolylcarbonylamino, methoxycarbonylamino, N-methoxycarbonyl-N-methylamino, methylsulphonylamino, formyl, acetyl, acetyl oxime, acetyl O-(methyl)oxime, trifluoromethylcarbonyl, carboxy, methoxycarbonyl, aminocarbonyl, methylaminocarbonyl, (hydroxyethyl)aminocarbonyl, (dimethylaminoethyl)aminocarbonyl, (1-hydroxyprop-2-yl)aminocarbonyl, dimethylaminocarbonyl, N-(cyanomethyl)-N-methylaminocarbonyl, N-(cyanoethyl)-N-methylaminocarbonyl, N-(hydroxyethyl)-N-methylaminocarbonyl, N-(methoxyethyl)-N-methylaminocarbonyl, N-(dimethylaminoethyl)-N-methylaminocarbonyl, N-isopropyl-N-methylaminocarbonyl, diethylaminocarbonyl, cyclopropylmethylaminocarbonyl, benzylaminocarbonyl, methylpiperidinylaminocarbonyl, N-(methyl)-N-(methylpiperidinyl)aminocarbonyl, piperidinylethylaminocarbonyl, pyrazolylaminocarbonyl, pyridinylmethylaminocarbonyl, azetidinylcarbonyl, hydroxyazetidinylcarbonyl, aminoazetidinylcarbonyl, tert-butoxycarbonylaminoazetidinylcarbonyl, pyrrolidinylcarbonyl, methylpyrrolidinylcarbonyl, methoxymethylpyrrolidinylcarbonyl, dimethylaminopyrrolidinylcarbonyl, thiazolidinylcarbonyl, oxothiazolidinylcarbonyl, piperidinylcarbonyl, methylpiperazinylcarbonyl, morpholinylcarbonyl, isopropylthio, isopropylsulphinyl, methylsulphonyl, isopropylsulphonyl, methylsulphonylmethyl, dimethylaminosulphonyl, tert-butoxycarbonyloxy, trimethylsilyl and tetramethyldioxaborolanyl.

Selected examples of illustrative substituents on $R^3$ and/or $R^4$ include fluoro, bromo, nitro, methyl, hydroxymethyl, pyrazolyl, methylpyrazolyl, dimethylpyrazolyl, propylpyrazolyl, isobutylpyrazolyl, benzylpyrazolyl, morpholinylethylpyrazolyl, methylimidazolyl, methylpyridinyl, pyrimidinyl, hydroxy, difluoromethoxy, trifluoromethoxy, pyridinyloxymethyl, difluoromethylenedioxy, amino, pyridinylamino, chloropyridinylamino, methylpyridinylamino, dimethylpyridinylamino, methoxypyridinylamino, dimethylaminomethyl, pyridinylaminomethyl, methylpiperazinylmethyl, morpholinylmethyl, formyl, carboxy, methoxycarbonyl, methylaminocarbonyl, (hydroxyethyl)aminocarbonyl, dimethylaminocarbonyl, N-(hydroxyethyl)-N-methylaminocarbonyl, benzylaminocarbonyl, azetidinylcarbonyl, piperidinylcarbonyl, methylpiperazinylcarbonyl, morpholinylcarbonyl and tert-butoxycarbonyloxy.

Selected values of $R^3$ include hydrogen, methyl, phenoxymethyl, phenylthiomethyl, aminomethyl, phenylaminomethyl, N-methyl-N-phenylaminomethyl, pyridinylamino-methyl, benzofurylcarbonylaminomethyl, phenylsulphonylaminomethyl, benzothienyl-methylaminocarbonylmethyl, phenyl, benzyl, chlorobenzyl, bromobenzyl, pyridinylaminobenzyl, chloropyridinylaminobenzyl, dimethylpyridinylaminobenzyl, methoxypyridinylaminobenzyl, pyrrolidinyl-benzyl, morpholinyl-benzyl, phenylethyl, naphthylmethyl, phenylpropynyl, biphenylmethyl, fluorobiphenylmethyl, difluorobiphenylmethyl, chlorobiphenylmethyl, dichlorobiphenylmethyl, bromobiphenylmethyl, cyanobiphenylmethyl, methylbiphenyl-methyl, (fluoro)(methyl)biphenylmethyl, dimethylbiphenylmethyl, hydroxymethylbiphenylmethyl, trifluoromethylbiphenylmethyl, bis(trifluoromethyl)biphenylmethyl, methoxybiphenylmethyl, dimethoxybiphenylmethyl, ethoxybiphenylmethyl, methylenedioxybiphenylmethyl, trifluoromethoxybiphenylmethyl, phenoxybiphenylmethyl, methylthiobiphenylmethyl, aminobiphenylmethyl, acetylaminobiphenylmethyl, methylsulphonylaminobiphenylmethyl, acetylbiphenylmethyl, aminocarbonylbiphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, methyl-1,2,3,4-tetrahydroquinolinylcarbonyl, methoxy-1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, fluoroindolylmethyl, nitroindolylmethyl, methyl-indolylmethyl, hydroxyindolylmethyl, difluoromethoxyindolylmethyl, trifluoromethoxyindolylmethyl, benzyloxyindolylmethyl, difluoromethylenedioxy-indolylmethyl, acetylindolylmethyl, methylsulphonyloxyindolylmethyl, carboxylndolylmethyl, methoxycarbonyl-indolylmethyl, methylaminocarbonyl-indolylmethyl, (hydroxyethyl)aminocarbonyl-indolylmethyl, dimethylaminocarbonyl-indolylmethyl, N-hydroxyethyl-N-methylaminocarbonylindolylmethyl, benzylaminocarbonyl-indolylmethyl, azetidinylcarbonyl-indolylmethyl, piperidinylcarbonyl-indolylmethyl, methylpiperazinylcarbonyl-indolylmethyl, morpholinylcarbonyl-indolylmethyl, pyrrolo[2,3-b]pyridinylmethyl, benzimidazolylmethyl, benzotriazolylmethyl, bromopyridinylmethyl, quinolinylmethyl, isoquinolinylmethyl, benzofurylbenzyl, thienylbenzyl, methylthienylbenzyl, acetylthienylbenzyl, benzothienylbenzyl, phenylsulphonylindolylbenzyl, dimethylisoxazolylbenzyl, methylpyrazolylbenzyl, benzylpyrazolylbenzyl, pyridinylbenzyl, fluoropyridinylbenzyl, chloropyridinylbenzyl, methoxypyridinylbenzyl, pyrimidinylbenzyl and phenylpyridinylmethyl.

Specific values of $R^3$ include hydrogen, methyl, phenoxymethyl, phenylthiomethyl, aminomethyl, phenylaminomethyl, N-methyl-N-phenylaminomethyl, pyridinylaminomethyl, benzofurylcarbonylaminomethyl, phenylsulphonylaminomethyl, benzothienylmethylaminocarbonylmethyl, phenyl, benzyl, chlorobenzyl, bromobenzyl, pyrrolidinylbenzyl, morpholinyl-benzyl, phenylethyl, naphthylmethyl, phenylpropynyl, biphenylmethyl, fluorobiphenylmethyl, difluorobiphenylmethyl, chlorobiphenylmethyl, dichlorobiphenylmethyl, bromobiphenylmethyl, cyanobiphenylmethyl, methylbiphenylmethyl, (fluoro)(methyl)biphenylmethyl, dimethylbiphenylmethyl, hydroxymethylbiphenylmethyl, trifluoromethylbiphenylmethyl, bis(trifluoromethyl)biphenylmethyl, methoxybiphenylmethyl, dimethoxybiphenylmethyl, ethoxybiphenylmethyl, methylenedioxybiphenylmethyl, trifluoromethoxybiphenylmethyl, phenoxybiphenylmethyl, methylthiobiphenylmethyl, aminobiphenylmethyl, acetylaminobiphenylmethyl, methylsulphonylaminobiphenylmethyl, acetylbiphenylmethyl, aminocarbonylbiphenylmethyl, naphthylbiphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, methyl-1,2,3,4-tetrahydroquinolinylcarbonyl, methoxy-1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, methylindolylmethyl, hydroxyindolylmethyl, benzyloxyindolylmethyl, acetylindolylmethyl, methylsulphonyloxyindolylmethyl, pyrrolo[2,3-b]pyridinylmethyl, benzimidazolylmethyl, benzotriazolylmethyl, bromopyridinylmethyl, quinolinylmethyl, isoquinolinylmethyl, benzofurylbenzyl, thienylbenzyl, methylthienylbenzyl, acetylthienylbenzyl, benzothienylbenzyl, phenylsulphonylindolylbenzyl, dimethylisoxazolylbenzyl, methylpyrazolylbenzyl, benzylpyrazolylbenzyl, pyridinylbenzyl, fluoropyridinylbenzyl, chloropyridinylbenzyl, methoxypyridinylbenzyl, pyrimidinylbenzyl and phenylpyridinylmethyl.

Definitive values of $R^3$ include hydrogen, propynyl, trimethylsilylpropynyl, bromobenzyl, methylenedioxyphenylaminobenzyl, morpholinylmethylphenylaminobenzyl, oxazolinylphenylaminobenzyl, (methyl)(oxo)pyrazolylphenylaminobenzyl, oxazolylphenylaminobenzyl, isoxazolylphenylaminobenzyl, triazolylphenylaminobenzyl, methyltriazolylphenylaminobenzyl, methylpyrimidinylphenylaminobenzyl, pyrazolylmethylphenylaminobenzyl, triazolylmethylphenylaminobenzyl, methylsulphonylaminophenylaminobenzyl, morpholinylcarbonylphenylaminobenzyl, methylsulphonylphenylaminobenzyl, morpholinylsulphonylphenylaminobenzyl, dihydrobenzofuranylaminobenzyl, methylsulphonylindolinylaminobenzyl, chromanonylaminobenzyl, dihydroquinolinonylaminobenzyl, benzoxazinonylaminobenzyl, benzothienylaminobenzyl, indolylaminobenzyl, dioxoindolylaminobenzyl, (bromo)(methyl)pyrazolylaminobenzyl, trimethylpyrazolylaminobenzyl, methylindazolylaminobenzyl, benzoxazolylaminobenzyl, benzoxazolonylaminobenzyl, dimethylisoxazolylaminobenzyl, benzothiazolylaminobenzyl, methylisothiazolylaminobenzyl, methylbenzimidazolylaminobenzyl, benzimidazolonylaminobenzyl, dimethylbenzimidazolonylaminobenzyl, methyloxadiazolylaminobenzyl, furyloxadiazolylaminobenzyl, pyridinylaminobenzyl, chloropyridinylaminobenzyl, methylpyridinylaminobenzyl, dimethylpyridinylaminobenzyl, methoxypyridinylaminobenzyl, oxopyridinylaminobenzyl, oxopyrimidinylaminobenzyl, thioxopyrimidinylaminobenzyl, (chloro)-(methoxy)pyridazinylaminobenzyl, methylcinnolinylaminobenzyl, quinoxalinylaminobenzyl, methylchromenylaminobenzyl, benzofuryl, cyanobenzofuryl, methoxycarbonylbenzofuryl, dimethylaminocarbonylbenzofuryl, azetidinylcarbonylbenzofuryl, indolylmethyl, fluoroindolylmethyl, cyanoindolylmethyl, (cyano)(methyl)indolylmethyl, nitroindolylmethyl, methylindolylmethyl, oxazolinylindolylmethyl, triazolylindolylmethyl, methoxyindolylmethyl, (chloro)(methoxy)indolylmethyl, di(methoxy)indolylmethyl, difluoromethoxyindolylmethyl, trifluoromethoxyindolylmethyl, (chloro)(trifluoromethoxy)indolylmethyl, cyclobutyloxyindolylmethyl, cyclopropylmethoxyindolylmethyl, morpholinylethoxyindolylmethyl, methylenedioxyindolylmethyl, difluoromethylenedioxyindolylmethyl, azetidinylindolylmethyl, morpholinylindolylmethyl, acetylaminoindolylmethyl, acetylaminomethylindolylmethyl, methoxycarbonylaminoindolylmethyl, N-methoxycarbonyl-N-methylaminoindolylmethyl, methylsulphonylaminoindolylmethyl, acetylindolylmethyl, [acetyl oxime]indolylmethyl, [acetyl O-(methyl)oxime]-indolylmethyl, trifluoromethylcarbonylindolylmethyl, carboxylndolylmethyl, (carboxy)-(methyl)indolylmethyl, methoxycarbonylindolylmethyl, (methoxycarbonyl)(methyl)-indolylmethyl, (chloro)(methoxycarbonyl)indolylmethyl, aminocarbonylindolylmethyl, (aminocarbonyl)(chloro)indolylmethyl, methylaminocarbonylindolylmethyl, (chloro)-(methylaminocarbonyl)indolylmethyl, (hydroxyethyl)aminocarbonylindolylmethyl, (dimethylaminoethyl)aminocarbonylindolylmethyl, (1-hydroxyprop-2-yl)aminocarbonylindolylmethyl, dimethylaminocarbonylindolylmethyl, (dimethylaminocarbonyl)(methyl)-indolylmethyl, (chloro)(dimethylaminocarbonyl)indolylmethyl, bis(dimethylaminocarbonyl)indolylmethyl, N-(cyanomethyl)-N-methylaminocarbonylindolylmethyl, [N-(cyanomethyl)-N-methylaminocarbonyl](methyl)indolylmethyl, N-(cyanoethyl)-N-methylaminocarbonylindolylmethyl, N-(hydroxyethyl)-N-methylaminocarbonylindolylmethyl, N-(methoxyethyl)-N-methylaminocarbonylindolylmethyl, [N-(methoxyethyl)-N-methylaminocarbonyl](methyl)indolylmethyl, N-(dimethylaminoethyl)-N-methylaminocarbonylindolylmethyl, N-isopropyl-N-methylaminocarbonylindolylmethyl, diethylaminocarbonylindolylmethyl, cyclopropylmethylaminocarbonylindolylmethyl, benzylaminocarbonylindolylmethyl, pyrazolylaminocarbonylindolylmethyl, pyridinylmethylaminocarbonylindolylmethyl, azetidinylcarbonylindolylmethyl, (azetidinylcarbonyl)(methyl)indolylmethyl, hydroxyazetidinylcarbonylindolylmethyl, aminoazetidinylcarbonylindolylmethyl, tert-butoxycarbonylaminoazetidinylcarbonylindolylmethyl, pyrrolidinylcarbonylindolylmethyl, methylpyrrolidinylcarbonylindolylmethyl, methoxymethylpyrrolidinylcarbonylindolylmethyl, dimethylaminopyrrolidinylcarbonylindolylmethyl, thiazolidinylcarbonylindolylmethyl, oxothiazolidinylcarbonylindolylmethyl, piperidinylcarbonylindolylmethyl, methylpiperazinylcarbonylindolylmethyl, morpholinylcarbonylindolylmethyl, methylsulphonylindolylmethyl, methylsulphonylmethylindolylmethyl, dimethylaminosulphonylindolylmethyl, trimethylsilylindolylmethyl and pyrrolo[3,2-c]pyridinylmethyl.

Particular values of $R^3$ include hydrogen, bromobenzyl, pyridinylaminobenzyl, chloropyridinylaminobenzyl, dimethylpyridinylaminobenzyl, methoxypyridinylaminobenzyl, indolylmethyl, fluoroindolylmethyl, nitroindolylmethyl, difluoromethoxyindolylmethyl, trifluoromethoxyindolylmethyl, difluoromethylenedioxy-indolylmethyl, carboxyln-dolylmethyl, methoxycarbonyl-indolylmethyl, methylaminocarbonylindolylmethyl, (hydroxyethyl)aminocarbonyl-indolylmethyl, dimethylaminocarbonylindolylmethyl, N-hydroxyethyl-N-methylaminocarbonyl-indolylmethyl, benzylaminocarbonyl-indolylmethyl, azetidinylcarbonyl-indolylmethyl, piperidinylcarbonyl-indolylmethyl, methylpiperazinylcarbonyl-indolylmethyl and morpholinylcarbonyl-indolylmethyl.

Typical values of $R^4$ include hydrogen and methyl. In a preferred embodiment, $R^4$ is hydrogen. In another embodiment, $R^4$ is $C_{1-6}$ alkyl, especially methyl.

Alternatively, $R^3$ and $R^4$, when both are attached to the same carbon atom, may together form an optionally substituted spiro linkage. Thus, $R^3$ and $R^4$, when both are attached to the same carbon atom, may represent, when taken together with the carbon atom to which they are both attached, $C_{3-7}$ cycloalkyl or $C_{3-7}$ heterocycloalkyl, either of which groups may be unsubstituted, or substituted by one or more, typically by one or two, substituents. In this context, $R^3$ and $R^4$, when taken together with the carbon atom to which they are both attached, may suitably represent an optionally substituted cyclopentyl, cyclohexyl, pyrrolidine or piperidine ring.

Alternatively, $R^3$ and $R^4$, when attached to adjacent carbon atoms, may together form an optionally benzo-fused and/or substituted cycloalkyl, phenyl or heteroaryl (e.g. pyridinyl) ring fused to the morpholine ring. Thus, $R^3$ and $R^4$, when attached to adjacent carbon atoms, may represent, when taken together with the carbon atoms to which they are attached, $C_{5-7}$ cycloalkyl, phenyl or heteroaryl (e.g. pyridinyl), any of which groups may be benzo-fused and/or unsubstituted, or substituted by one or more, typically by one or two, substituents. In this context, in one embodiment, $R^3$ and $R^4$, when taken together with the adjacent carbon atoms to which they are attached, suitably represent a phenyl ring fused to the morpholine ring, which phenyl ring may be unsubstituted, or substituted by one or more, typically by one or two, substituents. Also in this context, in another embodiment, $R^3$ and $R^4$, when taken together with the adjacent carbon atoms to which they are attached, suitably represent a benzo-fused cyclopentyl ring, i.e. an indanyl moiety fused to the morpholine ring, which indanyl moiety may be unsubstituted, or substituted by one or more, typically by one or two, substituents.

Definitive examples of suitable substituents on the fused rings referred to in the preceding paragraph include halogen, nitro, $C_{1-6}$ alkyl, $C_{2-6}$ alkenyl, $C_{3-7}$ cycloalkyl, $(C_{1-6})$-alkylaryl, di($C_{1-6}$)alkylaryl, piperidinyl($C_{1-6}$)alkylaryl, piperazinyl($C_{1-6}$)alkylaryl, ($C_{1-6}$)alkylpiperazinyl($C_{1-6}$)alkylaryl, morpholinyl($C_{1-6}$)alkylaryl, ($C_{1-6}$)alkoxyaryl, cyano($C_{1-6}$)alkoxyaryl, di($C_{1-6}$)alkylamino($C_{1-6}$)alkylaryl, ($C_{1-6}$)alkylaminocarbonylaryl, aryl($C_{1-6}$)alkyl, haloarylpyrrolidinyl, dioxopyrrolidinyl, aminopyrrolidinyl, di($C_{1-6}$)alkylaminopyrrolidinyl, indolinyl, oxoindolinyl, arylpiperidinyl, arylcarbonylpiperidinyl, di-($C_{1-6}$)alkylaminocarbonylpiperidinyl, piperazinyl, ($C_{1-6}$)alkylpiperazinyl, haloarylpiperazinyl, pyridinylpiperazinyl, furoylpiperazinyl, homopiperazinyl, ($C_{1-6}$)alkylhomopiperazinyl, ($C_{1-6}$)alkylpiperazinyl($C_{1-6}$) alkyl, morpholinyl($C_{1-6}$)alkyl, benzofuryl, benzothienyl, pyrazolyl, ($C_{1-6}$)alkylpyrazolyl, di($C_{1-6}$)alkylpyrazolyl, tri ($C_{1-6}$)alkylpyrazolyl, [di($C_{1-6}$)alkyl](trifluoromethyl)pyrazolyl, cyano($C_{1-6}$)alkylpyrazolyl, [cyano-($C_{1-6}$)alkyl][di ($C_{1-6}$)-alkyl]pyrazolyl, hydroxy($C_{1-6}$)alkylpyrazolyl, [hydroxy($C_{1-6}$)-alkyl][di($C_{1-6}$)alkyl]pyrazolyl, methoxy($C_{1-6}$) alkylpyrazolyl, [(hydroxy)(methoxy)($C_{1-6}$)-alkyl]pyrazolyl, amino($C_{1-6}$)alkylpyrazolyl, [($C_{1-6}$)alkyl][amino($C_{1-6}$)alkyl] pyrazolyl, [amino($C_{1-6}$)alkyl][di($C_{1-6}$)alkyl]pyrazolyl, di($C_{1-6}$)alkylamino($C_{1-6}$)alkylpyrazolyl, di($C_{1-6}$)alkoxyphosphono($C_{1-6}$)alkylpyrazolyl, ($C_{2-6}$)alkenylpyrazolyl, ($C_{3-7}$)cycloalkyl-($C_{1-6}$)alkylpyrazolyl, [($C_{3-7}$)cycloalkyl ($C_{1-6}$)alkyl][di($C_{1-6}$)alkyl]pyrazolyl, [($C_{1-6}$)alkyl]-(aryl) pyrazolyl, (aryl)(trifluoromethyl)pyrazolyl, aryl($C_{1-6}$)alkylpyrazolyl, aminoaryl-($C_{1-6}$)alkylpyrazolyl, piperidinylpyrazolyl, tetrahydropyranyl($C_{1-6}$)alkylpyrazolyl, [di-($C_{1-6}$) alkyl][tetrahydropyranyl($C_{1-6}$)alkyl]pyrazolyl, pyrrolidinyl ($C_{1-6}$)alkylpyrazolyl, piperidinyl($C_{1-6}$)alkylpyrazolyl, ($C_{1-6}$) alkylpiperidinyl($C_{1-6}$)alkylpyrazolyl, morpholinyl($C_{1-6}$) alkylpyrazolyl, pyridinyl($C_{1-6}$)alkylpyrazolyl, oxypyridinyl ($C_{1-6}$)alkylpyrazolyl, [arylcarbonyl($C_{1-6}$)alkyl][di($C_{1-6}$) alkyl]pyrazolyl, [($C_{1-6}$)alkyl](piperazinylcarbonyl) pyrazolyl, [($C_{1-6}$)alkylaminocarbonyl][($C_{1-6}$)alkylaryl] pyrazolyl, [($C_{1-6}$)alkyl]-[amino($C_{1-6}$)alkylaminocarbonyl] pyrazolyl, aminocarbonyl($C_{1-6}$)alkylpyrazolyl, [aminocarbonyl($C_{1-6}$)alkyl][di($C_{1-6}$)alkyl]pyrazolyl, di ($C_{1-6}$)alkylaminocarbonyl($C_{1-6}$)alkylpyrazolyl, pyrazolo[1, 5-a]pyridinyl, di($C_{1-6}$)alkylisoxazolyl, (amino)[($C_{1-6}$)alkyl]-isoxazolyl, thiazolyl, di($C_{1-6}$)alkylthiazolyl, imidazolyl, imidazo[1,2-a]pyridinyl, ($C_{1-6}$)alkylimidazo[1,2-a]pyridinyl, ($C_{1-6}$)-alkylimidazo[4,5-b]pyridinyl, imidazo[1,2-a]pyrimidinyl, imidazo[1,2-a]pyrazinyl, ($C_{1-6}$)-alkylthiadiazolyl, pyridinyl, halopyridinyl, ($C_{1-6}$)alkyl-pyridinyl, [($C_{1-6}$)alkyl] (halo)-pyridinyl, di($C_{1-6}$)alkylpyridinyl, ($C_{2-6}$)alkenylpyridinyl, ($C_{1-6}$)alkylpiperazinylpyridinyl, [($C_{1-6}$)alkyl](piperazinyl)pyridinyl, [($C_{1-6}$)alkoxycarbonylpiperazinyl][($C_{1-6}$) alkyl]-Pyridinyl, piperidinyl($C_{1-6}$)alkylpyridinyl, [($C_{1-6}$) alkyl](oxy)pyridinyl, hydroxypyridinyl, hydroxy($C_{1-6}$) alkylpyridinyl, ($C_{1-6}$)alkoxypyridinyl, [($C_{1-6}$)alkoxy][($C_{1-6}$) alkyl]pyridinyl, [($C_{1-6}$)alkoxy][di($C_{1-6}$)alkyl]pyridinyl, ($C_{1-6}$)alkoxy($C_{1-6}$)alkylpyridinyl, aminopyridinyl, carboxy ($C_{1-6}$)alkylpyridinyl, ($C_{1-6}$)alkoxycarbonyl($C_{1-6}$)alkylpyridinyl, pyridazinyl, ($C_{1-6}$)-alkylpyridazinyl, piperidinylpyridazinyl, oxypyridazinyl, ($C_{1-6}$)alkoxypyridazinyl, aminopyridazinyl, hydroxy($C_{1-6}$)alkylaminopyridazinyl, di($C_{1-6}$)alkylaminopyridazinyl, pyrimidinyl, ($C_{1-6}$)alkylpyrimidinyl, [($C_{1-6}$)alkyl](halo)pyrimidinyl, di($C_{1-6}$)alkylpyrimidinyl, pyrrolidinylpyrimidinyl, ($C_{1-6}$)alkylpiperazinylpyrimidinyl, [($C_{1-6}$)alkyl](piperazinyl)pyrimidinyl, [($C_{1-6}$) alkoxycarbonyl][($C_{1-6}$)alkyl]piperazinylpyrimidinyl, hydroxypyrimidinyl, [($C_{1-6}$)alkyl](hydroxy)pyrimidinyl, [($C_{1-6}$)alkyl]-[hydroxy($C_{1-6}$)alkyl]pyrimidinyl, [($C_{1-6}$)alkyl] [hydroxy($C_{2-6}$)alkynyl]pyrimidinyl, ($C_{1-6}$)-alkoxypyrimidinyl, aminopyrimidinyl, di($C_{1-6}$)alkylaminopyrimidinyl, [di ($C_{1-6}$)alkylamino](halo)pyrimidinyl, carboxypyrimidinyl, [($C_{1-6}$)alkoxycarbonyl($C_{1-6}$)alkyl][($C_{1-6}$)-alkyl]pyrimidinyl, aminocarbonylpyrimidinyl, pyrazinyl, ($C_{1-6}$)alkoxypyrazinyl, aminopyrazinyl, hydroxy, ($C_{1-6}$)alkoxy, aryl($C_{1-6}$) alkoxycarbonylpiperidinyloxy, morpholinyl-($C_{1-6}$)alkoxy, aryloxy, haloaryloxy, di($C_{1-6}$)alkylpyrazolyloxy, halopyridinyloxy, pyrrolidinylpyridinyloxy, ($C_{1-6}$)alkylpiperazinylpyridinyloxy, ($C_{1-6}$)alkylpyrazolylpyridinyloxy, ($C_{1-6}$)alkylaminopyridinyloxy, carboxypyridinyloxy, aminocarbonylpyridinyloxy, ($C_{1-6}$)alkylpyridazinyloxy, pyrimidinyloxy, ($C_{1-6}$)alkylpyrimidinyloxy, [($C_{1-6}$)alkyl] (halo)pyrimidinyloxy, hydroxy($C_{1-6}$)alkyl, dihydroxy($C_{1-6}$) alkyl, pyridinyloxy($C_{1-6}$)alkyl, amino, ($C_{1-6}$)alkylamino, dihydroxy($C_{1-6}$)alkylamino, ($C_{1-6}$)-alkoxy($C_{1-6}$)alkylamino, N—[($C_{1-6}$)alkoxy($C_{1-6}$)alkyl]-N—[($C_{1-6}$)alkyl]amino, di($C_{1-6}$)-alkylamino($C_{1-6}$)alkylamino, N—[($C_{1-6}$)alkyl]-N-[di($C_{1-6}$)alkylamino($C_{1-6}$)alkyl]amino, N—[($C_{1-6}$) alkyl]-N—[($C_{3-7}$)cycloalkyl]amino, haloarylamino, N—[($C_{1-6}$) alkyl]-N-(haloaryl)amino, N—[($C_{1-6}$)alkyl]-N-[aryl($C_{1-6}$) alkyl]amino, N-[di($C_{1-6}$)alkylamino($C_{1-6}$)alkyl]-N-[aryl ($C_{1-6}$)-alkyl]amino, cyanoaryl($C_{1-6}$)alkylamino, (cyano) (halo)aryl($C_{1-6}$) alkylamino, methylenedioxyaryl($C_{1-6}$)alkylamino, N—[($C_{1-6}$)alkyl]-N—[($C_{1-6}$)alkylpyrrolidinyl] amino, piperidinylamino, N—[($C_{1-6}$)alkyl]-N-(piperidinyl) amino, N—[($C_{3-7}$)cycloalkyl($C_{1-6}$)alkyl]-N-(piperidinyl) amino, ($C_{1-6}$)alkylpiperidinylamino, N—[($C_{1-6}$)alkyl]-N—($C_{1-6}$)alkylpiperidinyliamino, N—[($C_{1-6}$)alkyl]-N—[($C_{3-7}$)cycloalkylpiperidinyl]amino, N—[($C_{1-6}$)alkyl]-N—[($C_{2-6}$)alkylcarbonylpiperidinyl]amino, pyrrolidinyl($C_{1-6}$)alkylamino, N—[($C_{1-6}$)alkyl]-N-[pyrrolidinyl($C_{1-6}$)alkyl] amino, N—[($C_{1-6}$)alkyl]-N-[piperidinyl($C_{1-6}$)alkyl]amino, ($C_{1-6}$)-alkylpyrazolylamino, di($C_{1-6}$)alkylpyrazolylamino, tri($C_{1-6}$)alkylpyrazolylamino, N—[($C_{1-6}$)-alkyl]-N—[($C_{1-6}$) alkylpyrazolyl]amino, thiazolylamino, imidazolylamino, [($C_{1-6}$)alkoxycarbonyl][($C_{1-6}$)alkyl]imidazolylamino, ($C_{1-6}$) alkylthiadiazolylamino, pyridinylamino, halopyridinylamino, ($C_{1-6}$)alkylpyridinylamino, di($C_{1-6}$)alkylpyridinylamino, trifluoromethylpyridinylamino, hydroxypyridinylamino, hydroxy($C_{1-6}$)alkylpyridinylamino, dihydroxy($C_{1-6}$)alkylpyridinylamino, ($C_{1-6}$)alkoxypyridinylamino, dihydroxy($C_{1-6}$)alkoxypyridinylamino, di($C_{1-6}$) alkyldioxolanyl($C_{1-6}$)alkoxypyridinylamino, ($C_{1-6}$)alkoxy ($C_{1-6}$)-alkylpyridinylamino, ($C_{1-6}$)alkoxy($C_{2-6}$) alkenylpyridinylamino, dihydroxy($C_{1-6}$) alkylaminopyridinylamino, di($C_{1-6}$) alkylaminopyridinylamino, ($C_{1-6}$)alkylamino($C_{1-6}$) alkylpyridinylamino, di($C_{1-6}$)alkylamino($C_{1-6}$) alkylpyridinylamino, carboxypyridinylamino, N—[($C_{1-6}$) alkyl]-N—[($C_{1-6}$)alkylpyridinyl]amino, bis[($C_{1-6}$) alkylpyridinyl]amino, bis(trifluoromethylpyridinyl)amino, isoquinolinylamino, ($C_{1-6}$)alkylpyridazinylamino, N—[($C_{1-6}$)alkyl]-N—($C_{1-6}$)alkylpyridazinyliamino, N-[aryl ($C_{1-6}$)alkyl]-N—[($C_{1-6}$)alkylpyridazinyl]amino, di($C_{1-6}$) alkylpyridazinylamino, arylpyridazinylamino, piperidinylpyridazinylamino, ($C_{1-6}$)-alkoxypyridazinylamino, di ($C_{1-6}$)alkylaminopyridazinylamino, bis[($C_{1-6}$)alkylpyridazinyl]-amino, benzofuryl($C_{1-6}$)alkylamino, thienyl($C_{1-6}$)alkylamino, indolyl($C_{1-6}$)alkylamino, ($C_{1-6}$)alkylpyrazolyl($C_{1-6}$) alkylamino, [di($C_{1-6}$)alkyl](halo)pyrazolyl($C_{1-6}$)alkylamino, di($C_{1-6}$)alkylisoxazolyl($C_{1-6}$)alkylamino, thiazolyl($C_{1-6}$) alkylamino, imidazolyl($C_{1-6}$)alkylamino, ($C_{1-6}$)alkylimidazolyl($C_{1-6}$)alkylamino, pyridinyl($C_{1-6}$)alkylamino, ($C_{1-6}$) alkylpyridinyl($C_{1-6}$)alkylamino, N—[($C_{1-6}$)alkyl]-N-[pyridinyl($C_{1-6}$)alkyl]amino, N-[dihydroxy-($C_{1-6}$)alkyl]-N-[pyridinyl($C_{1-6}$)alkyl]amino, N—[($C_{1-6}$)alkylpyridinyl($C_{1-6}$)alkyl]-N-[dihydroxy($C_{1-6}$)alkyl]amino, amino($C_{1-6}$)alkyl, ($C_{1-6}$)alkylamino($C_{1-6}$)alkyl, di($C_{1-6}$)alkylamino($C_{1-6}$)alkyl, pyridinylamino($C_{1-6}$)alkyl, N—[($C_{2-6}$)alkylcarbonyl]-N—[($C_{1-6}$)alkylpyridinyl($C_{1-6}$)alkyl]amino, di($C_{1-6}$)alkylamino ($C_{1-6}$)alkylcarbonylamino, ($C_{3-7}$)cycloalkylcarbonylamino, ($C_{1-6}$)alkylpiperidinylcarbonylamino, ($C_{1-6}$)alkylimidazolylcarbonylamino, formyl, $C_{2-6}$ alkylcarbonyl, ($C_{1-6}$)alkylpiperidinylaminocarbonyl, N—[($C_{1-6}$)alkyl]-N—[($C_{1-6}$)-alkylpiperidinyl]aminocarbonyl, piperidinyl($C_{1-6}$) alkylaminocarbonyl, ($C_{1-6}$)alkylpiperazinylcarbonyl, $C_{1-6}$ alkylthio, $C_{1-6}$ alkylsulphinyl, $C_{1-6}$ alkylsulphonyl, $C_{2-6}$ alkoxycarbonyloxy and tetra($C_{1-6}$)alkyldioxaborolanyl.

Particular examples of suitable substituents on the fused rings referred to in the two preceding paragraphs include halogen, nitro, hydroxy($C_{1-6}$)alkyl, pyrazolyl, ($C_{1-6}$)alkylpyrazolyl, di($C_{1-6}$)alkylpyrazolyl, aryl($C_{1-6}$)alkylpyrazolyl, morpholinyl($C_{1-6}$)alkylpyrazolyl, ($C_{1-6}$)alkylimidazolyl, ($C_{1-6}$)alkylpyridinyl, pyrimidinyl, hydroxy, pyridinyloxy-($C_{1-6}$)alkyl, amino, ($C_{1-6}$)alkylpyridinylamino, di($C_{1-6}$)alkylamino($C_{1-6}$)alkyl, pyridinylamino($C_{1-6}$)alkyl, ($C_{1-6}$)alkylpiperazinyl($C_{1-6}$)alkyl, morpholinyl($C_{1-6}$)alkyl, formyl and $C_{2-6}$ alkoxycarbonyloxy.

Definitive examples of specific substituents on the fused rings referred to in the three preceding paragraphs include bromo, nitro, methyl, n-propyl, isopropyl, allyl, cyclopropyl, methylphenyl, dimethylphenyl, piperidinylmethylphenyl, piperazinylmethylphenyl, methylpiperazinylmethylphenyl, morpholinylmethylphenyl, methoxyphenyl, cyanomethoxyphenyl, dimethylaminomethylphenyl, methylaminocarbonylphenyl, benzyl, chlorophenylpyrrolidinyl, dioxopyrrolidinyl, aminopyrrolidinyl, dimethylaminopyrrolidinyl, indolinyl, oxoindolinyl, phenylpiperidinyl, benzoylpiperidinyl, diethylaminocarbonylpiperidinyl, piperazinyl, methylpiperazinyl, chlorophenylpiperazinyl, pyridinylpiperazinyl, furoylpiperazinyl, homopiperazinyl, methylhomopiperazinyl, methylpiperazinylmethyl, methylpiperazinylethyl, morpholinylmethyl, benzofuryl, benzothienyl, pyrazolyl, methylpyrazolyl, ethylpyrazolyl, propylpyrazolyl, 2-methyl-propylpyrazolyl, 3-methylbutylpyrazolyl, dimethylpyrazolyl, trimethylpyrazolyl, (dimethyl)(ethyl)pyrazolyl, (dimethyl)(isopropyl) pyrazolyl, (dimethyl)(2-methylpropyl)-pyrazolyl, (dimethyl) (3-methylbutyl)pyrazolyl, (dimethyl)(trifluoromethyl) pyrazolyl, cyanomethylpyrazolyl, (cyanomethyl)(dimethyl) pyrazolyl, hydroxyethylpyrazolyl, hydroxypropylpyrazolyl, 2-hydroxy-2-methylpropylpyrazolyl, (hydroxyethyl)(dimethyl)-pyrazolyl, (hydroxypropyl)(dimethyl)pyrazolyl, methoxypropylpyrazolyl, [(hydroxy)-(methoxy)propyl] pyrazolyl, aminoethylpyrazolyl, aminopropylpyrazolyl, (aminopropyl)-(methyl)pyrazolyl, (aminopropyl)(dimethyl) pyrazolyl, dimethylaminoethylpyrazolyl, dimethylaminopropylpyrazolyl, diethoxyphosphonopropylpyrazolyl, allylpyrazolyl, cyclopropylmethylpyrazolyl, (cyclopropylmethyl)(dimethyl)pyrazolyl, (methyl)(phenyl)-pyrazolyl, (phenyl)(trifluoromethyl)pyrazolyl, benzylpyrazolyl, aminobenzylpyrazolyl, piperidinylpyrazolyl, tetrahydropyranylmethylpyrazolyl, (dimethyl)(tetrahydropyranylmethyl)pyrazolyl, pyrrolidinylethylpyrazolyl, piperidinylethylpyrazolyl, methylpiperidinylethylpyrazolyl, morpholinylethylpyrazolyl, pyridinylmethylpyrazolyl, oxypyridinylmethylpyrazolyl, (dimethyl)(phenylcarbonylmethyl)pyrazolyl, (ethyl) (piperazinylcarbonyl)pyrazolyl, (methylaminocarbonyl) (methylphenyl)pyrazolyl, (aminoethylaminocarbonyl) (methyl)pyrazolyl, aminocarbonylmethylpyrazolyl, (aminocarbonylmethyl)(dimethyl)pyrazolyl, dimethylaminocarbonylmethylpyrazolyl, pyrazolo[1,5-a]pyridinyl, dimethylisoxazolyl, (amino)(methyl)isoxazolyl, thiazolyl, dimethylthiazolyl, imidazolyl, methylimidazolyl, dimethylimidazolyl, imidazo[1,2-a]pyridinyl, methylimidazo[1,2-a]pyridinyl, methylimidazo[4,5-b]pyridinyl, imidazo[1,2-a]pyrimidinyl, imidazo[1,2-a]pyrazinyl, methylthiadiazolyl, pyridinyl, fluoropyridinyl, methylpyridinyl, (fluoro)(methyl)pyridinyl, dimethylpyridinyl, vinylpyridinyl, (methylpiperazinyl)pyridinyl, (methyl)(piperazinyl)pyridinyl, (tert-butoxycarbonylpiperazinyl)-(methyl)pyridinyl, piperidinylmethylpyridinyl, (methyl)(oxy)pyridinyl, hydroxypyridinyl, hydroxymethylpyridinyl, hydroxyethylpyridinyl, methoxypyridinyl, (methoxy)(methyl)-pyridinyl, (dimethyl)(methoxy)pyridinyl, methoxymethylpyridinyl, aminopyridinyl, carboxymethylpyridinyl, ethoxycarbonylmethylpyridinyl, pyridazinyl, methylpyridazinyl, piperidinylpyridazinyl, oxypyridazinyl, methoxypyridazinyl, aminopyridazinyl, hydroxyethylaminopyridazinyl, dimethylaminopyridazinyl, pyrimidinyl, methylpyrimidinyl, (chloro)(methyl)pyrimidinyl, dimethylpyrimidinyl, pyrrolidinylpyrimidinyl, methylpiperazinylpyrimidinyl, (methyl)(piperazinyl)pyrimidinyl, (tert-butoxycarbonylpiperazinyl)(methyl)pyrimidinyl, hydroxypyrimidinyl, (hydroxy)(methyl)pyrimidinyl, (hydroxyethyl)(methyl)pyrimidinyl, (hydroxypropyl)(methyl)pyrimidinyl, (hydroxypropynyl)(methyl)pyrimidinyl, methoxypyrimidinyl, aminopyrimidinyl, dimethylaminopyrimidinyl, (dimethylamino)(fluoro)pyrimidinyl, carboxypyrimidinyl, (methoxycarbonylmethyl)(methyl)pyrimidinyl, aminocarbonylpyrimidinyl, pyrazinyl, methoxypyrazinyl, aminopyrazinyl, hydroxy, methoxy, isopropoxy, benzyloxycarbonylpiperidinyloxy, morpholinylethoxy, phenoxy, fluorophenoxy, dimethylpyrazolyloxy, bromopyridinyloxy, pyrrolidinylpyridinyloxy, methylpiperazinylpyridinyloxy, methylpyrazolylpyridinyloxy, isopropylaminopyridinyloxy, carboxypyridinyloxy, aminocarbonylpyridinyloxy, methylpyridazinyloxy, pyrimidinyloxy, methylpyrimidinyloxy, (chloro)(methyl)-pyrimidinyloxy, hydroxymethyl, 1-hydroxy-1-methylethyl, dihydroxypropyl, pyridinyloxymethyl, amino, isopropylamino, dihydroxypropylamino, methoxyethylamino, methoxypropylamino, N-(methoxyethyl)-N-(methyl)amino, N-(methoxypropyl)-N-(methyl)amino, dimethylaminoethylamino, dimethylaminopropylamino, N-(dimethylaminoethyl)-N-(methyl)amino, N-(diethylaminoethyl)-N-(methyl)amino, N-(dimethylaminopropyl)-N-(methyl)amino, N-(dimethylaminoethyl)-N-(ethyl)amino, N-(dimethylaminopropyl)-N-(ethyl)amino, N-(cyclohexyl)-N-(methyl)amino, fluorophenylamino, N-fluorophenyl-N-methylamino, N-benzyl-N-methylamino, N-(benzyl)-N-(dimethylaminoethyl)amino, cyanobenzylamino, (cyano)(phenyl)ethylamino, (cyano)(fluoro)benzylamino, methylenedioxybenzylamino, N-(methyl)-N-(methylpyrrolidinyl)amino, piperidinylamino, N-(methyl)-N-(piperidinyl)amino, N-(ethyl)-N-(piperidinyl)amino, N-(cyclopropylmethyl)-N-(piperidinyl)amino, methylpiperidinylamino, N-(methyl)-N-(methylpiperidinyl)amino, N-(methyl)-N-(2-methylpropylpiperidinyl)amino, N-(cyclopentylpiperidinyl)-N-(methyl)amino, N-(acetylpiperidinyl)-N-(methyl)amino, pyrrolidinylethylamino, pyrrolidinylpropylamino, N-(methyl)-N-(pyrrolidinylethyl)amino, N-(methyl)-N-(pyrrolidinylpropyl)amino, N-(methyl)-N-(piperidinylmethyl)amino, methylpyrazolylamino, dimethylpyrazolylamino, trimethylpyrazolylamino, N-(ethyl)-N-(methylpyrazolyl)amino, thiazolylamino, imidazolylamino, (ethoxycarbonyl)(methyl)imidazolylamino, methylthiadiazolylamino, pyridinylamino, bromopyridinylamino, methylpyridinylamino, dimethylpyridinylamino, trifluoromethylpyridinylamino, hydroxypyridinylamino, hydroxyethylpyridinylamino, dihydroxyethylpyridinylamino, methoxypyridinylamino, dihydroxypropoxypyridinylamino, dimethyldioxolanylmethoxypyridinylamino, methoxyethylpyridinylamino, methoxyvinylpyridinylamino, dihydroxypropylaminopyridinylamino, dimethylaminopyridinylamino, methylaminomethylpyridinylamino, dimethylaminomethylpyridinylamino, carboxypyridinylamino, N-(methyl)-N-(methylpyridinyl)amino, N-(ethyl)-N-(methylpyridinyl)amino, bis(methylpyridinyl)amino, bis(trifluoromethylpyridinyl)amino, isoquinolinylamino, methylpyridazinylamino, N-(methyl)-N-(methylpyridazinyl)amino, N-(benzyl)-N-(methylpyridazinyl)amino, dimethylpyridazinylamino, phenylpyridazinylamino, piperidinylpyridazinylamino, methoxypyridazinylamino, dimethylaminopyridazinylamino, bis(methylpyridazinyl)amino, benzofurylmethylamino, thienylmethylamino, indolylmethylamino, methylpyrazolylmethylamino, (chloro)(dimethyl)pyrazolylmethylamino, dimethylisoxazolylmethylamino, thiazolylmethylamino, imidazolylmethylamino, methylimidazolylmethylamino, pyridinylmethylamino, methylpyridinylmethylamino, N-(methyl)-N-(pyridinylethyl)amino, N-(dihydroxypropyl)-N-(pyridinylmethyl)-amino, N-(dihydroxypropyl)-N-(methylpyridinylmethyl)amino, aminomethyl, methylaminomethyl, dimethylaminomethyl, pyridinylaminomethyl, N-(acetyl)-N-(methylpyridinyl)amino, dimethylaminoethylcarbonylamino, cyclohexylcarbonylamino, methylpiperidinylcarbonylamino, methylimidazolylcarbonylamino, formyl, acetyl, methylpiperidinylaminocarbonyl, N-(methyl)-N-(methylpiperidinyl)aminocarbonyl, piperidinylethylaminocarbonyl, methylpiperazinylcarbonyl, isopropylthio, isopropylsulphinyl, isopropylsulphonyl, tert-butoxycarbonyloxy and tetramethyldioxaborolanyl.

Selected examples of such substituents include bromo, nitro, hydroxymethyl, pyrazolyl, methylpyrazolyl, dimethylpyrazolyl, propylpyrazolyl, isobutylpyrazolyl, benzylpyrazolyl, morpholinylethylpyrazolyl, methylimidazolyl, methylpyridinyl, pyrimidinyl, hydroxy, pyridinyloxymethyl, amino, methylpyridinylamino, dimethylaminomethyl, pyridinylaminomethyl, methylpiperazinylmethyl, morpholinylmethyl, formyl and tert-butoxycarbonyloxy.

In one embodiment, $R^5$ represents hydrogen. In another embodiment, $R^5$ represents $C_{1-6}$ alkyl, especially methyl.

Suitably, $R^6$ represents hydrogen or $C_{1-6}$ alkyl. In one embodiment, $R^6$ represents hydrogen. In another embodiment, $R^6$ represents $C_{1-6}$ alkyl, especially methyl.

In one embodiment, $R^7$ represents hydrogen. In another embodiment, $R^7$ represents $C_{1-6}$ alkyl, especially methyl.

Alternatively, $R^6$ and $R^7$ may together form an optionally substituted spiro linkage. Thus, $R^6$ and $R^7$, when taken together with the carbon atom to which they are both attached, may represent $C_{3-7}$ cycloalkyl or $C_{3-7}$ heterocycloalkyl, either of which groups may be unsubstituted, or substituted by one or more, typically by one or two, substituents. In this context, $R^6$ and $R^7$, when taken together with the carbon atom to which they are both attached, may suitably represent an optionally substituted cyclopentyl, cyclohexyl, pyrrolidine or piperidine ring.

Alternatively, $R^2$ and $R^6$ may form an optionally benzo-fused and/or substituted cycloalkyl, phenyl or heteroaryl (e.g. pyridinyl) ring fused to the ring containing the $NR^5$ moiety. Thus, $R^2$ and $R^6$, when taken together with the carbon atoms to which they are attached, may represent $C_{5-7}$ cycloalkyl, phenyl or heteroaryl (e.g. pyridinyl), any of which groups may be benzo-fused and/or unsubstituted, or substituted by one or more, typically by one or two, substituents. In this context, in one embodiment, $R^2$ and $R^6$, when taken together with the adjacent carbon atoms to which they are attached, suitably represent a cyclopentyl ring fused to the ring containing the $NR^5$ moiety. Also in this context, in another embodiment, $R^2$ and $R^6$, when taken together with the adjacent carbon atoms to which they are attached, suitably represent a phenyl ring fused to the ring containing the $NR^5$ moiety. Also in this context, in a further embodiment, $R^2$ and $R^6$, when taken together with the adjacent carbon atoms to which they are attached, suitably represent a benzo-fused cyclopentyl ring, i.e. an indanyl moiety fused to the ring containing the $NR^5$ moiety.

Suitable values of $R^8$ include hydrogen and $C_{1-6}$ alkyl. In one embodiment, $R^8$ represents hydrogen. In another embodiment, $R^8$ represents $C_{1-6}$ alkyl, especially methyl.

Alternatively, $R^2$ and $R^8$ may together form an optionally benzo-fused and/or substituted heterocycloalkyl (e.g. pyrrolidinyl) or heteroaryl (e.g. pyrrolyl, pyrazolyl, triazolyl or tetrazolyl) ring fused to the ring containing the $NR^5$ moiety. Thus, $R^2$ and $R^8$, when taken together with the carbon and nitrogen atoms to which they are respectively attached, may represent $C_{5-7}$ heterocycloalkyl (e.g. pyrrolidinyl) or heteroaryl (e.g. pyrrolyl, pyrazolyl, triazolyl or tetrazolyl), either of which groups may be benzo-fused and/or unsubstituted, or substituted by one or more, typically by one or two, substituents. In this context, in one embodiment, $R^2$ and $R^8$, when taken together with the carbon and nitrogen atoms to which they are respectively attached, suitably represent a pyrrolidinyl ring fused to the ring containing the $NR^5$ moiety (i.e. $R^2/R^8$ represents —$CH_2CH_2CH_2$—).

One sub-class of compounds according to the invention is represented by the compounds of formula (IIA), and pharmaceutically acceptable salts and solvates thereof:

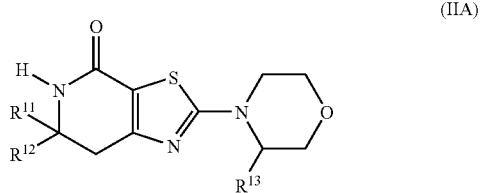

(IIA)

wherein $R^{11}$ represents hydrogen or $C_{1-6}$ alkyl; and $R^{12}$ represents hydrogen; or $C_{1-6}$ alkyl, $C_{1-6}$ alkoxy, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; or $R^{11}$ and $R^{12}$, when taken together with the carbon atom to which they are both attached, represent $C_{3-7}$ cycloalkyl or $C_{3-7}$ heterocycloalkyl, either of which groups may be optionally substituted by one or more substituents; and $R^{13}$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

Where any of the groups in the compounds of formula (IIA) above is stated to be optionally substituted, this group may be unsubstituted, or substituted by one or more substituents. Typically, such groups will be unsubstituted, or substituted by one or two substituents. Suitably, such groups will be unsubstituted or monosubstituted.

Typical values of $R^{11}$ include hydrogen, methyl and ethyl. In one embodiment, $R^{11}$ hydrogen. In another embodiment, $R^{11}$ is $C_{1-6}$ alkyl, especially methyl.

Suitably, $R^{12}$ represents hydrogen; or $C_{1-6}$ alkyl, $C_{3-7}$ cycloalkyl or aryl, any of which groups may be optionally substituted by one or more substituents.

Examples of typical substituents on $R^{12}$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)alkylaminosulphonyl; especially halogen, $C_{1-6}$ alkoxy or $C_{1-6}$ alkylthio.

Examples of particular substituents on $R^{12}$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, methoxy or methylthio.

Typical values of $R^{12}$ include hydrogen, methyl, n-propyl, isopropyl, isobutyl, cyclohexyl and phenyl. A particular value of $R^{12}$ is methyl.

Alternatively, $R^{11}$ and $R^{12}$ may together form an optionally substituted spiro linkage. Thus, $R^{11}$ and $R^{12}$, when taken together with the carbon atom to which they are both attached, may represent $C_{3-7}$ cycloalkyl or $C_{3-7}$ heterocycloalkyl, either of which groups may be unsubstituted, or substituted by one or more, typically by one or two, substituents. In this context, $R^{11}$ and $R^{12}$, when taken together with the carbon atom to which they are both attached, may suitably represent an optionally substituted cyclopentyl, cyclohexyl, pyrrolidine or piperidine ring.

Typically, $R^{13}$ represents hydrogen; or $C_{1-6}$ alkyl, aryl ($C_{1-6}$)alkyl, aryl($C_{2-6}$)alkynyl, biaryl($C_{1-6}$)alkyl, $C_{3-7}$ heterocycloalkyl($C_{1-6}$)alkyl, $C_{3-7}$ heterocycloalkylcarbonyl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

Generally, $R^{13}$ represents hydrogen; or $C_{2-6}$ alkynyl, aryl ($C_{1-6}$)alkyl or heteroaryl-($C_{1-6}$)alkyl, any of which groups may be optionally substituted by one or more substituents. More particularly, $R^{13}$ represents aryl($C_{1-6}$)alkyl or heteroaryl($C_{1-6}$)alkyl, either of which groups may be optionally substituted by one or more substituents.

In one specific embodiment, $R^{13}$ represents hydrogen.

In a representative embodiment, $R^{13}$ represents $C_{1-6}$ alkyl, aryl($C_{1-6}$)alkyl, biaryl-($C_{1-6}$)alkyl, heteroaryl($C_{1-6}$)alkyl or heteroaryl-aryl($C_{1-6}$)alkyl, any of which groups may be optionally substituted by one or more substituents. Preferably, $R^{13}$ represents methyl, arylmethyl, biarylmethyl, heteroarylmethyl or heteroaryl-arylmethyl, any of which groups may be optionally substituted by one or more substituents.

In a particular embodiment, $R^{13}$ represents substituted or unsubstituted indolyl-($C_{1-6}$)alkyl. Advantageously, $R^{13}$ represents substituted or unsubstituted indolylmethyl.

In a typical embodiment, $R^{13}$ represents substituted or unsubstituted phenyl-($C_{1-6}$)alkyl. Advantageously, $R^{13}$ represents substituted or unsubstituted benzyl.

In another embodiment, $R^{13}$ represents substituted or unsubstituted benzofuryl-($C_{1-6}$)alkyl. Advantageously, $R^{13}$ represents substituted or unsubstituted benzofurylmethyl.

In a further embodiment, $R^{13}$ represents substituted or unsubstituted pyrrolo[3,2-c]-pyridinyl($C_{1-6}$)alkyl. Advantageously, $R^{13}$ represents substituted or unsubstituted pyrrolo [3,2-c]pyridinylmethyl.

Illustratively, $R^{13}$ represents hydrogen; or methyl, benzyl, phenylethyl, naphthylmethyl, phenylpropynyl, biphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, pyrrolo[2,3-b]pyridinylmethyl, benzimidazolylmethyl, benzotriazolylmethyl, pyridinylmethyl, quinolinylmethyl, isoquinolinylmethyl, benzofurylbenzyl, thienylbenzyl, benzothienylbenzyl, indolylbenzyl, isoxazolylbenzyl, pyrazolylbenzyl, pyridinylbenzyl, pyrimidinylbenzyl or phenylpyridinylmethyl, any of which groups may be optionally substituted by one or more substituents. Additionally, $R^{13}$ may represent propynyl, benzofurylmethyl or pyrrolo[3,2-c]pyridinylmethyl, any of which groups may be optionally substituted by one or more substituents.

Definitive examples of suitable substituents on $R^{13}$ include halogen, cyano, nitro, $C_{1-6}$ alkyl, $C_{2-6}$ alkenyl, $C_{3-7}$ cycloalkyl, $(C_{1-6})$alkylaryl, di$(C_{1-6})$alkylaryl, piperidinyl $(C_{1-6})$alkylaryl, piperazinyl$(C_{1-6})$alkylaryl, $(C_{1-6})$alkylpiperazinyl$(C_{1-6})$alkylaryl, morpholinyl$(C_{1-6})$alkylaryl, $(C_{1-6})$alkoxyaryl, cyano$(C_{1-6})$alkoxyaryl, di$(C_{1-6})$alkylamino-$(C_{1-6})$alkylaryl, $(C_{1-6})$alkylaminocarbonylaryl, aryl$(C_{1-6})$alkyl, oxazolinyl, azetidinyl, haloarylpyrrolidinyl, dioxopyrrolidinyl, aminopyrrolidinyl, di$(C_{1-6})$alkylaminopyrrolidinyl, indolinyl, oxoindolinyl, arylpiperidinyl, arylcarbonylpiperidinyl, di$(C_{1-6})$alkylaminocarbonylpiperidinyl, piperazinyl, $(C_{1-6})$alkylpiperazinyl, haloarylpiperazinyl, pyridinylpiperazinyl, furoylpiperazinyl, homopiperazinyl, $(C_{1-6})$alkylhomopiperazinyl, morpholinyl, $(C_{1-6})$alkylpiperazinyl$(C_{1-6})$alkyl, morpholinyl$(C_{1-6})$alkyl, benzofuryl, benzothienyl, pyrazolyl, $(C_{1-6})$alkylpyrazolyl, di$(C_{1-6})$alkylpyrazolyl, tri$(C_{1-6})$alkylpyrazolyl, [di$(C_{1-6})$alkyl](trifluoromethyl)pyrazolyl, cyano$(C_{1-6})$alkylpyrazolyl, [cyano-$(C_{1-6})$alkyl][di$(C_{1-6})$alkyl]pyrazolyl, hydroxy$(C_{1-6})$alkylpyrazolyl, [hydroxy$(C_{1-6})$-alkyl][di$(C_{1-6})$alkyl]pyrazolyl, methoxy$(C_{1-6})$alkylpyrazolyl, [(hydroxy)(methoxy)$(C_{1-6})$-alkyl]pyrazolyl, amino$(C_{1-6})$alkylpyrazolyl, [$(C_{1-6})$alkyl][amino$(C_{1-6})$alkyl]pyrazolyl, [amino$(C_{1-6})$alkyl][di$(C_{1-6})$alkyl]pyrazolyl, di$(C_{1-6})$alkylamino$(C_{1-6})$alkylpyrazolyl, di$(C_{1-6})$alkoxyphosphono$(C_{1-6})$alkylpyrazolyl, $(C_{2-6})$alkenylpyrazolyl, $(C_{3-7})$cycloalkyl-$(C_{1-6})$alkylpyrazolyl, [$(C_{3-7})$cycloalkyl$(C_{1-6})$alkyl][di$(C_{1-6})$alkyl]pyrazolyl, [$(C_{1-6})$alkyl]-(aryl)pyrazolyl, (aryl)(trifluoromethyl)pyrazolyl, aryl$(C_{1-6})$alkylpyrazolyl, aminoaryl-$(C_{1-6})$alkylpyrazolyl, piperidinylpyrazolyl, tetrahydropyranyl$(C_{1-6})$alkylpyrazolyl, [di-$(C_{1-6})$alkyl][tetrahydropyranyl$(C_{1-6})$alkyl]pyrazolyl, pyrrolidinyl$(C_{1-6})$alkylpyrazolyl, piperidinyl$(C_{1-6})$alkylpyrazolyl, $(C_{1-6})$alkylpiperidinyl$(C_{1-6})$alkylpyrazolyl, morpholinyl$(C_{1-6})$alkylpyrazolyl, pyridinyl$(C_{1-6})$alkylpyrazolyl, oxypyridinyl$(C_{1-6})$alkylpyrazolyl, [arylcarbonyl$(C_{1-6})$alkyl][di$(C_{1-6})$alkyl]pyrazolyl, [$(C_{1-6})$alkyl](piperazinylcarbonyl)pyrazolyl, [$(C_{1-6})$alkylaminocarbonyl][$(C_{1-6})$alkylaryl]pyrazolyl, [$(C_{1-6})$alkyl]-[amino$(C_{1-6})$alkylaminocarbonyl]pyrazolyl, aminocarbonyl$(C_{1-6})$alkylpyrazolyl, [aminocarbonyl$(C_{1-6})$alkyl][di$(C_{1-6})$alkyl]pyrazolyl, di$(C_{1-6})$alkylaminocarbonyl$(C_{1-6})$alkylpyrazolyl, pyrazolo[1,5-a]pyridinyl, di$(C_{1-6})$alkylisoxazolyl, (amino)[$(C_{1-6})$alkyl]-isoxazolyl, thiazolyl, di$(C_{1-6})$alkylthiazolyl, imidazolyl, $(C_{1-6})$alkylimidazolyl, di$(C_{1-6})$-alkylimidazolyl, imidazo[1,2-a]pyridinyl, $(C_{1-6})$alkylimidazo[1,2-a]pyridinyl, $(C_{1-6})$-alkylimidazo[4,5-b]pyridinyl, imidazo[1,2-a]pyrimidinyl, imidazo[1,2-a]pyrazinyl, $(C_{1-6})$-alkylthiadiazolyl, triazolyl, pyridinyl, halopyridinyl, $(C_{1-6})$alkylpyridinyl, [$(C_{1-6})$alkyl]-(halo)pyridinyl, di$(C_{1-6})$alkylpyridinyl, $(C_{2-6})$alkenylpyridinyl, $(C_{1-6})$alkylpiperazinylpyridinyl, [$(C_{1-6})$alkyl](piperazinyl)pyridinyl, [$(C_{1-6})$alkoxycarbonylpiperazinyl][$(C_{1-6})$-alkyl]pyridinyl, piperidinyl$(C_{1-6})$alkylpyridinyl, [$(C_{1-6})$alkyl](oxy)pyridinyl, hydroxypyridinyl, hydroxy$(C_{1-6})$alkylpyridinyl, $(C_{1-6})$alkoxypyridinyl, [$(C_{1-6})$alkoxy]-[$(C_{1-6})$alkyl]pyridinyl, [$(C_{1-6})$alkoxy][di$(C_{1-6})$alkyl]pyridinyl, $(C_{1-6})$alkoxy$(C_{1-6})$alkylpyridinyl, aminopyridinyl, carboxy$(C_{1-6})$alkylpyridinyl, $(C_{1-6})$alkoxycarbonyl$(C_{1-6})$alkylpyridinyl, pyridazinyl, $(C_{1-6})$alkylpyridazinyl, piperidinylpyridazinyl, oxypyridazinyl, $(C_{1-6})$alkoxypyridazinyl, aminopyridazinyl, hydroxy$(C_{1-6})$alkylaminopyridazinyl, di$(C_{1-6})$alkylaminopyridazinyl, pyrimidinyl, $(C_{1-6})$alkylpyrimidinyl, [$(C_{1-6})$alkyl](halo)-pyrimidinyl, di$(C_{1-6})$alkylpyrimidinyl, pyrrolidinylpyrimidinyl, $(C_{1-6})$alkylpiperazinylpyrimidinyl, [$(C_{1-6})$alkyl](piperazinyl)pyrimidinyl, [$(C_{1-6})$alkoxycarbonyl][$(C_{1-6})$alkyl]-piperazinylpyrimidinyl, hydroxypyrimidinyl, [$(C_{1-6})$alkyl](hydroxy)pyrimidinyl, [$(C_{1-6})$-alkyl][hydroxy$(C_{1-6})$alkyl]pyrimidinyl, [$(C_{1-6})$alkyl][hydroxy$(C_{2-6})$alkynyl]pyrimidinyl, $(C_{1-6})$alkoxypyrimidinyl, aminopyrimidinyl, di$(C_{1-6})$alkylaminopyrimidinyl, [di$(C_{1-6})$alkylamino](halo)pyrimidinyl, carboxypyrimidinyl, [$(C_{1-6})$alkoxycarbonyl$(C_{1-6})$alkyl][$(C_{1-6})$-alkyl]pyrimidinyl, aminocarbonylpyrimidinyl, pyrazinyl, $(C_{1-6})$alkoxypyrazinyl, aminopyrazinyl, hydroxy, $(C_{1-6})$alkoxy, difluoromethoxy, trifluoromethoxy, $C_{3-7}$ cycloalkoxy, $C_{3-7}$ cycloalkyl$(C_{1-6})$alkoxy, aryl$(C_{1-6})$alkoxycarbonylpiperidinyloxy, morpholinyl$(C_{1-6})$-alkoxy, aryloxy, haloaryloxy, di$(C_{1-6})$alkylpyrazolyloxy, halopyridinyloxy, pyrrolidinylpyridinyloxy, $(C_{1-6})$alkylpiperazinylpyridinyloxy, $(C_{1-6})$alkylpyrazolylpyridinyloxy, $(C_{1-6})$alkylaminopyridinyloxy, carboxypyridinyloxy, aminocarbonylpyridinyloxy, $(C_{1-6})$alkylpyridazinyloxy, pyrimidinyloxy, $(C_{1-6})$alkylpyrimidinyloxy, [$(C_{1-6})$alkyl](halo)pyrimidinyloxy, hydroxy$(C_{1-6})$alkyl, dihydroxy$(C_{1-6})$alkyl, pyridinyloxy$(C_{1-6})$alkyl, amino, $(C_{1-6})$alkylamino, dihydroxy$(C_{1-6})$alkylamino, alkoxy$(C_{1-6})$alkylamino, N—[$(C_{1-6})$alkoxy$(C_{1-6})$alkyl]-N—[$(C_{1-6})$alkyl]amino, di$(C_{1-6})$-alkylamino$(C_{1-6})$alkylamino, N—[$(C_{1-6})$alkyl]-N-[di$(C_{1-6})$alkylamino$(C_{1-6})$alkyl]amino, N—[$(C_{1-6})$alkyl]-N—[$(C_{3-7})$cycloalkyl]amino, haloarylamino, N—[$(C_{1-6})$alkyl]-N-(haloaryl)amino, methylenedioxyphenylamino, morpholinyl$(C_{1-6})$alkylphenylamino, oxazolinylphenylamino, [$(C_{1-6})$alkyl](oxo)pyrazolylphenylamino, oxazolylphenylamino, isoxazolylphenylamino, triazolylphenylamino, $(C_{1-6})$alkyltriazolylphenylamino, $(C_{1-6})$alkylpyrimidinylphenylamino, pyrazolyl$(C_{1-6})$alkylphenylamino, triazolyl$(C_{1-6})$alkylphenylamino, $C_{1-6}$ alkylsulphonylaminophenylamino, morpholinylcarbonylphenylamino, $C_{1-6}$ alkylsulphonylphenylamino, morpholinylsulphonylphenylamino, N—[$(C_{1-6})$alkyl]-N-[aryl$(C_{1-6})$alkyl]amino, N-[di$(C_{1-6})$alkylamino$(C_{1-6})$alkyl]-N-[aryl$(C_{1-6})$alkyl]amino, cyanoaryl$(C_{1-6})$alkylamino, (cyano)(halo)aryl$(C_{1-6})$alkylamino, methylenedioxyaryl$(C_{1-6})$-alkylamino, dihydrobenzofuranylamino, N—[$(C_{1-6})$alkyl]-N—[$(C_{1-6})$alkylpyrrolidinyl]amino, $C_{1-6}$ alkylsulphonylindolinylamino, chromanonylamino, piperidinylamino, N—[$(C_{1-6})$alkyl]-N-(piperidinyl)amino, N—[$(C_{3-7})$cycloalkyl$(C_{1-6})$alkyl]-N-(piperidinyl)amino, $(C_{1-6})$alkylpiperidinylamino, N—[$(C_{1-6})$alkyl]-N—[$(C_{1-6})$alkylpiperidinyl]amino, N—[$(C_{1-6})$alkyl]-N—[$(C_{3-7})$cycloalkylpiperidinyl]amino, N—[$(C_{1-6})$alkyl]-N—[$(C_{2-6})$alkylcarbonylpiperidinyl]-amino, dihydroquinolinonylamino, benzoxazinonylamino, pyrrolidinyl$(C_{1-6})$alkylamino, N—[$(C_{1-6})$alkyl]-N-[pyrrolidinyl$(C_{1-6})$alkyl]amino, N—[$(C_{1-6})$alkyl]-N-[piperidinyl$(C_{1-6})$-alkyl]amino, benzothienylamino, indolylamino, dioxoindolylamino, $(C_{1-6})$alkylpyrazolylamino, [$(C_{1-6})$alkyl](halo)pyrazolylamino, di$(C_{1-6})$alkylpyrazolylamino, tri$(C_{1-6})$alkylpyrazolylamino, N—[$(C_{1-6})$alkyl]-N—[$(C_{1-6})$alkylpyrazolyl]amino, $(C_{1-6})$alkylindazolylamino, benzoxazolylamino, benzoxazolonylamino, di$(C_{1-6})$alkylisoxazolylamino, thiazolylamino, benzothiazolylamino, $(C_{1-6})$alkylisothiazolylamino, imidazolylamino, [$(C_{1-6})$alkoxycarbonyl][$(C_{1-6})$alkyl]imidazolylamino, $(C_{1-6})$alkylbenzimidazolylamino, benzimidazolonylamino, di$(C_{1-6})$alkylbenzimidazolonylamino, $(C_{1-6})$alkyloxadiazolylamino, furyloxadiazolylamino, $(C_{1-6})$alkylthiadiazolylamino, pyridinylamino, halopyridinylamino, $(C_{1-6})$alkylpyridinylamino, di$(C_{1-6})$alkylpyridinylamino, trifluoromethylpyridinylamino, hydroxypyridinylamino, hydroxy$(C_{1-6})$alkylpyridinylamino, dihydroxy$(C_{1-6})$alkylpyridinylamino, $(C_{1-6})$alkoxypyridinylamino, dihydroxy$(C_{1-6})$alkoxypyridinylamino, di$(C_{1-6})$alkyldioxolanyl$(C_{1-6})$ alkoxypyridinylamino, $(C_{1-6})$alkoxy$(C_{1-6})$-alkylpyridinylamino, $(C_{1-6})$alkoxy$(C_{2-6})$alkenylpyridinylamino, dihydroxy$(C_{1-6})$alkylaminopyridinylamino, di$(C_{1-6})$alkylaminopyridinylamino, $(C_{1-6})$alkylamino$(C_{1-6})$alkylpyridinylamino, di$(C_{1-6})$alkylamino$(C_{1-6})$alkylpyridinylamino, oxopyridinylamino, carboxypyridinylamino, N—[$(C_{1-6})$alkyl]-N—[$(C_{1-6})$alkylpyridinyl]amino, bis[$(C_{1-6})$alkylpyridinyl]amino, bis(trifluoromethylpyridinyl)amino, isoquinolinylamino, $(C_{1-6})$alkylpyridazinylamino, N—[$(C_{1-6})$alkyl]-N—[$(C_{1-6})$alkylpyridazinyl]amino, N-[aryl$(C_{1-6})$alkyl]-N—[$(C_{1-6})$alkylpyridazinyl]amino, di$(C_{1-6})$alkylpyridazinylamino, arylpyridazinylamino, piperidinylpyridazinylamino, $(C_{1-6})$alkoxypyridazinylamino, [$(C_{1-6})$alkoxy](halo)-pyridazinylamino, di$(C_{1-6})$alkylaminopyridazinylamino, bis[$(C_{1-6})$alkylpyridazinyl]amino, $(C_{1-6})$alkylcinnolinylamino, oxopyrimidinylamino, thioxopyrimidinylamino, quinoxalinylamino, $(C_{1-6})$alkylchromenylamino, benzofuryl$(C_{1-6})$alkylamino, thienyl$(C_{1-6})$-alkylamino, indolyl$(C_{1-6})$alkylamino, $(C_{1-6})$alkylpyrazolyl$(C_{1-6})$alkylamino, [di$(C_{1-6})$alkyl]-(halo)pyrazolyl$(C_{1-6})$alkylamino, di$(C_{1-6})$alkylisoxazolyl$(C_{1-6})$alkylamino, thiazolyl$(C_{1-6})$-alkylamino, imidazolyl$(C_{1-6})$alkylamino, $(C_{1-6})$alkylimidazolyl$(C_{1-6})$alkylamino, pyridinyl$(C_{1-6})$alkylamino, $(C_{1-6})$alkylpyridinyl$(C_{1-6})$alkylamino, N—[$(C_{1-6})$alkyl]-N-[pyridinyl$(C_{1-6})$alkyl]amino, N-[dihydroxy$(C_{1-6})$alkyl]-N-[pyridinyl$(C_{1-6})$alkyl]amino, N—[$(C_{1-6})$alkylpyridinyl$(C_{1-6})$alkyl]-N-[dihydroxy$(C_{1-6})$alkyl]amino, amino$(C_{1-6})$alkyl, $(C_{1-6})$-alkylamino$(C_{1-6})$alkyl, di$(C_{1-6})$alkylamino$(C_{1-6})$alkyl, pyridinylamino$(C_{1-6})$alkyl, $C_{2-6}$ alkylcarbonylamino, N—[$(C_{2-6})$alkylcarbonyl]-N—[$(C_{1-6})$alkylpyridinyl$(C_{1-6})$alkyl]amino, di$(C_{1-6})$alkylamino$(C_{1-6})$alkylcarbonylamino, $C_{2-6}$ alkylcarbonylaminomethyl, $(C_{3-7})$-cycloalkylcarbonylamino, $(C_{1-6})$alkylpiperidinylcarbonylamino, $(C_{1-6})$alkylimidazolylcarbonylamino, $C_{2-6}$ alkoxycarbonylamino, [$(C_{2-6})$alkoxycarbonyl][$(C_{1-6})$alkyl]amino, $C_{1-6}$ alkylsulphonylamino, formyl, $C_{2-6}$ alkylcarbonyl, $C_{2-6}$ alkylcarbonyl oxime, $C_{2-6}$ alkylcarbonyl O-(methyl) oxime, trifluoromethylcarbonyl, carboxy, $C_{2-6}$ alkoxycarbonyl, aminocarbonyl, $C_{1-6}$ alkylaminocarbonyl, [hydroxy$(C_{1-6})$alkyl]aminocarbonyl, [di$(C_{1-6})$-alkylamino$(C_{1-6})$alkyl]aminocarbonyl, di$(C_{1-6})$alkylaminocarbonyl, [$(C_{1-6})$alkyl][cyano-$(C_{1-6})$alkyl]aminocarbonyl, [$(C_{1-6})$alkyl][hydroxy$(C_{1-6})$alkyl]aminocarbonyl, [$(C_{1-6})$alkoxy-$(C_{1-6})$alkyl][$(C_{1-6})$alkyl]aminocarbonyl, [di$(C_{1-6})$alkylamino$(C_{1-6})$alkyl][$(C_{1-6})$alkyl]aminocarbonyl, $C_{3-7}$ cycloalkyl$(C_{1-6})$alkylaminocarbonyl, aryl$(C_{1-6})$alkylaminocarbonyl, $(C_{1-6})$-alkylpiperidinylaminocarbonyl, N—[$(C_{1-6})$alkyl]-N—[$(C_{1-6})$-alkylpiperidinyl]aminocarbonyl, piperidinyl$(C_{1-6})$alkylaminocarbonyl, heteroarylaminocarbonyl, heteroaryl$(C_{1-6})$alkylaminocarbonyl, azetidinylcarbonyl, hydroxyazetidinylcarbonyl, aminoazetidinylcarbonyl, $C_{2-6}$ alkoxycarbonylaminoazetidinylcarbonyl, pyrrolidinylcarbonyl, $(C_{1-6})$alkylpyrrolidinylcarbonyl, $C_{1-6}$ alkoxy$(C_{1-6})$alkylpyrrolidinylcarbonyl, di$(C_{1-6})$alkylaminopyrrolidinylcarbonyl, thiazolidinylcarbonyl, oxothiazolidinylcarbonyl, piperidinylcarbonyl, $(C_{1-6})$alkylpiperazinylcarbonyl, morpholinylcarbonyl, $C_{1-6}$ alkylthio, $C_{1-6}$ alkylsulphinyl, $C_{1-6}$ alkylsulphonyl, $C_{1-6}$ alkylsulphonylmethyl, di$(C_{1-6})$alkylaminosulphonyl, $C_{2-6}$ alkoxycarbonyloxy, trimethylsilyl and tetra$(C_{1-6})$alkyldioxaborolanyl.

Examples of typical substituents on $R^{13}$ include halogen, cyano, nitro, $C_{1-6}$ alkyl, hydroxy$(C_{1-6})$alkyl, trifluoromethyl, pyrazolyl, $(C_{1-6})$alkylpyrazolyl, di$(C_{1-6})$alkylpyrazolyl, aryl$(C_{1-6})$alkylpyrazolyl, morpholinyl$(C_{1-6})$alkylpyrazolyl, $(C_{1-6})$alkylimidazolyl, $(C_{1-6})$alkylpyridinyl, pyrimidinyl, aryl$(C_{1-6})$alkyl, hydroxy, $C_{1-6}$ alkoxy, difluoromethoxy, trifluoromethoxy, aryloxy, aryl$(C_{1-6})$alkoxy, pyridinyloxy$(C_{1-6})$alkyl, methylenedioxy, difluoromethylenedioxy, $C_{1-6}$ alkylthio, arylthio, $C_{1-6}$ alkylsulphinyl, arylsulphinyl, $C_{1-6}$ alkylsulphonyl, arylsulphonyl, $C_{1-6}$ alkylsulphonyloxy, amino, $C_{1-6}$ alkylamino, di$(C_{1-6})$alkylamino, phenylamino, [$(C_{1-6})$alkyl](phenyl)amino, pyridinylamino, halopyridinylamino, $(C_{1-6})$alkylpyridinylamino, di$(C_{1-6})$alkylpyridinylamino, $(C_{1-6})$alkoxypyridinylamino, pyrrolidinyl, morpholinyl, $C_{2-6}$ alkylcarbonylamino, benzofurylcarbonylamino, $C_{2-6}$ alkoxycarbonylamino, $C_{1-6}$ alkylsulphonylamino, arylsulphonylamino, amino$(C_{1-6})$alkyl, $(C_{1-6})$alkylamino$(C_{1-6})$alkyl, di$(C_{1-6})$alkylamino$(C_{1-6})$alkyl, pyridinylamino$(C_{1-6})$alkyl, $(C_{1-6})$alkylpiperazinyl$(C_{1-6})$alkyl, morpholinyl$(C_{1-6})$alkyl, formyl, $C_{2-6}$ alkylcarbonyl, carboxy, $C_{2-6}$ alkoxycarbonyl, aminocarbonyl, $C_{1-6}$ alkylaminocarbonyl, [hydroxy$(C_{1-6})$alkyl]aminocarbonyl, di$(C_{1-6})$alkylaminocarbonyl, [$(C_{1-6})$alkyl][hydroxy$(C_{1-6})$alkyl]aminocarbonyl, aryl$(C_{1-6})$alkylaminocarbonyl, benzothienylmethylaminocarbonyl, azetidinylcarbonyl, pyrrolidinylcarbonyl, piperidinylcarbonyl, $(C_{1-6})$alkylpiperazinylcarbonyl, morpholinylcarbonyl, aminosulphonyl, $C_{1-6}$ alkylaminosulphonyl, di$(C_{1-6})$alkylaminosulphonyl and $C_{2-6}$ alkoxycarbonyloxy.

Examples of suitable substituents on $R^{13}$ include halogen, cyano, nitro, $C_{1-6}$ alkyl, hydroxy$(C_{1-6})$alkyl, trifluoromethyl, aryl$(C_{1-6})$alkyl, hydroxy, $C_{1-6}$ alkoxy, difluoromethoxy, trifluoromethoxy, aryloxy, aryl$(C_{1-6})$alkoxy, methylenedioxy, $C_{1-6}$ alkylthio, arylthio, $C_{1-6}$ alkylsulphinyl, arylsulphinyl, $C_{1-6}$ alkylsulphonyl, arylsulphonyl, $C_{1-6}$ alkylsulphonyloxy, amino, $C_{1-6}$ alkylamino, di$(C_{1-6})$alkylamino, phenylamino, [$(C_{1-6})$alkyl](phenyl)amino, pyridinylamino, pyrrolidinyl, morpholinyl, $C_{2-6}$ alkylcarbonylamino, benzofurylcarbonylamino, $C_{2-6}$ alkoxycarbonylamino, $C_{1-6}$ alkylsulphonylamino, arylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di$(C_{1-6})$alkylaminocarbonyl, benzothienylmethylaminocarbonyl, aminosulphonyl, $C_{1-6}$ alkylaminosulphonyl and di$(C_{1-6})$alkylaminosulphonyl.

Selected examples of typical substituents on $R^{13}$ include halogen, nitro, $C_{1-6}$ alkyl, hydroxy$(C_{1-6})$alkyl, pyrazolyl, $(C_{1-6})$alkylpyrazolyl, di$(C_{1-6})$alkylpyrazolyl, aryl$(C_{1-6})$alkylpyrazolyl, morpholinyl$(C_{1-6})$alkylpyrazolyl, $(C_{1-6})$alkylimidazolyl, $(C_{1-6})$alkylpyridinyl, pyrimidinyl, hydroxy, difluoromethoxy, trifluoromethoxy, pyridinyloxy$(C_{1-6})$alkyl, difluoromethylenedioxy, amino, pyridinylamino, halopyridinylamino, $(C_{1-6})$alkylpyridinylamino, di$(C_{1-6})$alkylpyridinylamino, $(C_{1-6})$alkoxypyridinylamino, di$(C_{1-6})$alkylamino$(C_{1-6})$alkyl, pyridinylamino$(C_{1-6})$alkyl, $(C_{1-6})$alkylpiperazinyl$(C_{1-6})$alkyl, morpholinyl$(C_{1-6})$alkyl, formyl, carboxy, $C_{2-6}$ alkoxycarbonyl, $C_{1-6}$ alkylaminocarbonyl, [hydroxy$(C_{1-6})$alkyl]aminocarbonyl, di$(C_{1-6})$alkylaminocarbonyl, [$(C_{1-6})$alkyl][hydroxy$(C_{1-6})$alkyl]aminocarbonyl, aryl$(C_{1-6})$alkylaminocarbonyl, azetidinylcarbonyl, piperidinylcarbonyl, $(C_{1-6})$alkylpiperazinylcarbonyl, morpholinylcarbonyl and $C_{2-6}$ alkoxycarbonyloxy.

Examples of illustrative substituents on $R^{13}$ include fluoro, chloro, bromo, cyano, nitro, methyl, hydroxymethyl, trifluoromethyl, pyrazolyl, methylpyrazolyl, dimethylpyrazolyl, propylpyrazolyl, isobutylpyrazolyl, benzylpyrazolyl, morpholinylethylpyrazolyl, methylimidazolyl, methylpyridinyl, pyrimidinyl, benzyl, hydroxy, methoxy, ethoxy, difluoromethoxy, trifluoromethoxy, phenoxy, benzyloxy, pyridinyloxymethyl, methylenedioxy, difluoromethylenedioxy, methylthio, phenylthio, methylsulphinyl, phenylsulphinyl, methylsulphonyl, phenylsulphonyl, methylsulphonyloxy, amino, methylamino, dimethylamino, phenylamino, N-methyl-N-phenylamino, pyridinylamino, chloropyridinylamino, methylpyridinylamino, dimethylpyridinylamino, methoxypyridinylamino, pyrrolidinyl, morpholinyl, acetylamino, benzofurylcarbonylamino, methoxycarbonylamino, methylsulphonylamino, phenylsulphonylamino, aminomethyl, methylaminomethyl, dimethylaminomethyl, pyridinylaminomethyl, methylpiperazinylmethyl, morpholinylmethyl, formyl, acetyl, carboxy, methoxycarbonyl, aminocarbonyl, methylaminocarbonyl, (hydroxyethyl)aminocarbonyl, dimethylaminocarbonyl, N-(hydroxyethyl)-N-methylaminocarbonyl, benzylaminocarbonyl, benzothienylmethylaminocarbonyl, azetidinylcarbonyl, pyrrolidinylcarbonyl, piperidinylcarbonyl, methylpiperazinylcarbonyl, morpholinylcarbonyl, aminosulphonyl, methylaminosulphonyl, dimethylaminosulphonyl and tert-butoxycarbonyloxy.

Examples of representative substituents on $R^{13}$ include fluoro, chloro, bromo, cyano, nitro, methyl, hydroxymethyl, trifluoromethyl, benzyl, hydroxy, methoxy, ethoxy, difluoromethoxy, trifluoromethoxy, phenoxy, benzyloxy, methylenedioxy, methylthio, phenylthio, methylsulphinyl, phenylsulphinyl, methylsulphonyl, phenylsulphonyl, methylsulphonyloxy, amino, methylamino, dimethylamino, phenylamino, N-methyl-N-phenylamino, pyridinylamino, pyrrolidinyl, morpholinyl, acetylamino, benzofurylcarbonylamino, methoxycarbonylamino, methylsulphonylamino, phenylsulphonylamino, formyl, acetyl, carboxy, methoxycarbonyl, aminocarbonyl, methylaminocarbonyl, dimethylaminocarbonyl, benzothienylmethylaminocarbonyl, aminosulphonyl, methylaminosulphonyl and dimethylaminosulphonyl.

Definitive examples of specific substituents on $R^{13}$ include fluoro, chloro, bromo, cyano, nitro, methyl, n-propyl, isopropyl, allyl, cyclopropyl, methylphenyl, dimethylphenyl, piperidinylmethylphenyl, piperazinylmethyl-phenyl, methylpiperazinylmethylphenyl, morpholinylmethylphenyl, methoxyphenyl, cyanomethoxyphenyl, dimethylaminomethylphenyl, methylaminocarbonylphenyl, benzyl, oxazolinyl, azetidinyl, chlorophenylpyrrolidinyl, dioxopyrrolidinyl, aminopyrrolidinyl, dimethylaminopyrrolidinyl, indolinyl, oxoindolinyl, phenylpiperidinyl, benzoylpiperidinyl, diethylaminocarbonylpiperidinyl, piperazinyl, methylpiperazinyl, chlorophenylpiperazinyl, pyridinylpiperazinyl, furoylpiperazinyl, homopiperazinyl, methylhomopiperazinyl, morpholinyl, methylpiperazinylmethyl, methylpiperazinylethyl, morpholinylmethyl, benzofuryl, benzothienyl, pyrazolyl, methylpyrazolyl, ethylpyrazolyl, propylpyrazolyl, 2-methylpropylpyrazolyl, 3-methylbutylpyrazolyl, dimethylpyrazolyl, trimethylpyrazolyl, (dimethyl)(ethyl)pyrazolyl, (dimethyl)(isopropyl)pyrazolyl, (dimethyl)(2-methylpropyl)pyrazolyl, (dimethyl)(3-methylbutyl)pyrazolyl, (dimethyl)(trifluoromethyl)pyrazolyl, cyanomethylpyrazolyl, (cyanomethyl)(dimethyl)pyrazolyl, hydroxyethylpyrazolyl, hydroxypropylpyrazolyl, 2-hydroxy-2-methylpropylpyrazolyl, (hydroxyethyl)(dimethyl)-pyrazolyl, (hydroxypropyl)(dimethyl)pyrazolyl, methoxypropylpyrazolyl, [(hydroxy)-(methoxy)propyl]pyrazolyl, aminoethylpyrazolyl, aminopropylpyrazolyl, (aminopropyl)-(methyppyrazolyl, (aminopropyl)(dimethyl)pyrazolyl, dimethylaminoethylpyrazolyl, dimethylaminopropylpyrazolyl, diethoxyphosphonopropylpyrazolyl, allylpyrazolyl, cyclopropylmethylpyrazolyl, (cyclopropylmethyl)(dimethyl)pyrazolyl, (methyl)(phenyl)-pyrazolyl, (phenyl)(trifluoromethyl)pyrazolyl, benzylpyrazolyl, aminobenzylpyrazolyl, piperidinylpyrazolyl, tetrahydropyranylmethylpyrazolyl, (dimethyl)(tetrahydropyranylmethyl)pyrazolyl, pyrrolidinylethylpyrazolyl, piperidinylethylpyrazolyl, methylpiperidinylethylpyrazolyl, morpholinylethylpyrazolyl, pyridinylmethylpyrazolyl, oxypyridinylmethylpyrazolyl, (dimethyl)(phenylcarbonylmethyl)pyrazolyl, (ethyl)(piperazinylcarbonyl)pyrazolyl, (methylaminocarbonyl)(methylphenyl)pyrazolyl, (aminoethylaminocarbonyl)(methyl)pyrazolyl, aminocarbonylmethylpyrazolyl, (aminocarbonylmethyl)(dimethyl)pyrazolyl, dimethylaminocarbonylmethylpyrazolyl, pyrazolo[1,5-a]pyridinyl, dimethylisoxazolyl, (amino)(methyl)isoxazolyl, thiazolyl, dimethylthiazolyl, imidazolyl, methylimidazolyl, dimethylimidazolyl, imidazo[1,2-a]pyridinyl, methylimidazo[1,2-a]pyridinyl, methylimidazo[4,5-b]pyridinyl, imidazo[1,2-a]pyrimidinyl, imidazo[1,2-a]pyrazinyl, methylthiadiazolyl, triazolyl, pyridinyl, fluoropyridinyl, methylpyridinyl, (fluoro)(methyl)pyridinyl, dimethylpyridinyl, vinylpyridinyl, (methylpiperazinyl)pyridinyl, (methyl)(piperazinyl)pyridinyl, (tertbutoxycarbonylpiperazinyl)(methyl)pyridinyl, piperidinylmethylpyridinyl, (methyl)(oxy)-pyridinyl, hydroxypyridinyl, hydroxymethylpyridinyl, hydroxyethylpyridinyl, methoxypyridinyl, (methoxy)(methyl)pyridinyl, (dimethyl)(methoxy)pyridinyl, methoxymethylpyridinyl, aminopyridinyl, carboxymethylpyridinyl, ethoxycarbonylmethylpyridinyl, pyridazinyl, methylpyridazinyl, piperidinylpyridazinyl, oxypyridazinyl, methoxypyridazinyl, aminopyridazinyl, hydroxyethylaminopyridazinyl, dimethylaminopyridazinyl, pyrimidinyl, methylpyrimidinyl, (chloro)(methyl)pyrimidinyl, dimethylpyrimidinyl, pyrrolidinylpyrimidinyl, methylpiperazinylpyrimidinyl, (methyl)-(piperazinyl)pyrimidinyl, (tert-butoxycarbonylpiperazinyl)(methyl)pyrimidinyl, hydroxypyrimidinyl, (hydroxy)(methyl)pyrimidinyl, (hydroxyethyl)(methyl)pyrimidinyl, (hydroxypropyl)(methyl)pyrimidinyl, (hydroxypropynyl)(methyl)pyrimidinyl, methoxypyrimidinyl, aminopyrimidinyl, dimethylaminopyrimidinyl, (dimethylamino)-(fluoro)pyrimidinyl, carboxypyrimidinyl, (methoxycarbonylmethyl)(methyl)pyrimidinyl, aminocarbonylpyrimidinyl, pyrazinyl, methoxypyrazinyl, aminopyrazinyl, hydroxy, methoxy, isopropoxy, difluoromethoxy, trifluoromethoxy, cyclobutyloxy, cyclopropylmethoxy, benzyloxycarbonylpiperidinyloxy, morpholinylethoxy, phenoxy, fluorophenoxy, dimethylpyrazolyloxy, bromopyridinyloxy, pyrrolidinylpyridinyloxy, methylpiperazinylpyridinyloxy, methylpyrazolylpyridinyloxy, isopropylaminopyridinyloxy, carboxypyridinyloxy, aminocarbonylpyridinyloxy, methylpyridazinyloxy, pyrimidinyloxy, methylpyrimidinyloxy, (chloro)(methyl)pyrimidinyloxy, hydroxymethyl, 1-hydroxy-1-methylethyl, dihydroxypropyl, pyridinyloxymethyl, amino, isopropylamino, dihydroxypropylamino, methoxyethylamino, methoxypropylamino, N-(methoxyethyl)-N-(methyl)amino, N-(methoxypropyl)-N-(methyl)amino, dimethylaminoethylamino, dimethylaminopropylamino, N-(dimethylaminoethyl)-N-(methyl)amino, N-(diethylaminoethyl)-N-(methyl)amino, N-(dimethylaminopropyl)-N-(methyl)amino, N-(dimethylaminoethyl)-N-(ethyl)amino, N-(dimethylaminopropyl)-N-(ethyl)amino, N-(cyclohexyl)-N-(methyl)amino, fluorophenylamino, N-fluorophenyl-N-methylamino, methylenedioxyphenylamino, morpholinylmethylphenylamino, oxazolinylphenylamino, (methyl)(oxo)pyrazolylphenylamino, oxazolylphenylamino, isoxazolylphenylamino, triazolylphenylamino, methyltriazolylphenylamino, methylpyrimidinylphenylamino, pyrazolylmethylphenylamino, triazolylmethylphenylamino, methylsulphonylaminophenylamino, morpholinylcarbonylphenylamino, methylsulphonylphenylamino, morpholinylsulphonylphenylamino, N-benzyl-N-methylamino, N-(benzyl)-N-(dimethylaminoethyl)amino, cyanobenzylamino, (cyano)(phenyl)ethylamino, (cyano)(fluoro)-benzylamino, methylenedioxybenzylamino, dihydrobenzofuranylamino, N-(methyl)-N-(methylpyrrolidinyl)amino, methylsulphonylindolinylamino, chromanonylamino, piperidinylamino, N-(methyl)-N-(piperidinyl)amino, N-(ethyl)-N-(piperidinyl)amino, N-(cyclopropylmethyl)-N-(piperidinyl)amino, methylpiperidinylamino, N-(methyl)-N-(methylpiperidinyl)amino, N-(methyl)-N-(2-methylpropylpiperidinyl)amino, N-(cyclopentylpiperidinyl)-N-(methyl)amino, N-(acetylpiperidinyl)-N-(methyl)amino, dihydroquinolinonylamino, benzoxazinonylamino, pyrrolidinylethylamino, pyrrolidinylpropylamino, N-(methyl)-N-(pyrrolidinylethyl)amino, N-(methyl)-N-(pyrrolidinylpropyl)amino, N-(methyl)-N-(piperidinylmethyl)amino, benzothienylamino, indolylamino, dioxoindolylamino, methylpyrazolylamino, (bromo)(methyl)pyrazolylamino, dimethylpyrazolylamino, trimethylpyrazolylamino, N-(ethyl)-N-(methylpyrazolyl)-amino, methylindazolylamino, benzoxazolylamino, benzoxazolonylamino, dimethylisoxazolylamino, thiazolylamino, benzothiazolylamino, methylisothiazolylamino, imidazolylamino, (ethoxycarbonyl)(methyl)imidazolylamino, methylbenzimidazolylamino, benzimidazolonylamino, dimethylbenzimidazolylamino, methyloxadiazolylamino, furyloxadiazolylamino, methylthiadiazolylamino, pyridinylamino, chloropyridinylamino, bromopyridinylamino, methylpyridinylamino, dimethylpyridinylamino, trifluoromethylpyridinylamino, hydroxypyridinylamino, hydroxyethylpyridinylamino, dihydroxyethylpyridinylamino, methoxypyridinylamino, dihydroxypropoxypyridinylamino, dimethyldioxolanylmethoxypyridinylamino, methoxyethylpyridinylamino, methoxyvinylpyridinylamino, dihydroxypropylaminopyridinylamino, dimethylaminopyridinylamino, methylaminomethylpyridinylamino, dimethylaminomethylpyridinylamino, oxopyridinylamino, carboxypyridinylamino, N-(methyl)-N-(methylpyridinyl)-amino, N-(ethyl)-N-(methylpyridinyl)amino, bis(methylpyridinyl)amino, bis(trifluoromethylpyridinyl)amino, isoquinolinylamino, methylpyridazinylamino, N-(methyl)-N-(methylpyridazinyl)amino, N-(benzyl)-N-(methylpyridazinyl)amino, dimethylpyridazinylamino, phenylpyridazinylamino, piperidinylpyridazinylamino, methoxypyridazinylamino, (chloro)(methoxy)pyridazinylamino, dimethylaminopyridazinylamino, bis(methylpyridazinyl)amino, methylcinnolinylamino, oxopyrimidinylamino, thioxopyrimidinylamino, quinoxalinylamino, methylchromenylamino, benzofurylmethylamino, thienylmethylamino, indolylmethylamino, methylpyrazolylmethylamino, (chloro)(dimethyl)pyrazolylmethylamino, dimethylisoxazolylmethylamino, thiazolylmethylamino, imidazolylmethylamino, methylimidazolylmethylamino, pyridinylmethylamino, methylpyridinylmethylamino, N-(methyl)-N-(pyridinylethyl)-amino, N-(dihydroxypropyl)-N-(pyridinylmethyl)amino, N-(dihydroxypropyl)-N-(methylpyridinylmethyl)amino, aminomethyl, methylaminomethyl, dimethylaminomethyl, pyridinylaminomethyl, acetylamino, N-(acetyl)-N-(methylpyridinyl)amino, dimethylaminoethylcarbonylamino, acetylaminomethyl, cyclohexylcarbonylamino, methylpiperidinylcarbonylamino, methylimidazolylcarbonylamino, methoxycarbonylamino, N-methoxycarbonyl-N-methylamino, methylsulphonylamino, formyl, acetyl, acetyl oxime, acetyl O-(methyl)oxime, trifluoromethylcarbonyl, carboxy, methoxycarbonyl, aminocarbonyl, methylaminocarbonyl, (hydroxyethyl)aminocarbonyl, (dimethylaminoethyl)aminocarbonyl, (1-hydroxyprop-2-yl)aminocarbonyl, dimethylaminocarbonyl, N-(cyanomethyl)-N-methylaminocarbonyl, N-(cyanoethyl)-N-methylaminocarbonyl, N-(hydroxyethyl)-N-methylaminocarbonyl, N-(methoxyethyl)-N-methylaminocarbonyl, N-(dimethylaminoethyl)-N-methylaminocarbonyl, N-isopropyl-N-methylaminocarbonyl, diethylaminocarbonyl, cyclopropylmethylaminocarbonyl, benzylaminocarbonyl, methylpiperidinylaminocarbonyl, N-(methyl)-N-(methylpiperidinyl)aminocarbonyl, piperidinylethylaminocarbonyl, pyrazolylaminocarbonyl, pyridinylmethylaminocarbonyl, azetidinylcarbonyl, hydroxyazetidinylcarbonyl, aminoazetidinylcarbonyl, tert-butoxycarbonylaminoazetidinylcarbonyl, pyrrolidinylcarbonyl, methylpyrrolidinylcarbonyl, methoxymethylpyrrolidinylcarbonyl, dimethylaminopyrrolidinylcarbonyl, thiazolidinylcarbonyl, oxothiazolidinylcarbonyl, piperidinylcarbonyl, methylpiperazinylcarbonyl, morpholinylcarbonyl, isopropylthio, isopropylsulphinyl, methylsulphonyl, isopropylsulphonyl, methylsulphonylmethyl, dimethylaminosulphonyl, tert-butoxycarbonyloxy, trimethylsilyl and tetramethyldioxaborolanyl.

Selected examples of illustrative substituents on $R^{13}$ include fluoro, bromo, nitro, methyl, hydroxymethyl, pyrazolyl, methylpyrazolyl, dimethylpyrazolyl, propylpyrazolyl, isobutylpyrazolyl, benzylpyrazolyl, morpholinylethylpyrazolyl, methylimidazolyl, methylpyridinyl, pyrimidinyl, hydroxy, difluoromethoxy, trifluoromethoxy, pyridinyloxymethyl, difluoromethylenedioxy, amino, pyridinylamino, chloropyridinylamino, methylpyridinylamino, dimethylpyridinylamino, methoxypyridinylamino, dimethylaminomethyl, pyridinylaminomethyl, methylpiperazinylmethyl, morpholinylmethyl, formyl, carboxy, methoxycarbonyl, methylaminocarbonyl, (hydroxyethyl)aminocarbonyl, dimethylaminocarbonyl, N-(hydroxyethyl)-N-methylaminocarbonyl, benzylaminocarbonyl, azetidinylcarbonyl, piperidinylcarbonyl, methylpiperazinylcarbonyl, morpholinylcarbonyl and tert-butoxycarbonyloxy.

Selected values of $R^{13}$ include hydrogen, methyl, phenoxymethyl, phenylthiomethyl, aminomethyl, phenylaminomethyl, N-methyl-N-phenylaminomethyl, pyridinylamino-methyl, benzofurylcarbonylaminomethyl, phenylsulphonylaminomethyl, benzothienyl-methylaminocarbonylmethyl, phenyl, benzyl, chlorobenzyl, bromobenzyl, pyridinylaminobenzyl, chloropyridinylaminobenzyl, dimethylpyridinylaminobenzyl, methoxypyridinylaminobenzyl, pyrrolidinyl-benzyl, morpholinyl-benzyl, phenylethyl, naphthylmethyl, phenylpropynyl, biphenylmethyl, fluorobiphenylmethyl, difluorobiphenylmethyl, chlorobiphenylmethyl, dichlorobiphenylmethyl, bromobiphenylmethyl, cyanobiphenylmethyl, methylbiphenyl-methyl, (fluoro)(methyl)biphenylmethyl, dimethylbiphenylmethyl, hydroxymethylbiphenylmethyl, trifluoromethylbiphenylmethyl, bis(trifluoromethyl)biphenylmethyl, methoxybiphenylmethyl, dimethoxybiphenylmethyl, ethoxybiphenylmethyl, methylenedioxybiphenylmethyl, trifluoromethoxybiphenylmethyl, phenoxybiphenylmethyl, methylthiobiphenylmethyl, aminobiphenylmethyl, acetylaminobiphenylmethyl, methylsulphonylaminobiphenylmethyl, acetylbiphenylmethyl, aminocarbonylbiphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, methyl-1,2,3,4-tetrahydroquinolinylcarbonyl, methoxy-1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, fluoroindolylmethyl, nitroindolylmethyl, methyl-indolylmethyl, hydroxyindolylmethyl, difluoromethoxyindolylmethyl, trifluoromethoxyindolylmethyl, benzyloxyindolylmethyl, difluoromethylenedioxy-indolylmethyl, acetylindolylmethyl, methylsulphonyloxyindolylmethyl, carboxylndolylmethyl, methoxycarbonyl-indolylmethyl, methylaminocarbonyl-indolylmethyl, (hydroxyethyl)aminocarbonyl-indolylmethyl, dimethylaminocarbonylindolylmethyl, N-hydroxyethyl-N-methylaminocarbonylindolylmethyl, benzylaminocarbonylindolylmethyl, azetidinylcarbonyl-indolylmethyl, piperidinylcarbonyl-indolylmethyl, methylpiperazinylcarbonyl-indolylmethyl, morpholinylcarbonyl-indolylmethyl, pyrrolo[2,3-b]pyridinylmethyl, benzimidazolylmethyl, benzotriazolylmethyl, bromopyridinylmethyl, quinolinylmethyl, isoquinolinylmethyl, benzofurylbenzyl, thienylbenzyl, methylthienylbenzyl, acetylthienylbenzyl, benzothienylbenzyl, phenylsulphonylindolylbenzyl, dimethylisoxazolylbenzyl, methylpyrazolylbenzyl, benzylpyrazolylbenzyl, pyridinylbenzyl, fluoropyridinylbenzyl, chloropyridinylbenzyl, methoxypyridinylbenzyl, pyrimidinylbenzyl and phenylpyridinylmethyl.

Specific values of $R^{13}$ include hydrogen, phenoxymethyl, phenylthiomethyl, aminomethyl, phenylaminomethyl, N-methyl-N-phenylaminomethyl, pyridinylaminomethyl, benzofurylcarbonylaminomethyl, phenylsulphonylaminomethyl, benzothienylmethylaminocarbonylmethyl, benzyl, chlorobenzyl, bromobenzyl, pyrrolidinylbenzyl, morpholinyl-benzyl, phenylethyl, naphthylmethyl, phenylpropynyl, biphenylmethyl, fluorobiphenylmethyl, difluorobiphenylmethyl, chlorobiphenylmethyl, dichlorobiphenylmethyl, bromobiphenylmethyl, cyanobiphenylmethyl, methylbiphenylmethyl, (fluoro)(methyl)biphenylmethyl, dimethylbiphenylmethyl, hydroxymethylbiphenylmethyl, trifluoromethylbiphenylmethyl, bis(trifluoromethyl)biphenylmethyl, methoxybiphenylmethyl, dimethoxybiphenylmethyl, ethoxybiphenylmethyl, methylenedioxybiphenylmethyl, trifluoromethoxybiphenylmethyl, phenoxybiphenylmethyl, methylthiobiphenylmethyl, aminobiphenylmethyl, acetylaminobiphenylmethyl, methylsulphonylaminobiphenylmethyl, acetylbiphenylmethyl, aminocarbonylbiphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, methyl-1,2,3,4-tetrahydroquinolinylcarbonyl, methoxy-1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, methylindolylmethyl, hydroxyindolylmethyl, benzyloxyindolylmethyl, acetylindolylmethyl, methylsulphonyloxyindolylmethyl, pyrrolo[2,3-b]pyridinylmethyl, benzimidazolylmethyl, benzotriazolylmethyl, bromopyridinylmethyl, quinolinylmethyl, isoquinolinylmethyl, benzofurylbenzyl, thienylbenzyl, methylthienylbenzyl, acetylthienylbenzyl, benzothienylbenzyl, phenylsulphonylindolylbenzyl, dimethylisoxazolylbenzyl, methylpyrazolylbenzyl, benzylpyrazolylbenzyl, pyridinylbenzyl, fluoropyridinylbenzyl, chloropyridinylbenzyl, methoxypyridinylbenzyl, pyrimidinylbenzyl and phenylpyridinylmethyl.

Definitive values of $R^{13}$ include hydrogen, propynyl, trimethylsilylpropynyl, bromobenzyl, methylenedioxyphenylaminobenzyl, morpholinylmethylphenylaminobenzyl, oxazolinylphenylaminobenzyl, (methyl)(oxo)pyrazolylphenylaminobenzyl, oxazolylphenylaminobenzyl, isoxazolylphenylaminobenzyl, triazolylphenylaminobenzyl, methyltriazolylphenylaminobenzyl, methylpyrimidinylphenylaminobenzyl, pyrazolylmethylphenylaminobenzyl, triazolylmethylphenylaminobenzyl, methylsulphonylaminophenylaminobenzyl, morpholinylcarbonylphenylaminobenzyl, methylsulphonylphenylaminobenzyl, morpholinylsulphonylphenylaminobenzyl, dihydrobenzofuranylaminobenzyl, methylsulphonylindolinylaminobenzyl, chromanonylaminobenzyl, dihydroquinolinonylaminobenzyl, benzoxazinonylaminobenzyl, benzothienylaminobenzyl, indolylaminobenzyl, dioxoindolylaminobenzyl, (bromo)(methyl)pyrazolylaminobenzyl, trimethylpyrazolylaminobenzyl, methylindazolylaminobenzyl, benzoxazolylaminobenzyl, benzoxazolonylaminobenzyl, dimethylisoxazolylaminobenzyl, benzothiazolylaminobenzyl, methylisothiazolylaminobenzyl, methylbenzimidazolylaminobenzyl, benzimidazolonylaminobenzyl, dimethylbenzimidazolonylaminobenzyl, methyloxadiazolylaminobenzyl, furyloxadiazolylaminobenzyl, pyridinylaminobenzyl, chloropyridinylaminobenzyl, methylpyridinylaminobenzyl, dimethylpyridinylaminobenzyl, methoxypyridinylaminobenzyl, oxopyridinylaminobenzyl, oxopyrimidinylaminobenzyl, thioxopyrimidinylaminobenzyl, (chloro)-(methoxy)pyridazinylaminobenzyl, methylcinnolinylaminobenzyl, quinoxalinylaminobenzyl, methylchromenylaminobenzyl, benzofuryl, cyanobenzofuryl, methoxycarbonylbenzofuryl, dimethylaminocarbonylbenzofuryl, azetidinylcarbonylbenzofuryl, indolylmethyl, fluoroindolylmethyl, cyanoindolylmethyl, (cyano)(methyl)indolylmethyl, nitroindolylmethyl, methylindolylmethyl, oxazolinylindolylmethyl, triazolylindolylmethyl, methoxyindolylmethyl, (chloro)(methoxy)indolylmethyl, di(methoxy)indolylmethyl, difluoromethoxyindolylmethyl, trifluoromethoxyindolylmethyl, (chloro)(trifluoromethoxy)indolylmethyl, cyclobutyloxyindolylmethyl, cyclopropylmethoxyindolylmethyl, morpholinylethoxyindolylmethyl, methylenedioxyindolylmethyl, difluoromethylenedioxyindolylmethyl, azetidinylindolylmethyl, morpholinylindolylmethyl, acetylaminoindolylmethyl, acetylaminomethylindolylmethyl, methoxycarbonylaminoindolylmethyl, N-methoxycarbonyl-N-methylaminoindolylmethyl, methylsulphonylaminoindolylmethyl, acetylindolylmethyl, [acetyl oxime]indolylmethyl, [acetyl O-(methyl)oxime]-indolylmethyl, trifluoromethylcarbonylindolylmethyl, carboxylndolylmethyl, (carboxy)-(methyl)indolylmethyl, methoxycarbonylindolylmethyl, (methoxycarbonyl)(methyl)-indolylmethyl (chloro)(methoxycarbonyl)indolylmethyl, aminocarbonylindolylmethyl, (aminocarbonyl)(chloro)indolylmethyl, methylaminocarbonylindolylmethyl, (chloro)-(methylaminocarbonyl)indolylmethyl, (hydroxyethyl)aminocarbonylindolylmethyl, (dimethylaminoethyl)aminocarbonylindolylmethyl, (1-hydroxyprop-2-yl)aminocarbonylindolylmethyl, dimethylaminocarbonylindolylmethyl, (dimethylaminocarbonyl)(methyl)-indolylmethyl, (chloro)(dimethylaminocarbonyl)indolylmethyl, bis(dimethylaminocarbonyl)indolylmethyl, N-(cyanomethyl)-N-methylaminocarbonylindolylmethyl, [N-(cyanomethyl)-N-methylaminocarbonyl](methyl)indolylmethyl, N-(cyanoethyl)-N-methylaminocarbonylindolylmethyl, N-(hydroxyethyl)-N-methylaminocarbonylindolylmethyl, N-(methoxyethyl)-N-methylaminocarbonylindolylmethyl, [N-(methoxyethyl)-N-methylaminocarbonyl](methyl)indolylmethyl, N-(dimethylaminoethyl)-N-methylaminocarbonylindolylmethyl, N-isopropyl-N-methylaminocarbonylindolylmethyl, diethylaminocarbonylindolylmethyl, cyclopropylmethylaminocarbonylindolylmethyl, benzylaminocarbonylindolylmethyl, pyrazolylaminocarbonylindolylmethyl, pyridinylmethylaminocarbonylindolylmethyl, azetidinylcarbonylindolylmethyl, (azetidinylcarbonyl)(methyl)indolylmethyl, hydroxyazetidinylcarbonylindolylmethyl, aminoazetidinylcarbonylindolylmethyl, tert-butoxycarbonylaminoazetidinylcarbonylindolylmethyl, pyrrolidinylcarbonylindolylmethyl, methylpyrrolidinylcarbonylindolylmethyl, methoxymethylpyrrolidinylcarbonylindolylmethyl, dimethylaminopyrrolidinylcarbonyl indolylmethyl, thiazolidinylcarbonylindolylmethyl, oxothiazolidinylcarbonylindolylmethyl, piperidinylcarbonylindolylmethyl, methylpiperazinylcarbonylindolylmethyl, morpholinylcarbonylindolylmethyl, methylsulphonylindolylmethyl, methylsulphonylmethylindolylmethyl, dimethylaminosulphonylindolylmethyl, trimethylsilylindolylmethyl and pyrrolo[3,2-c]pyridinylmethyl.

Particular values of $R^{13}$ include hydrogen, bromobenzyl, pyridinylaminobenzyl, chloropyridinylaminobenzyl, dimethylpyridinylaminobenzyl, methoxypyridinylaminobenzyl, indolylmethyl, fluoroindolylmethyl, nitroindolylmethyl, difluoromethoxyindolylmethyl, trifluoromethoxyindolylmethyl, difluoromethylenedioxy-indolylmethyl, carboxyindolylmethyl, methoxycarbonyl-indolylmethyl, methylaminocarbonylindolylmethyl, (hydroxyethyl)aminocarbonyl-indolylmethyl, dimethylaminocarbonylindolylmethyl, N-hydroxyethyl-N-methylaminocarbonyl-indolylmethyl, benzylaminocarbonyl-indolylmethyl, azetidinylcarbonyl-indolylmethyl, piperidinylcarbonyl-indolylmethyl, methylpiperazinylcarbonyl-indolylmethyl and morpholinylcarbonyl-indolylmethyl.

One particular sub-group of the compounds of formula (IIA) is represented by the compounds of formula (IIB), and pharmaceutically acceptable salts and solvates thereof:

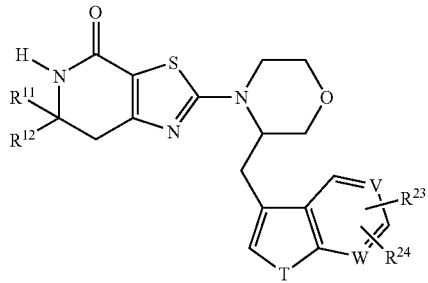

(IIB)

wherein
$R^{11}$ and $R^{12}$ are as defined above;
T represents oxygen or N—$R^{25}$;
V represents carbon or nitrogen;
W represents carbon or nitrogen;
$R^{23}$ represents hydrogen, halogen, cyano, nitro, $C_{1-6}$ alkyl, hydroxy($C_{1-6}$)alkyl, trifluoromethyl, aryl($C_{1-6}$)alkyl, oxazolinyl, triazolyl, hydroxy, $C_{1-6}$ alkoxy, difluoromethoxy, trifluoromethoxy, $C_{3-7}$ cycloalkoxy, $C_{3-7}$ cycloalkyl($C_{1-6}$)alkoxy, morpholinyl($C_{1-6}$)alkoxy, aryloxy, aryl($C_{1-6}$)alkoxy, $C_{1-6}$ alkylthio, $C_{1-6}$ alkylsulphinyl, arylsulphinyl, arylsulphonyl, $C_{1-6}$ alkylsulphonyloxy, amino, azetidinyl, morpholinyl, $C_{2-6}$ alkylcarbonylamino, $C_{2-6}$ alkylcarbonylaminomethyl, $C_{2-6}$ alkoxycarbonylamino, [($C_{2-6}$)alkoxycarbonyl][($C_{1-6}$)alkyl]amino, $C_{1-6}$ alkylsulphonylamino, $C_{2-6}$ alkylcarbonyl, $C_{2-6}$ alkylcarbonyl oxime, $C_{2-6}$ alkylcarbonyl O-(methyl) oxime, trifluoromethylcarbonyl, carboxy, $C_{2-6}$ alkoxycarbonyl, aminocarbonyl, $C_{1-6}$ alkylaminocarbonyl, [hydroxy($C_{1-6}$)-alkyl]aminocarbonyl, [di($C_{1-6}$)alkylamino($C_{1-6}$)alkyl]aminocarbonyl, di($C_{1-6}$)alkylaminocarbonyl, [($C_{1-6}$)alkyl][cyano($C_{1-6}$)alkyl]aminocarbonyl, [($C_{1-6}$)alkyl][hydroxy($C_{1-6}$)-alkyl]aminocarbonyl, [($C_{1-6}$)alkoxy($C_{1-6}$)alkyl][($C_{1-6}$)alkyl]aminocarbonyl, [di($C_{1-6}$)alkylamino($C_{1-6}$)alkyl][($C_{1-6}$)alkyl]aminocarbonyl, $C_{3-7}$ cycloalkyl($C_{1-6}$)alkylaminocarbonyl, aryl($C_{1-6}$)alkylaminocarbonyl, heteroarylaminocarbonyl, heteroaryl($C_{1-6}$)alkylaminocarbonyl, azetidinylcarbonyl, hydroxyazetidinylcarbonyl, aminoazetidinylcarbonyl, $C_{2-6}$ alkoxycarbonylaminoazetidinylcarbonyl, pyrrolidinylcarbonyl, ($C_{1-6}$)alkylpyrrolidinylcarbonyl, $C_{1-6}$ alkoxy($C_{1-6}$)alkylpyrrolidinylcarbonyl, di($C_{1-6}$)alkylaminopyrrolidinylcarbonyl, thiazolidinylcarbonyl, oxothiazolidinylcarbonyl, piperidinylcarbonyl, ($C_{1-6}$)-alkylpiperazinylcarbonyl, morpholinylcarbonyl, $C_{1-6}$ alkylsulphonyl, $C_{1-6}$ alkylsulphonylmethyl or di($C_{1-6}$)alkylaminosulphonyl; and $R^{24}$ represents hydrogen, halogen, $C_{1-6}$ alkoxy or di($C_{1-6}$)alkylaminocarbonyl; or $R^{23}$ and $R^{24}$, when situated on adjacent carbon atoms, together represent methylenedioxy or difluoromethylenedioxy; and $R^{25}$ represents hydrogen or $C_{1-6}$ alkyl.

The present invention also provides a compound of formula (IIB) as depicted above, or a pharmaceutically acceptable salt or solvate thereof, wherein
$R^{11}$, $R^{12}$ and W are as defined above;
T represents NH;
V represents carbon;
$R^{23}$ represents hydrogen, halogen, cyano, nitro, $C_{1-6}$ alkyl, hydroxy($C_{1-6}$)alkyl, trifluoromethyl, aryl($C_{1-6}$)alkyl, hydroxy, $C_{1-6}$ alkoxy, difluoromethoxy, trifluoromethoxy, aryloxy, aryl($C_{1-6}$)alkoxy, $C_{1-6}$ alkylthio, $C_{1-6}$ alkylsulphinyl, arylsulphinyl, arylsulphonyl, $C_{1-6}$ alkylsulphonyloxy, amino, $C_{2-6}$ alkylcarbonylamino, $C_{1-6}$ alkylsulphonylamino, $C_{2-6}$ alkylcarbonyl, carboxy, $C_{2-6}$ alkoxycarbonyl, aminocarbonyl, $C_{1-6}$ alkylaminocarbonyl, [hydroxy($C_{1-6}$)alkyl]aminocarbonyl, di($C_{1-6}$)alkylaminocarbonyl, [($C_{1-6}$)alkyl][hydroxy-($C_{1-6}$)alkyl]aminocarbonyl, aryl($C_{1-6}$)alkylaminocarbonyl, azetidinylcarbonyl, pyrrolidinylcarbonyl, piperidinylcarbonyl, ($C_{1-6}$)alkylpiperazinylcarbonyl or morpholinylcarbonyl; and $R^{24}$ represents hydrogen.

The present invention further provides a compound of formula (IIB) as depicted above, or a pharmaceutically acceptable salt or solvate thereof, wherein
$R^{11}$, $R^{12}$ and W are as defined above;
T represents NH;
V represents carbon;
$R^{23}$ represents hydrogen, halogen, cyano, $C_{1-6}$ alkyl, hydroxy($C_{1-6}$)alkyl, trifluoromethyl, aryl($C_{1-6}$)alkyl, hydroxy, $C_{1-6}$ alkoxy, trifluoromethoxy, aryloxy, aryl($C_{1-6}$)alkoxy, $C_{1-6}$ alkylthio, $C_{1-6}$ alkylsulphinyl, arylsulphinyl, arylsulphonyl, $C_{1-6}$ alkylsulphonyloxy, amino, $C_{2-6}$ alkylcarbonylamino, $C_{1-6}$ alkylsulphonylamino, $C_{2-6}$ alkylcarbonyl or aminocarbonyl; and $R^{24}$ represents hydrogen.

In a preferred embodiment, T is N—$R^{25}$. In another embodiment, T is oxygen.

In a preferred embodiment, V is carbon. In another embodiment, V is nitrogen.

In a preferred embodiment, W is carbon. In another embodiment, W is nitrogen.

Particular values of $R^{23}$ include hydrogen, halogen, cyano, nitro, oxazolinyl, triazolyl, $C_{1-6}$ alkoxy, difluoromethoxy, trifluoromethoxy, $C_{3-7}$ cycloalkoxy, $C_{3-7}$ cycloalkyl($C_{1-6}$)alkoxy, morpholinyl($C_{1-6}$)alkoxy, azetidinyl, morpholinyl, $C_{2-6}$ alkylcarbonylamino, $C_{2-6}$ alkylcarbonylaminomethyl, $C_{2-6}$ alkoxycarbonylamino, [($C_{2-6}$)alkoxycarbonyl][($C_{1-6}$)alkyl]amino, $C_{1-6}$ alkylsulphonylamino, $C_{2-6}$ alkylcarbonyl, $C_{2-6}$ alkylcarbonyl oxime, $C_{2-6}$ alkylcarbonyl O-(methyl)

oxime, trifluoromethylcarbonyl, carboxy, $C_{2-6}$ alkoxycarbonyl, aminocarbonyl, $C_{1-6}$ alkylaminocarbonyl, [hydroxy($C_{1-6}$)-alkyl]aminocarbonyl, [di($C_{1-6}$)alkylamino($C_{1-6}$)alkyl]aminocarbonyl, di($C_{1-6}$)alkylaminocarbonyl, [($C_{1-6}$)alkyl][cyano($C_{1-6}$)alkyl]aminocarbonyl, [($C_{1-6}$)alkyl][hydroxy($C_{1-6}$)-alkyl]aminocarbonyl, [($C_{1-6}$)alkoxy($C_{1-6}$)alkyl][($C_{1-6}$)alkyl]aminocarbonyl, [di($C_{1-6}$)alkylamino($C_{1-6}$)alkyl][($C_{1-6}$)alkyl]aminocarbonyl, $C_{3-7}$ cycloalkyl($C_{1-6}$)alkylaminocarbonyl, aryl($C_{1-6}$)alkylaminocarbonyl, heteroarylaminocarbonyl, heteroaryl($C_{1-6}$)alkylaminocarbonyl, azetidinylcarbonyl, hydroxyazetidinylcarbonyl, aminoazetidinylcarbonyl, $C_{2-6}$ alkoxycarbonylaminoazetidinylcarbonyl, pyrrolidinylcarbonyl, ($C_{1-6}$)alkylpyrrolidinylcarbonyl, $C_{1-6}$ alkoxy($C_{1-6}$)alkylpyrrolidinylcarbonyl, di($C_{1-6}$)alkylaminopyrrolidinylcarbonyl, thiazolidinylcarbonyl, oxothiazolidinylcarbonyl, piperidinylcarbonyl, ($C_{1-6}$)-alkylpiperazinylcarbonyl, morpholinylcarbonyl, $C_{1-6}$ alkylsulphonyl, $C_{1-6}$ alkylsulphonylmethyl and di($C_{1-6}$)alkylaminosulphonyl.

Typical values of $R^{23}$ include hydrogen, halogen, nitro, difluoromethoxy, trifluoromethoxy, carboxy, $C_{2-6}$ alkoxycarbonyl, alkylaminocarbonyl, [hydroxy-($C_{1-6}$)alkyl]aminocarbonyl, di($C_{1-6}$)alkylaminocarbonyl, [($C_{1-6}$)alkyl][hydroxy($C_{1-6}$)alkyl]-aminocarbonyl, aryl($C_{1-6}$)alkylaminocarbonyl, azetidinylcarbonyl, piperidinylcarbonyl, ($C_{1-6}$)alkylpiperazinylcarbonyl and morpholinylcarbonyl.

Suitable values of $R^{23}$ include hydrogen, $C_{1-6}$ alkyl, hydroxy, aryl($C_{1-6}$)alkoxy and $C_{1-6}$ alkylsulphonyloxy.

Illustrative values of $R^{23}$ include hydrogen, fluoro, chloro, bromo, cyano, nitro, methyl, hydroxymethyl, trifluoromethyl, benzyl, hydroxy, methoxy, ethoxy, difluoromethoxy, trifluoromethoxy, phenoxy, benzyloxy, methylthio, methylsulphinyl, phenylsulphinyl, phenylsulphonyl, methylsulphonyloxy, amino, acetylamino, methylsulphonylamino, acetyl, carboxy, methoxycarbonyl, aminocarbonyl, methylaminocarbonyl, (hydroxyethyl)aminocarbonyl, dimethylaminocarbonyl, N-(hydroxyethyl)-N-methylaminocarbonyl, benzylaminocarbonyl, azetidinylcarbonyl, pyrrolidinylcarbonyl, piperidinylcarbonyl, methylpiperazinylcarbonyl and morpholinylcarbonyl.

Specific values of $R^{23}$ include hydrogen, fluoro, chloro, bromo, cyano, methyl, hydroxymethyl, trifluoromethyl, benzyl, hydroxy, methoxy, ethoxy, trifluoromethoxy, phenoxy, benzyloxy, methylthio, methylsulphinyl, phenylsulphinyl, phenylsulphonyl, methylsulphonyloxy, amino, acetylamino, methylsulphonylamino, acetyl and aminocarbonyl; especially hydrogen, methyl, hydroxy, benzyloxy or methylsulphonyloxy.

Definitive values of $R^{23}$ include hydrogen, fluoro, chloro, cyano, nitro, oxazolinyl, triazolyl, methoxy, difluoromethoxy, trifluoromethoxy, cyclobutyloxy, cyclopropylmethoxy, morpholinylethoxy, azetidinyl, morpholinyl, acetylamino, acetylaminomethyl, methoxycarbonylamino, N-methoxycarbonyl-N-methylamino, methylsulphonylamino, acetyl, acetyl oxime, acetyl O-(methyl)oxime, trifluoromethylcarbonyl, carboxy, methoxycarbonyl, aminocarbonyl, methylaminocarbonyl, (hydroxyethyl)aminocarbonyl, (dimethylaminoethyl)aminocarbonyl, (1-hydroxyprop-2-yl)aminocarbonyl, dimethylaminocarbonyl, N-(cyanomethyl)-N-methylaminocarbonyl, N-(cyanoethyl)-N-methylaminocarbonyl, N-(hydroxyethyl)-N-methylaminocarbonyl, N-(methoxyethyl)-N-methylaminocarbonyl, N-(dimethylaminoethyl)-N-methylaminocarbonyl, N-isopropyl-N-methylaminocarbonyl, diethylaminocarbonyl, cyclopropylmethylaminocarbonyl, benzylaminocarbonyl, pyrazolylaminocarbonyl, pyridinylmethylaminocarbonyl, azetidinylcarbonyl, hydroxyazetidinylcarbonyl, aminoazetidinylcarbonyl, tert-butoxycarbonylaminoazetidinylcarbonyl, pyrrolidinylcarbonyl, methylpyrrolidinylcarbonyl, methoxymethylpyrrolidinylcarbonyl, dimethylaminopyrrolidinylcarbonyl, thiazolidinylcarbonyl, oxothiazolidinylcarbonyl, piperidinylcarbonyl, methylpiperazinylcarbonyl, morpholinylcarbonyl, methylsulphonyl, methylsulphonylmethyl and dimethylaminosulphonyl.

Selected values of $R^{23}$ include hydrogen, fluoro, nitro, difluoromethoxy, trifluoromethoxy, carboxy, methoxycarbonyl, methylaminocarbonyl, (hydroxyethyl)-aminocarbonyl, dimethylaminocarbonyl, N-(hydroxyethyl)-N-methylaminocarbonyl, benzylaminocarbonyl, azetidinylcarbonyl, piperidinylcarbonyl, methylpiperazinylcarbonyl and morpholinylcarbonyl.

A particular value of $R^{23}$ is hydrogen.

Definitive values of $R^{24}$ include hydrogen, chloro, methoxy and dimethylaminocarbonyl. A particular value of $R^{24}$ is hydrogen.

In one embodiment, $R^{25}$ is hydrogen. In another embodiment, $R^{25}$ is $C_{1-6}$ alkyl, especially methyl.

Another particular sub-group of the compounds of formula (IIA) is represented by the compounds of formula (IIC), and pharmaceutically acceptable salts and solvates thereof:

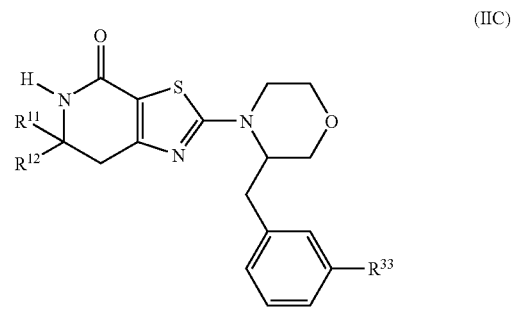

(IIC)

wherein
$R^{11}$ and $R^{12}$ are as defined above;
$R^{33}$ represents halogen or —$NHR^{34}$; or aryl or heteroaryl, either of which groups may be optionally substituted by one or more substituents; and
$R^{34}$ represents methylenedioxyphenyl, morpholinyl($C_{1-6}$)alkylphenyl, oxazolinylphenyl, [($C_{1-6}$)alkyl](oxo)pyrazolylphenyl, oxazolylphenyl, isoxazolylphenyl, triazolylphenyl, ($C_{1-6}$)alkyltriazolylphenyl, ($C_{1-6}$)alkylpyrimidinylphenyl, pyrazolyl($C_{1-6}$)alkylphenyl, triazolyl($C_{1-6}$)alkylphenyl, $C_{1-6}$ alkylsulphonylaminophenyl, morpholinylcarbonylphenyl, $C_{1-6}$ alkylsulphonylphenyl, morpholinylsulphonylphenyl, dihydrobenzofuranyl, $C_{1-6}$ alkylsulphonylindolinyl, chrontanonyl, dihydroquinolinonyl, benzoxazinonyl, benzothienyl, indolyl, dioxoindolyl, [($C_{1-6}$)alkyl](halo)pyrazolyl, tri($C_{1-6}$)alkylpyrazolyl, ($C_{1-6}$)alkylindazolyl, benzoxazolyl, benzoxazolonyl, di($C_{1-6}$)alkylisoxazolyl, benzothiazolyl, ($C_{1-6}$)alkylisothiazolyl, ($C_{1-6}$)alkylbenzimidazolyl, benzimidazolonyl, di($C_{1-6}$)alkylbenzimidazolonyl, ($C_{1-6}$)alkyloxadiazolyl, furyloxadiazolyl, pyridinyl, halopyridinyl, ($C_{1-6}$)alkylpyridinyl, di($C_{1-6}$)alkylpyridinyl, ($C_{1-6}$)alkoxypyridinyl, oxopyridinyl, oxopyrimidinyl, thioxopyrimidinyl, [($C_{1-6}$)alkoxy](halo)pyridazinyl, ($C_{1-6}$)alkylcinnolinyl, quinoxalinyl or ($C_{1-6}$)alkylchromenyl.

Suitably, $R^{33}$ represents halogen or —$NHR^{34}$, in which $R^{34}$ is as defined above. In one embodiment, $R^{33}$ represents halogen, especially bromo. In another embodiment, $R^{33}$ represents —$NHR^{34}$, in which $R^{34}$ is as defined above.

In one embodiment, $R^{33}$ represents unsubstituted or substituted aryl. In another embodiment, $R^{33}$ represents unsubstituted or substituted heteroaryl.

Typical values of $R^{34}$ include pyridinyl, halopyridinyl, $(C_{1-6})$alkylpyridinyl, di$(C_{1-6})$alkylpyridinyl and $(C_{1-6})$alkoxypyridinyl.

Definitive values of $R^{34}$ include methylenedioxyphenyl, morpholinylmethylphenyl, oxazolinylphenyl, (methyl)(oxo)pyrazolylphenyl, oxazolylphenyl, isoxazolylphenyl, triazolylphenyl, methyltriazolylphenyl, methylpyrimidinylphenyl, pyrazolylmethylphenyl, triazolylmethylphenyl, methylsulphonylaminophenyl, morpholinylcarbonylphenyl, methylsulphonylphenyl, morpholinylsulphonylphenyl, dihydrobenzofuranyl, methylsulphonylindolinyl, chromanonyl, dihydroquinolinonyl, benzoxazinonyl, benzothienyl, indolyl, dioxoindolyl, (bromo)(methyl)pyrazolyl, trimethylpyrazolyl, methylindazolyl, benzoxazolyl, benzoxazolonyl, dimethylisoxazolyl, benzothiazolyl, methylisothiazolyl, methylbenzimidazolyl, benzimidazolonyl, dimethylbenzimidazolonyl, methyloxadiazolyl, furyloxadiazolyl, pyridinyl, chloropyridinyl, methylpyridinyl, dimethylpyridinyl, methoxypyridinyl, oxopyridinyl, oxopyrimidinyl, thioxopyrimidinyl, (chloro)(methoxy)pyridazinyl, methylcinnolinyl, quinoxalinyl and methylchromenyl.

Suitable values of $R^{34}$ include pyridinyl, chloropyridinyl, methylpyridinyl, dimethylpyridinyl and methoxypyridinyl.

Illustratively, $R^{33}$ represents halogen or —$NHR^{34}$, in which $R^{34}$ is as defined above. Additionally, $R^{33}$ represents phenyl, naphthyl, benzofuryl, thienyl, benzothienyl, indolyl, isoxazolyl, pyrazolyl, pyridinyl or pyrimidinyl, any of which groups may be optionally substituted by one or more substituents.

Selected examples of suitable substituents on $R^{33}$ include halogen, cyano, $C_{1-6}$ alkyl, hydroxy$(C_{1-6})$alkyl, trifluoromethyl, $C_{1-6}$ alkoxy, trifluoromethoxy, aryloxy, methylenedioxy, $C_{1-6}$ alkylthio, arylsulphonyl, amino, $C_{2-6}$ alkylcarbonylamino, $C_{1-6}$ alkylsulphonylamino, $C_{2-6}$ alkylcarbonyl and aminocarbonyl.

Selected examples of representative substituents on $R^{33}$ include fluoro, chloro, bromo, cyano, methyl, hydroxymethyl, trifluoromethyl, methoxy, ethoxy, trifluoromethoxy, phenoxy, methylenedioxy, methylthio, phenylsulphonyl, amino, acetylamino, methylsulphonylamino, acetyl and aminocarbonyl.

Specific values of $R^{33}$ include bromo, pyridinylamino, chloropyridinylamino, methylpyridinylamino, dimethylpyridinylamino, methoxypyridinylamino, phenyl, fluorophenyl, difluorophenyl, chlorophenyl, dichlorophenyl, bromophenyl, cyanophenyl, methylphenyl, (fluoro)(methyl)phenyl, dimethylphenyl, hydroxymethylphenyl, trifluoromethylphenyl, bis(trifluoromethyl)phenyl, methoxyphenyl, dimethoxyphenyl, ethoxyphenyl, methylenedioxyphenyl, trifluoromethoxyphenyl, phenoxyphenyl, methylthiophenyl, aminophenyl, acetylamino-phenyl, methylsulphonylaminophenyl, acetylphenyl, aminocarbonylphenyl, naphthyl, benzofuryl, thienyl, methylthienyl, acetylthienyl, benzothienyl, phenylsulphonylindolyl, dimethylisoxazolyl, methylpyrazolyl, benzylpyrazolyl, pyridinyl, fluoropyridinyl, chloropyridinyl, methoxypyridinyl and pyrimidinylbenzyl.

Definitive values of $R^{33}$ include bromo, methylenedioxyphenylamino, morpholinylmethylphenylamino, oxazolinylphenylamino, (methyl)(oxo)pyrazolylphenylamino, oxazolylphenylamino, isoxazolylphenylamino, triazolylphenylamino, methyltriazolylphenylamino, methylpyrimidinylphenylamino, pyrazolylmethylphenylamino, triazolylmethylphenylamino, methylsulphonylaminophenylamino, morpholinylcarbonylphenylamino, methylsulphonylphenylamino, morpholinylsulphonylphenylamino, dihydrobenzofuranylamino, methylsulphonylindolinylamino, chromanonylamino, dihydroquinolinonylamino, benzoxazinonylamino, benzothienylamino, indolylamino, dioxoindolylamino, (bromo)(methyl)pyrazolylamino, trimethylpyrazolylamino, methylindazolylamino, benzoxazolylamino, benzoxazolonylamino, dimethylisoxazolylamino, benzothiazolylamino, methylisothiazolylamino, methylbenzimidazolylamino, benzimidazolonylamino, dimethylbenzimidazolonylamino, methyloxadiazolylamino, furyloxadiazolylamino, pyridinylamino, chloropyridinylamino, methylpyridinylamino, dimethylpyridinylamino, methoxypyridinylamino, oxopyridinylamino, oxopyrimidinylamino, thioxopyrimidinylamino, (chloro)(methoxy)pyridazinylamino, methylcinnolinylamino, quinoxalinylamino and methylchromenylamino.

Particular values of $R^{33}$ include bromo, pyridinylamino, chloropyridinylamino, dimethylpyridinylamino and methoxypyridinylamino.

Other sub-classes of compounds according to the invention are represented by the compounds of formula (IID-1) and (IID-2), and pharmaceutically acceptable salts and solvates thereof:

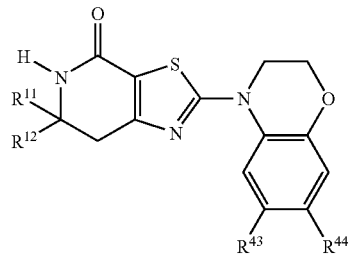

(IID-1)

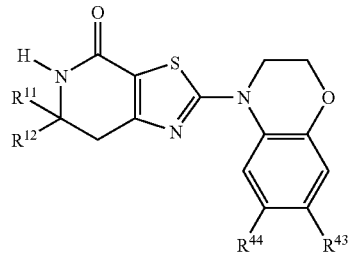

(IID-2)

wherein $R^{11}$ and $R^{12}$ are as defined above;

$R^{43}$ represents hydrogen, halogen, nitro, $C_{1-6}$ alkyl, $C_{2-6}$ alkenyl, $C_{3-7}$ cycloalkyl, $(C_{1-6})$alkylaryl, di$(C_{1-6})$alkylaryl, piperidinyl$(C_{1-6})$alkylaryl, piperazinyl$(C_{1-6})$alkylaryl, $(C_{1-6})$alkylpiperazinyl$(C_{1-6})$alkylaryl, morpholinyl$(C_{1-6})$alkylaryl, $(C_{1-6})$alkoxyaryl, cyano$(C_{1-6})$alkoxyaryl, di$(C_{1-6})$alkylamino$(C_{1-6})$alkylaryl, $(C_{1-6})$alkylaminocarbonylaryl, aryl$(C_{1-6})$alkyl, haloarylpyrrolidinyl, dioxopyrrolidinyl, aminopyrrolidinyl, di$(C_{1-6})$alkylaminopyrrolidinyl, indolinyl, oxoindolinyl, arylpiperidinyl, arylcarbonylpiperidinyl, di-$(C_{1-6})$alkylaminocarbonylpiperidinyl, piperazinyl, $(C_{1-6})$alkylpiperazinyl, haloarylpiperazinyl, pyridinylpiperazinyl, furoylpiperazinyl, homopiperazinyl, $(C_{1-6})$alkylhomopiperazinyl, $(C_{1-6})$alkylpiperazinyl$(C_{1-6})$alkyl, morpholinyl$(C_{1-6})$alkyl, benzofuryl, benzothienyl, pyrazolyl, $(C_{1-6})$alkylpyrazolyl, di$(C_{1-6})$alkylpyrazolyl, tri$(C_{1-6})$alkylpyrazolyl, [di (C₁₋₆)alkyl](trifluoromethyl)pyrazolyl, cyano(C₁₋₆)alkylpyrazolyl, [cyano-(C₁₋₆)alkyl][di(C₁₋₆)alkyl]pyrazolyl, hydroxy(C₁₋₆)alkylpyrazolyl, [hydroxy(C₁₋₆)-alkyl][di(C₁₋₆)alkyl]pyrazolyl, methoxy(C₁₋₆)alkylpyrazolyl, [(hydroxy)(methoxy)(C₁₋₆)-alkyl]pyrazolyl, amino(C₁₋₆)alkylpyrazolyl, [(C₁₋₆)alkyl][amino(C₁₋₆)alkyl]pyrazolyl, [amino(C₁₋₆)alkyl][di(C₁₋₆)alkyl]pyrazolyl, di(C₁₋₆)alkylamino(C₁₋₆)alkylpyrazolyl, di(C₁₋₆)alkoxyphosphono(C₁₋₆)alkylpyrazolyl, (C₂₋₆)alkenylpyrazolyl, (C₃₋₇)cycloalkyl-(C₁₋₆)alkylpyrazolyl, [(C₃₋₇)cycloalkyl(C₁₋₆)alkyl][di(C₁₋₆)alkyl]pyrazolyl, [(C₁₋₆)alkyl]-(aryl)pyrazolyl, (aryl)(trifluoromethyl)pyrazolyl, aryl(C₁₋₆)alkylpyrazolyl, aminoaryl-(C₁₋₆)alkylpyrazolyl, piperidinylpyrazolyl, tetrahydropyranyl(C₁₋₆)alkylpyrazolyl, [di-(C₁₋₆)alkyl][tetrahydropyranyl(C₁₋₆)alkyl]pyrazolyl, pyrrolidinyl(C₁₋₆)alkylpyrazolyl, piperidinyl(C₁₋₆)alkylpyrazolyl, (C₁₋₆)alkylpiperidinyl(C₁₋₆)alkylpyrazolyl, morpholinyl(C₁₋₆)alkylpyrazolyl, pyridinyl(C₁₋₆)alkylpyrazolyl, oxypyridinyl(C₁₋₆)alkylpyrazolyl, [arylcarbonyl(C₁₋₆)alkyl][di(C₁₋₆)alkyl]pyrazolyl, [(C₁₋₆)alkyl](piperazinylcarbonyl)pyrazolyl, [(C₁₋₆)alkylaminocarbonyl][(C₁₋₆)alkylaryl]pyrazolyl, [(C₁₋₆)alkyl]-[amino(C₁₋₆)alkylaminocarbonyl]pyrazolyl, aminocarbonyl(C₁₋₆)alkylpyrazolyl, [aminocarbonyl(C₁₋₆)alkyl][di(C₁₋₆)alkyl]pyrazolyl, di(C₁₋₆)alkylaminocarbonyl(C₁₋₆)alkylpyrazolyl, pyrazolo[1,5-a]pyridinyl, di(C₁₋₆)alkylisoxazolyl, (amino)[(C₁₋₆)alkyl]isoxazolyl, thiazolyl, di(C₁₋₆)alkylthiazolyl, imidazolyl, imidazo[1,2-a]pyridinyl, (C₁₋₆)alkylimidazo[1,2-a]pyridinyl, (C₁₋₆)-alkylimidazo[4,5-b]pyridinyl, imidazo[1,2-a]pyrimidinyl, imidazo[1,2-a]pyrazinyl, (C₁₋₆)-alkylthiadiazolyl, pyridinyl, halopyridinyl, (C₁₋₆)alkyl-pyridinyl, [(C₁₋₆)alkyl](halo)-pyridinyl, di(C₁₋₆)alkylpyridinyl, (C₂₋₆)alkenylpyridinyl, (C₁₋₆)alkylpiperazinylpyridinyl, [(C₁₋₆)alkyl](piperazinyl)pyridinyl, [(C₁₋₆)alkoxycarbonylpiperazinyl][(C₁₋₆)alkyl]-pyridinyl, piperidinyl(C₁₋₆)alkylpyridinyl, [(C₁₋₆)alkyl](oxy)pyridinyl, hydroxypyridinyl, hydroxy(C₁₋₆)alkylpyridinyl, (C₁₋₆)alkoxypyridinyl, [(C₁₋₆)alkoxy][(C₁₋₆)alkyl]pyridinyl, [(C₁₋₆)alkoxy][di(C₁₋₆)alkyl]pyridinyl, (C₁₋₆)alkoxy(C₁₋₆)alkylpyridinyl, aminopyridinyl, carboxy(C₁₋₆)alkylpyridinyl, (C₁₋₆)alkoxycarbonyl(C₁₋₆)alkylpyridinyl, pyridazinyl, (C₁₋₆)-alkylpyridazinyl, piperidinylpyridazinyl, oxypyridazinyl, (C₁₋₆)alkoxypyridazinyl, aminopyridazinyl, hydroxy(C₁₋₆)alkylaminopyridazinyl, di(C₁₋₆)alkylaminopyridazinyl, pyrimidinyl, (C₁₋₆)alkylpyrimidinyl, [(C₁₋₆)alkyl](halo)pyrimidinyl, di(C₁₋₆)alkylpyrimidinyl, pyrrolidinylpyrimidinyl, (C₁₋₆)alkylpiperazinylpyrimidinyl, [(C₁₋₆)alkyl](piperazinyl)pyrimidinyl, [(C₁₋₆)alkoxycarbonyl][(C₁₋₆)alkyl]piperazinylpyrimidinyl, hydroxypyrimidinyl, [(C₁₋₆)alkyl](hydroxy)pyrimidinyl, [(C₁₋₆)alkyl]-[hydroxy(C₁₋₆)alkyl]pyrimidinyl, [(C₁₋₆)alkyl][hydroxy(C₂₋₆)alkynyl]pyrimidinyl, (C₁₋₆)-alkoxypyrimidinyl, aminopyrimidinyl, di(C₁₋₆)alkylaminopyrimidinyl, [di(C₁₋₆)alkylamino](halo)pyrimidinyl, carboxypyrimidinyl, [(C₁₋₆)alkoxycarbonyl(C₁₋₆)alkyl][(C₁₋₆)-alkyl]pyrimidinyl, aminocarbonylpyrimidinyl, pyrazinyl, (C₁₋₆)alkoxypyrazinyl, aminopyrazinyl, hydroxy, (C₁₋₆)alkoxy, aryl(C₁₋₆)alkoxycarbonylpiperidinyloxy, morpholinyl-(C₁₋₆)alkoxy, aryloxy, haloaryloxy, di(C₁₋₆)alkylpyrazolyloxy, halopyridinyloxy, pyrrolidinylpyridinyloxy, (C₁₋₆)alkylpiperazinylpyridinyloxy, (C₁₋₆)alkylpyrazolylpyridinyloxy, (C₁₋₆)alkylaminopyridinyloxy, carboxypyridinyloxy, aminocarbonylpyridinyloxy, (C₁₋₆)alkylpyridazinyloxy, pyrimidinyloxy, (C₁₋₆)alkylpyrimidinyloxy, [(C₁₋₆)alkyl](halo)pyrimidinyloxy, hydroxy(C₁₋₆)alkyl, dihydroxy(C₁₋₆)alkyl, pyridinyloxy(C₁₋₆)alkyl, amino, (C₁₋₆)alkylamino, dihydroxy(C₁₋₆)alkylamino, (C₁₋₆)-alkoxy(C₁₋₆)alkylamino, N—[(C₁₋₆)alkoxy(C₁₋₆)alkyl]-N—[(C₁₋₆)alkyl]amino, di(C₁₋₆)-alkylamino(C₁₋₆)alkylamino, N—[(C₁₋₆)alkyl]-N-[di(C₁₋₆)alkylamino(C₁₋₆)alkyl]amino, N—[(C₁₋₆)alkyl]-N—[(C₃₋₇)cycloalkyl]amino, haloarylamino, N—[(C₁₋₆)alkyl]-N-(haloaryl)amino, N—[(C₁₋₆)alkyl]-N-[aryl(C₁₋₆)alkyl]amino, N-[di(C₁₋₆)alkylamino(C₁₋₆)alkyl]-N-[aryl(C₁₋₆)-alkyl]amino, cyanoaryl(C₁₋₆)alkylamino, (cyano)(halo)aryl(C₁₋₆)alkylamino, methylenedioxyaryl(C₁₋₆)alkylamino, N—[(C₁₋₆)alkyl]-N—[(C₁₋₆)alkylpyrrolidinyl]amino, piperidinylamino, N—[(C₁₋₆)alkyl]-N-(piperidinyl)amino, N—[(C₃₋₇)cycloalkyl(C₁₋₆)alkyl]-N-(piperidinyl)amino, (C₁₋₆)alkylpiperidinylamino, N—[(C₁₋₆)alkyl]-N—[(C₁₋₆)alkylpiperidinyl]amino, N—[(C₁₋₆)alkyl]-N—[(C₃₋₇)cycloalkylpiperidinyl]amino, N—[(C₁₋₆)alkyl]-N—[(C₂₋₆)alkylcarbonylpiperidinyl]amino, pyrrolidinyl(C₁₋₆)alkylamino, N—[(C₁₋₆)alkyl]-N-[pyrrolidinyl(C₁₋₆)alkyl]amino, N—[(C₁₋₆)alkyl]-N-[piperidinyl(C₁₋₆)alkyl]amino, (C₁₋₆)-alkylpyrazolylamino, di(C₁₋₆)alkylpyrazolylamino, tri(C₁₋₆)alkylpyrazolylamino, N—[(C₁₋₆)-alkyl]-N—[(C₁₋₆)alkylpyrazolyl]amino, thiazolylamino, imidazolylamino, [(C₁₋₆)alkoxycarbonyl][(C₁₋₆)alkyl]imidazolylamino, (C₁₋₆)alkylthiadiazolylamino, pyridinylamino, halopyridinylamino, (C₁₋₆)alkylpyridinylamino, di(C₁₋₆)alkylpyridinylamino, trifluoromethylpyridinylamino, hydroxypyridinylamino, hydroxy(C₁₋₆)alkylpyridinylamino, dihydroxy(C₁₋₆)alkylpyridinylamino, (C₁₋₆)alkoxypyridinylamino, dihydroxy(C₁₋₆)alkoxypridinylamino, di(C₁₋₆)alkyldioxolanyl(C₁₋₆)alkoxypyridinylamino, (C₁₋₆)alkoxy(C₁₋₆)-alkylpyridinylamino, (C₁₋₆)alkoxy(C₂₋₆)alkenylpyridinylamino, dihydroxy(C₁₋₆)alkylaminopyridinylamino, di(C₁₋₆)alkylaminopyridinylamino, (C₁₋₆)alkylamino(C₁₋₆)alkylpyridinylamino, di(C₁₋₆)alkylamino(C₁₋₆)alkylpyridinylamino, carboxypyridinylamino, N—[(C₁₋₆)alkyl]-N—[(C₁₋₆)alkylpyridinyl]amino, bis[(C₁₋₆)alkylpyridinyl]amino, bis(trifluoromethylpyridinyl)amino, isoquinolinylamino, (C₁₋₆)alkylpyridazinylamino, N—[(C₁₋₆)alkyl]-N—[(C₁₋₆)alkylpyridazinyl]amino, N-[aryl(C₁₋₆)alkyl]-N—[(C₁₋₆)alkylpyridazinyl]amino, di(C₁₋₆)alkylpyridazinylamino, arylpyridazinylamino, piperidinylpyridazinylamino, (C₁₋₆)-alkoxypyridazinylamino, di(C₁₋₆)alkylaminopyridazinylamino, bis[(C₁₋₆)alkylpyridazinyl]-amino, benzofuryl(C₁₋₆)alkylamino, thienyl(C₁₋₆)alkylamino, indolyl(C₁₋₆)alkylamino, (C₁₋₆)alkylpyrazolyl(C₁₋₆)alkylamino, [di(C₁₋₆)alkyl](halo)pyrazolyl(C₁₋₆)alkylamino, di(C₁₋₆)alkylisoxazolyl(C₁₋₆)alkylamino, thiazolyl(C₁₋₆)alkylamino, imidazolyl(C₁₋₆)alkylamino, (C₁₋₆)alkylimidazolyl(C₁₋₆)alkylamino, pyridinyl(C₁₋₆)alkylamino, (C₁₋₆)alkylpyridinyl(C₁₋₆)alkylamino, N—[(C₁₋₆)alkyl]-N-[pyridinyl(C₁₋₆)alkyl]amino, N-[dihydroxy-(C₁₋₆)alkyl]-N-[pyridinyl(C₁₋₆)alkyl]amino, N—[(C₁₋₆)alkylpyridinyl(C₁₋₆)alkyl]-N-[dihydroxy(C₁₋₆)alkyl]amino, amino(C₁₋₆)alkyl, (C₁₋₆)alkylamino(C₁₋₆)alkyl, di(C₁₋₆)alkylamino(C₁₋₆)alkyl, pyridinylamino(C₁₋₆)alkyl, N—[(C₂₋₆)alkylcarbonyl]-N—[(C₁₋₆)alkylpyridinyl(C₁₋₆)alkyl]amino, di(C₁₋₆)alkylamino(C₁₋₆)alkylcarbonylamino, (C₃₋₇)cycloalkylcarbonylamino, (C₁₋₆)alkylpiperidinylcarbonylamino, (C₁₋₆)alkylimidazolylcarbonylamino, formyl, C₂₋₆ alkylcarbonyl, (C₁₋₆)alkylpiperidinylaminocarbonyl, N—[(C₁₋₆)alkyl]-N—[(C₁₋₆)-alkylpiperidinyl]aminocarbonyl, piperidinyl(C₁₋₆)alkylaminocarbonyl, (C₁₋₆)alkylpiperazinylcarbonyl, C₁₋₆ alkylthio, C₁₋₆ alkylsulphinyl, C₁₋₆ alkylsulphonyl, C₂₋₆ alkoxycarbonyloxy or tetra(C₁₋₆)alkyldioxaborolanyl; and R⁴⁴ represents hydrogen, halogen, C₁₋₆ alkyl or C₁₋₆ alkoxy.

The present invention also provides a compound of formula (IID-1) as depicted above, or a pharmaceutically acceptable salt or solvate thereof, wherein $R^{11}$ and $R^{12}$ are as defined above;

$R^{43}$ represents hydrogen, halogen, nitro, hydroxy($C_{1-6}$)alkyl, pyrazolyl, ($C_{1-6}$)alkylpyrazolyl, di($C_{1-6}$)alkylpyrazolyl, aryl($C_{1-6}$)alkylpyrazolyl, morpholinyl-($C_{1-6}$)alkylpyrazolyl, imidazolyl, ($C_{1-6}$)alkylimidazolyl, pyridinyl, ($C_{1-6}$)alkylpyridinyl, pyrimidinyl, hydroxy, pyridinyloxy ($C_{1-6}$)alkyl, amino, pyridinylamino, halopyridinylamino, ($C_{1-6}$)alkylpyridinylamino, di($C_{1-6}$)alkylpyridinylamino, ($C_{1-6}$)alkoxypyridinylamino, amino($C_{1-6}$)alkyl, ($C_{1-6}$)alkylamino($C_{1-6}$)alkyl, di($C_{1-6}$)alkylamino-($C_{1-6}$)alkyl, pyridinylamino($C_{1-6}$)alkyl, ($C_{1-6}$)alkylpiperazinyl($C_{1-6}$)alkyl, morpholinyl-($C_{1-6}$)alkyl, formyl or $C_{2-6}$ alkoxycarbonyloxy; and $R^{44}$ represents hydrogen.

Suitable values of $R^{43}$ include halogen, nitro, hydroxy ($C_{1-6}$)alkyl, pyrazolyl, ($C_{1-6}$)alkylpyrazolyl, di($C_{1-6}$)alkylpyrazolyl, aryl($C_{1-6}$)alkylpyrazolyl, morpholinyl-($C_{1-6}$)alkylpyrazolyl, ($C_{1-6}$)alkylimidazolyl, ($C_{1-6}$)alkylpyridinyl, pyrimidinyl, hydroxy, pyridinyloxy($C_{1-6}$)alkyl, amino, ($C_{1-6}$)alkylpyridinylamino, di($C_{1-6}$)alkylamino($C_{1-6}$)alkyl, pyridinylamino($C_{1-6}$)alkyl, ($C_{1-6}$)alkylpiperazinyl($C_{1-6}$)alkyl, morpholinyl($C_{1-6}$)alkyl, formyl and $C_{2-6}$ alkoxycarbonyloxy.

Definitive values of $R^{43}$ include bromo, nitro, methyl, n-propyl, isopropyl, allyl, cyclopropyl, methylphenyl, dimethylphenyl, piperidinylmethylphenyl, piperazinylmethylphenyl, methylpiperazinylmethylphenyl, morpholinylmethylphenyl, methoxyphenyl, cyanomethoxyphenyl, dimethylaminomethylphenyl, methylaminocarbonylphenyl, benzyl, chlorophenylpyrrolidinyl, dioxopyrrolidinyl, aminopyrrolidinyl, dimethylaminopyrrolidinyl, indolinyl, oxoindolinyl, phenylpiperidinyl, benzoylpiperidinyl, diethylaminocarbonylpiperidinyl, piperazinyl, methylpiperazinyl, chlorophenylpiperazinyl, pyridinylpiperazinyl, furoylpiperazinyl, homopiperazinyl, methylhomopiperazinyl, methylpiperazinylmethyl, methylpiperazinylethyl, morpholinylmethyl, benzofuryl, benzothienyl, pyrazolyl, methylpyrazolyl, ethylpyrazolyl, propylpyrazolyl, 2-methylpropylpyrazolyl, 3-methylbutylpyrazolyl, dimethylpyrazolyl, trimethylpyrazolyl, (dimethyl)(ethyl)pyrazolyl, (dimethyl)(isopropyl)pyrazolyl, (dimethyl)(2-methylpropyl)pyrazolyl, (dimethyl)(3-methylbutyl)pyrazolyl, (dimethyl)(trifluoromethyl)pyrazolyl, cyanomethylpyrazolyl, (cyanomethyl)(dimethyl)pyrazolyl, hydroxyethylpyrazolyl, hydroxypropylpyrazolyl, 2-hydroxy-2-methylpropylpyrazolyl, (hydroxyethyl)(dimethyl)-pyrazolyl, (hydroxypropyl)(dimethyl)pyrazolyl, methoxypropylpyrazolyl, [(hydroxy)-(methoxy)propyl]pyrazolyl, aminoethylpyrazolyl, aminopropylpyrazolyl, (aminopropyl)-(methyl)pyrazolyl, (aminopropyl)(dimethyl)pyrazolyl, dimethylaminoethylpyrazolyl, dimethylaminopropylpyrazolyl, diethoxyphosphonopropylpyrazolyl, allylpyrazolyl, cyclopropylmethylpyrazolyl, (cyclopropylmethyl)(dimethyl)pyrazolyl, (methyl)(phenyl)-pyrazolyl, (phenyl)(trifluoromethyl)pyrazolyl, benzylpyrazolyl, aminobenzylpyrazolyl, piperidinylpyrazolyl, tetrahydropyranylmethylpyrazolyl, (dimethyl)(tetrahydropyranylmethyl)pyrazolyl, pyrrolidinylethylpyrazolyl, piperidinylethylpyrazolyl, methylpiperidinylethylpyrazolyl, morpholinylethylpyrazolyl, pyridinylmethylpyrazolyl, oxypyridinylmethylpyrazolyl, (dimethyl)(phenylcarbonylmethyl)pyrazolyl, (ethyl)(piperazinylcarbonyl)pyrazolyl, (methylaminocarbonyl)(methylphenyl)pyrazolyl, (aminoethylaminocarbonyl)(methyl)pyrazolyl, aminocarbonylmethylpyrazolyl, (aminocarbonylmethyl)(dimethyl]pyrazolyl, dimethylaminocarbonylmethylpyrazolyl, pyrazolo[1,5-a]pyridinyl, dimethylisoxazolyl, (amino)(methyl)isoxazolyl, thiazolyl, dimethylthiazolyl, imidazolyl, methylimidazolyl, dimethylimidazolyl, imidazo[1,2-a]pyridinyl, methylimidazo[1,2-a]pyridinyl, methylimidazo[4,5-b]pyridinyl, imidazo[1,2-a]pyrimidinyl, imidazo[1,2-a]pyrazinyl, methylthiadiazolyl, pyridinyl, fluoropyridinyl, methylpyridinyl, (fluoro)(methyl)pyridinyl, dimethylpyridinyl, vinylpyridinyl, (methylpiperazinyl)pyridinyl, (methyl)(piperazinyl)pyridinyl, (tert-butoxycarbonylpiperazinyl)-(methyl)pyridinyl, piperidinylmethylpyridinyl, (methyl)(oxy)pyridinyl, hydroxypyridinyl, hydroxymethylpyridinyl, hydroxyethylpyridinyl, methoxypyridinyl, (methoxy)(methyl)-pyridinyl, (dimethyl)(methoxy)pyridinyl, methoxymethylpyridinyl, aminopyridinyl, carboxymethylpyridinyl, ethoxycarbonylmethylpyridinyl, pyridazinyl, methylpyridazinyl, piperidinylpyridazinyl, oxypyridazinyl, methoxypyridazinyl, aminopyridazinyl, hydroxyethylaminopyridazinyl, dimethylaminopyridazinyl, pyrimidinyl, methylpyrimidinyl, (chloro)(methyl)pyrimidinyl, dimethylpyrimidinyl, pyrrolidinylpyrimidinyl, methylpiperazinylpyrimidinyl, (methyl)(piperazinyl)pyrimidinyl, (tert-butoxycarbonylpiperazinyl)(methyl)pyrimidinyl, hydroxypyrimidinyl, (hydroxy)(methyl)pyrimidinyl, (hydroxyethyl)(methyl)pyrimidinyl, (hydroxypropyl)(methyl)pyrimidinyl, (hydroxypropynyl)(methyl)pyrimidinyl, methoxypyrimidinyl, aminopyrimidinyl, dimethylaminopyrimidinyl, (dimethylamino)(fluoro)pyrimidinyl, carboxypyrimidinyl, (methoxycarbonylmethyl)(methyl)pyrimidinyl, aminocarbonylpyrimidinyl, pyrazinyl, methoxypyrazinyl, aminopyrazinyl, hydroxy, methoxy, isopropoxy, benzyloxycarbonylpiperidinyloxy, morpholinylethoxy, phenoxy, fluorophenoxy, dimethylpyrazolyloxy, bromopyridinyloxy, pyrrolidinylpyridinyloxy, methylpiperazinylpyridinyloxy, methylpyrazolylpyridinyloxy, isopropylaminopyridinyloxy, carboxypyridinyloxy, aminocarbonylpyridinyloxy, methylpyridazinyloxy, pyrimidinyloxy, methylpyrimidinyloxy, (chloro)(methyl)-pyrimidinyloxy, hydroxymethyl, 1-hydroxy-1-methylethyl, dihydroxypropyl, pyridinyloxymethyl, amino, isopropylamino, dihydroxypropylamino, methoxyethylamino, methoxypropylamino, N-(methoxyethyl)-N-(methyl)amino, N-(methoxypropyl)-N-(methyl)amino, dimethylaminoethylamino, dimethylaminopropylamino, N-(dimethylaminoethyl)-N-(methyl)amino, N-(diethylaminoethyl)-N-(methyl)amino, N-(dimethylaminopropyl)-N-(methyl)amino, N-(dimethylaminoethyl)-N-(ethyl)amino, N-(dimethylaminopropyl)-N-(ethyl)amino, N-(cyclohexyl)-N-(methyl)amino, fluorophenylamino, N-fluorophenyl-N-methylamino, N-benzyl-N-methylamino, N-(benzyl)-N-(dimethylaminoethyl)amino, cyanobenzylamino, (cyano)(phenyl)ethylamino, (cyano)(fluoro)benzylamino, methylenedioxybenzylamino, N-(methyl)-N-(methylpyrrolidinyl)amino, piperidinylamino, N-(methyl)-N-(piperidinyl)amino, N-(ethyl)-N-(piperidinyl)amino, N-(cyclopropylmethyl)-N-(piperidinyl)amino, methylpiperidinylamino, N-(methyl)-N-(methylpiperidinyl)amino, N-(methyl)-N-(2-methylpropylpiperidinyl)amino, N-(cyclopentylpiperidinyl)-N-(methyl)amino, N-(acetylpiperidinyl)-N-(methyl)amino, pyrrolidinylethylamino, pyrrolidinylpropylamino, N-(methyl)-N-(pyrrolidinylethyl)amino, N-(methyl)-N-(pyrrolidinylpropyl)amino, N-(methyl)-N-(piperidinylmethyl)amino, methylpyrazolylamino, dimethylpyrazolylamino, trimethylpyrazolylamino, N-(ethyl)-N-(methylpyrazolyl)amino, thiazolylamino, imidazolylamino, (ethoxycarbonyl)(methyl)imidazolylamino, methylthiadiazolylamino, pyridinylamino, bromopyridinylamino, methylpyridinylamino, dimethylpyridinylamino, trifluoromethylpyridinylamino, hydroxypyridinylamino, hydroxyethylpyridinylamino, dihydroxyethylpyridinylamino, methoxypyridinylamino, dihydroxypropoxypyridinylamino, dimethyldioxolanylmethoxypyridinylamino, methoxyethylpyridinylamino, methoxyvinylpyridinylamino, dihydroxypropylaminopyridinylamino, dimethylaminopyridinylamino, methylaminomethylpyridinylamino, dimethylaminomethylpyridinylamino, carboxypyridinylamino, N-(methyl)-N-(methylpyridinyl)amino, N-(ethyl)-N-(methylpyridinyl)amino, bis(methylpyridinyl)amino, bis(trifluoromethylpyridinyl)amino, isoquinolinylamino, methylpyridazinylamino, N-(methyl)-N-(methylpyridazinyl)amino, N-(benzyl)-N-(methylpyridazinyl)amino, dimethylpyridazinylamino, phenylpyridazinylamino, piperidinylpyridazinylamino, methoxypyridazinylamino, dimethylaminopyridazinylamino, bis(methylpyridazinyl)amino, benzofurylmethylamino, thienylmethylamino, indolylmethylamino, methylpyrazolylmethylamino, (chloro)(dimethyl)pyrazolylmethylamino, dimethylisoxazolylmethylamino, thiazolylmethylamino, imidazolylmethylamino, methylimidazolylmethylamino, pyridinylmethylamino, methylpyridinylmethylamino, N-(methyl)-N-(pyridinylethyl)amino, N-(dihydroxypropyl)-N-(pyridinylmethyl)-amino, N-(dihydroxypropyl)-N-(methylpyridinylmethyl)amino, aminomethyl, methylaminomethyl, dimethylaminomethyl, pyridinylaminomethyl, N-(acetyl)-N-(methylpyridinyl)amino, dimethylaminoethylcarbonylamino, cyclohexylcarbonylamino, methylpiperidinylcarbonylamino, methylimidazolylcarbonylamino, formyl, acetyl, methylpiperidinylaminocarbonyl, N-(methyl)-N-(methylpiperidinyl)aminocarbonyl, piperidinylethylaminocarbonyl, methylpiperazinylcarbonyl, isopropylthio, isopropylsulphinyl, isopropylsulphonyl, tert-butoxycarbonyloxy and tetramethyldioxaborolanyl.

Specific values of $R^{43}$ include bromo, nitro, hydroxymethyl, pyrazolyl, methylpyrazolyl, dimethylpyrazolyl, propylpyrazolyl, isobutylpyrazolyl, benzylpyrazolyl, morpholinylethylpyrazolyl, methylimidazolyl, methylpyridinyl, pyrimidinyl, hydroxy, pyridinyloxymethyl, amino, methylpyridinylamino, dimethylaminomethyl, pyridinylaminomethyl, methylpiperazinylmethyl, morpholinylmethyl, formyl and tertbutoxycarbonyloxy.

In relation to formula (IID-1), $R^{44}$ suitably represents hydrogen, halogen or $C_{1-6}$ alkoxy. In relation to formula (IID-2), $R^{44}$ suitably represents hydrogen, halogen or $C_{1-6}$ alkyl.

In one embodiment, $R^{44}$ represents hydrogen. In another embodiment, $R^{44}$ represents halogen, especially bromo. In a further embodiment, $R^{44}$ represents $C_{1-6}$ alkyl, especially methyl. In an additional embodiment, $R^{44}$ represents $C_{1-6}$ alkoxy, especially methoxy.

A further sub-class of compounds according to the invention is represented by the compounds of formula (IIE), and pharmaceutically acceptable salts and solvates thereof:

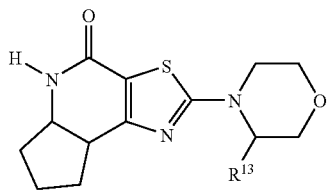

(IIE)

wherein
$R^{13}$ is as defined above.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III) with a compound of formula (IV):

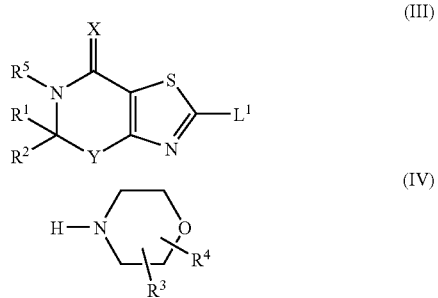

wherein $R^1$, $R^2$, $R^3$, $R^4$, $R^5$, X and Y are as defined above, and $L^1$ represents a suitable leaving group.

The leaving group $L^1$ is typically a halogen atom, e.g. bromo.

The reaction is conveniently effected at an elevated temperature in a suitable solvent, e.g. a lower alkanol such as isopropanol or a cyclic ether such as tetrahydrofuran, typically under basic conditions, e.g. in the presence of an organic base such as N,N-diisopropylethylamine or 2,6-lutidine.

Alternatively, the reaction may be effected at an elevated temperature in a solvent such as 2-ethoxyethanol in the presence of a catalytic quantity of a mineral acid, e.g. concentrated hydrochloric acid.

In another alternative, the reaction may be effected at an elevated temperature in a suitable solvent, e.g. a cyclic ether such as tetrahydrofuran, or an aromatic solvent such as toluene, typically under basic conditions, e.g. in the presence of an inorganic base such as sodium tert-butoxide, in the presence of a transition metal catalyst. The transition metal catalyst is suitably palladium(II) acetate, in which case the reaction will ideally be performed in the presence of tert-butylphosphonium tetrafluoroborate or dicyclohexyl diphenylphosphine.

The intermediates of formula (III) above wherein $L^1$ is bromo may be prepared from a compound of formula (V):

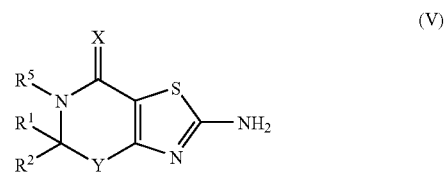

wherein $R^1$, $R^2$, $R^5$, X and Y are as defined above; by diazotization/bromination.

The reaction is conveniently effected by stirring compound (V) with tert-butyl nitrite and copper(II) bromide in a suitable solvent, e.g. acetonitrile.

The intermediates of formula (V) above may be prepared by reacting thiourea with a compound of formula (VI):

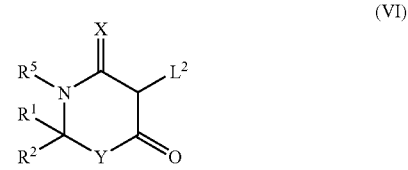

wherein $R^1$, $R^2$, $R^5$, X and Y are as defined above, and $L^2$ represents a suitable leaving group.

The leaving group $L^2$ is typically a halogen atom, e.g. bromo.

The reaction is conveniently effected at an elevated temperature in a suitable solvent, e.g. a cyclic ether such as tetrahydrofuran, typically under basic conditions, e.g. in the presence of an organic base such as N,N-diisopropylethylamine.

Alternatively, the reaction may be accomplished by heating the reactants in a lower alkanol solvent, e.g. a $C_{1-6}$ alkyl alcohol such as ethanol.

In another procedure, the compounds of formula (I) may be prepared by a process which comprises reacting a compound of formula (VI) as defined above with a compound of formula (VII):

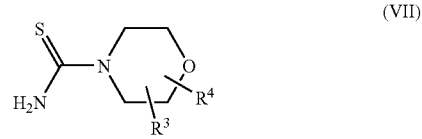

wherein $R^3$ and $R^4$ are as defined above; under conditions analogous to those described above for the reaction between thiourea and compound (VI).

In an additional procedure, the compounds of formula (I) wherein X is oxygen and R⁵ is hydrogen may be prepared by a process which comprises reacting a compound of formula (VIII):

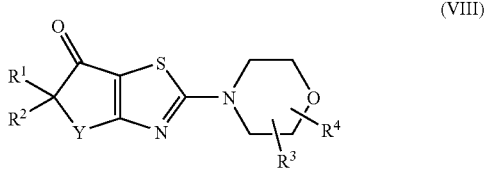
(VIII)

wherein Y, R¹, R², R³ and R⁴ are as defined above; with sodium azide.

The reaction may conveniently be effected at ambient temperature in a suitable solvent, e.g. a chlorinated solvent such as chloroform, in the presence of a mineral acid, e.g. concentrated sulphuric acid.

The intermediates of formula (VIII) may be prepared by reacting a compound of formula (VII) as defined above with a compound of formula (IX):

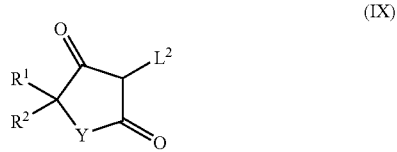
(IX)

wherein Y, R¹, R² and L² are as defined above.

The reaction is conveniently effected by heating the reactants in a suitable solvent, e.g. N,N-dimethylformamide.

In a further procedure, the compounds of formula (I) wherein X is oxygen, Y is NH and R⁵ is hydrogen may be prepared by a process which comprises reacting a compound of formula (X):

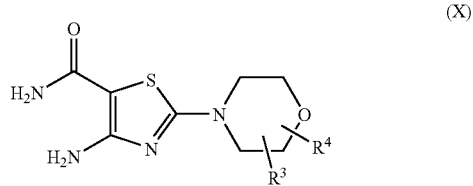
(X)

wherein R³ and R⁴ are as defined above; with a compound of formula (XI), or a carbonyl-protected form thereof:

(XI)

wherein R¹ and R² are as defined above.

Suitable carbonyl-protected forms of the compounds of formula (XI) include the di(C₁₋₆)alkyl (e.g. dimethyl or diethyl)acetal or ketal derivatives.

The reaction may conveniently be effected at an elevated temperature in a suitable solvent, e.g. acetone or a chlorinated solvent such as 1,2-dichloroethane, in the presence of a catalytic quantity of p-toluenesulphonic acid.

Where they are not commercially available, the starting materials of formula (IV), (VI), (VII), (IX), (X) and (XI) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (IA) may be converted into the corresponding compound of formula (IB) by treatment with Lawesson's Reagent (i.e. 2,4-bis(4-methoxyphenyl)-1,3-dithia-2,4-diphosphetane-2,4-disulphide).

Similarly, a compound of formula (IC) may be converted into the corresponding compound of formula (ID) by treatment with Lawesson's Reagent.

A compound of formula (I) wherein R² represents —CH₂CH₂CH₂Cl and R⁸ is hydrogen may be converted under standard N-alkylation conditions into the corresponding compound wherein R²/R⁸ represents —CH₂CH₂CH₂—.

A compound of formula (I) wherein R³ and/or R⁴ contains an aryl or heteroaryl moiety may be halogenated (e.g. brominated) on the aryl or heteroaryl moiety by treatment with the appropriate N-halosuccinimide (e.g. N-bromosuccinimide).

A compound of formula (I) wherein R³ and/or R⁴ contains a halogen atom (e.g. bromo) may be converted into the corresponding compound wherein the halogen atom is replaced by amino (—NH₂) by treatment with benzophenone imine and tris(dibenzylideneacetone)dipalladium(0) in the presence of 2,2'-bis(diphenylphosphino)-1,1'-binaphthyl (BINAP) and a strong base such as sodium tert-butoxide.

A compound of formula (I) wherein R³ contains a halogen atom, e.g. bromo, may be converted into the corresponding compound of formula (I) wherein the halogen atom is replaced by an optionally substituted C₃₋₇ cycloalkyl, aryl, aryl(C₁₋₆)alkyl or heteroaryl moiety by treatment with, respectively, an appropriately-substituted C₃₋₇ cycloalkyl, aryl, aryl(C₁₋₆)alkyl or heteroaryl boronic acid or a cyclic ester thereof, e.g. a pinacol ester thereof, in the presence of a catalyst. More particularly, a compound of formula (I) wherein R³ represents aryl(C₁₋₆)alkyl, substituted on the aryl moiety by a halogen atom such as bromo, may be converted into the corresponding compound wherein R³ represents biaryl(C₁₋₆)alkyl or heteroarylaryl(C₁₋₆)alkyl by treatment with, respectively, an aryl or heteroaryl boronic acid, in the presence of a catalyst. Similarly, a compound of formula (I) wherein R³ represents heteroaryl(C₁₋₆)alkyl, substituted on the heteroaryl moiety by a halogen atom such as bromo, may be converted into the corresponding compound wherein R³ represents aryl-heteroaryl(C₁₋₆)alkyl by treatment with an aryl boronic acid, in the presence of a catalyst. Furthermore, a compound of formula (I) wherein R³ contains a cyclic borane moiety, e.g. 4,4,5,5-tetramethyl[1,3,2]dioxaborolan-2-yl, may be converted into the corresponding compound wherein the cyclic borane moiety is replaced by an optionally substituted aryl or heteroaryl moiety by treatment with, respectively, an appropriately-substituted aryl or heteroaryl halide, e.g. chloride, bromide or iodide, in the presence of a catalyst. The catalyst may typically be a transition metal catalyst. A suitable catalyst is tetrakis(triphenylphosphine)palladium(0), in which case the transformation may conveniently be effected at an elevated temperature in the presence of a base such as sodium carbonate, potassium carbonate or potassium phosphate, in an inert solvent such as 1,2-dimethoxyethane, tetrahydrofuran or 1,4-dioxane, optionally in the presence of tetra-n-butylammonium bromide. Alternatively, the catalyst may be palladium(II) acetate, in which case the transformation may conveniently be effected at an elevated temperature in the presence of 2-dicyclohexylphosphino-2',6'-dimethoxybiphenyl and potassium phosphate.

A compound of formula (I) wherein $R^3$ represents hydroxymethyl may be converted into the corresponding compound wherein $R^3$ represents a substituted aminomethyl moiety, e.g. phenylaminomethyl, N-methyl-N-phenylaminomethyl, pyridin-3-ylaminomethyl, indolin-1-ylmethyl, 1,2,3,4-tetrahydroquinolin-1-ylmethyl or 1,2,3,4-tetrahydroisoquinolin-2-ylmethyl, by a two-stage procedure which comprises (i) Swern oxidation of the hydroxymethyl derivative by treatment with oxalyl chloride and dimethyl sulphoxide in the presence of triethylamine; and (ii) reductive amination of the formyl derivative thereby obtained by treatment with the appropriate amine, e.g. aniline, N-methylaniline, 3-aminopyridine, indoline, 1,2,3,4-tetrahydroquinoline or 1,2,3,4-tetrahydroisoquinoline, in the presence of a reducing agent such as sodium cyanoborohydride.

In general, any compound of formula (I) which contains a carbonyl-containing functionality, e.g. formyl or a ketone moiety, may be converted into a substituted amino analogue thereof by application of the reductive amination procedure described in step (ii) in the preceding paragraph, which comprises treatment with the appropriately-substituted amine in the presence of a reducing agent, e.g. sodium cyanoborohydride or sodium triacetoxyborohydride.

Any compound of formula (I) wherein $R^3$ contains an amino moiety can be alkylated on the amino moiety by a reductive amination procedure which comprises treatment with the appropriate aldehyde in the presence of a reducing agent, e.g. sodium cyanoborohydride or sodium triacetoxyborohydride.

A compound of formula (I) wherein $R^3$ represents hydroxymethyl may be converted into the corresponding compound wherein $R^3$ represents an optionally substituted $C_{3-7}$ heterocycloalkylcarbonyl moiety, e.g. piperidin-1-ylcarbonyl, 1,2,3,4-tetrahydroquinolin-1-ylcarbonyl, 6-methyl-1,2,3,4-tetrahydroquinolin-1-ylcarbonyl, 6-methoxy-1,2,3,4-tetrahydroquinolin-1-ylcarbonyl, 1,2,3,4-tetrahydroisoquinolin-2-ylcarbonyl or 1,2,3,4-tetrahydroquinoxalin-1-ylcarbonyl, by a two-stage procedure which comprises (i) oxidation of the hydroxymethyl moiety by treatment with potassium permanganate; and (ii) reaction of the carboxy derivative thereby obtained with the appropriate amine, e.g. piperidine, 1,2,3,4-tetrahydroquinoline, 6-methyl-1,2,3,4-tetrahydroquinoline, 6-methoxy-1,2,3,4-tetrahydroquinoline, 1,2,3,4-tetrahydroisoquinoline or 1,2,3,4-tetrahydroquinoxaline, in the presence of a condensing agent such as 1-(3-dimethylaminopropyl)-3-ethylcarbodiimide, or O-(benzotriazol-1-yl)-N,N,N',N'-tetramethyluronium hexafluorophosphate (HBTU).

A compound of formula (I) wherein $R^3$ contains a phenyl moiety substituted by chloro may be converted into the corresponding compound wherein the phenyl ring is substituted by morpholin-4-yl by treatment with morpholine in the presence of tris(dibenzylideneacetone)dipalladium(0), 2-(di-tert-butylphosphino)biphenyl and sodium tert-butoxide. A compound of formula (I) wherein $R^3$ contains a phenyl moiety substituted by bromo may be converted into the corresponding compound wherein the phenyl ring is substituted by pyrrolidin-1-yl by treatment with pyrrolidine in the presence of tris(dibenzylideneacetone)dipalladium(0), 2-dicyclohexylphosphino-2',4',6'-triisopropyl-1,1'-biphenyl and a base such as potassium carbonate. Similarly, a compound of formula (I) wherein $R^3$ contains a phenyl moiety substituted by bromo may be converted into the corresponding compound wherein the phenyl ring is substituted by an amino moiety (e.g. a group of formula —$NHR^{34}$ as defined above) by treatment with the appropriate amine (e.g. a compound of formula $H_2N$—$R^{34}$) in the presence of tris(dibenzylideneacetone)dipalladium(0), 2-(dicyclohexylphosphino)-2',4',6'-triisopropyl-1,1'-biphenyl (X-Phos) and a base such as sodium tert-butoxide.

A compound of formula (I) wherein $R^3/R^4$ contains a halogen atom (e.g. bromo) may be converted into the corresponding compound wherein the halogen atom is replaced by carboxy (—$CO_2H$) by treatment with n-butyllithium followed by carbon dioxide.

A compound of formula (I) wherein $R^3$ contains an indole moiety may be methylated on the indole ring by treatment with a methyl halide, e.g. iodomethane, in the presence of a strong base such as sodium hydride. A compound of formula (I) wherein $R^3$ contains an indole moiety may be acetylated on the indole ring by treatment with acetic anhydride and 4-dimethylamino-pyridine, typically in the presence of an organic base such as triethylamine. A compound of formula (I) wherein $R^3$ contains an indoline moiety may be converted into the corresponding compound wherein $R^3$ contains an indole moiety by treatment with an oxidising agent such as manganese dioxide. A compound of formula (I) wherein $R^3$ contains a hydroxy substituent may be converted into the corresponding compound wherein $R^3$ contains a $C_{1-6}$ alkylsulphonyloxy substituent, e.g. methylsulphonyloxy, by treatment with a $C_{1-6}$ alkylsulphonyl halide, e.g. methanesulphonyl chloride. A compound of formula (I) wherein $R^3$ contains an amino (—$NH_2$) or carboxy (—$CO_2H$) moiety may be converted into the corresponding compound wherein $R^3$ contains an amido moiety (—NHCO— or —CONH— respectively) by treatment with, respectively, a compound containing a carboxy or amino group, in the presence of 0-(benzotriazol-1-yl)-N,N,N',N'-tetramethyluronium hexafluorophosphate (HBTU), typically in a dipolar aprotic solvent such as N,N-dimethylformamide; or in the presence of 1-(3-dimethylaminopropyl)-3-ethylcarbodiimide and 1-hydroxybenzotriazole. A compound of formula (I) wherein $R^3$ contains an amino substituent may be converted into the corresponding compound wherein $R^3$ contains an alkyl- or arylsulphonylamino substituent, e.g. methylsulphonylamino or phenylsulphonylamino, by treatment with an alkyl- or arylsulphonyl halide, e.g. methanesulphonyl chloride or benzenesulphonyl chloride.

A compound of formula (I) wherein $R^3$ contains an amino moiety may be acylated by treatment with a $C_{2-6}$ alkylcarbonyl halide, e.g. acetyl chloride; or a $C_{2-6}$ alkylcarbonyl anhydride, e.g. acetic anhydride. A compound of formula (I) wherein $R^3$ contains an amino moiety may be converted into the corresponding carbamate ester by treatment with a $C_{1-6}$ alkyl haloformate, e.g. methyl chloroformate.

A compound of formula (I) wherein $R^3$ contains a $C_{2-6}$ alkoxycarbonyl substituent, e.g. methoxycarbonyl, may be converted into the corresponding compound wherein $R^3$ contains a carboxy (—$CO_2H$) substituent under standard saponification conditions, e.g. by treatment with a base such as lithium hydroxide. A compound of formula (I) wherein $R^3$ contains a carboxy (—$CO_2H$) substituent may be converted into the corresponding compound wherein $R^3$ contains an amido substituent, e.g. methylaminocarbonyl, 2-hydroxyethylaminocarbonyl, dimethylaminocarbonyl, N-(2-hydroxyethyl)-N-methylaminocarbonyl, benzylaminocarbonyl, azetidin-1-ylcarbonyl, pyrrolidin-1-ylcarbonyl, piperidin-1-ylcarbonyl, 4-methylpiperazin-1-ylcarbonyl or morpholin-4-ylcarbonyl, by a two-stage procedure which comprises (i) treatment of the carboxy derivative with pentafluorophenol in the presence of a condensing agent such as 1-(3-dimethylaminopropyl)-3-ethylcarbodiimide; and (ii)

reaction of the pentafluorophenyl ester thereby obtained with the appropriate amine, e.g. methylamine, 2-hydroxyethylamine, dimethylamine, N-(2-hydroxyethyl)-N-methylamine, benzylamine, azetidine, pyrrolidine, piperidine, 1-methylpiperazine or morpholine.

A compound of formula (I) wherein $R^3/R^4$ contains a nitro moiety may be converted into the corresponding compound wherein $R^3/R^4$ contains an amino (—$NH_2$) moiety by catalytic hydrogenation, typically by treatment with hydrogen in the presence of a hydrogenation catalyst, e.g. palladium on charcoal. A compound of formula (I) wherein $R^3/R^4$ contains an amino (—$NH_2$) moiety may be converted into the corresponding compound wherein $R^3/R^4$ contains a heteroarylamino moiety, e.g. 6-methylpyridin-3-ylamino, by treatment with the appropriate heteroaryl halide, e.g. 5-bromo-2-methylpyridine, in the presence of palladium(II) acetate, 2-bis(dicyclohexylphosphino)-biphenyl and a base such as sodium tert-butoxide.

In general, any compound of formula (I) wherein $R^3/R^4$ contains a halogen atom, e.g. bromo, may be converted into the corresponding compound wherein the halogen atom is replaced by a substituted amino functionality by treatment with the appropriately-substituted amine derivative and palladium(II) acetate in the presence of a base, e.g. sodium tert-butoxide, and tri-tert-butylphosphonium tetrafluoroborate. Alternatively, the reaction may be effected by treatment with the appropriately-substituted amine derivative and [1,1'-bis(di-tert-butylphosphino)ferrocene]palladium(II) dichloride in the presence of a base, e.g. sodium tert-butoxide. Conversely, any compound of formula (I) wherein $R^3/R^4$ contains an amino functionality may be converted into the corresponding compound wherein the amino functionality is substituted by an optionally substituted aryl or heteroaryl moiety by treatment with an appropriately-substituted aryl or heteroaryl halide (e.g. bromide) and [1,1'-bis(di-tert-butylphosphino)ferrocene]palladium(II) dihloride in the presence of a base, e.g. sodium tert-butoxide.

A compound of formula (I) wherein $R^3/R^4$ contains a benzo moiety substituted by a halogen atom, e.g. bromo, may be converted into the corresponding compound wherein $R^3/R^4$ contains a benzo moiety substituted by a heteroaryl group, e.g. pyrazol-3-yl, 1-methylpyrazol-4-yl, 1-propylpyrazol-4-yl, 1-isobutylpyrazol-4-yl, 1-benzylpyrazol-4-yl, 1-[2-(morpholin-4-yl)ethyl]pyrazol-4-yl, 6-methylpyridin-3-yl or pyrimidin-5-yl, by treatment with the appropriate heteroaryl boronic acid or a cyclic ester thereof formed with an organic diol, e.g. pinacol, in the presence of a catalyst. Similarly, a compound of formula (I) wherein $R^3/R^4$ contains a benzo moiety substituted by a boronic acid [—$B(OH)_2$] moiety may be converted into the corresponding compound wherein $R^3/R^4$ contains a benzo moiety substituted by a heteroaryl group, e.g. methylimidazolyl, by treatment with the appropriate heteroaryl halide, e.g. bromide, derivative in the presence of a catalyst. The catalyst may typically be a transition metal catalyst. A suitable catalyst is tetrakis(triphenylphosphine)palladium(0), in which case the transformation may conveniently be effected at an elevated temperature in the presence of a base such as sodium carbonate, potassium carbonate or potassium phosphate, optionally in the presence of tetrabutylammonium bromide.

A compound of formula (I) wherein $R^3/R^4$ contains a benzo moiety substituted by a halogen atom, e.g. bromo, may be converted into the corresponding compound wherein $R^3/R^4$ contains a benzo moiety substituted by a formyl (—CHO) group by treatment with a strong base, e.g. n-butyllithium, and N,N-dimethylformamide. A compound of formula (I) wherein $R^3/R^4$ contains a benzo moiety substituted by a formyl (—CHO) group may be converted into the corresponding compound wherein $R^3/R^4$ contains a benzo moiety substituted by hydroxymethyl by treatment with a reducing agent such as sodium borohydride. A compound of formula (I) wherein $R^3/R^4$ contains a benzo moiety substituted by a formyl (—CHO) group may be converted into the corresponding compound wherein $R^3/R^4$ contains a benzo moiety substituted by an aminomethyl moiety (e.g. dimethylaminomethyl, pyridin-3-ylaminomethyl, 4-methylpiperazin-1-ylmethyl or morpholin-4-ylmethyl) by treatment with the appropriate amine (e.g. dimethylamine, pyridin-3-ylamine, 1-methylpiperazine or morpholine) and a reducing agent which typically consists of a mixture of phenylsilane and dibutyltin dichloride. Conversely, a compound of formula (I) wherein $R^3/R^4$ contains an amino moiety may be converted into the corresponding compound wherein $R^3/R^4$ is methylated on the amino moiety by treatment with formaldehyde and a reducing agent which typically consists of a mixture of phenylsilane and dibutyltin dichloride. A compound of formula (I) wherein $R^3/R^4$ contains a benzo moiety substituted by a formyl (—CHO) group may be converted into the corresponding compound wherein $R^3/R^4$ contains a benzo moiety substituted by a pyridinyloxymethyl moiety by treatment with the appropriate hydroxypyridine in the presence of a mixture of triphenylphosphine and diethyl azodicarboxylate. A compound of formula (I) wherein $R^3/R^4$ contains a benzo moiety substituted by a $C_{2-6}$ alkoxycarbonyloxy group, e.g. tert-butoxycarbonyloxy, may be converted into the corresponding compound wherein $R^3/R^4$ contains a benzo moiety substituted by hydroxy under standard hydrolytic conditions, e.g. by treatment with trifluoroacetic acid.

A compound of formula (I) wherein $R^3/R^4$ contains a halogen atom, e.g. bromo, may be converted into the corresponding compound wherein $R^3/R^4$ contains hydroxy by treatment with sodium hydroxide in the presence of tris(dibenzylideneacetone)-dipalladium(0) and 2-(di-tert-butylphosphino)-2',4',6'-triisopropyl-1,1'-biphenyl.

A compound of formula (I) wherein $R^3/R^4$ contains hydroxy may be converted into the corresponding compound wherein $R^3/R^4$ contains optionally substituted $C_{1-6}$ alkoxy, $C_{3-7}$ heterocycloalkoxy or $C_{3-7}$ heterocycloalkyl($C_{1-6}$)alkoxy by treatment with the appropriately substituted $C_{1-6}$ alkyl, $C_{3-7}$ heterocycloalkyl or $C_{3-7}$ heterocycloalkyl($C_{1-6}$)-alkyl halide, e.g. bromide, ideally at an elevated temperature in the presence of cetylammonium bromide. Alternatively, a compound of formula (I) wherein $R^3/R^4$ contains hydroxy may be converted into the corresponding compound wherein $R^3/R^4$ contains optionally substituted pyridinyloxy, pyrimidinyloxy or pyrazinyloxy by treatment with the appropriately substituted pyridinyl, pyrimidinyl or pyrazinyl halide, e.g. fluoride or chloride, typically in the presence of a strong base such as sodium tert-butoxide.

A compound of formula (I) wherein $R^3/R^4$ contains a halogen atom (e.g. bromo) may be converted into the corresponding compound wherein $R^3/R^4$ contains optionally substituted aryloxy or heteroaryloxy by treatment with an appropriately-substituted hydroxyaryl or hydroxyheteroaryl derivative and a base such as caesium carbonate, ideally in the presence of a copper(I) halide, e.g. copper(I) chloride or copper(I) bromide.

A compound of formula (I) wherein $R^3/R^4$ contains an amino (—$NH_2$) group may be converted into the corresponding compound wherein $R^3/R^4$ contains 2,5-dioxopyrrolidin-1-yl by treatment with succinic anhydride.

A compound of formula (I) wherein $R^3/R^4$ contains an aryl or heteroaryl moiety substituted by a halogen atom, e.g. chloro, may have the halogen atom removed by catalytic hydrogenation.

A compound of formula (I) wherein $R^3/R^4$ contains a benzo moiety may be alkylated on the aromatic ring by treatment with n-butyllithium and an alkyl halide (e.g. iodopropane); or by treatment with an organozinc reagent (e.g. isopropylzinc bromide) in the presence of [1,1'-bis(di-tert-butylphosphino)ferrocene]palladium(II) dichloride and copper(I) iodide.

A compound of formula (I) wherein $R^3/R^4$ contains a halogen atom (e.g. chloro) may be converted into the corresponding compound wherein the halogen atom is replaced by an optionally substituted alkynyl moiety (e.g. 3-hydroxyprop-1-yn-1-yl) by treatment with an appropriately-substituted alkyne derivative (e.g. 3-hydroxyprop-1-yne) and a catalyst such as tetrakis(triphenylphosphine)palladium(0), typically in the presence of copper(I) iodide and a base such as triethylamine.

A compound of formula (I) wherein $R^3/R^4$ contains a halogen atom (e.g. bromo) may be converted into the corresponding compound wherein the halogen atom is replaced by acetyl by a two-stage procedure which comprises (i) treatment with butyl vinyl ether and palladium acetate, suitably in the presence of 1,3-bis(diphenylphosphino)propane and an organic base such as triethylamine; and (ii) hydrolysis with a mineral acid such as hydrochloric acid.

A compound of formula (I) wherein $R^3/R^4$ contains a halogen atom (e.g. bromo) may be converted into the corresponding compound wherein the halogen atom is replaced by 1-hydroxy-1-methylethyl by treatment with n-butyllithium and acetone.

A compound of formula (I) wherein $R^3/R^4$ contains a halogen atom (e.g. bromo) may be converted into the corresponding compound wherein the halogen atom is replaced by $C_{1-6}$ alkylthio (e.g. isopropylthio) by treatment with n-butyllithium and the appropriate disulphide derivative (e.g isopropyl disulphide). Conversion of the $C_{1-6}$ alkylthio moiety into $C_{1-6}$ alkylsulphinyl or $C_{1-6}$ alkylsulphonyl may be accomplished by treatment with an oxidising agent, e.g. m-chloroperbenzoic acid.

A compound of formula (I) wherein $R^3/R^4$ contains a pyridinyl moiety may be converted into the corresponding pyridine-N-oxide analogue by treatment with peracetic acid.

A compound of formula (I) wherein $R^3/R^4$ contains a carbonyl-containing moiety (e.g. acetyl) may be converted into the corresponding oxime analogue by treatment with an appropriately-substituted hydroxylamine derivative.

A compound of formula (I) wherein $R^3/R^4$ contains a formyl moiety may be converted into the corresponding compound wherein $R^3/R^4$ contains a vinyl moiety by treatment with methyltriphenylphosphonium bromide and a strong base such as sodium hexamethyldisilazide.

A compound of formula (I) wherein $R^3/R^4$ contains a formyl moiety may be converted into the corresponding compound wherein $R^3/R^4$ contains a 1-hydroxyethyl moiety by treatment with methyllithium.

A compound of formula (I) wherein $R^3/R^4$ contains a (2-hydroxyethyl)aminocarbonyl group may be converted into the corresponding compound wherein $R^3/R^4$ contains an oxazolin-1-yl moiety by treatment with thionyl chloride.

A compound of formula (I) wherein $R^3/R^4$ contains an ester functionality (e.g. methoxycarbonyl) may be converted into the corresponding compound wherein $R^3/R^4$ contains an amide functionality (e.g. methylaminocarbonyl) by treatment with an appropriately-substituted amine (e.g. methylamine) in the presence of trimethylaluminium.

Alkenyl-containing compounds may be converted into the corresponding vic-dihydroxy analogues by treatment with osmium tetroxide.

Alkenyl- and alkynyl-containing compounds may be converted into the corresponding alkyl analogues by catalytic hydrogenation.

A compound of formula (I) wherein $R^5$ represents hydrogen may be converted into the corresponding compound wherein $R^5$ represents $C_{1-6}$ alkyl by treatment with the appropriate alkyl halide, e.g. a methyl halide such as iodomethane, in the presence of a strong base such as sodium hydride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (α, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 µM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the $IC_{50}$.

When tested in the above assay, the compounds of the accompanying Examples were all found to possess $IC_{50}$ values for inhibition of activity of human PI3Kα and/or PI3Kβ and/or PI3Kγ and/or PI3Kδ of 50 µM or better.

EXAMPLES

| Abbreviations | |
|---|---|
| BOC: | tert-butoxycarbonyl |
| DMF: | N,N-dimethylformamide |
| DMSO: | dimethylsulphoxide; |
| Et$_2$O: | diethyl ether |
| r.t.: | room temperature |
| DMAP: | 4-(dimethylamino)pyridine |
| MeOH: | methanol |
| EtOH: | ethanol |
| RT: | retention time |
| h: | hour |
| cat.: | catalytic |
| SiO$_2$: | silica |
| w or wt: | weight |
| $^t$Bu: | tert-butyl |
| BuOH: | butanol |
| DCE: | 1,2-dichloroethane |
| brine: | saturated aqueous sodium chloride solution |
| HPLC: | High Performance Liquid Chromatography |
| LCMS: | Liquid Chromatography Mass Spectrometry |
| DIPEA: | N,N-diisopropylethylamine |
| ES+: | Electrospray Positive Ionisation |
| ES−: | Electrospray Negative Ionisation |
| EDC: | 1-(3-dimethylaminopropyl)-3-ethylcarbodiimide hydrochloride |
| Meldrum's acid: | 2,2-dimethyl-1,3-dioxane-4,6-dione |
| DMPU: | 1,3-dimethyl-3,4,5,6-tetrahydro-2(1H)-pyrimidinone |
| DDQ: | 2,3-dichloro-5,6-dicyano-1,4-benzoquinone |
| X-Phos: | 2-(dicyclohexylphosphino)-2',4',6'-triisopropyl-1,1'-biphenyl |
| DCM: | dichloromethane |
| DME: | ethylene glycol dimethyl ether |
| $^i$Pr: | isopropyl |
| THF: | tetrahydrofuran |
| sat.: | saturated |
| EtOAc: | ethyl acetate |
| AcOH: | acetic acid |
| IPA: | isopropyl alcohol |
| Me: | methyl |
| conc.: | concentrated |
| MeCN: | acetonitrile |
| br.: | broad |
| M: | mass |
| v: | volume |
| NBS: | N-bromosuccinimide |
| TFA: | trifluoroacetic acid |

Analytical Conditions

All NMRs were obtained either at 300 MHz or 400 MHz.

Compounds were named with the aid of ACD Labs Name (v. 7.0, 9.0 or 10.0) supplied by Advanced Chemical Development, Toronto, Canada.

All reactions involving air- or moisture-sensitive reagents were performed under a nitrogen atmosphere using dried solvents and glassware.

Examples 5-10 were prepared as a library and final purities were determined by LCMS using a Luna C18, 4.6 mm, 5 µm column. Mobile phase A: 99.9% water, 0.1% formic acid. Mobile phase B: 99.9% MeCN, 0.1% formic acid.

Gradient program (flow rate 6.5 mL/min, column temperature 35° C.):

| Time | A % | B % |
|---|---|---|
| 0.00 | 95.0 | 5.0 |
| 4.40 | 5.0 | 5.0 |
| 5.30 | 5.0 | 95.0 |
| 5.32 | 95.0 | 5.0 |
| 6.50 | 95.0 | 5.0 |

Examples 13-15 were purified by preparative HPLC at pH 5.8 using a Luna C18 250 mm×21.2 mm, 5 µm column. Mobile phase A: 10 mM ammonium acetate in water. Mobile phase B: 10 mM ammonium acetate in MeCN.

All other compound purities and retention times were determined by LCMS using one of the Methods 1-9 below.

Preparative HPLC for all other compounds that required it was performed using one of the Methods 10-13 below.

Method 1: Luna C18(2) 100×4.6 mm, 5 µm column. Mobile phase A: 99.92% water, 0.08% formic acid. Mobile phase B: 99.92% MeCN, 0.08% formic acid.

Gradient program (flow rate 3.0 mL/min, column temperature 35° C.):

| Time | A % | B % |
|---|---|---|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Method 2: Luna C18(2) 100×4.6 mm, 5 µm column. Mobile phase A: 5 mM NH$_4$OAc, pH 5.8. Mobile phase B: 95:5 MeCN:100 mM NH$_4$OAc, pH 5.8.

Gradient program (flow rate 3.0 mL/min, column temperature 35° C.):

| Time | A % | B % |
|---|---|---|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Method 3: Gemini C18 50×4.6 mm, 5 µm column. Mobile phase A: 99.9% 10 mM ammonium formate, 0.1% formic acid. Mobile phase B: 94.9% MeCN, 0.1% formic acid, 5% mobile phase A.

Gradient program (flow rate 0.9 mL/min, column temperature 40° C.):

| Time | A % | B % |
|---|---|---|
| 0.00 | 95.0 | 5.0 |
| 2.00 | 5.0 | 95.0 |
| 5.50 | 5.0 | 95.0 |

Method 4: Gemini C18 50×4.6 mm, 5 μm column. Mobile phase A: 99.9% 10 mM ammonium formate, 0.1% ammonia. Mobile phase B: 94.9% MeCN, 0.1% ammonia, 5% mobile phase A.

Gradient program (flow rate 3.0 mL/min, column temperature 40° C.):

| Time | A % | B % |
| --- | --- | --- |
| 0.00 | 95.0 | 5.0 |
| 2.00 | 5.0 | 95.0 |
| 5.50 | 5.0 | 95.0 |

Method 5: Gemini C18 50×4.6 mm, 5 μm column. Mobile phase A: 99.9% ammonium formate, 0.1% formic acid. Mobile phase B: 94.9% MeCN, 0.1% formic acid, 5% mobile phase A.

Gradient program (flow rate 0.9 mL/min, column temperature 40° C.):

| Time | A % | B % |
| --- | --- | --- |
| 0.00 | 95.0 | 5.0 |
| 2.00 | 5.0 | 95.0 |
| 4.00 | 5.0 | 95.0 |

Method 6: Gemini C18 30×3.0 mm, 3 μm column. Mobile phase A: 99.9% 10 mM ammonium formate, 0.1% formic acid. Mobile phase B: 94.9% MeCN, 0.1% formic acid, 5% mobile phase A.

Gradient program (flow rate 1.2 mL/min, column temperature 40° C.):

| Time | A % | B % |
| --- | --- | --- |
| 0.00 | 95.0 | 5.0 |
| 4.00 | 5.0 | 95.0 |
| 5.50 | 5.0 | 95.0 |

Method 7: Gemini C18 30×3.0 mm, 3 μm column. Mobile phase A: 99.9% 10 mM ammonium formate, 0.1% ammonia solution. Mobile phase B: 94.9% MeCN, 0.1% ammonia solution, 5% mobile phase A.

Gradient program (flow rate 1.2 mL/min, column temperature 40° C.):

| Time | A % | B % |
| --- | --- | --- |
| 0.00 | 95.0 | 5.0 |
| 4.00 | 5.0 | 95.0 |
| 5.50 | 5.0 | 95.0 |

Method 8: Gemini C18 30×3.0 mm, 3 μm column. Mobile phase A: 99.9% 10 mM ammonium formate, 0.1% formic acid. Mobile phase B: 100% MeCN.

Gradient program (flow rate 1.2 mL/min, column temperature 40° C.):

| Time | A % | B % |
| --- | --- | --- |
| 0.00 | 95.0 | 5.0 |
| 2.30 | 5.0 | 95.0 |
| 3.40 | 5.0 | 95.0 |
| 3.50 | 95.0 | 5.0 |

Method 9: Gemini C18 30×3.0 mm, 3 μm column. Mobile phase A: 99.9% 10 mM ammonium formate, 0.1% ammonia solution. Mobile phase B: 100% MeCN.

Gradient program (flow rate 1.2 mL/min, column temperature 40° C.):

| Time | A % | B % |
| --- | --- | --- |
| 0.00 | 95.0 | 5.0 |
| 2.30 | 5.0 | 95.0 |
| 3.40 | 5.0 | 95.0 |
| 3.50 | 95.0 | 5.0 |

Method 10: Luna C18(2) 250×21.2 mm, 5 μm column. Mobile phase A: 99.92% water, 0.08% formic acid. Mobile phase B: 99.92% MeCN, 0.08% formic acid.

Gradient program (flow rate 25.0 mL/min), column temperature: ambient, variable gradient.

Method 11: Luna C18(2) 250×21.2 mm, 5 μm column. Mobile phase A: 10 mM $NH_4OAc$, pH 5.8. Mobile phase B: 95% MeCN, 5% 200 mM $NH_4OAc$, pH 5.8.

Gradient program (flow rate 25.0 mL/min), column temperature: ambient, variable gradient.

Method 12: Gemini C18 150×21.2 mm, 10 μm column. Mobile phase A: 99.9% ammonium formate, 0.1% formic acid. Mobile phase B: 94.9% MeCN, 0.1% formic acid, 5% mobile phase A.

Gradient program (flow rate 20.0 mL/min), column temperature: ambient, variable gradient.

Method 13: Gemini C18 150×21.2 mm, 10 μm column. Mobile phase A: 99.9% ammonium formate, 0.1% ammonia solution. Mobile phase B: 94.9% MeCN, 0.1% ammonia solution, 5% mobile phase A.

Gradient program (flow rate 20.0 mL/min), column temperature: ambient, variable gradient.

Examples 240-284 were prepared as a library and final purities were determined by LCMS using Method 14.

Method 14: BEH C18 2.1×30 mm, 1.7 μm column. Mobile phase A: $NH_4HCO_3$ (15.8 g), 30% $NH_4OH$ (2 mL), water (4 L). Mobile phase B: $NH_4OH$ (500 mL), $CH_3CN$ (2.5 L).

Gradient program (flow rate 6.5 mL/min, column temperature 35° C.):

| Time | Flow rate (ml/min) | A % | B % |
| --- | --- | --- | --- |
| 0.00 | 0.4 | 95.0 | 5.0 |
| 0.40 | 0.4 | 95.0 | 5.0 |
| 2.40 | 0.4 | 10.0 | 90.0 |
| 4.00 | 0.6 | 10.0 | 90.0 |
| 5.00 | 0.6 | 5.0 | 95.0 |
| 5.10 | 0.4 | 95.0 | 5.0 |
| 6.00 | 0.4 | 95.0 | 5.0 |

Intermediate 1

Ethyl 3-amino-3-methylbutanoate hydrochloride

To a stirred solution of ethyl 3,3-dimethylacrylate (5.0 g, 39.1 mmol) in EtOH (20 mL) in a Parr® reactor at 0° C. was added liquid $NH_3$ (ca 20 mL). The reactor was sealed and heated to 90° C. for 24 h. The reaction mixture was then cooled to r.t., bubbled with nitrogen to remove the residual $NH_3$ and treated with 4M HCl in dioxane (10 mL). The reaction mixture was stirred for 30 minutes at r.t. and then evaporated in vacuo to dryness. The resulting grey paste was triturated with DCM, filtered and dried to give the title compound (5.0 g, 70%) as a grey solid that was used without further purification. $\delta_H$ ($CDCl_3$) 8.27 (3H, br. s), 4.10 (2H, q, J 7.1 Hz), 2.65 (2H, s), 1.26 (6H, s), 1.20 (3H, t, J 7.1 Hz).

Intermediate 2

Ethyl 3-[(3-ethoxy-3-oxopropanoyl)amino]-3-methylbutanoate

To a stirred suspension of Intermediate 1 (5.0 g, 27.4 mmol) in DCM (40 mL) was added $NEt_3$ (11.1 g, 15.3 mL, 109.6 mmol). The reaction mixture was then cooled to 0° C. and ethyl malonyl chloride (4.4 g, 3.7 mL, 28.8 mmol) was added dropwise. The suspension was stirred at r.t. for 2 h before it was diluted with DCM (50 mL) and washed with aqueous 1M HCl (50 mL) and water (2×50 mL). The organics were dried over $MgSO_4$, filtered and concentrated in vacuo to give the title compound (5.0 g, 71%) as an orange oil that was used without further purification. $\delta_H$ (DMSO-$d_6$) 7.75 (1H, br. s), 4.15-3.95 (4H, m), 3.14 (2H, s), 2.71 (2H, s), 1.29 (6H, s), 1.21-1.11 (6H, m).

Intermediate 3

6,6-Dimethylpiperidine-2,4-dione

To a stirred solution of NaOEt, prepared in situ from Na (0.53 g, 23.16 mmol) in EtOH (30 mL), was added dropwise a solution of Intermediate 2 (5.00 g, 19.30 mmol) in toluene (30 mL) and the reaction mixture was heated to 80° C. for 2 h. The solution was then concentrated to ca 10 mL and the residue was dissolved in toluene (30 mL) and extracted with water (3×30 mL). The combined aqueous layers were acidified to pH 2-3 with aqueous 1M HCl and extracted with EtOAc (4×50 mL). The combined organic fractions were dried ($MgSO_4$), filtered and evaporated in vacuo to give a pale yellow solid that was dissolved in MeCN (90 mL) containing 1% water. The solution was heated to reflux for 2 h and then evaporated in vacuo to dryness. The resulting solid was triturated with diisopropyl ether, filtered and dried to give the title compound (1.55 g, 57%) as a cream solid that was used without further purification. Both the keto and enol forms were observed (ratio 3.6:1 keto/enol). $\delta_H$ (DMSO-$d_6$) 10.29 (1H, br. s, enol), 8.14 (1H, br. s, keto), 6.66 (1H, s, enol), 4.81 (1H, s, enol), 3.15 (2H, s), 2.51 (2H, s), 1.20 (6H, s, keto), 1.18 (6H, s, enol).

Intermediate 4

2-Amino-6,6-dimethyl-6,7-dihydro[1,3]thiazolo[5,4-c]pyridin-4(5H)-one

To a stirred suspension of Intermediate 3 (0.50 g, 3.55 mmol) in THF (10 mL) was added $Br_2$ (0.59 g, 0.19 mL, 3.72 mmol) dropwise at 0° C. The reaction mixture was then allowed to warm to r.t. and thiourea (0.27 g, 3.55 mmol), DIPEA (1.37 g, 1.85 mL, 10.65 mmol) and THF (5 mL) were added. The reaction mixture was heated to 85° C. for 1 h, cooled to r.t., and then EtOAc (10 mL) and water (10 mL) were added. The aqueous layer was extracted with EtOAc (2×15 mL) and the combined organic layers were washed with aqueous sat. $NaHCO_3$ solution (15 mL) and brine (3×15 mL), dried ($MgSO_4$), filtered and concentrated in vacuo to give the title compound (0.37 g, 53%) as a yellow solid that was used without further purification. $\delta_H$ (DMSO-$d_6$) 7.63 (2H, s), 7.17 (1H, s), 2.62 (2H, s), 1.23 (6H, s). LCMS (ES+) 198.0 $(M+H)^+$.

Intermediate 5

2-Bromo-6,6-dimethyl-6,7-dihydro[1,3]thiazolo[5,4-c]pyridin-4(5H)-one

To a stirred suspension of Intermediate 4 (0.37 g, 1.89 mmol) in MeCN (10 mL) at r.t. was added $CuBr_2$ (0.34 g, 1.54 mmol) followed by the dropwise addition of tert-butyl nitrite (0.20 g, 0.23 mL, 1.96 mmol). The reaction mixture was stirred at r.t. for 2.5 h before aqueous 1M HCl (10 mL) was added, and the stirring was then continued for 10 minutes. The reaction mixture was partitioned between DCM (20 mL) and water (15 mL) and the aqueous layer was further extracted with DCM (3×20 mL). The combined organic layers were washed with brine (3×30 mL), dried ($MgSO_4$), filtered and concentrated in vacuo to give the title compound (0.33 g, 66%) as a yellow solid that was used without further purification. $\delta_H$ (DMSO-$d_6$) 8.04 (1H, s), 2.97 (2H, s), 1.28 (6H, s). LCMS (ES+) 261.0 and 263.0 $(M+H)^+$.

Intermediate 6

2-Bromocyclopentane-1,3-dione

To a stirred solution of cyclopentane-1,3-dione (2.5 g, 25.5 mmol) in AcOH (50 mL) at r.t. was added $Br_2$ (4.3 g, 1.4 mL, 26.8 mmol) dropwise. The reaction mixture was stirred for 45 minutes and then the product was isolated by filtration. The precipitate was washed twice with $Et_2O$ (50 mL) and dried in vacuo to give the title compound (3.2 g, 70%) as a yellow solid that was used without further purification. LCMS (ES+) 177.0 and 179.0 $(M+H)^+$.

Intermediate 7

Morpholine-4-carbothioamide

To a stirred solution of 1,1'-thiocarbonyldiimidazole (10.0 g, 56.1 mmol) in THF (150 mL) was added morpholine (4.2 g, 4.2 mL, 48.7 mmol). The reaction mixture was then stirred for 72 h at r.t. before it was concentrated in vacuo to 30 mL and $NH_3$ (60.0 mL, 2.0M in MeOH) was added. The reaction mixture was stirred at r.t. in a sealed flask for 18 h, filtered and the resultant solid washed with $Et_2O$ to give the title compound (2.0 g, 28%) as a white solid that was used without further purification. $\delta_H$ (DMSO-$d_6$) 7.46 (2H, br. s), 3.82-3.61 (4H, m), 3.60-3.53 (4H, m).

Intermediate 8

2-(Morpholin-4-yl)-4,5-dihydro-6H-cyclopenta[d][1,3]thiazol-6-one

To a stirred solution of Intermediate 6 (2.0 g, 11.3 mmol) in DMF (15 mL) was added Intermediate 7 (1.7 g, 11.3 mmol).

The reaction mixture was heated to 85° C. for 16 h, poured into aqueous sat. NaHCO$_3$ solution (70 mL) and extracted with DCM (2×70 mL). The combined organic fractions were dried over MgSO$_4$, filtered and concentrated in vacuo to give the title compound (1.1 g, 44%) as a yellow solid that was used without further purification. LCMS (ES+) 225.0 (M+H)$^+$.

Intermediate 9

Method A (2S)-2-Amino-3-(1H-indol-3-yl)propan-1-ol

To a stirred solution of (S)-tryptophan (4.0 g, 20.0 mmol) in THF (100 mL) at 0° C. was slowly added BH$_3$.Me$_2$S complex (5.9 mL, 10M solution in THF, 59.0 mmol). The reaction mixture was heated to 70° C. for 16 h and, after cooling, the excess borane was quenched by the addition of MeOH (10 mL) at 0° C. The reaction mixture was then concentrated in vacuo and the resultant white solid was dissolved in EtOAc (100 mL) and washed with aqueous 20% NaOH solution (2×70 mL). The organic layer was then extracted into aqueous 2M HCl (2×100 mL). The combined acidic aqueous layers were basified to pH 14 (addition of solid NaOH) and were re-extracted with EtOAc (2×150 mL). The combined organic fractions were washed with brine (70 mL), dried over MgSO$_4$, filtered and concentrated in vacuo to give the title compound (3.5 g, 92%) as a white solid that required no further purification. $\delta_H$ (CD$_3$OD) 7.46 (1H, d, J 7.9 Hz), 7.21 (1H, d, J 8.0 Hz), 6.96 (3H, m), 3.79 (1H, dd, J 11.3 and 3.6 Hz), 3.54 (1H, dd, J 11.2 and 6.2 Hz), 3.05 (1H, m), 2.80 (1H, m), 2.61 (1H, m). Exchangeable protons were not observed.

Intermediate 10

Method B

2-Chloro-N-[(1S)-2-hydroxy-1-(1H-indol-3-ylmethyl)ethyl]acetamide

To a stirred solution of Intermediate 9 (2.0 g, 10.0 mmol) and NEt$_3$ (1.3 g, 1.8 mL, 13.0 mmol) in THF (120 mL) at 0° C. was added chloroacetyl chloride (1.3 g, 1.0 mL, 12.0 mmol) dropwise. The reaction mixture was stirred at r.t. for 1.5 h and was then quenched by the addition of water (5 mL). The reaction mixture was diluted with EtOAc (120 mL) and partitioned with water (100 mL). The organic fraction was washed with brine (100 mL), dried over MgSO$_4$, filtered and concentrated in vacuo to give the title compound (2.4 g, 90%) as a beige solid that was used without further purification. $\delta_H$ (CDCl$_3$) 8.15 (1H, br. s), 7.59 (1H, d, J 7.9 Hz), 7.28 (1H, d, J 8.0 Hz), 7.11 (3H, m), 6.97 (1H, d, J 2.3 Hz), 4.19 (1H, m), 3.92 (2H, d, J 2.9 Hz), 3.59 (2H, m), 2.98 (2H, d, J 6.0 Hz), 2.52 (1H, br. s).

Intermediate 11

Method C (5S)-5-(1H-Indol-3-ylmethyl)morpholin-3-one

To a stirred solution of Intermediate 10 (2.4 g, 9.5 mmol) in THF (100 mL) at 0° C. was added NaH (0.8 g, 60% dispersion in oil, 19.0 mmol) portionwise. The reaction mixture was stirred at r.t. for 1.5 h and then quenched at 0° C. by the addition of ice. The solution was partitioned between EtOAc (100 mL) and water (100 mL) and the organic fraction was dried over MgSO$_4$, filtered and concentrated in vacuo to give the title compound (1.8 g, 82%) as a yellow solid that was used without further purification. $\delta_H$ (CD$_3$OD) 7.46 (1H, d, J 7.8 Hz), 7.25 (1H, d, J 7.8 Hz), 6.95 (3H, m), 3.99 (2H, s), 3.65 (2H, m), 3.52 (1H, m), 2.91 (2H, d, J 6.3 Hz). Exchangeable protons were not observed. LCMS (ES+) 231.0 (M+H)$^+$.

Intermediate 12

3-[(3S)-Morpholin-3-ylmethyl]-1H-indole

To a stirred solution of Intermediate 11 (1.8 g, 7.8 mmol) in THF (100 mL) at 0° C. was slowly added LiAlH$_4$ (1.0 g, 27.0 mmol). After stirring for 16 h at r.t. the reaction mixture was quenched by the dropwise addition of aqueous sat. NaHCO$_3$ solution (20 mL). The resulting mixture was filtered through Celite® and the filtrate was concentrated in vacuo. The resulting solid was azeotroped from toluene. Purification by column chromatography (SiO$_2$, EtOAc) gave the title compound (1.5 g, 89%) as a cream solid. $\delta_H$ (CDCl$_3$) 8.11 (1H, br. s), 7.55 (1H, d, J 7.8 Hz), 7.28 (1H, d, J 8.0 Hz), 7.11 (3H, m), 3.83 (1H, dd, J 10.9 and 2.8 Hz), 3.71 (1H, dt, J 11.3 and 2.2 Hz), 3.47 (1H, m), 3.24 (1H, t, J 9.8 Hz), 3.06 (1H, m), 2.78 (3H, m), 2.56 (1H, m), 1.92 (1H, br. s). LCMS (ES+) 217.0 (M+H)$^+$.

Intermediate 13

Method D tert-Butyl 2,4-dioxooctahydro-1H-cyclopenta[b]pyridine-1-carboxylate

To a stirred solution of 2-[(tert-butoxycarbonyl)amino]cyclopentanecarboxylic acid (0.24 g, 1.06 mmol) in DCM (4.5 mL) was added EDC (0.31 g, 1.59 mmol), DMAP (0.19 g, 1.59 mmol) and Meldrum's acid (0.15 g, 1.06 mmol). After stirring for 18 h at r.t., the reaction mixture was poured into aqueous 1M NaHSO$_4$ solution (5 mL) and extracted with DCM (3×20 mL). The combined organics were dried over MgSO$_4$, filtered and concentrated in vacuo to give a clear yellow oil which was dissolved in EtOAc (5 mL) and heated to 80° C. for 18 h. The reaction mixture was then cooled and concentrated in vacuo to give the title compound (0.25 g, 42%) as a yellow solid that was used without further purification. $\delta_H$ (CDCl$_3$) 4.64-4.55 (1H, m), 2.98-2.92 (1H, m), 2.37-2.20 (2H, m), 1.99-1.60 (6H, m), 1.58 (9H, s). LCMS (ES+) 198.0 ((M−$^t$Bu)+H)$^+$.

Intermediate 14 tert-Butyl 3-bromo-2,4-dioxooctahydro-1H-cyclopenta[b]pyridine-1-carboxylate

To a stirred solution of Intermediate 13 (0.245 g, 0.968 mmol) in THF (10 mL) was added polymer-supported tribromide (Amberlyst® A-26, 1.070 g, 1.070 mmol) and the reaction mixture was stirred at r.t. for 1.5 h. The crude reaction mixture was then filtered, washed with THF (10 mL) and the solvent removed in vacuo to give the title compound as a brown oil, in quantitative yield, that was used without further purification. LCMS (ES−) 332.1 and 330.1 (M)−.

Intermediate 15 tert-Butyl 2,4-dioxo-6-phenylpiperidine-1-carboxylate

The title compound was prepared from 3-[(tert-butoxycarbonyl)amino]-3-phenylpropanoic acid according to Method D and was used as a crude intermediate.

Intermediate 16 tert-Butyl 4,6-dioxo-2-methylpiperidine-1-carboxylate

The title compound was prepared from 3-[(tert-butoxycarbonyl)amino]butanoic acid according to Method D and was used as a crude intermediate.

Intermediate 17 tert-Butyl 4,6-dioxo-2-isopropylpiperidine-1-carboxylate

The title compound was prepared from 3-[(tert-butoxycarbonyl)amino]-4-methylpentanoic acid according to Method D and was used as a crude intermediate.

Intermediate 18 tert-Butyl 4,6-dioxo-2-isobutylpiperidine-1-carboxylate

The title compound was prepared from 3-[(tert-butoxycarbonyl)amino]-5-methylhexanoic acid according to Method D and was used as a crude intermediate.

Intermediate 19 tert-Butyl 2,4-dioxo-6-propylpiperidine-1-carboxylate

The title compound was prepared from 3-[(tert-butoxycarbonyl)amino]hexanoic acid according to Method D and was used as a crude intermediate.

Intermediate 20 tert-Butyl 2-cyclohexyl-4,6-dioxopiperidine-1-carboxylate

The title compound was prepared from 3-[(tert-butoxycarbonyl)amino]-3-cyclohexylpropanoic acid according to Method D and was used as a crude intermediate.

Intermediate 21 tert-Butyl 2,4-dioxo-5-methylpiperidine-1-carboxylate

The title compound was prepared from 3-[(tert-butoxycarbonyl)amino]-2-methylpropanoic acid according to Method D and was used as a crude intermediate.

Intermediate 22

Method E (3S)-3-(1H-Indol-3-ylmethyl)morpholine-4-carbothioamide

To a stirred solution of 1,1'-thiocarbonyldiimidazole (28.6 g, 160.0 mmol) in THF (950 mL) was added Intermediate 12 (31.5 g, 145.8 mmol) in THF (300 mL) dropwise over 1 h. The reaction mixture was stirred at r.t. for 15 minutes and then concentrated in vacuo. A sat. solution of $NH_3$ in MeOH (600 mL) was added and the reaction mixture was stirred at 60° C. in a sealed flask for 12 h. The solution was then concentrated in vacuo and the oily residue purified by column chromatography ($SiO_2$, EtOAc) to give the title compound (17.6 g, 44%) as an orange foam. $\delta_H$(DMSO-$d_6$) 10.85 (1H, br. s), 7.86 (1H, d, J 7.2 Hz), 7.49 (2H, br. s), 7.33 (1H, d, J 8.0 Hz), 7.18 (1H, d, J 2.2 Hz), 7.09-7.01 (1H, m), 7.00-6.94 (1H, m), 3.87 (1H, m), 3.60 (1H, d, J 11.6 Hz), 3.36-3.18 (6H, m), 2.81 (1H, dd, J 13.6 and 4.8 Hz). LCMS (ES+) 276.0 $(M+H)^+$.

Intermediate 23

(3a,R)-Tetrahydro-3H-[1,2,3]oxathiazolo[4,3-c][1,4]oxazine 1,1-dioxide

To a solution of Intermediate 54 (30 g, 257 mmol) dissolved in anhydrous DCM (250 mL) was added pyridine (43.5 mL, 539 mmol) and the solution was cooled to −70° C. ($CO_2$/IPA bath). Sulphuryl chloride (21.7 mL, 270 mmol) dissolved in anhydrous DCM (200 mL) was added dropwise over 1 h (so as to maintain the reaction temperature below −60° C.). The reaction was stirred at −70° C. for 2 h and at −10 to −20° C. (MeOH/ice bath) for 2 h before being quenched by the addition of water (15 mL) and warming to r.t. The solution was separated and the aqueous fraction extracted with further DCM (2×100 mL). The combined organic fractions were washed with water (15 mL), brine (15 mL), dried ($Na_2SO_4$), filtered and concentrated in vacuo to give the title compound (24.7 g, 54%) as a yellow oil which solidified to an orange sticky solid on standing at r.t. that was used without further purification. $\delta_H$ ($CDCl_3$) 4.51 (1H, dd, J 8.1 and J 6.4 Hz), 4.23 (1H, dd, J 9.1 and J 8.1 Hz), 3.95 (1H, dd, J 11.6 and J 3.4 Hz), 3.84-3.64 (3H, m), 3.54 (1H, dd, J 11.6 and J 7.7 Hz), 3.29 (1H, dt, J 12.0 and J 3.4 Hz), 3.06 (1H, m).

Intermediate 24

(3S)-3-(Prop-2-yn-1-yl)morpholine

To a solution of trimethylsilyl acetylene (27.59 mL, 195.25 mmol) dissolved in anhydrous THF (250 mL) at 0° C. was added n-butyllithium (78.1 mL, 201 mmol, 2.5M in hexanes) dropwise over 15 minutes. After stirring at this temperature for 40 minutes, a solution of Intermediate 23 (11.65 g, 65.083 mmol) dissolved in DMPU (11 mL) was added slowly over 15 minutes and the reaction mixture was allowed to warm to r.t. After stirring at r.t. for 18 h, the reaction mixture was quenched by the addition of water (ca 4 mL) and the solvent (not DMPU) was removed in vacuo. To the resultant dark oil were added aqueous HCl (10% v/v, 200 mL) and MeOH (100 mL) and the reaction mixture was stirred at r.t. for 18 h. The solution was then concentrated in vacuo to give the title compound (17.059 g, ca 74% yield) as a crude dark oil (containing ca 11 mL DMPU) that was used without further purification. $\delta_H$ ($CD_3OD$) 3.89 (1H, dd, J 11.2 and J 3.1 Hz), 3.76

(1H, dt, J 11.2 and J 2.7 Hz), 3.45-3.56 (1H, m), 3.25 (1H, m), 2.89 (3H, m), 2.39 (1H, t, J 2.7 Hz), 2.25 (2H, dd, J 6.8 and J 2.7 Hz). Exchangeable proton was not observed.

Intermediate 25 tert-Butyl (3S)-3-(prop-2-yn-1-yl)morpholine-4-carboxylate

To a solution of crude Intermediate 24 (17.059 g, containing 11 mL DMPU), dissolved in anhydrous DCM (300 mL) at 0° C., was added DIPEA (13.04 mL, 74.85 mmol) and di-tert-butyl dicarbonate (15.624 g, 71.59 mmol) and the reaction mixture warmed to r.t. After stirring for 18 h, the reaction mixture was washed with brine and the organic fraction was dried using an Isolute® phase separator cartridge and concentrated in vacuo to give a dark brown oil. Purification by column chromatography (SiO$_2$, 10:1 EtOAc/hexanes) gave the title compound (8.79 g, 59% from Intermediate 23) as a yellow oil. $\delta_H$ (CD$_3$OD) 3.95 (1H, m), 3.75 (1H, d, J 14.2 Hz), 3.70 (1H, m), 3.58 (1H, m), 3.42 (1H, m), 3.30 (1H, m), 2.95 (1H, m), 2.51 (1H, m), 2.37 (1H, m), 2.19 (1H, t, J 2.7 Hz), 1.35 (9H, s).

Intermediate 26

Method H tert-Butyl (3S)-3-[3-(trimethylsilyl)prop-2-yn-1-yl]morpholine-4-carboxylate To a solution of Intermediate 25 (8.05 g, 35.7 mmol) dissolved in anhydrous THF (250 mL) at 0° C. was added n-butyllithium (15.7 mL, 39.3 mmol, 2.5 M in hexanes) dropwise over 15 minutes. After stirring for 30 minutes, chlorotrimethylsilane was added slowly over 5 minutes and the reaction mixture stirred for 45 minutes and then allowed to warm to r.t. After stirring at r.t. for 18 h, the reaction mixture was quenched by the addition of water (ca 1 mL) and the solvent was removed in vacuo. The crude mixture was dissolved in DCM and washed with water, the aqueous phase was extracted with further DCM (500 mL) and the combined organic fractions were dried using an Isolute® phase separator cartridge and concentrated in vacuo to give a dark brown oil. Purification by column chromatography (SiO$_2$, 5-20% EtOAc/hexanes) gave the title compound (8.1 g, 76%) as a colourless oil and recovered starting material (1.25 g, 15%). $\delta_H$ (CD$_3$OD) 3.91 (1H, m), 3.82 (1H, d, J 11.7 Hz), 3.70 (1H, dd, J 3.6 and J 11.4 Hz), 3.58 (1H, dd, J 2.9 and J 13.7 Hz), 3.40-3.20 (2H, m), 2.95 (1H, m), 2.60 (1H, dd, J 9.1 and J 16.7 Hz), 2.38 (1H, dd, J 6.4 and J 16.7 Hz), 1.35 (9H, s), 0.00 (9H, s).

Intermediate 27

Method I tert-Butyl (3S)-3-{[5-(difluoromethoxy)-2-(trimethylsilyl)-1H-indol-3-yl]methyl}morpholine-4-carboxylate To a solution of Intermediate 26 (0.571 g, 1.93 mmol) dissolved in DMF (23 mL) was added Intermediate 71 (0.55 g, 1.93 mmol), LiCl (0.082 g, 1.93 mmol), Na$_2$CO$_3$ (0.409 g, 3.86 mmol) and Pd(OAc)$_2$ (0.017 g, 0.08 mmol) and the reaction mixture was degassed under vacuum and then purged with nitrogen. The reaction mixture was then heated at 100° C. for 6 h. The crude reaction mixture was cooled to r.t. and the solvent removed in vacuo to give a brown oil. Purification by column chromatography (SiO$_2$, 10-30% EtOAc/hexanes; followed by SiO$_2$, DCM) gave the title compound (0.462 g, 53%) as a yellow oil. LCMS (ES+) 399.0 ((M−$^t$Bu)+H)$^+$, RT 3.95 minutes (Method 5).

Intermediate 28

Method J

5-(Difluoromethoxy)-3-[(3S)-morpholin-3-ylmethyl]-1H-indole

To Intermediate 27 (0.285 g, 0.63 mmol) at 0° C. was added 4M HCl in 1,4-dioxane (8 mL) and the reaction mixture was stirred at r.t. for 2 h. The reaction mixture was concentrated in vacuo and the crude residue was dissolved in DCM (25 mL) and washed with aqueous sat. NaHCO$_3$ solution (5 mL). The aqueous fraction was further extracted with DCM (3×20 mL) and the combined organic fractions were dried (Na$_2$SO$_4$), filtered and concentrated in vacuo to give the title compound (0.197 g, quantitative) as a yellow oil that was used without further purification. LCMS (ES+) 283.0 (M+H)$^+$, RT 2.27 minutes (Method 5).

Intermediate 29

Method K

(3S)-3-{[5-(Difluoromethoxy)-1H-indol-3-yl]methyl}morpholine-4-carbothioamide To a solution of 1,1'-thiocarbonyldiimidazole (0.137 g, 0.77 mmol) in THF (5 mL) was added Intermediate 28 (0.197 g, 0.70 mmol) dissolved in THF (5 mL) and the reaction mixture was stirred at r.t. for 18 h. The reaction mixture was concentrated in vacuo and dissolved in MeCN (7 mL) and aqueous NH$_3$ (20% v/v, 7 mL) added. The reaction mixture was stirred at 60° C. for 4 h. After cooling to r.t., the reaction mixture was concentrated in vacuo to give a yellow oil. The crude material was purified by column chromatography (SiO$_2$, 9:10 EtOAc/hexanes) to give the title compound (0.106 g, 44%) as a yellow oil. LCMS (ES+) 342.0 (M+H)$^+$, RT 2.91 minutes (Method 5).

Intermediate 30 tert-Butyl (3S)-3-{[2,2-difluoro-6-(trimethylsilyl)-5H-[1,3]dioxolo[4,5-f]indol-7-yl]methyl}morpholine-4-carboxylate The title compound was prepared from 2,2-difluoro-5-amino-6-iodo-1,3-benzodioxole and Intermediate 26 according to Method I and was isolated as a yellow gum (30%) after purification by column chromatography (SiO$_2$, 5-20% EtOAc/hexanes). LCMS (ES+) 414.0 ((M−$^t$Bu)+H)$^+$, RT 4.34 minutes (Method 5).

Intermediate 31

2,2-Difluoro-7-[(3S)-morpholin-3-ylmethyl]-5H-[1,3]dioxolo[4,5-f]indole

The title compound was prepared from Intermediate 30 according to Method J and was isolated as a brown gum (quantitative) that was used as a crude intermediate. LCMS (ES+) 297.0 (M+H)+, RT 2.08 minutes (Method 3).

Intermediate 32

(3S)-3-[(2,2-Difluoro-5H-[1,3]dioxolo[4,5-f]indol-7-yl)methyl]morpholine-4-carbothioamide The title compound was prepared from Intermediate 31 according to Method K and was isolated as a yellow gum (58%) after purification by column chromatography (SiO$_2$, 0-2% MeOH/DCM). LCMS (ES+) 356.0 (M+H)+, RT 3.03 minutes (Method 5).

Intermediate 33

Benzyl (3S)-3-(prop-2-yn-1-yl)morpholine-4-carboxylate

To a solution of crude Intermediate 24 (2.806 g) dissolved in DCM (50 mL) cooled to 0° C. was added NEt$_3$ (6.5 mL, 46.8 mmol) followed by benzyl chloroformate (4.85 mL, 33.9 mmol). The mixture was stirred at r.t. for 18 h. The reaction mixture was diluted further with DCM (100 mL) and washed with aqueous sat. NaHCO$_3$ solution (20 mL). The aqueous fraction was further extracted with DCM (3×50 mL). The combined organic fractions were concentrated in vacuo to give a brown oil. The crude material was purified by column chromatography (SiO$_2$, 0.5-1% MeOH/DCM; followed by SiO$_2$, EtOAc) to yield the title compound (4.01 g, 68% from Intermediate 23) as a yellow oil. $\delta_H$ (DMSO-d$_6$) 7.42-7.27 (5H, m), 4.73 (2H, br. s), 4.03-3.97 (1H, m), 3.77-3.74 (2H, m), 3.64 (1H, dd, J 13.6 and J 2.6 Hz), 3.44 (1H, dd, J 11.7 and J 3.1 Hz), 3.35-3.26 (1H, m), 3.09-3.03 (1H, m), 2.83 (1H, t, J 2.6 Hz), 2.58-2.57 (1H, m), 2.48-2.46 (1H, m). LCMS (ES+) 260.1 (M+H)+, RT 3.25 minutes (Method 5).

Intermediate 34

Benzyl (3S)-3-[3-(trimethylsilyl)prop-2-yn-1-yl]morpholine-4-carboxylate

The title compound was prepared from Intermediate 33 according to Method H and was isolated as a yellow oil (12%) after purification by column chromatography (SiO$_2$, 1:10 EtOAc/hexanes). $\delta_H$ (CD$_3$OD) 7.28-7.15 (5H, m), 5.03 (2H, br. s), 4.06-4.00 (1H, m), 3.79-3.70 (1H, m), 3.66 (1H, dd, J 13.7 and J 3.0 Hz), 3.42 (1H, dd, J 12.0 and J 3.2 Hz), 3.32 (1H, dt, J 12.0 and J 3.0 Hz), 3.20 (1H, quint, J 1.6 Hz), 3.10-3.00 (1H, m), 2.63-2.54 (2H, m), 0.00 (9H, s). LCMS (ES+) 332.0 (M+H)+, RT 3.83 minutes (Method 5).

Intermediate 35

Benzyl (3S)-3-{[5-(trifluoromethoxy)-2-(trimethylsilyl)-1H-indol-3-yl]methyl}morpholine-4-carboxylate The title compound was prepared from Intermediate 34 and 2-iodo-4-trifluoromethoxyaniline according to Method I and was isolated as a yellow oil (46%) after purification by column chromatography (SiO$_2$, 5-10% EtOAc/hexanes). $\delta_H$ (CD$_3$OD) 7.70-7.40 (1H, br. m), 7.29-7.19 (6H, m), 6.89-6.86 (1H, m), 5.07 (2H, s), 4.13-4.00 (1H, m), 3.83-3.77 (2H, m), 3.55-3.51 (1H, m), 3.44-3.26 (4H, m), 2.89-2.75 (1H, m), 0.28 (9H, s). Exchangeable proton was not observed. LCMS (ES+) 507.0 (M+H)+, RT 4.12 minutes (Method 5).

Intermediate 36

3-[(3S)-Morpholin-3-ylmethyl]-5-(trifluoromethoxy)-1H-indole

To a solution of Intermediate 35 (0.290 g, 0.57 mmol) dissolved in MeCN (8 mL) at 0° C. was added iodotrimethylsilane (0.312 mL, 2.29 mmol) and the reaction mixture was stirred at 0° C. for 4 h. Aqueous HCl (10% v/v, 2 mL) was added to the reaction mixture at 0° C. and the aqueous fraction extracted with Et$_2$O (20 mL). The aqueous fraction was basified with aqueous NaOH (2M, 5 mL) and extracted with DCM (30 mL). The organic fraction was concentrated in vacuo to yield the title compound (0.160 g, 93%) as a yellow oil. The crude material was used without further purification. $\delta_H$ (CD$_3$OD) 7.47 (1H, s), 7.40 (1H, d, J 8.8 Hz), 7.22 (1H, s), 7.02 (1H, dd, J 8.8 and J 1.1 Hz), 3.82-3.74 (2H, m), 3.59-3.46 (1H, m), 3.39-3.24 (1H, m), 3.10-3.01 (1H, m), 2.88-2.84 (2H, m), 2.81-2.73 (2H, m). Exchangeable protons were not observed. LCMS (ES+) 301.0 (M+H)+, RT 2.38 minutes (Method 5).

Intermediate 37

(3S)-3-{[5-(Trifluoromethoxy)-1H-indol-3-yl]methyl}morpholine-4-carbothioamide

The title compound was prepared from Intermediate 36 according to Method E (at 50° C.) and was isolated as a colourless oil (53%) after purification by column chromatography (SiO$_2$, 30-50% EtOAc/DCM). $\delta_H$ (CDCl$_3$) 8.39 (1H, br. s), 7.63 (1H, br. s), 7.27 (1H, d, J 8.8 Hz), 7.12 (1H, d, J 2.3 Hz), 6.99 (1H, dd, J 8.8 and J 1.1 Hz), 5.63 (2H, br. s), 3.98-3.86 (1H, m), 3.77 (1H, d, J 11.9 Hz), 3.52-3.38 (3H, m), 3.20-3.04 (2H, m). LCMS (ES+) 360.0 (M+H)+, RT 2.52 minutes (Method 3).

Intermediate 38 tert-Butyl (3S)-3-{[5-nitro-2-(trimethylsilyl)-1H-indol-3-yl]methyl}morpholine-4-carboxylate The title compound was prepared from 2-iodo-4-nitroaniline and Intermediate 26 according to Method I and was isolated as an orange oil (39%) after purification by column chromatography (SiO$_2$, 30:70 EtOAc/hexanes). LCMS (ES+) 334.0 (M−BOC)+, RT 3.92 minutes (Method 5).

Intermediate 39

3-[(3S)-Morpholin-3-ylmethyl]-5-nitro-1H-indole

The title compound was prepared from Intermediate 38 according to Method J and was isolated as an orange-brown solid (80%) that was used as a crude intermediate. LCMS (ES+) 262.0 (M+H)+, RT 2.18 minutes (Method 5).

Intermediate 40

(3S)-3-[5-Nitro-1H-indol-3-yl)methyl]morpholine-4-carbothioamide

The title compound was prepared from Intermediate 39 according to Method K and was isolated as an orange solid (quantitative) after purification by column chromatography

Intermediate 41

Methyl 3-{[(3S)-4-(tert-butoxycarbonyl)morpholin-3-yl]methyl}-2-(trimethylsilyl)-1H-indole-5-carboxylate The title compound was prepared from methyl 4-amino-3-iodobenzoate and Intermediate 26 according to Method I and was isolated as a yellow sticky solid (59%) after purification by column chromatography (SiO$_2$, 10-25% EtOAc/hexanes). LCMS (ES+) 392.0 ((M−$^t$Bu)+H)$^+$, RT 3.58 minutes (Method 3).

Intermediate 42

Methyl 3-[(3S)-morpholin-3-ylmethyl]-1H-indole-5-carboxylate

The title compound was prepared from Intermediate 41 according to Method J and was isolated as a brown gum (quantitative) that was used as a crude intermediate. LCMS (ES+) 275.0 (M+H)$^+$, RT 2.30 minutes (Method 5).

Intermediate 43

Methyl 3-{[(3S)-4-(aminocarbonothioyl)morpholin-3-yl]methyl}-1H-indole-5-carboxylate The title compound was prepared from Intermediate 42 according to Method K and was isolated as a yellow solid (99%) after purification by column chromatography (SiO$_2$, 0-4% MeOH/DCM). LCMS (ES+) 334.0 (M+H)$^+$, RT 2.25 minutes (Method 4).

Intermediate 44

Pentafluorophenyl 3-{[(3S)-4-(6,6-dimethyl-4-oxo-4,5,6,7-tetrahydro[1,3]thiazolo[5,4-c]pyridin-2-yl)morpholin-3-yl]methyl}-1H-indole-5-carboxylate To a solution of Example 21 (1.96 g, 4.46 mmol) in DMF (10 mL) and DCM (150 mL) was added pentafluorophenol (0.86 g, 4.68 mmol) and EDC (0.94 g, 4.91 mmol) and the reaction mixture was stirred at r.t. for 16 h. DIPEA (1.15 g, 1.56 mL, 8.92 mmol), and further pentafluorophenol (0.22 g, 1.20 mmol) and EDC (0.24 g, 1.25 mmol), were added and stirred for an additional 2 h at r.t. The reaction mixture was washed with water (2×50 mL), brine (50 mL), dried (Na$_2$SO$_4$), filtered and concentrated in vacuo. Purification by column chromatography (SiO$_2$, 0-6% MeOH/DCM) gave the title compound (1.41 g, 52%) as a brown gum. LCMS (ES+) 607.3 (M+H)$^+$, RT 3.23 minutes (Method 3).

Intermediate 45

(3S)-3-(3-Bromobenzyl)morpholine-4-carbothioamide

To a stirred solution of 1,1'-thiocarbonyldiimidazole (13.31 g, 74.8 mmol) in THF (250 mL) was added dropwise over a period of 30 minutes a solution of Intermediate 59 (17.35 g, 68.0 mmol) in THF (250 mL). The reaction mixture was stirred at r.t. for 24 h then concentrated in vacuo. The intermediate was re-dissolved in MeCN (200 mL) and aqueous NH$_3$ (20% v/v, 300 mL) was added. The solution was heated at 60° C. for 8 h. Another portion of aqueous NH$_3$ was added and the mixture was stirred at r.t. for 24 h then concentrated in vacuo. The residue was re-dissolved in DCM (200 mL) and the solution was washed with aqueous sat. NH$_4$Cl solution (2×150 mL), dried (Na$_2$SO$_4$), filtered and concentrated in vacuo to give the title compound (22 g, quantitative) as a yellow solid that was used without further purification. LCMS (ES+) 315.0 and 317.0 (1:1 ratio) (M+H)$^+$, RT 2.69 minutes (Method 3).

Intermediate 46

3-Bromo-6,6-dimethylpiperidine-2,4-dione

To a stirred suspension of Intermediate 3 (10.00 g, 70.9 mmol) in THF (200 mL) was added NaHSO$_4$ (2.12 g, 17.7 mmol). The suspension was cooled to 0° C. and NBS (12.62 g, 70.9 mmol) was added portionwise. The reaction mixture was stirred at r.t. for 5 h then DCM (200 mL) and water (100 mL) were added. The aqueous fraction was extracted with DCM (2×100 mL). The combined organic fractions were washed with water (3×200 mL), dried (Na$_2$SO$_4$), filtered and the solvent evaporated in vacuo. The white solid was triturated with IPA (3×50 mL), then filtered to give the title compound (10.3 g, 66%) as a white solid. $\delta_H$ (DMSO-d$_6$) 10.80 (1H, br. s), 7.26 (1H, br. s), 2.50 (2H, s) for the main tautomer. LCMS (ES+) 220.0 and 222.0 (1:1 ratio) (M+H)$^+$, RT 1.94 minutes (Method 3).

Intermediate 47

2-Amino-3-(6-fluoro-1H-indol-3-yl)propan-1-ol

6-Fluorotryptophan (1.9 g, 9.153 mmol) was dissolved in THF (50 mL) and cooled to 0° C. in an ice bath. BH$_3$.Me$_2$S complex (2.55 mL, 26.87 mmol) was added and the reaction mixture was heated at reflux for 21 h. The reaction mixture was then cooled in an ice bath and cautiously quenched by the dropwise addition of MeOH (5 mL). The crude reaction mixture was then concentrated in vacuo. The crude product was dissolved in EtOAc (50 mL) and extracted with aqueous NaOH (20% w/v, 2×50 mL) after which the combined aqueous fractions were extracted with EtOAc (2×50 mL), and the combined organic fractions were washed with brine (50 mL), dried (MgSO$_4$), filtered and concentrated in vacuo to give the title compound (2.24 g, quantitative) as a white semi-solid that was used without further purification. $\delta_H$ (CD$_3$OD) 7.28 (1H, dd, J 8.9 and J 5.5 Hz), 6.85 (1H, s), 6.83 (1H, dd, J 10.0 and J 2.3 Hz), 6.57 (1H, dt, J 8.1 and J 8.6 Hz), 3.37 (1H, dd, J 10.7 and J 4.3 Hz), 3.19 (1H, dd, J 10.7 and J 6.8 Hz), 2.92 (1H, m), 2.67 (1H, dd, J 14.1 and J 5.8 Hz), 2.47 (1H, dd, J 14.3 and J 7.5 Hz). No exchangeable protons were observed. LCMS (ES+) 208.0 (M)$^+$, RT 1.30 minutes (Method 1).

Intermediate 48

2-Chloro-N-[2-(6-fluoro-1H-indol-3-yl)-1-(hydroxymethyl)ethyl]acetamide

Crude Intermediate 47 (2.24 g) was dissolved in THF (120 mL) and cooled to 0° C. in an ice bath. NEt$_3$ (1.58 mL, 11.88 mmol) was added followed by the dropwise addition of chloroacetyl chloride (0.84 mL, 10.546 mmol). The reaction mixture was allowed to warm to r.t. and left to stir for 3 h. The reaction mixture was quenched by the addition of water (5 mL) and concentrated in vacuo. The crude product was dissolved in EtOAc (100 mL) and washed with water (2×100

(SiO$_2$, 1:20 MeOH/DCM) and used as a crude intermediate. LCMS (ES+) 321.0 (M+H)$^+$, RT 2.76 minutes (Method 5).

mL), brine (50 mL), dried (MgSO$_4$), filtered and concentrated in vacuo. Purification by column chromatography (SiO$_2$, heptane-EtOAc) gave the title compound (1.8 g, 72%) as a colourless oil. $\delta_H$ (CD$_3$OD) 7.57 (1H, dd, J 8.7 and J 5.3 Hz), 7.07 (1H, s), 7.01 (1H, dd, J 10.0 and J 2.3 Hz), 6.79 (1H, dt, J 8.1 and J 2.4 Hz), 4.20 (1H, m), 4.00 (2H, d, J 1.1 Hz), 3.58 (2H, dd, J 9.7 and J 5.2 Hz), 3.02 (1H, dd, J 14.5 and J 7.0 Hz), 2.91 (1H, dd, J 14.5 and J 6.9 Hz). No exchangeable protons were observed. LCMS (ES+) 285.0 (M+H)$^+$, RT 2.44 minutes (Method 1).

Intermediate 49

5-(6-Fluoro-1H-indol-3-ylmethyl)morpholin-3-one

Intermediate 48 (1.8 g, 6.3 mmol) was dissolved in THF (60 mL) and cooled to 0° C. in an ice bath. NaH (0.529 g, 60% dispersion in oil, 13.22 mmol) was added portionwise over 5 minutes. The reaction mixture was then allowed to warm to r.t. and left to stir for 90 minutes. The reaction mixture was quenched by the addition of ice (ca 50 mL) and extracted with EtOAc (2×50 mL). The combined organic fractions were washed with brine, dried (MgSO$_4$), filtered and concentrated in vacuo. Purification by column chromatography (SiO$_2$, 0-50% MeOH/DCM) gave the title compound (0.726 g, 46%) as a colourless foam. $\delta_H$ (CD$_3$OD) 7.50 (1H, dd, J 8.9 and J 5.5 Hz), 7.11 (1H, s), 7.04 (1H, dd, J 10.0 and J 2.1 Hz), 6.77-6.87 (1H, m), 4.10 (2H, s), 3.68-3.80 (2H, m), 3.54-3.67 (1H, m), 3.00 (2H, m). Exchangeable protons were not observed. LCMS (ES+) 249.0 (M+H)$^+$, RT 2.47 minutes (Method 1).

Intermediate 50

6-Fluoro-3-(morpholin-3-ylmethyl)-1H-indole

Intermediate 49 (0.726 g, 2.92 mmol) was dissolved in THF (100 mL) and cooled to 0° C. in an ice bath. BH$_3$.Me$_2$S complex (0.61 mL, 6.40 mmol) was added dropwise and the reaction mixture allowed to warm to r.t. The reaction mixture was heated to reflux for 5 h and allowed to cool to r.t. The reaction mixture was quenched with aqueous 2N NaOH (25 mL) and stirred at r.t. for 72 h. The reaction mixture was concentrated in vacuo and dissolved in EtOAc (100 mL), washed with aqueous 2N HCl (2×50 mL) and the combined aqueous fractions basified with solid NaOH pellets (ca 10 g) to raise the pH to pH 12. The aqueous fraction was extracted with EtOAc (3×50 mL) and the combined organic fractions were dried (MgSO$_4$), filtered and concentrated in vacuo. The material from the initial EtOAc extraction was combined with the concentrated material and purified by column chromatography (SiO$_2$, 0-25% [MeOH/DCM/NH$_4$OH (50:50:1)]/DCM) to afford 0.493 g as a mixture of 6-fluoro-3-(morpholin-3-ylmethyl)indoline and title compound (1:3). The resulting mixture was dissolved in THF (7.5 mL) followed by the addition of DDQ (0.102 g, 0.452 mmol). The reaction mixture was irradiated in the microwave at 100° C. for 10 minutes. The reaction mixture was diluted with EtOAc (50 mL), washed with aqueous 2N NaOH (20 mL), brine (20 mL), dried (MgSO$_4$), filtered, concentrated in vacuo and purified by column chromatography (SiO$_2$, 0-25% [MeOH/DCM/NH$_4$OH (50:50:1)]/DCM) to give the title compound (0.430 g, 61%) as an amber oil. $\delta_H$ (CDCl$_3$) 8.04 (1H, br. s), 7.52 (1H, dd, J 8.7 and J 5.3 Hz), 7.00-7.09 (2H, m), 6.85-6.95 (1H, m), 3.90 (1H, dd, J 10.9 and J 2.8 Hz), 3.76-3.85 (1H, m), 3.49-3.61 (1H, m), 3.24-3.36 (1H, m), 3.17-3.03 (1H, m), 2.95-2.76 (3H, m), 2.62 (1H, dd, J 14.3 and J 9.0 Hz), 1.78 (1H, br. s). LCMS (ES+) 235.0 (M+H)$^+$, RT 1.85 minutes (Method 2).

Intermediate 51

N-Benzyl-D-serine

To a stirred solution of D-serine (14.7 g, 140.0 mmol) in aqueous 2M NaOH (70 mL) was added benzaldehyde (14.6 g, 14.0 mL, 138.0 mmol). The reaction mixture was then stirred at r.t. for 1 h before cooling to 5° C. NaBH$_4$ (1.5 g, 40.0 mmol) was added portionwise such that an internal temperature of between 6 and 10° C. was maintained. After addition, the reaction mixture was allowed to stir at 5° C. for 30 minutes and then at r.t. for 1 h. The reaction mixture was cooled to 5° C. and a further portion of NaBH$_4$ (1.5 g, 40.0 mmol) was added portionwise such that an internal temperature of <10° C. was maintained. The ice bath was removed on completion of addition and the reaction mixture stirred at r.t. for 16 h. The reaction mixture was then extracted with Et$_2$O (3×100 mL) and the aqueous phase acidified to pH 5 with conc. HCl. The resultant white precipitate was filtered and washed with water. The product was dried in vacuo to give the title compound (24.0 g, 88%) as a white solid. $\delta_H$ (DMSO-d$_6$) 7.45-7.30 (5H, m), 4.04-3.91 (2H, m), 3.70-3.61 (3H, m), 3.17 (1H, t, J 5.8 Hz).

Intermediate 52

(3R)-4-Benzyl-5-oxomorpholine-3-carboxylic acid

To a stirred solution of Intermediate 51 (35.0 g, 179.0 mmol) in aqueous NaOH solution (9.3 g, 200.0 mL, 232.5 mmol) at 0° C. was slowly added chloroacetyl chloride (24.2 g, 17.0 mL, 214.0 mmol). The reaction mixture was allowed to warm to r.t. and then stirred for 30 minutes. Aqueous 10M NaOH solution (45.0 mL, 465.0 mmol) was added and the reaction mixture heated to 45° C. for 4 h. The reaction mixture was then cooled to 10° C. and acidified to pH 1 with conc. HCl. On standing at 4° C. the product crystallised from the mixture and was collected by filtration, washed with cold water and then dried in vacuo to give the title compound (18.0 g, 43%) as a white solid. $\delta_H$ (DMSO-d$_6$) 13.51-12.53 (1H, br. s), 7.38-7.25 (5H, m), 5.27 (1H, d, J 15.3 Hz), 4.24-4.10 (3H, m), 3.94-3.88 (2H, m), 3.83 (1H, d, J 15.3 Hz). LCMS (ES+) 236.0 (M+H)$^+$.

Intermediate 53

[(3S)-(4-Benzylmorpholin-3-yl)]methanol

To a stirred solution of Intermediate 52 (17.7 g, 75.3 mmol) in THF (300 mL) was added NEt$_3$ (7.3 g, 10.0 mL, 72.0 mmol). The solution was then cooled to 0° C. and BH$_3$.Me$_2$S complex (10M in THF, 45.0 mL, 450.0 mmol) was added slowly. The reaction mixture was heated at reflux for 12 h and, after cooling to r.t., the excess borane was destroyed by slow addition of MeOH at 0° C. The reaction mixture was concentrated in vacuo and the resultant white solid was dissolved in EtOAc (120 mL) and washed with aqueous NaOH solution (20% v/v, 2×100 mL). The organic fraction was then extracted into aqueous 2M HCl (2×150 mL). The combined acidic aqueous fractions were then basified to pH 14 (addition of solid NaOH) and were re-extracted with EtOAc (2×150 mL). The combined organic fractions were washed with brine (150 mL), dried (MgSO$_4$), filtered and concentrated in vacuo to give the title compound (13.5 g, 87%) as a clear oil that required no further purification. $\delta_H$ (CDCl$_3$) 7.29-7.16 (5H, m), 4.05 (1H, d, J 12.8 Hz), 3.88 (1H, dd, J 11.5 and J 4.5 Hz), 3.78 (1H, m), 3.70-3.53 (2H, m), 3.51-3.40 (2H, m), 3.20 (1H, d, J 13.2 Hz), 2.68 (1H, dt, J 12.1 and J 2.8 Hz), 2.48 (1H, m), 2.27 (1H, m), 2.20-2.15 (1H, br. s).

Intermediate 54

(3S)-Morpholin-3-ylmethanol

To a nitrogen-flushed solution of Intermediate 53 (10.0 g, 48.3 mmol) in MeOH (300 mL) was added 10 wt % palladium on carbon (2.0 g) and the reaction mixture placed in a Parr® apparatus under 50 psi of H$_2$ for 18 h. The resulting mixture was then filtered through Celite® and concentrated in vacuo to give the title compound (5.2 g, 92%) as a colourless oil. $\delta_H$ (CDCl$_3$) 3.81-3.76 (2H, m), 3.58-3.43 (3H, m), 3.35-3.28 (1H, m), 2.99-2.91 (5H, br. m). LCMS (ES+) 118.0 (M+H)$^+$.

Intermediate 55

3-Bromo-L-phenylalanine (2S)-3-(3-Bromophenyl)-2-(tert-butoxycarbonylamino) propionic acid (5.0 g, 14.5 mmol) was suspended in 4M HCl in 1,4-dioxane (75 mL) and stirred for 16 h at r.t. The white precipitate was filtered and washed with Et$_2$O to give the title compound (3.2 g, 89%) as a white solid that required no further purification. $\delta_H$ (CDCl$_3$) 8.32 (2H, s), 7.50-7.48 (2H, m), 7.34-7.29 (2H, m), 4.22 (1H, t, J 6.2 Hz), 3.13-3.11 (2H, m).

Intermediate 56

(2S)-2-Amino-3-(3-bromophenyl)propan-1-ol

The title compound was prepared from Intermediate 55 according to Method A and was isolated as a colourless oil (56%) that required no further purification. $\delta_H$ (CDCl$_3$) 7.42-7.35 (2H, m), 7.29-7.19 (2H, m), 3.59 (1H, m), 3.39 (1H, m), 3.10 (1H, m), 2.78 (1H, dd, J 13.5 and J 5.3 Hz), 2.51 (1H, dd, J 13.5 and J 8.5 Hz).

Intermediate 57

N-[(1S)-1-(3-Bromobenzyl)-2-hydroxyethyl]-2-chloroacetamide

The title compound was prepared from Intermediate 56 according to Method B and was isolated as a yellow oil (77%) after purification by column chromatography (SiO$_2$, 1:1 EtOAc/DCM). $\delta_H$ (DMSO-d$_6$) 8.06 (1H, d, J 8.4 Hz), 7.42 (1H, s), 7.39-7.35 (1H, m), 7.26-7.19 (2H, m), 4.85 (1H, t, J 5.6 Hz), 3.98 (2H, s), 3.87 (1H, m), 3.39-3.15 (2H, m), 2.84 (1H, dd, J 13.7 and J 5.4 Hz), 2.65 (1H, dd, J 13.7 and J 8.6 Hz).

Intermediate 58

(5S)-5-(3-Bromobenzyl)morpholin-3-one

The title compound was prepared from Intermediate 57 according to Method C and was isolated as a white solid (50%) after purification by column chromatography (SiO$_2$, 1:1 EtOAc/DCM). $\delta_H$ (CDCl$_3$) 7.36-7.32 (1H, m), 7.28 (1H, s), 7.19-7.11 (1H, m), 7.06-7.03 (1H, m), 6.26 (1H, br. s), 4.09 (2H, s), 3.81 (1H, dd, J 11.7 and J 3.6 Hz), 3.71-3.62 (1H, m), 3.50 (1H, dd, J 11.6 and J 6.0 Hz), 2.79 (1H, dd, J 13.6 and J 6.1 Hz), 2.67 (1H, dd, J 13.6 and J 8.2 Hz). LCMS (ES+) 270.0 and 272.0 (M+H)$^+$.

Intermediate 59

(3S)-3-(3-Bromobenzyl)morpholine

To a stirred solution of Intermediate 58 (0.8 g, 3.0 mmol) in THF (100 mL) at 0° C. was added BH$_3$.Me$_2$S complex (1.7 mL, 10 M solution in THF, 17.7 mmol) dropwise. The reaction was then carried out according to Method A to give the title compound (0.7 g, 83%) as a colourless oil. LCMS (ES+) 256.0 and 258.0 (M+H)$^+$.

Intermediate 60

Method L

6-Bromo-4H-benzo[1,4]oxazin-3-one

NEt$_3$ (2.4 mL, 17 mmol) was added to 2-amino-4-bromophenol (2.5 g, 13 mmol) in THF (80 mL). The reaction mixture was cooled to 0° C., chloroacetyl chloride (1.12 mL, 14 mmol) was added portionwise and then stirred at 0° C. for 10 minutes before being allowed to warm to r.t. and stirred for a further 2 h. The reaction mixture was cooled to 0° C. and NaH (1.05 g, 60% dispersion in oil, 26 mmol) was added portionwise. The reaction mixture was stirred at 0° C. for 20 minutes then at r.t. for 2 h before being quenched with water (20 mL). The solvent was removed in vacuo and the resulting mixture diluted with water (100 mL). The precipitate was filtered, washed with water (3×50 mL) and dried in vacuo to give the title compound (2.14 g, 70%) as a beige solid. $\delta_H$ (DMSO-d$_6$) 10.81 (1H, br. s), 7.08 (1H, dd, J 8.5 and J 2.3 Hz), 7.02 (1H, d, J 2.3 Hz), 6.92 (1H, d, J 8.5 Hz), 4.60 (2H, s).

Intermediate 61

6-Nitro-4H-benzo[1,4]oxazin-3-one

The title compound was prepared from 2-amino-4-nitrophenol according to Method L and was isolated as a grey solid (33%). $\delta_H$ (DMSO-d$_6$) 11.09 (1H, s), 7.84 (1H, dd, J 8.9 and J 2.6 Hz), 7.74 (1H, d, J 2.4 Hz), 7.15 (1H, d, J 8.9 Hz), 4.78 (2H, s).

Intermediate 62

Method M

6-Bromo-3,4-dihydro-2H-benzo[1,4]oxazine

Borane-THF (13.2 mL, 1M solution in THF, 13.2 mmol) was added portionwise to Intermediate 60 (2.0 g, 8.0 mmol) in THF (50 mL) at r.t. The resulting solution was stirred at r.t. for 10 minutes, heated to reflux for 1 h and then allowed to cool to r.t. The reaction mixture was cooled to 0° C. and quenched with water (20 mL) and aqueous 2N NaOH (20 mL). The solvent was removed in vacuo and the resulting mixture diluted with water (100 mL). The aqueous fraction was extracted with EtOAc (100 mL), washed with brine (100 mL), dried (MgSO$_4$), filtered and concentrated in vacuo to yield the title compound (2 g, quantitative) as a brown oil. $\delta_H$ (DMSO-d$_6$) 6.68 (3H, m), 4.25-4.18 (2H, m), 3.81 (1H, br. s), 3.44-3.36 (2H, m).

Intermediate 63

6-Nitro-3,4-dihydro-2H-benzo[1,4]oxazine

The title compound was prepared from Intermediate 61 according to Method M and was isolated as a red solid (49%). $\delta_H$ (DMSO-d$_6$) 7.49-7.36 (2H, m), 6.83 (1H, d, J 8.9 Hz), 4.28-4.21 (2H, m), 3.37-3.30 (3H, m).

Intermediate 64

4-(Aminocarbonothioyl)-3,4-dihydro-2H-benzo[1,4]oxazin-6-yl tert-butyl carbonate NEt$_3$ (0.72 mL, 5.1 mmol) was added to 3,4-dihydro-2H-benzo[1,4]oxazin-6-ol hydrobromide (0.4 g, 1.7 mmol) in THF (25 mL). The reaction mixture was stirred for 5 minutes before addition of di-tert-butyl dicarbonate (0.75 g, 3.4 mmol) and DMAP (0.02 g, cat), and then stirred for 3 h before being concentrated in vacuo and the residue partitioned between DCM (100 mL) and water (100 mL). The organic fraction was washed with water (100 mL) and brine (100 mL), dried (MgSO$_4$), filtered and concentrated in vacuo to give a brown oil which was dissolved in THF (15 mL). 1,1'-Thiocarbonyldiimidazole (0.178 g, 3.4 mmol) was added, and the mixture heated to 120° C. under microwave irradiation for 15 minutes. After cooling to r.t., NH$_3$ (15 mL, 7N solution in MeOH, 105 mmol) was added, and the mixture stirred at r.t. for 3 h. The reaction mixture was then concentrated in vacuo and then partitioned between DCM (100 mL) and aqueous 1N HCl (100 mL). The organic fraction was washed with water (100 mL) and brine (100 mL), dried (MgSO$_4$), filtered and concentrated in vacuo. The residue was triturated with Et$_2$O/ hepane to give the title compound (0.160 g, 30%) as a beige solid. $\delta_H$ (DMSO-d$_6$) 8.13 (2H, br. s), 7.30 (1H, d, J 1.9 Hz), 6.94-6.90 (2H, m), 4.32-4.17 (4H, m), 1.48 (9H, s).

Intermediate 65

6-Bromo-3,4-dihydro-2H-benzo[1,4]oxazine-4-carbothioic acid amide

Intermediate 62 (1.7 g, 8 mmol) and 1,1'-thiocarbonyldiimidazole (2.84 g, 16 mmol) were combined in THF (15 mL) and heated to 120° C. under microwave irradiation for 15 minutes. After cooling to r.t., NH$_3$ (40 mL, 7N solution in MeOH, 280 mmol) was added, and the mixture stirred at r.t. for 3 h. The reaction mixture was concentrated in vacuo and then partitioned between EtOAc (100 mL) and water (100 mL). The organic fraction was washed with water (100 mL) and brine (100 mL), dried (MgSO$_4$), filtered and concentrated in vacuo. The residue was triturated with Et$_2$O and heptane to give the title compound (0.5 g, 23%) as a white solid. $\delta_H$ (DMSO-d$_6$) 8.20 (2H, br. s), 7.60 (1H, d, J 2.3 Hz), 7.21 (1H, dd, J 8.7 and J 2.3 Hz), 6.88 (1H, d, J 8.9 Hz), 4.30-4.16 (4H, m).

Intermediate 66

2-(3,4-Dihydro-2H-benzo[1,4]oxazin-4-yl-6-boronic acid)-6,6-dimethyl-6,7-dihydro-5H-thiazolo[5,4-c]pyridin-4-one A solution of Example 39 (0.2 g, 0.5 mmol) in THF (25 mL) was cooled to −70° C., n-butyllithium (0.8 mL, 2.5M solution in hexanes, 2 mmol) was added portionwise, and the mixture stirred at −70° C. for 40 minutes before addition of trimethyl borate (0.28 mL, 2.5 mmol). The reaction mixture was allowed to warm to 0° C. and stirred for 90 minutes. Aqueous NH$_4$Cl solution (20 mL) was added and stirring continued for 10 minutes at 0° C. and 30 minutes at r.t. The reaction mixture was then concentrated in vacuo and the residue partitioned between EtOAc (100 mL) and aqueous NH$_4$Cl (100 mL). The organic fraction was washed with water (100 mL) and brine (100 mL), dried (MgSO$_4$), filtered and concentrated in vacuo. The crude material was triturated with Et$_2$O to give the title compound (0.085 g, 47%) as a yellow solid. LCMS (ES+) 360.0 (M+H)$^+$.

Intermediate 67

3,5-Dimethyl-4-(4,4,5,5-tetramethyl-[1,3,2]dioxaborolan-2-yl)-1-(2-trimethylsilanylethoxymethyl)-1H-pyrazole A stirred suspension of 3,5-dimethyl-4-(4,4,5,5-tetramethyl-[1,3,2]dioxaborolan-2-yl)-1H-pyrazole (0.15 g, 0.68 mmol) in THF (5 mL) was treated with NaH (0.032 g, 60% dispersion in oil, 0.81 mmol) at r.t. After 5 minutes [2-(chloromethoxy)ethyl]-trimethylsilane (0.14 mL, 0.81 mmol) was added and the reaction mixture stirred for 1.5 h. The reaction mixture was quenched with water (5 mL), diluted with EtOAc (20 mL) and the organic fraction separated. The organic fraction was dried (MgSO$_4$), filtered and concentrated in vacuo. Purification by column chromatography (SiO$_2$, 0-40% EtOAc/hexanes) gave the title compound (0.206 g, 86%) as a clear oil. $\delta_H$ (CDCl$_3$) 5.35 (2H, s), 3.60 (2H, m), 2.50 (3H, s), 2.35 (3H, s), 1.35 (12H, s), 0.90 (2H, m), 0.00 (9H, s). LCMS (ES+) 353.0 (M+H)$^+$.

Intermediate 68

Methyl 3-{[(3S)-4-(tert-butoxycarbonyl)morpholin-3-yl]methyl}-2-(trimethylsilyl)-1H-indole-6-carboxylate The title compound was prepared from methyl 3-amino-4-iodobenzoate and Intermediate 26 according to Method I and was isolated as a yellow solid (77%) after purification by column chromatography (SiO$_2$, 10% EtOAc/hexanes). $\delta_H$ (DMSO-d$_6$) 10.98 (1H, s), 8.07 (1H, s), 7.75 (1H, br. s), 7.57 (1H, d, J 8.3 Hz), 4.10 (1H, m), 3.88 (1H, d, J 10.9 Hz), 3.86 (3H, s), 3.74 (1H, m), 3.50 (1H, m), 3.33 (4H, m), 2.85 (1H, br. s), 1.32 (9H, br. s), 0.41 (9H, s). LCMS (ES+) 469.0 (M+Na)$^+$, RT 3.97 minutes (Method 5).

Intermediate 69

Methyl 3-[(3S)-morpholin-3-ylmethyl]-1H-indole-6-carboxylate

The title compound was prepared from Intermediate 68 according to Method J and was isolated as an orange oil (84%) that was used as a crude intermediate. $\delta_H$ (DMSO-d$_6$) 11.27 (1H, s), 8.00 (1H, s), 7.60 (2H, m), 7.39 (1H, d, J 2.1 Hz), 3.83 (3H, s), 3.61 (2H, d, J 10.8 Hz), 3.33 (1H, m), 3.07 (1H, t, J 10.2 Hz), 2.89 (1H, m), 2.67 (4H, br. m). LCMS (ES+) 275.0 (M+H)$^+$, RT 2.17 minutes (Method 5).

Intermediate 70

Methyl 3-{[(3S)-4-(aminocarbonothioyl)morpholin-3-yl]methyl}-1H-indole-6-carboxylate The title compound was prepared from Intermediate 69 according to Method K and was isolated as a yellow foam (76%) after purification by column chromatography (SiO$_2$, 5% MeOH/DCM). $\delta_H$ (DMSO-d$_6$) 11.18 (1H, s), 8.04 (1H, d, J 0.8 Hz), 7.88 (1H, d, J 8.4 Hz), 7.61 (1H, dd, J 8.4 and J 1.4 Hz), 7.44 (1H, d, J 2.2 Hz), 7.30 (2H, s), 4.99 (1H, m), 4.20 (1H, m), 3.91 (1H, d, J 8.1 Hz), 3.87 (3H, s), 3.63 (1H, d, J 11.7 Hz), 3.38 (3H, m), 3.26 (1H, m), 2.92 (1H, dd, J 13.7 and J 4.7 Hz). LCMS (ES+) 334.0 (M+H)$^+$, RT 2.75 minutes (Method 5).

Intermediate 71

2-Iodo-4-difluoromethoxyaniline

A solution of 4-(difluoromethoxy)aniline (1.0 g, 6.30 mmol) in AcOH (6 mL) was heated to 60° C. and iodine monochloride (1.07 g, 6.6 mmol) in AcOH (15 mL) was added dropwise. The reaction mixture was then heated to 85° C. and stirred for 1.5 h. The reaction mixture was cooled to r.t. and poured into cold water and the resulting suspension filtered. The filtrate was concentrated in vacuo to give a dark brown oil. Purification by column chromatography (SiO$_2$, 10-20% EtOAc/hexanes) gave the title compound (0.40 g, 22%) as a dark brown oil. $\delta_H$ (DMSO-d$_6$) 7.38 (1H, d, J 2.7 Hz), 6.98-6.94 (1H, m), 6.97 (1H, t, J 74.8 Hz), 6.75 (1H, d, J 8.8 Hz), 5.20 (2H, br. s). LCMS (ES+) 286.0 (M+H)$^+$, RT 3.28 minutes (Method 5).

Intermediate 72

Pyridazine 1-oxide

To a stirred solution of pyridazine (0.25 g, 3.12 mmol) in DCM (10 ml) was added peracetic acid (3.75 g, 36-40 wt % in AcOH, 18.72 mmol). The reaction mixture was stirred at r.t. for 24 h, then concentrated in vacuo. The residue was dissolved in a mixture of DCM (10 mL) and heptane (10 mL), and the solvents were again removed in vacuo. This last step was repeated twice to give the title compound (0.29 g, 97%) as a yellow oil that was used without further purification. $\delta_H$ (CDCl$_3$) 8.49 (1H, s), 8.18 (1H, d, J 6.4 Hz), 7.69-7.56 (1H, m), 7.08 (1H, ddd, J 7.7, 5.3 and 0.8 Hz).

Intermediate 73

6-{[4-(6,6-Dimethyl-4-oxo-4,5,6,7-tetrahydro[1,3] thiazolo[5,4-c]pyridin-2-yl)-3,4-dihydro-2H-1,4-benzoxazin-6-yl]amino}pyridine-2-carbaldehyde A stirred solution of Example 42 (0.08 g, 0.24 mmol), [1,1'-bis(di-tertbutylphosphino)ferrocene]palladium(II) dichloride (0.01 g, 0.016 mmol), sodium tert-butoxide (0.07 g, 0.726 mmol) and 2-bromopyridine-6-carboxaldehyde dimethyl acetal (0.056 g, 0.24 mmol) in toluene (2 mL) was heated to 140° C. under microwave irradiation in a sealed tube for 2 h, and then concentrated in vacuo. DCM (20 mL) and water (20 mL) were added. The organic fraction was separated and concentrated in vacuo. The residue was dissolved in MeOH (3 mL) and 2M aqueous HCl (3 mL). The solution was stirred at 60° C. for 2 days, then concentrated in vacuo. DCM (5 mL) and water (5 mL) were added. The organic fraction was separated, dried (MgSO$_4$), filtered and concentrated in vacuo to give the title compound (0.075 g, 80%) that was used without further purification. LCMS (ES+) 436.4 (M+H)$^+$, RT 3.20 minutes (Method 1).

Intermediate 74

3-[(6-bromopyridin-2-yl)amino]propane-1,2-diol

A stirred solution of 2,6-dibromopyridine (0.76 g, 3.20 mmol), 1-amino-2,3-dihydroxypropane (0.29 g, 3.20 mmol) and DIPEA (0.56 mL, 3.24 mmol) in toluene (3.2 mL) was heated to 160° C. under microwave irradiation in a sealed tube for 2 h, and then concentrated in vacuo. Water (5 mL) was added, the mixture sonicated for 10 minutes, and then filtered through Celite®. The filtrate was concentrated in vacuo to yield the title compound (0.239 g, 30%) as a white solid that was used without further purification. $\delta_H$ (DMSO-d$_6$) 7.29-7.18 (1H, m), 6.92-6.79 (1H, m), 6.61 (1H, d, J 7.3 Hz), 6.51 (1H, d, J 8.3 Hz), 4.79 (1H, d, J 4.9 Hz), 4.58 (1H, t, J 5.8 Hz), 3.65-3.54 (1H, m), 3.15-3.04 (1H, m). Exchangeable protons were not observed. LCMS (ES+) 247.0 and 249.0 (1:1 ratio) (M+H)$^+$, RT 2.07 minutes (Method 1).

Intermediate 75

2-Chloro-6[(2,2-dimethyl-1,3-dioxolan-4-yl)methoxy]pyridine

To a stirred solution of 2-chloro-6-hydroxypyridine (0.58 g, 4.50 mmol) and 2,2-dimethyl-1,3-dioxolan-4-ylmethyl p-toluenesulfonate (1.29 g, 4.50 mmol) in DMF (10 mL) was added cesium carbonate (2.97 g, 9.00 mmol). The reaction mixture was stirred at 85° C. for 18 h, and then partitioned between EtOAc (50 mL) and water (50 mL). The organic fraction was separated, washed with water (2×50 mL), then brine (50 mL), dried (MgSO$_4$), filtered and concentrated in vacuo to give the title compound (1.03 g, 94%) as an off-white solid that was used without further purification. $\delta_H$ (DMSO-d$_6$) 7.78 (1H, dd, J 8.1 and 7.5 Hz), 7.11 (1H, dd, J 7.5 and 0.6 Hz), 6.86 (1H, dd, J 8.1 and 0.6 Hz), 4.45-4.35 (1H, m), 4.33-4.18 (2H, m), 4.11-4.01 (1H, m), 3.77 (1H, dd, J 8.5 and 6.2 Hz), 1.34 (3H, s), 1.29 (3H, s). LCMS (ES+) 244.1 (M+H)$^+$, RT 3.63 minutes (Method 1).

Intermediate 76

Methyl 3-{[(3S)-4-(tert-butoxycarbonyl)morpholin-3-yl]methyl}-1-methyl-2-(trimethylsilyl)-1H-indole-5-carboxylate To a stirred solution of Intermediate 41 (2.0 g, 4.48 mmol) in THF (30 mL) at 0° C. was added NaH (0.19 g, 60% dispersion in oil, 4.93 mmol). The reaction mixture was stirred at this temperature for 30 minutes. Methyl iodide (0.33 mL, 5.37 mmol) was then added, and the reaction mixture allowed to warm to r.t., then stirred for 18 h. Water (1 mL) was added, and the reaction mixture concentrated in vacuo. DCM (25 mL) and water (10 mL) were added. The organic fraction was separated, washed with brine (10 mL), dried (Na$_2$SO$_4$), filtered and concentrated in vacuo. Purification by column chromatography (SiO$_2$, 10-25% EtOAc/hexanes) gave the title compound (1.95 g, 95%) as a pale yellow oil. LCMS (ES+) 405.1 ((M−$^t$Bu)+H)$^+$, RT 3.80 minutes (Method 3).

Intermediate 77

Methyl 1-methyl-3-[(3S)-morpholin-3-ylmethyl]-1H-indole-5-carboxylate

To a stirred solution of Intermediate 76 (1.95 g, 4.23 mmol) in MeOH (15 mL) was added 4M HCl in 1,4-dioxane (20 mL). The reaction mixture was stirred at r.t. for 16 h, then concentrated in vacuo. Water (10 mL) and DCM (10 mL) were added. The aqueous fraction was separated, basified by the addition of aqueous sat. $NaHCO_3$, then extracted with DCM (5×30 mL). The combined organic fractions were dried ($Na_2SO_4$), filtered and concentrated in vacuo to give the title compound (1.02 g, 84%) as a yellow solid that was used without further purification. LCMS (ES+) 289.2 $(M+H)^+$, RT 2.00 minutes (Method 3).

Intermediate 78

Methyl 3-{[(3S)-4-(aminocarbonothioyl)morpholin-3-yl]methyl}-1-methyl-1H-indole-5-carboxylate The title compound was prepared from Intermediate 77 according to Method K and was isolated as a brown gum (80%) after purification by column chromatography ($SiO_2$, 0-6% MeOH/DCM). LCMS (ES+) 348.2 $(M+H)^+$, RT 2.63 minutes (Method 3).

Intermediate 79

Pentafluorophenyl 3-{[(3S)-4-(6,6-dimethyl-4-oxo-4,5,6,7-tetrahydro[1,3]thiazolo[5,4-c]pyridin-2-yl)morpholin-3-yl]methyl}-1-methyl-1H-indole-5-carboxylate To a stirred solution of Example 123 (1.0 g, 2.20 mmol) in DMF (20 mL) was added pentafluorophenol (0.49 g, 2.64 mmol), DIPEA (0.77 mL, 4.41 mmol) and EDC (0.55 g, 2.86 mmol). The reaction mixture was stirred at r.t. for 16 h, then concentrated in vacuo. DCM (15 mL) and water (15 mL) were added. The organic fraction was separated, dried ($Na_2SO_4$), filtered and concentrated in vacuo. Purification by column chromatography ($SiO_2$, 0-4% MeOH/DCM) gave the title compound (1.04 g, 76%) as a yellow gum. LCMS (ES+) 621.3 $(M+H)^+$, RT 3.52 minutes (Method 4).

Intermediate 80

Methyl 3-{[(3S)-4-(tert-butoxycarbonyl)morpholin-3-yl]methyl}-5-chloro-2-(trimethylsilyl)-1H-indole-7-carboxylate The title compound was prepared from Intermediate 26 and methyl 2-amino-5-chloro-3-iodobenzoate according to Method I and was isolated as a yellow solid (48%) after purification by column chromatography ($SiO_2$, 10-15% EtOAc/hexanes). LCMS (ES+) 425.2 $((M-^tBu)+H)^+$, RT 4.63 minutes (Method 3).

Intermediate 81

Methyl 5-chloro-3-[(3S)-morpholin-3-ylmethyl]-1H-indole-7-carboxylate

The title compound was prepared from Intermediate 80 (dissolved in MeOH) according to Method J and was isolated as a yellow gum (95%). LCMS (ES+) 309.1 $(M+H)^+$, RT 2.20 minutes (Method 3).

Intermediate 82

Methyl 3-{[(3S)-4-(aminocarbonothioyl)morpholin-3-yl]methyl}-5-chloro-1H-indole-7-carboxylate The title compound was prepared from Intermediate 81 according to Method K and was isolated as a yellow solid (44%). LCMS (ES+) 368.0 $(M+H)^+$, RT 2.84 minutes (Method 3).

Intermediate 83

5-Chloro-3-{[(3S)-4-(6,6-dimethyl-4-oxo-4,5,6,7-tetrahydro[1,3]thiazolo[5,4-c]pyridin-2-yl)morpholin-3-yl]methyl}-1H-indole-7-carboxylic acid To a stirred suspension of Example 128 (1.15 g, 2.46 mmol) in 1,4-dioxane (20 mL) and MeOH (5 mL) was added a solution of $LiOH.H_2O$ (0.21 g, 4.91 mmol) in water (5 mL). The reaction mixture was stirred at 60° C. for 16 h, then concentrated in vacuo. DCM (200 mL) and water (100 mL) were added. The aqueous fraction was separated, acidified to pH 1 by the addition of 1M aqueous HCl then extracted with EtOAc (4×200 mL). The combined organic fractions were concentrated in vacuo to give the title compound (0.08 g, quantitative) as a yellow solid that was used without further purification. LCMS (ES+) 475.1 $(M+H)^+$, RT 2.48 minutes (Method 3).

Intermediate 84

Pentafluorophenyl 3-{[(3S)-4-(6,6-dimethyl-4-oxo-4,5,6,7-tetrahydro[1,3]thiazolo[5,4-c]pyridin-2-yl)morpholin-3-yl]methyl}-1H-indole-6-carboxylate To a stirred solution of Example 130 (1.6 g, 3.63 mmol) in DMF (10 mL) was added pentafluorophenol (0.66 g, 3.81 mmol) and EDC (0.76 g, 3.99 mmol). The reaction mixture was stirred at r.t. for 16 h. Water (25 mL) and EtOAc (25 mL) were added. The organic fraction was separated, dried ($Na_2SO_4$), filtered and concentrated in vacuo to give the title compound (1.85 g, 83%) as a yellow solid. $\delta_H$ (DMSO-$d_6$) 11.53 (1H, s), 8.23 (1H, d, J 1.2 Hz), 7.98 (1H, d, J 8.4 Hz), 7.81 (1H, d, J 8.4 and 1.4 Hz), 7.62 (1H, d, J 2.3 Hz), 7.27 (1H, s), 4.31-4.22 (1H, m), 4.00 (1H, d, J 9.3 Hz), 3.76 (1H, d, J 11.5 Hz), 3.68-3.51 (4H, m), 3.33-3.25 (1H, m), 3.09 (1H, dd, J 14.2 and 5.6 Hz), 2.69 (1H, d, J 16.7 Hz), 2.56 (1H, d, J 16.7 Hz), 1.23 (3H, s), 1.21 (3H, s). LCMS (ES+) 607.0 $(M+H)^+$, RT 3.56 minutes (Method 5).

Intermediate 85

2-{(3S)-3-[(5-Amino-1H-indol-3-yl)methyl]morpholin-4-yl}-6,6-dimethyl-6,7-dihydro[1,3]thiazolo[5,4-c]pyridin-4(5H)-one To a stirred solution of Example 19 (1.65 g, 3.73 mmol) in EtOH (30 mL) and AcOH (5 mL) was added 10% w/w palladium on carbon (0.20 g). The reaction mixture was stirred under an atmosphere of $H_2$ at r.t. for 24 h, then filtered and concentrated in vacuo. The residue was dissolved in DCM (100 mL) and washed with aqueous sat. $NaHCO_3$ (10 mL). The organic fraction was separated, then dried ($MgSO_4$) to give the title compound (1.16 g, 75%) as a purple solid that was used without further purification. LCMS (ES+) 412.2 $(M+H)^+$ RT 2.21 minutes (Method 4).

Intermediate 86 tert-Butyl (3S)-3-{[2-(trimethylsilyl)-1H-pyrrolo[3,2-c]pyridin-3-yl]methyl}morpholine-4-carboxylate The title compound was prepared from Intermediate 26 and 3-iodopyridin-4-ylamine according to Method I and was isolated as a brown gum (23%) after purification by column chromatography (SiO$_2$, 30-100% EtOAc/hexanes). LCMS (ES+) 390.2 (M+H)$^+$, RT 2.44 minutes (Method 3).

Intermediate 87

3-[(3S)-Morpholin-3-ylmethyl]-1H-pyrrolo[3,2-c]pyridine

To a stirred solution of Intermediate 86 (0.55 g, 1.41 mmol) in MeOH (10 mL) was added 4M HCl in 1,4-dioxane (20 mL). The reaction mixture was stirred for 2 days, then concentrated in vacuo. Water (10 mL) and DCM (20 mL) were added. The aqueous fraction was basified by the addition of aqueous NH$_3$ solution (20% v/v), then concentrated in vacuo. The residue was dissolved in THF (10 mL), tetrabutylammonium fluoride (2.8 mL, 1.0M in THF, 2.82 mmol) added, and the reaction mixture stirred at r.t. for 16 h. Additional tetrabutylammonium fluoride (5.6 mL, 5.64 mmol) was added. The reaction mixture was stirred at 60° C. for 16 h, and then concentrated in vacuo to give the title compound (0.20 g, 66%) as a brown gum that was used without further purification. LCMS (ES+) 218.1 (M+H)$^+$, RT 1.87 minutes (Method 4).

Intermediate 88

(3S)-3-(1H-Pyrrolo[3,2-c]pyridin-3-ylmethyl)morpholine-4-carbothioamide

The title compound was prepared from Intermediate 87 according to Method K and was isolated as a yellow gum (86%) after purification by column chromatography (SiO$_2$, 0-15% MeOH/DCM with 1% NH$_4$OH added). LCMS (ES+) 277.1 (M+H)$^+$, RT 1.79 minutes (Method 4).

Intermediate 89 tert-Butyl (3S)-3-{[5-cyano-2-(trimethylsilyl)-1H-indol-3-yl]methyl}morpholine-4-carboxylate The title compound was prepared from Intermediate 26 and 4-amino-3-iodobenzonitrile according to Method I and was isolated as a yellow solid (50%) after work-up (EtOAc and water) and purification by column chromatography (SiO$_2$, 5-100% EtOAc/hexanes). LCMS (ES+) 414.0 (M+H)$^+$, RT 3.92 minutes (Method 5).

Intermediate 90

3-[(3S)-Morpholin-3-ylmethyl]-1H-indole-5-carbonitrile

The title compound was prepared from Intermediate 89 (dissolved in MeOH) according to Method J and was isolated as a brown solid (87%) that was used without further purification. LCMS (ES+) 242.0 (M+H)$^+$, RT 2.15 minutes (Method 5).

Intermediate 91

(3S)-3-[(5-Cyano-1H-indol-3-yl)methyl]morpholine-4-carbothioamide

The title compound was prepared from Intermediate 90 according to Method K and was isolated as an off-white solid (39%) after purification by column chromatography (SiO$_2$, 0-5% MeOH/DCM). LCMS (ES+) 301.0 (M+H)$^+$, RT 2.77 minutes (Method 5).

Intermediate 92

4-Amino-3-iodo-N,N-dimethylbenzenesulfonamide

To a stirred solution of 4-amino-N,N-dimethylbenzenesulfonamide (3.0 g, 14.98 mmol) in EtOH (165 mL) at 50° C. was added a slurry of iodine (1.3 g, 4.99 mmol) and silver sulfate (2.8 g, 9.00 mmol) in EtOH (40 mL). The same addition was repeated after 1 h of stirring at 50° C., then the reaction mixture was stirred at 50° C. for 16 h. Iodine (0.76 g, 3.00 mmol) was again added, and the mixture stirred at 50° C. for 2 h before being filtered through Celite®. The filtrate was concentrated in vacuo, and EtOH (70 mL) was added. The suspension was stirred at 50° C. for 1 h, cooled to r.t., then filtered to give the title compound (2.7 g, 55%) as a brown solid that was used without further purification. $\delta_H$ (DMSO-d$_6$) 7.81 (1H, d, J 2.1 Hz), 7.42 (1H, dd, J 8.6 and 2.1 Hz), 6.83 (1H, d, J 8.6 Hz), 6.12 (2H, br. s), 2.58 (6H, s). LCMS (ES+) 326.9 (M+H)$^+$, RT 2.50 minutes (Method 3).

Intermediate 93 tert-Butyl (3S)-3-({5-[(dimethylamino)sulfonyl]-2-(trimethylsilyl)-1H-indol-3-yl}methyl)morpholine-4-carboxylate The title compound was prepared from Intermediate 26 and Intermediate 92 according to Method I and was isolated as a yellow oil (80%) after work-up (DCM and water) and purification by column chromatography (SiO$_2$, 0-10% EtOAc/DCM). $\delta_H$ (DMSO-d$_6$) 11.05 (1H, s), 7.84 (1H, s), 7.51-7.39 (1H, m), 7.32 (1H, dd, J 8.6 and 1.5 Hz), 4.00-3.86 (1H, m), 3.85-3.72 (1H, m), 3.71-3.53 (1H, m), 3.53-3.36 (1H, m), 3.30-3.12 (5H, m), 2.45 (6H, s), 1.45-0.91 (9H, m), 0.29 (9H, s). LCMS (ES+) 496.4 (M+H)$^+$, RT 3.12 minutes (Method 3).

Intermediate 94

N,N-Dimethyl-3-[(3S)-morpholin-3-ylmethyl]-1H-indole-5-sulfonamide

The title compound was prepared from Intermediate 93 (dissolved in MeOH) according to Method J and was isolated as a yellow oil (92%) that was used without further purification. LCMS (ES+) 324.2 (M+H)$^+$, RT 1.70 minutes (Method 3).

Intermediate 95

(3S)-3-({5-[(Dimethylamino)sulfonyl]-1H-indol-3-yl}methyl)morpholine-4-carbothioamide The title compound was prepared from Intermediate 94 according to Method K and was isolated as a white solid (64%) after purification by column chromatography (SiO$_2$, 0-3% MeOH/DCM). LCMS (ES+) 383.2 (M+H)$^+$, RT 2.12 minutes (Method 3).

Intermediate 96 tert-Butyl [4-(cyclopropylmethoxy)phenyl]carbamate

To a stirred solution of 4-[N-(tert-butoxycarbonyl)amino] phenol (5.0 g, 23.89 mmol) in DMF (140 mL) was added cesium carbonate (19.5 g, 59.73 mmol). The reaction mixture was stirred at r.t. for 20 minutes, and then cyclopropylmethyl bromide (2.3 mL, 23.89 mmol) was added. The reaction mixture was stirred at r.t. for 2 days, cooled to r.t., filtered and partitioned between Et$_2$O (2×25 mL) and water (100 mL). The layers were separated, and the aqueous fraction was further extracted with Et$_2$O (3×50 mL). The combined organic fractions were washed with water (3×150 mL), dried (Na$_2$SO$_4$), filtered and concentrated in vacuo to give the title compound (5.1 g, 81%) as a light pink solid that was used without further purification. $\delta_H$ (DMSO-d$_6$) 8.82 (1H, br. s), 7.09-7.06 (2H, m), 6.59-6.54 (2H, m), 3.50 (2H, d, J 6.9 Hz), 1.22 (9H, s), 0.97-0.90 (1H, m), 0.34-0.28 (2H, m), 0.08-0.03 (2H, m). LCMS (ES+) 207.0 ((M−$^t$Bu)+H)$^+$, RT 3.20 minutes (Method 3).

Intermediate 97

Method X tert-Butyl [4-(cyclopropylmethoxy)-2-iodophenyl]carbamate

To a stirred solution of Intermediate 96 (5.0 g, 19.01 mmol) in Et$_2$O (140 mL) at −20° C. was added tert-butyllithium (28 mL, 1.7 M in pentane, 47.53 mmol) dropwise. After stirring at this temperature for 3 h, the reaction mixture was cooled to −78° C. A solution of 1,2-diiodoethane (8.0 g, 28.52 mmol) in Et$_2$O (60 mL) was added dropwise, and the reaction mixture gradually warmed to r.t. and stirred for 16 h. Aqueous sat. Na$_2$S$_2$O$_3$ (100 mL) was added, and the mixture stirred for 15 minutes. The aqueous fraction was separated, and then extracted with Et$_2$O (3×40 mL). The combined organic fractions were washed with water (3×100 mL), dried (Na$_2$SO$_4$), filtered and concentrated in vacuo. Purification by column chromatography (SiO$_2$, 5% EtOAc/hexanes) gave the title compound (5.0 g, 68%) as an orange oil. $\delta_H$ (DMSO-d$_6$) 8.13 (1H, s), 7.13 (1H, d, J 2.8 Hz), 6.93 (1H, d, J 8.8 Hz), 6.68 (1H, dd, J 8.7 and 2.8 Hz), 3.56 (2H, d, J 7.0 Hz), 1.20 (9H, s), 0.99-0.89 (1H, m), 0.62-0.29 (2H, m), 0.09-0.05 (2H, m). LCMS (ES+) 375.0 (M−Me)$^+$, RT 3.25 minutes (Method 3).

Intermediate 98

4-(Cyclopropylmethoxy)-2-iodoaniline

The title compound was prepared from Intermediate 97 (dissolved in MeOH) according to Method J and was isolated as an orange solid (95%) that was used without further purification. LCMS (ES+) 290.0 (M+H)$^+$, RT 1.87 minutes (Method 3).

Intermediate 99 tert-Butyl (3S)-3-{[5-(cyclopropylmethoxy)-2-(trimethylsilyl)-1H-indol-3-yl]methyl}morpholine-4-carboxylate The title compound was prepared from Intermediate 26 and Intermediate 98 according to Method I and was isolated as a yellow oil (76%) after work-up (DCM and water) and purification by column chromatography (SiO$_2$, 0-5% EtOAc/DCM). $\delta_H$ (DMSO-d$_6$) 10.21 (1H, s), 7.07 (1H, d, J 8.7 Hz), 7.27-6.94 (1H, m), 6.57 (1H, dd, J 8.9 and 2.4 Hz), 3.98-3.87 (1H, m), 3.77-3.68 (1H, m), 3.67-3.61 (2H, m), 3.59-3.48 (1H, m), 3.38 (1H, d, J 11.3 Hz), 3.25-3.02 (5H, m), 2.70-2.46 (1H, m), 1.30-1.14 (9H, m), 0.48-0.33 (2H, m), 0.20 (9H, s), 0.18-0.08 (2H, m). LCMS (ES+) 359.4 (M−BOC+H)$^+$, RT 3.56 minutes (Method 3).

Intermediate 100

5-(Cyclopropylmethoxy)-3-[(3S)-morpholin-3-ylmethyl]-1H-indole

The title compound was prepared from Intermediate 99 (dissolved in MeOH) according to Method J and was isolated as an orange solid (95%) that was used without further purification. LCMS (ES+) 287.2 (M+H)$^+$, RT 1.87 minutes (Method 3).

Intermediate 101

(3S)-3-{[5-(Cyclopropylmethoxy)-1H-indol-3-yl] methyl}morpholine-4-carbothioamide The title compound was prepared from Intermediate 100 according to Method K and was isolated as a white solid (54%) after purification by column chromatography (SiO$_2$, 0-3% MeOH/DCM). LCMS (ES+) 346.2 (M+H)$^+$, RT 2.42 minutes (Method 3).

Intermediate 102 tert-Butyl (3S)-3-[3-(triethylsilyl)prop-2-yn-1-yl] morpholine-4-carboxylate

To a stirred solution of triethylsilyl acetylene (6.3 mL, 35.0 mmol) in anhydrous THF (80 mL) at 0° C. was added n-butyllithium (14 mL, 2.5M in hexanes, 35.0 mmol) dropwise over 20 minutes. After stirring at this temperature for 30 minutes, this reaction mixture was added to a cool (0° C.) suspension of Intermediate 23 (2.5 g, 14.0 mmol) in DMPU (3.2 mL) and THF (15 mL) dropwise. The reaction mixture was stirred at 0° C. for 30 minutes, then at r.t. for 30 minutes, then quenched by the addition of 2M aqueous HCl (5 mL). MeOH (20 mL) and additional 2M aqueous HCl (20 mL) were added, and the reaction mixture was stirred at r.t. for 3 h before being concentrated in vacuo. The residue was dissolved in DCM (80 mL), and the solution cooled at 0° C. DIPEA (3.7 mL, 21.0 mmol) was added, followed by di-tert-butyl dicarbonate (4.6 g, 21.0 mmol). The reaction mixture was stirred at r.t. for 16 h. Water (150 mL) was added. The organic fraction was separated, washed with brine (150 mL), dried (Na$_2$SO$_4$), filtered and concentrated in vacuo. Purification by column chromatography (SiO$_2$, 5-10% EtOAc/hexanes) gave the title compound (2.8 g, 60%) as a colourless oil. $\delta_H$ (DMSO-d$_6$) 4.03 (1H, d, J 11.6 Hz), 3.96 (1H, dd, J 2.3 and 1.3 Hz), 3.77 (1H, dd, J 11.1 and 2.8 Hz), 3.65 (1H, d, J 12.9 Hz), 3.44 (1H, ddd, J 11.6, 3.3 and 1.3 Hz), 3.37 (1H, td, J 12.1 and 3.0 Hz), 3.12-2.95 (1H, m), 2.76 (1H, dd, J 16.4 and 10.6 Hz), 2.31 (1H, ddd, J 16.2, 4.5 and 0.8 Hz), 1.40 (9H, s), 0.90 (9H, t, J 8.1 Hz), 0.49 (6H, d, J 7.8 Hz).

Intermediate 103

1-[(Methylsulfonyl)methyl]-4-nitrobenzene

To a stirred solution of 4-nitrobenzyl bromide (10.0 g, 46.3 mmol) in DMF (25 mL) was added sodium methanesulfinate (7.1 g, 69.4 mmol). The reaction mixture was stirred at 65° C. for 30 minutes, and then partitioned between water (30 mL) and EtOAc (30 mL). The organic fraction was separated, washed with water (2×30 ml), dried ($Na_2SO_4$), filtered and concentrated in vacuo to give the title compound (7.5 g, 75%) as a yellow solid that was used without further purification. $\delta_H$ (DMSO-$d_6$) 8.28 (2H, d, J 8.8 Hz), 7.70 (2H, d, J 8.8 Hz), 4.72 (2H, s), 2.97 (3H, s).

Intermediate 104

4-[(Methylsulfonyl)methyl]aniline

A solution of Intermediate 103 (0.94 g, 4.36 mmol) in EtOAc (88 mL) was passed through a H-Cube® flow hydrogenator using continuous $H_2$ over Pd/C at a rate of 1.5 mL/minute at 40° C. The reaction mixture was concentrated in vacuo to give the title compound as a white solid (0.80 g, 98%) that was used without any further purification. $\delta_H$ (DMSO-$d_6$) 7.03 (2H, d, J 8.3 Hz), 6.54 (2H, d, J 8.3 Hz), 5.21 (2H, s), 4.21 (2H, s), 2.80 (3H, s). LCMS (ES+) 186.0 (M+H)$^+$, RT 0.88 minutes (Method 5).

Intermediate 105

2-Iodo-4-[(methylsulfonyl)methyl]aniline

To a stirred solution of Intermediate 104 (0.80 g, 4.31 mmol) in DCM (25 mL), AcOH (2 mL) and MeOH (1 mL) at −15° C. was added a solution of iodine monochloride (0.84 g, 5.17 mmol) in DCM (25 mL) dropwise over 30 minutes. The reaction mixture was allowed to warm to r.t., and then concentrated in vacuo. The residue was dissolved in EtOAc and basified with the addition of aqueous sat. $Na_2CO_3$ solution. The organic layer was separated, dried ($Na_2SO_4$), filtered and concentrated in vacuo to give the title compound (1.48 g, quantitative) as a brown solid that was used without further purification. LCMS (ES+) 312.0 (M+H)$^+$, RT 2.79 minutes (Method 5).

Intermediate 106 tert-Butyl (3S)-3-({5-[(methylsulfonyl)methyl]-2-(triethylsilyl)-1H-indol-3-yl}methyl)morpholine-4-carboxylate The title compound was prepared from Intermediate 102 and Intermediate 105 according to Method I and was isolated as an orange oil (57%) after purification by column chromatography ($SiO_2$, 30% EtOAc/hexanes). LCMS (ES+) 523.0 (M+H)$^+$, RT 3.91 minutes (Method 5).

Intermediate 107

5-[(Methylsulfonyl)methyl]-3-[(3S)-morpholin-3-ylmethyl]-1H-indole

The title compound was prepared from Intermediate 106 (dissolved in MeOH) according to Method J and was isolated as a pale brown oil (73%) that was used without further purification. LCMS (ES+) 309.0 (M+H)$^+$, RT 1.95 minutes (Method 5).

Intermediate 108

(3S)-3-({5-[(Methylsulfonyl)methyl]-1H-indol-3-yl}methyl)morpholine-4-carbothioamide The title compound was prepared from Intermediate 107 according to Method K and was isolated as a white solid (30%) after purification by column chromatography ($SiO_2$, 100% EtOAc). LCMS (ES+) 368.0 (M+H)$^+$, RT 2.60 minutes (Method 5).

Intermediate 109

1-(4-Amino-3-iodophenyl)-2,2,2-trifluoroethanone

To a stirred solution of 1-(4-aminophenyl)-2,2,2-trifluoroethanone (1.0 g, 5.28 mmol) in 1M aqueous HCl solution (70 mL) was added iodine monochloride (0.77 g, 4.76 mmol). The reaction mixture was stirred at r.t. for 2 h, then basified with the addition of aqueous sat. $NaHCO_3$ solution and extracted with EtOAc (2×100 mL). The combined organic fractions were dried ($Na_2SO_4$), filtered and concentrated in vacuo. Purification by column chromatography ($SiO_2$, 15-20% EtOAc/hexanes) gave the title compound (0.983 g, 59%) as a cream solid. $\delta_H$ ($CDCl_3$) 8.40 (1H, d, J 1.0 Hz), 7.92-7.85 (1H, m), 6.76 (1H, d, J 8.6 Hz), 4.91 (2H, br. s). LCMS (ES+) RT 2.86 minutes (Method 3).

Intermediate 110 tert-Butyl (3S)-3-{[5-(trifluoroacetyl)-2-(trimethylsilyl)-1H-indol-3-yl]methyl}morpholine-4-carboxylate The title compound was prepared from Intermediate 26 and Intermediate 109 according to Method I and was isolated as a yellow gum (88%) after purification by column chromatography ($SiO_2$, 10-15% EtOAc/hexanes). LCMS (ES+) 429.1 ((M−$^t$Bu)+H)$^+$, RT 3.50 minutes (Method 3).

Intermediate 111

1-{3-[(3S)-Morpholin-3-ylmethyl]-1H-indol-5-yl}-2,2,2-trifluoroethanone

The title compound was prepared from Intermediate 110 (dissolved in MeOH) according to Method J and was isolated as a yellow gum (76%) that was used without further purification. LCMS (ES+) 313.0 (M+H)$^+$, RT 1.89 minutes (Method 3).

Intermediate 112

(3S)-3-{[5-(Trifluoroacetyl)-1H-indol-3-yl]methyl}morpholine-4-carbothioamide The title compound was prepared from Intermediate 111 according to Method K and was isolated as a yellow gum (84%) after purification by column chromatography ($SiO_2$, 0-5% MeOH/DCM). LCMS (ES+) 372.2 (M+H)$^+$, RT 2.44 minutes (Method 3).

Intermediate 113 tert-Butyl [4-(cyclobutyloxy)phenyl]carbamate

To a stirred solution of 4-[N-(tert-butoxycarbonyl)amino]phenol (3.1 g, 14.81 mmol) in DMF (40 mL) was added cesium carbonate (12.1 g, 37.02 mmol) and cyclobutyl bromide (2.0 g, 14.81 mmol). The reaction mixture was stirred at r.t. for 3 days, and then at 60° C. for 19 h. The reaction mixture was cooled to r.t., filtered and partitioned between water (50 mL) and $Et_2O$ (100 mL). The layers were separated, and the aqueous fraction was further extracted with $Et_2O$ (3×50 mL). The combined organic fractions were washed with brine (50 mL), dried (Na$_2$SO$_4$), filtered and concentrated in vacuo. Purification by column chromatography (SiO$_2$, 5-8% EtOAc/hexanes) gave the title compound (1.6 g, 41%) as a white solid. δ$_H$ (CDCl$_3$) 7.24 (2H, d, J 8.9 Hz), 6.82-6.72 (2H, m), 6.31 (1H, br. s), 4.67-6.54 (1H, m), 2.52-2.36 (2H, m), 2.25-2.08 (2H, m), 1.94-1.78 (1H, m), 1.77-1.62 (1H, m), 1.53 (9H, s). LCMS (ES+) 208.0 ((M−$^t$Bu)+H)$^+$, RT 3.10 minutes (Method 3).

Intermediate 114 tert-Butyl [4-(cyclobutyloxy)-2-iodophenyl]carbamate

The title compound was prepared from Intermediate 113 according to Method X and was isolated as a brown oil (94%) after purification by column chromatography (SiO$_2$, 10% EtOAc/hexanes). δ$_H$(CDCl$_3$) 7.80 (1H, d, J 9.0 Hz), 7.24 (1H, d, J 2.8 Hz), 6.81 (1H, dd, 1H, d, J 9.0 and 2.8 Hz), 6.53 (1H, br. s), 4.66-4.52 (1H, m), 2.52-2.36 (2H, m), 2.24-2.07 (2H, m), 1.98-1.78 (1H, m), 1.78-1.59 (1H, m), 1.54 (9H, s). LCMS (ES+) 334.0 ((M−$^t$Bu)+H)$^+$, RT 3.32 minutes (Method 3).

Intermediate 115

4-(Cyclobutyloxy)-2-iodoaniline

The title compound was prepared from Intermediate 114 (dissolved in MeOH) according to Method J and was isolated as a brown gum (97%) that was used without further purification. LCMS (ES+) 290.0 (M+H)$^+$, RT 2.93 minutes (Method 3).

Intermediate 116 tert-Butyl (3S)-3-{[5-(cyclobutyloxy)-2-(trimethylsilyl)-1H-indol-3-yl]methyl}-morpholine-4-carboxylate The title compound was prepared from Intermediate 26 and Intermediate 115 according to Method I and was isolated as a brown gum (36%) after purification by column chromatography (SiO$_2$, 10-15% EtOAc/hexanes). LCMS (ES+) 403.3 ((M−$^t$Bu)+H)$^+$, RT 3.73 minutes (Method 3).

Intermediate 117

5-(Cyclobutyloxy)-3-[(3S)-morpholin-3-ylmethyl]-1H-indole

The title compound was prepared from Intermediate 116 (dissolved in MeOH) according to Method J and was isolated as a brown gum (83%) that was used without further purification. LCMS (ES+) 287.1 (M+H)$^+$, RT 1.89 minutes (Method 3).

Intermediate 118

(3S)-3-{[5-(Cyclobutyloxy)-1H-indol-3-yl] methyl}morpholine-4-carbothioamide

The title compound was prepared from Intermediate 117 according to Method K and was isolated as a yellow gum (69%) after purification by column chromatography (SiO$_2$, 0-4% MeOH/DCM). LCMS (ES+) 346.1 (M+H)$^+$, RT 2.44 minutes (Method 3).

Intermediates 119 and 120

(3S)-3-[3-(Trimethylsilyl)prop-2-yn-1-yl]morpholine-4-carbothioamide and (3S)-3-(Prop-2-yn-1-yl)morpholine-4-carbothioamide respectively To a stirred solution of trimethylsilyl acetylene (30.3 mL, 215.0 mmol) in THF (300 mL) at 0° C. was added n-butyl-lithium (86.2 mL, 2.5M in hexanes, 215.0 mmol) dropwise over 15 minutes. After stirring at this temperature for 30 minutes, Intermediate 23 (19.3 g, 107.7 mmol) was added over 5 minutes. The reaction mixture was stirred at 0° C. for 20 minutes, and then allowed to warm to r.t. After stirring at r.t. for 40 minutes, the reaction mixture was quenched by the addition of 2M aqueous HCl (80 mL) and MeOH (50 mL), then stirred at r.t. for 3 h. The reaction mixture was concentrated in vacuo. The residue was dissolved in THF (60 mL). DIPEA (4.9 mL, 28.4 mmol) then 1,1'-thiocarbonyldiimidazole (5.3 g, 29.7 mmol) were added. The reaction mixture was stirred at r.t. for 16 h, then partitioned between DCM (50 mL) and water (30 mL). The organic fraction was dried (Na$_2$SO$_4$), filtered and concentrated in vacuo. Purification by column chromatography (SiO$_2$, 0-2% MeOH/DCM, followed by SiO$_2$, 60-80% EtOAc/hexanes) gave the first title compound (2.35 g, 34%) as a brown gum, LCMS (ES+) 257.0 (M+H)$^+$, RT 3.206 minutes (Method 5), followed by the second title compound (1.55 g, 31%) as a brown gum, LCMS (ES+) 185.0 (M+H)$^+$, RT 2.47 minutes (Method 5). They were both used individually without further purification.

Intermediate 121

Methyl 3-{[(3S)-4-(6,6-dimethyl-4-oxo-4,5,6,7-tetrahydro[1,3]thiazolo[5,4-c]pyridin-2-yl)morpholin-3-yl]methyl}-2-(trimethylsilyl)-1-benzofuran-5-carboxylate The title compound was prepared from Example 155 and methyl 4-hydroxy-3-iodobenzoate according to Method I and was isolated as a brown gum (49%) after purification by column chromatography (SiO$_2$, 60-100% EtOAc/hexanes). LCMS (ES+) 528.2 (M+H)$^+$, RT 3.46 minutes (Method 9).

Intermediate 122

3-{[(3S)-4-(6,6-Dimethyl-4-oxo-4,5,6,7-tetrahydro [1,3]thiazolo[5,4-c]pyridin-2-yl)morpholin-3-yl] methyl}-1-benzofuran-5-carboxylic acid To a stirred solution of Intermediate 121 (0.326 g, 0.62 mmol) in 1,4-dioxane (8 mL) was added a solution of LiOH.H$_2$O (0.054 g, 1.29 mmol) in water (5 mL). The reaction mixture was stirred at r.t. for 1 h, then at 60° C. for 1 h, and then at r.t. for 18 h before being concentrated in vacuo. The residue was dissolved in water (20 mL) and the solution washed with DCM (3×25 mL). The aqueous fraction was separated, acidified with 1M aqueous HCl, then extracted with EtOAc (4×50 mL). The combined organic fractions were dried (Na$_2$SO$_4$), filtered and concentrated in vacuo to give the title compound (0.135 g, 49%) as an off-white solid that was used without further purification. LCMS (ES+) 442.2 (M+H)$^+$, RT 1.82 minutes (Method 9).

Intermediate 123

Pentafluorophenyl 3-{[(3S)-4-(6,6-dimethyl-4-oxo-4,5,6,7-tetrahydro[1,3]thiazolo[5,4-c]pyridin-2-yl) morpholin-3-yl]methyl}-1-benzofuran-5-carboxylate To a stirred solution of Intermediate 122 (0.135 g, 0.31 mmol) in DMF (8 mL) was added pentafluorophenol (0.062 g, 0.34 mmol) and EDC (0.070 g, 0.37 mmol). The reaction mixture was stirred at r.t. for 16 h, then used as such for the next step. LCMS (ES+) 608.1 (M+H)$^+$, RT 3.39 minutes (Method 9).

Intermediate 124 tert-Butyl 6-bromo-2,3-dihydro-4H-1,4-benzoxazine-4-carboxylate

To a stirred solution of 6-bromo-3,4-dihydro-2H-1,4-benzoxazine (4.0 g, 18.69 mmol) in THF (50 mL) was added NEt$_3$ (2.8 mL, 18.69 mmol), followed by DMAP (0.02 g, 0.16 mmol) and di-tert-butyl dicarbonate (4.0 g, 18.69 mmol). The reaction mixture was stirred at 70° C. for 3 h, cooled to r.t., and then concentrated in vacuo. Purification by column chromatography (SiO$_2$, 0-50% EtOAc/heptane) gave the title compound (2.19 g, 37%) as a colourless oil. $\delta_H$ (CDCl$_3$) 7.94 (1H, s), 6.99 (1H, dd, J 8.7 and 2.3 Hz), 6.67 (1H, d, J 8.9 Hz), 4.22-4.09 (2H, m), 3.82-3.72 (2H, m), 1.49 (9H, s). LCMS (ES+) 315.0 (M+H)$^+$, RT 4.52 minutes (Method 1).

Intermediate 125 tert-Butyl 6-(1H-pyrazol-1-yl)-2,3-dihydro-4H-1,4-benzoxazine-4-carboxylate

A stirred suspension of Intermediate 124 (0.079 g, 0.25 mmol), cesium carbonate (0.162 g, 0.50 mmol), copper(I) oxide (0.002 g, 0.025 mmol), pyrazole (0.026 g, 0.37 mmol) and salicylaldehyde hydrazone (0.07 g, 0.05 mmol) in MeCN (1 mL) was stirred at 80° C. for 3 days. The reaction mixture was then concentrated in vacuo. Purification by column chromatography (SiO$_2$, 0-50% EtOAc/heptane) gave the title compound (0.070 g, 93%) as an off-white solid. $\delta_H$ (CDCl$_3$) 8.26 (1H, s), 7.84 (1H, d, J 2.3 Hz), 7.70 (1H, d, J 1.7 Hz), 7.33 (1H, dd, J 8.9 and 2.6 Hz), 6.96 (1H, d, J 8.7 Hz), 6.44 (1H, t, J 2.1 Hz), 4.35-4.20 (2H, m), 3.84-3.98 (2H, m), 1.59 (9H, s). LCMS (ES+) 302.0 (M+H)$^+$, RT 4.08 minutes (Method 2).

Intermediate 126

6-(1H-Pyrazol-1-yl)-3,4-dihydro-2H-1,4-benzoxazine

A stirred solution of Intermediate 125 (0.07 g, 0.23 mmol) in TFA (4 mL) was stirred at r.t. for 3 h, then concentrated in vacuo. The residue was dissolved in DCM (5 mL), and the solution treated with aqueous sat. Na$_2$CO$_3$ solution. The organic fraction was separated, then concentrated in vacuo to give the title compound (0.045 g, 96%) as an off-white solid. $\delta_H$ (CDCl$_3$) 7.71 (1H, d, J 2.4 Hz), 7.59 (1H, d, J 1.7 Hz), 6.92 (1H, d, J 2.3 Hz), 6.85-6.69 (2H, m), 6.33 (1H, t, J 2.3 Hz), 4.26-4.15 (2H, m), 3.44-3.34 (2H, m), 3.27-2.54 (1H, m). LCMS (ES+) 202.0 (M+H)$^+$, RT 2.75 minutes (Method 2).

Intermediate 127

Method AC

1-Cyclopropylmethyl-4-(4,4,5,5-tetramethyl-[1,3,2]dioxaborolan-2-yl)-1H-pyrazole To a stirred solution of pyrazole-4-boronic acid pinacol ester (0.25 g, 1.29 mmol) in THF (5 mL) was added a solution of sodium bis(trimethylsilyl)amide (0.71 mL, 2M in THF, 1.42 mmol), followed by (bromomethyl)cyclopropane (0.19 mL, 1.93 mmol). The reaction mixture was stirred at r.t. in a sealed tube for 16 h, then at 80° C. for 4 h. Additional (bromomethyl)cyclopropane (0.06 mL, 0.65 mmol) was added. The reaction mixture was stirred at 80° C. for 16 h, then concentrated in vacuo. EtOAc (30 mL) and aqueous sat. NH$_4$Cl (15 mL) were added. The organic fraction was separated, washed with H$_2$O (15 mL), then brine (15 mL), dried (MgSO$_4$), filtered and concentrated in vacuo to give the title compound (0.27 g, 84%) as a clear yellow oil that was used without further purification. $\delta_H$ (CDCl$_3$) 7.82 (1H, s), 7.80 (1H, s), 3.99 (2H, d, J 7.2 Hz), 1.32 (12H, s), 1.32-1.19 (1H, m), 0.70-0.59 (2H, m), 0.42-0.33 (2H, m). LCMS (ES+) 249.0 (M+H)$^+$, RT 3.42 minutes (Method 1).

Intermediate 128

1-(3-Methoxypropyl)-4-(4,4,5,5-tetramethyl-[1,3,2]dioxaborolan-2-yl)-1H-pyrazole The title compound was prepared from pyrazole-4-boronic acid pinacol ester and 1-bromo-3-methoxypropane according to Method AC (90° C.) and was isolated as an orange gum (quantitative) that was used without further purification. LCMS (ES+) 267.0 (M+H)$^+$, RT 2.96 minutes (Method 1).

Intermediate 129

1-Methoxy-3-[4-(4,4,5,5-tetramethyl-[1,3,2]dioxaborolan-2-yl)-1H-pyrazol-1-yl]propan-2-ol To a stirred solution of pyrazole-4-boronic acid pinacol ester (0.25 g, 1.29 mmol) in THF (5 mL) was added a solution of sodium bis(trimethylsilyl)amide (0.71 mL, 2M in THF, 1.42 mmol), followed by 1-chloro-3-methoxy-2-propanol (0.24 g, 2.58 mmol). The reaction mixture was stirred in a sealed vial at 90° C. for 6 days. Additional 1-chloro-3-methoxy-2-propanol (0.24 g, 2.58 mmol) was added, followed by triethylamine (0.35 mL, 2.60 mmol). The reaction mixture was stirred at 90° C. for 3 days, then cooled to r.t. Water (2 mL) and EtOAc (5 mL) were added. The organic fraction was separated, washed with H$_2$O (2×2 mL), then brine (2 mL), dried (MgSO$_4$), filtered and concentrated in vacuo to give the title compound (0.38 g, 96%) as an orange oil that was used without further purification. LCMS (ES+) 283.0 (M+H)$^+$, RT 2.52 minutes (Method 1).

Intermediate 130

1-Allyl-4-(4,4,5,5-tetramethyl-[1,3,2]dioxaborolan-2-yl)-1H-pyrazole

The title compound was prepared from pyrazole-4-boronic acid pinacol ester and allyl bromide according to Method AC (after initial stirring at r.t. for 16 h, an additional 0.3 equivalent of sodium bis(trimethylsilyl)amide was added and the reaction mixture was stirred at 90° C. for 16 h) and was isolated as an amber oil (quantitative) that was used without further purification. LCMS (ES+) 235.0 (M+H)$^+$, RT 3.09 minutes (Method 1).

Intermediate 131

Method AE 4-(4-Nitrophenyl)morpholine

To a stirred solution of 4-fluoronitrobenzene (5.0 g, 35.43 mmol) in DMF (40 mL) were added morpholine (4.7 mL, 53.15 mmol) and cesium carbonate (17.3 g, 53.15 mmol). The reaction mixture was stirred at 60° C. for 48 h, then water (50 mL) was added. The solid formed was filtered and washed with water (5×100 mL), then Et$_2$O (3×50 mL) to give the title compound (6.5 g, 88%) as a yellow solid that was used without further purification. $\delta_H$ (DMSO-d$_6$) 8.12-8.02 (2H, m), 7.09-7.00 (2H, m), 3.79-3.68 (4H, m), 4.46-3.37 (4H, m). LCMS (ES+) 208.9 (M+H)$^+$, RT 2.49 minutes (Method 3).

Intermediate 132

Method AF 4-(Morpholin-4-yl)aniline

To a stirred suspension of Intermediate 131 (6.5 g, 31.25 mmol) in EtOH (170 mL) was added 10% w/w palladium on carbon (0.33 g). The reaction mixture was stirred under an atmosphere of H$_2$ at r.t. for 16 h, then filtered through Celite®, washed with MeOH (5×100 mL) and concentrated in vacuo to give the title compound (4.8 g, 86%) as a purple solid that was used without further purification. $\delta_H$ (DMSO-d$_6$) 6.72-6.65 (2H, m), 6.58-6.54 (2H, m), 4.55 (2H, br. s), 3.73-3.66 (4H, m), 4.91-2.84 (4H, m). LCMS (ES+) 178.9 (M+H)$^+$, RT 1.86 minutes (Method 4).

Intermediate 133

Method AG tert-Butyl [4-(morpholin-4-yl)phenyl]carbamate

To a stirred solution of Intermediate 132 (4.8 g, 26.97 mmol) in DCM (70 mL) was added DIPEA (5.6 mL, 32.36 mmol), followed by di-tert-butyl dicarbonate (7.1 g, 32.36 mmol). The reaction mixture was stirred at r.t. for 16 h. Water (50 mL) was added, and the layers were separated. The aqueous fraction was extracted with DCM (2×30 mL). The combined organic fractions were washed with water (3×100 mL), dried (Na$_2$SO$_4$), filtered and concentrated in vacuo. The residue was triturated with hexanes, then filtered to give the title compound (7.03 g, 93%) as a purple solid. $\delta_H$ (DMSO-d$_6$) 9.01 (1H, br. s), 7.34-7.25 (2H, d, J 8.7 Hz), 6.87-6.79 (2H, d, J 9.0 Hz), 3.78-3.65 (4H, m), 3.07-2.93 (4H, m), 1.46 (9H, s). LCMS (ES+) 279.0 (M+H)$^+$, RT 2.70 minutes (Method 4).

Intermediate 134 tert-Butyl [2-iodo-4-(morpholin-4-yl)phenyl]carbamate

The title compound was prepared from Intermediate 133 according to Method X and was isolated as a pale yellow solid (48%) after purification by column chromatography (SiO$_2$, 0-30% EtOAc/hexanes). $\delta_H$ (DMSO-d$_6$) 8.31 (1H, s), 7.32 (1H, d, J 2.8 Hz), 7.13 (1H, d, J 8.9 Hz), 6.94 (1H, dd, J 2.8 and 8.9 Hz), 3.78-3.66 (4H, m), 3.14-3.02 (4H, m), 1.44 (9H, s). LCMS (ES+) 405.1 (M+H)$^+$, RT 2.80 minutes (Method 10).

Intermediate 135

2-Iodo-4-(morpholin-4-yl)aniline

The title compound was prepared from Intermediate 134 (dissolved in MeOH) according to Method J and was isolated as a yellow solid (71%) that was used without further purification. $\delta_H$ (DMSO-d$_6$) 7.11 (1H, d, J 2.8 Hz), 6.83 (1H, dd, J 8.8 and 2.8 Hz), 6.71 (1H, d, J 8.8 Hz), 4.72 (2H, br. s), 3.72-3.66 (4H, m), 2.92-2.85 (4H, m). LCMS (ES+) 305.1 (M+H)$^+$, RT 1.76 minutes (Method 10).

Intermediate 136

1-(4-Nitrophenyl)azetidine

The title compound was prepared from 4-fluoronitrobenzene and azetidine hydrochloride according to Method AE and was isolated as a yellow solid (69%) after trituration in water, and then in Et$_2$O. $\delta_H$ (DMSO-d$_6$) 8.10-7.99 (2H, m), 6.48-6.35 (2H, m), 4.04 (4H, t, J 7.5 Hz), 2.47-2.31 (2H, m). LCMS (ES+) 178.9 (M+H)$^+$, RT 2.71 minutes (Method 3).

Intermediate 137

4-(Azetidin-1-yl)aniline

The title compound was prepared from Intermediate 136 according to Method AF and was isolated as a purple solid (70%) that was used without further purification. $\delta_H$ (DMSO-d$_6$) 6.50-6.43 (2H, m), 6.23-6.16 (2H, m), 4.33 (2H, br. s), 3.61 (4H, t, J 7.0 Hz), 2.26-2.14 (2H, m). LCMS (ES+) 148.9 (M+H)$^+$, RT 2.06 minutes (Method 4).

Intermediate 138 tert-Butyl [4-(azetidin-1-yl)phenyl]carbamate

The title compound was prepared from Intermediate 137 according to Method AG and was isolated as a purple solid (81%) after trituration in hexanes. $\delta_H$ (DMSO-d$_6$) 8.87 (1H, br. s), 7.21 (2H, d, J 8.7 Hz), 6.32 (2H, d, J 8.9 Hz), 3.71 (4H, t, J 7.0 Hz), 2.36-2.18 (2H, m), 1.45 (9H, s). LCMS (ES+) 249.9 (M+H)$^+$, RT 2.91 minutes (Method 4).

Intermediate 139 tert-Butyl [4-(azetidin-1-yl)-2-iodophenyl)carbamate

The title compound was prepared from Intermediate 138 according to Method X and was isolated as a pale yellow solid (43%) after purification by column chromatography (SiO$_2$, 0-30% EtOAc/hexanes). $\delta_H$ (DMSO-d$_6$) 8.26 (1H, s), 7.03 (1H, d, J 8.5 Hz), 6.80 (1H, d, J 2.6 Hz), 6.38 (1H, dd, J 8.6 and 2.6 Hz), 3.78 (4H, t, J 7.2 Hz), 2.37-2.20 (2H, m), 1.43 (9H, s). LCMS (ES+) 405.1 (M+H)$^+$, RT 2.80 minutes (Method 10).

Intermediate 140

4-(Azetidin-1-yl)-2-iodoaniline

The title compound was prepared from Intermediate 139 (dissolved in MeOH) according to Method J and was isolated as a yellow oil (15%) that was used without further purification. LCMS (ES+) 274.0 (M+H)$^+$, RT 2.06 minutes (Method 10).

Intermediate 141

6,6-Dimethyl-2-[(3S)-3-{[5-(morpholin-4-yl)-2-(trimethylsilyl)-1H-indol-3-yl]methyl}morpholin-4-yl]-6,7-dihydro[1,3]thiazolo[5,4-c]pyridin-4(5H)-one The title compound was prepared from Example 155 and Intermediate 135 according to Method I and was isolated as a

Intermediate 142

2-[(3S)-3-{[5-(Azetidin-1-yl)-2-(trimethylsilyl)-1H-indol-3-yl]methyl}morpholin-4-yl]-6,6-dimethyl-6,7-dihydro[1,3]thiazolo[5,4-c]pyridin-4(5H)-one The title compound was prepared from Example 155 and Intermediate 140 according to Method I and was isolated as a yellow gum (21%) after work-up (DCM and water) and purification by column chromatography (SiO$_2$, 0-5% MeOH/DCM). LCMS (ES+) 524.3 (M+H)$^+$, RT 2.15 minutes (Method 9).

Intermediate 143 tert-Butyl (4-aminobenzyl)carbamate

To a stirred solution of 4-aminobenzylamine (10.0 g, 81.8 mmol) in MeOH (100 mL) was added di-tert-butyl dicarbonate (17.9 g, 81.8 mmol) portionwise over 30 minutes. The reaction mixture was then concentrated in vacuo. EtOAc (100 mL) was added and the solution washed with 0.5M aqueous NaH$_2$PO$_4$ (3×100 ml), dried (Na$_2$SO$_4$), filtered and concentrated in vacuo to give the title compound (15.34 g, 84%) as a pale orange solid that was used without further purification. $\delta_H$(DMSO-d$_6$) 7.16-7.08 (1H, m), 6.89 (2H, d, J 8.1 Hz), 6.49 (2H, d, J 8.1 Hz), 4.91 (2H, s), 3.93 (2H, d, J 6.1 Hz), 1.38 (9H, s).

Intermediate 144 tert-Butyl (4-amino-3-iodobenzyl)carbamate

To a stirred solution of Intermediate 143 (15.3 g, 69.0 mmol) in MeOH (100 mL) was added CaCO$_3$ (8.6 g, 83.0 mmol), followed by iodine (17.5 g, 69.0 mmol). The reaction mixture was stirred at 70° C. for 16 h, then concentrated in vacuo. Aqueous sat. Na$_2$S$_2$O$_3$ (100 mL) and EtOAc (100 mL) were added. The organic fraction was separated, dried (Na$_2$SO$_4$), filtered and concentrated in vacuo. Purification by column chromatography (SiO$_2$, 0-15% EtOAc/hexanes) gave the title compound (3.46 g, 14%) as an orange oil. LCMS (ES+) 371.0 (M+Na)$^+$, RT 3.34 minutes (Method 5).

Intermediate 145

4-(Aminomethyl)-2-iodo aniline

The title compound was prepared from Intermediate 144 (dissolved in MeOH) according to Method J and was isolated as a yellow oil (94%) that was used without further purification. $\delta_H$(DMSO-d$_6$) 7.51 (1H, d, J 1.5 Hz), 7.02 (1H, dd, J 8.3 and 1.8 Hz), 6.70 (1H, d, J 8.1 Hz), 5.01 (2H, s), 3.51 (2H, s), 2.00 (2H, s).

Intermediate 146

N-(4-Amino-3-iodobenzyl)acetamide

To a stirred solution of Intermediate 145 (0.97 g, 3.91 mmol) in DCM (50 mL) at 0° C. was added NEt$_3$ (0.65 mL, 4.69 mmol), followed by the slow addition of acetyl chloride (0.26 mL, 3.71 mmol). The reaction mixture was stirred at r.t. for 16 h. Water (40 mL) was added. The aqueous fraction was separated and extracted with DCM (2×20 mL). The combined organic fractions were washed with brine (60 mL), separated via an Isolute® phase separator cartridge, then concentrated in vacuo. Purification by column chromatography (SiO$_2$, 30-100% EtOAc/hexanes) gave the title compound (0.56 g, 50%) as a yellow solid. $\delta_H$(DMSO-d$_6$) 8.17 (1H, s), 7.43 (1H, d, J 1.5 Hz), 6.97 (1H, dd, J 8.1 and 1.5 Hz), 6.70 (1H, d, J 8.2 Hz), 5.11 (2H, s), 4.04 (2H, d, J 5.8 Hz), 1.83 (3H, s). LCMS (ES+) 291.0 (M+H)$^+$, 313 (M+Na)$^+$, RT 2.63 minutes (Method 5).

Intermediate 147

N-{[3-{[(3S)-4-(6,6-Dimethyl-4-oxo-4,5,6,7-tetrahydro[1,3]thiazolo[5,4-c]pyridin-2-yl)morpholin-3-yl]methyl}-2-(trimethylsilyl)-1H-indol-5-yl]methyl}acetamide The title compound was prepared from Example 155 and Intermediate 146 according to Method I (additional LiCl (1 equivalent) and Pd(OAc)$_2$ (0.05 equivalent) were added after 16 h, and the reaction mixture stirred at 100° C. for a further 5 h) and was isolated as a yellow oil (25%) after work-up (EtOAc and water) and purification by column chromatography (SiO$_2$, 0-1% MeOH/DCM). $\delta_H$ (CDCl$_3$) 8.03 (1H, s), 7.93 (1H, s), 7.33-7.27 (1H, m), 7.15 (1H, dd, J 8.3 and 1.3 Hz), 6.56-6.14 (1H, m), 5.15 (1H, s), 4.64-4.43 (2H, m), 4.38-4.25 (1H, m), 4.17-4.07 (1H, m), 3.84 (1H, d, J 11.9 Hz), 3.78-3.62 (3H, m), 3.58-3.37 (2H, m), 3.24-3.13 (1H, m), 2.85 (2H, s), 2.04 (3H, s), 1.37 (6H, d, J 5.5 Hz), 0.43 (9H, s). LCMS (ES+) 468 (M+H-TMS)$^+$, RT 2.20 minutes (Method 5).

Intermediate 148 tert-Butyl (3S)-3-{[5-cyano-1-methyl-2-(trimethylsilyl)-1H-indol-3-yl]methyl}morpholine-4-carboxylate To a stirred solution of Intermediate 89 (1.6 g, 3.87 mmol) in THF (20 mL) at −78° C. was added n-butyllithium (1.9 mL, 2.5M in THF, 4.85 mmol). After stirring at this temperature for 10 minutes, MeI (0.3 mL, 4.84 mmol) was added, and the reaction mixture warmed to r.t. over 1 h. EtOAc (10 mL) and brine (20 mL) were added. The aqueous fraction was separated and extracted with EtOAc (3×20 mL). The combined organic fractions were dried (Na$_2$SO$_4$), filtered and evaporated in vacuo. Purification by column chromatography (SiO$_2$, 15-60% EtOAc/hexanes) gave the title compound (1.60 g, quantitative) as an off-white solid. LCMS (ES+) 427.0 (M+H)$^+$, RT 2.51 minutes (Method 12).

Intermediate 149

1-Methyl-3-[(3S)-morpholin-3-ylmethyl]-1H-indole-5-carbonitrile

The title compound was prepared from Intermediate 148 according to Method J and was isolated as a yellow oil (71%) that was used without further purification. LC, RT 1.45 minutes (Method 12).

Intermediate 150

(3S)-3-[(5-Cyano-1-methyl-1H-indol-3-yl)methyl]morpholine-4-carbothioamide

The title compound was prepared from Intermediate 149 according to Method K and was isolated a brown solid (92%) that was used without further purification. LCMS (ES+) 298.0 (M–NH$_2$)$^+$, RT 1.76 minutes (Method 12).

Intermediate 151 tert-Butyl (3S)-3-{[2-(trimethylsilyl)-1H-indol-3-yl]methyl}morpholine-4-carboxylate The title compound was prepared from Intermediate 26 and 2-iodoaniline according to Method I and was isolated as a white solid (40%) after purification by column chromatography (SiO$_2$, 15-60% EtOAc/hexanes). LCMS (ES+) 333.0 ((M–tBu)+H)$^+$, 2.50 minutes (Method 12).

Intermediate 152 tert-Butyl (3S)-3-{[1-methyl-2-(trimethylsilyl)-1H-indol-3-yl]methyl}morpholine-4-carboxylate The title compound was prepared from Intermediate 151 according to Method W (using only 1.1 equivalent of NaH, doing the work-up in EtOAc and water, and drying the separated organic fraction with Na$_2$SO$_4$) and was isolated as a yellow oil (24%) after purification by column chromatography (SiO$_2$, 15-60% EtOAc/hexanes). $\delta_H$ (DMSO-d$_6$) 7.90-7.60 (1H, br. s), 7.39 (1H, d, J 8.3 Hz), 7.25-7.10 (1H, m), 7.10-7.00 (1H, m), 4.07-4.05 (1H, m), 3.88-3.85 (1H, m), 3.80 (3H, s), 3.70-3.60 (1H, br. s), 3.48-3.39 (2H, m), 3.31-3.24 (1H, m), 3.24-3.22 (2H, m), 2.90-2.75 (1H, m), 1.38 (9H, s), 0.47 (9H, s). LCMS (ES+) 403.0 (M+H)$^+$, 347.0 ((M–$^t$Bu)+H), RT 2.66 minutes (Method 12).

Intermediate 153

1-Methyl-3-[(3S)-morpholin-3-ylmethyl]-1H-indole

The title compound was prepared from Intermediate 152 according to Method J and was isolated as a colourless oil (88%) that was used without further purification. LCMS (ES+) 230.0 (M+H)$^+$, RT 1.53 minutes (Method 12).

Intermediate 154

(3S)-3-[(1-Methyl-1H-indol-3-yl)methyl]morpholine-4-carbothioamide

The title compound was prepared from Intermediate 153 according to Method K and was isolated as a yellow solid (48%) that was used without further purification. LCMS (ES+) 290.0 (M+H)$^+$, RT 1.66 minutes (Method 12).

Intermediate 155

4-[2-(2-Nitrophenoxy)ethyl]morpholine

To a stirred solution of 4-(2-hydroxyethyl)morpholine (1.7 g, 12.96 mmol) in DMF (2 mL) was added NaH (0.52 g, 60% dispersion in oil, 12.96 mmol). The reaction mixture was stirred at r.t. for 10 minutes, then cooled to 0° C. A solution of 2-fluoronitrobenzene (1.5 g, 10.63 mmol) in DMF (2 mL) was added over 5 min. The reaction mixture was allowed to warm to r.t., then was stirred for 2 h before the addition of 2M aqueous HCl (50 mL). The aqueous fraction was separated, neutralised with aqueous sat. NaHCO$_3$ and extracted with EtOAc (2×50 mL). The combined organic fractions were dried (Na$_2$SO$_4$), filtered and concentrated in vacuo to give the title compound (2.4 g, 90%) as a yellow oil that was used without further purification. LCMS (ES+) 253.0 (M+H)$^+$, RT 2.06 minutes (Method 5).

Intermediate 156

2-[2-(Morpholin-4-yl)ethoxy]aniline

To a stirred solution of Intermediate 155 (2.4 g, 9.51 mmol) in EtOH (20 mL) was added tin(II) chloride (6.5 g, 28.53 mmol). The reaction mixture was stirred at 60° C. for 3 h, then cooled to r.t. before addition of 2M aqueous NaOH (50 mL). The reaction mixture was stirred at r.t. for 1 h. The aqueous fraction was separated and extracted with tert-butyl methyl ether (2×100 mL). The combined organic fractions were dried (Na$_2$SO$_4$), filtered and concentrated in vacuo to give the title compound (1.7 g, 80%) as a yellow oil that was used without further purification. LCMS (ES+) 223.0 (M+H)$^+$, RT 1.07 minutes (Method 5).

Intermediate 157 tert-Butyl {2-[2-(morpholin-4-yl)ethoxy]phenyl}carbamate

The title compound was prepared from Intermediate 156 according to Method AG and was isolated as a yellow oil (90%) after purification by column chromatography (SiO$_2$, 0-5% MeOH/DCM with 1% NEt$_3$ added). LCMS (ES+) 323.0 (M+H)$^+$, RT 2.40 minutes (Method 5).

Intermediate 158 tert-Butyl {2-iodo-6-[2-(morpholin-4-yl)ethoxy]phenyl}carbamate

The title compound was prepared from Intermediate 157 according to Method X and was isolated as a dark yellow solid (65%) after purification by column chromatography (SiO$_2$, 0-100% EtOAc/DCM with 1% NEt$_3$ added). LCMS (ES+) 449.0 (M+H)$^+$, RT 2.36 minutes (Method 5).

Intermediate 159

2-Iodo-6-[2-(morpholin-4-yl)ethoxy]aniline

The title compound was prepared from Intermediate 158 according to Method J and was isolated as a brown oil (72%) after purification by column chromatography (SiO$_2$, 0-100% EtOAc/DCM with 1% Et$_3$N added). LCMS (ES+) 349.0 (M+H)$^+$, RT 2.28 minutes (Method 5).

Intermediate 160 tert-Butyl (3S)-3-{[7-(2-(morpholin-4-yl)ethoxy)-2-(triethylsilyl)-1H-1-indol-3-yl]methyl}morpholine-4-carboxylate The title compound was prepared from Intermediate 102 and Intermediate 159 according to Method I and was isolated as a yellow oil (40%) after purification by column chroma-

Intermediate 161

(3S)-3-{[7-(2-(Morpholin-4-yl)ethoxy)-1H-indol-3-yl]methyl}morpholine-4-carbothioamide The title compound was prepared from Intermediate 160 according to Method J, followed by Method K, and was isolated as a yellow oil (33%) that was used without further purification. LCMS (ES+) 405.0 (M+H)$^+$, RT 2.01 minutes (Method 5).

Intermediate 162

Dimethyl 4-nitrobenzene-1,3-dicarboxylate

To a stirred solution of methyl 3-formyl-4-nitrobenzoate (1.5 g, 7.18 mmol) in formic acid (2 mL) was added hydrogen peroxide (2.5 mL, 30% in water). The reaction mixture was stirred at r.t. for 16 h. Additional hydrogen peroxide (2.5 mL, 30% in water) was added, and the reaction mixture stirred at r.t. for 8 h before being concentrated in vacuo. The residue was dissolved in 2% HCl in MeOH (40 mL). The solution was stirred at 70° C. for 4 days, then concentrated in vacuo. The residue was dissolved in DCM (10 mL), and the solution washed with aqueous sat. NaHCO$_3$ (2×10 mL), dried (MgSO$_4$), filtered and concentrated in vacuo to give the title compound (1.52 g, 87%) as a colourless oil. $\delta_H$ (CDCl$_3$) 8.43 (1H, s), 8.29 (1H, dd, J 1.8 and 8.6 Hz), 7.92 (1H, d, J 8.3 Hz), 3.99 (3H, s), 3.95 (3H, s). LCMS (ES+) 240.0 (M+H)$^+$, RT 1.80 minutes (Method 12).

Intermediate 163

4-Nitro-N,N,N',N'-tetramethylbenzene-1,3-dicarboxamide

The title compound was prepared from Intermediate 162 and dimethylamine hydrochloride according to Method AH (the reaction mixture was neutralised using AcOH before work-up with DCM and aqueous sat. NaHCO$_3$) and was isolated as a colourless oil (90%) after purification by column chromatography (SiO$_2$, 2.5% MeOH/DCM). $\delta_H$ (CDCl$_3$) 8.23 (1H, d, J 8.3 Hz), 7.59 (1H, dd, J 1.8 and 8.3 Hz), 7.43 (1H, s), 3.16 (6H, s), 2.85 (6H, s). LCMS (ES+) 266.0 (M+H)$^+$, RT 1.07 minutes (Method 12).

Intermediate 164

4-Amino-N,N,N',N'-tetramethylbenzene-1,3-dicarboxamide

To a stirred solution of Intermediate 163 (1.5 g, 5.66 mmol) in THF (15 mL) was added Raney® nickel (ca. 0.5 g). The reaction mixture was stirred under an atmosphere of H$_2$ at r.t. for 3 h, then filtered and concentrated in vacuo. Trituration in Et$_2$O gave the title compound (1.1 g, 83%) as a white solid. $\delta_H$ (CDCl$_3$) 7.31-7.27 (1H, m), 7.25 (1H, d, J 1.4 Hz), 6.70 (1H, d, J 6.2 Hz), 4.62 (2H, br. s), 3.06 (3H, s), 3.05 (3H, s), 3.04 (6H, s). LCMS (ES+) 236 (M+H)$^+$, RT 0.90 minutes (Method 12).

Intermediate 165

4-Amino-5-iodo-N,N,N',N'-tetramethylbenzene-1,3-dicarboxamide

To a stirred solution of Intermediate 164 (1.1 g, 4.68 mmol) in DCM (16 mL) was added dipyridineiodonium tetrafluoroborate (1.6 g, 4.25 mmol), followed by tetrafluoroboric acid (0.7 mL, 54% in Et$_2$O, 4.24 mmol). The reaction mixture was stirred at r.t. for 10 minutes. DCM (10 mL) was added, and the reaction mixture washed with aqueous sat. NaHCO$_3$ (2×10 mL). The organic fraction was dried (MgSO$_4$), filtered and concentrated in vacuo to give the title compound (1.4 g, 58%) as an off-white solid. $\delta_H$ (CDCl$_3$) 7.80 (1H, s), 7.21 (1H, d, J 0.8 Hz), 5.01 (2H, br. s), 3.04 (12H, s). LCMS (ES+) 262.0 (M+H)$^+$, RT 1.27 minutes (Method 12).

Intermediate 166 tert-Butyl (3S)-3-({5,7-bis[(dimethylamino)carbonyl]-2-(trimethyl silyl)-1H-indol-3-yl}methyl)morpholine-4-carboxylate The title compound was prepared from Example 26 and Intermediate 165 according to Method I and was isolated as a colourless oil (89%) after work-up (DCM and brine) and purification by column chromatography (SiO$_2$, 2.5% MeOH/DCM). LCMS (ES+) 531.0 (M+1)$^+$, RT 2.06 minutes (Method 12).

Intermediate 167

3-{[(3S)-4-(Aminocarbonothioyl)morpholin-3-yl]methyl}-N,N,N',N'-tetramethyl-1H-indole-5,7-dicarboxamide The title compound was prepared from Intermediate 166 according to Method J, followed by Method K, and was isolated as an off-white solid (95%) after purification by column chromatography (SiO$_2$, 10% MeOH/DCM). LC/MS (ES+) 418.0 (M+H)$^+$, RT 1.22 minutes (Method 12).

Intermediate 168

Methyl N-methyl-N-(4-nitrophenyl)carbamate

The title compound was prepared from N-methyl-4-nitroaniline and methyl chloroformate according to Method Y and was isolated as a pale yellow solid (84%) after trituration in cold MeOH. $\delta_H$ (DMSO-d$_6$) 8.22 (2H, d, J 9.3 Hz), 7.64 (2H, d, J 9.3 Hz), 3.70 (3H, s), 3.32 (3H, s).

Intermediate 169

Methyl N-(4-aminophenyl)-N-methylcarbamate

The title compound was prepared from Intermediate 168 according to Method AF and was isolated as a brown solid (95%) that was used without further purification. $\delta_H$ (DMSO-d$_6$) 6.87 (2H, d, J 8.6 Hz), 6.51 (2H, d, J 8.7 Hz), 5.09 (2H, br. s), 3.53 (3H, s), 3.09 (3H, s). LCMS (ES+) 181.9 (M+H)$^+$, RT 1.85 minutes (Method 9).

Intermediate 170

Methyl N-(4-amino-3-iodophenyl)-N-methylcarbamate

To a stirred solution of Intermediate 169 (3.1 g, 17.36 mmol) in 1M aqueous HCl (200 mL) was added a solution of iodine monochloride (2.5 g, 15.62 mmol) in 1M aqueous HCl (50 mL) over 30 minutes. The reaction mixture was stirred for 3 h at r.t., and then concentrated in vacuo. Purification by column chromatography (SiO$_2$, 30% EtOAc/hexanes) gave the title compound (1.62 g, 30%) as a pale yellow oil. $\delta_H$ (DMSO) 7.44 (1H, d, J 2.4 Hz), 6.99 (1H, dd, J 8.5 and 2.4 Hz), 6.72 (1H, d, J 8.6 Hz), 5.21 (2H, br. s), 3.55 (3H, s), 3.09 (3H, s). LCMS (ES+) 306.9 (M+H)$^+$, RT 1.89 minutes (Method 11).

Intermediate 171 tert-Butyl (3S)-3-({5-[N-(methoxycarbonyl)-N-(methyl)amino]-2-(trimethylsilyl)-1H-indol-3-yl}methyl)morpholine-4-carboxylate The title compound was prepared from Intermediate 26 and Intermediate 170 according to Method I and was isolated as an orange oil (78%) after purification by column chromatography (SiO$_2$, 50% EtOAc/hexanes). LCMS (ES+) 476.0 (M+H)$^+$, RT 3.29 minutes (Method 11).

Intermediate 172

Methyl N-methyl-N-{3-[(3S)-morpholin-3-ylmethyl]-1H-indol-5-yl}carbamate

The title compound was prepared from Intermediate 171 according to Method J and was isolated as an orange oil (quantitative) that was used without further purification. LCMS (ES+) 304.1 (M+H)$^+$, RT 1.06 minutes (Method 11).

Intermediate 173

Methyl N-(3-{[(3S)-4-(aminocarbonothioyl)morpholin-3-yl]methyl}-1H-indol-5-yl)-N-methylcarbamate The title compound was prepared from Intermediate 172 according to Method K and was isolated as an orange oil (quantitative) after purification by column chromatography (SiO$_2$, 10% EtOAc/hexanes). LCMS (ES+) 362.0 (M)$^+$, RT 1.50 minutes (Method 12).

Intermediate 174

1-(4-Amino-3-iodophenyl)ethanone

To a stirred suspension of CaCO$_3$ (4.5 g, 45.27 mmol) in H$_2$O (15 mL) was added a solution of 4-acetylaniline (4.1 g, 30.18 mmol) in MeOH (25 mL), followed by a solution of iodine monochloride (5.2 g, 31.88 mmol) in MeOH (20 mL) dropwise. The reaction was stirred at r.t. for 45 minutes, then diluted with Et$_2$O (150 mL). The organic fraction was separated, washed with water (100 mL), then brine (100 mL), dried (Na$_2$SO$_4$), filtered and concentrated in vacuo to give the title compound (3.5 g, 44%) as a brown oil that was used without further purification. $\delta_H$ (DMSO-d$_6$) 8.14 (1H, d, J 1.8 Hz), 7.70 (1H, dd, J 8.3 and 1.8 Hz), 6.75 (1H, d, J 8.3 Hz), 6.10 (2H, s), 2.41 (3H, s). LCMS (ES+) 261 (M)$^+$, 283 (M+Na)$^+$, RT 3.026 minutes (Method 5).

Intermediate 175 tert-Butyl (3S)-3-{[5-acetyl-2-(trimethylsilyl)-1H-indol-3-yl]methyl}morpholine-4-carboxylate The title compound was prepared from Intermediate 26 and Intermediate 174 according to Method I and was isolated as a yellow oil (61%) after work-up (EtOAc and water) and purification by column chromatography (SiO$_2$, 10% EtOAc/hexanes). LCMS (ES+) 453.0 (M+Na)$^+$, 375 ((M-$^t$Bu)+H)$^+$, RT 3.87 minutes (Method 5).

Intermediate 176

1-{3-[(3S)-Morpholin-3-ylmethyl]-1H-indol-5-yl}ethanone

The title compound was prepared from Intermediate 175 according to Method J and was isolated as a brown oil (95%) that was used without further purification. $\delta_H$ (DMSO-d$_6$) 11.12 (1H, s), 8.13 (1H, s), 7.60 (1H, d, J 8.6 Hz), 7.28 (1H, d, J 8.6 Hz), 7.15 (1H, d, J 1.7 Hz), 3.54-3.49 (2H, m), 3.44 (2H, s), 3.00 (1H, t, J 10.0 Hz), 2.83-2.78 (1H, m), 2.64-2.51 (4H, m), 2.51 (3H, s). LCMS (ES+) 259.0 (M+H)$^+$, RT 2.12 minutes (Method 5).

Intermediate 177

(3S)-3-[(5-Acetyl-1H-indol-3-yl)methyl]morpholine-4-carbothioamide

The title compound was prepared from Intermediate 176 according to Method K and was isolated as a brown oil (81%) after purification by column chromatography (SiO$_2$, 0-10% MeOH/DCM). LCMS (ES+) 318.1 (M+H)$^+$, RT 2.68 minutes (Method 5).

Intermediate 178 tert-Butyl (4-chloro-2-hydroxyphenyl)carbamate

To a stirred solution of 2-amino-5-chlorophenol (5.0 g, 34.82 mmol) in THF (70 mL) was added di-tert-butyl dicarbonate (15.2 g, 69.65 mmol). The reaction mixture was stirred at 50° C. for 3 h, then concentrated in vacuo. The solid was triturated with hexanes, filtered and washed with cyclohexane to give the title compound (7.3 g, 86%) as a brown solid. $\delta_H$ (CDCl$_3$) 8.45 (1H, br. s), 7.00-6.96 (2H, m), 6.85 (1H, dd, J 8.5 and 2.2 Hz), 6.60 (1H, br. s), 1.50 (9H, s).

Intermediate 179 tert-Butyl (4-chloro-2-methoxyphenyl)carbamate

To a stirred solution of Intermediate 178 (4.6 g, 18.9 mmol) in anhydrous acetone (50 mL) was added K$_2$CO$_3$ (1.5 g, 108.7 mmol), followed by methyl iodide (4.5 mL, 72.0 mmol). The reaction mixture was stirred at 70° C. for 16 h, then cooled to r.t., filtered through Celite® and the filtrate concentrated in vacuo. Purification by column chromatography (SiO$_2$, 20-80% EtOAc/hexanes) gave the title compound (4.8 g, quantitative) as a pale brown liquid. $\delta_H$ (CDCl$_3$) 8.05 (1H, d, J 8.6 Hz), 7.04 (1H, br. s), 6.93 (1H, dd, J 8.7 and 2.2 Hz), 6.84 (1H, d, J 2.2 Hz), 3.87 (3H, s), 1.54 (9H, s).

Intermediate 180 tert-Butyl (4-chloro-2-iodo-6-methoxyphenyl)carbamate

To a stirred solution of Intermediate 179 (2.0 g, 7.76 mmol) in THF (50 mL) at −20° C. was added sec-butyllithium (11 mL, 1.4M in cyclohexane, 15.52 mmol) dropwise. After stirring at this temperature for 10 minutes, the reaction mixture was cooled to −78° C. A solution of 1,2-diiodoethane (3.3 g, 11.64 mmol) in THF (10 mL) was added dropwise, and the reaction mixture gradually warmed to r.t. and stirred for 16 h. Water (10 mL) was added dropwise, and the mixture stirred for 5 minutes then diluted with EtOAc (150 mL). The organic fraction was separated, washed with water (3×50 mL), then brine (50 mL), dried ($Na_2SO_4$), filtered and concentrated in vacuo to give the title compound (2.6 g, 87%) as a brown solid that was used without further purification. $\delta_H$ ($CDCl_3$) 7.36 (1H, d, J 2.2 Hz), 6.79 (1H, d, J 2.2 Hz), 5.86 (1H, br. s), 3.78 (3H, s), 1.42 (9H, s).

Intermediate 181

4-Chloro-2-iodo-6-methoxyaniline

To a stirred solution of Intermediate 180 (2.6 g, 6.78 mmol) in DCM (30 mL) was added TFA (10 mL). The reaction mixture was stirred at r.t. for 1 h, then concentrated in vacuo. The residue was dissolved in DCM (30 mL), and the solution washed with $NaHCO_3$ (3×10 mL), then water (10 mL), and brine (10 mL), dried ($MgSO_4$), filtered and concentrated in vacuo. Purification by column chromatography ($SiO_2$, 5% EtOAc/hexanes) gave the title compound (1.5 g, 79%) as a brown solid. $\delta_H$ ($CDCl_3$) 7.15 (1H, d, J 2.1 Hz), 6.65 (1H, d, J 2.1 Hz), 4.15 (2H, br. s), 3.74 (3H, s).

Intermediate 182 tert-Butyl (3S)-3-{[5-chloro-7-methoxy-2-(trimethylsilyl)-1H-indol-3-yl]methyl}morpholine-4-carboxylate The title compound was prepared from Intermediate 26 and Intermediate 181 according to Method I and was isolated as a yellow oil (66%) after purification by column chromatography ($SiO_2$, 10% EtOAc/hexanes). $\delta_H$ ($CDCl_3$) 8.15 (1H, br. s), 7.45 (1H, br. s), 6.61 (1H, d, J 1.3 Hz), 4.35-4.20 (1H, m), 4.00-3.80 (5H, m), 3.70-3.20 (5H, m), 2.95-2.85 (1H, m), 1.55 (9H, s), 0.44 (9H, s).

Intermediate 183

5-Chloro-7-methoxy-3-[(3S)-morpholin-3-ylmethyl]-1H-indole

The title compound was prepared from Intermediate 182 according to Method J and was isolated as a white solid (60%) after purification by column chromatography ($SiO_2$, 5% MeOH/DCM). $\delta_H$ ($CDCl_3$) 8.39 (1H, br. s), 7.28 (1H, s), 7.05 (1H, s), 6.65 (1H, s), 3.95 (3H, s), 3.94-3.70 (2H, m), 3.60-3.50 (1H, m), 3.40-3.25 (1H, m), 3.20-3.00 (1H, m), 2.99-2.50 (4H, m). One exchangeable proton was not observed.

Intermediate 184

(3S)-3-[(5-Chloro-7-methoxy-1H-indol-3-yl)methyl]morpholine-4-carbothioamide

The title compound was prepared from Intermediate 183 according to Method K and was isolated as a white solid (46%) after purification by column chromatography ($SiO_2$, 50% EtOAc/hexanes). $\delta_H$ (DMSO-$d_6$) 11.21 (1H, s), 7.50 (2H, br. s), 7.14 (1H, s), 6.66 (1H, s), 5.00 (1H, br. s), 3.92-3.85 (4H, m), 3.55 (1H, d, J 10.6 Hz), 3.38-3.31 (5H, m), 3.25-3.10 (1H, m), 2.85-2.70 (1H, m). One exchangeable proton was not observed.

Intermediate 185

4-Chloro-2-iodo-6-(trifluoromethoxy)aniline

To a stirred solution of 4-chloro-2-(trifluoromethoxy)aniline (1.0 g, 4.7 mmol) in EtOH (50 mL) at 50° C. was added a slurry of iodine (1.2 g, 9.6 mmol) and silver sulfate (2.6 g, 8.4 mmol) in EtOH (30 mL). The reaction mixture was stirred in darkness at 50° C. for 24 h, then cooled to r.t. and filtered through Celite®. The filtrate was concentrated in vacuo. Purification by column chromatography ($SiO_2$, 0-55% ethyl acetate/hexanes) gave the title compound (1.6 g, quantitative) as a pale brown solid. $\delta_H$ ($CDCl_3$) 7.59 (1H, d, J 1.7 Hz), 7.18 (1H, d, J 1.7 Hz), 4.35 (2H, br. s). LCMS (ES+) 337.8 (M+H)$^+$, RT 3.81 minutes (Method 5).

Intermediate 186 tert-Butyl (3S)-3-{[5-chloro-7-(trifluoromethoxy)-2-(trimethylsilyl)-1H-indol-3-yl]methyl}morpholine-4-carboxylate The title compound was prepared from Intermediate 26 and Intermediate 185 according to Method I and was isolated as a yellow oil (66%) after purification by column chromatography ($SiO_2$, 10% EtOAc/hexanes). $\delta_H$ ($CDCl_3$) 7.95 (1H, s), 7.60 (1H, br. s), 6.93 (1H, s), 4.20-4.05 (1H, m), 3.90-3.10 (7H, m), 2.85-2.70 (1H, m), 1.34 (9H, s), 0.30 (9H, s).

Intermediate 187

5-Chloro-3-[(3S)-morpholin-3-ylmethyl]-7-(trifluoromethoxy)-1H-indole

The title compound was prepared from Intermediate 186 according to Method J and was isolated as a white solid (57%) that was used without further purification. LCMS (ES+) 335.0 (M+H)$^+$, RT 2.46 minutes (Method 5).

Intermediate 188

(3S)-3-{[5-Chloro-7-(trifluoromethoxy)-1H-indol-3-yl]methyl}morpholine-4-carbothioamide The title compound was prepared from Intermediate 187 according to Method K and was isolated as a white solid (15%) after purification by column chromatography ($SiO_2$, 0-50% EtOAc/hexanes). LCMS (ES+) 393.9 (M)$^+$, RT 3.29 minutes (Method 5).

Intermediate 189

3-{[(3S)-4-(Aminocarbonothioyl)morpholin-3-yl]methyl}-5-chloro-1H-indole-7-carboxamide The title compound was prepared from Intermediate 81 according to Method K (after stirring at 50° C. for 8 h, additional aqueous $NH_3$ (20% v/v, excess) was added, and the reaction mixture stirred at r.t. for 16 h) and was isolated as a brown oil (24%) after purification by column chromatography ($SiO_2$, EtOAc). LCMS (ES+) 353.0 (M+H)$^+$, RT 1.42 minutes (Method 12).

Intermediate 190

6,6-Dimethyl-2-[(3S)-3-{[2-(trimethylsilyl)-1-benzo-furan-3-yl]methyl}morpholin-4-yl]-6,7-dihydro[1,3]thiazolo[5,4-c]pyridin-4(5H)-one The title compound was prepared from Example 155 and 2-iodophenol according to Method I and was isolated as a yellow oil (77%) after purification by column chromatography (SiO$_2$, 0-50% EtOAc/hexanes). δ$_H$ (CDCl$_3$) 7.84-7.81 (1H, m), 7.27-7.25 (1H, m), 7.11-7.07 (2H, m), 5.00-4.90 (1H, m), 4.30-4.20 (1H, m), 4.00-3.86 (1H, m), 3.60-3.20 (7H, m), 1.41 (2H, s), 1.98-1.20 (6H, m), 0.22 (9H, s).

Intermediate 191

4-Hydroxy-3-iodobenzaldehyde

To a stirred solution of 4-hydroxybenzaldehyde (2.0 g, 16.39 mmol) in AcOH (30 mL) was added N-iodosuccinimide (4.5 g, 19.67 mmol). The reaction mixture was stirred at r.t. for 16 h, then filtered. The filtrate was poured onto water (100 mL) and EtOAc (50 mL) was added. The aqueous fraction was separated, then extracted with EtOAc (3×50 mL). The combined organic fractions were washed with water (2×20 mL), dried (Na$_2$SO$_4$), filtered and concentrated in vacuo to give the title compound (2.0 g, 50%) as a white solid that was used without further purification. LCMS (ES−) 247.1 (M−H)$^-$, RT 1.44 minutes (Method 9).

Intermediate 192

4-Hydroxy-3-iodobenzonitrile

To a stirred solution of Intermediate 191 (5.2 g, 20.97 mmol) in formic acid (60 mL) was added sodium acetate (2.1 g, 25.16 mmol), followed by hydroxylamine hydrochloride (8.7 g, 125.8 mmol). The reaction mixture was stirred at 105° C. for 3 h, then cooled to r.t. and poured onto water. The solid formed was filtered to give the title compound (3.0 g, 58%) as a white solid that was used without further purification. LCMS (ES+) 246.1 (M+H)$^+$, RT 1.64 minutes (Method 11).

Intermediate 193

3-[(3S)-Morpholin-3-ylmethyl]-1-benzofuran-5-carbonitrile

The title compound was prepared from Intermediate 26 and Intermediate 192 according to Method I, followed by Method J then Method AI, and was isolated as a yellow solid (10%) after purification by column chromatography (SiO$_2$, 0-10% MeOH/DCM). LCMS (ES+) 243.1 (M+H)$^+$, RT 1.41 minutes (Method 12).

Intermediate 194

(3S)-3-[(5-Cyano-1-benzofuran-3-yl)methyl]morpholine-4-carbothioamide

The title compound was prepared from Intermediate 193 according to Method K and was isolated as a yellow solid (quantitative) that was used without further purification. LCMS (ES+) 302.1 (M+H$^+$), RT 1.54 minutes (Method 12).

Intermediate 195

N-(4,5-Dimethoxy-2-iodophenyl)acetamide

To a solution of N-(3,4-dimethoxyphenyl)acetamide (6.3 g, 32.0 mmol) in DCM (100 mL) and AcOH (6.5 mL) was added a solution of iodine monochloride (6.3 g, 39 mmol) in DCM (50 mL) dropwise. The reaction mixture was stirred at r.t. for 16 h. Aqueous sat. Na$_2$S$_2$O$_3$ (500 mL) was added. The organic fraction was separated, washed with water (2×250 mL), then brine (100 mL), dried (Na$_2$SO$_4$), filtered and concentrated in vacuo. Purification by column chromatography (SiO$_2$, 50% EtOAc/hexanes) gave the title compound (7.5 g, 72%) as a dark solid. LCMS (ES+) 321.8 (M+H)$^+$, RT 2.67 minutes (Method 5).

Intermediate 196

4,5-Dimethoxy-2-iodoaniline

A suspension of Intermediate 195 (7.0 g, 21.8 mmol) and NaOH (44.0 g, 1100 mmol) in EtOH (500 mL) and water (200 mL) was stirred at 100° C. for 3 h. The reaction mixture was cooled to r.t., then concentrated vacuo. CHCl$_3$ (300 mL) and water (300 mL) were added. The organic fraction was separated, washed with water (2×300 mL), dried (Na$_2$SO$_4$) and concentrated in vacuo to give the title compound (5.2 g, 84%) as a pale pink oil that was used without further purification. LCMS (ES+) 279.8 (M+H)$^+$, RT 2.95 minutes (Method 5).

Intermediate 197 tert-Butyl (3S)-3-{[5,6-dimethoxy-2-(trimethylsilyl)-1H-indol-3-yl]methyl}morpholine-4-carboxylate The title compound was prepared from Intermediate 26 and Intermediate 196 according to Method I and was isolated as a yellow oil (66%) after work-up (EtOAc and water) and purification by column chromatography (SiO$_2$, 20-33% EtOAc/hexanes). δ$_H$ (CDCl$_3$) 7.55 (1H, br. s), 7.40-7.10 (1H, m), 6.66 (1H, s), 4.18-3.99 (1H, m), 3.77 (3H, s), 3.74 (1H, br. s), 3.71 (3H, s), 3.62 (1H, d, J 7.3 Hz), 3.53 (1H, d, J 11.7 Hz), 3.36-3.07 (4H, m), 2.69 (1H, d, J 14.3 Hz), 1.26 (9H, s), 0.20 (9H, s).

Intermediate 198

5,6-Dimethoxy-3-[(3S)-morpholin-3-ylmethyl]-1H-indole

The title compound was prepared from Intermediate 197 (dissolved in MeOH) according to Method J and was isolated as a yellow oil (25%) after purification by column chromatography (SiO$_2$, 0-20% MeOH/DCM). LCMS (ES+) 277.1 (M+H)$^+$, RT 2.03 minutes (Method 5).

Intermediate 199

(3S)-3-[(5,6-Dimethoxy-1H-indol-3-yl)methyl]morpholine-4-carbothioamide

The title compound was prepared from Intermediate 198 according to Method K and was isolated as a yellow foam (38%) that was used without further purification. LCMS (ES+) 336.0 (M+H)$^+$, RT 2.57 minutes (Method 5).

Intermediate 200 tert-Butyl (3S)-3-{[6-methoxy-2-(trimethylsilyl)-1H-indol-3-yl]methyl}morpholine-4-carboxylate The title compound was prepared from Intermediate 26 and 2-iodo-5-methoxyaniline according to Method I and was isolated as a clear glass (80%) after work-up (EtOAc and water) and purification by column chromatography (SiO$_2$, 0-10% EtOAc/hexanes). LCMS (ES+) 419.1 (M+H)$^+$, RT 3.87 minutes (Method 5).

Intermediate 201

6-Methoxy-3-[(3S)-morpholin-3-ylmethyl]-1H-indole

The title compound was prepared from Intermediate 200 (dissolved in MeOH) according to Method J and was isolated as a white foam (97%) that was used without further purification. LCMS (ES+) 247.1 (M+H)$^+$, RT 2.07 minutes (Method 5).

Intermediate 202

2-Iodo-4-(methylsulfonyl)aniline

To a stirred suspension of 4-(methylsulfonyl)aniline hydrochloride (2.0 g, 9.7 mmol) in EtOH (40 mL) was added KO$^t$Bu (1.3 g, 11.4 mmol). The reaction mixture was stirred for 15 minutes, then a slurry of silver sulfate (3.3 g, 10.6 mmol) and iodine (2.4 g, 9.6 mmol) in EtOH (100 mL) was added. The reaction mixture was stirred at 50° C. for 3 h, then cooled to r.t., filtered through Celite®, and the filtrate concentrated in vacuo. Recrystallisation from EtOH gave the title compound (1.9 g, 66%) as an off-white solid. LCMS (ES+) 319.8 (M+Na)$^+$, RT 2.77 minutes (Method 5).

Intermediate 203 tert-Butyl (3S)-3-{[5-(methylsulfonyl)-2-(trimethylsilyl)-1H-indol-3-yl]methyl}morpholine-4-carboxylate The title compound was prepared from Intermediate 26 and Intermediate 202 according to Method I and was isolated as a white foam (48%) after work-up (EtOAc and water) and purification by column chromatography (SiO$_2$, 0-33% EtOAc/hexanes). δ$_H$ (CDCl$_3$) 8.71-8.30 (1H, br. s), 8.26 (1H, br. s), 7.75 (1H, d, J 8.8 Hz), 7.48 (1H, d, J 8.6 Hz), 4.31-4.20 (1H, m), 3.98-3.80 (2H, m), 3.69 (1H, d, J 11.4 Hz), 3.60-3.19 (5H, m), 3.12 (3H, s), 1.28 (9H, s), 0.47 (9H, s).

Intermediate 204

5-(Methylsulfonyl)-3-[(3S)-morpholin-3-ylmethyl]-1H-indole

The title compound was prepared from Intermediate 203 (dissolved in MeOH) according to Method J and was isolated as an off-white foam (quantitative) that was used without further purification. LCMS (ES+) 295.0 (M+H)$^+$, RT 1.90 minutes (Method 5).

Intermediate 205

(3S)-3-{[5-(Methylsulfonyl)-1H-indol-3-yl]methyl}morpholine-4-carbothioamide

The title compound was prepared from Intermediate 204 according to Method K and was isolated as a white solid (58%) that was used without further purification. LCMS (ES+) 354.0 (M+H)$^+$, RT 2.54 minutes (Method 5).

Intermediate 206

N-(6-Iodo-1,3-benzodioxol-5-yl)acetamide

To a stirred solution of 3,4-methylenedioxyacetanilide (7.7 g, 43.0 mmol) in DCM (100 mL) and AcOH (6.5 mL) was added a solution of iodine monochloride (6.3 g, 38.8 mmol) in DCM (50 mL). The reaction mixture was stirred at r.t. for 16 h. Aqueous sat. Na$_2$S$_2$O$_3$ (500 mL) was added. The organic fraction was separated, dried (Na$_2$SO$_4$), filtered and concentrated in vacuo. Purification by column chromatography (SiO$_2$, 50% EtOAc/hexanes) gave the title compound (7.5 g, 57%) as a brown solid. LCMS (ES+) 306.0 (M+H)$^+$, RT 2.75 minutes (Method 5).

Intermediate 207

6-Iodo-1,3-benzodioxol-5-amine

To a stirred solution of Intermediate 206 (5.0 g, 16.4 mmol) in EtOH (150 mL) was added a solution of sodium hydroxide (20.0 g, 500 mmol) in water (120 mL). The reaction mixture was stirred at 90° C. for 16 h, then cooled to r.t. and extracted with DCM (4×200 mL). The combined organic fractions were washed with brine (100 mL), dried (Na$_2$SO$_4$), filtered and concentrated in vacuo to give the title compound (3.5 g, 83%) as a white solid. δ$_H$ (CDCl$_3$) 7.08 (1H, s), 6.40 (1H, s), 5.90 (2H, s), 3.80 (2H, br. s).

Intermediate 208 tert-Butyl (3S)-3-{[6-(trimethylsilyl)-5H-[1,3]dioxolo[4,5-f]indol-7-yl]methyl}morpholine-4-carboxylate The title compound was prepared from Intermediate 26 and Intermediate 207 according to Method I and was isolated as a white foam (80%) after work-up (EtOAc and water) and purification by column chromatography (SiO$_2$, 0-10% EtOAc/hexanes). LCMS (ES+) 433.0 (M+H)$^+$, RT 3.89 minutes (Method 5).

Intermediate 209

7-[(3S)-Morpholin-3-ylmethyl]-5H-[1,3]dioxolo[4,5-f]indole

The title compound was prepared from Intermediate 208 (dissolved in MeOH) according to Method J and was isolated as a white foam (96%) after purification by column chromatography (SiO$_2$, 0-10% MeOH/DCM). LCMS (ES+) 261.0 (M+H)$^+$, RT 2.11 minutes (Method 5).

Intermediate 210

(3S)-3-(5H-[1,3]Dioxolo[4,5-f]indol-7-ylmethyl)morpholine-4-carbothioamide

The title compound was prepared from Intermediate 209 according to Method K and was isolated as an off-white solid

Intermediate 211

Methyl 3-{[(3S)-4-(tert-butoxycarbonyl)morpholin-3-yl]methyl}-6-chloro-2-(trimethylsilyl)-1H-indole-5-carboxylate The title compound was prepared from Intermediate 26 and methyl 4-amino-2-chloro-5-iodobenzoate according to Method I and was isolated as a white foam (49%) after work-up (EtOAc and water) and purification by column chromatography (SiO$_2$, 0-10% EtOAc/hexanes). $\delta_H$ (CDCl$_3$) 8.50 (1H, br. s), 7.96 (1H, s), 7.34 (1H, s), 4.28-4.12 (1H, m), 3.92-3.82 (4H, m), 3.70 (1H, br. s), 3.61-3.12 (5H, m), 2.98-2.78 (1H, m), 1.39 (9H, s), 0.36 (9H, s). LCMS (ES+) 424.9 and 426.9 ((M−$^t$Bu)+H)$^+$, RT 3.91 minutes (Method 5).

Intermediate 212

Methyl 3-{[(3S)-4-(aminocarbonothioyl)morpholin-3-yl]methyl}-6-chloro-1H-indole-5-carboxylate The title compound was prepared from Intermediate 211 according to Method J, followed by Method K, and was isolated as a pale yellow foam (42%) that was used without further purification. LCMS (ES+) 389.9 and 391.0 (M+Na)$^+$, RT 2.83 minutes (Method 5).

Intermediate 213

2-Iodo-4-(1H-1,2,4-triazol-1-yl)aniline

To a stirred solution of 1-(4-aminophenyl)-1,2,4-triazole (1.0 g, 6.25 mmol) in MeOH (10 mL) and water (10 mL) was added CaCO$_3$ (1.2 g, 12.0 mmol), followed by a solution of iodine monochloride (1.2 g, 7.38 mmol) in MeOH (10 mL). The reaction mixture was stirred at r.t. for 1.5 h, and then partitioned between EtOAc (100 mL) and aqueous sat. Na$_2$S$_2$O$_3$ (100 mL). The organic fraction was separated, washed with aqueous sat. Na$_2$S$_2$O$_3$ (100 mL), then water (100 mL), brine (50 mL), dried (Na$_2$SO$_4$), filtered and concentrated in vacuo. Purification by column chromatography (SiO$_2$, 0-100% EtOAc/hexanes) gave the title compound (1.2 g, 67%). LCMS (ES+) 286.9 (M+H)$^+$, RT 2.78 minutes (Method 5).

Intermediate 214 tert-Butyl (3S)-3-{[5-(1H-1,2,4-triazol-1-yl)-2-(trimethylsilyl)-1H-indol-3-yl]methyl}morpholine-4-carboxylate The title compound was prepared from Intermediate 26 and Intermediate 213 according to Method I and was isolated as a yellow solid (44%) after work-up (EtOAc and water) and purification by column chromatography (SiO$_2$, 0-33% EtOAc/hexanes). LCMS (ES+) 498.2 (M+H)$^+$, RT 4.03 minutes (Method 5).

Intermediate 215

3-[(3S)-Morpholin-3-ylmethyl]-5-(1H-1,2,4-triazol-1-yl)-1H-indole

The title compound was prepared from Intermediate 214 (dissolved in MeOH) according to Method J and was isolated as a pale yellow solid (78%) after trituration in Et$_2$O. LCMS (ES+) 284.0 (M+H)$^+$, RT 2.05 minutes (Method 5).

Intermediate 216

(3S)-3-{[5-(1H-1,2,4-Triazol-1-yl)-1H-indol-3-yl]methyl}morpholine-4-carbothioamide The title compound was prepared from Intermediate 215 according to Method K and was isolated as an off-white foam (quantitative) that was used without further purification. LCMS (ES+) 343.0 (M+H)$^+$, RT 2.53 minutes (Method 5).

Intermediate 217

7-Bromo-6-methyl-2H-1,4-benzoxazin-3(4H)-one

To a suspension of 6-methyl-2H-1,4-benzoxazin-3(4H)-one (10.0 g, 61.3 mmol) in DCM (200 mL) and THF (200 mL) at 0° C. was added bromine (15.0 g, 93.7 mmol) dropwise. The reaction mixture was stirred at this temperature for 30 minutes, then filtered. The solid was washed with Et$_2$O (200 mL) to give the title compound (11.95 g, 80%) as a white solid that was used without further purification. $\delta_H$ (CDCl$_3$) 8.95 (1H, s), 7.16 (1H, s), 6.70 (1H, s), 4.59 (2H, s), 2.31 (3H, s).

Intermediate 218

7-Bromo-6-methyl-3,4-dihydro-2H-1,4-benzoxazine

The title compound was prepared from Intermediate 217 according to Method M and was isolated as a white solid (95%) that was used without further purification. LCMS (ES+) 228.0 (M)$^+$, RT 3.52 minutes (Method 1).

Intermediate 219

Method AK

7-Bromo-6-methyl-2,3-dihydro-4H-1,4-benzoxazine-4-carbothioamide

To a stirred suspension of Intermediate 218 (11.1 g, 48.66 mmol) in THF (130 mL) was added 1,1'-thiocarbonyldiimidazole (13.0 g, 72.99 mmol). The reaction mixture was heated to 120° C. under microwave irradiation in a sealed tube for 20 minutes, then cooled to r.t. NH$_3$ (200 mL, 7N solution in MeOH, 1400 mmol) was added. The reaction mixture was stirred for 3 days, then concentrated in vacuo. Aqueous HCl (1M, 50 mL) and Et$_2$O (100 mL) were added, and the solid formed was filtered to give the title compound (9.6 g, 69%) as a pale brown solid. $\delta_H$ (DMSO-d$_6$) 8.65 (2H, br. s), 7.38 (1H, s), 7.16 (1H, s), 4.30-4.22 (4H, m), 2.25 (3H, s). LCMS (ES+) 287.2 and 289.1 (M+H)$^+$, RT 3.41 minutes (Method 1).

Intermediate 220 tert-Butyl 4-{[4-(6,6-dimethyl-4-oxo-4,5,6,7-tetrahydro[1,3]thiazolo[5,4-c]pyridin-2-yl)-6-methyl-3,4-dihydro-2H-1,4-benzoxazin-7-yl]amino}piperidine-1-carboxylate The title compound was prepared from Example 210 and 4-amino-1-BOC-piperidine according to Method U and was isolated as a yellow glass (57%) after purification by column

Intermediate 221 tert-Butyl 4-{N-[4-(6,6-dimethyl-4-oxo-4,5,6,7-tetrahydro[1,3]thiazolo[5,4-c]pyridin-2-yl)-6-methyl-3,4-dihydro-2H-1,4-benzoxazin-7-yl]-N-(methyl)amino}piperidine-1-carboxylate To a stirred solution of Intermediate 220 (0.047 g, 0.09 mmol) in DMF (2 mL) was added $K_2CO_3$ (0.026 g, 0.187 mmol), followed by methyl iodide (0.06 mL, 0.962 mmol). The reaction mixture was stirred at r.t. for 3 days, then concentrated in vacuo. Purification by column chromatography ($SiO_2$, 20-100% EtOAc/heptane, followed by $SiO_2$, 15% MeOH/DCM with 2% $NH_4OH$ added) gave the title compound (0.033 g, 67%) as a yellow solid. LCMS (ES+) 542.1 (M+H)$^+$, RT 3.52 minutes (Method 1).

Intermediate 222

7-Bromo-3,4-dihydro-2H-1,4-benzoxazine

The title compound was prepared from 7-bromo-2H-1,4-benzoxazin-3(4H)-one according to Method M and was isolated as an off-white oil (76%) after purification by column chromatography ($SiO_2$, 0-100% EtOAc/heptane). $\delta_H$ (DMSO-$d_6$) 6.82-6.77 (2H, m), 6.50 (1H, d, J 9.0 Hz), 6.04-5.86 (1H, br. s), 4.10 (2H, t, J 4.0 Hz), 3.29-3.23 (2H, m). LCMS (ES+) 213.9 and 215.9 (M+H)$^+$, RT 3.28 minutes (Method 1).

Intermediate 223

7-Bromo-2,3-dihydro-4H-1,4-benzoxazine-4-carbothioamide

The title compound was prepared from Intermediate 222 according to Method AK and was isolated as a cream solid (62%) after trituration in water, then in Et$_2$O. $\delta_H$ (DMSO-$d_6$) 8.25 (2H, br. s), 7.39 (1H, d, J 8.7 Hz), 7.15 (1H, d, J 2.3 Hz), 7.07 (1H, dd, J 8.7 and 2.3 Hz), 4.30-4.21 (4H, m). LCMS (ES+) 272.9 and 274.9 (M+H)$^+$, RT 3.14 minutes (Method 1).

Intermediate 224

{3-[4-(4,4,5,5-Tetramethyl-[1,3,2]dioxaborolan-2-yl)pyrazol-1-yl]propyl}-phosphonic acid diethyl ester The title compound was prepared from pyrazole-4-boronic acid pinacol ester and diethyl (3-bromopropyl)phosphonate according to Method AC (stirred in a sealed vial at r.t. for 16 h, then heating to 80° C. for 4 h before addition of further diethyl (3-bromopropyl)phosphonate, and heating to 90° C. for a further 3 days) and was isolated as a brown gum (64%). LCMS (ES+) 373 (M+H)$^+$, RT 3.73 minutes (Method 1).

Intermediate 225

1-(Tetrahydropyran-2-ylmethyl)-4-(4,4,5,5-tetramethyl-[1,3,2]dioxaborolan-2-yl)-1H-pyrazole The title compound was prepared from pyrazole-4-boronic acid pinacol ester and 2-(bromomethyl)tetrahydro-2H-pyran according to Method AC (stirred in a sealed vial at r.t. for 16 h, then heating to 80° C. for 4 h before addition of further 2-(bromomethyl)-tetrahydro-2H-pyran, and heating to 80° C. for a further 2 days) and was isolated as a brown gum (75%). LCMS (ES+) 293 (M+H)$^+$, RT 3.41 minutes (Method 1).

Intermediate 226

N,N-Dimethyl-2-[4-(4,4,5,5-tetramethyl-[1,3,2]dioxaborolan-2-yl)pyrazol-1-yl]-acetamide The title compound was prepared from pyrazole-4-boronic acid pinacol ester and 2-chloro-N,N-dimethylacetamide according to Method AC (heating to 90° C. for 4 h) and was isolated as an orange gum (quantitative). LCMS (ES+) 280 (M+H)$^+$, RT 2.38 minutes (Method 1).

Intermediate 227

3-[4-(4,4,5,5-Tetramethyl-[1,3,2]dioxaborolan-2-yl)pyrazol-1-yl]propan-1-ol

The title compound was prepared from pyrazole-4-boronic acid pinacol ester and 3-chloro-1-propanol according to Method AC (heating to 90° C. for 6 days before addition of further 3-chloro-1-propanol and triethylamine, and heating to 90° C. for a further 3 days) and was isolated as a brown gum (quantitative). LCMS (ES+) 253 (M+H)$^+$, RT 2.53 minutes (Method 1).

Intermediate 228

1-{2-[4-(4,4,5,5-Tetramethyl-[1,3,2]dioxaborolan-2-yl)pyrazol-1-yl]ethyl}piperidine The title compound was prepared from pyrazole-4-boronic acid pinacol ester and 1-(2-chloroethyl)piperidine hydrochloride according to Method AC (heating to 90° C. for 6 days before addition of further 1-(2-chloroethyl)piperidine hydrochloride, and heating to 90° C. for a further 3 days) and was isolated as a brown gum (69%). LCMS (ES+) 305 (M+H)$^+$, RT 1.91 minutes (Method 1).

Intermediate 229

1-[2-(Pyrrolidin-1-yl)ethyl]-4-(4,4,5,5-tetramethyl-[1,3,2]dioxaborolan-2-yl)-1H-pyrazole The title compound was prepared from pyrazole-4-boronic acid pinacol ester and 1-(2-chloroethyl)pyrrolidine hydrochloride according to Method AC (heating to 90° C. for 6 days before addition of further 1-(2-chloroethyl)pyrrolidine hydrochloride, and heating to 90° C. for a further 3 days) and was isolated as a brown gum (45%). LCMS (ES+) 292 (M+H)$^+$, RT 1.81 minutes (Method 1).

Intermediate 230

N,N-Dimethyl-N-{2-[4-(4,4,5,5-tetramethyl-[1,3,2]dioxaborolan-2-yl)pyrazol-1-yl]ethyl}-amine The title compound was prepared from pyrazole-4-boronic acid pinacol ester and 2-chloro-N,N-(dimethyl)ethylamine hydrochloride according to Method AC (heating to 90° C. for 6 days before addition of further 2-chloro-N,N-(dimethyl)ethylamine hydrochloride and triethylamine, then heating to 90° C. for a further 3 days) and was isolated as a brown oil (43%). LCMS (ES+) 266 (M+H)$^+$, RT 1.73 minutes (Method 1).

chromatography ($SiO_2$, 40-100% EtOAc/heptane). LCMS (ES+) 528.1 (M+H)$^+$, RT 3.83 minutes (pH 2.5) (Method 1).

Intermediate 231

3-[4-(4,4,5,5-Tetramethyl-[1,3,2]dioxaborolan-2-yl) pyrazol-1-ylmethyl]pyridine The title compound was prepared from pyrazole-4-boronic acid pinacol ester and 3-picolyl chloride (prepared from the hydrochloride salt using a pre-swelled suspension of morpholinomethyl polystyrene in DMF) according to Method AC (heating to 100° C. under microwave irradiation for 2 h) and was isolated as a brown oil (71%). LCMS (ES+) 286 (M+H)$^+$, RT 1.98 minutes (Method 1).

Intermediate 232

N,N-Dimethyl-N-{3-[4-(4,4,5,5-tetramethyl-[1,3,2] dioxaborolan-2-yl)pyrazol-1-yl]-propyl}amine The title compound was prepared from pyrazole-4-boronic acid pinacol ester and 3-chloro-N,N-(dimethyl)propylamine hydrochloride according to Method AC (heating to 90° C. for 6 days before addition of further 3-chloro-N,N-(dimethyl) propylamine hydrochloride and triethylamine, then heating to 90° C. for a further 3 days) and was isolated as a brown oil (42%). LCMS (ES+) 280 (M+H)$^+$, RT 1.75 minutes (Method 1).

Intermediate 233

1-Methyl-(2RS)-2-{2-[4-(4,4,5,5-tetramethyl-[1,3,2] dioxaborolan-2-yl)pyrazol-1-yl]-ethyl}piperidine The title compound was prepared from pyrazole-4-boronic acid pinacol ester and 2-(2-chloroethyl)-1-methylpiperidine hydrochloride according to Method AC (heating to 90° C. for 6 days before addition of further 2-(2-chloroethyl)-1-methylpiperidine hydrochloride and triethylamine, then heating to 90° C. for a further 3 days) and was isolated as a brown oil (quantitative). LCMS (ES+) 320 (M+H)$^+$, RT 1.85 minutes (Method 1).

Intermediate 234

5-[4-(6,6-Dimethyl-4-oxo-4,5,6,7-tetrahydrothiazolo [5,4-c]pyridin-2-yl)-3,4-dihydro-2H-1,4-benzoxazin-6-yl]pyridine-2-carboxaldehyde To a suspension of Example 292 (400 mg, 0.907 mmol) in THF (12 mL) and water (3 mL) was added tetra-n-butylammonium bromide (438 mg, 1.36 mmol), potassium phosphate (384 mg, 1.81 mmol), 5-bromo-2-formylpyridine (337 mg, 1.81 mmol) and tetrakis(triphenylphosphine)palladium(0) (107 mg, 0.091 mmol). The reaction was heated at 120° C. under microwave irradiation for 30 minutes. The resulting mixture was triturated with water (3×30 mL), Et$_2$O (3×30 mL) and EtOAc (2×30 mL) and the solid was dried in vacuo to yield the title compound (110 mg, 29%) as an off-white solid (90% purity). LCMS (ES+) 421.0 (M+H)$^+$, RT 3.17 minutes (Method 1).

Intermediate 235

5-Bromopyrimidine-2-carboxamide

To a solution of 5-bromopyrimidine-2-carboxylic acid (135 mg, 0.665 mmol) under nitrogen in DCM (10 mL) was added oxalyl chloride (0.082 ml, 0.931 mmol) and DMF (2 drops). The reaction was allowed to stir for 1 h and was then concentrated in vacuo. THF (10 mL) and ammonium hydroxide (2 mL) were added and the mixture was stirred for a further 1 h. The resulting mixture was concentrated in vacuo to give the title compound (95 mg, 71%), which was used without further purification. LCMS (ES+) 202.0 (M+H)$^+$, RT 1.35 minutes (Method 2).

Intermediate 236

5-Bromo-2-(methoxymethyl)pyridine

To a stirred solution of 5-bromo-2-(hydroxymethyl)pyridine (150 mg, 0.798 mmol) in THF (8 mL) under nitrogen at r.t. was added sodium hydride (60% dispersion in oil, 64 mg, 1.60 mmol). After 30 minutes iodomethane was added and the reaction mixture was heated to 60° C. for 3 h, then cooled to r.t. and concentrated in vacuo. The residue was partitioned between DCM (50 mL) and water (50 mL); the organic fraction was washed with brine (50 mL), dried (MgSO$_4$), and concentrated in vacuo to give the title compound (70 mg, 65%) as 70% pure material. LCMS (ES+) 202.0 (M+H)$^+$, RT 2.40 minutes (Method 1).

Intermediate 237

N-Benzyl-6-methylpyridazin-3-amine

To a stirred solution of 3-chloro-6-methylpyridazine (215 mg, 1.66 mmol) and benzylamine (267 mg, 2.5 mmol) in toluene (20 mL) was added sodium tert-butoxide (480 mg, 5.0 mmol) and [1,1'-bis(di-tert-butylphosphino)ferrocene]palladium(II) dichloride (20 mg). The reaction mixture was stirred at 140° C. under microwave irradiation for 2 h, then cooled to room temperature and concentrated in vacuo. The residue was purified by column chromatography (SiO$_2$, 0-100% EtOAc/heptane) to give the title compound (302 mg, 91%) as an off-white solid. $\delta_H$ (CDCl$_3$) 7.25-7.41 (5H, m), 7.02 (1H, d, J 9.0 Hz), 6.55 (1H, d, J 9.0 Hz), 4.91 (1H, s), 4.60 (2H, d, J 5.8 Hz), 2.53 (3H, s). LCMS (ES+) 200 (M+H)$^+$, RT 2.50 minutes (Method 2).

Intermediate 238

2-Bromo-6-[(E)-2-methoxyvinyl]pyridine

To a suspension of (methoxymethyl)triphenylphosphonium chloride (7.37 g, 21.5 mmol) in THF (100 mL) at −10° C. was added LDA (1.8M in THF/hexane/ethylbenzene, 11.94 mL, 21.5 mmol). The resulting red suspension was stirred at −10° C. for 1 h. To this was added a solution of 6-bromopyridine-2-carboxaldehyde (2.0 g, 10.8 mmol) in THF (60 mL). The resulting colourless suspension was slowly warmed to r.t. over 2.5 h. The reaction mixture was poured into water and extracted with Et$_2$O (3×75 mL). The combined organic phases were washed with brine, dried (MgSO$_4$) and concentrated in vacuo to give a pale yellow oil. Purification by column chromatography (SiO$_2$, 20:1 heptane: EtOAc) gave the title compound (506 mg, 22%) as a yellow oil. $\delta_H$ (CDCl$_3$) 7.61 (1H, d, J 12.6 Hz), 7.37 (1H, t, J 7.7 Hz), 7.16 (1H, dd, J 7.9 and 0.8 Hz), 6.98 (1H, dd, J 7.5 and 0.6 Hz), 5.78 (1H, d, J 12.6 Hz), 3.73 (3H, s). LCMS (ES+) 215.97 (M+H)$^+$, RT 3.50 minutes (Method 1).

Intermediate 239

8-Methyl-2H-1,4-benzoxazin-3(4H)-one

A solution of chloroacetyl chloride (0.71 mL, 8.94 mmol) in THF (5 mL) was added dropwise to a solution/suspension of 2-amino-6-methylphenol (1 g, 8.13 mmol) and triethylamine (1.24 mL, 8.94 mmol) in THF (50 mL) which had been pre-cooled in an ice-water bath. After stirring for 5 minutes a further portion of triethylamine (1.24 mL, 8.94 mmol) was added. The mixture was stirred and warmed to r.t. After 24 h the reaction was allowed to stand overnight. The mixture was concentrated in vacuo and the residue was partitioned between water (100 mL) and EtOAc (50 mL). Brine (20 mL) was added to the aqueous phase, and this was further extracted with EtOAc (50 mL). The combined organic fractions were dried (MgSO$_4$), concentrated in vacuo, and purified by column chromatography (SiO$_2$, 20-100% EtOAc/heptane) to give an orange-brown solid (1.04 g), which was dissolved in THF (10 mL) and triethylamine (2 mL), and the mixture left to stand for 3 days. The mixture was concentrated in vacuo and purified by column chromatography (SiO$_2$, 10-50% EtOAc/heptane) to give a cream solid (0.6 g). This was dissolved in DCM (40 mL), and the solution was washed with aqueous NaOH (2M, 10 mL). The organic fraction was dried (MgSO$_4$) and concentrated in vacuo to give the title compound (0.29 g, 22%) as a beige solid. LCMS (ES+) 164 (M+H)$^+$, RT 2.61 minutes (Method 1).

Intermediate 240

8-Methyl-2,3-dihydro-4H-1,4-benzoxazine-4-carbothioamide

Borane (1M in THF, 4 mL, 4 mmol) was added to a solution of Intermediate 239 (0.26 g, 1.60 mmol) in THF (10 mL). The mixture was heated at 70° C. for 2 h. After cooling to r.t. it was poured into water (20 mL). Brine (10 mL) was added, and the mixture extracted with DCM (30 mL then 10 mL). The combined organic fractions were dried (MgSO$_4$) and concentrated in vacuo to give a brown oil (0.26 g). This oil was dissolved in THF (4 mL) together with 1,1'-thiocarbonyldiimidazole (0.46 g, 2.6 mmol). It was heated at 120° C. under microwave irradiation for 20 minutes, then poured into EtOH:NH$_4$OH (1:1, 20 mL) and left to stand overnight. The mixture was partitioned between water-brine (1:1, 50 mL) and EtOAc (50 mL). The aqueous phase was further extracted with EtOAc (30 mL), and the combined organic fractions were dried (MgSO$_4$) and concentrated in vacuo. The residue was purified by column chromatography (SiO$_2$, 10-100% EtOAc/heptane) to give the title compound (0.127 g, 38%) as a beige solid. $\delta_H$ (CDCl$_3$) 7.19 (1H, dd, J 7.5 and 1.0 Hz), 7.01 (1H, dd, J 17.5 and 1.0 Hz), 6.85 (1H, t, J 7.5 Hz), 6.64 (2H, br. s), 4.51-4.45 (2H, m), 4.44-4.38 (2H, m), 2.22 (3H, s). LCMS (ES+) 209 (M+H)$^+$, RT 3.95 minutes (Method 1).

Intermediate 241

3-Chloro-4,6-dimethylpyridazine

To a mixture of 3-chloro-6-methylpyridazine (0.2 g, 1.55 mmol), acetic acid (0.2 mL, 3.49 mmol), sulphuric acid (0.124 mL, 2.33 mmol) and silver nitrate (0.026 g, 0.16 mmol) in water (4.5 mL) was added dropwise a solution of ammonium persulfate in water (1.5 mL). The mixture was held at 75° C. for 30 minutes, allowed to cool to r.t. and poured onto ice. The mixture was basified to pH 9-10 with ammonium hydroxide and extracted with DCM (50 mL). The organic fraction was washed with aqueous sodium hydroxide (1.0N, 2×15 mL), dried (MgSO$_4$), concentrated in vacuo and purified by preparative HPLC (Method 6). The product was dissolved in DCM (15 mL), washed with aqueous potassium carbonate solution (0.7M) and concentrated in vacuo to give the title compound (0.111 g, 50%) as a pink solid. $\delta_H$ (DMSO-d$_6$) 7.62 (1H, s), 2.57-2.54 (3H, m), 2.33 (3H, s). LCMS (ES+) 142.97 (M+H)$^+$, RT 1.93 minutes (Method 1).

Intermediate 242

2-(6-Chloropyridin-3-yl)ethanol

To a stirred solution of 2-chloropyridine-5-acetic acid (800 mg, 4.60 mmol) in THF (30 mL) at 0° C. under a nitrogen atmosphere was added triethylamine (2.20 mL, 10.3 mmol) and isobutyl chloroformate (1.20 mL, 9.33 mmol). The reaction was stirred for 50 minutes then sodium borohydride (1.77 g, 46 mmol) was added and the suspension stirred at r.t. for 16 h then at reflux for a further 4 h. The resulting mixture was partitioned between DCM (50 mL) and water (50 mL). The organic fraction was washed with brine (50 mL), dried (MgSO$_4$) and concentrated in vacuo to yield the title compound (800 mg, quantitative) as a brown oil. LCMS (ES+) 158.0 (M+H)$^+$, RT 1.81 minutes (85% purity) (Method 1).

Intermediate 243

4-(6-Chloro-2-methylpyrimidin-4-yl)piperazine-1-carboxylic acid tert-butyl ester To a solution of 4,6-dichloro-2-methylpyrimidine (300 mg, 1.84 mmol) in THF (4 mL) were added tert-butyl piperazine-1-carboxylate (376 mg, 2.02 mmol) and DIPEA (0.48 mL, 2.76 mmol), and the reaction was heated at 145° C. under microwave irradiation for 30 minutes. The resulting mixture was concentrated in vacuo and the residue was partitioned between DCM (50 mL) and water (50 mL). The organic fraction was washed with brine (50 mL), dried (MgSO$_4$) and concentrated in vacuo to yield the title compound (400 mg, 70%) as an off-white solid. LCMS (ES+) 313.0 (M+H)$^+$, RT 3.63 minutes (Method 1).

Intermediate 244

4-Chloro-2-methyl-6-(piperazin-1-yl)pyrimidine dihydrochloride

To a solution of Intermediate 243 (200 mg, 0.64 mmol) in DCM (8 mL) was added a solution of HCl in Et$_2$O (2M, 1.6 mL, 3.23 mmol) and the reaction was allowed to stir at r.t. for 16 h. The resulting mixture was concentrated in vacuo to yield the title compound (135 mg, 100%) as an off-white solid. LCMS (ES+) 213.0 (M+H)$^+$, RT 1.38 minutes (Method 2).

Intermediate 245

2-(6-Chloro-2-methylpyrimidin-4-yl)malonic acid dimethyl ester

To a solution of dimethyl malonate (0.39 mL, 3.37 mmol) in THF (20 mL) was added sodium hydride (60% dispersion in oil, 138 mg, 3.37 mmol) portionwise. The reaction mixture was stirred for 10 minutes at r.t. then 4,6-dichloro-2-methylpyrimidine (500 mg, 3.07 mmol) was added and the mixture heated to reflux for 2 h. The resulting suspension was concentrated in vacuo, triturated with Et$_2$O (3×30 mL) and the mother liquors were evaporated in vacuo to yield the title compound (300 mg, 40%) as an off-white solid. LCMS (ES+) 259.0 (M+H)$^+$, RT 2.93 minutes (90% purity) (Method 2).

Intermediate 246

Method BG

1-(2-Chloropyridin-4-yl)-4-methylpiperazine

To a mixture of 2-chloro-4-iodopyridine (300 mg, 1.24 mmol) in toluene (4 mL) was added 1-methylpiperazine (0.14 mL, 1.24 mmol), sodium tert-butoxide (239 mg, 2.44 mmol), [1,1'-bis(di-tert-butylphosphino)ferrocene]palladium(II) dichloride (30 mg, 10% wt) and the suspension was heated to 115° C. under microwave irradiation for 30 minutes. The resulting mixture was concentrated in vacuo and partitioned between DCM (50 mL) and water (50 mL). The organic phase was washed with brine (50 mL), dried (MgSO$_4$), and evaporated in vacuo to give the title compound (200 mg, 77%) as a brown oil. LCMS (ES+) 212.0 (M+H)$^+$, RT 1.78 minutes (70% purity) (Method 2).

Intermediate 247

1-(6-Chloropyridin-3-yl)-4-methylpiperazine

The title compound was prepared from 5-bromo-2-chloropyridine and 1-methylpiperazine according to Method BG and was isolated as a brown oil (27%). LCMS (ES+) 212.0 (M+H)$^+$, RT 1.97 minutes (70% purity) (Method 2).

Intermediate 248

5-Bromo-4,6-dimethyl-1H-pyridin-2-one

To a solution of 2-amino-5-bromo-4,6-dimethylpyridine (0.7 g, 3.48 mmol) in water (6.4 mL) was added an aqueous solution of hypophosphorous acid (50%, 2.9 mL, 27.84 mmol). The mixture was cooled to about 0° C. and a solution of sodium nitrite (0.281 g, 4.07 mmol) in water (1.4 mL) was added with vigorous stirring, maintaining the temperature below 5° C. The mixture was stirred for 30 minutes at 0° C. and was then allowed to warm up to r.t. overnight. The solution was neutralized to pH 6-7 with an aqueous solution of sodium hydroxide (2.0M) and cooled to 5° C. for 5 h. The resulting precipitate was filtered off and washed with cold water. The solid obtained was dried in vacuo to give the title compound (0.681 g, 97%) as a white solid. $\delta_H$ (CDCl$_3$) 6.35 (1H, s), 2.47 (3H, s), 2.29 (3H, s). LCMS (ES+) 201/203 (M+H)$^+$, RT 2.16 minutes (Method 1).

Intermediate 249

3-Bromo-2,4-dimethyl-6-methoxypyridine

Silver carbonate (0.5 g, 2.47 mmol) and iodomethane (1.541 mL, 24.7 mmol) were added to a solution of Intermediate 248 (0.5 g, 2.47 mmol) in DCM (25 mL) in the dark. The reaction mixture was stirred at r.t. for 24 h. The inorganic solids were removed by filtration and washed with DCM. The filtrate was evaporated in vacuo to give the title compound (0.493 g, 92%) as an orange oil. LCMS (ES+) 216/218 (M+H)$^+$, RT 4.22 minutes (Method 1).

Intermediate 250

(6-Chloropyridin-2-yl)acetic acid ethyl ester

To a solution of 6-chloro-2-picoline (2.0 g, 15.7 mmol) in THF (60 mL) at −20° C. was added n-butyllithium (2.5M in hexanes, 9.4 mL, 23.5 mmol). The resulting dark red solution was stirred at −20° C. for 15 minutes, then cooled to −78° C. and diethyl carbonate (2.85 mL, 23.5 mmol) was added dropwise. The reaction mixture was stirred at −78° C. for 30 minutes then slowly warmed to r.t. overnight. The reaction mixture was quenched with sat. aqueous ammonium chloride solution (100 mL) and extracted with EtOAc (3×60 mL). The combined organic fractions were washed with brine (60 mL), dried (MgSO$_4$) and concentrated in vacuo. Purification by column chromatography (SiO$_2$, 0-40% EtOAc/heptane, followed by SiO$_2$, 20% EtOAc/heptane) gave the title compound (120 mg, 25%) as a pale yellow oil. LCMS (ES+) 321.11 (M+H)$^+$, RT 4.43 min (Method 1).

Intermediate 251

7-Methoxy-2H-1,4-benzoxazin-3(4H)-one

DIPEA (2.2 mL, 12.5 mmol) was added to 2-amino-5-methoxyphenol hydrochloride (1 g, 5.7 mmol) in THF (13 mL). The reaction mixture was cooled to 0° C., chloroacetyl chloride (0.5 mL, 6.3 mmol) was added portionwise and then stirred at 0° C. for 5 minutes. Further DIPEA (1.1 mL, 6.3 mmol) was added and the mixture was allowed to warm to r.t. and stirred for 3 days. The majority of the THF was removed in vacuo. EtOAc (50 mL) and water (50 mL) were added. The aqueous layer was extracted with EtOAc (2×50 mL) and the combined organic fractions were washed with brine (20 mL), dried (MgSO$_4$), filtered and the solvent was evaporated in vacuo. To a portion of the crude material (0.250 g, 1.159 mmol) in MeCN (6 mL) was added potassium carbonate (0.449 g, 3.246 mmol) followed by THF (2 mL). The reaction mixture was stirred at r.t. for 5 h and then concentrated in vacuo. Water (5 mL) was added and the solid collected by filtration, washed with water (3×5 mL) and dried in vacuo to give the title compound (0.173 g, 17%) as a red solid. $\delta_H$ (DMSO-d$_6$) 10.53 (1H, br s), 6.80 (1H, d, J 8.5 Hz), 6.58-6.51 (2H, m), 4.52 (2H, s), 3.69 (3H, s). LCMS (ES+) 180.1 (M+H)$^+$, RT 2.27 minutes (Method 1).

Intermediate 252

7-Methoxy-3,4-dihydro-2H-1,4-benzoxazine hydrochloride

Borane-THF complex (44.9 mL, 1M solution in THF, 44.9 mmol) was added portionwise to Intermediate 251 (5.36 g, 29.9 mmol) in THF (100 mL) at r.t. under nitrogen. The resulting solution was heated to reflux for 4.5 h and then allowed to cool to r.t. After stirring at r.t. for 2 days the reaction mixture was quenched with water (50 mL) and then the mixture was heated to 100° C. for 40 minutes. The mixture was allowed to cool to r.t. and the majority of the THF was removed in vacuo. DCM (50 mL) was added and the aqueous layer was extracted with DCM (2×50 mL). The combined organic fractions were washed with brine (10 mL), dried (MgSO$_4$), filtered and the solvent was evaporated in vacuo. Et$_2$O (50 mL) and DCM (10 mL) were added and the solution was cooled in an ice-bath. HCl in Et$_2$O (2M, 15 mL) was slowly added. The resulting precipitate was sonicated, collected by filtration, washed with Et$_2$O (10 mL) and dried in vacuo to give the title compound (5.275 g, 87%) as a grey solid. $\delta_H$ (CDCl$_3$) 11.96-11.48 (2H, s), 7.47 (1H, d, J 8.9 Hz), 6.57 (1H, dd, J 8.9 and 2.6 Hz), 6.48 (1H, d, J 2.6 Hz), 4.52-4.47 (2H, m), 3.69-3.63 (2H, m), 3.78 (3H, s). LCMS (ES+) 166.0 (M+H)$^+$, RT 1.46 minutes (Method 1).

Intermediate 253

7-Methoxy-2,3-dihydro-4H-1,4-benzoxazine-4-carbothioamide

To a stirred suspension of Intermediate 252 (5.247 g, 26.02 mmol) in THF (110 mL) was added 1,1'-thiocarbonyldiimidazole (6.96 g, 39.03 mmol) followed by DIPEA (4.53 mL, 26.02 mmol). The reaction mixture was heated to 70° C. under nitrogen for 4.5 h, then cooled to r.t. Ammonia (7N solution in EtOH, 29.94 mL, 208 mmol) was added and the reaction mixture was stirred at r.t. overnight and then in a sealed vessel at 35° C. for 45 minutes. Aqueous ammonia (18.1M, 11.5 mL, 208 mmol) was added and the mixture was heated in a sealed vessel at 35° C. for 1 h. The reaction was stirred at r.t. overnight and then at 50° C. for 1.5 h. After cooling to r.t. the solvent was removed in vacuo. Water (50 mL), aqueous HCl (2M, 50 mL) and $Et_2O$ (50 mL) were added, and the solid formed was collected by filtration, washed with water (3×30 mL) and $Et_2O$ (2×25 mL) and dried in vacuo to give the title compound (4.788 g, 82%) as a light brown solid. $\delta_H$ ($CDCl_3$) 7.25-7.22 (1H, m), 6.54-6.48 (2H, m), 6.34-6.25 (2H, m), 4.52-4.47 (2H, m), 4.39-4.34 (2H, m), 3.78 (3H, s). LCMS (ES+) 225.1 (M+H)$^+$, RT 2.74 minutes (Method 2).

Intermediate 254 tert-Butyl 4-{4-[4-(6,6-dimethyl-4-oxo-4,5,6,7-tetrahydro[1,3]thiazolo[5,4-c]pyridin-2-yl)-3,4-dihydro-2H-1,4-benzoxazin-6-yl]-1H-pyrazol-1-yl}piperidine-1-carboxylate A solution of Example 513 (0.06 g, 0.16 mmol) in DMF (2 mL) was added to sodium hydride (0.022 g, 0.55 mmol) and the mixture stirred at r.t. for 5 minutes before addition of 4-(methanesulphonyloxy)piperidine-1-carboxylic acid tert-butyl ester (0.067 g, 0.24 mmol). The reaction was heated to 150° C. After cooling to r.t. the mixture was filtered, concentrated in vacuo and purified by preparative HPLC (Method 6) to give the title compound (0.033 g, 36%) as a clear glass. $\delta_H$ ($CDCl_3$) 7.97 (1H, d, J 2.1 Hz), 7.72 (1H, s), 7.60 (1H, s), 7.15 (1H, dd, J 8.5 and 2.1 Hz), 6.95 (1H, d, J 8.5 Hz), 4.45 (1H, s), 4.36-4.23 (6H, m), 4.22-4.17 (2H, m), 2.98-2.93 (3H, m), 2.22-2.11 (2H, m), 2.08-1.89 (2H, m), 1.48 (9H, s), 1.40 (6H, s). LCMS (ES+) 565.28 (M+H)$^+$, RT 3.77 minutes (Method 1).

Example 1

6,6-Dimethyl-2-(morpholin-4-yl)-6,7-dihydro[1,3]thiazolo[5,4-c]pyridin-4(5H)-one To a stirred suspension of Intermediate 3 (0.10 g, 0.71 mmol) in THF (3 mL) was added $Br_2$ (0.12 g, 0.04 mL, 0.74 mmol) dropwise at 0° C. The reaction mixture was allowed to warm to r.t. and Intermediate 7 (0.16 g, 0.71 mmol), DIPEA (0.19 g, 0.25 mL, 1.42 mmol) and THF (3 mL) were added. After stirring at 85° C. for 1 h, the reaction mixture was poured into water (5 mL) and the aqueous layer was extracted with EtOAc (2×5 mL). The combined organic layers were washed with water (3×7 mL), dried ($MgSO_4$), filtered and concentrated in vacuo. The residue was purified by column chromatography ($SiO_2$, 1:1 EtOAc/hexanes) to give the title compound (0.07 g, 35%) as a yellow solid. $\delta_H$ (DMSO-$d_6$) 7.30 (1H, br. s), 3.70 (4H, t, J 4.9 Hz), 3.47 (4H, t, J 4.9 Hz), 2.70 (2H, s), 1.24 (6H, s). LCMS (ES+) 268.0 (M+H)$^+$.

Example 2

6,6-Dimethyl-2-[(3S)-3-(1H-indol-3-ylmethyl)morpholin-4-yl]-6,7-dihydro[1,3]thiazolo[5,4-c]pyridin-4(5H)-one A stirred suspension of Intermediate 5 (0.17 g, 0.65 mmol), Intermediate 12 (0.42 g, 1.94 mmol) and DIPEA (0.28 g, 0.37 mL, 2.13 mmol) in IPA (2 mL) was heated to 180° C. in a sealed tube, under microwave irradiation, for 6 h. After cooling, the reaction mixture was poured into water (5 mL) and extracted with DCM (3×5 mL). The combined organic layers were washed with brine (2×10 mL), dried ($MgSO_4$), filtered and concentrated in vacuo. Purification by column chromatography ($SiO_2$, 1:1 EtOAc/hexanes), followed by preparative HPLC (Method 8), gave the title compound (0.09 g, 18%) as a pale yellow solid. $\delta_H$ (DMSO-$d_6$) 10.91 (1H, br. s), 7.76 (1H, d, J 7.8 Hz), 7.36-7.32 (2H, m), 7.20 (1H, d, J 1.9 Hz), 7.08 (1H, t, J 7.1 Hz), 7.02 (1H, t, J 7.3 Hz), 4.09 (1H, br. s), 3.98 (1H, d, J 7.5 Hz), 3.73-3.69 (2H, m), 3.55 (2H, d, J 8.4 Hz), 3.50-3.47 (1H, m), 3.41-3.33 (1H, m), 2.91 (1H, dd, J 13.8 and 4.2 Hz), 2.74 (2H, d, J 3.8 Hz), 1.26 (6H, s). LCMS (ES+) 397.0 (M+H)$^+$.

Example 3

2-(Morpholin-4-yl)-6,7-dihydro[1,3]thiazolo[5,4-c]pyridin-4(5H)-one

To a stirred solution of Intermediate 8 (0.35 g, 1.56 mmol) in $CHCl_3$ (15 mL) was added conc. $H_2SO_4$ (1 mL, excess) and $NaN_3$ (0.11 g, 1.72 mmol). The reaction mixture was stirred for 72 h at r.t. and then the solvent was decanted off and ice was added to the resulting oil. Aqueous sat. $Na_2CO_3$ solution was added slowly up to pH 9 and the resulting solid was filtered and washed several times with water and then $Et_2O$ to give the title compound (0.21 g, 56%) as a white solid. $\delta_H$ (DMSO-$d_6$) 7.35 (1H, s), 3.70 (4H, t, J 4.8 Hz), 3.47 (4H, t, J 4.8 Hz), 3.39-3.36 (2H, m), 2.72 (2H, t, J 7.0 Hz). LCMS (ES+) 240.0 (M+H)$^+$.

Example 4

2-(Morpholin-4-yl)-5,5a,6,7,8,8a-hexahydro-4H-cyclopenta[b][1,3]thiazolo[4,5-d]pyridin-4-one To a stirred solution of Intermediate 14 (0.26 g, 0.79 mmol) in EtOH (10 mL) was added Intermediate 7 (0.12 g, 0.83 mmol) and the reaction mixture was stirred at 70° C. for 6 h. The reaction mixture was then partitioned between EtOAc (15 mL) and aqueous sat. $NaHCO_3$ solution (15 mL) and the organics were dried ($MgSO_4$), filtered and concentrated in vacuo. Purification by column chromatography ($SiO_2$, EtOAc), followed by preparative HPLC, gave the title compound (0.03 g, 14%) as an off-white solid. $\delta_H$ ($CD_3OD$) 4.17-4.11 (1H, m), 3.82-3.79 (4H, m), 3.58-3.55 (4H, m), 3.27-3.19 (1H, m), 2.25-2.19 (1H, m), 2.17-2.02 (1H, m), 2.00-1.64 (4H, m). Exchangeable proton not observed. LCMS (ES+) 280.0 (M+H)$^+$.

Example 5

Method F

2-(Morpholin-4-yl)-6-phenyl-6,7-dihydro[1,3]thiazolo[5,4-c]pyridin-4(5H)-one To a stirred solution of Intermediate 15 (0.05 g, 0.16 mmol) in THF (1 mL) was added polymer-supported tribromide (Amberlyst® A-26, 0.18 g, 0.17 mmol) and the reaction mixture was stirred at r.t. for 1.5 h. The crude reaction mixture was then filtered, washed with THF (1 mL) and the solvent removed in vacuo. The crude intermediate was then re-dissolved in EtOH (1 mL) and Intermediate 4 (0.02 g, 0.16 mmol) was added. After stirring at 70° C. for 6 h, the reaction mixture was cooled and concentrated in vacuo. Purification by preparative HPLC gave the title compound (0.01 g, 19%) as an off-white solid. LCMS (ES+) 316.0 (M+H)$^+$, RT 2.56 minutes.

Example 6

6-Methyl-2-(morpholin-4-yl)-6,7-dihydro[1,3]thiazolo[5,4-c]pyridin-4(5H)-one

The title compound was prepared from Intermediate 16 according to Method F and was isolated (9%) after purification by preparative HPLC. LCMS (ES+) 254.0 (M+H)$^+$, RT 1.85 minutes.

Example 7

6-Isopropyl-2-(morpholin-4-yl)-6,7-dihydro[1,3]thiazolo[5,4-c]pyridin-4(5H)-one

The title compound was prepared from Intermediate 17 according to Method F and was isolated (22%) after purification by preparative HPLC. LCMS (ES+) 282.0 (M+H)$^+$, RT 2.36 minutes.

Example 8

6-Isobutyl-2-(morpholin-4-yl)-6,7-dihydro[1,3]thiazolo[5,4-c]pyridin-4(5H)-one

The title compound was prepared from Intermediate 18 according to Method F and was isolated (19%) after purification by preparative HPLC. LCMS (ES+) 296.0 (M+H)$^+$, RT 2.72 minutes.

Example 9

2-(Morpholin-4-yl)-6-propyl-6,7-dihydro[1,3]thiazolo[5,4-c]pyridin-4(5H)-one

The title compound was prepared from Intermediate 19 according to Method F and was isolated (28%) after purification by preparative HPLC. LCMS (ES+) 282.0 (M+H)$^+$, RT 2.45 minutes.

Example 10

6-Cyclohexyl-2-(morpholin-4-yl)-6,7-dihydro[1,3]thiazolo[5,4-c]pyridin-4(5H)-one The title compound was prepared from Intermediate 20 according to Method F and was isolated (30%) after purification by preparative HPLC. LCMS (ES+) 322.0 (M+H)$^+$, RT 3.01 minutes.

Example 11

7-Methyl-2-(morpholin-4-yl)-6,7-dihydro[1,3]thiazolo[5,4-c]pyridin-4(5H)-one

The title compound was prepared from Intermediate 21 according to Method F and was isolated after purification by preparative HPLC. LCMS (ES+) 254.0 (M+H)$^+$, RT 1.92 minutes.

Example 12

2-[(3S)-3-(1H-Indol-3-ylmethyl)morpholin-4-yl]-5,5a,6,7,8,8a-hexahydro-4H-cyclopenta[b][1,3]thiazolo[4,5-d]pyridin-4-one To a stirred solution of Intermediate 14 (0.79 g, 2.36 mmol) in THF (15 mL) was added Intermediate 22 (0.69 g, 2.48 mmol) and DIPEA (0.32 g, 0.43 mL, 2.48 mmol) and the reaction mixture was stirred at 70° C. for 7 h. After cooling, the volatiles were removed in vacuo to give a brown oil which was partitioned between EtOAc (20 mL) and aqueous sat. NaHCO$_3$ solution (20 mL). The organic layer was dried over MgSO$_4$, filtered and concentrated in vacuo to give an orange oil. Purification by column chromatography (SiO$_2$, EtOAc; followed by SiO$_2$, 1-4% MeOH/DCM) gave the title compound (0.16 g, 16%) as a yellow solid. $\delta_H$ (DMSO-d$_6$) 10.88 (1H, s), 7.87-7.81 (1H, m), 7.36-7.33 (2H, m), 7.19 (1H, t, J 2.4 Hz), 7.10-7.00 (2H, m), 4.17 (1H, br. s), 3.99-3.97 (2H, m), 3.73-3.70 (1H, m), 3.62-3.46 (4H, m), 3.33-3.15 (2H, m), 2.94-2.88 (1H, m), 2.18-2.06 (1H, m), 1.94-1.85 (2H, m), 1.68-1.60 (3H, m). LCMS (ES+) 409.0 (M+H)$^+$.

Example 13

5,5-Dimethyl-2-(morpholin-4-yl)-5,6-dihydro[1,3]thiazolo[4,5-d]pyrimidin-7(4H)-one A mixture of 4-amino-2-(morpholin-4-yl)-1,3-thiazole-5-carboxamide (0.22 g, 0.98 mmol; prepared according to Liebigs Annalen der Chemie, 1986, 4, 780-4), 2,2-dimethoxypropane (3 mL, excess), acetone (2 mL, excess) and p-toluenesulfonic acid monohydrate (cat. amount) was heated to 100° C. in a sealed tube, under microwave irradiation, for 1 h. The reaction mixture was then concentrated in vacuo and purification by preparative HPLC gave the title compound (0.04 g, 16%) as an off-white solid. $\delta_H$ (DMSO-d$_6$) 7.54 (1H, s), 7.01 (1H, s), 3.73-3.63 (4H, m), 3.49-3.38 (4H, m), 1.38 (6H, s). LCMS (ES+) 269.0 (M+H)$^+$.

Example 14

Method G

5a-Methyl-2-(morpholin-4-yl)-5a,6,7,8-tetrahydropyrrolo[1,2-a][1,3]thiazolo[5,4-e]pyrimidin-4(5H)-one A stirred solution of 4-amino-2-(morpholin-4-yl)-1,3-thiazole-5-carboxamide (0.22 g, 0.99 mmol), 5-chloro-2-pentanone (0.5 mL, excess) and p-toluenesulfonic acid monohydrate (cat. amount) in DCE (4 mL) was heated to 100° C. in a sealed tube, under microwave irradiation, for 1 h. The reaction mixture was then concentrated in vacuo and purification by preparative HPLC gave the title compound (0.03 g, 10%) as an off-white solid. $\delta_H$ (DMSO-d$_6$) 7.29 (1H, s), 3.73-3.64

(4H, m), 3.57-3.39 (6H, m), 2.08-1.96 (2H, m), 1.93-1.83 (2H, m), 1.36 (3H, s). LCMS (ES+) 295.2 (M+H)+.

Example 15

5-Ethoxy-5-ethyl-2-(morpholin-4-yl)-5,6-dihydro[1,3]thiazolo[4,5-d]pyrimidin-7(4H)-one The title compound was prepared from 4-amino-2-(morpholin-4-yl)-1,3-thiazole-5-carboxamide and triethyl orthopropionate according to Method G and was isolated as a white solid (39%) after purification by preparative HPLC. $\delta_H$ (DMSO-$d_6$) 7.26 (1H, br. s), 7.06 (1H, br. s), 4.19 (2H, q, J 7.0 Hz), 3.74-3.66 (4H, m), 3.46-3.36 (4H, m), 2.55-2.47 (2H, m), 1.29 (3H, t, J 7.0 Hz), 1.10 (3H, t, J 7.5 Hz). LCMS (ES+) 313.0 (M+H)+.

Example 16

Method N

2-[(3S)-3-{[5-(Difluoromethoxy)-1H-indol-3-yl]methyl}morpholin-4-yl]-6,6-dimethyl-6,7-dihydro[1,3]thiazolo[5,4-c]pyridin-4(5H)-one To a solution of Intermediate 29 (0.07 g, 0.21 mmol) in THF (3 mL) was added Intermediate 46 (0.048 g, 0.22 mmol) and DIPEA (0.059 mL, 0.41 mmol) and the reaction mixture was stirred at 60° C. for 1.5 h. The reaction mixture was concentrated in vacuo to give a yellow oil. Purification by column chromatography ($SiO_2$, 1-2% MeOH/DCM; followed by $SiO_2$, 80-100% EtOAc/DCM) and freeze-drying (MeCN/water) gave the title compound (0.019 g, 20%) as an off-white solid. $\delta_H$ ($CD_3OD$) 7.73 (1H, d, J 2.1 Hz), 7.32 (1H, d, J 8.7 Hz), 7.20 (1H, s), 6.93 (1H, dd, J 8.7 and J 2.3 Hz), 6.72 (1H, t, J 75.6 Hz), 4.38-4.30 (1H, m), 4.09-4.06 (1H, m), 3.90 (1H, d, J 11.8 Hz), 3.71-3.46 (4H, m), 3.40-3.31 (1H, m), 3.10-3.04 (1H, m), 2.83 (2H, s), 1.36 (6H, s). Exchangeable protons were not observed. LCMS (ES+) 463.0 (M+H)+, RT 3.07 minutes (Method 5).

Example 17

6,6-Dimethyl-2-[(3S)-3-{[5-(trifluoromethoxy)-1H-indol-3-yl]methyl}morpholin-4-yl]-6,7-dihydro[1,3]thiazolo[5,4-c]pyridin-4(5H)-one The title compound was prepared from Intermediate 37 and Intermediate 46 according to Method N and was isolated as a colourless oil after purification by column chromatography ($SiO_2$, 60-90% EtOAc/DCM; followed by $SiO_2$, 60-80% EtOAc/DCM). The sample was freeze-dried (MeCN/water) to give the title compound (45%) as a white fluffy solid. $\delta_H$ ($CD_3OD$) 7.75 (1H, s), 7.25 (1H, d, J 8.8 Hz), 7.14 (1H, s), 6.90 (1H, dd, J 8.8 and J 1.1 Hz), 4.28-4.25 (1H, m), 3.97-3.95 (1H, m), 3.77 (1H, d, J 11.7 Hz), 3.63-3.54 (2H, m), 3.49-3.37 (2H, m), 3.29-3.23 (1H, m), 2.95 (1H, dd, J 13.9 and J 4.7 Hz), 2.71 (2H, d, J 2.2 Hz), 1.25 (3H, s), 1.24 (3H, s). Exchangeable protons were not observed. LCMS (ES+) 481.0 (M+H)+, RT 3.29 minutes (Method 5).

Example 18

2-{(3S)-3-[(2,2-Difluoro-5H-[1,3]dioxolo[4,5-f]indol-7-yl)methyl]morpholin-4-yl}-6,6-dimethyl-6,7-dihydro[1,3]thiazolo[5,4-c]pyridin-4(5H)-one The title compound was prepared from Intermediate 32 and Intermediate 46 according to Method N and was isolated as a colourless oil after purification by column chromatography ($SiO_2$, 50-100% EtOAc/hexanes). The sample was freeze-dried (MeCN/water) to give the title compound (0.058 g, 48%) as an off-white solid. $\delta_H$ ($CD_3OD$) 7.48 (1H, s), 7.03 (1H, s), 6.99 (1H, s), 4.19 (1H, m), 3.92 (1H, m), 3.75 (1H, d, J 11.7 Hz), 3.50 (4H, m), 3.18 (1H, m), 2.95 (1H, m), 2.65 (2H, dd, J 16.8 and J 23.6 Hz), 1.24 (3H, s), 1.23 (3H, s). Exchangeable protons were not observed. LCMS (ES+) 477.0 (M+H)+, RT 3.25 minutes (Method 5).

Example 19

6,6-Dimethyl-2-{(3S)-3-[5-nitro-1H-indol-3-yl)methyl]morpholin-4-yl}-6,7-dihydro[1,3]thiazolo[5,4-c]pyridin-4(5H)-one The title compound was prepared from Intermediate 40 and Intermediate 46 according to Method N and was isolated as a yellow solid (29%) after purification by column chromatography ($SiO_2$, 20:80 EtOAc/hexanes). $\delta_H$ (DMSO-$d_6$) 11.68 (1H, s), 8.93 (1H, s), 8.04 (1H, d, J 11.2 Hz), 7.57 (1H, s), 7.54 (1H, s), 7.33 (1H, s), 4.20 (1H, m), 3.80 (1H, m), 3.53 (4H, m), 3.09 (1H, dd, J 4.9 and J 4.2 Hz), 2.80 (2H, s), 1.30 (6H, s). $\delta_H$ (DMSO-$d_6$ & $D_2O$) 8.78 (1H, s), 7.95 (1H, d, J 8.9 Hz), 7.48 (1H, s), 7.45 (1H, s), 7.39 (1H, s), 7.14 (1H, s), 4.29 (1H, m), 3.73 (1H, d, J 11.7 Hz), 3.49 (4H, m), 3.26 (1H, m), 3.03 (1H, m), 2.65 (2H, d, J 6.5 Hz), 1.20 (3H, s), 1.18 (3H, s). Exchangeable protons were observed. LCMS (ES+) 442.0 (M+H)+, RT 2.98 minutes (Method 5).

Example 20

Methyl 3-{[(3S)-4-(6,6-dimethyl-4-oxo-4,5,6,7-tetrahydro[1,3]thiazolo[5,4-c]pyridin-2-yl)morpholin-3-yl]methyl}-1H-indole-5-carboxylate The title compound was prepared from Intermediate 43 and Intermediate 46 according to Method N and was isolated as a yellow solid (69%) after purification by column chromatography ($SiO_2$, 0-5% MeOH/DCM). $\delta_H$ ($CD_3OD$) 8.62 (1H, d, J 1.0 Hz), 7.81 (1H, dd, J 8.6 and J 1.6 Hz), 7.39 (1H, d, J 8.6 Hz), 7.24 (1H, s), 4.37 (1H, m), 4.07 (1H, m), 3.95 (3H, s), 3.90 (1H, d, J 11.7 Hz), 3.73-3.52 (4H, m), 3.38 (1H, m), 3.18 (1H, dd, J 13.9 and J 5.4 Hz), 2.87 (1H, d, J 16.9 Hz), 2.81 (1H, d, J 16.9 Hz), 1.37 (3H, s), 1.36 (3H, s). Exchangeable protons were not observed. LCMS (ES+) 455.0 (M+H)+, RT 2.59 minutes (Method 4).

Example 21

3-{[(3S)-4-(6,6-Dimethyl-4-oxo-4,5,6,7-tetrahydro[1,3]thiazolo[5,4-c]pyridin-2-yl)morpholin-3-yl]methyl}-1H-indole-5-carboxylic acid To Example 20 (2.18 g, 4.80 mmol) dissolved in 1,4-dioxane (20 mL) was added a solution of LiOH.$H_2O$ (0.40 g, 9.60 mmol) in water (20 mL) and the reaction mixture stirred at r.t. for 16 h. Further LiOH.$H_2O$ (0.10 g, 2.40 mmol) in water (5 mL) was added and the reaction mixture stirred at 50° C. for 3 h. The reaction mixture was concentrated in vacuo and the crude residue was partitioned between water (100 mL) and DCM (200 mL). The aqueous phase was acidified to pH 1 by the addition of aqueous HCl (10% v/v) and extracted with EtOAc (3×200 mL) and the combined organic fractions were concentrated in vacuo to give the title compound (2.37 g, quantitative) as a yellow solid. $\delta_H$ (DMSO-$d_6$) 12.35 (1H, br. s), 11.23 (1H, s), 8.58 (1H, s), 7.71 (1H, dd, J 8.6 and J 1.5 Hz), 7.38 (1H, d, J 8.6 Hz), 7.30 (1H, d, J 2.1 Hz), 7.27 (1H, s), 4.27 (1H, m), 3.98 (1H, m), 3.73 (1H, d, J 11.6 Hz), 3.62-3.43 (4H, m), 3.28 (1H, m), 2.96 (1H, dd, J 13.9 and J 3.9 Hz), 2.83 (1H, d, J 16.9 Hz), 2.76 (1H, d, J 16.9 Hz), 1.26 (6H, s). LCMS (ES+) 441.0 (M+H)$^+$, RT 2.65 minutes (Method 5).

Example 22

Method O 6,6-Dimethyl-2-[(3S)-3-{[5-(piperidin-1-ylcarbonyl)-1H-indol-3-yl]methyl}morpholin-4-yl]-6,7-dihydro[1,3]thiazolo[5,4-c]pyridin-4(5H)-one To Intermediate 44 (0.206 g, 0.34 mmol) dissolved in DCM (5 mL) was added piperidine (0.035 g, 0.04 mL, 0.409 mmol) and the reaction mixture stirred at r.t. for 1 h. The reaction mixture was concentrated in vacuo and the crude residue was purified by column chromatography (SiO$_2$, 0-5% MeOH/DCM). The sample was freeze-dried (MeCN/water) to give the title compound (0.086 g, 50%) as a white powder. $\delta_H$ (DMSO-d$_6$) 11.07 (1H, s), 7.91 (1H, s), 7.36 (1H, d, J 8.3 Hz), 7.29 (1H, s), 7.27 (1H, d, J 1.9 Hz), 7.10 (1H, dd, J 8.5 and J 1.3 Hz), 4.19 (1H, m), 3.98 (1H, d, J 6.0 Hz), 3.74 (1H, d, J 11.7 Hz), 3.57 (4H, br. s), 3.50 (4H, m), 3.36-3.22 (1H, m), 2.92 (1H, dd, J 13.9 and J 4.1 Hz), 2.71 (2H, t, J 17.1 Hz), 1.66-1.49 (6H, m), 1.26 (6H, s). LCMS (ES+) 508.0 (M+H)$^+$, RT 2.88 minutes (Method 5).

Example 23

2-[(3S)-3-{[5-(Azetidin-1-ylcarbonyl)-1H-indol-3-yl]methyl}morpholin-4-yl]-6,6-dimethyl-6,7-dihydro[1,3]thiazolo[5,4-c]pyridin-4(5H)-one The title compound was prepared from Intermediate 44 and azetidine.HCl according to Method O with the addition of DIPEA and was isolated as a white powder (61%) after purification by column chromatography (SiO$_2$, 0-10% MeOH/DCM) and freeze-drying (MeCN/water). $\delta_H$ (CD$_3$OD) 8.20 (1H, d, J 0.8 Hz), 7.45 (1H, dd, J 8.5 and J 1.5 Hz), 7.40 (1H, dd, J 8.5 and J 0.8 Hz), 7.24 (1H, s), 4.49 (2H, m), 4.35 (1H, m), 4.26 (2H, m), 4.08 (1H, m), 3.88 (1H, d, J 11.7 Hz), 3.75-3.54 (4H, m), 3.42 (1H, dd, J 13.9 and J 10.2 Hz), 3.12 (1H, m), 2.86 (2H, s), 2.40 (2H, quint, J 7.7 Hz), 1.39 (3H, s), 1.38 (3H, s). Exchangeable protons were not observed. LCMS (ES+) 480.0 (M+H)$^+$, RT 2.67 minutes (Method 5).

Example 24

6,6-Dimethyl-2-[(3S)-3-({5-[(4-methylpiperazin-1-yl)carbonyl]-1H-indol-3-yl}methyl)morpholin-4-yl]-6,7-dihydro[1,3]thiazolo[5,4-c]pyridin-4(5H)-one The title compound was prepared from Intermediate 44 and 1-methylpiperazine according to Method O and was isolated as a white powder (51%) after purification by column chromatography (SiO$_2$, 0-10% MeOH/DCM) and freeze-drying (MeCN/water). $\delta_H$ (CD$_3$OD) 8.05 (1H, d, J 0.9 Hz), 7.41 (1H, dd, J 8.3 and J 0.4 Hz), 7.25 (1H, s), 7.20 (1H, dd, J 8.3 and J 1.5 Hz), 4.40-4.30 (1H, m), 4.12-4.03 (1H, m), 3.89 (1H, d, J 11.7 Hz), 3.79-3.55 (8H, m), 3.46-3.29 (1H, m), 3.12 (1H, m), 2.81 (2H, s), 2.51 (4H, br. s), 2.35 (3H, s), 1.37 (6H, s). Exchangeable protons were not observed. LCMS (ES+) 523.1 (M+H)$^+$, RT 2.22 minutes (Method 5).

Example 25

3-{[(3S)-4-(6,6-Dimethyl-4-oxo-4,5,6,7-tetrahydro[1,3]thiazolo[5,4-c]pyridin-2-yl)morpholin-3-yl]methyl}-N-(2-hydroxyethyl)-N-methyl-1H-indole-5-carboxamide The title compound was prepared from Intermediate 44 and 2-(methylamino)-ethanol according to Method O and was isolated as a white powder (63%) after purification by column chromatography (SiO$_2$, 0-10% MeOH/DCM) and freeze-drying (MeCN/water). $\delta_H$ (CD$_3$OD) 8.09 (1H, s), 7.41 (1H, d, J 8.5 Hz), 7.23 (2H, m), 4.35 (1H, m), 4.06 (1H, m), 3.89 (1H, d, J 11.7 Hz), 3.84-3.48 (8H, m), 3.39 (1H, dd, J 13.9 and J 10.2 Hz), 3.19 (3H, s), 3.11 (1H, m), 2.82 (2H, s), 1.37 (6H, s). Exchangeable protons were not observed. LCMS (ES+) 498.0 (M+H)$^+$, RT 2.51 minutes (Method 5).

Example 26

3-{[(3S)-4-(6,6-Dimethyl-4-oxo-4,5,6,7-tetrahydro[1,3]thiazolo[5,4-c]pyridin-2-yl)morpholin-3-yl]methyl}-N-(2-hydroxyethyl)-1H-indole-5-carboxamide The title compound was prepared from Intermediate 44 and ethanolamine according to Method O and was isolated as a white powder (78%) after purification by column chromatography (SiO$_2$, 0-10% MeOH/DCM) and freeze-drying (MeCN/water). $\delta_H$ (CD$_3$OD) 8.33 (1H, d, J 1.1 Hz), 7.61 (1H, dd, J 8.7 and J 1.7 Hz), 7.37 (1H, dd, J 8.5 and J 0.4 Hz), 7.22 (1H, s), 4.43 (1H, m), 4.08 (1H, m), 3.92 (1H, d, J 11.9 Hz), 3.78 (2H, t, J 5.8 Hz), 3.71 (1H, s), 3.69-3.56 (5H, m), 3.41-3.21 (2H, m), 2.73 (2H, dd, J 19.6 and J 17.0 Hz), 1.33 (3H, s), 1.32 (3H, s). Exchangeable protons were not observed. LCMS (ES+) 484.0 (M+H)$^+$, RT 2.48 minutes (Method 5).

Example 27

3-{[(3S)-4-(6,6-Dimethyl-4-oxo-4,5,6,7-tetrahydro[1,3]thiazolo[5,4-c]pyridin-2-yl)morpholin-3-yl]methyl}-N-methyl-1H-indole-5-carboxamide The title compound was prepared from Intermediate 44 and methylamine according to Method O and was isolated as a white powder (72%) after purification by column chromatography (SiO$_2$, 0-10% MeOH/DCM) and freeze-drying (MeCN/water). $\delta_H$ (CD$_3$OD) 8.31 (1H, d, J 1.1 Hz), 8.28 (1H, d, J 4.3 Hz), 7.58 (1H, dd, J 8.5 and J 1.7 Hz), 7.37 (1H, m), 7.21 (1H, s), 4.43 (1H, m), 4.08 (1H, d, J 7.5 Hz), 3.91 (1H, d, J 11.7 Hz), 3.78-3.57 (4H, m), 3.38 (1H, m), 3.22 (1H, dd, J 13.9 and J 6.0 Hz), 3.00 (1H, s), 2.98 (2H, d, J 1.1 Hz), 2.74 (2H, dd, J 18.5 and J 16.8 Hz), 1.34 (3H, s), 1.33 (3H, s). Exchangeable protons were not observed. LCMS (ES+) 454.4 (M+H)$^+$, RT 2.25 minutes (Method 3).

Example 28

3-{[(3S)-4-(6,6-Dimethyl-4-oxo-4,5,6,7-tetrahydro[1,3]thiazolo[5,4-c]pyridin-2-yl)morpholin-3-yl]methyl}-N,N-dimethyl-1H-indole-5-carboxamide The title compound was prepared from Intermediate 44 and dimethylamine according to Method O and was isolated as a white powder (70%) after purification by column chromatography (SiO$_2$, 0-10% MeOH/DCM) and freeze-drying (MeCN/water). $\delta_H$ (CD$_3$OD) 8.08 (1H, d, J 0.9 Hz), 7.41 (1H, dd, J 8.3 and J 0.6 Hz), 7.24 (1H, s), 7.21 (1H, dd, J 8.5 and J 1.7 Hz), 4.35 (1H, m), 4.07 (1H, m), 3.89 (1H, d, J 11.7 Hz), 3.76-3.54 (4H, m), 3.42 (1H, dd, J 13.9 and J 10.2 Hz), 3.18-3.05 (7H, m), 2.82 (2H, s), 1.38 (6H, s). Exchangeable protons were not observed. LCMS (ES+) 468.5 (M+H)$^+$, RT 2.36 minutes (Method 3).

Example 29

6,6-Dimethyl-2-[(3S)-3-{[5-(morpholin-4-ylcarbonyl)-1H-indol-3-yl]methyl}morpholin-4-yl]-6,7-dihydro[1,3]thiazolo[5,4-c]pyridin-4(5H)-one The title compound was prepared from Intermediate 44 and morpholine according to Method O and was isolated as a white powder (64%) after purification by column chromatography (SiO$_2$, 0-10% MeOH/DCM) and freeze-drying (MeCN/water). $\delta_H$ (CD$_3$OD) 8.04 (1H, d, J 0.8 Hz), 7.42 (1H, dd, J 8.3 and J 0.6 Hz), 7.25 (1H, s), 7.21 (1H, dd, J 8.5 and J 1.5 Hz), 4.33 (1H, m), 4.08 (1H, m), 3.88 (1H, d, J 11.7 Hz), 3.73-3.56 (12H, m), 3.41 (1H, dd, J 13.9 and J 10.0 Hz), 3.12 (1H, dd, J 13.8 and J 5.1 Hz), 2.81 (2H, s), 1.37 (6H, s). Exchangeable protons were not observed. LCMS (ES+) 510.5 (M+H)$^+$, RT 2.33 minutes (Method 3).

Example 30

N-Benzyl-3-{[(3S)-4-(6,6-dimethyl-4-oxo-4,5,6,7-tetrahydro[1,3]thiazolo[5,4-c]pyridin-2-yl)morpholin-3-yl]methyl}-1H-indole-5-carboxamide The title compound was prepared from Intermediate 44 and benzylamine according to Method O and was isolated as a white powder (81%) after purification by column chromatography (SiO$_2$, 0-10% MeOH/DCM) and freeze-drying (MeCN/water). $\delta_H$ (CD$_3$OD) 8.35 (1H, d, J 1.3 Hz), 7.63 (1H, dd, J 8.5 and J 1.7 Hz), 7.38 (5H, m), 7.27 (1H, m), 7.23 (1H, s), 4.66 (2H, t, J 16.0 Hz), 4.46 (1H, m), 4.08 (1H, m), 3.95 (1H, d, J 11.7 Hz), 3.91-3.60 (4H, m), 3.56 (1H, m), 3.32 (1H, m), 2.62 (2H, dd, J 23.4 and J 17.0 Hz), 1.26 (3H, s), 1.24 (3H, s). Exchangeable protons were not observed. LCMS (ES+) 530.4 (M+H)$^+$, RT 2.62 minutes (Method 3).

Example 31

2-[(3S)-3-(3-Bromobenzyl)morpholin-4-yl]-6,6-dimethyl-6,7-dihydro[1,3]thiazolo[5,4-c]pyridin-4(5H)-one The title compound was prepared from Intermediate 45 and Intermediate 46 according to Method N and was isolated as a yellow solid (66%) after purification by column chromatography (SiO$_2$, DCM-EtOAc). $\delta_H$ (DMSO-d$_6$) 7.45 (1H, d, J 1.6 Hz), 7.38-7.35 (1H, m), 7.32-7.19 (2H, m), 4.20-4.10 (1H, m), 3.96-3.93 (1H, m), 3.70-3.54 (5H, m), 3.04 (2H, d, J 7.4 Hz), 2.63 (2H, d, J 5.1 Hz), 1.22 (6H, s). LCMS (ES+) 436.0 and 438.0 (1:1 ratio) (M+H)$^+$, RT 2.89 minutes (Method 3).

Example 32

Method P 6,6-Dimethyl-2-{(3S)-3-[3-(pyridin-4-ylamino)benzyl]morpholin-4-yl}-6,7-dihydro[1,3]thiazolo[5,4-c]pyridin-4(5H)-one A flask was charged with Example 31 (0.300 g, 0.69 mmol), Pd$_2$dba$_3$ (0.013 g, 0.014 mmol), X-Phos (0.033 g, 0.069 mmol), sodium tert-butoxide (0.165 g, 1.72 mmol) and 4-aminopyridine (0.097 g, 1.03 mmol). tert-BuOH (5 mL) was then added. The reaction mixture was stirred for 16 h at 95° C. The solvent was evaporated in vacuo and DCM (5 mL) and water (5 mL) were added. The aqueous fraction was extracted with DCM (3×5 mL). The combined organic fractions were washed with water (3×10 mL), dried (NaSO$_4$), filtered and the solvent evaporated in vacuo. The oily residue was purified by column chromatography (SiO$_2$, 0-3% MeOH/DCM) to give the title compound (0.176 g, 57%) as a white solid. $\delta_H$ (DMSO-d$_6$) 8.80 (1H, s), 8.17 (2H, d, J 4.8 Hz), 7.28-7.23 (2H, m), 7.12 (1H, s), 7.02 (1H, d, J 8.0 Hz), 6.94 (1H, d, J 7.6 Hz), 6.87 (2H, d, J 6.0 Hz), 4.01-3.95 (2H, m), 3.69-3.78 (2H, m), 3.53-3.60 (3H, m), 3.27-2.92 (2H, m), 2.62 (2H, s), 1.21 (3H, s), 1.20 (3H, s). LCMS (ES+) 450.0 (M+H)$^+$, RT 1.95 minutes (Method 3).

Example 33

2-[(3S)-3-{3-[(6-Chloropyridin-3-yl)amino]benzyl}morpholin-4-yl]-6,6-dimethyl-6,7-dihydro[1,3]thiazolo[5,4-c]pyridin-4(5H)-one The title compound was prepared from Example 31 and 5-amino-2-chloropyridine according to Method P and was isolated as a white solid (19%) after purification by column chromatography (SiO$_2$, 0-3% MeOH/DCM), followed by preparative HPLC (Method 8) and freeze-drying (MeCN/water). $\delta_H$ (DMSO-d$_6$) 8.49 (1H, s), 8.13 (1H, d, J 2.7 Hz), 7.48 (1H, dd, J 8.7 and J 3.0 Hz), 7.30 (2H, t, J 8.6 Hz), 7.20 (1H, d, J 7.7 Hz), 7.05 (1H, s), 6.92 (1H, d, J 7.9 Hz), 6.81 (1H, d, J 7.6 Hz), 4.00-3.95 (2H, m), 3.72-3.68 (2H, m), 3.57-3.51 (3H, m), 3.03 (1H, dd, J 13.0 and J 8.9 Hz), 2.89 (1H, dd, J 13.2 and J 5.5 Hz), 2.63 (2H, s), 1.22 (6H, s). LCMS (ES+) 484.0 and 486.0 (3:1 ratio, M+H)$^+$, RT 3.13 minutes (Method 5).

Example 34

2-[(3S)-3-{3-[(2,6-Dimethylpyridin-4-yl)amino]benzyl}morpholin-4-yl]-6,6-dimethyl-6,7-dihydro[1,3]thiazolo[5,4-c]pyridin-4(5H)-one The title compound was prepared from Example 31 and 2,6-dimethylpyridin-4-yl-amine according to Method P and was isolated as a white solid (19%) after purification by column chromatography (SiO$_2$, 0-3% MeOH/DCM), followed by preparative HPLC (Method 8) and freeze-drying (MeCN/water). $\delta_H$ (DMSO-d$_6$) 8.62 (1H, s), 7.25 (2H, t, J 7.7 Hz), 7.08 (1H, s), 6.99 (1H, d, J 8.0 Hz), 6.90 (1H, d, J 7.8 Hz), 6.59 (2H, s), 3.98-3.95 (2H, m), 3.79-3.69 (2H, s), 3.59-3.53 (3H, m), 3.06 (1H, dd, J 13.2 and J 8.8 Hz), 2.93 (1H, dd, J 13.0 and J 6.0 Hz), 2.63 (2H, s), 2.29 (6H, s), 1.21 (3H, s), 1.20 (3H, s). LCMS (ES+), 478.0 (M+H)$^+$, RT 2.32 minutes (Method 5).

Example 35

6,6-Dimethyl-2-[(3S)-3-{3-[(2-methoxypyridin-4-yl)amino]benzyl}morpholin-4-yl]-6,7-dihydro[1,3]thiazolo[5,4-c]pyridin-4(5H)-one The title compound was prepared from Example 31 and 2-methoxypyridin-4-yl-amine according to Method P and was isolated as a white solid (78%) after purification by column chromatography (SiO$_2$, 0-3% MeOH/DCM) and freeze-drying (MeCN/water). $\delta_H$ (DMSO-d$_6$) 8.71 (1H, s), 7.82 (1H, d, J 5.8 Hz), 7.27-7.22 (2H, m), 7.10 (1H, s), 6.99 (1H, d, J 8.0 Hz), 6.90 (1H, d, J 7.5 Hz), 6.55 (1H, dd, J 5.8 and J 2.0 Hz), 6.25 (1H, d, J 1.9 Hz), 4.02-3.91 (2H, m), 3.77 (3H, s), 3.71-3.67 (2H, m), 3.60-3.48 (3H, m) 3.06 (1H, dd, J 13.1 and J 9.0 Hz), 2.92 (1H, dd, J 13.2 and J 5.9 Hz), 2.64 (2H, s), 1.21 (6H, s). LCMS (ES+), 480.0 (M+H)$^+$, RT 2.31 minutes (Method 5).

Example 36

2-(Morpholin-4-yl)-6,7-dihydro[1,3]thiazolo[5,4-c]pyridin-4(5H)-thione

To a stirred solution of Example 3 (0.139 g, 0.58 mmol) in THF (10 mL) was added Lawesson's reagent (2.36 g, 5.8 mmol). The suspension was stirred for 1 week. DCM (10 mL) and water (10 mL) were added. The aqueous fraction was extracted with DCM (3×15 mL). The combined organic fractions were washed with water (3×20 mL), dried (MgSO$_4$), filtered and the solvent evaporated in vacuo. The oily residue was purified by column chromatography (SiO$_2$, 1:1 EtOAc/hexanes). Fractions containing the title compound were concentrated and the residue washed with Et$_2$O to give the title compound (0.088 g, 51%) as a yellow solid. $\delta_H$ (DMSO-d$_6$) 9.38 (1H, s), 3.69 (4H, t, J 4.8 Hz), 3.51 (4H, t, J 4.8 Hz), 3.44-3.48 (2H, m), 2.74 (2H, t, J 7.6 Hz). LCMS (ES+), 256.0 (M+H)$^+$, RT 2.60 minutes (Method 5).

Example 37

6,6-Dimethyl-2-{3-[(6-fluoro-1H-indol-3-yl)methyl]morpholin-4-yl}-6,7-dihydro[1,3]thiazolo[5,4-c]pyridin-4(5H)-one A microwave tube was charged with Intermediate 50 (0.43 g, 1.84 mmol) and dissolved in THF (3 mL) followed by the addition of Intermediate 5 (0.255 g, 0.979 mmol) and DIPEA (0.160 mL, 0.943 mmol). The tube was sealed and heated at 130° C. for 5 days after which time it was allowed to cool to r.t. The crude reaction mixture was diluted with EtOAc (30 mL), washed with water (20 mL), treated with brine (20 mL) and dried (MgSO$_4$), filtered and concentrated in vacuo. Purification by column chromatography (SiO$_2$, heptane-EtOAc) gave the title compound (0.184 g, 48%) as a yellow resin. $\delta_H$ (CDCl$_3$) 8.42 (1H, s), 7.80 (1H, dd, J 8.7 and J 5.3 Hz), 7.05 (2H, m), 6.92 (1H, m), 5.33 (1H, s), 4.09 (2H, m), 3.85 (1H, d, J 11.7 Hz), 3.62 (4H, m), 3.39 (1H, dd, J 13.8 and J 11.1 Hz), 3.03 (1H, dd, J 13.9 and J 4.1 Hz), 2.84 (2H, s), 1.39 (6H, s). LCMS (ES+) 415.0 (M+H)$^+$, RT 3.08 minutes (Method 1). This sample was further purified on Chiralpak IA column and repurified by column chromatography (SiO$_2$, heptane-EtOAc) to give the enantiomers (S) RT=5.1 minutes and (R) RT=6.0 minutes as colourless resins.

Example 38

2-{(3S)-3-[(1-Methyl-1H-indol-3-yl)methyl]morpholin-4-yl}-5,6,6-trimethyl-6,7-dihydro[1,3]thiazolo[5,4-c]pyridin-4(5H)-one To a solution of Example 2 (0.05 g, 0.12 mmol) in THF (5 mL) was added NaH (0.01 g, 60% dispersion in oil, 0.25 mmol) and the reaction mixture was stirred at r.t. for 10 minutes. Methyl iodide (0.017 g, 0.0075 ml, 0.12 mmol) was then added and the reaction mixture stirred at r.t. for 1 h. The reaction mixture was concentrated in vacuo and purified by preparative HPLC (Method 6) to give the title compound (0.004 g, 8%) as a colourless glass. $\delta_H$ (CDCl$_3$) 7.89 (1H, d, J 7.9 Hz), 7.35-7.25 (2H, m), 7.15-7.22 (1H, m), 7.01 (1H, s), 3.99-4.12 (2H, m), 3.90 (1H, d, J 11.7 Hz), 3.76-3.85 (4H, m), 3.75-3.60 (2H, m), 3.60-3.40 (2H, m), 3.10 (1H, d, J 3.6 Hz), 3.05 (3H, s), 2.89 (2H, s), 1.40 (6H, s). LCMS (ES+) 425.0 and 426.0 (M+H)$^+$, RT 3.68 minutes (Method 1).

Example 39

2-(6-Bromo-2,3-dihydrobenzo[1,4]oxazin-4-yl)-6,6-dimethyl-6,7-dihydro-[1,3]thiazolo[5,4-d]pyridin-4(5H)-one Two batches each of Intermediate 46 (0.25 g, 1.14 mmol), Intermediate 65 (0.25 g, 0.87 mmol) and DIPEA (0.23 mL, 1.3 mmol) in THF (4 mL) were heated to 120° C. under microwave irradiation for 20 minutes. After cooling to r.t., the reaction mixtures were combined and partitioned between EtOAc (100 mL) and water (100 mL). The organic fraction was separated, washed with brine (100 mL) and concentrated in vacuo. The crude material was purified by preparative HPLC (Method 6) to give the title compound (0.101 g, 15%) as an off-white solid. $\delta_H$ (CDCl$_3$) 8.18 (1H, d, J 2.3 Hz), 7.08 (1H, dd, J 8.9 and J 2.3 Hz), 6.76 (1H, d, J 8.7 Hz), 5.28 (1H, br. s), 4.29-4.22 (2H, m), 4.04-3.98 (2H, m), 2.83 (2H, s), 1.33 (6H, s). LCMS (ES+) 394.0 (M+H)$^+$, RT 3.64 minutes (Method 1).

Example 40

Tert-butyl 4-(6,6-dimethyl-4-oxo-4,5,6,7-tetrahydro[1,3]thiazolo[5,4-c]pyridin-2-yl)-3,4-dihydro-2H-benzo[1,4]oxazin-6-yl carbonate Intermediate 64 (0.160 g, 0.5 mmol), Intermediate 46 (0.147 g, 0.6 mmol) and DIPEA (0.24 mL, 1.3 mmol) in THF (4 mL) were heated to 120° C. under microwave irradiation for 20 minutes. After cooling to r.t., the reaction mixture was concentrated in vacuo and partitioned between DCM (50 mL) and water (50 mL). The organic fraction was washed with aqueous 1N HCl (50 mL) and brine (50 mL) then dried (MgSO$_4$), filtered and concentrated in vacuo. The resulting material was triturated with Et$_2$O to give the title compound (0.046 g, 21%) as a yellow solid. $\delta_H$ (CDCl$_3$) 8.01 (1H, d, J 2.4 Hz), 6.97-6.84 (2H, m), 5.25 (1H, br. s), 4.39-4.29 (2H, m), 4.13-4.03 (2H, m), 2.89 (2H, s), 1.61 (3H, s), 1.56 (6H, s), 1.40 (6H, s). LCMS (ES+) 432.0 (M+H)$^+$, RT 3.87 minutes (Method 2).

Example 41

6,6-Dimethyl-2-(6-nitro-2,3-dihydrobenzo[1,4]oxazin-4-yl)-6,7-dihydro-[1,3]thiazolo[5,4-c]pyridin-4(5H)-one A stirred solution of Intermediate 5 (0.20 g, 0.77 mmol), Intermediate 63 (0.166 g, 0.92 mmol), sodium tert-butoxide (0.022 g, 2.3 mmol), palladium(II) acetate (0.017 g, 0.07 mmol) and tert-butylphosphonium tetrafluoroborate (0.044 g, 0.15 mmol) in THF (4 mL) was heated to 100° C. under microwave irradiation for 1 h. After cooling to r.t. the reaction mixture was filtered through Celite® and concentrated in vacuo before being purified by preparative HPLC (Method 6) to give the title compound (0.020 g, 7%) as a yellow solid. $\delta_H$ (CDCl$_3$) 9.34 (1H, d, J 2.6 Hz), 7.97 (1H, dd, J 9.0 and J 2.6 Hz), 7.07 (1H, d, J 9.0 Hz), 5.32 (1H, br. s), 4.52-4.45 (2H, m), 4.13-4.05 (2H, m), 2.97 (2H, s), 1.44 (6H, s). LCMS (ES+) 361.0 (M+H)$^+$, RT 3.24 minutes (Method 1).

Example 42

2-(6-Amino-2,3-dihydrobenzo[1,4]oxazin-4-yl)-6,6-dimethyl-6,7-dihydro-[1,3]thiazolo[5,4-c]pyridin-4(5H)-one Example 41 (0.016 g, 0.04 mmol) was dissolved in EtOAc (7.5 mL) and MeOH (7.5 ml). 5% wt Palladium on carbon (0.032 g) was added and the mixture stirred under an atmosphere of H$_2$ overnight. The reaction mixture was then filtered through Celite® and concentrated in vacuo to give the title compound (0.014 g, 95%) as an off-white solid. $\delta_H$ (CDCl$_3$) 7.27 (1H, d, J 2.6 Hz), 6.70 (1H, d, J 8.7 Hz), 6.36 (1H, dd, J 8.7 and J 2.6 Hz), 5.25 (1H, br. s), 4.22-4.14 (2H, m), 4.08-4.00 (2H, m), 3.50 (2H, br. s), 2.80 (2H, s), 1.32 (6H, s). LCMS (ES+) 331.0 (M+H)$^+$, RT 2.57 minutes (Method 2).

Example 43

6,6-Dimethyl-2-[6-(1-methyl-1H-pyrazol-4-yl)-2,3-dihydrobenzo[1,4]oxazin-4-yl]-6,7-dihydro[1,3]thiazolo[5,4-c]pyridin-4(5H)-one A stirred suspension of Example 39 (0.090 g, 0.23 mmol), 1-methyl-4-(4,4,5,5-tetramethyl-[1,3,2]dioxaborolan-2-yl)-1H-pyrazole (0.142 g, 0.69 mmol), Na$_2$CO$_3$ (0.073 g, 0.69 mmol), tetra-n-butylammonium bromide (0.212 g, 0.69 mmol) and tetrakis-(triphenylphosphine)palladium(0) (0.026 g, 0.02 mmol) in THF (4 mL) was heated to 150° C. under microwave irradiation for 40 minutes. After cooling to r.t., the reaction mixture was partitioned between EtOAc (50 mL) and water (50 mL) and washed with brine (50 mL). The organic fraction was dried (MgSO$_4$), filtered and concentrated in vacuo. The residue was then purified by preparative HPLC (Method 6), the resulting material being partitioned between EtOAc (100 mL) and aqueous sat. NaHCO$_3$ solution (100 mL). The organic fractions were combined and washed with a mixture of brine and water (100 mL), dried (MgSO$_4$), filtered and concentrated in vacuo. This residue was then triturated with EtOAc (100 mL) and the mother liquors decanted to give the title compound (0.024 g, 27%) as a white solid. $\delta_H$ (CDCl$_3$) 7.92 (1H, d, J 2.1 Hz), 7.62 (1H, s), 7.49 (1H, s), 7.10 (1H, dd, J 8.5 and J 2.1 Hz), 6.88 (1H, d, J 8.5 Hz), 5.26 (1H, s), 4.30-4.23 (2H, m), 4.16-4.09 (2H, m), 3.88 (3H, s), 2.81 (2H, s), 1.33 (6H, s). LCMS (ES+) 396.0 (M+H)$^+$, RT 2.87 minutes (Method 1).

Example 44

6,6-Dimethyl-2-[6-(1-isobutyl-1H-pyrazol-4-yl)-2,3-dihydrobenzo[1,4]oxazin-4-yl]-6,7-dihydro[1,3]thiazolo[5,4-c]pyridin-4(5H)-one Example 39 (0.094 g, 0.238 mmol), 1-isobutyl-4-(4,4,5,5-tetramethyl-[1,3,2]dioxaborolan-2-yl)-1H-pyrazole (0.082 g, 0.33 mmol), K$_2$CO$_3$ (0.123 g, 0.9 mmol), tetra-n-butylammonium bromide (0.283 g, 0.9 mmol), tetrakis(triphenylphosphine)-palladium(0) (0.017 g, 0.014 mmol) and water (1 mL) in THF (2.5 mL) were heated to 120° C. under microwave irradiation for 10 minutes. After cooling to r.t., the reaction mixture was diluted with EtOAc (15 mL), washed with water (2×10 mL) and brine (10 mL) then dried (MgSO$_4$) and filtered before being concentrated in vacuo. The crude material was purified by column chromatography (SiO$_2$, 0-100% [9:1 EtOAc/MeOH]/heptane) to yield the title compound (0.045 g, 47%) as a white solid. $\delta_H$ (DMSO-d$_6$) 8.21 (1H, d, J 2.1 Hz), 8.05 (1H, s), 7.77 (1H, s), 7.55 (1H, s), 7.28 (1H, dd, J 8.5 and J 2.1 Hz), 6.95 (1H, d, J 8.3 Hz), 4.32-4.25 (2H, m), 4.12-4.06 (2H, m), 3.91 (2H, d, J 7.2 Hz), 2.83 (2H, s), 2.21-2.07 (1H, m), 1.28 (6H, s), 0.85 (6H, d, J 6.8 Hz). LCMS (ES+) 438.0 (M+H)$^+$, RT 3.75 minutes (Method 1).

Example 45

6,6-Dimethyl-2-[6-(1-propyl-1H-pyrazol-4-yl)-2,3-dihydrobenzo[1,4]oxazin-4-yl]-6,7-dihydro[1,3]thiazolo[5,4-c]pyridin-4(5H)-one Example 39 (0.094 g, 0.24 mmol), 1-propyl-4-(4,4,5,5-tetramethyl-[1,3,2]dioxaborolan-2-yl)-1H-pyrazole (0.175 g, 0.74 mmol), K$_2$CO$_3$ (0.123 g, 0.9 mmol), tetra-n-butylammonium bromide (0.28 g, 0.9 mmol), tetrakis(triphenylphosphine)palladium(0) (0.018 g, 0.015 mmol) and water (1 mL) in THF (2.5 mL) were heated to 120° C. for 10 minutes. After cooling to r.t. the reaction mixture was diluted with EtOAc (15 mL), washed with water (3×10 mL) and brine (10 mL) then dried (MgSO$_4$), filtered and concentrated in vacuo. The crude material was purified by column chromatography (SiO$_2$, 0-100% [9:1 EtOAc/MeOH]/heptane) to give the title compound (0.060 g, 59%) as a cream solid. $\delta_H$ (CD$_3$OD) 8.11 (1H, d, J 2.1 Hz), 7.90 (1H, s), 7.77 (1H, s), 7.29 (1H, dd, J 8.5 and J 2.1 Hz), 6.96 (1H, d, J 8.5 Hz), 4.36-4.30 (2H, m), 4.21-4.09 (4H, m), 2.90 (2H, s), 1.98-1.84 (2H, m), 1.40 (6H, s), 0.95 (3H, t, J 7.3 Hz). Exchangeable proton was not observed. LCMS (ES+) 424.0 (M+H)$^+$, RT 3.27 minutes (Method 1).

Example 46

6,6-Dimethyl-2-(6-{1-[2-(morpholin-4-yl)ethyl]-1H-pyrazol-4-yl}-2,3-dihydrobenzo[1,4]oxazin-4-yl)-6,7-dihydro[1,3]thiazolo[5,4-c]pyridin-4(5H)-one A stirred solution of Example 39 (0.1 g, 0.326 mmol), 4-{2-[4-(4,4,5,5-tetramethyl-[1,3,2]dioxaborolan-2-yl)-1H-pyrazol-1-yl]ethyl}morpholine (0.051 g, 0.165 mmol), K$_2$CO$_3$ (0.054 g, 0.395 mmol), tetra-n-butylammonium bromide (0.122 g, 0.377 mmol), tetrakis(triphenylphosphine) palladium(0) (0.007 g, 0.006 mmol) and H$_2$O (0.5 mL) in THF (1 mL) was heated at 125° C. in a sealed vessel for 2.5 days. After cooling to r.t. the reaction mixture was diluted with EtOAc and washed with water and brine. The organic fraction was dried (MgSO$_4$), filtered and concentrated in vacuo. Purification by column chromatography (SiO$_2$, 0-100% [9:1 EtOAc/MeOH]/heptane) followed by trituration with Et$_2$O gave the title compound (0.026 g, 41%) as a white solid. $\delta_H$ (CDCl$_3$) 8.00 (1H, d, J 2.1 Hz), 7.72 (1H, s), 7.68 (1H, s), 7.20 (1H, dd, J 8.5 and J 2.1 Hz), 6.97 (1H, d, J 8.5 Hz), 5.27 (1H, br. s), 4.39-4.26 (4H, m), 4.25-4.19 (2H, m), 3.78-3.69 (4H, m), 2.95-2.83 (4H, m), 2.61-2.49 (4H, m), 1.42 (6H, s). LCMS (ES+) 495.5 (M+H)$^+$, RT 2.04 minutes (Method 1).

Example 47

2-[6-(1-Benzyl-1H-pyrazol-4-yl)-2,3-dihydrobenzo[1,4]oxazin-4-yl]-6,6-dimethyl-6,7-dihydro[1,3]thiazolo[5,4-c]pyridin-4(5H)-one A stirred solution of Example 39 (0.051 g, 0.129 mmol), 1-benzyl-4-(4,4,5,5-tetramethyl-[1,3,2]dioxaborolan-2-yl)-

1H-pyrazole (0.049 g, 0.173 mmol), $K_2CO_3$ (0.054 g, 0.388 mmol), tetra-n-butylammonium bromide (0.124 g, 0.385 mmol), tetrakis-(triphenylphosphine)palladium(0) (0.010 g, 0.009 mmol) and $H_2O$ (0.5 mL) in THF (1 mL) was heated to 125° C. under microwave irradiation for 1 h. The reaction mixture was diluted with EtOAc and washed with water and brine. The organic fractions were dried ($MgSO_4$), filtered and concentrated in vacuo. The crude material was triturated with $Et_2O$ to give the title compound (0.041 g, 68%) as a beige solid. $\delta_H$ ($CDCl_3$) 8.03 (1H, d, J 1.9 Hz), 7.78 (1H, s), 7.60 (1H, s), 7.40-7.25 (5H, m), 7.18 (1H, dd, J 8.5 and J 2.1 Hz), 6.96 (1H, d, J 8.3 Hz), 5.37 (2H, s), 5.26 (1H, br. s), 4.38-4.32 (2H, m), 4.22-4.16 (2H, m), 2.89 (2H, s), 1.42 (6H, s). LCMS (ES+) 472.0 $(M+H)^+$, RT 3.53 minutes (Method 1).

Example 48

6,6-Dimethyl-2-[6-(6-methylpyridin-3-yl)-2,3-dihydrobenzo[1,4]oxazin-4-yl]-6,7-dihydro[1,3]thiazolo[5,4-c]pyridin-4(5H)-one A stirred solution of Example 39 (0.090 g, 0.23 mmol), 2-methylpyridine-5-boronic acid (0.094 g, 0.69 mmol), $Na_2CO_3$ (0.073 g, 0.69 mmol) and tetrakis-(triphenylphosphine)palladium(0) (0.026 g, 0.02 mmol) in THF (3 mL) was heated to 160° C. under microwave irradiation for 30 minutes. After cooling to r.t., water (10 mL) was added and the resulting precipitate filtered off, washed with water (3×20 mL) and dried in vacuo. The solid was then triturated with EtOAc (3×20 mL) and DCM (2×20 mL), then concentrated in vacuo to give the title compound (0.027 g, 29%) as an off-white solid. $\delta_H$ ($CDCl_3$) 8.71 (1H, d, J 2.3 Hz), 8.22 (1H, d, J 2.1 Hz), 7.75 (1H, dd, J 8.1 and J 2.4 Hz), 7.29 (1H, dd, J 7.9 and J 2.3 Hz), 7.22 (1H, d, J 7.9 Hz), 7.05 (1H, d, J 8.5 Hz), 5.30 (1H, br. s), 4.43-4.37 (2H, m), 4.22-4.16 (2H, m), 2.89 (2H, s), 2.60 (3H, s), 1.40 (6H, s). LCMS (ES+) 407.0 $(M+H)^+$, RT 1.99 minutes (Method 1).

Example 49

6,6-Dimethyl-2-[6-(pyrimidin-5-yl)-2,3-dihydrobenzo[1,4]oxazin-4-yl]-6,7-dihydro-[1,3]thiazolo[5,4-c]pyridin-4(5H)-one A mixture of Example 39 (0.135 g, 0.34 mmol), 5-pyrimidinylboronic acid (0.084 g, 0.68 mmol), $K_3PO_4$ (0.143 g, 0.68 mmol), water (1 mL) and tetrakis(triphenylphosphine)palladium(0) (catalytic) in DME (5 mL) was heated to 120° C. under microwave irradiation for 30 minutes. After cooling to r.t. the reaction mixture was filtered and purified by preparative HPLC (Method 7) to give the title compound (0.008 g, 6%) as a pale yellow solid. $\delta_H$ ($CD_3OD$) 9.12 (1H, s), 9.01 (2H, s), 8.44 (1H, d, J 2.3 Hz), 7.40 (1H, dd, J 8.5 and J 2.3 Hz), 7.14 (1H, d, J 8.5 Hz), 4.47-4.40 (2H, m), 4.21-4.14 (2H, m), 2.92 (2H, s), 1.41 (6H, s). Exchangeable proton was not observed. LCMS (ES+) 393.0 $(M)^+$, RT 2.83 minutes (Method 2).

Example 50

4-(6,6-Dimethyl-4-oxo-4,5,6,7-tetrahydrothiazolo[5,4-c]pyridin-2-yl)-3,4-dihydro-2H-benzo[1,4]oxazine-6-carbaldehyde A solution of Example 39 (0.700 g, 1.75 mmol) in THF (100 mL) was cooled to −70° C. before dropwise addition of n-butyllithium (2.8 mL, 2.5M solution in hexanes, 7.0 mmol). The mixture was stirred at −70° C. for 30 minutes. DMF (3.5 mL) was added. Stirring was continued at −70° C. for 30 minutes; the mixture was then allowed to warm to r.t. over 1 h, and stirred at r.t. for 30 minutes. The reaction mixture was concentrated in vacuo and water (10 mL) was added to the residue. The resulting precipitate was removed by filtration, washed with water (4×40 mL) and dried in vacuo to give the title compound (0.380 g, 63%) as a white solid. A small sample (0.030 g) of this material was purified further by preparative HPLC (Method 6). $\delta_H$ ($CDCl_3$) 9.89 (1H, s), 8.64 (1H, d, J 1.9 Hz), 7.62 (1H, dd, J 8.3 and J 1.9 Hz), 7.09 (1H, d, J 8.3 Hz), 5.34 (1H, br. s), 4.47-4.40 (2H, m), 4.17-4.11 (2H, m), 2.92 (2H, s), 1.41 (6H, s). LCMS (ES+) 344.0 $(M+H)^+$, RT 2.86 minutes (Method 1).

Example 51

6,6-Dimethyl-2-(6-hydroxymethyl-2,3-dihydrobenzo[1,4]oxazin-4-yl)-6,7-dihydro-[1,3]thiazolo[5,4-c]pyridin-4(5H)-one Example 50 (0.060 g, 0.18 mmol) and $NaBH_4$ (0.014 g, 0.36 mmol) were combined in THF (10 mL) and stirred for 18 h at r.t. The mixture was concentrated in vacuo and the residue partitioned between DCM (50 mL) and water (50 mL). The organic fraction was washed with brine (50 mL), dried ($MgSO_4$), filtered and concentrated in vacuo. The crude material was purified by preparative HPLC (Method 6) to give the title compound (0.020 g, 32%) as a white solid. $\delta_H$ ($CDCl_3$) 7.94 (1H, d, J 1.9 Hz), 7.07 (1H, dd, J 8.7 and 2.3 Hz), 6.93 (1H, d, J 8.6 Hz), 5.36 (2H, br. s), 4.63 (2H, s), 4.37-4.29 (2H, m), 4.18-4.12 (2H, m), 2.87 (2H, s), 1.39 (6H, s). LCMS (ES+) 346.0 $(M+H)^+$, RT 2.47 minutes (Method 1).

Example 52

6,6-Dimethyl-2-[6-(4-methylpiperazin-1-ylmethyl)-2,3-dihydrobenzo[1,4]oxazin-4-yl]-6,7-dihydro[1,3]thiazolo[5,4-c]pyridin-4(5H)-one Example 50 (0.060 g, 0.17 mmol), phenylsilane (0.046 mL, 0.35 mmol), dibutyltin dichloride (0.005 g, 0.02 mmol) and 1-methylpiperazine (0.04 mL, 0.13 mmol) in THF (4 mL) were heated to 100° C. under microwave irradiation for 20 minutes. The mixture was concentrated in vacuo. The crude material was purified by preparative HPLC (Method 6) to give the title compound (0.008 g, 11%) as a white solid. $\delta_H$ ($CDCl_3$) 7.85 (1H, d, J 1.7 Hz), 7.01 (1H, dd, J 8.3 and J 1.9 Hz), 6.89 (1H, d, J 8.2 Hz), 5.19 (1H, br. s), 4.35-4.28 (2H, m), 4.19-4.13 (2H, m), 3.46 (2H, s), 2.87 (2H, s), 2.49 (4H, br. s), 2.30 (3H, s), 1.80 (4H, br. m), 1.40 (6H, s). LCMS (ES+) 428.0 $(M+H)^+$, RT 1.72 minutes (Method 1).

Example 53

6,6-Dimethyl-2-[6-(morpholin-4-ylmethyl)-2,3-dihydrobenzo[1,4]oxazin-4-yl]-6,7-dihydro[1,3]thiazolo[5,4-c]pyridin-4(5H)-one Example 50 (0.040 g, 0.16 mmol), phenylsilane (0.03 mL, 0.23 mmol), dibutyltin dichloride (0.003 g, 0.016 mmol) and morpholine (0.02 mL, 0.25 mmol) in THF (3 mL) were heated to 100° C. under microwave irradiation for 20 minutes. The crude material was purified by preparative HPLC (Method 6). The resulting material was partitioned between DCM (50 mL) and aqueous sat. $NaHCO_3$ solution (50 mL). The organic fraction was washed with brine (50 mL), dried (MgSO$_4$), filtered and concentrated in vacuo, and then triturated with Et$_2$O (3×20 mL) to give the title compound (0.005 g, 8%) as a white solid. δ$_H$ (CDCl$_3$) 7.85 (1H, d, J 1.9 Hz), 7.02 (1H, dd, J 8.1 and J 1.9 Hz), 6.90 (1H, d, J 8.1 Hz), 5.20 (1H, br. s), 4.37-4.27 (2H, m), 4.21-4.13 (2H, m), 3.79-3.67 (4H, m), 3.45 (2H, s), 2.87 (2H, s), 2.52-2.40 (4H, m), 1.40 (6H, s). LCMS (ES+) 415.0 (M+H)$^+$, RT 1.73 minutes (Method 1).

Example 54

6,6-Dimethyl-2-[6-(pyridin-3-ylaminomethyl)-2,3-dihydrobenzo[1,4]oxazin-4-yl]-6,7-dihydro[1,3]thiazolo[5,4-c]pyridin-4(5H)-one Example 50 (0.040 g, 0.16 mmol), phenylsilane (0.03 mL, 0.23 mmol), dibutyltin dichloride (0.003 g, 0.016 mmol) and 3-aminopyridine (0.033 g, 0.3 mmol) in THF (3 mL) were heated to 100° C. under microwave irradiation for 20 minutes. The crude material was triturated with Et$_2$O (3×20 mL) followed by water (2×20 mL) then Et$_2$O (2×20 mL), dried in vacuo and purified by preparative HPLC (Method 6) to give the title compound (0.009 g, 13%) as a white solid. δ$_H$ (CDCl$_3$) 8.06 (1H, d, J 2.6 Hz), 8.00-7.93 (2H, m), 7.13-7.02 (2H, m), 6.94 (1H, d, J 8.5 Hz), 6.93-6.87 (2H, m), 5.31 (1H, br. s), 4.31 (2H, s), 4.37-4.28 (2H, m), 4.18-4.09 (2H, m), 2.84 (2H, s), 1.39 (6H, s). LCMS (ES+) 422.0 (M+H)$^+$, RT 1.86 minutes (Method 1).

Example 55

2-(6-Dimethylaminomethyl-2,3-dihydrobenzo[1,4]oxazin-4-yl)-6,6-dimethyl-6,7-dihydro[1,3]thiazolo[5,4-c]pyridin-4(5H)-one Example 50 (0.040 g, 0.16 mmol), phenylsilane (0.03 mL, 0.23 mmol), dibutyltin dichloride (0.003 g, 0.016 mmol) and dimethylamine (0.6 mL, 2M solution in THF, 1.2 mmol) in THF (3 mL) were heated to 100° C. under microwave irradiation for 20 minutes. The crude material was triturated with Et$_2$O (3×20 mL) followed by water (2×20 mL) then Et$_2$O (2×20 mL), dried in vacuo and purified by preparative HPLC (Method 6) to give the title compound (0.002 g, 3%) as a white solid. δ$_H$ (CDCl$_3$) 7.85 (1H, d, J 1.9 Hz), 7.06 (1H, dd, J 8.3 and J 1.9 Hz), 6.93 (1H, d, J 8.3 Hz), 5.19 (1H, br. s), 4.36-4.30 (2H, m), 4.19-4.13 (2H, m), 3.48 (2H, s), 2.88 (2H, s), 2.33 (6H, s), 1.40 (6H, s). LCMS (ES+) 373.0 (M+H)$^+$, RT 1.70 minutes (Method 1).

Example 56

6,6-Dimethyl-2-[6-(pyridin-3-yloxymethyl)-2,3-dihydrobenzo[1,4]oxazin-4-yl]-6,7-dihydro[1,3]thiazolo[5,4-c]pyridin-4(5H)-one A mixture of Example 50 (0.050 g, 0.14 mmol), 3-hydroxypyridine (0.015 g, 0.14 mmol), and triphenylphosphine (0.042 g, 0.16 mmol) in THF (15 mL) was cooled to 0° C. Diethyl azodicarboxylate (0.03 mL, 0.16 mmol) was added, and the reaction mixture stirred for 30 minutes at 0° C., then at r.t. for 3 h. Further portions of 3-hydroxypyridine (0.015 g, 0.14 mmol) and triphenylphosphine (0.021 g, 0.08 mmol) were added, and stirring continued for 2 h. The mixture was concentrated in vacuo and the residue partitioned between DCM (50 mL) and water (50 mL). The organic fraction was washed with water (50 mL) and brine (50 mL), dried (MgSO$_4$), filtered and concentrated in vacuo. The crude material was purified by preparative HPLC (Method 6) to give the title compound (0.0045 g, 8%) as a white solid. δ$_H$ (CDCl$_3$) 8.32 (2H, br. s), 8.06 (1H, d, J 1.7 Hz), 7.38-7.31 (2H, m), 7.13 (1H, dd, J 8.5 and J 1.9 Hz), 6.99 (1H, d, J 8.5 Hz), 5.07 (2H, s), 5.21 (1H, br. s), 4.38-4.32 (2H, m), 4.18-4.11 (2H, m), 2.88 (2H, s), 1.40 (6H, s). LCMS (ES+) 423.0 (M+H)$^+$, RT 2.27 minutes (Method 1).

Example 57

6,6-Dimethyl-2-(6-hydroxy-2,3-dihydrobenzo[1,4]oxazin-4-yl)-6,7-dihydro-[1,3]thiazolo[5,4-c]pyridin-4(5H)-one Example 40 (0.040 g, 0.09 mmol) and TFA (15 mL, 10% v/v solution in DCM) were combined and stirred for 18 h at r.t. The mixture was concentrated in vacuo and azeotroped with heptane and DCM to give the title compound (0.029 g, quantitative) as a brown solid. δ$_H$ (CDCl$_3$/CD$_3$OD) 7.39 (1H, d, J 2.6 Hz), 6.70 (1H, d, J 8.9 Hz), 6.46 (1H, dd, J 8.9 and J 2.8 Hz), 4.68 (2H, br. s), 4.21-4.14 (2H, m), 4.02 (2H, m), 2.79 (2H, s), 1.31 (6H, s). LCMS (ES+) 332.0 (M+H)$^+$, RT 2.69 minutes (Method 2).

Example 58

2-[6-(3,5-Dimethyl-1H-pyrazol-4-yl)-2,3-dihydrobenzo[1,4]oxazin-4-yl]-6,6-dimethyl-6,7-dihydro[1,3]thiazolo[5,4-c]pyridin-4(5H)-one A stirred suspension of Example 39 (0.053 g, 0.13 mmol), Intermediate 67 (0.071 g, 0.20 mmol), K$_3$PO$_4$ (0.085 g, 0.40 mmol) and tetrakis(triphenylphosphine)palladium(0) (0.005 g) in a mixture of DME (4 mL) and water (1 mL) was heated to 120° C. in a sealed tube, under microwave irradiation, for 30 minutes. After cooling to r.t., the reaction mixture was concentrated in vacuo. The residue was treated with 4M HCl in 1,4-dioxane (5 mL) and stirred at r.t. for 3 h. The reaction mixture was concentrated in vacuo. Purification by preparative HPLC (Method 6), gave the title compound (0.015 g, 29%) as an off-white solid. δ$_H$ (CDCl$_3$) 8.20 (1H, s), 7.90 (1H, s), 7.00 (2H, m), 5.75 (1H, s), 4.40 (2H, m), 4.20 (2H, m), 2.90 (2H, s), 2.30 (6H, s), 1.40 (6H, s). LCMS (ES+) 410.0 (M+H)$^+$, RT 2.62 minutes (Method 1).

Example 59

6,6-Dimethyl-2-[6-(2H-pyrazol-3-yl)-2,3-dihydrobenzo[1,4]oxazin-4-yl]-6,7-dihydro-5H-thiazolo[5,4-c]pyridin-4-one A stirred suspension of Example 39 (0.050 g, 0.14 mmol), 3-pyrazoleboronic acid (0.055 g, 0.42 mmol), Na$_2$CO$_3$ (0.045 g, 0.42 mmol) and tetrakis(triphenylphosphine)-palladium (0) (0.005 g) in a mixture of DME (4 mL) and water (1 mL) was heated to 140° C. in a sealed tube, under microwave irradiation, for 30 minutes. After cooling to r.t., the reaction mixture was concentrated in vacuo. Purification by preparative HPLC (Method 7) gave the title compound (0.0318 g, 60%) as an off-white solid. δ$_H$ (CDCl$_3$/CD$_3$OD) 8.20 (1H, s), 7.60 (1H, s), 7.40 (1H, dd, J 8.7 and J 2.1 Hz), 7.00 (1H, d, J 8.5 Hz), 6.50 (1H, s), 4.40 (2H, m), 4.10 (2H, m), 2.90 (2H, s), 1.40 (6H, s). LCMS (ES+) 381.0 (M)$^+$, RT 2.85 minutes (Method 2).

Example 60

6,6-Dimethyl-2-[6-(6-methylpyridin-3-ylamino)-2,3-dihydrobenzo[1,4]oxazin-4-yl]-6,7-dihydro[1,3]thiazolo[5,4-c]pyridin-4(5H)-one A stirred suspension of Example 42 (0.050 g, 0.15 mmol), 5-bromo-2-methylpyridine (0.052 g, 0.30 mmol), palladium (II) acetate (0.010 g), 2-bis(dicyclohexylphosphino)biphenyl (0.030 g) and sodium tert-butoxide (0.044 g, 0.46 mmol) in toluene (5 mL) was heated to 120° C. in a sealed tube, under microwave irradiation, for 5 h. After cooling to r.t., the reaction mixture was concentrated in vacuo. Purification by preparative HPLC (Method 7), gave the title compound (0.0178 g, 28%) as an off-white solid. $\delta_H$ (CDCl$_3$) 8.30 (1H, s), 7.80 (1H, s), 7.30 (1H, dd, J 8.5 and J 3.0 Hz), 7.10 (1H, d, J 8.5 Hz), 6.90 (1H, d, J 8.5 Hz), 6.80 (1H, dd, J 8.7 and J 2.4 Hz), 5.60 (1H, br. s), 5.20 (1H, br. s), 4.40 (1H, m), 4.10 (2H, m), 2.90 (2H, m), 2.50 (3H, s), 1.40 (6H, s). LCMS (ES+) 422.0 (M+H)$^+$, RT 3.10 minutes (Method 2).

Example 61

Methyl 3-{[(3S)-4-(6,6-dimethyl-4-oxo-4,5,6,7-tetrahydro[1,3]thiazolo[5,4-c]pyridin-2-yl)morpholin-3-yl]methyl}-1H-indole-6-carboxylate The title compound was prepared from Intermediate 70 and Intermediate 46 according to Method N and was isolated as a yellow oil (81%) after purification by column chromatography (SiO$_2$, 2% MeOH/DCM). $\delta_H$ (DMSO-d$_6$) 11.33 (1H, s), 8.02 (1H, d, J 0.8 Hz), 7.86 (1H, d, J 8.4 Hz), 7.65 (1H, dd, J 8.4 and J 1.4 Hz), 7.48 (1H, d, J 2.3 Hz), 7.30 (1H, s), 4.17 (1H, m), 3.99 (1H, d, J 7.2 Hz), 3.86 (3H, s), 3.73 (1H, d, J 11.6 Hz), 3.58 (4H, m), 3.27 (1H, m), 3.00 (1H, dd, J 13.8 and J 4.8 Hz), 2.73 (1H, d, J 16.7 Hz), 2.66 (1H, d, J 16.7 Hz), 1.25 (6H, s). LCMS (ES+) 455.0 (M+H)$^+$, RT 2.93 minutes (Method 5).

Example 62

Method O 6,6-Dimethyl-2-[6-(1-methyl-1H-imidazol-2-yl)-2,3-dihydrobenzo[1,4]oxazin-4-yl]-6,7-dihydro[1,3]thiazolo[5,4-c]pyridin-4(5H)-one A mixture of Intermediate 66 (0.050 g, 0.14 mmol), 1-methyl-2-bromoimidazole (0.067 g, 0.4 mmol), tetra-n-butylammonium bromide (0.135 g, 0.4 mmol), Na$_2$CO$_3$ (0.045 g, 0.4 mmol), tetrakis(triphenylphosphine)palladium(0) (0.016 g, 0.014 mmol) and water (1 mL) in THF (3 mL) was heated to 140° C. under microwave irradiation for 20 minutes. Additional portions of 1-methyl-2-bromoimidazole (0.033 g, 0.2 mmol) and tetrakis(triphenylphosphine)palladium(0) (0.016 g, 0.014 mmol) were added, and heating continued for a further 40 minutes. After cooling to r.t., the reaction mixture was concentrated in vacuo, and the residue partitioned between DCM (50 mL) and water (50 mL). The organic fraction was washed with water (50 mL) and brine (50 mL), dried (MgSO$_4$), filtered and concentrated in vacuo. The crude material was purified by preparative HPLC (Method 6) to give the title compound (0.002 g, 4%) as a white solid. $\delta_H$ (CDCl$_3$) 8.18 (1H, d, J 1.9 Hz), 7.33 (1H, dd, J 8.5 and J 1.9 Hz), 7.02 (1H, d, J 1.3 Hz), 6.98 (1H, d, J 8.5 Hz), 6.89 (1H, d, J 1.1 Hz), 5.10 (1H, br. s), 4.36-4.29 (2H, m), 4.12-4.04 (2H, m), 3.74 (3H, s), 2.80 (2H, s), 1.32 (6H, s). LCMS (ES+) 396.0 (M+H)$^+$, RT 1.66 minutes (Method 1).

Example 63

6,6-Dimethyl-2-[6-(3-methyl-3H-imidazol-4-yl)-2,3-dihydrobenzo[1,4]oxazin-4-yl]-6,7-dihydro[1,3]thiazolo[5,4-c]pyridin-4(5H)-one The title compound was prepared from Intermediate 66 and 1-methyl-5-bromoimidazole according to Method Q and was isolated as a white solid (13%) after purification by preparative HPLC (Method 6). $\delta_H$ (CDCl$_3$) 8.09 (1H, d, J 2.3 Hz), 7.51 (1H, s), 7.13-7.00 (3H, m), 5.22 (1H, br. s), 4.43-4.34 (2H, m), 4.18-4.10 (2H, m), 3.72 (3H, s), 2.87 (2H, s), 1.40 (6H, s). LCMS (ES+) 396.0 (M+H)$^+$, RT 1.76 minutes (Method 1).

Example 64

6,6-Dimethyl-2-[6-(1-methyl-1H-imidazol-4-yl)-2,3-dihydrobenzo[1,4]oxazin-4-yl]-6,7-dihydro[1,3]thiazolo[5,4-c]pyridin-4(5H)-one The title compound was prepared from Intermediate 66 and 1-methyl-4-bromoimidazole according to Method Q and was isolated as a white solid (5%) after purification by preparative HPLC (Method 6). $\delta_H$ (CDCl$_3$) 8.10 (1H, d, J 1.9 Hz), 7.57 (1H, br. s), 7.12-7.00 (3H, m), 5.19 (1H, br. s), 4.43-4.35 (2H, m), 4.19-4.10 (2H, m), 3.72 (3H, s), 2.87 (2H, s), 1.40 (6H, s). LCMS (ES+) 396.0 (M+H)$^+$, RT 1.81 minutes (Method 1).

Example 65

6,6-Dimethyl-2-[6-(2-oxypyridazin-3-yl)-2,3-dihydrobenzo[1,4]oxazin-4-yl]-6,7-dihydro[1,3]thiazolo[5,4-c]pyridin-4(5H)-one A stirred suspension of Example 39 (0.10 g, 0.25 mmol), Intermediate 72 (0.073 g, 0.76 mmol), potassium carbonate (0.07 g, 0.51 mmol), palladium acetate (0.003 g, 0.01 mmol) and tri-tert-butylphosphonium tetrafluoroborate (0.011 g, 0.04 mmol) in 1,4-dioxane (10 mL) was heated at 110° C. for 16 h, then concentrated in vacuo. Purification by preparative HPLC (Method 6) gave the title compound (0.016 g, 16%) as an orange oil. $\delta_H$ (CD$_3$OD) 8.73 (1H, d, J 2.3 Hz), 8.62-8.53 (1H, m), 8.21 (1H, s), 8.13 (1H, dd, J 7.9 and 2.3 Hz), 7.66 (1H, dd, J 8.7 and 2.1 Hz), 7.45 (1H, dd, J 8.1 and 5.3 Hz), 7.12 (1H, d, J 8.7 Hz), 4.53-4.36 (2H, m), 4.28-4.17 (2H, m), 2.90 (2H, s), 1.39 (6H, s). LCMS (ES+) 410.1 (M+H)$^+$, RT 2.39 minutes (Method 1).

Example 66

6,6-Dimethyl-2-[6-(2-methyl-3H-imidazo[4,5-b]pyridin-3-yl)-2,3-dihydro-4H-1,4-benzoxazin-4-yl]-6,7-dihydro[1,3]thiazolo[5,4-c]pyridin-4(5H)-one To a stirred solution of Example 42 (0.09 g, 0.27 mmol) in EtOH (3 mL) was added DIPEA (0.09 mL, 0.55 mmol) and 2-chloro-3-nitropyridine (0.043 g, 0.27 mmol). The reaction mixture was heated to 80° C. for 3 days, then cooled to r.t., poured into water (10 mL), and extracted with DCM (2×10 mL). The combined organic fractions were dried (MgSO$_4$), filtered and concentrated in vacuo. The residue was dissolved in EtOH (5 mL) and 20% w/w palladium on carbon (0.020 g)

was added. The reaction mixture was stirred under an atmosphere of H₂ at r.t. for 3 days, then filtered and concentrated in vacuo. The residue was dissolved in DCM (3 mL). AcOH (0.02 mL), EDC (0.095 g, 0.5 mmol) and HOBT (0.01 g, 0.05 mmol) were added and the reaction mixture stirred at r.t. for 18 h. DCM (5 mL) and aqueous sat. NaHCO₃ solution (5 mL) were added. The organic fraction was separated, then concentrated in vacuo and the residue dissolved in AcOH (2 mL). The reaction mixture was heated to 120° C. under microwave irradiation in a sealed tube for 10 minutes, and then concentrated in vacuo. The residue was dissolved in DCM (10 mL), then washed with aqueous sat. NaHCO₃ solution (2×10 mL). The organic fraction was separated and concentrated in vacuo. Purification by preparative HPLC (Method 6) gave the title compound (0.024 g, 20%) as a brown solid. $\delta_H$ (CDCl₃) 8.26 (1H, d, J 2.3 Hz), 8.23 (1H, dd, J 4.7 and 1.3 Hz), 8.04 (1H, dd, J 7.9 and 1.3 Hz), 7.25 (1H, dd, J 7.9 and 4.7 Hz), 7.20-7.15 (1H, m), 7.15-7.10 (1H, m), 5.31 (1H, s), 4.42-4.29 (2H, m), 4.09-3.96 (2H, m), 2.76 (2H, s), 2.56 (3H, s), 1.28 (6H, s). LCMS (ES+) 447.4 (M+H)⁺, RT 2.36 minutes (Method 1).

Example 67

2-(6-Amino-7-bromo-2,3-dihydro-4H-1,4-benzoxazin-4-yl)-6,6-dimethyl-6,7-dihydro[1,3]thiazolo[5,4-c]pyridin-4(5H)-one To a stirred solution of Example 42 (0.04 g, 0.12 mmol) in DCM (1 mL) was added NBS (0.02 g, 0.12 mmol) and the reaction mixture stirred for 1 h at r.t. Water (2 mL) was added, the layers were separated and the organic fraction was concentrated in vacuo. Purification by preparative HPLC (Method 6) gave the title compound (0.006 g, 12%) as a white solid. $\delta_H$ (CDCl₃) 7.56 (1H, s), 7.05 (1H, s), 5.30 (1H, s), 4.29-4.23 (2H, m), 4.11-4.05 (2H, m), 2.88 (2H, s), 1.40 (6H, s). LCMS (ES+) 409.2 and 411.2 (1:1 ratio) (M+H)⁺, RT 3.06 minutes (Method 1).

Example 68

2-(6-{[6-(1,2-Dihydroxyethyl)pyridin-2-yl]amino}-2,3-dihydro-4H-1,4-benzoxazin-4-yl)-6,6-dimethyl-6,7-dihydro[1,3]thiazolo[5,4-c]pyridin-4(5H)-one To a stirred suspension of methyltriphenylphosphonium bromide (0.186 g, 0.52 mmol) in THF (3 mL) at 0° C. was added sodium hexamethyldisilazide (0.55 mL, 1.0M in THF, 0.55 mmol). After stirring at this temperature for 1 h, the reaction mixture was cooled to −78° C., and a solution of Intermediate 73 (0.074 g, 0.17 mmol) in THF (1 mL) was added. The reaction mixture was allowed to warm to r.t. over 2 h, then partitioned between DCM (5 mL) and water (5 mL). The organic fraction was separated, dried (MgSO₄), filtered and concentrated in vacuo. The residue was dissolved in acetone (2 mL) and water (0.2 mL). Osmium tetroxide (0.05 mL, 0.033 g/mL solution in tert-BuOH, 0.006 mmol) and N-methylmorpholine oxide (0.040 g, 0.34 mmol) were added. The reaction mixture was stirred at r.t. for 18 h, then concentrated in vacuo. Purification by preparative HPLC (Method 6) gave the title compound (0.06 g, 8%) as a green solid. $\delta_H$ (CD₃OD) 8.46 (1H, d, J 2.4 Hz), 7.54 (1H, dd, J 8.3 and 7.5 Hz), 7.12 (1H, dd, J 8.9 and 2.4 Hz), 6.95-6.85 (2H, m), 6.70 (1H, d, J 8.1 Hz), 4.68 (1H, dd, J 7.0 and 4.0 Hz), 4.35-4.27 (2H, m), 4.24-4.16 (2H, m), 3.87 (1H, dd, J 11.3 and 4.1 Hz), 3.65 (1H, dd, J 11.3 and 7.0 Hz), 2.68 (2H, s), 1.40 (6H, s). Exchangeable protons were not observed. LCMS (ES+) 468.4 (M+H)⁺, RT 1.93 minutes (Method 1).

Example 69

Method S 6,6-Dimethyl-2-[6-({6-[(methylamino)methyl]pyridin-2-yl}amino)-2,3-dihydro-4H-1,4-benzoxazin-4-yl]-6,7-dihydro[1,3]thiazolo[5,4-c]pyridin-4(5H)-one To a stirred solution of Intermediate 73 (0.048 g, 0.11 mmol) in 5% AcOH in MeOH (1 mL) was added methylamine (1 mL, 20% in MeOH), followed by sodium cyanoborohydride (0.020 g, 0.33 mmol). The reaction mixture was stirred at r.t. for 10 minutes, then partitioned between DCM (5 mL) and aqueous sat. NaHCO₃ solution (5 mL). The organic fraction was separated, then concentrated in vacuo. Purification by preparative HPLC (Method 6) gave the title compound (0.008 g, 16%) as a brown solid. $\delta_H$ (CD₃OD) 8.27 (1H, d, J 2.3 Hz), 7.97 (1H, dd, J 8.9 and 7.2 Hz), 7.24-7.02 (4H, m), 4.45-4.36 (4H, m), 4.25-4.13 (2H, m), 2.90 (2H, m), 2.83 (3H, s), 1.38 (6H, m). Exchangeable protons were not observed. LCMS (ES+) 451.4 (M+H)⁺, RT 2.07 minutes (Method 1).

Example 70

2-[6-({6-[(Dimethylamino)methyl]pyridin-2-yl}amino)-2,3-dihydro-4H-1,4-benzoxazin-4-yl]-6,6-dimethyl-6,7-dihydro[1,3]thiazolo[5,4-c]pyridin-4(5H)-one diacetate The title compound was prepared from Intermediate 73 and dimethylamine according to Method S and was isolated as a brown solid (20%) after purification by preparative HPLC (Method 6). $\delta_H$ (CD₃OD) 8.41 (1H, d, J 2.3 Hz), 7.60 (1H, dd, J 8.3 and 7.3 Hz), 7.09 (1H, dd, J 8.9 and 2.4 Hz), 6.93 (1H, d, J 18.9 Hz), 6.86-6.80 (2H, m), 4.37-4.28 (2H, m), 4.28-4.20 (2H, m), 4.13 (2H, s), 2.90 (2H, s), 2.74 (6H, s), 1.95 (6H, s, AcOH), 1.40 (6H, s). Exchangeable protons were not observed. LCMS (ES+) 465.3 (M+H)⁺, RT 2.09 minutes (Method 1).

Example 71

6,6-Dimethyl-2-(6-{[6-(1-hydroxyethyl)pyridin-2-yl]amino}-2,3-dihydro-4H-1,4-benzoxazin-4-yl)-6,7-dihydro[1,3]thiazolo[5,4-c]pyridin-4(5H)-one To a stirred solution of Intermediate 73 (0.15 g, 0.33 mmol) in THF (2 mL) at −78° C. was added methyllithium (0.8 mL, 1.6M in THF, 1.32 mmol). The reaction mixture was allowed to warm to r.t., then partitioned between DCM (5 mL) and water (5 mL). The organic fraction was separated, then concentrated in vacuo. A portion of the residue was purified by preparative HPLC (Method 6) to give the title compound (0.003 g) as an orange solid. $\delta_H$ (CDCl₃) 8.09 (1H, d, J 2.3 Hz), 7.54-7.47 (1H, m), 7.03-6.90 (2H, m), 6.73-6.66 (2H, m), 6.45 (1H, s), 5.27 (1H, br. s), 4.79 (1H, q, J 6.6 Hz), 4.37-4.31 (2H, m), 4.17-4.11 (2H, m), 2.88 (2H, s), 2.62 (1H, s), 1.48 (3H, d), 1.39 (6H, s). LCMS (ES+) 451.4 (M+H)⁺, RT 2.07 minutes (Method 1).

Example 72

Method T

N-[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]-1-methyl-1H-imidazole-5-carboxamide To a stirred solution of Example 42 (0.025 g, 0.08 mmol) in DCM (1 mL) were added 1-methylimidazol-5-ylcarboxylic acid (0.013 g, 0.10 mmol), DIPEA (0.02 mL, 0.10 mmol), EDC (0.030 g, 0.16 mmol) and HOBT (0.05 g, 0.04 mmol). The reaction mixture was stirred at r.t. for 18 h, then concentrated in vacuo. Purification by preparative HPLC (Method 6) gave the title compound (0.01 g, 29%) as a yellow oil. $\delta_H$ (CDCl$_3$) 9.25 (1H, s), 8.46-8.43 (1H, m), 7.33 (1H, dd, J 8.9 and 2.4 Hz), 7.07 (1H, d, J 0.9 Hz), 7.02 (1H, d, J 0.8 Hz), 6.94 (1H, d, J 8.9 Hz), 5.56 (1H, br. s), 4.36-4.29 (2H, m), 4.16-4.09 (2H, m), 4.11 (3H, s), 2.90 (2H, s), 1.40 (6H, s). LCMS (ES+) 439.4 (M+H)$^+$, RT 2.69 minutes (Method 1).

Example 73

N-[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]-1-methylpiperidine-4-carboxamide The title compound was prepared from Example 42 and 1-methylpiperidine-4-carboxylic acid according to Method T and was isolated as a yellow solid (27%) after purification by preparative HPLC (Method 6). $\delta_H$ (CD$_3$OD) 8.51 (1H, s), 8.33 (1H, d, J 2.3 Hz), 7.25 (1H, dd, J 8.9 and 2.4 Hz), 6.92 (1H, d, J 8.9 Hz), 4.35-4.26 (2H, m), 4.20-4.11 (2H, m), 3.62-3.48 (2H, m), 3.06 (2H, td, J 12.2 and 3.6 Hz), 2.91 (2H, s), 2.86 (3H, s), 2.78-2.60 (2H, m), 2.24-1.94 (4H, m), 1.39 (6H, s). LCMS (ES+) 456.5 (M+H)$^+$, RT 1.98 minutes (Method 1).

Examples 74 and 75

Method U 6,6-Dimethyl-2-{6-[(6-methylpyridin-2-yl)amino]-2,3-dihydro-4H-1,4-benzoxazin-4-yl}-6,7-dihydro[1,3]thiazolo[5,4-c]pyridin-4(5H)-one formate and 2-{6-[Bis(6-methylpyridin-2-yl)amino]-2,3-dihydro-4H-1,4-benzoxazin-4-yl}-6,6-dimethyl-6,7-dihydro[1,3]thiazolo[5,4-c]pyridin-4(5H)-one formate respectively A stirred solution of Example 42 (0.04 g, 0.12 mmol), [bis-1,1'-(di-tert-butyl)-phosphinoferrocenyl]palladium(II) dichloride (0.005 g, 0.008 mmol), sodium tert-butoxide (0.035 g, 0.36 mmol) and 2-bromo-6-methylpyridine (0.04 g, 0.24 mmol) in toluene (2 mL) was heated to 140° C. under microwave irradiation in a sealed tube for 2 h, and then concentrated in vacuo. DCM (20 mL) and water (20 mL) were added. The organic fraction was separated, then concentrated in vacuo. Purification by preparative HPLC (Method 6) gave the first title compound (0.010 g, 20%) as a yellow solid [$\delta_H$ (CDCl$_3$) 10.67 (1H, br. s), 8.50 (1H, s), 8.03 (1H, s, formic acid), 7.55 (1H, dd, J 8.7 and 7.5 Hz), 6.96 (2H, s), 6.85 (1H, d, J 8.9 Hz), 6.55 (1H, d, J 7.3 Hz), 5.52 (1H, br. s), 4.39-4.31 (2H, m), 4.16-4.07 (2H, m), 2.87 (2H, s), 2.51 (3H, s), 1.39 (6H, s). LCMS (ES+) 422.4 (M+H)$^+$, RT 1.99 minutes (Method 1)], followed by the second title compound (0.012 g, 20%) as a yellow solid [$\delta_H$ (CDCl$_3$) 8.07 (1H, s, formic acid), 7.60 (1H, dd, J 1.7 and 0.6 Hz), 7.47 (2H, t, J 7.9 Hz), 6.93-6.87 (2H, m), 6.84-6.76 (4H, m), 5.63 (1H, br. s), 4.36-4.29 (2H, m), 4.21-4.13 (2H, m), 2.79 (2H, s), 2.44 (6H, s), 1.36 (6H, s). LCMS (ES+) 513.5 (M+H)$^+$, RT 2.38 minutes (Method 1)].

Example 76

6,6-Dimethyl-2-{6-[(2-methylpyridin-3-yl)amino]-2,3-dihydro-4H-1,4-benzoxazin-4-yl}-6,7-dihydro[1,3]thiazolo[5,4-c]pyridin-4(5H)-one The title compound was prepared from Example 42 and 3-bromo-2-methylpyridine according to Method U and was isolated as a yellow solid (63%) after purification by preparative HPLC (Method 6). $\delta_H$ (CDCl$_3$) 8.26 (1H, s), 8.09 (1H, d, J 5.1 Hz), 7.84 (1H, d, J 2.4 Hz), 7.50 (1H, d, J 8.3 Hz), 7.17 (1H, dd, J 8.1 and 4.9 Hz), 7.00-6.91 (1H, m), 6.81 (1H, dd, J 8.7 and 2.4 Hz), 6.12 (1H, s), 4.40-4.32 (2H, m), 4.17-4.09 (2H, m), 2.87 (2H, s), 2.60 (3H, s), 1.41 (6H, s). LCMS (ES+) 422.4 (M+H)$^+$, RT 2.04 minutes (Method 1).

Example 77

6,6-Dimethyl-2-{6-[(4-methylpyridin-3-yl)amino]-2,3-dihydro-4H-1,4-benzoxazin-4-yl}-6,7-dihydro[1,3]thiazolo[5,4-c]pyridin-4(5H)-one The title compound was prepared from Example 42 and 3-bromo-4-methylpyridine according to Method U and was isolated as a yellow solid (43%) after purification by preparative HPLC (Method 6). $\delta_H$ (CDCl$_3$) 8.30 (1H, s), 8.22 (1H, s), 8.10 (1H, d, J 5.1 Hz), 7.81 (1H, d, J 2.4 Hz), 7.24 (1H, d, J 5.1 Hz), 6.98-6.93 (1H, m), 6.82 (1H, dd, J 8.7 and 2.4 Hz), 6.15 (1H, s), 4.39-4.33 (2H, m), 4.17-4.12 (2H, m), 2.89 (2H, s), 2.37 (3H, s), 1.41 (6H, s). LCMS (ES+) 422.4 (M+H)$^+$, RT 2.05 minutes (Method 1).

Example 78

6-{[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]amino}pyridine-2-carboxylic acid The title compound was prepared from Example 42 and 2-bromopyridine-6-carboxylic acid according to Method U and was isolated as a yellow solid (3%) after purification by preparative HPLC (Method 6). $\delta_H$ (DMSO-d$_6$) 9.22 (1H, d, J 0.9 Hz), 8.36 (1H, br. s), 7.73-7.61 (3H, m), 7.52 (1H, s), 7.37 (1H, d, J 7.3 Hz), 6.99 (1H, d, J 8.7 Hz), 6.90 (1H, d, J 8.9 Hz), 4.32-4.22 (2H, m), 4.15-4.06 (2H, m), 2.80 (2H, s), 1.28 (6H, s). LCMS (ES+) 452.3 (M+H)$^+$, RT 2.21 minutes (Method 1).

Example 79

2-[6-({6-[(2,3-Dihydroxypropyl)amino]pyridin-2-yl}amino)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 42 and Intermediate 74 according to Method U and was isolated as a yellow oil (4%) after purification by preparative HPLC (Method 6). $\delta_H$ (CD$_3$OD) 8.12 (1H, d, J 2.4 Hz), 7.22-7.12 (1H, m), 6.98 (1H, dd, J 8.9 and 2.4 Hz), 6.77 (1H, d, J 8.9 Hz), 5.95 (1H, d, J 7.7 Hz), 5.83 (1H, d, J 8.1 Hz), 4.23-4.15 (2H, m), 4.09-4.01 (2H, m), 3.69-3.60 (1H, m), 3.25-3.15 (1H, m), 3.42-3.28 (3H, m), 2.77 (2H, s), 1.27 (6H, s). LCMS (ES+) 497.0 (M+H)+, RT 2.00 minutes (Method 1).

Example 80

2-[6-({6-[(2,2-Dimethyl-1,3-dioxolan-4-yl)methoxy]pyridin-2-yl}amino)-2,3-dihydro-4H-1,4-benzoxazin-4-yl]-6,6-dimethyl-6,7-dihydro[1,3]thiazolo[5,4-c]pyridin-4(5H)-one

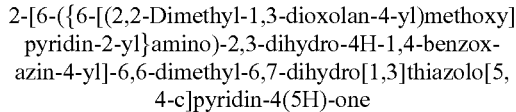

The title compound was prepared from Example 42 and Intermediate 75 according to Method U and was isolated as a yellow oil (54%) after purification by column chromatography (SiO$_2$, gradient of EtOAc/heptane). $\delta_H$(CDCl$_3$) 8.01 (1H, d, J 2.4 Hz), 7.41 (1H, t, J 7.9 Hz), 7.05 (1H, dd, J 8.7 and 2.4 Hz), 6.92 (1H, d, J 8.7 Hz), 6.38 (1H, d, J 17.7 Hz), 6.30 (1H, br. s), 6.21 (1H, d, J 7.9 Hz), 5.34 (1H, br. s), 4.53-4.44 (1H, m), 4.39-4.25 (4H, m), 4.16-4.07 (3H, m), 3.83 (1H, dd, J 8.5 and 6.2 Hz), 2.87 (2H, s), 1.46 (3H, s), 1.39 (9H, s). LCMS (ES+) 538.0 (M+H)+, RT 3.64 minutes (Method 1).

Example 81

2-(6-{[6-(2,3-Dihydroxypropoxy)pyridin-2-yl]amino}-2,3-dihydro-4H-1,4-benzoxazin-4-yl)-6,6-dimethyl-6,7-dihydro[1,3]thiazolo[5,4-c]pyridin-4(5H)-one To a stirred solution of Example 80 (0.07 g, 0.13 mmol) in THF (3 mL) was added 2M aqueous HCl (3 mL). The reaction mixture was heated to 85° C. for 18 h, then concentrated in vacuo to give the title compound (0.06 g, 93%) as a yellow oil that required no further purification. $\delta_H$ (CD$_3$OD) 8.19 (1H, br.s), 8.01 (1H, t, J 8.5 Hz), 7.11-7.07 (2H, m), 6.70 (1H, d, J 8.7 Hz), 6.58 (1H, d, J 8.3 Hz), 4.48-4.28 (3H, m), 4.20-4.00 (3H, m), 3.76-3.64 (3H, m), 2.89 (2H, s), 1.40 (6H, s). LCMS (ES+) 498.0 (M+H)+, RT 2.58 minutes (Method 1).

Example 82

2-{6-[(6-Bromopyridin-2-yl)amino]-2,3-dihydro-4H-1,4-benzoxazin-4-yl}-6,6-dimethyl-6,7-dihydro[1,3]thiazolo[5,4-c]pyridin-4(5H)-one

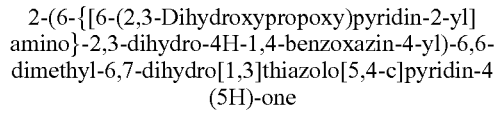

The title compound was prepared from Example 42 and 2,6-dibromopyridine according to Method U and was isolated as a clear oil (5%) after purification by preparative HPLC (Method 6). $\delta_H$ (CDCl$_3$) 8.09 (1H, d, J 2.1 Hz), 7.32 (1H, t, J 7.9 Hz), 6.98-6.94 (2H, m), 6.87 (1H, dd, J 7.5 and 0.6 Hz), 6.74 (1H, dd, J 8.3 and 0.4 Hz), 6.57 (1H, s), 5.27 (1H, br. s), 4.40-4.31 (2H, m), 4.16-4.05 (2H, m), 2.88 (2H, s), 1.40 (6H, s). LCMS (ES+) 485.9 and 487.9 (1:1 ratio) (M+H)+, RT 3.65 minutes (Method 1).

Example 83

6,6-Dimethyl-2-{6-[(6-hydroxypyridin-2-yl)amino]-2,3-dihydro-4H-1,4-benzoxazin-4-yl}-6,7-dihydro[1,3]thiazolo[5,4-c]pyridin-4(5H)-one

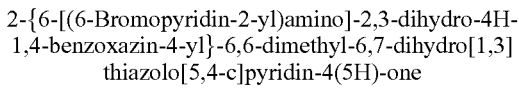

The title compound was prepared from Example 42 and 2-bromo-6-hydroxypyridine according to Method U and was isolated as an off-white solid (10%) after purification by preparative HPLC (Method 6). $\delta_H$ (CD$_3$OD) 7.98 (1H, d, J 2.3 Hz), 7.57-7.53 (3H, m), 7.42-7.34 (1H, m), 6.99 (1H, d, J 8.7 Hz), 6.92 (1H, dd, J 8.7 and 2.4 Hz), 5.94-5.78 (2H, m), 4.42-4.33 (2H, m), 4.18-4.09 (2H, m), 2.89 (2H, s), 1.41 (6H, s). LCMS (ES+) 424.0 (M+H)+, RT 2.43 minutes (Method 1).

Example 84

Method V 6,6-Dimethyl-2-(6-{[(1-methyl-1H-imidazol-5-yl)methyl]amino}-2,3-dihydro-4H-1,4-benzoxazin-4-yl)-6,7-dihydro[1,3]thiazolo[5,4-c]pyridin-4(5H)-one

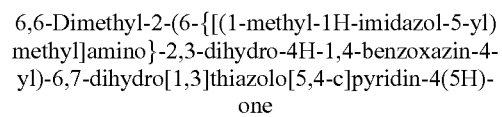

To a stirred solution of Example 42 (0.03 g, 0.10 mmol) in 5% AcOH in MeOH (1 mL) was added 1-methyl-5-imidazolecarboxaldehyde (0.01 g, 0.14 mmol). The reaction mixture was stirred at r.t. for 20 minutes. Sodium cyanoborohydride (0.02 g, 0.39 mmol) was then added, and the reaction mixture stirred for a further 10 minutes before being concentrated in vacuo. Purification by preparative HPLC (Method 6) gave the title compound (0.01 g, 32%) as a yellow oil. $\delta_H$ (CDCl$_3$) 8.28 (1H, s), 8.17 (1H, s), 7.22 (1H, s), 7.17 (1H, d, J 2.6 Hz), 6.82 (1H, d, J 8.7 Hz), 6.47 (1H, dd, J 8.9 and 2.8 Hz), 5.82 (1H, s), 4.34 (2H, s), 4.29-4.22 (2H, m), 4.19-4.11 (2H, m), 3.86 (3H, s), 2.86 (2H, s), 1.39 (6H, s). LCMS (ES+) 425.42 (M+H)+, RT 1.85 minutes (Method 1).

Example 85

6,6-Dimethyl-2-{6-[(pyridin-3-ylmethyl)amino]-2,3-dihydro-4H-1,4-benzoxazin-4-yl}-6,7-dihydro[1,3]thiazolo[5,4-c]pyridin-4(5H)-one

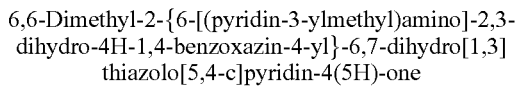

The title compound was prepared from Example 42 and pyridine-3-carboxaldehyde according to Method V and was isolated as a yellow solid (27%) after purification by preparative HPLC (Method 6). $\delta_H$ (CDCl$_3$) 8.65 (1H, br. s), 8.58-8.51 (1H, m), 8.15 (1H, s), 7.82-7.75 (1H, m), 7.35 (1H, dd, J 7.7 and 5.1 Hz), 7.22 (1H, d, J 2.6 Hz), 6.80 (1H, d, J 8.9 Hz), 6.39 (1H, dd, J 8.9 and 2.8 Hz), 5.79 (1H, br. s), 4.36 (2H, s), 4.29-4.21 (2H, m), 4.14-4.08 (2H, m), 2.84 (2H, s), 1.39 (6H, s). LCMS (ES+) 422.4 (M+H)+, RT 2.00 minutes (Method 1).

Example 86

6,6-Dimethyl-2-{6-[(pyridin-2-ylmethyl)amino]-2,3-dihydro-4H-1,4-benzoxazin-4-yl}-6,7-dihydro[1,3]thiazolo[5,4-c]pyridin-4(5H)-one

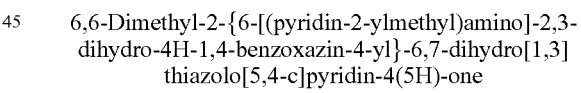

The title compound was prepared from Example 42 and pyridine-2-carboxaldehyde according to Method V and was isolated as a green oil after purification by preparative HPLC (Method 6). $\delta_H$ (CDCl$_3$) 8.66-8.54 (1H, m), 7.68 (1H, td, J 7.7 and 1.7 Hz), 7.37 (1H, d, J 7.9 Hz), 7.25-7.17 (3H, m), 6.80 (1H, d, J 8.9 Hz), 6.44 (1H, dd, J 8.7 and 2.6 Hz), 5.26 (1H, br. s), 4.42 (2H, s), 4.30-4.20 (2H, m), 4.17-4.09 (2H, m), 2.85 (2H, s), 1.39 (6H, s). LCMS (ES+) 422.3 (M+H)+, RT 2.01 minutes (Method 1).

Example 87

2-{6-[(2,3-Dihydroxypropyl)amino]-2,3-dihydro-4H-1,4-benzoxazin-4-yl}-6,6-dimethyl-6,7-dihydro[1,3]thiazolo[5,4-d]pyridin-4(5H)-one

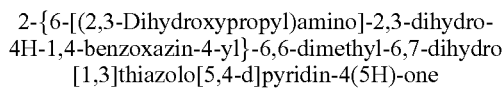

The title compound was prepared from Example 42 and glyceraldehyde according to Method V and was isolated as a yellow solid (15%) after purification by preparative HPLC (Method 6). δ$_H$ (CD$_3$OD) 8.82 (1H, br. s), 7.24 (1H, d, J 2.6 Hz), 6.77 (1H, d, J 8.9 Hz), 6.50 (1H, dd, J 8.9 and 2.6 Hz), 4.28-4.19 (2H, m), 4.18-4.11 (2H, m), 3.92-3.81 (1H, m), 3.52-3.14 (2H, m), 3.27 (1H, dd, J 12.8 and 4.7 Hz), 3.05 (1H, dd, J 13.0 and 7.2 Hz), 2.88 (2H, s), 1.40 (6H, s). All but one exchangeable protons were not observed. LCMS (ES+) 405.1 (M+H)$^+$, RT 1.83 minutes (Method 1).

Example 88

6,6-Dimethyl-2-{6-[(1H-imidazol-2-ylmethyl)amino]-2,3-dihydro-4H-1,4-benzoxazin-4-yl}-6,7-dihydro[1,3]thiazolo[5,4-c]pyridin-4(5H)-one The title compound was prepared from Example 42 and imidazole-2-carboxaldehyde according to Method V and was isolated as a yellow solid (22%) after purification by preparative HPLC (Method 6). δ$_H$ (CD$_3$OD) 8.31-8.25 (2H, m), 7.32 (2H, s), 7.07-7.04 (1H, m), 6.82 (1H, d, J 8.9 Hz), 6.50 (1H, dd, J 8.9 and 2.8 Hz), 4.55 (2H, s), 4.22-4.19 (2H, m), 4.17-4.11 (2H, m), 2.83 (2H, s), 1.40 (6H, s). One exchangeable proton was not observed. LCMS (ES+) 411.1 (M+H)$^+$, RT 1.85 minutes (Method 1).

Example 89

6,6-Dimethyl-2-(6-{[(4-methyl-1H-imidazol-5-yl)methyl]amino}-2,3-dihydro-4H-1,4-benzoxazin-4-yl)-6,7-dihydro[1,3]thiazolo[5,4-c]pyridin-4(5H)-one The title compound was prepared from Example 42 and 4-methylimidazole-5-carboxaldehyde according to Method V and was isolated as a yellow solid (33%) after purification by preparative HPLC (Method 6). δ$_H$ (CD$_3$OD) 8.46 (1H, br. s), 8.32 (1H, s), 7.02 (1H, d, J 2.6 Hz), 6.80 (1H, d, J 8.7 Hz), 6.51 (1H, dd, J 8.7 and 2.6 Hz), 4.32 (2H, s), 4.19-4.23 (2H, m), 4.17-4.12 (2H, m), 2.87 (2H, s), 2.33 (3H, s), 1.40 (6H, s). Some exchangeable protons were not observed. LCMS (ES+) 425.1 (M+H)$^+$, RT 1.94 minutes (Method 1).

Example 90

6,6-Dimethyl-2-{6-[(1,3-thiazol-2-ylmethyl)amino]-2,3-dihydro-4H-1,4-benzoxazin-4-yl}-6,7-dihydro[1,3]thiazolo[5,4-c]pyridin-4(5H)-one The title compound was prepared from Example 42 and thiazole-2-carboxaldehyde according to Method V and was isolated as a white solid (33%) after purification by preparative HPLC (Method 6). δ$_H$ (CD$_3$OD) 8.55 (1H, br. s), 7.73 (1H, d, J 3.2 Hz), 7.48 (1H, d, J 3.2 Hz), 7.17 (1H, d, J 2.6 Hz), 6.76 (1H, d, J 8.9 Hz), 6.47 (1H, dd, J 8.9 and 2.6 Hz), 4.60 (2H, s), 4.22-4.18 (2H, m), 4.11-4.06 (2H, m), 2.83 (2H, s), 1.41 (6H, s). One exchangeable proton was not observed. LCMS (ES+) 428.0 (M+H)$^+$, RT 2.83 minutes (Method 1).

Example 91

6,6-Dimethyl-2-(6-{[(1-methyl-1H-pyrazol-4-yl)methyl]amino}-2,3-dihydro-4H-1,4-benzoxazin-4-yl)-6,7-dihydro[1,3]thiazolo[5,4-c]pyridin-4(5H)-one The title compound was prepared from Example 42 and 1-methylpyrazole-4-carboxaldehyde according to Method V and was isolated as a yellow solid (16%) after purification by preparative HPLC (Method 6). δ$_H$ (CD$_3$OD) 8.35 (1H, s), 7.55 (1H, s), 7.45 (1H, s), 7.26 (1H, d, J 2.6 Hz), 6.77 (1H, d, J 8.9 Hz), 6.52 (1H, dd, J 8.7 and 2.6 Hz), 4.25-4.19 (2H, m), 4.07 (2H, s), 4.16-4.10 (2H, m), 3.87 (3H, s), 2.88 (2H, s), 1.40 (6H, s). LCMS (ES+) 425.1 (M+H)$^+$, RT 1.98 minutes (Method 1).

Example 92

2-(6-{[(3,5-Dimethylisoxazol-4-yl)methyl]amino}-2,3-dihydro-4H-1,4-benzoxazin-4-yl)-6,6-dimethyl-6,7-dihydro[1,3]thiazolo[5,4-c]pyridin-4(5H)-one The title compound was prepared from Example 42 and 3,5-dimethylisoxazole-4-carboxaldehyde according to Method V and was isolated as a yellow solid (32%) after purification by preparative HPLC (Method 6). δ$_H$ (CD$_3$OD) 8.07 (1H, s), 7.28 (1H, d, J 2.6 Hz), 6.78 (1H, d, J 8.7 Hz), 6.49 (1H, dd, J 8.9 and 2.6 Hz), 4.25-4.22 (2H, m), 4.17-4.12 (2H, m), 4.05 (2H, s), 2.88 (2H, s), 2.39 (3H, s), 2.26 (3H, s), 1.39 (6H, s). One exchangeable proton was not observed. LCMS (ES+) 440.9 (M+H)$^+$, RT 2.73 minutes (Method 1).

Example 93

6,6-Dimethyl-2-(6-{[(6-methylpyridin-2-yl)methyl]amino}-2,3-dihydro-4H-1,4-benzoxazin-4-yl)-6,7-dihydro[1,3]thiazolo[5,4-c]pyridin-4(5H)-one The title compound was prepared from Example 42 and 2-methylpyridine-6-carboxaldehyde according to Method V and was isolated as a yellow solid (23%) after purification by preparative HPLC (Method 6). δ$_H$ (CD$_3$OD) 7.73-7.64 (1H, m), 7.32 (1H, d, J 7.9 Hz), 7.18 (1H, d, J 7.9 Hz), 7.06 (1H, d, J 2.6 Hz), 6.75 (1H, d, J 8.9 Hz), 6.47 (1H, dd, J 8.9 and 2.6 Hz), 4.38 (2H, s), 4.24-4.15 (2H, m), 4.13-4.05 (2H, m), 2.82 (2H, s), 2.68 (3H, s), 1.38 (6H, s). Exchangeable protons were not observed. LCMS (ES+) 436.1 (M+H)$^+$, RT 2.04 minutes (Method 1).

Example 94

6,6-Dimethyl-2-(6-{[(3-methylpyridin-2-yl)methyl]amino}-2,3-dihydro-4H-1,4-benzoxazin-4-yl)-6,7-dihydro[1,3]thiazolo[5,4-c]pyridin-4(5H)-one The title compound was prepared from Example 42 and 3-methylpyridine-2-carboxaldehyde according to Method V and was isolated as a white solid (23%) after purification by preparative HPLC (Method 6). δ$_H$ (CD$_3$OD) 8.53 (1H, s), 8.35 (1H, dd, J 4.9 and 1.1 Hz), 7.66-7.61 (1H, m), 7.31-7.19 (2H, m), 6.78 (1H, d, J 8.9 Hz), 6.56 (1H, dd, J 8.7 and 2.6 Hz), 5.51 (1H, s), 4.39 (2H, s), 4.27-4.18 (2H, m), 4.18-4.07 (2H, m), 2.87 (2H, s), 2.44 (3H, s), 1.39 (6H, s). LCMS (ES+) 436.1 (M+H)$^+$, RT 1.95 minutes (Method 1).

Example 95

6,6-Dimethyl-2-{6-[(2-thienylmethyl)amino]-2,3-dihydro-4H-1,4-benzoxazin-4-yl}-6,7-dihydro[1,3]thiazolo[5,4-c]pyridin-4(5H)-one The title compound was prepared from Example 42 and thiophene-2-carboxaldehyde according to Method V and was isolated as a white solid (23%) after purification by preparative HPLC (Method 6). δ$_H$ (CDCl$_3$) 7.28 (1H, d, J 2.6 Hz), 7.23 (1H, dd, J 5.1 and 1.3 Hz), 7.03 (1H, m), 6.97 (1H, dd, J 4.9 and 3.4 Hz), 6.81 (1H, d, J 8.7 Hz), 6.46 (1H, dd, J 8.9 and 2.6 Hz), 4.48 (2H, d, J 0.6 Hz), 4.31-4.22 (2H, m), 4.16-4.08 (2H, m), 2.86 (2H, s), 1.40 (6H, s). Exchangeable protons were not observed. LCMS (ES+) 427.0 (M+H)$^+$, RT 3.23 minutes (Method 1).

Example 96

2-{6-[(1,3-Benzodioxol-5-ylmethyl)amino]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 42 and 3,4-(methylenedioxy)-benzaldehyde according to Method V and was isolated as a white solid (22%) after purification by preparative HPLC (Method 6). $\delta_H$ (CD$_3$OD) 7.21 (1H, s), 6.89 (1H, d, J 1.3 Hz), 6.92-6.84 (1H, m), 6.82-6.76 (2H, m), 6.44 (1H, dd, J 8.9 and 2.6 Hz), 5.96 (2H, s), 4.29-4.25 (2H, m), 4.20 (2H, s), 4.17-4.10 (2H, m), 2.86 (2H, s), 1.42 (6H, s). Exchangeable protons were not observed. LCMS (ES+) 465.1 (M+H)$^+$, RT 2.99 minutes (Method 1).

Example 97

4-({[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]amino}methyl)benzonitrile The title compound was prepared from Example 42 and 4-cyanobenzaldehyde according to Method V and was isolated as a yellow solid (25%) after purification by preparative HPLC (Method 6). $\delta_H$ (CD$_3$OD) 7.68-7.60 (2H, m), 7.56-7.45 (2H, m), 7.13 (1H, d, J 2.6 Hz), 6.78 (1H, d, J 8.7 Hz), 6.35 (1H, dd, J 8.7 and 2.6 Hz), 4.40 (2H, s), 4.27-4.22 (2H, m), 4.13-4.10 (2H, m), 2.81 (2H, s), 1.40 (6H, s). Exchangeable protons were not observed. LCMS (ES+) 446.1 (M+H)$^+$, RT 3.29 minutes (Method 1).

Example 98

3-{[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]amino}-2-phenylpropanenitrile The title compound was prepared from Example 42 and α-formylphenylacetonitrile according to Method V and was isolated as a yellow solid (25%) after purification by preparative HPLC (Method 6). $\delta_H$ (CDCl$_3$) 7.47-7.33 (6H, m), 6.85 (1H, d, J 8.9 Hz), 6.40 (1H, dd, J 8.9 and 2.8 Hz), 5.26 (1H, s), 4.32-4.26 (2H, m), 4.26-4.11 (2H, m), 4.11-3.97 (1H, m), 3.76-3.64 (1H, m), 3.62-3.51 (1H, m), 2.88 (2H, s), 1.40 (3H, s), 1.39 (3H, s). One exchangeable proton was not observed. LCMS (ES+) 460.1 (M+H)$^+$, RT 3.44 minutes (Method 1).

Example 99

5-({[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]amino}methyl)-2-fluorobenzonitrile The title compound was prepared from Example 42 and 2-fluoro-5-formylbenzonitrile according to Method V and was isolated as a white solid (22%) after purification by preparative HPLC (Method 6). $\delta_H$ (CD$_3$OD) 7.70-7.63 (2H, m), 7.23 (1H, s), 7.13 (1H, d, J 2.6 Hz), 6.79 (1H, d, J 8.7 Hz), 6.36 (1H, dd, J 8.9 and 2.6 Hz), 4.34 (2H, s), 4.30-4.20 (2H, m), 4.18-4.08 (2H, m), 2.83 (2H, s), 1.40 (6H, s). Exchangeable protons were not observed. LCMS (ES+) 464.0 (M+H)$^+$, RT 3.38 minutes (Method 1).

Example 100

6,6-Dimethyl-2-{6-[(1H-indol-5-ylmethyl)amino]-2,3-dihydro-4H-1,4-benzoxazin-4-yl}-6,7-dihydro[1,3]thiazolo[5,4-c]pyridin-4(5H)-one The title compound was prepared from Example 42 and indole-5-carboxaldehyde according to Method V and was isolated as a white solid (11%) after purification by preparative HPLC (Method 6). $\delta_H$ (CDCl$_3$) 8.27-8.20 (1H, m), 7.69-7.63 (1H, m), 7.42-7.37 (1H, m), 7.23-7.20 (1H, m), 6.80 (1H, d, J 8.7 Hz), 6.54-6.51 (1H, m), 6.44 (1H, dd, J 8.9 and 2.6 Hz), 5.20 (1H, d, J 0.8 Hz), 4.37 (2H, s), 4.28-4.22 (2H, m), 4.15-4.08 (2H, m), 2.82 (2H, s), 1.37 (6H, s). Exchangeable protons were not observed. LCMS (ES+) 460.1 (M+H)$^+$, RT 2.51 minutes (Method 1).

Example 101

2-{6-[(1-Benzofuran-2-ylmethyl)amino]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 42 and benzofuran-2-carboxaldehyde according to Method V and was isolated as a white solid (22%) after purification by preparative HPLC (Method 6). $\delta_H$ (CD$_3$OD) 7.56-7.49 (2H, m), 7.48-7.38 (2H, m), 7.30-7.14 (2H, m), 6.80 (1H, d, J 8.7 Hz), 6.66 (1H, s), 6.56-6.49 (1H, m), 4.45 (2H, s), 4.31-4.21 (2H, m), 4.17-4.05 (2H, m), 2.76 (2H, s), 1.37 (6H, s). One exchangeable proton was not observed. LCMS (ES+) 461.1 (M+H)$^+$, RT 3.65 minutes (Method 1).

Example 102

Method R

2-{6-[N-(2,3-Dihydroxypropyl)-N-(pyridin-2-ylmethyl)amino]-2,3-dihydro-4H-1,4-benzoxazin-4-yl}-6,6-dimethyl-6,7-dihydro[1,3]thiazolo[5,4-c]pyridin-4(5H)-one To a stirred solution of Example 86 (0.23 g, 0.54 mmol) in DCM (10 mL) were added DIPEA (0.19 mL, 1.08 mmol) and allyl bromide (0.09 mL, 1.2 mmol). The reaction mixture was heated to 40° C. for 24 h, then concentrated in vacuo. The residue was purified by column chromatography (C$_{18}$—SiO$_2$, gradient of MeOH/water). The resulting material was dissolved in acetone (3 mL) and water (0.3 mL). Osmium tetroxide (0.05 mL, 0.033 g/mL solution in tert-BuOH, 0.006 mmol) and N-methylmorpholine oxide (0.08 g, 0.68 mmol) were added. The reaction mixture was stirred at r.t. for 18 h, then concentrated in vacuo. Purification by preparative HPLC (Method 6) gave the title compound (0.018 g, 7%) as a green solid. $\delta_H$ (CD$_3$OD) 8.41-8.32 (1H, m), 7.65 (1H, td, J 7.7 and 1.7 Hz), 7.27 (1H, d, J 7.9 Hz), 7.23-7.15 (1H, m), 7.12 (1H, d, J 2.8 Hz), 6.65 (1H, d, J 9.0 Hz), 6.43 (1H, dd, J 9.0 and 3.0 Hz), 4.61 (2H, d, J 5.3 Hz), 4.13-4.01 (2H, m), 4.02-3.89 (3H, m), 3.69 (1H, dd, J 15.1 and 4.0 Hz), 3.54-3.48 (2H, m), 3.32 (1H, dd, J 15.1 and 8.1 Hz), 2.71 (2H, s), 1.25 (6H, s). Exchangeable protons were not observed. LCMS (ES+) 496.4 (M+H)$^+$, RT 1.91 minutes (Method 1).

Example 103

2-(6-{N-(2,3-Dihydroxypropyl)-N-[(6-methylpyridin-2-yl)methyl]amino}-2,3-dihydro-4H-1,4-benzoxazin-4-yl)-6,6-dimethyl-6,7-dihydro[1,3]thiazolo[5,4-c]pyridin-4(5H)-one The title compound was prepared from Example 93 according to Method R and was isolated as an off-white solid (26%) after purification by preparative HPLC (Method 6). $\delta_H$ (CD$_3$OD) 7.69-7.58 (1H, m), 7.19-7.10 (3H, m), 6.74 (1H, d, J 9.0 Hz), 6.52 (1H, dd, J 9.0 and 3.0 Hz), 4.77-4.55 (2H, m), 4.22-4.17 (2H, m), 4.16-4.04 (3H, m), 3.89-3.78 (1H, m), 3.68-3.61 (2H, m), 3.36-3.48 (1H, m), 2.82 (2H, s), 2.51 (3H, s), 1.39 (6H, s). Exchangeable protons were not observed. LCMS (ES+) 510.1 (M+H)$^+$, RT 1.91 minutes (Method 1).

Example 104

3-{[(3S)-4-(6,6-Dimethyl-4-oxo-4,5,6,7-tetrahydro[1,3]thiazolo[5,4-c]pyridin-2-yl)morpholin-3-yl]methyl}-N-(pyridin-4-ylmethyl)-1H-indole-5-carboxamide The title compound was prepared from Intermediate 44 and 4-(aminomethyl)-pyridine according to Method O and was isolated as a white solid (47%) after purification by column chromatography (SiO$_2$, 0-10% MeOH/DCM). $\delta_H$ (CD$_3$OD) 8.54-3.48 (2H, m), 8.42 (1H, d, J 1.2 Hz), 7.67 (1H, dd, J 8.6 and 1.7 Hz), 7.50-7.45 (2H, m), 7.39 (1H, d, J 8.5 Hz), 7.24 (1H, s), 4.70 (2H, s), 4.49-4.40 (1H, m), 4.11-4.03 (1H, m), 3.93 (1H, d, J 11.7 Hz), 3.80-3.55 (4H, m), 3.44-3.21 (1H, m), 3.25 (1H, m), 2.68 (2H, s), 1.27 (3H, s), 1.26 (3H, s). Exchangeable protons were not observed. LCMS (ES+) 531.0 (M+H)$^+$, RT 2.25 minutes (Method 5).

Example 105

6,6-Dimethyl-2-[(3S)-3-({5-[(3-Hydroxyazetidin-1-yl)carbonyl]-1H-indol-3-yl}methyl)morpholin-4-yl]-6,7-dihydro[1,3]thiazolo[5,4-c]pyridin-4(5H)-one The title compound was prepared from Intermediate 44 and 3-hydroxyazetidine hydrochloride according to Method O (with the addition of 1.2 equivalents of DIPEA) and was isolated as a white solid (7%) after purification by column chromatography (SiO$_2$, 0-10% MeOH/DCM), followed by dissolution of material in DCM, washing with 1M aqueous HCl, extraction of the aqueous layer with 5% MeOH/DCM (4×20 mL), filtration of the combined organic fractions through an Isolute® phase separation cartridge, and concentration in vacuo. $\delta_H$ (CD$_3$OD) 8.21 (1H, s), 7.52-7.36 (2H, m), 7.25 (1H, s), 4.73-1.35 (16H, m), 1.40 (6H, s). Exchangeable protons were not observed. LCMS (ES+) 496.4 (M+H)$^+$, RT 2.17 minutes (Method 3).

Example 106

6,6-Dimethyl-2-[(3S)-3-{[5-(pyrrolidin-1-ylcarbonyl)-1H-indol-3-yl]methyl}morpholin-4-yl]-6,7-dihydro[1,3]thiazolo[5,4-c]pyridin-4(5H)-one The title compound was prepared from Intermediate 44 and pyrrolidine according to Method O and was isolated as a white solid (77%) after purification by column chromatography (SiO$_2$, 0-10% MeOH/DCM). $\delta_H$ (CD$_3$OD) 8.15 (1H, d, J 0.8 Hz), 7.40 (1H, dd, J 8.4 and 0.5 Hz), 7.31 (1H, dd, J 8.4 and 1.5 Hz), 7.24 (1H, s), 4.42-4.30 (1H, m), 4.14-4.00 (1H, m), 3.89 (1H, d, J 11.7 Hz), 3.75-3.56 (8H, m), 3.42 (1H, dd, J 13.9 and 10.2 Hz), 3.10 (1H, dd, J 13.9 and 4.7 Hz), 2.81 (2H, s), 2.04 (2H, m), 1.92 (2H, m), 1.37 (6H, s). Exchangeable protons were not observed. LCMS (ES+) 494.3 (M+H)$^+$, RT 2.44 minutes (Method 3).

Example 107

3-{[(3S)-4-(6,6-Dimethyl-4-oxo-4,5,6,7-tetrahydro[1,3]thiazolo[5,4-c]pyridin-2-yl)morpholin-3-yl]methyl}-N-isopropyl-N-methyl-1H-indole-5-carboxamide The title compound was prepared from Intermediate 44 and N-methylisopropylamine according to Method O (50° C.) and was isolated as a white solid (80%) after purification by column chromatography (SiO$_2$, 0-10% MeOH/DCM). $\delta_H$ (CD$_3$OD) 8.05 (1H, br. s), 7.41 (1H, d, J 8.4 Hz), 7.23 (1H, s), 7.15 (1H, d, J 8.4 Hz), 4.44-4.32 (1H, m), 4.28-3.98 (2H, m), 3.89 (1H, d, J 11.7 Hz), 3.75-3.55 (4H, m), 3.41 (1H, dd, J 13.8 and 10.2 Hz), 3.09 (1H, dd, J 13.8 and 4.4 Hz), 2.98 (3H, s), 2.81 (2H, s), 1.37 (6H, s), 1.30-1.09 (6H, m). Exchangeable protons were not observed. LCMS (ES+) 496.3 (M+H)$^+$, RT 2.54 minutes (Method 3).

Example 108

N,N-Diethyl-3-{[(3S)-4-(6,6-dimethyl-4-oxo-4,5,6,7-tetrahydro[1,3]thiazolo[5,4-c]pyridin-2-yl)morpholin-3-yl]methyl}-1H-indole-5-carboxamide The title compound was prepared from Intermediate 44 and diethylamine according to Method O (50° C.) and was isolated as a white solid (41%) after purification by column chromatography (SiO$_2$, 0-10% MeOH/DCM). $\delta_H$ (CD$_3$OD) 8.03 (1H, d, J 0.9 Hz), 7.41 (1H, dd, J 8.3 and 0.5 Hz), 7.23 (1H, s), 7.14 (1H, dd, J 8.3 and 1.5 Hz), 4.45-4.32 (1H, m), 4.12-4.00 (1H, m), 3.89 (1H, d, J 11.7 Hz), 3.75-3.35 (9H, m), 3.14-3.03 (1H, m), 2.81 (2H, s), 1.37 (6H, s), 1.33-3.11 (6H, m). Exchangeable protons were not observed. LCMS (ES+) 496.1 (M+H)$^+$, RT 2.44 minutes (Method 3).

Example 109

3-{[(3S)-4-(6,6-Dimethyl-4-oxo-4,5,6,7-tetrahydro[1,3]thiazolo[5,4-c]pyridin-2-yl)morpholin-3-yl]methyl}-N-(2-methoxyethyl)-N-methyl-1H-indole-5-carboxamide The title compound was prepared from Intermediate 44 and N-(2-methoxyethyl)-methylamine according to Method O and was isolated as a white solid (62%) after purification by column chromatography (SiO$_2$, 0-8% MeOH/DCM). $\delta_H$ (CD$_3$OD) 8.09 (1H, br. s), 7.42 (1H, dd, J 8.3 and 0.5 Hz), 7.23 (1H, s), 7.19 (1H, dd, J 8.3 and 1.4 Hz), 4.42-4.32 (1H, m), 4.13-4.02 (1H, m), 3.89 (1H, d, J 11.7 Hz), 3.75-3.20 (12H, m), 3.17 (3H, s), 3.14-3.04 (1H, m), 2.82 (2H, s), 1.37 (6H, s). Exchangeable protons were not observed. LCMS (ES+) 512.3 (M+H)$^+$, RT 2.38 minutes (Method 3).

Example 110

N-[2-(Dimethylamino)ethyl]-3-{[(3S)-4-(6,6-dimethyl-4-oxo-4,5,6,7-tetrahydro-[1,3]thiazolo[5,4-c]pyridin-2-yl)morpholin-3-yl]methyl}-N-methyl-1H-indole-5-carboxamide The title compound was prepared from Intermediate 44 and N,N,N'-trimethylethylenediamine according to Method O and was isolated as a white solid (64%) after purification by column chromatography (SiO$_2$, 0-10% MeOH/DCM). δ$_H$ (CD$_3$OD) 8.09 (1H, br. s), 7.42 (1H, d, J 8.4 Hz), 7.28-7.17 (2H, m), 4.41-4.26 (1H, m), 4.12-4.01 (1H, m), 3.88 (1H, d, J 11.7 Hz), 3.84-3.50 (6H, m), 3.42 (1H, dd, J 13.8 and 10.5 Hz), 3.15 (3H, s), 3.30-3.02 (1H, m), 2.83 (2H, s), 2.71-2.25 (5H, m), 2.09 (3H, br. s), 1.38 (6H, s). Exchangeable protons were not observed. LCMS (ES+) 525.3 (M+H)$^+$, RT 2.95 minutes (Method 3).

Example 111

6,6-Dimethyl-2-{(3S)-3-[(5-{[(2S)-2-(methoxymethyl)pyrrolidin-1-yl]carbonyl}-1H-indol-3-yl)methyl]morpholin-4-yl}-6,7-dihydro[1,3]thiazolo[5,4-c]pyridin-4(5H)-one The title compound was prepared from Intermediate 44 and (R)-(−)-2-(methoxymethyl)pyrrolidine according to Method O and was isolated as a white solid (77%) after purification by column chromatography (SiO$_2$, 0-8% MeOH/DCM). δ$_H$ (CD$_3$OD) 8.11 (1H, br. s), 7.40 (1H, d, J 8.4 Hz), 7.35-7.26 (1H, m), 7.24 (1H, s), 4.52-4.39 (1H, m), 4.39-4.28 (1H, m), 4.12-4.03 (1H, m), 3.88 (1H, d, J 11.7 Hz), 3.72-3.56 (7H, m), 3.49-3.36 (3H, m), 3.17-3.00 (2H, m), 2.86 (1H, d, J 17.0 Hz), 2.78 (1H, d, J 17.0 Hz), 2.17-1.93 (4H, m), 1.89-1.71 (1H, m), 1.38 (3H, s), 1.37 (3H, s). Exchangeable protons were not observed. LCMS (ES+) 538.3 (M+H)$^+$, RT 2.50 minutes (Method 3).

Example 112

6,6-Dimethyl-2-{(3S)-3-[(5-{[(2R)-2-(Methoxymethyl)pyrrolidin-1-yl]carbonyl}-1H-indol-3-yl)methyl]morpholin-4-yl}-6,7-dihydro [1,3]thiazolo pyridin-4(5H)-one The title compound was prepared from Intermediate 44 and (S)-(+)-2-(methoxymethyl)pyrrolidine according to Method O and was isolated as a white solid (78%) after purification by column chromatography (SiO$_2$, 0-8% MeOH/DCM). δ$_H$ (CD$_3$OD) 8.10 (1H, br. s), 7.40 (1H, d, J 8.4 Hz), 7.34-7.25 (1H, m), 7.23 (1H, s), 4.50-4.31 (1H, m), 4.10-4.03 (1H, m), 3.88 (1H, d, J 11.7 Hz), 3.70-3.56 (7H, m), 3.48-3.39 (3H, m), 3.19-2.97 (2H, m), 2.81 (2H, s), 2.22-1.93 (4H, m), 1.91-1.70 (1H, m), 1.37 (3H, s), 1.36 (3H, s). Exchangeable protons were not observed. LCMS (ES+) 538.3 (M+H)$^+$, RT 2.49 minutes (Method 3).

Example 113

N-(Cyanomethyl)-3-{[(3S)-4-(6,6-dimethyl-4-oxo-4,5,6,7-tetrahydro[1,3]thiazolo[5,4-c]pyridin-2-yl)morpholin-3-yl]methyl}-N-methyl-1H-indole-5-carboxamide The title compound was prepared from Intermediate 44 and (methylamino)-acetonitrile hydrochloride according to Method O (at 55° C. for 4 h with the addition of 1.2 equivalents of DIPEA) and was isolated as a white solid (57%) after purification by column chromatography (SiO$_2$, 0-8% MeOH/DCM). δ$_H$(CD$_3$OD) 8.18 (1H, d, J 0.9 Hz), 7.44 (1H, dd, J 8.4 and 0.5 Hz), 7.28 (1H, dd, J 8.4 and 1.6 Hz), 7.26 (1H, s), 4.59 (1H, d, J 17.3 Hz), 4.52 (1H, d, J 17.3 Hz), 4.45-4.34 (1H, m), 4.12-4.01 (1H, m), 3.88 (1H, d, J 11.7 Hz), 3.75-3.65 (2H, m), 3.65-3.52 (2H, m), 3.41 (1H, dd, J 13.9 and 10.0 Hz), 3.24 (3H, s), 3.13 (1H, dd, J 13.9 and 4.9 Hz), 2.83 (2H, s), 1.38 (3H, s), 1.37 (3H, s). Exchangeable protons were not observed. LCMS (ES+) 493.3 (M+H)$^+$, RT 2.47 minutes (Method 3).

Example 114

N-(2-Cyanoethyl)-3-{[(3S)-4-(6,6-dimethyl-4-oxo-4,5,6,7-tetrahydro[1,3]thiazolo[5,4-c]pyridin-2-yl)morpholin-3-yl]methyl}-N-methyl-1H-indole-5-carboxamide The title compound was prepared from Intermediate 44 and 3-(methylamino)-propionitrile according to Method O (55° C. for 4 h) and was isolated as a white solid (11%) after purification by column chromatography (SiO$_2$, 0-8% MeOH/DCM), followed by preparative HPLC (Method 13). δ$_H$ (CD$_3$OD) 8.08 (1H, s), 7.42 (1H, d, J 8.4 Hz), 7.28-7.21 (2H, m), 4.38-4.28 (1H, m), 4.11-4.01 (1H, m), 3.89 (1H, d, J 11.8 Hz), 3.90-3.78 (2H, m), 3.76-3.55 (4H, m), 3.41 (1H, dd, J 13.9 and 9.9 Hz), 3.20 (3H, s), 3.13 (1H, dd, J 13.9 and 5.1 Hz), 2.95-2.83 (2H, m), 2.80 (2H, s), 1.37 (6H, s). Exchangeable protons were not observed. LCMS (ES+) 507.2 (M+H)$^+$, RT 2.40 minutes (Method 3).

Example 115

6,6-Dimethyl-2-[(3S)-3-({5-[(2-methylpyrrolidin-1-yl)carbonyl]-1H-indol-3-yl}methyl)morpholin-4-yl]-6,7-dihydro[1,3]thiazolo[5,4-c]pyridin-4(5H)-one The title compound was prepared from Intermediate 44 and 2-methylpyrrolidine according to Method O and was isolated as a white solid (51%) after purification by column chromatography (SiO$_2$, 0-8% MeOH/DCM). δ$_H$ (CD$_3$OD) 8.14-8.07 (1H, m), 7.40 (1H, d, J 8.4 Hz), 7.34-7.26 (1H, m), 7.23 (1H, d, J 1.7 Hz), 4.43-4.23 (2H, m), 4.13-4.01 (1H, m), 3.88 (1H, d, J 11.7 Hz), 3.72-3.56 (6H, m), 3.48-3.36 (1H, m), 3.17-3.04 (1H, m), 2.84-2.78 (2H, m), 2.28-2.13 (1H, m), 2.11-1.87 (1H, m), 1.91-1.65 (2H, m), 1.47-1.39 (3H, m), 1.39-1.33 (6H, m). Exchangeable protons were not observed. LCMS (ES+) 508.3 (M+H)$^+$, RT 2.61 minutes (Method 3).

Example 116

2-{(3S)-3-[(5-{[(3R)-3-(Dimethylamino)pyrrolidin-1-yl]carbonyl}-1H-indol-3-yl)methyl]morpholin-4-yl}-6,6-dimethyl-6,7-dihydro [1,3]thiazolo[5,4-c]pyridin-4(5H)-one The title compound was prepared from Intermediate 44 and (3R)-3-(dimethylamino)pyrrolidine according to Method O and was isolated as a white solid (51%) after purification by column chromatography (SiO$_2$, 0-10% MeOH/DCM with 1% NH$_3$). δ$_H$ (CD$_3$OD) 8.13 (1H, s), 7.41 (1H, d, J 8.4 Hz), 7.38-7.29 (1H, m), 7.25 (1H, s), 4.37-4.26 (1H, m), 4.16-4.03 (1H, m), 3.97-3.35 (11H, m), 3.17-3.05 (1H, m), 3.02-2.88 (1H, m), 2.87-2.75 (2H, m), 2.36 (3H, s), 2.24 (3H, s), 2.00-1.74 (1H, m), 1.37 (6H, s). Exchangeable protons were not observed. LCMS (ES+) 537.4 (M+H)$^+$, RT 2.03 minutes (Method 3).

Example 117

2-{(3S)-3-[(5-{[(3S)-3-(Dimethylamino)pyrrolidin-1-yl]carbonyl}-1H-indol-3-yl)methyl]morpholin-4-yl}-6,6-dimethyl-6,7-dihydro [1,3]thiazolo[5,4-c]pyridin-4(5H)-one The title compound was prepared from Intermediate 44 and (3S)-3-(dimethylamino)pyrrolidine according to Method O and was isolated as a white solid (77%) after purification by column chromatography (SiO$_2$, 0-10% MeOH/DCM with 1% NH$_4$OH added). $\delta_H$ (CD$_3$OD) 8.17 (1H, s), 7.45-7.38 (1H, m), 7.31 (1H, dd, J 8.5 and 1.3 Hz), 7.24 (1H, s), 4.46-4.29 (1H, m), 4.13-4.02 (1H, m), 3.95-3.35 (11H, m), 3.16-3.06 (1H, m), 3.02-2.89 (1H, m), 2.87-2.78 (2H, m), 2.36 (3H, s), 2.22 (3H, s), 1.99-1.76 (1H, m), 1.38 (3H, s), 1.37 (3H, s). Exchangeable protons were not observed. LCMS (ES+) 537.4 (M+H)$^+$, RT 2.02 minutes (Method 3).

Example 118 tert-Butyl {1-[(3-{[(3S)-4-(6,6-dimethyl-4-oxo-4,5, 6,7-tetrahydro[1,3]thiazolo[5,4-c]pyridin-2-yl)morpholin-3-yl]methyl}-1H-indol-5-yl)carbonyl]azetidin-3-yl}carbamate The title compound was prepared from Intermediate 44 and azetidin-3-yl-carbamic acid tert-butyl ester according to Method O and was isolated as a white solid (63%) after purification by column chromatography (SiO$_2$, 0-8% MeOH/DCM). $\delta_H$ (CD$_3$OD) 8.19 (1H, s), 7.46 (1H, dd, J 8.5 and 1.5 Hz), 7.40 (1H, d, J 8.5 Hz), 7.25 (1H, s), 4.76-4.56 (1H, m), 4.53-4.39 (2H, m), 4.39-4.22 (2H, m), 4.13-4.01 (2H, m), 3.88 (1H, d, J 13.9 Hz), 3.71-3.55 (4H, m), 3.42 (1H, dd, J 13.8 and 10.0 Hz), 3.18-3.06 (1H, m), 2.84 (2H, s), 1.45 (9H, s), 1.39 (3H, s), 1.37 (3H, s). Exchangeable protons were not observed. LCMS (ES+) 595.4 (M+H)$^+$, RT 2.63 minutes (Method 3).

Example 119

6,6-Dimethyl-2-[(3S)-3-{[5-(1,3-thiazolidin-3-ylcarbonyl)-1H-indol-3-yl]methyl}morpholin-4-yl]-6,7-dihydro[1,3]thiazolo[5,4-c]pyridin-4(5H)-one The title compound was prepared from Intermediate 44 and thiazolidine according to Method O and was isolated as a white solid (77%) after purification by column chromatography (SiO$_2$, 0-8% MeOH/DCM). $\delta_H$ (CD$_3$OD) 8.21 (1H, d, J 0.8 Hz), 7.43 (1H, dd, J 8.5 and 0.6 Hz), 7.34 (1H, dd, J 8.5 and 1.5 Hz), 7.25 (1H, s), 4.75 (2H, s), 4.46-4.34 (1H, m), 4.13-4.04 (1H, m), 4.05-3.92 (2H, m), 3.88 (1H, d, J 11.7 Hz), 3.76-3.56 (4H, m), 3.41 (1H, dd, J 13.8 and 10.2 Hz), 3.17-3.03 (3H, m), 2.83 (2H, s), 1.37 (6H, s). Exchangeable protons were not observed. LCMS (ES+) 595.4 (M+H)$^+$, RT 2.63 minutes (Method 3).

Example 120

6,6-Dimethyl-2-[(3S)-3-({5-[(1-oxido-1,3-thiazolidin-3-yl)carbonyl]-1H-indol-3-yl}methyl)morpholin-4-yl]-6,7-dihydro[1,3]thiazolo[5,4-c]pyridin-4(5H)-one To a stirred solution of Example 119 (0.14 g, 0.27 mmol) in acetone (5 mL) was added sodium periodate (0.09 g, 0.41 mmol) in water (5 mL), and the reaction mixture was stirred at r.t. for 16 h. Additional sodium periodate (0.03 g, 0.16 mmol) in water (1 mL) was added. The reaction mixture was stirred for 3 days at r.t., then concentrated in vacuo. Purification by column chromatography (SiO$_2$, 0-10% MeOH/DCM) gave the title compound (0.087 g, 61%) as a white solid. $\delta_H$ (CD$_3$OD) 8.22 (1H, d, J 7.4 Hz), 7.47-7.35 (2H, m), 7.27 (1H, s), 5.01-4.89 (1H, m), 4.72 (1H, d, J 12.9 Hz), 4.60-4.40 (1H, m), 4.39-4.27 (1H, m), 4.26-4.12 (1H, m), 4.11-4.00 (1H, m), 3.94-3.86 (1H, m), 3.71-3.56 (4H, m), 3.41 (1H, dd, J 13.9 and 10.3 Hz), 3.28-3.06 (3H, m), 2.83-2.77 (2H, m), 1.35 (6H, s). Exchangeable protons were not observed. LCMS (ES+) 528.2 (M+H)$^+$, RT 2.20 minutes (Method 3).

Example 121

2-[(3S)-3-({5-[(3-Aminoazetidin-1-yl)carbonyl]-1H-indol-3-yl}methyl)morpholin-4-yl]-6,6-dimethyl-6, 7-dihydro[1,3]thiazolo[5,4-c]pyridin-4(5H)-one To a stirred solution of Example 118 (0.12 g, 0.21 mmol) in DCM (8 mL) was added TFA (2 mL). The reaction mixture was stirred at r.t. for 1 h, then concentrated in vacuo. Purification by column chromatography (SiO$_2$, 0-10% MeOH/DCM with 1% NH$_4$OH added) gave the title compound (0.095 g, 90%) as a white solid. $\delta_H$ (CD$_3$OD) 8.17 (1H, br.s), 7.50-7.37 (2H, m), 7.25 (1H, s), 4.73-4.55 (1H, m), 4.52-4.36 (1H, m), 4.31-4.02 (3H, m), 4.00-3.80 (3H, m), 3.69 (3H, s), 3.64-3.52 (1H, m), 3.43 (1H, dd, J 13.9 and 10.1 Hz), 3.18-3.07 (1H, m), 2.83 (2H, s), 1.38 (3H, s), 1.37 (3H, s). Exchangeable protons were not observed. LCMS (ES+) 495.0 (M+H)$^+$, RT 2.24 minutes (Method 5).

Example 122

Methyl 3-{[(3S)-4-(6,6-dimethyl-4-oxo-4,5,6,7-tetrahydro[1,3]thiazolo[5,4-c]pyridin-2-yl)morpholin-3-yl]methyl}-1-methyl-1H-indole-5-carboxylate The title compound was prepared from Intermediate 78 and Intermediate 46 according to Method N and was isolated as a white solid (91%) after purification by column chromatography (SiO$_2$, 0-4% MeOH/DCM, followed by SiO$_2$, 0-2% MeOH/EtOAc), then preparative HPLC ((Method 13). $\delta_H$ (CD$_3$OD) 8.62-8.59 (1H, m), 7.86 (1H, dd, J 8.7 and 1.6 Hz), 7.41-7.35 (1H, m), 7.18 (1H, s), 4.41-4.31 (1H, m), 4.13-4.02 (1H, m), 3.95 (3H, s), 3.90 (1H, d, J 11.8 Hz), 3.79 (3H, s), 3.76-3.55 (4H, m), 3.44-3.36 (1H, m), 3.15 (1H, dd, J 13.9 and 5.4 Hz), 2.85 (1H, d, J 16.9 Hz), 2.80 (1H, d, J 16.9 Hz), 1.36 (3H, s), 1.35 (3H, s). Exchangeable proton was not observed. LCMS (ES+) 469.3 (M+H)$^+$, RT 2.88 minutes (Method 4).

Example 123

3-{[(3S)-4-(6,6-Dimethyl-4-oxo-4,5,6,7-tetrahydro [1,3]thiazolo[5,4-c]pyridin-2-yl)morpholin-3-yl] methyl}-1-methyl-1H-indole-5-carboxylic acid To a stirred suspension of Example 122 (1.15 g, 2.46 mmol) in 1,4-dioxane (20 mL) and MeOH (5 mL) was added a solution of LiOH.H$_2$O (0.21 g, 4.91 mmol) in water (5 mL). The reaction mixture was stirred at 60° C. for 16 h, then concentrated in vacuo. Water (100 mL) and DCM (200 mL) were added. The aqueous fraction was separated, acidified to pH 1 by the addition of 1M aqueous HCl, then extracted with EtOAc (4×200 mL). The combined organic fractions were dried (Na$_2$SO$_4$), filtered and concentrated in vacuo. The solid was washed with EtOAc to give the title compound (1.0 g, 90%) as a white solid. $\delta_H$ (CD$_3$OD) 8.64 (1H, d, J 1.1 Hz), 7.88 (1H, dd, J 8.7 and 1.5 Hz), 7.36 (1H, d, J 8.7 Hz), 7.15 (1H, s), 4.52-4.39 (1H, m), 4.12-4.02 (1H, m), 3.91 (1H, d, J 11.7 Hz), 3.79 (3H, s), 3.76-3.65 (2H, m), 3.64-3.50 (2H, m), 3.44-3.34 (1H, m), 3.16 (1H, dd, J 13.9 and 5.3 Hz), 2.87 (1H, d, J 17.0 Hz), 2.81 (1H, d, J 17.0 Hz), 1.36 (3H, s), 1.35 (3H,

Example 124

3-{[(3S)-4-(6,6-Dimethyl-4-oxo-4,5,6,7-tetrahydro
[1,3]thiazolo[5,4-c]pyridin-2-yl)-morpholin-3-yl]
methyl}-N,1-dimethyl-N-(2-methoxyethyl)-1H-indole-5-carboxamide The title compound was prepared from Intermediate 79 and N-(2-methoxyethyl)-methylamine according to Method O and was isolated as a white solid (70%) after purification by column chromatography (SiO$_2$, 0-6% MeOH/DCM). $\delta_H$ (CD$_3$OD) 8.09 (1H, br. s), 7.40 (1H, d, J 8.4 Hz), 7.26 (1H, dd, J 8.4 and 1.4 Hz), 7.17 (1H, s), 4.42-4.32 (1H, m), 4.13-4.02 (1H, m), 3.89 (1H, d, J 11.7 Hz), 3.79 (3H, s), 3.74-3.25 (12H, m), 3.16 (3H, s), 3.14-3.04 (1H, m), 2.81 (2H, s), 1.37 (6H, s). Exchangeable proton was not observed. LCMS (ES+) 526.3 (M+H)$^+$, RT 2.58 minutes (Method 3).

Example 125

N-(Cyanomethyl)-3-{[(3S)-4-(6,6-dimethyl-4-oxo-4,
5,6,7-tetrahydro[1,3]thiazolo[5,4-c]pyridin-2-yl)
morpholin-3-yl]methyl}-N,1-dimethyl-1H-indole-5-
carboxamide The title compound was prepared from Intermediate 79 and (methylamino)-acetonitrile hydrochloride according to Method O (with the addition of 1.2 equivalents of DIPEA) and was isolated as a white solid (63%) after purification by column chromatography (SiO$_2$, 0-6% MeOH/DCM). $\delta_H$ (CD$_3$OD) 8.17 (1H, d, J 0.9 Hz), 7.44 (1H, d, J 8.6 Hz), 7.34 (1H, dd, J 8.6 and 1.5 Hz), 7.20 (1H, s), 4.59 (1H, d, J 17.3 Hz), 4.51 (1H, d, J 17.3 Hz), 4.41-4.30 (1H, m), 4.11-4.01 (1H, m), 3.88 (1H, d, J 11.7 Hz), 3.80 (3H, s), 3.75-3.50 (4H, m), 3.45-3.33 (1H, m), 3.24 (3H, s), 3.11 (1H, dd, J 13.9 and 4.9 Hz), 2.81 (2H, s), 1.37 (3H, s), 1.36 (3H, s). Exchangeable proton was not observed. LCMS (ES+) 507.2 (M+H)$^+$, RT 2.62 minutes (Method 3).

Example 126

2-[(3S)-3-{[5-(Azetidin-1-ylcarbonyl)-1-methyl-1H-
indol-3-yl]methyl}morpholin-4-yl]-6,6-dimethyl-6,
7-dihydro[1,3]thiazolo[5,4-c]pyridin-4(5H)-one The title compound was prepared from Intermediate 79 and azetidine hydrochloride according to Method O (with the addition of 1.2 equivalents of DIPEA) and was isolated as a white solid (65%) after purification by column chromatography (SiO$_2$, 0-6% MeOH/DCM). $\delta_H$ (CD$_3$OD) 8.19 (1H, d, J 1.0 Hz), 7.50 (1H, dd, J 8.6 and 1.6 Hz), 7.40 (1H, d, J 8.6 Hz), 7.18 (1H, s), 4.53-4.45 (2H, m), 4.36-4.28 (1H, m), 4.29-4.18 (2H, m), 4.11-4.01 (1H, m), 3.87 (1H, d, J 11.8 Hz), 3.79 (3H, s), 3.74-3.55 (4H, m), 3.39 (1H, dd, J 13.9 and 10.2 Hz), 3.10 (1H, dd, J 13.9 and 4.9 Hz), 2.84 (2H, s), 2.44-2.35 (2H, m), 1.38 (3H, s), 1.37 (3H, s). Exchangeable proton was not observed. LCMS (ES+) 494.3 (M+H)$^+$, RT 2.59 minutes (Method 3).

Example 127

3-{[(3S)-4-(6,6-Dimethyl-4-oxo-4,5,6,7-tetrahydro
[1,3]thiazolo[5,4-c]pyridin-2-yl)morpholin-3-yl]
methyl}-N,N,1-trimethyl-1H-indole-5-carboxamide The title compound was prepared from Intermediate 79 and dimethylamine (40% v/v in water) according to Method O (in MeCN) and was isolated as a white solid (92%) after purification by column chromatography (SiO$_2$, 0-6% MeOH/DCM). $\delta_H$ (CD$_3$OD) 8.07 (1H, d, J 1.0 Hz), 7.41 (1H, d, J 8.5 Hz), 7.27 (1H, dd, J 8.5 and 1.6 Hz), 7.18 (1H, s), 4.39-4.29 (1H, m), 4.13-4.01 (1H, m), 3.88 (1H, d, J 11.7 Hz), 3.79 (3H, s), 3.75-3.55 (4H, m), 3.39 (1H, dd, J 13.9 and 10.1 Hz), 3.14 (6H, br. s), 3.12-3.02 (1H, m), 2.80 (2H, s), 1.37 (6H, s). Exchangeable proton was not observed. LCMS (ES+) 482.3 (M+H)$^+$, RT 2.57 minutes (Method 3).

Example 128

Methyl 5-chloro-3-{[(3S)-4-(6,6-dimethyl-4-oxo-4,
5,6,7-tetrahydro[1,3]thiazolo[5,4-c]pyridin-2-yl)
morpholin-3-yl]methyl}-1H-indole-7-carboxylate The title compound was prepared from Intermediate 82 and Intermediate 46 according to Method N and was isolated as a white solid (30%) after purification by column chromatography (SiO$_2$, 0-6% MeOH/DCM), followed by (SiO$_2$, 0-5% MeOH/EtOAc), then trituration in EtOAc. $\delta_H$ (CD$_3$OD) 8.23 (1H, d, J 2.0 Hz), 7.78 (1H, d, J 2.0 Hz), 7.31 (1H, s), 4.47-4.36 (1H, m), 4.13-4.03 (1H, m), 4.00 (3H, s), 3.89 (1H, d, J 11.8 Hz), 3.78-3.50 (4H, m), 3.42-3.34 (1H, m), 3.18-3.06 (1H, m), 2.84 (1H, d, J 16.9 Hz), 2.78 (1H, d, J 16.9 Hz), 1.36 (3H, s), 1.33 (3H, s). Exchangeable protons were not observed. LCMS (ES+) 489.1 (M+H)$^+$, RT 3.11 minutes (Method 3).

Example 129

5-Chloro-3-{[(3S)-4-(6,6-dimethyl-4-oxo-4,5,6,7-
tetrahydro[1,3]thiazolo[5,4-c]pyridin-2-yl)morpho-
lin-3-yl]methyl}-N,N-dimethyl-1H-indole-7-car-
boxamide To a stirred solution of Intermediate 83 (0.08 g, 0.17 mmol) in DMF (5 mL) was added pentafluorophenol (0.03 g, 0.19 mmol) and EDC (0.04 g, 0.20 mmol). The reaction mixture was stirred at r.t. for 16 h, then dimethylamine (5 mL, 40% v/v in water) was added. The reaction mixture was stirred at r.t. for 2 h, then concentrated in vacuo. DCM (20 mL) and water (20 mL) were added. The organic fraction was separated via an Isolute® phase separator cartridge, then concentrated in vacuo. Purification by column chromatography (SiO$_2$, 0-5% MeOH/DCM) gave the title compound (0.020 g, 23%) as a white solid. $\delta_H$ (CD$_3$OD) 8.04 (1H, d, J 1.9 Hz), 7.26 (1H, s), 7.13 (1H, d, J 1.9 Hz), 4.44-4.30 (1H, m), 4.12-4.02 (1H, m), 3.88 (1H, d, J 11.7 Hz), 3.78-3.52 (4H, m), 3.42-3.33 (1H, m), 3.25-2.88 (6H, m), 2.87-2.83 (3H, m), 1.36 (3H, s), 1.35 (3H, s). Exchangeable protons were not observed. LCMS (ES+) 502.2 (M+H)$^+$, RT 2.42 minutes (Method 3).

Example 130

3-{[(3S)-4-(6,6-Dimethyl-4-oxo-4,5,6,7-tetrahydro
[1,3]thiazolo[5,4-c]pyridin-2-yl)morpholin-3-yl]
methyl}-1H-indole-6-carboxylic acid To a stirred solution of Example 61 (2.0 g, 4.4 mmol) in 1,4-dioxane (30 mL) was added a solution of LiOH.H$_2$O (0.6 g, 13.2 mmol) in water (10 mL). The reaction mixture was stirred at r.t. for 3 days, then concentrated in vacuo. DCM (100 mL) and water (50 mL) were added. The aqueous fraction was separated, then acidified to pH 1 with 2M aqueous HCl. The precipitate was filtered, washed with Et$_2$O and dried at r.t. under vacuum to give the title compound (1.6 g, 83%) as a yellow solid. $\delta_H$ (DMSO-d$_6$) 12.43 (1H, br. s), 11.28 (1H, s), 8.00 (1H, d, J 0.7 Hz), 7.84 (1H, d, J 8.4 Hz), 7.64 (1H, dd, J 8.4 and 1.4 Hz), 7.44 (1H, d, J 2.3 Hz), 7.30 (1H, s), 4.22-4.12 (1H, m), 3.99 (1H, d, J 7.1 Hz), 3.73 (1H, d, J 11.6 Hz), 3.70-3.46 (4H, m), 3.38-3.24 (1H, m), 2.98 (1H, dd, J 13.9 and 4.7 Hz), 2.74 (1H, d, J 16.7 Hz), 2.67 (1H, d, J 16.7 Hz), 1.25 (6H, s). LCMS (ES+) 441.0 (M+H)$^+$, RT 2.74 minutes (Method 5).

Example 131

6,6-Dimethyl-2-[(3S)-3-{[6-(piperidin-1-ylcarbonyl)-1H-indol-3-yl]methyl}morpholin-4-yl]-6,7-dihydro[1,3]thiazolo[5,4-c]pyridin-4(5H)-one The title compound was prepared from Intermediate 84 and piperidine according to Method O and was isolated as a white solid (15%) after purification by column chromatography (SiO$_2$, 3-10% MeOH/DCM). $\delta_H$ (DMSO-d$_6$) 11.14 (1H, s), 7.85 (1H, d, J 8.2 Hz), 7.41 (1H, br. s), 7.39-7.34 (2H, m), 7.10 (1H, d, J 8.2 Hz), 4.26-4.15 (1H, m), 4.04 (1H, d, J 11.7 Hz), 3.78 (1H, d, J 11.7 Hz), 3.75-3.43 (9H, m), 3.00 (1H, dd, J 13.5 and 3.8 Hz), 2.85-2.70 (2H, m), 1.74-1.64 (2H, m), 1.64-1.49 (4H, m), 1.31 (6H, s). LCMS (ES+) 508.0 (M+H)$^+$, RT 2.97 minutes (Method 5).

Example 132

3-{[(3S)-4-(6,6-Dimethyl-4-oxo-4,5,6,7-tetrahydro[1,3]thiazolo[5,4-c]pyridin-2-yl)morpholin-3-yl]methyl}-N,N-dimethyl-1H-indole-6-carboxamide The title compound was prepared from Intermediate 84 and dimethylamine (40% v/v in water) according to Method O and was isolated as a white solid (61%) after purification by column chromatography (SiO$_2$, 4% MeOH/DCM). $\delta_H$ (DMSO-d$_6$) 11.09 (1H, s), 7.89 (1H, d, J 8.2 Hz), 7.39 (1H, br. s), 7.35-7.26 (2H, m), 7.08 (1H, dd, J 8.2 and 1.2 Hz), 4.22-4.07 (1H, m), 3.98 (1H, d, J 7.4 Hz), 3.79-3.43 (5H, m), 3.45-3.22 (1H, m), 2.99 (6H, s), 3.05-2.90 (1H, m), 2.74 (1H, d, J 16.7 Hz), 2.68 (1H, d, J 16.7 Hz), 1.26 (6H, s). LCMS (ES+) 468.0 (M+H)$^+$, RT 2.74 minutes (Method 5).

Example 133

2-[(3S)-3-{[6-(Azetidin-1-ylcarbonyl)-1H-indol-3-yl]methyl}morpholin-4-yl]-6,6-dimethyl-6,7-dihydro[1,3]thiazolo[5,4-c]pyridin-4(5H)-one The title compound was prepared from Intermediate 84 and azetidine hydrochloride according to Method O with the addition of DIPEA and was isolated as a white solid (65%) after purification by column chromatography (SiO$_2$, 4% MeOH/DCM). $\delta_H$ (DMSO-d$_6$) 11.15 (1H, s), 7.79 (1H, d, J 8.3 Hz), 7.65 (1H, s), 7.34-7.28 (3H, m), 4.41-4.25 (2H, m), 4.21-4.01 (3H, m), 3.98 (1H, d, J 7.3 Hz), 3.76-3.45 (5H, m), 3.32-3.24 (1H, m), 2.95 (1H, dd, J 13.9 and 4.5 Hz), 2.75 (1H, d, J 16.7 Hz), 2.68 (1H, d, J 16.7 Hz), 2.34-2.20 (2H, m), 1.26 (6H, s). LCMS (ES+) 480.0 (M+H)$^+$, RT 2.76 minutes (Method 5).

Example 134

3-{[(3S)-4-(6,6-Dimethyl-4-oxo-4,5,6,7-tetrahydro[1,3]thiazolo[5,4-c]pyridin-2-yl)morpholin-3-yl]methyl}-N-(2-methoxyethyl)-N-methyl-1H-indole-6-carboxamide The title compound was prepared from Intermediate 84 and N-(2-methoxyethyl)-methylamine according to Method O and was isolated as a white solid (61%) after purification by column chromatography (SiO$_2$, 5% MeOH/DCM). $\delta_H$ (DMSO-d$_6$) 11.08 (1H, br. s), 7.80 (1H, d, J 8.2 Hz), 7.38 (1H, s), 7.34-7.28 (2H, m), 7.06 (1H, dd, J 8.1 and 1.2 Hz), 4.18-4.10 (1H, m), 3.98 (1H, d, J 7.3 Hz), 3.70-3.40 (9H, m), 3.33-3.16 (4H, m), 2.99 (3H, s), 2.94 (1H, dd, J 14.0 and 4.5 Hz), 2.74 (1H, d, J 16.7 Hz), 2.69 (1H, d, J 16.7 Hz), 1.26 (6H, s). LCMS (ES+) 512.0 (M+H)$^+$, RT 2.77 minutes (Method 5).

Example 135

N-Benzyl-3-{[(3S)-4-(6,6-dimethyl-4-oxo-4,5,6,7-tetrahydro[1,3]thiazolo[5,4-c]pyridin-2-yl)morpholin-3-yl]methyl}-1H-indole-6-carboxamide The title compound was prepared from Intermediate 84 and benzylamine according to Method O and was isolated as a white solid (45%) after purification by column chromatography (SiO$_2$, 4% MeOH/DCM). $\delta_H$ (DMSO-d$_6$) 11.22 (1H, s), 8.98-8.90 (1H, m), 7.95 (1H, s), 7.81 (1H, d, J 8.3 Hz), 7.62 (1H, d, J 8.3 Hz), 7.41-7.28 (6H, m), 7.28-7.17 (1H, m), 4.51 (2H, d, J 5.8 Hz), 4.20-4.09 (1H, m), 3.98 (1H, d, J 7.2 Hz), 3.69-3.46 (5H, m), 3.35-3.24 (1H, m), 2.97 (1H, dd, J 13.7 and 4.2 Hz), 2.73 (1H, d, J 16.7 Hz), 2.67 (1H, d, J 16.7 Hz), 1.25 (6H, s). LCMS (ES+) 530.0 (M+H)$^+$, RT 3.01 minutes (Method 5).

Example 136

N-(Cyanomethyl)-3-{[(3S)-4-(6,6-dimethyl-4-oxo-4,5,6,7-tetrahydro[1,3]thiazolo[5,4-c]pyridin-2-yl)morpholin-3-yl]methyl}-N-methyl-1H-indole-6-carboxamide The title compound was prepared from Intermediate 84 and (methylamino)-acetonitrile hydrochloride according to Method O (with the addition of 1.2 equivalents of DIPEA) and was isolated as a white solid (52%) after purification by column chromatography (SiO$_2$, 3% MeOH/DCM). $\delta_H$ (DMSO-d$_6$) 11.20 (1H, s), 7.68 (1H, d, J 8.2 Hz), 7.48 (1H, s), 7.37 (1H, d, J 1.2 Hz), 7.30 (1H, s), 7.15 (1H, d, J 8.3 Hz), 4.53 (2H, s), 4.21-4.11 (1H, m), 3.99 (1H, d, J 7.2 Hz), 3.69-3.46 (5H, m), 3.33-3.24 (1H, m), 3.08 (3H, s), 2.97 (1H, dd, J 13.9 and 4.5 Hz), 2.74 (1H, d, J 16.7 Hz), 2.68 (1H, d, J 16.7 Hz), 1.25 (6H, s). LCMS (ES+) 493.0 (M+H)$^+$, RT 2.80 minutes (Method 5).

Example 137

3-{[(3S)-4-(6,6-Dimethyl-4-oxo-4,5,6,7-tetrahydro[1,3]thiazolo[5,4-c]pyridin-2-yl)morpholin-3-yl]methyl}-N-(2-hydroxy-1-methylethyl)-1H-indole-6-carboxamide The title compound was prepared from Intermediate 84 and (DL)-2-amino-1-propanol according to Method O and was isolated as a white solid (15%) after purification by column chromatography (SiO$_2$, 5% MeOH/DCM). $\delta_H$ (DMSO-d$_6$) 11.22 (1H, s), 8.00 (1H, d, J 8.0 Hz), 7.95 (1H, s), 7.83 (1H, d, J 8.4 Hz), 7.61 (1H, dd, J 8.4 and 1.1 Hz), 7.41 (1H, d, J 2.2 Hz), 7.36 (1H, s), 4.76 (1H, t, J 5.8 Hz), 4.23-4.14 (1H, m), 4.14-3.99 (2H, m), 3.82-3.68 (2H, m), 3.69-3.48 (4H, m), 3.47-3.29 (2H, m), 3.02 (1H, dd, J 14.0 and 4.7 Hz), 2.79 (1H, d, J 16.7 Hz), 2.73 (1H, d, J 16.7 Hz), 1.30 (6H, s), 1.20 (3H, d, J 6.7 Hz). LCMS (ES+) 498.0 (M+H)$^+$, RT 2.62 minutes (Method 5).

Example 138

6,6-Dimethyl-2-[(3S)-3-({6-[(4-methylpiperazin-1-yl)carbonyl]-1H-indol-3-yl}methyl)morpholin-4-yl]-6,7-dihydro[1,3]thiazolo[5,4-c]pyridin-4(5H)-one The title compound was prepared from Intermediate 84 and 1-methylpiperazine according to Method O and was isolated as a white solid (50%) after purification by column chromatography (SiO$_2$, 5% MeOH/DCM). $\delta_H$ (DMSO-d$_6$) 11.10 (1H, s), 7.80 (1H, d, J 8.1 Hz), 7.38 (1H, s), 7.34-7.29 (2H, m), 7.06 (1H, d, J 8.1 Hz), 4.21-4.08 (1H, m), 3.98 (1H, d, J 7.3 Hz), 3.72 (1H, d, J 11.6 Hz), 3.69-3.41 (8H, m), 3.35-3.24 (1H, m), 2.95 (1H, dd, J 13.9 and 4.6 Hz), 2.74 (1H, d, J 16.7 Hz), 2.68 (1H, d, J 16.7 Hz), 2.39-2.24 (4H, m), 2.20 (3H, s), 1.25 (6H, s). LCMS (ES+) 523.0 (M+H)$^+$, RT 2.26 minutes (Method 5).

Example 139

3-{[(3S)-4-(6,6-Dimethyl-4-oxo-4,5,6,7-tetrahydro[1,3]thiazolo[5,4-c]pyridin-2-yl)morpholin-3-yl]methyl}-1H-indole-6-carboxamide The title compound was prepared from Intermediate 84 and aqueous NH$_3$ (20% v/v) according to Method O and was isolated as a white solid (58%) after purification by column chromatography (SiO$_2$, 5-10% MeOH/DCM). $\delta_H$ (DMSO-d$_6$) 11.20 (1H, s), 7.92 (1H, s), 7.87 (1H, br. s), 7.79 (1H, d, J 8.4 Hz), 7.59 (1H, dd, J 8.4 and 1.3 Hz), 7.36 (1H, d, J 2.2 Hz), 7.31 (1H, s), 7.12 (1H, br. s), 4.19-4.09 (1H, m), 3.98 (1H, d, J 7.3 Hz), 3.72 (1H, d, J 11.6 Hz), 3.70-3.46 (4H, m), 3.32-3.24 (1H, m), 2.95 (1H, dd, J 13.9 and 4.5 Hz), 2.74 (1H, d, J 16.7 Hz), 2.68 (1H, d, J 16.7 Hz), 1.26 (6H, s). LCMS (ES+) 440.0 (M+H)$^+$, RT 2.60 minutes (Method 5).

Example 140

3-{[(3S)-4-(6,6-Dimethyl-4-oxo-4,5,6,7-tetrahydro[1,3]thiazolo[5,4-c]pyridin-2-yl)morpholin-3-yl]methyl}-N-(1H-pyrazol-3-yl)-1H-indole-6-carboxamide The title compound was prepared from Intermediate 84 and 3-aminopyrazole according to Method O and was isolated as a white solid (56%) after purification by column chromatography (SiO$_2$, 5% MeOH/DCM). $\delta_H$ (DMSO-d$_6$) 12.38 (1H, s), 11.28 (1H, s), 10.61 (1H, s), 8.07 (1H, s), 7.84 (1H, d, J 8.4 Hz), 7.74 (1H, d, J 9.0 Hz), 7.64 (1H, s), 7.40 (1H, d, J 1.7 Hz), 7.32 (1H, s), 6.65 (1H, s), 4.23-4.12 (1H, m), 3.99 (1H, d, J 7.2 Hz), 3.73 (1H, d, J 11.6 Hz), 3.70-3.47 (4H, m), 3.35-3.30 (1H, m), 2.97 (1H, dd, J 13.8 and 4.3 Hz), 2.76 (1H, d, J 16.7 Hz), 2.70 (1H, d, J 16.7 Hz), 1.26 (6H, s). LCMS (ES+) 506.0 (M+H)$^+$, RT 2.68 minutes (Method 5).

Example 141

N-[2-(Dimethylamino)ethyl]-3-{[(3S)-4-(6,6-dimethyl-4-oxo-4,5,6,7-tetrahydro-[1,3]thiazolo[5,4-c]pyridin-2-yl)morpholin-3-yl]methyl}-1H-indole-6-carboxamide The title compound was prepared from Intermediate 84 and N,N-dimethylethylenediamine according to Method O and was isolated as a white solid (49%) after purification by column chromatography (SiO$_2$, 8% MeOH/DCM). $\delta_H$ (DMSO-d$_6$) 11.19 (1H, s), 8.27-8.20 (1H, m), 7.88 (1H, s), 7.79 (1H, d, J 8.4 Hz), 7.54 (1H, d, J 8.4 Hz), 7.36 (1H, d, J 2.0 Hz), 7.31 (1H, s), 4.19-4.08 (1H, m), 3.98 (1H, d, J 7.3 Hz), 3.72 (1H, d, J 11.6 Hz), 3.70-3.45 (4H, m), 3.42-3.33 (2H, m), 3.35-3.27 (1H, m), 2.96 (1H, dd, J 13.9 and 4.6 Hz), 2.74 (1H, d, J 16.7 Hz), 2.68 (1H, d, J 16.7 Hz), 2.41 (2H, t, J 6.9 Hz), 2.19 (6H, s), 1.25 (6H, s). LCMS (ES+) 511.0 (M+H)$^+$, RT 2.28 minutes (Method 5).

Example 142

N-(Cyclopropylmethyl)-3-{[(3S)-4-(6,6-dimethyl-4-oxo-4,5,6,7-tetrahydro[1,3]thiazolo-[5,4-c]pyridin-2-yl)morpholin-3-yl]methyl}-1H-indole-6-carboxamide The title compound was prepared from Intermediate 84 and (cyclopropylmethyl)-amine according to Method O and was isolated as a white solid (64%) after purification by column chromatography (SiO$_2$, 8% MeOH/DCM). $\delta_H$ (DMSO-d$_6$) 11.19 (1H, s), 8.47-8.38 (1H, m), 7.90 (1H, s), 7.79 (1H, d, J 8.4 Hz), 7.57 (1H, dd, J 8.4 and 1.0 Hz), 7.36 (1H, d, J 2.1 Hz), 7.30 (1H, s), 4.20-4.08 (1H, m), 3.98 (1H, d, J 7.3 Hz), 3.73 (1H, d, J 11.6 Hz), 3.71-3.45 (4H, m), 3.34-3.28 (1H, m), 3.17 (2H, t, J 6.2 Hz), 2.96 (1H, dd, J 13.8 and 4.5 Hz), 2.74 (1H, d, J 16.7 Hz), 2.68 (1H, d, J 16.7 Hz), 1.25 (6H, s), 1.14-0.99 (1H, m), 0.47-0.39 (2H, m), 0.29-0.19 (2H, m). LCMS (ES+) 494.0 (M+H)$^+$, RT 2.89 minutes (Method 5).

Example 143

Method Y

N-(3-{[(3S)-4-(6,6-Dimethyl-4-oxo-4,5,6,7-tetrahydro[1,3]thiazolo[5,4-c]pyridin-2-yl)morpholin-3-yl]methyl}-1H-indol-5-yl)acetamide To a stirred solution of Intermediate 85 (0.21 g, 0.49 mmol) in DCM (10 mL) was added DIPEA (0.08 mL, 0.49 mmol), followed by acetyl chloride (0.03 mL, 0.49 mmol) dropwise. The reaction mixture was stirred at r.t. for 24 h, and then concentrated in vacuo. DCM (75 mL) and water (25 mL) were added. The organic fraction was separated via an Isolute® phase separator cartridge, and then concentrated in vacuo. Purification by preparative HPLC (Method 8) gave the title compound (0.041 g, 19%) as a white solid. $\delta_H$ (DMSO-d$_6$) 10.81 (1H, s), 9.67 (1H, s), 7.91 (1H, s) 7.28-7.22 (2H, m) 7.19-7.11 (2H, m), 4.18-4.08 (1H, m), 3.98 (1H, d, J 7.0 Hz), 3.73 (1H, d, J 11.6 Hz), 3.67-3.46 (4H, m), 2.86 (1H, d, J 16.3 Hz), 2.76 (2H, d, J 10.9 Hz), 2.03 (3H, s), 1.25 (6H, s). One exchangeable proton was not observed. LCMS (ES+) 454.0 (M+H)$^+$, RT 2.66 minutes (Method 4).

Example 144

Methyl (3-{[(3S)-4-(6,6-dimethyl-4-oxo-4,5,6,7-tetrahydro[1,3]thiazolo[5,4-c]pyridin-2-yl)morpholin-3-yl]methyl}-1H-indol-5-yl)carbamate The title compound was prepared from Intermediate 85 and methyl chloroformate according to Method Y and was isolated as a pale yellow solid (18%) after purification by preparative HPLC (Method 13). $\delta_H$ (DMSO-d$_6$) 10.79 (1H, s), 9.23 (1H, br. s), 7.85 (1H, s), 7.25 (1H, d, J 4.5 Hz), 7.22 (1H, s), 7.16 (1H, d, J 2.1 Hz), 7.02 (1H, dd, J 8.7 and 1.7 Hz), 4.20-4.09 (1H, m), 3.98 (1H, d, J 6.5 Hz), 3.73 (1H, d, J 11.5 Hz), 3.65 (3H, s), 3.63-3.44 (4H, m), 3.27-3.18 (1H, m), 2.96-2.81 (1H, m), 2.76 (2H, d J 7.3 Hz), 1.26 (6H, d, J 1.1 Hz). LCMS (ES+) 470.0 (M+H)⁺, RT 2.47 minutes (Method 10).

Example 145

N-(3-{[(3S)-4-(6,6-Dimethyl-4-oxo-4,5,6,7-tetrahydro[1,3]thiazolo[5,4-c]pyridin-2-yl)morpholin-3-yl]methyl}-1H-indol-5-yl)methanesulfonamide The title compound was prepared from Intermediate 85 and methanesulfonyl chloride according to Method Y and was isolated as a white solid (37%) after purification by preparative HPLC (Method 13). $\delta_H$ (DMSO-d$_6$) 10.94 (1H, s), 9.14 (1H, br. s), 7.67 (1H, s), 7.30 (1H, d, J 8.7 Hz,), 7.26 (1H, s), 7.23 (1H, d, J 2.1 Hz,), 6.98 (1H, dd, J 8.7 and 2.1 Hz), 4.16-4.05 (1H, m), 3.98 (1H, d, J 7.2 Hz), 3.74 (1H, d, J 11.7 Hz,), 3.70-3.45 (4H, m), 3.30-3.18 (1H, m), 2.93 (1H, d, J 4.5 Hz), 2.89 (3H, s), 2.76 (2H, d, J 16.8 Hz), 1.24 (6H, s). LCMS (ES+) 490.0 (M+H)⁺, RT 2.38 minutes (Method 4).

Example 146

Methyl 3-{[(3S)-4-(6,6-dimethyl-4-oxo-4,5,6,7-tetrahydro[1,3]thiazolo[5,4-c]pyridin-2-yl)morpholin-3-yl]methyl}-1H-indole-7-carboxylate To a stirred solution of Example 128 (0.096 g, 0.19 mmol) in MeOH (10 mL) was added 10% w/w palladium on carbon and the reaction mixture was stirred under an atmosphere of H₂ at r.t. for 16 h. Ammonium formate (0.062 g, 0.98 mmol) and additional 10% w/w palladium on carbon (0.02 g) were added. The reaction mixture was heated to 170° C. for 90 minutes in a sealed tube under microwave irradiation, filtered through Celite®, then partitioned between DCM (20 mL) and water (20 mL). The organic fraction was separated via an Isolute® phase separation cartridge and concentrated in vacuo. Purification by column chromatography (SiO₂, 0-5% MeOH/DCM), followed by preparative HPLC (Method 8) gave the title compound (0.014 g, 16%) as a white solid. $\delta_H$ (CD₃OD) 8.01 (1H, dd, J 7.9 and 1.0 Hz), 7.77 (1H, d, J 7.6 Hz), 7.19 (1H, s), 7.13-7.04 (1H, m), 4.28-4.18 (1H, m), 4.03-3.96 (1H, m), 3.90 (3H, s), 3.81 (1H, d, J 11.7 Hz), 3.70-3.45 (4H, m), 3.32 (1H, dd, J 14.1 and 9.5 Hz), 3.10 (1H, dd, J 14.1 and 5.8 Hz), 2.69 (1H, d, J 16.8 Hz), 2.58 (1H, d, J 16.8 Hz), 1.26 (3H, s), 1.23 (3H, s). Exchangeable protons were not observed. LCMS (ES+) 455.2 (M+H)⁺, RT 2.58 minutes (Method 3).

Example 147

6,6-Dimethyl-2-[(3S)-3-(1H-pyrrolo[3,2-c]pyridin-3-ylmethyl)morpholin-4-yl]-6,7-dihydro[1,3]thiazolo[5,4-c]pyridin-4(5H)-one The title compound was prepared from Intermediate 46 and Intermediate 88 according to Method N and was isolated as a yellow solid (2%) after purification by column chromatography (SiO₂, 0-15% DCM/MeOH with 1% NH₄OH added). $\delta_H$ (CD₃OD) 9.40 (1H, s), 8.37 (1H, d, J 6.3 Hz), 7.78 (1H, d, J 6.3 Hz), 7.65 (1H, s), 4.66-4.54 (1H, m), 4.26-4.17 (1H, m), 4.02 (1H, d, J 11.8 Hz), 3.90-3.65 (4H, m), 3.62-3.41 (2H, m), 2.90 (1H, d, J 16.9 Hz), 2.79 (1H, d, J 16.9 Hz), 1.46 (3H, s), 1.45 (3H, s). Exchangeable protons were not observed. LCMS (ES+) 398.2 (M+H)⁺, RT 1.96 minutes (Method 4).

Example 148

3-{[(3S)-4-(6,6-Dimethyl-4-oxo-4,5,6,7-tetrahydro[1,3]thiazolo[5,4-c]pyridin-2-yl)morpholin-3-yl]methyl}-1H-indole-5-carbonitrile The title compound was prepared from Intermediate 46 and Intermediate 91 according to Method N and was isolated as a yellow solid (35%) after purification by recrystallisation from MeOH. $\delta_H$ (DMSO-d$_6$) 11.45 (1H, s), 8.44 (1H, s), 7.49 (1H, d, J 8.5 Hz), 7.43-7.40 (2H, m), 7.29 (1H, s), 4.33-4.22 (1H, m), 3.99 (1H, d, J 7.0 Hz), 3.73 (1H, d, J 11.6 Hz), 3.59-3.16 (5H, m), 2.97 (1H, dd, J 113.9 and 4.7 Hz), 2.75 (2H, s), 1.25 (6H, s). LCMS (ES+) 422.0 (M+H)⁺, RT 3.02 minutes (Method 5).

Example 149

3-{[(3S)-4-(6,6-Dimethyl-4-oxo-4,5,6,7-tetrahydro[1,3]thiazolo[5,4-d]pyridin-2-yl)morpholin-3-yl]methyl}-N,N-dimethyl-1H-indole-5-sulfonamide The title compound was prepared from Intermediate 46 and Intermediate 95 according to Method N and was isolated as a white solid (8%) after purification by column chromatography (SiO₂, 0-4% MeOH/DCM). $\delta_H$ (DMSO-d$_6$) 11.46 (1H s), 8.25 (1H, d, J 1.1 Hz), 7.55 (1H, d, J 8.7 Hz), 7.49-7.38 (2H, m), 7.25 (1H, s), 4.29-4.15 (1H, m), 3.99 (1H, d, J 7.0 Hz), 3.74 (1H, d, J 11.7 Hz), 3.68-3.47 (4H, m), 3.39-3.30 (1H, m), 3.03 (1H, dd, J 13.8 and 4.9 Hz), 2.75 (2H, s), 2.58 (6H, s), 1.24 (3H, s), 1.23 (3H, s). LCMS (ES+) 504.3 (M+H)⁺, RT 2.34 minutes (Method 3), RT 2.30 minutes (Method 4).

Example 150

2-[(3S)-3-{[5-(Cyclopropylmethoxy)-1H-indol-3-yl]methyl}morpholin-4-yl]-6,6-dimethyl-6,7-dihydro[1,3]thiazolo[5,4-c]pyridin-4(5H)-one The title compound was prepared from Intermediate 46 and Intermediate 101 according to Method N and was isolated as a white solid (68%) after purification by column chromatography (SiO₂, 0-3% MeOH/DCM). $\delta_H$ (DMSO-d$_6$) 10.70 (1H, s), 7.31 (1H, s), 7.25 (1H, d, J 2.3 Hz), 7.22 (1H, d, J 8.9 Hz), 7.13 (1H, d, J 2.3 Hz), 6.73 (1H, dd, J 8.7 and 2.3 Hz), 4.17-4.07 (1H, m), 4.01-3.94 (1H, m), 3.84 (2H, d, J 6.8 Hz), 3.75-3.40 (5H m), 3.28-3.19 (1H, m), 2.85 (1H, dd, J 14.1 and 4.1 Hz), 2.75 (2H, s), 1.28 (3H, s), 1.27 (3H, s), 1.26-1.22 (1H, m), 0.61-0.54 (2H, m), 0.40-0.33 (2H, m). LCMS (ES+) 467.3 (M+H)⁺, RT 2.65 minutes (Methods 3 and 4).

Example 151

6,6-Dimethyl-2-[(3S)-3-({5-[methylsulfonyl)methyl]-1H-indol-3-yl}methyl)morpholin-4-yl]-6,7-dihydro[1,3]thiazolo[5,4-c]pyridin-4(5H)-one The title compound was prepared from Intermediate 46 and Intermediate 108 according to Method N and was isolated as a white solid (16%) after purification by column chromatography (SiO₂, 100% EtOAc). $\delta_H$ (DMSO-d$_6$) 11.01 (1H, s), 7.86 (1H, s), 7.35 (1H, d, J 8.3 Hz), 7.29 (1H, s), 7.25 (1H, s), 7.13 (1H, d, J 8.8 Hz), 4.50 (1H, d, J 13.7 Hz), 4.43 (1H, d, J 13.7 Hz), 4.24-4.15 (1H, m), 3.98 (1H, d, J 6.7 Hz), 3.75 (1H, d, J 11.6 Hz), 3.64-3.47 (4H, m), 3.31-3.21 (1H, m), 2.93 (1H, dd, J 14.1 and 4.5 Hz), 2.88 (3H, s), 2.79 (1H, d, J 16.8 Hz), 2.74 (1H, d, J 16.8 Hz), 1.25 (6H, s). LCMS (ES+) 489.0 (M+H)+, RT 2.79 minutes (Method 5).

Example 152

6,6-Dimethyl-2-[(3S)-3-{[5-(trifluoroacetyl)-1H-indol-3-yl]methyl}morpholin-4-yl]-6,7-dihydro[1,3]thiazolo[5,4-c]pyridin-4(5H)-one The title compound was prepared from Intermediate 46 and Intermediate 112 according to Method N and was isolated as a yellow solid (57%) after purification by column chromatography (SiO$_2$, 60-80% EtOAc/hexanes). $\delta_H$ (CD$_3$OD) (mixture of ketone and hydrate forms): 8.68 and 8.22 (1H, s), 7.85 and 7.49 (1H, d, J 8.8 Hz), 7.43-7.38 (1H, m), 7.36-7.33 and 7.18-7.15 (1H, m), 4.51-4.39 (1H, m), 4.13-4.03 (1H, m), 3.94-3.87 (1H, m), 3.87-3.52 (4H, m), 3.45-3.35 (1H, m), 3.24-3.08 (1H, m), 2.90-2.81 (2H, m), 1.40-1.30 (6H, m). Exchangeable protons were not observed. LCMS (ES+) 493.1 (M+H)+, RT 3.29 minutes (Method 5).

Example 153

Method W

N,N,1-Trimethyl-3-{[(3S)-4-(5,6,6-trimethyl-4-oxo-4,5,6,7-tetrahydro[1,3]thiazolo[5,4-c]pyridin-2-yl)morpholin-3-yl]methyl}-1H-indole-5-carboxamide To a stirred solution of Example 28 (0.103 g, 0.22 mmol) in DMF (5 mL) was added NaH (0.019 g, 60% dispersion in oil, 0.48 mmol) and the reaction mixture was stirred at r.t. for 10 minutes. Methyl iodide (0.34 mL, 0.55 mmol) was added. The reaction mixture was stirred at r.t. for 2 h, then quenched with the addition of water (0.5 mL) and concentrated in vacuo. DCM (20 mL) and water (20 mL) were added. The organic fraction was separated via an Isolute® phase separation cartridge and concentrated in vacuo. Purification by column chromatography (SiO$_2$, 0-3% MeOH/DCM) gave the title compound (0.085 g, 78%) as a white solid. $\delta_H$ (CD$_3$OD) 8.08 (1H, d, J 0.9 Hz), 7.41 (1H, d, J 8.5 Hz), 7.27 (1H, dd, J 8.5 and 1.5 Hz), 7.18 (1H, s), 4.38-4.27 (1H, m), 4.13-4.00 (1H, m), 3.88 (1H, d, J 11.8 Hz), 3.80 (3H, s), 3.73-3.52 (4H, m), 3.46-3.34 (1H, m), 3.23-3.02 (7H, m), 2.99 (3H, s), 2.87 (2H, s), 1.40 (3H, s), 1.39 (3H, s). LCMS (ES+) 496.3 (M+H)+, RT 2.45 minutes (Method 3).

Example 154

2-[(3S)-3-{[5-(Cyclobutyloxy)-1H-indol-3-yl]methyl}morpholin-4-yl]-6,6-dimethyl-6,7-dihydro[1,3]thiazolo[5,4-c]pyridin-4(5H)-one The title compound was prepared from Intermediate 46 and Intermediate 118 according to Method N and was isolated as a yellow solid (24%) after purification by column chromatography (SiO$_2$, 60-80% EtOAc/hexanes, followed by SiO$_2$, 0-3% MeOH/DCM). $\delta_H$ (CD$_3$OD) 7.25-7.18 (2H, m), 7.10 (1H, s), 6.72 (1H, dd, J 8.7 and 2.5 Hz), 4.80-4.68 (1H, m), 4.25-4.14 (1H, m), 4.13-4.03 (1H, m), 3.89 (1H, d, J 11.7 Hz), 3.78-3.63 (3H, m), 3.62-3.52 (1H, m), 3.44-3.34 (1H, m), 3.01 (1H, dd, J 13.9 and 4.7 Hz), 2.84 (2H, s), 2.60-2.45 (2H, m), 2.26-2.08 (2H, m), 1.94-1.69 (2H, m), 1.38 (6H, s). Exchangeable protons were not observed. LCMS (ES+) 467.2 (M+H)+, RT 2.601 minutes (Method 4).

Example 155

6,6-Dimethyl-2-{(3S)-3-[3-(trimethylsilyl)prop-2-yn-1-yl]morpholin-4-yl}-6,7-dihydro[1,3]thiazolo[5,4-c]pyridin-4(5H)-one The title compound was prepared from Intermediate 46 and Intermediate 119 according to Method N and was isolated as a yellow solid (70%) after purification by column chromatography (SiO$_2$, 60-80% EtOAc/hexanes). A portion (0.10 g) of this material was further purified by column chromatography (SiO$_2$, 0-2% MeOH/DCM) to give the title compound (0.06 g) as a white solid. $\delta_H$ (CD$_3$OD) 4.22-4.08 (1H, m), 4.02-3.83 (2H, m), 3.71-3.50 (3H, m), 3.49-3.33 (1H, m), 2.76-2.66 (4H, m), 1.29 (3H, s), 1.28 (3H, s), 0.00 (9H, s). Exchangeable proton was not observed. LCMS (ES+) 378.2 (M+H)+, RT 2.86 minutes (Method 4).

Example 156

6,6-Dimethyl-2-[(3S)-3-(prop-2-yn-1-yl)morpholin-4-yl]-6,7-dihydro [1,3]thiazolo[5,4-c]pyridin-4(5H)-one The title compound was prepared from Intermediate 46 and Intermediate 120 according to Method N and was isolated as a yellow solid (68%) after purification by column chromatography (SiO$_2$, 65-100% EtOAc/hexanes). A portion (0.10 g) of this material was further purified by column chromatography (SiO$_2$, 0-2% MeOH/DCM) to give the title compound (0.06 g) as an off-white solid. $\delta_H$ (CD$_3$OD) 4.18-4.08 (1H, m), 4.05 (1H, d, J 11.9 Hz), 3.90 (1H, dd, J 11.2 and 3.7 Hz), 3.69-3.50 (3H, m), 3.46-3.32 (1H, m), 2.85-2.68 (3H, m), 2.61-2.47 (1H, m), 2.30 (1H, t, J 2.7 Hz), 1.29 (6H, s). Exchangeable proton was not observed. LCMS (ES+) 306.1 (M+H)+, RT 2.24 minutes (Method 4).

Example 157

6,6-Dimethyl-2-[(3S)-3-{[2-(trimethylsilyl)-1H-indol-3-yl]methyl}morpholin-4-yl]-6,7-dihydro[1,3]thiazolo[5,4-c]pyridin-4(5H)-one The title compound was prepared from Example 155 and 2-iodoaniline according to Method I and was isolated as an off-white solid (57%) after purification by column chromatography (SiO$_2$, 0-2% MeOH/DCM, followed by SiO$_2$, 60% EtOAc/hexanes). $\delta_H$ (CD$_3$OD) 7.90 (1H, d, J 7.8 Hz), 7.35-7.26 (1H, m), 7.08-6.99 (1H, m), 6.99-6.89 (1H, m), 4.44-4.32 (1H, m), 4.08-3.93 (1H, m), 3.77-3.32 (6H, m), 3.09-2.94 (1H, m), 2.79 (2H, s), 1.31 (6H, s), 0.37 (9H, s). Exchangeable protons were not observed. LCMS (ES+) 469.2 (M+H)+, RT 3.05 minutes (Method 4).

Example 158

6,6-Dimethyl-2-[(3S)-3-(1H-Indol-2-ylmethyl)morpholin-4-yl]-6,7-dihydro[1,3]thiazolo-[5,4-c]pyridin-4(5H)-one The title compound was prepared from Example 156 and 2-iodoaniline according to Method I and was isolated as a yellow solid (7%) after purification by column chromatography (SiO$_2$, 40-100% EtOAc/hexanes). $\delta_H$ (CD$_3$OD) 7.01-6.89 (3H, m), 6.61 (1H, d, J 7.9 Hz), 6.51-6.41 (1H, m), 4.34-4.22 (1H, m), 4.07-3.85 (2H, m), 3.72-3.45 (4H, m), 3.07-2.89 (2H, m), 2.69 (2H, s), 1.25 (6H, s). Exchangeable protons were not observed. LCMS (ES+) 397.2 (M+H)$^+$, RT 2.45 minutes (Method 4).

Example 159

Methyl 3-{[(3S)-4-(6,6-dimethyl-4-oxo-4,5,6,7-tetrahydro[1,3]thiazolo[5,4-c]pyridin-2-yl)morpholin-3-yl]methyl}-1-benzofuran-5-carboxylate The title compound was prepared from Intermediate 121 (dissolved in MeOH) according to Method J and was isolated as a white solid (44%) after purification by column chromatography (SiO$_2$, 60-100% EtOAc/hexanes). $\delta_H$ (CD$_3$OD) 8.59 (1H, d, J 1.4 Hz), 7.93 (1H, dd, J 8.7 and 1.7 Hz), 7.69 (1H, s), 7.44 (1H, dd, J 8.7 and 0.4 Hz), 4.55-4.39 (1H, m), 4.05-3.94 (1H, m), 3.89 (3H, s), 3.82 (1H, d, J 11.9 Hz), 3.70-3.40 (4H, m), 3.35-3.24 (1H, m), 3.08 (1H, dd, J 14.1 and 5.8 Hz), 2.77 (1H, d, J 17.0 Hz), 2.70 (1H, d, J 17.0 Hz), 1.28 (3H, s), 1.25 (3H, s). Exchangeable proton was not observed. LCMS (ES+) 456.1 (M+H)$^+$, RT 2.68 minutes (Method 9).

Example 160

3-{[(3S)-4-(6,6-Dimethyl-4-oxo-4,5,6,7-tetrahydro[1,3]thiazolo[5,4-c]pyridin-2-yl)morpholin-3-yl]methyl}-N,N-dimethyl-1-benzofuran-5-carboxamide The title compound was prepared from Intermediate 123 and dimethylamine (40% v/v in water, 3 mL) according to Method O and was isolated as a white solid (33% from Intermediate 122) after purification by column chromatography (SiO$_2$, 0-4% MeOH/DCM). $\delta_H$ (CD$_3$OD) 8.16 (1H, d, J 1.3 Hz), 7.76 (1H, s), 7.54 (1H, dd, J 8.5 and 0.4 Hz), 7.39 (1H, dd, J 8.5 and 1.7 Hz), 4.55-4.45 (1H, m), 4.14-4.01 (1H, m), 3.90 (1H, d, J 11.9 Hz), 3.79-3.59 (3H, m), 3.59-3.49 (1H, m), 3.45-3.34 (1H, m), 3.24-3.00 (7H, m), 2.81 (1H, d, J 16.9 Hz), 2.75 (1H, d, J 16.9 Hz), 1.37 (3H, s), 1.35 (3H, s). Exchangeable proton was not observed. LCMS (ES+) 469.1 (M+H)$^+$, RT 1.95 minutes (Method 9), RT 1.50 minutes (Method 10).

Example 161

2-[(3S)-3-{[5-(Azetidin-1-ylcarbonyl)-1-benzofuran-3-yl]methyl}morpholin-4-yl]-6,6-dimethyl-6,7-dihydro[1,3]thiazolo[5,4-c]pyridin-4(5H)-one The title compound was prepared from Intermediate 123 and azetidine hydrochloride (40% v/v in water, 3 mL) according to Method O (with the addition of 1.2 equivalents of DIPEA) and was isolated as a white solid (28% from Intermediate 122) after purification by column chromatography (SiO$_2$, 0-4% MeOH/DCM, followed by SiO$_2$, 0-5% MeOH/EtOAc). $\delta_H$(CD$_3$OD) 8.27 (1H, d, J 1.3 Hz), 7.77 (1H, s), 7.61 (1H, dd, J 8.6 and 1.7 Hz), 7.53 (1H, d, J 8.6 Hz), 4.53-4.45 (3H, m), 4.36-4.28 (2H, m), 4.15-4.02 (1H, m), 3.89 (1H, d, J 11.9 Hz), 3.77-3.54 (4H, m), 3.37 (1H, m), 3.12 (1H, dd, J 14.0 and 5.4 Hz), 2.85 (1H, d, J 16.8 Hz), 2.79 (1H, d, J 16.8 Hz), 2.44-2.35 (2H, m) 1.37 (3H, s), 1.35 (3H, s). Exchangeable proton was not observed. LCMS (ES+) 481.1 (M+H)$^+$, RT 1.89 minutes (Method 9).

Example 162

Method Z 6,6-Dimethyl-2-[6-(1,3,5-trimethyl-1H-pyrazol-4-yl)-2,3-dihydro-4H-1,4-benzoxazin-4-yl]-6,7-dihydro[1,3]thiazolo[5,4-c]pyridin-4(5H)-one A stirred solution of Example 39 (0.055 g, 0.14 mmol), 1,3,5-trimethyl-4-(4,4,5,5-tetramethyl-[1,3,2]dioxaborolan-2-yl)-1H-pyrazole (0.066 g, 0.28 mmol), potassium phosphate (0.089 g, 0.42 mmol) and tetrakis(triphenylphosphine)palladium(0) (0.05 g, 0.004 mmol) in DME (4 mL) and water (1 mL) was heated to 140° C. under microwave irradiation in a sealed tube for 30 minutes, and then concentrated in vacuo. Purification by preparative HPLC (Method 7) gave the title compound (0.020 g, 34%) as an off-white solid. $\delta_H$ (CDCl$_3$) 7.84 (1H, d, J 1.9 Hz), 7.08-6.99 (2H, m), 5.45 (1H, s), 4.43-4.35 (2H, m), 4.22-4.16 (2H, m), 3.79 (3H, s), 2.87 (2H, s), 2.29 (6H, s), 1.40 (6H, s). LCMS (ES+) 424.0 (M+H)$^+$, RT 3.17 minutes (Method 2).

Example 163

2-[6-(3,5-Dimethylisoxazol-4-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 39 and 3,5-dimethylisoxazole-4-boronic acid according to Method Z and was isolated as an off-white solid (21%) after purification by preparative HPLC (Method 7). $\delta_H$ (CDCl$_3$) 7.91 (1H, s), 7.00-6.84 (2H, m), 5.26 (1H, s), 4.37-4.28 (2H, m), 4.12-4.03 (2H, m), 2.80 (2H, s), 2.38 (3H, s), 2.24 (3H, s), 1.33 (6H, s). LCMS (ES+) 411.0 (M+H)$^+$, RT 3.47 minutes (Method 2).

Example 164

6,6-Dimethyl-2-[6-(pyridazin-3-yl)-2,3-dihydro-4H-1,4-benzoxazin-4-yl]-6,7-dihydro[1,3]thiazolo[5,4-c]pyridin-4(5H)-one The title compound was prepared from Example 39 and 3-(tributylstannyl)-pyridazine according to Method Z (120° C.) and was isolated as an off-white solid (37%) after purification by preparative HPLC (Method 7). $\delta_H$ (CDCl$_3$) 9.50 (1H, s), 9.23 (1H, d, J 5.1 Hz), 8.55 (1H, d, J 2.3 Hz), 7.70 (1H, dd, J 5.5 and 2.5 Hz), 7.42 (1H, dd, J 8.7 and 2.3 Hz), 7.14 (1H, d, J 8.5 Hz), 5.70 (1H, s), 4.50-4.39 (2H, m), 4.22-4.12 (2H, m), 2.90 (2H, s), 1.40 (6H, s). LCMS (ES+) 394.0 (M+H)$^+$, RT 2.66 minutes (Method 2).

Example 165

6,6-Dimethyl-2-[6-(1,3-thiazol-4-yl)-2,3-dihydro-4H-1,4-benzoxazin-4-yl]-6,7-dihydro[1,3]thiazolo[5,4-c]pyridin-4(5H)-one The title compound was prepared from Example 39 and 4-(tributylstannyl)thiazole according to Method Z (120° C.) and was isolated as an off-white solid (16%) after purification by preparative HPLC (Method 7). $\delta_H$ (CDCl$_3$) 8.79 (1H, d, J 2.1 Hz), 8.42 (1H, d, J 2.1 Hz), 7.59 (1H, dd, J 8.5 and 2.1 Hz), 7.38 (1H, d, J 8.5 Hz), 6.95 (1H, d, J 8.5 Hz), 5.20 (1H, s), 4.33-27 (2H, m), 4.18-12 (2H, m), 2.80 (2H, s), 1.30 (6H, s). LCMS (ES+) 399.0 (M+H)$^+$, RT 3.34 minutes (Method 2).

Example 166

6,6-Dimethyl-2-[6-(6-methylpyridazin-3-yl)-2,3-dihydro-4H-1,4-benzoxazin-4-yl]-6,7-dihydro[1,3]thiazolo[5,4-c]pyridin-4(5H)-one The title compound was prepared from Intermediate 66 and 3-chloro-6-methylpyridazine according to Method Z (120° C.) and was isolated as an off-white solid (37%) after purification by preparative HPLC (Method 6). $\delta_H$ (CDCl$_3$) 8.60 (1H, d, J 2.1 Hz), 7.87 (1H, dd, J 8.7 and 2.1 Hz), 7.70 (1H, d, J 8.9 Hz), 7.40 (1H, d, J 8.9 Hz), 7.10 (1H, d, J 8.7 Hz), 5.20 (1H, s), 4.43-4.37 (2H, m), 4.23-4.18 (2H, m), 2.90 (2H, s), 2.75 (3H, s), 1.40 (6H, s). LCMS (ES+) 407.0 (M+H)$^+$, RT 2.53 minutes (Method 1).

Example 167

Method AB 6,6-Dimethyl-2-[6-(1H-pyrazol-1-yl)-2,3-dihydro-4H-1,4-benzoxazin-4-yl]-6,7-dihydro[1,3]thiazolo[5,4-c]pyridin-4(5H)-one A stirred suspension of Intermediate 5 (0.09 g, 0.34 mmol), Intermediate 126 (0.045 g, 0.23 mmol), sodium tert-butoxide (0.098 g, 1.02 mmol), palladium acetate (0.03 g, 0.13 mmol) and dicyclohexyl diphenylphosphine (0.10 g, 0.28 mmol) in toluene (4 mL) was heated to 120° C. under microwave irradiation in a sealed tube for 5 h. The reaction mixture was then concentrated in vacuo. Purification by preparative HPLC (Method 7) gave the title compound (0.025 g, 19%) as an off-white solid. $\delta_H$ (CDCl$_3$/CD$_3$OD) 8.35 (1H, d, J 2.5 Hz), 7.80 (1H, m), 7.62 (1H, d, J 1.7 Hz), 7.33-7.27 (2H, m), 7.00 (1H, d, J 8.9 Hz), 6.40 (1H, t, J 2.3 Hz), 4.35-4.28 (2H, m), 4.11-4.03 (2H, m), 2.80 (2H, s), 1.30 (6H, s). LCMS (ES+) 382.0 (M+H)$^+$, RT 3.22 minutes (Method 2).

Example 168

6,6-Dimethyl-2-[6-(1H-imidazol-4-yl)-2,3-dihydro-4H-1,4-benzoxazin-4-yl]-6,7-dihydro[1,3]thiazolo[5,4-c]pyridin-4(5H)-one The title compound was prepared from Example 39 and 1-[2-(trimethylsilyl)-ethoxymethyl]-1H-imidazole-5-boronic acid according to Method Z (120° C.), followed by treatment with 4M HCl in 1,4-dioxane at r.t. for 16 h, concentration of the reaction mixture in vacuo, dissolution in DCM, neutralisation with Na$_2$CO$_3$, filtration and concentration of the filtrate in vacuo, and was isolated as an off-white solid (29%) after purification by preparative HPLC (Method 7). $\delta_H$ (CDCl$_3$) 8.21 (1H, d, J 1.9 Hz), 7.70 (1H, s), 7.47 (1H, dd, J 8.5 and 1.9 Hz), 7.29-7.23 (1H, m), 7.00 (1H, d, J 8.5 Hz), 5.30 (1H, s), 4.40-4.30 (2H, m), 4.27-4.16 (2H, m), 2.90 (2H, s), 1.40 (6H, s). One exchangeable proton was not observed. LCMS (ES+) 382.0 (M+H)$^+$, RT 2.53 minutes (Method 2).

Example 169

Method AA 6,6-Dimethyl-2-{6-[N-methyl-N-(6-methylpyridin-3-yl)amino]-2,3-dihydro-4H-1,4-benzoxazin-4-yl}-6,7-dihydro[1,3]thiazolo[5,4-c]pyridin-4(5H)-one A stirred solution of Example 60 (0.017 g, 0.04 mmol), paraformaldehyde (0.04 g, 0.28 mmol), dibutyltin dichloride (0.0015 g, 0.004 mmol) and phenyl silane (0.01 g, 0.08 mmol) in THF (4 mL) was heated to 100° C. under microwave irradiation in a sealed tube for 1 h. The reaction mixture was concentrated in vacuo. Purification by preparative HPLC (Method 7) gave the title compound (0.020 g, 34%) as an off-white solid. $\delta_H$ (CDCl$_3$) 8.20 (1H, d, J 2.8 Hz), 7.70 (1H, d, J 2.5 Hz), 7.16 (1H, d, J 8.5 Hz), 7.05-6.99 (1H, m), 6.93-6.87 (1H, m), 6.78 (1H, dd, J 8.7 and 2.5 Hz), 5.15 (1H, s), 4.36-4.29 (2H, m), 4.18-4.10 (2H, m), 3.20 (3H, s), 2.80 (2H, s), 2.50 (3H, s), 1.40 (6H, s). LCMS (ES+) 436 (M+H)$^+$, RT 3.30 minutes (Method 2).

Example 170

6,6-Dimethyl-2-{6-[N-ethyl-N-(6-methylpyridin-3-yl)amino]-2,3-dihydro-4H-1,4-benzoxazin-4-yl}-6,7-dihydro[1,3]thiazolo[5,4-c]pyridin-4(5H)-one The title compound was prepared from Example 60 and acetyldehyde according to Method AA and was isolated as an off-white solid (34%) after purification by preparative HPLC (Method 7). $\delta_H$ (CDCl$_3$) 8.15 (1H, d, J 2.6 Hz), 7.61 (1H, d, J 2.5 Hz), 7.10 (1H, dd, J 8.5 and 2.8 Hz), 7.05-6.99 (1H, m), 6.93-6.87 (1H, m), 6.76 (1H, dd, J 8.7 and 2.5 Hz), 5.30 (1H, s), 4.44-4.35 (2H, m), 3.75-3.62 (2H, m), 3.20 (3H, s), 2.80 (2H, s), 2.50 (3H, s), 1.40 (6H, s). LCMS (ES+) 450 (M+H)$^+$, RT 3.52 minutes (Method 2).

Example 171

6,6-Dimethyl-2-{6-[(6-methoxypyridin-3-yl)amino]-2,3-dihydro-4H-1,4-benzoxazin-4-yl}-6,7-dihydro[1,3]thiazolo[5,4-c]pyridin-4(5H)-one The title compound was prepared from Example 42 and 5-bromo-2-methoxypyridine according to Method AB and was isolated as an off-white solid (11%) after purification by preparative HPLC (Method 7). $\delta_H$ (CDCl$_3$) 7.97 (1H, d, J 2.6 Hz), 7.67 (1H, d, J 2.6 Hz), 7.40 (1H, dd, J 8.8 and 2.8 Hz), 6.85 (1H, d, J 8.7 Hz), 6.73 (1H, d, J 8.7 Hz), 6.64 (1H, dd, J 8.7 and 2.6 Hz), 5.40 (1H, s), 5.20 (1H, s), 4.34-4.25 (2H, m), 4.13-4.05 (2H, m), 3.90 (3H, s), 2.90 (2H, s), 1.40 (6H, s). LCMS (ES+) 438.0 (M+H)$^+$, RT 3.32 minutes (Method 2).

Example 172

2-(6-{[6-(Dimethylamino)pyridin-3-yl]amino}-2,3-dihydro-4H-1,4-benzoxazin-4-yl)-6,6-dimethyl-6,7-dihydro[1,3]thiazolo[5,4-c]pyridin-4(5H)-one acetate The title compound was prepared from Example 42 and 5-bromo-2-(dimethylamino)pyridine according to Method AB and was isolated as an off-white solid (70%) after purification by preparative HPLC (Method 7). $\delta_H$ (CDCl$_3$) 8.05 (1H, d, J 2.5 Hz), 7.49 (1H, d, J 2.6 Hz), 7.38 (1H, dd, J 9.0 and 2.8 Hz), 6.80 (1H, d, J 8.8 Hz), 6.61-6.49 (2H, m), 5.40 (1H, s), 5.20 (1H, s), 4.31-4.23 (2H, m), 4.14-4.05 (2H, m), 3.08 (3H, s), 2.85 (3H, s), 2.02 (2H, s), 1.40 (6H, s). LCMS (ES+) 451.0 (M+H)$^+$, RT 3.26 minutes (Method 2).

Example 173

6,6-Dimethyl-2-{6-[(6-methylpyridazin-3-yl)amino]-2,3-dihydro-4H-1,4-benzoxazin-4-yl}-6,7-dihydro[1,3]thiazolo[5,4-c]pyridin-4(5H)-one The title compound was prepared from Example 42 and 3-chloro-6-methylpyridazine according to Method AB and was isolated as an off-white solid (7%) after purification by preparative HPLC (Method 7). $\delta_H$ (CDCl$_3$) 8.00 (1H, d, J 2.5 Hz), 7.29-7.25 (2H, m), 7.17-6.91 (3H, m), 5.40 (1H, s), 4.37-4.30 (2H, m), 4.16-4.08 (2H, m), 2.90 (2H, s), 2.60 (3H, s), 1.40 (6H, s). LCMS (ES+) 423.0 (M+H)$^+$, RT 2.73 minutes (Method 2).

Example 174

6,6-Dimethyl-2-(6-{[6-(trifluoromethyl)pyridin-3-yl]amino}-2,3-dihydro-4H-1,4-benzoxazin-4-yl)-6,7-dihydro[1,3]thiazolo[5,4-c]pyridin-4(5H)-one The title compound was prepared from Example 42 and 5-bromo-2-(trifluoromethyl)pyridine according to Method AB (using [1,1'-bis(di-tert-butyl-phosphino)ferrocene]palladium(II) dichloride) and was isolated as an off-white solid (7%) after purification by preparative HPLC (Method 7). $\delta_H$ (CDCl$_3$) 8.36 (1H, d, J 2.6 Hz), 8.08 (1H, d, J 2.5 Hz), 7.53-7.46 (1H, m), 7.36-7.30 (1H, m), 7.01-6.93 (1H, m), 6.90-6.83 (1H, m), 5.90 (1H, s), 5.20 (1H, s), 4.41-4.31 (2H, m), 4.13-4.04 (2H, m), 2.90 (2H, s), 1.40 (6H, s). LCMS (ES+) 476.0 (M+H)$^+$, RT 3.70 minutes (Method 2).

Example 175

2-[6-(2,3-Dihydro-1H-indol-1-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 39 and indoline according to Method AB (using [1,1'-bis(di-tert-butylphosphino)ferrocene]palladium(II) dichloride) and was isolated as an off-white solid (70%) after purification by preparative HPLC (Method 7). $\delta_H$ (CDCl$_3$) 7-98-7.92 (1H, m), 7.20-7.02 (3H, m), 7.00-6.90 (2H, m), 6.78-6.69 (1H, m), 5.25 (1H, s), 4.38-4.29 (2H, m), 4.17-4.08 (2H, m), 3.90 (2H, t, J 8.3 Hz), 3.10 (2H, t, J 8.3 Hz), 2.90 (2H, s), 1.40 (6H, s). LCMS (ES+) 433.0 (M+H)$^+$, RT 4.26 minutes (Method 2).

Example 176

6,6-Dimethyl-2-{6-[(6-phenylpyridazin-3-yl)amino]-2,3-dihydro-4H-1,4-benzoxazin-4-yl}-6,7-dihydro[1,3]thiazolo[5,4-c]pyridin-4(5H)-one The title compound was prepared from Example 42 and 3-chloro-6-phenylpyridazine according to Method AB (using [1,1'-bis(di-tert-butylphosphino)ferrocene]-palladium(II) dichloride) and was isolated as an off-white solid (51%) after purification by preparative HPLC (Method 7). $\delta_H$ (CDCl$_3$) 8.15 (1H, d, J 2.4 Hz), 7.99 (2H, d, J 6.8 Hz), 7.69 (1H, d, J 9.4 Hz), 7.55-7.35 (3H, m), 7.22-7.05 (3H, m), 7.01-6.94 (1H, m), 5.41 (1H, s), 4.40-4.32 (2H, m), 4.19-4.08 (2H, m), 2.89 (2H, s), 1.40 (6H, s). LCMS (ES+) 485.0 (M+H)$^+$, RT 3.48 minutes (Method 2).

Example 177

2-{6-[(2,6-Dimethylpyridin-3-yl)amino]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 42 and 3-bromo-2,6-dimethylpyridine according to Method AB (using [1,1'-bis(di-tert-butylphosphino)-ferrocene]palladium(II) dichloride) and was isolated as an off-white solid (17%) after purification by preparative HPLC (Method 7). $\delta_H$ (CDCl$_3$) 7.66 (1H, d, J 2.6 Hz), 7.35 (1H, d, J 8.1 Hz), 7.00-6.81 (2H, m), 6.66 (1H, dd, J 8.9 and 2.6 Hz), 5.42 (1H, br. s), 5.19 (1H, br. s), 4.40-4.26 (2H, m), 4.15-4.08 (2H, m), 2.85 (2H, s), 2.52 (3H, s), 2.43 (3H, s), 1.39 (6H, s). LCMS (ES+) 436.0 (M+H)$^+$, RT 3.05 minutes (Method 2).

Example 178

6,6-Dimethyl-2-{6-[(6-methoxypyridazin-3-yl)amino]-2,3-dihydro-4H-1,4-benzoxazin-4-yl}-6,7-dihydro[1,3]thiazolo[5,4-c]pyridin-4(5H)-one The title compound was prepared from Example 42 and 3-chloro-6-methoxypyridazine according to Method AB (using [1,1'-bis(di-tert-butylphosphino)ferrocene]-palladium(II) dichloride) and was isolated as an off-white solid (30%) after purification by preparative HPLC (Method 7). $\delta_H$ (CDCl$_3$) 8.01 (1H, d, J 2.1 Hz), 7.16-7.00 (2H, m), 6.99-6.86 (2H, m), 6.60 (1H, s) 5.23 (1H, s), 4.38-4.28 (2H, m), 4.17-4.07 (2H, m), 4.00 (3H, s), 2.88 (2H, s), 1.40 (6H, s). LCMS (ES+) 439.0 (M+H)$^+$, RT 2.97 minutes (Method 2).

Example 179

2-(6-{[6-(Dimethylamino)pyridazin-3-yl]amino}-2,3-dihydro-4H-1,4-benzoxazin-4-yl)-6,6-dimethyl-6,7-dihydro[1,3]thiazolo[5,4-c]pyridin-4(5H)-one The title compound was prepared from Example 42 and 3-chloro-6-(dimethylamino)pyridazine according to Method AB (using [1,1'-bis(di-tert-butylphosphino)-ferrocene]palladium(II) dichloride) and was isolated as an off-white solid (35%) after purification by preparative HPLC (Method 7). $\delta_H$ (CDCl$_3$) 7.89 (1H, d, J 2.1 Hz), 7.16-7.00 (2H, m), 6.99-6.86 (2H, m), 5.23 (1H, s), 4.38-4.28 (2H, m), 4.17-4.07 (2H, m), 3.10 (6H, s), 2.88 (2H, s), 1.40 (6H, s). One exchangeable proton was not observed. LCMS (ES+) 452.0 (M+H)$^+$, RT 2.68 minutes (Method 2).

Example 180

Method AD

2-[6-(1-Cyclopropylmethyl-1H-pyrazol-4-yl)-2,3-dihydro-4H-1,4-benzoxazin-4-yl]-6,6-dimethyl-6,7-dihydro[1,3]thiazolo[5,4-c]pyridin-4(5H)-one A stirred mixture of Example 39 (0.100 g, 0.254 mmol), Intermediate 127 (0.042 g, 0.168 mmol), K$_2$CO$_3$ (0.053 g, 0.381 mmol), tetra-n-butylammonium bromide (0.123 g, 0.381 mmol) and tetrakis(triphenylphosphine)palladium(0) (0.015 g, 0.013 mmol) in THF (2 mL) and water (0.5 mL) was heated to 100° C. in a sealed vessel for 4 h. EtOAc (5 mL) was added, and the layers were separated. The organic fraction was washed with water (5 ml), then brine (5 mL), dried (MgSO$_4$), filtered and concentrated in vacuo. Purification by trituration in a mixture of heptane and Et$_2$O gave the title compound (0.025 g, 23%) as a beige solid. $\delta_H$ (CDCl$_3$) 8.01 (1H, d, J 1.9 Hz), 7.71 (1H, s), 7.67 (1H, s), 7.19 (1H, dd, J 8.5 and 2.1 Hz), 6.95 (1H, d, J 8.3 Hz), 5.31 (1H, s), 4.37-4.31 (2H, m), 4.05-3.99 (2H, m), 4.02 (2H, d, J 7.2 Hz), 2.88 (2H, s), 1.40 (6H, s), 1.38-1.17 (1H, m), 0.73-0.63 (2H, m), 0.46-0.38 (2H, m). LCMS (ES+) 436.0 (M+H)$^+$, RT 3.32 minutes (Method 1).

Example 181

6,6-Dimethyl-2-{6-[1-(3-methoxypropyl)-1H-pyrazol-4-yl]-2,3-dihydro-4H-1,4-benzoxazin-4-yl}-6,7-dihydro[1,3]thiazolo[5,4-c]pyridin-4(5H)-one The title compound was prepared from Example 39 and Intermediate 128 according to Method AD (90° C.) and was isolated as a colourless oil (37%) after purification by preparative HPLC (Method 6). $\delta_H$ (CDCl$_3$) 8.02 (1H, d, J 1.9 Hz), 7.72 (1H, s), 7.59 (1H, s), 7.17 (1H, dd, J 8.5 and 1.9 Hz), 6.95 (1H, d, J 8.5 Hz), 5.80 (1H, s), 4.36-4.30 (2H, m), 4.26 (2H, t, J 6.8 Hz), 4.21-4.15 (2H, m), 3.36 (2H, t, J 5.8 Hz), 3.35 (3H, s), 2.88 (2H, s), 2.21-2.10 (2H, m), 1.40 (6H, s). LCMS (ES+) 454 (M+H)$^+$, RT 3.08 minutes (Method 1).

Example 182

6,6-Dimethyl-2-{6-[1-(2-(R,S)-hydroxy-3-methoxypropyl)-1H-pyrazol-4-yl]-2,3-dihydro-4H-1,4-benzoxazin-4-yl}-6,7-dihydro[1,3]thiazolo[5,4-c]pyridin-4(5H)-one The title compound was prepared from Example 39 and Intermediate 129 according to Method AD (after stirring at 90° C. for 24 h, additional Intermediate 129 (1 equivalent) was added and the reaction mixture was stirred at 100° C. for 24 h) and was isolated as a colourless oil (13%) after purification by preparative HPLC (Method 6). $\delta_H$ (CDCl$_3$) 8.02 (1H, d, J 1.9 Hz), 7.73 (1H, d, J 0.4 Hz), 7.65 (1H, s), 7.18 (1H, dd, J 8.5 and 2.1 Hz), 6.96 (1H, d, J 8.5 Hz), 5.35 (1H, s), 4.35-4.15 (7H, m), 3.42-3.34 (5H, m), 2.89 (2H, s), 1.41 (6H, s). One exchangeable proton was not observed. LCMS (ES+) 470.0 (M+H)$^+$, RT 2.68 minutes (Method 1).

Example 183

2-[6-(1-Allyl-1H-pyrazol-4-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 39 and Intermediate 130 according to Method AD (90° C.) and was isolated as a white foam (36%) after purification by column chromatography (SiO$_2$, 10% MeOH/heptane). $\delta_H$ (CD$_3$OD) 8.12 (1H, d, J 2.1 Hz), 7.92 (1H, s), 7.76 (1H, d, J 0.8 Hz), 7.26 (1H, dd, J 8.5 and 2.1 Hz), 6.95 (1H, d, J 8.5 Hz), 4.38-4.25 (3H, m), 4.23-4.09 (3H, m), 4.07-3.94 (1H, m), 3.58-3.47 (2H, m), 2.89 (2H, s), 1.38 (6H, s). Exchangeable proton was not observed. LCMS (ES+) 422.0 (M+H)$^+$, RT 3.20 minutes (Method 1).

Example 184

6,6-Dimethyl-2-{6-[1-(2-hydroxyethyl)-1H-pyrazol-4-yl]-2,3-dihydro-4H-1,4-benzoxazin-4-yl}-6,7-dihydro[1,3]thiazolo[5,4-c]pyridin-4(5H)-one The title compound was prepared from Example 292 and 2-(4-bromo-1H-pyrazol-1-yl)ethanol according to Method AD (90° C.) and was isolated as a white solid (45%) after purification by preparative HPLC (Method 6). $\delta_H$ (CDCl$_3$) 7.99 (1H, d, J 1.9 Hz), 7.72 (1H, s), 7.65 (1H, s), 7.16 (1H, dd, J 8.3 and 1.9 Hz), 6.95 (1H, d, J 8.3 Hz), 5.52 (1H, s), 4.37-4.31 (2H, m), 4.31-4.25 (2H, m), 4.21-4.15 (2H, m), 4.07-4.01 (2H, m), 2.87 (2H, s), 1.40 (6H, s). One exchangeable proton was not observed. LCMS (ES+) 426.0 (M+H)$^+$, RT 2.59 minutes (Method 1).

Example 185

6,6-Dimethyl-2-{(3S)-3-[(5-(morpholin-4-yl)-1H-indol-3-yl)methyl]morpholin-4-yl}-6,7-dihydro[1,3]thiazolo[5,4-c]pyridin-4(5H)-one The title compound was prepared from Intermediate 141 according to Method J and was isolated as a white solid (67%) after purification by column chromatography (SiO$_2$, 0-4% MeOH/DCM). $\delta_H$ (CD$_3$OD) 7.41 (1H, d, J 2.0 Hz), 7.29 (1H, d, J 8.8 Hz), 7.11 (1H, s), 6.96 (1H, dd, J 9.2 and 2.2 Hz), 4.24-4.13 (1H, m), 4.05-3.94 (1H, m), 3.98-3.83 (5H, m), 3.75-3.51 (4H, m), 3.46-3.34 (1H, m), 3.17 (4H, m), 3.03 (1H, dd, J 13.9 and 4.6 Hz), 2.79 (2H, s), 1.36 (6H, s). Exchangeable protons were not observed. LCMS (ES+) 482.2 (M+H)$^+$, RT 1.46 minutes (Method 9), RT 1.98 minutes (Method 10).

Example 186

2-{(3S)-3-[(5-(Azetidin-1-yl)-1H-indol-3-yl)methyl]morpholin-4-yl}-6,6-dimethyl-6,7-dihydro[1,3]thiazolo[5,4-c]pyridin-4(5H)-one The title compound was prepared from Intermediate 142 according to Method J (4M HCl in 1,4-dioxane at r.t. for 16 h, then at 100° C. for 4 h; the reaction mixture was then stirred in DCM and TFA, 3:1 ratio, at r.t. for 30 minutes) and was isolated as a white solid (6%) after purification by column chromatography (SiO$_2$, 0-10% MeOH/DCM with 0-1% NH$_4$OH added, followed by SiO$_2$, 0-4% MeOH/EtOAc). $\delta_H$ (CD$_3$OD) 7.23 (1H, d, J 8.6 Hz), 7.08 (1H, s), 6.93 (1H, d, J 2.0 Hz), 6.51 (1H, dd, J 8.6 and 2.2 Hz), 4.23-4.10 (1H, m), 4.11-4.02 (1H, m), 3.97-3.84 (5H, m), 3.78-3.54 (4H, m), 3.46-3.33 (1H, m), 3.08-2.98 (1H, m), 2.79 (2H, s), 2.46-2.30 (2H, m), 1.36 (6H, s). Exchangeable protons were not observed. LCMS (ES+) 452.1 (M+H)$^+$, RT 0.78 minutes (Method 9), RT 1.86 minutes (Method 10).

Example 187

N-[(3-{[(3S)-4-(6,6-Dimethyl-4-oxo-4,5,6,7-tetrahydro[1,3]thiazolo[5,4-c]pyridin-2-yl)morpholin-3-yl]methyl}-1H-indol-5-yl)methyl]acetamide The title compound was prepared from Intermediate 147 (dissolved in MeOH) according to Method J and was isolated as a white solid (44%) after purification by column chromatography (SiO$_2$, 0-3% MeOH/DCM). $\delta_H$ (CDCl$_3$) 8.20 (1H, s), 7.81 (1H, s), 7.32 (1H, d, J 8.3 Hz), 7.17 (1H, dd, J 8.6 and 1.5 Hz), 7.11 (1H, d, J 2.3 Hz), 6.20-6.11 (1H, m), 5.58 (1H, s), 4.62-4.46 (2H, m), 4.09-3.99 (2H, m), 3.82 (1H, d, J 11.6 Hz), 3.89 (1H, d, J 11.6 Hz), 3.71-3.51 (3H, m), 3.41 (1H, dd, J 13.9 and 10.9 Hz), 3.05 (1H, dd, J 13.6 and 4.0 Hz), 2.83 (2H, d, J 0.8 Hz), 2.03 (3H, s), 1.39 (6H, s). LCMS (ES+) 468.0 (M+H)$^+$, RT 2.19 minutes (Method 5).

Example 188

3-{[(3S)-4-(6,6-Dimethyl-4-oxo-4,5,6,7-tetrahydro[1,3]thiazolo[5,4-c]pyridin-2-yl)morpholin-3-yl]methyl}-1-methyl-1H-indole-5-carbonitrile The title compound was prepared from Intermediate 46 and Intermediate 150 according to Method N and was isolated as a white solid (38%) after purification by column chromatography (SiO$_2$, 0-10% MeOH/EtOAc), followed by preparative HPLC (Method 13). δ$_H$ (DMSO-d$_6$) 8.45 (1H s), 7.64-7.56 (1H, m), 7.50 (1H, dd, J 8.6 and 1.3 Hz), 7.43 (1H, s), 7.35-7.32 (1H, m), 4.29-4.21 (1H, m), 4.02-3.97 (1H, m), 3.78 (3H, s), 3.74 (1H, d, J 11.9 Hz), 3.60-3.45 (4H, m), 3.32-3.24 (1H, m), 2.93 (1H, dd, J 14.1 and 11.8 Hz), 2.77 (2H, s), 1.26 (6H, s). LCMS (ES+) 436.2 (M+H)$^+$, RT 2.37 minutes (Method 12).

Example 189

3-{[(3S)-4-(6,6-Dimethyl-4-oxo-4,5,6,7-tetrahydro [1,3]thiazolo[5,4-c]pyridin-2-yl)morpholin-3-yl] methyl}-1-methyl-1H-indole The title compound was prepared from Intermediate 46 and Intermediate 154 according to Method N and was isolated as a white solid (39%) after purification by preparative HPLC (Method 13). δ$_H$ (DMSO-d$_6$) 7.77 (1H, d, J 8.8 Hz), 7.39 (1H, d, J 8.1 Hz), 7.32 (1H, s), 7.20 (1H, s), 7.23-7.10 (1H, m), 7.06 (1H, s), 4.06-3.99 (1H, m), 4.10-3.85 (1H, m), 3.72 (3H, s), 3.70-3.60 (1H, m), 3.56-3.54 (2H, m), 3.49-3.47 (1H, m), 3.33-3.31 (2H, m), 2.85 (1H, dd, J 13.8 and 4.0 Hz), 2.73 (2H, d, J 3.2 Hz), 1.26 (6H, s). LCMS (ES+) 411.2 (M+H)$^+$, RT 2.49 minutes (Method 12).

Example 190

6,6-Dimethyl-2-[(3S)-3-{[7-(2-(morpholin-4-yl) ethoxy)-1H-indol-3-yl]methyl}-morpholin-4-yl]-6,7-dihydro[1,3]thiazolo[5,4-c]pyridin-4(5H)-one The title compound was prepared from Intermediate 46 and Intermediate 161 according to Method N and was isolated as a white solid (59%) after purification by column chromatography (SiO$_2$, 0-100% EtOAc/hexanes). δ$_H$ (CDCl$_3$) 9.28 (1H, br. s), 7.55 (1H, d, J 8.0 Hz), 7.14 (1H, s), 7.08 (1H, dd, J 8.0 and 7.6 Hz), 6.71 (1H, d, J 7.6 Hz), 5.11 (1H, br. s), 4.31-4.28 (2H, m), 4.12-4.02 (2H, m), 3.91-3.40 (10H, m), 3.07-2.60 (9H, m), 1.41 (6H, s). LCMS (ES+) 526.0 (M+H)$^+$, RT 2.35 minutes (Method 5).

Example 191

Method AH

5-Chloro-3-{[(3S)-4-(6,6-dimethyl-4-oxo-4,5,6,7-tetrahydro[1,3]thiazolo[5,4-c]pyridin-2-yl)morpholin-3-yl]methyl}-N-methyl-1H-indole-7-carboxamide To a stirred suspension of methylamine hydrochloride (0.06 g, 0.92 mmol) in THF (2 mL) at 0° C. was added trimethylaluminium (0.46 mL, 2M in toluene, 0.92 mmol) dropwise. The reaction mixture was warmed to r.t., then stirred for 30 minutes. A solution of Example 128 (0.15 g, 0.307 mmol) in THF (3 mL) was then added and the reaction mixture stirred at 75° C. for 1.5 h. DCM (10 mL) and brine (10 mL) were added. The organic fraction was separated, dried (MgSO$_4$), filtered and concentrated in vacuo. Purification by column chromatography (SiO$_2$, 5% MeOH/DCM), followed by crystallisation with Et$_2$O and preparative HPLC (Method 13) gave the title compound (0.036 g, 24%) as a white solid. δ$_H$ (CDCl$_3$) 10.10 (1H, s), 8.25 (1H, s), 7.32 (1H, d, J 1.5 Hz), 7.23 (1H, d, J 1.8 Hz), 6.39-6.31 (1H, m), 5.17 (1H, s), 4.36-4.28 (1H, m), 4.10-4.04 (1H, m), 3.84 (1H, d, J 12.0 Hz), 3.74-3.65 (1H, m), 3.64-3.55 (1H, m), 3.55-3.43 (1H, m), 3.42-3.33 (1H, m), 3.06 (3H, d, J 4.8 Hz), 2.98-2.91 (4H, m), 1.40 (6H, s). LCMS (ES+) 488.0 (M+H)$^+$, RT 2.12 minutes (Method 12).

Example 192

3-{[(3S)-4-(6,6-Dimethyl-4-oxo-4,5,6,7-tetrahydro [1,3]thiazolo[5,4-c]pyridin-2-yl)morpholin-3-yl] methyl}-N,N,N',N'-tetramethyl-1H-indole-5,7-dicarboxamide The title compound was prepared from Intermediate 46 and Intermediate 167 according to Method N and was isolated as a white solid (24%) after purification by preparative HPLC (Method 13). δ$_H$ (DMSO-d$_6$) 11.00 (1H, br. s), 8.05 (1H, s), 7.31-7.27 (2H, m), 7.12 (1H, s), 4.24-4.16 (1H, m), 4.02-3.96 (1H, m), 3.76 (1H, d, J 11.7 Hz), 3.57-3.47 (3H, m), 3.30 (6H, s), 3.02 (6H, s), 3.02-2.84 (3H, m), 2.70 (2H, s), 1.25 (6H, s). LCMS (ES+) 539.0 (M+H)$^+$, RT 1.64 minutes (Method 12).

Example 193

Methyl N-(3-{[(3S)-4-(6,6-dimethyl-4-oxo-4,5,6,7-tetrahydro[1,3]thiazolo[5,4-c]pyridin-2-yl)morpholin-3-yl]methyl}-1H-indol-5-yl)-N-methylcarbamate The title compound was prepared from Intermediate 46 and Intermediate 173 according to Method N and was isolated as an off-white solid (25%) after purification by column chromatography (SiO$_2$, 10% MeOH/DCM, followed by SiO$_2$, 100% EtOAc). δ$_H$ (DMSO-d$_6$) 10.94 (1H, s), 7.82 (1H, s), 7.35-7.28 (3H, m), 6.97 (1H, d, J 8.5 and 1.9 Hz), 4.20-4.17 (1H, d, J 8.9 Hz), 3.98 (1H, d, J 7.5 Hz), 3.74 (1H, d, J 11.6 Hz), 3.65-3.47 (5H, m), 3.33-3.24 (6H, d, J 16.1 Hz), 2.84 (1H, d, J 10.2 Hz), 2.70 (2H, s), 1.26 (6H, s). LCMS (ES+) 484.0 (M+H)$^+$. RT 2.05 minutes (Method 11).

Example 194

2-{(3S)-3-[(5-Acetyl-1H-indol-3-yl)methyl]morpholin-4-yl}-6,6-dimethyl-6,7-dihydro[1,3]thiazolo[5,4-c]pyridin-4(5H)-one The title compound was prepared from Intermediate 46 and Intermediate 177 according to Method N and was isolated as a yellow solid (43%) after purification by column chromatography (SiO$_2$, 80-100% EtOAc/hexanes). δ$_H$ (DMSO-d$_6$) 11.29 (1H, s), 8.47 (1H, s), 7.73 (1H, d, J 8.6 Hz), 7.41 (1H, d, J 8.6 Hz), 7.33 (1H, d, J 2.0 Hz), 7.29 (1H, s), 4.27-4.16 (1H, m), 4.06-3.99 (1H, m), 3.75 (1H, d, J 11.6 Hz), 3.65-3.51 (4H, m), 3.37-3.34 (1H, m), 3.03 (1H, dd, J 13.8 and 4.8 Hz), 2.73 (2H, s), 2.63 (3H, s), 1.24 (6H, s). LCMS (ES+) 439.0 (M+H)$^+$, RT 2.87 minutes (Method 5).

Example 195

6,6-Dimethyl-2-[(3S)-3-({5-[N-(hydroxy)ethanimidoyl]-1H-indol-3-yl}methyl)-morpholin-4-yl]-6,7-dihydro[1,3]thiazolo[5,4-c]pyridin-4(5H)-one To a stirred suspension of hydroxylamine hydrochloride (0.03 g, 0.41 mmol) and anhydrous potassium carbonate (0.06 g, 0.41 mmol) in EtOH (10 mL) was added a solution of Example 194 (0.17 g, 0.39 mmol) in EtOH (10 mL) dropwise. The reaction mixture was stirred at 80° C. for 16 h, then cooled to r.t., filtered and the filtrate concentrated in vacuo.

Et$_2$O (100 mL) and water (100 mL) were added. The aqueous fraction was separated, then extracted with Et$_2$O (2×50 mL). The combined organic fractions were dried (Na$_2$SO$_4$), filtered and concentrated in vacuo. Purification by column chromatography (SiO$_2$, 60-80% EtOAc/hexanes) gave the title compound (0.11 g, 63%) as a pale yellow solid. $\delta_H$ (DMSO-d$_6$) 11.01 (1H, s), 10.83 (1H, s), 7.98 (1H, s), 7.50 (1H, dd, J 8.6 and 1.3 Hz), 7.34-7.30 (2H, m), 7.22 (1H, d, J 2.0 Hz), 4.19-4.08 (1H, m), 4.01-3.96 (1H, m), 3.76-3.71 (2H, m), 3.59-3.48 (3H, m), 3.37-3.28 (1H, m), 2.94 (1H, dd, J 13.9 and 4.3 Hz), 2.71 (2H, s), 2.25 (3H, s), 1.25 (6H, s). LCMS (ES+) 454.0 (M+H)$^+$, 476 (M+Na)$^+$, RT 2.87 minutes (Method 5).

Example 196

2-{(3S)-3-[(5-Chloro-7-methoxy-1H-indol-3-yl)methyl]morpholin-4-yl}-6,6-dimethyl-6,7-dihydro[1,3]thiazolo[5,4-c]pyridin-4(5H)-one The title compound was prepared from Intermediate 46 and Intermediate 184 according to Method N and was isolated as a white solid (80%) after purification by column chromatography (SiO$_2$, 0-5% EtOH/DCM), followed by trituration in Et$_2$O. $\delta_H$ (CDCl$_3$) 8.32 (1H, s), 7.71 (1H, s), 7.09 (1H,$), 6.65 (1H, s), 5.19 (1H, s), 4.31 (1H, d, J 10.8 Hz), 4.09-4.06 (1H, m), 3.95 (3H, s), 3.89-3.86 (1H, d, J 11.7 Hz), 3.74-3.52 (4H, m), 3.38-3.32 (1H, t, J 11.2 Hz), 3.02-2.91 (3H, m), 1.42 (6H, s). LCMS (ES+) 461.1 (M+H)$^+$, RT 3.27 minutes (Method 5).

Example 197

2-{(3S)-3-[(5-Chloro-7-trifluoromethoxy-1H-indol-3-yl)methyl]morpholin-4-yl}-6,6-dimethyl-6,7-dihydro[1,3]thiazolo[5,4-c]pyridin-4(5H)-one The title compound was prepared from Intermediate 46 and Intermediate 188 according to Method N and was isolated as a white solid (38%) after purification by column chromatography (SiO$_2$, EtOAc), followed by trituration in Et$_2$O. $\delta_H$ (CDCl$_3$) 8.43 (1H, s), 8.10 (1H, d, J 0.8 Hz), 7.20 (1H, d, J 2.0 Hz), 7.14 (1H, s), 5.17 (1H, s), 4.41-4.32 (1H, m), 4.09 (1H, dd, J 10.9 and 2.8 Hz), 3.86 (1H, d, J 11.8 Hz), 3.75-3.47 (4H, m), 3.41-3.35 (1H, m), 3.05-3.00 (1H, m), 2.98 (2H, d, J 6.8 Hz), 1.42 (6H, s). LCMS (ES+) 515.0 (M+H)$^+$, RT 3.57 minutes (Method 5).

Example 198

2-{(3S)-3-[(7-Methoxy-1H-indol-3-yl)methyl]morpholin-4-yl}-6,6-dimethyl-6,7-dihydro[1,3]thiazolo[5,4-c]pyridin-4(5H)-one To a stirred solution of Example 196 (0.10 g, 0.22 mmol) in MeOH (5 mL) was added ammonium formate (0.14 g, 2.17 mmol), followed by 10% w/w palladium on carbon (0.03 g). The reaction mixture was heated to 170° C. for 2 h in a sealed tube under microwave irradiation, then filtered through Celite®, and the filtrate concentrated in vacuo. Purification by preparative HPLC (Method 13) gave the title compound (0.025 g, 27%) as a white solid. $\delta_H$ (CDCl$_3$) 8.30 (1H, s), 7.51 (1H, d, J 8.0 Hz), 7.13-7.09 (2H, m), 6.69 (1H, d, J 7.8 Hz), 5.16 (1H, s), 4.12-4.06 (2H, m), 3.98 (3H, s), 3.91-3.41 (6H, m), 3.08-3.04 (1H, m), 2.87 (2H, s), 1.41 (6H, s). LCMS (ES+) 427.1 (M+H)$^+$, RT 3.11 minutes (Method 5).

Example 199

6,6-Dimethyl-2-[(3S)-3-({5-[N-methoxyethanimidoyl]-1H-indol-3-yl}methyl)morpholin-4-yl]-6,7-dihydro[1,3]thiazolo[5,4-c]pyridin-4(5H)-one A mixture of Example 194 (0.145 g, 0.33 mmol), methoxyamine hydrochloride (0.055 g, 0.66 mmol) and conc. HCl (0.5 mL) was stirred at 80° C. for 24 h, then cooled to r.t. and concentrated in vacuo. Purification by column chromatography (SiO$_2$, 1-10% MeOH/DCM), followed by preparative HPLC (Method 13) gave the title compound (51%). $\delta_H$ (CDCl$_3$) 8.22 (1H, br. s), 8.09 (1H, d, J 1.1 Hz), 7.68-7.62 (1H, m), 7.35 (1H, d, J 8.6 Hz), 7.12 (1H, d, J 2.3 Hz), 5.15 (1H, s), 4.28-4.21 (1H, m), 4.20-4.08 (4H, m), 3.88 (1H, d, J 11.7 Hz), 3.80-3.61 (3H, m), 3.58-3.38 (2H, m), 3.10-3.13 (1H, m), 2.84 (2H, s), 2.38 (3H, s), 1.39 (6H, s). LCMS (ES+) 468.1 (M+H)$^+$, RT 1.86 minutes (Method 12).

Example 200

5-Chloro-3-{[(3S)-4-(6,6-dimethyl-4-oxo-4,5,6,7-tetrahydro[1,3]thiazolo[5,4-c]pyridin-2-yl)morpholin-3-yl]methyl}-1H-indole-7-carboxamide The title compound was prepared from Intermediate 46 and Intermediate 189 according to Method N and was isolated as a white solid (45%) after purification by column chromatography (SiO$_2$, 5% MeOH/DCM). $\delta_H$ (DMSO-d$_6$) 11.07 (1H, d, J 1.5 Hz), 8.19-8.07 (2H, m), 7.75 (1H, d, J 1.8 Hz), 7.48 (1H, s), 7.32 (1H, s), 7.26 (1H, d, J 2.3 Hz), 4.26-4.18 (1H, m), 4.03-3.92 (1H, m), 3.70 (1H, m), 3.61-6.46 (4H, m), 3.27 (1H, dd, J 14.1 and 10.1 Hz), 2.92 (1H, dd, J 13.9 and 4.3 Hz), 2.76 (2H, s), 1.26 (3H, s), 1.25 (3H, s). LCMS (ES+) 475 (M+H)$^+$, RT 2.00 minutes (Method 12).

Example 201

Method AI

2-[(3S)-3-(1-Benzofuran-3-ylmethyl)morpholin-4-yl]-6,6-dimethyl-6,7-dihydro[1,3]thiazolo[5,4-c]pyridin-4(5H)-one To a stirred solution of Intermediate 190 (0.25 g, 0.53 mmol) in 1,4-dioxane (4 mL) was added a solution of lithium hydroxide monohydrate (0.047 g, 1.11 mmol) in water (2 mL). The reaction mixture was stirred at 60° C. for 2 h. EtOAc (20 mL) was added. The organic fraction was separated, washed with water (3×5 mL), dried (MgSO$_4$), filtered and concentrated in vacuo. Purification by column chromatography (SiO$_2$, EtOAc), followed by preparative HPLC (Method 13) gave the title compound (0.050 g, 24%), as a white solid. $\delta_H$ (CDCl$_3$) 7.92-7.90 (1H, m), 7.56 (1H, s), 7.51-7.50 (1H, m), 7.36-7.30 (2H, m), 5.17 (1H, s), 4.30-4.28 (1H, m), 4.09-4.07 (1H, m), 3.90-3.87 (1H, m), 3.74-3.57 (4H, m), 3.42-3.36 (1H, m), 3.03-2.98 (1H, m), 2.87-2.86 (2H, m), 1.41 (6H, m). LCMS (ES+) 398.2 (M+H)$^+$, RT 2.50 minutes (Method 12).

Example 202

2-[(3S)-3-{[5-(4,5-Dihydro-1,3-oxazol-2-yl)-1H-indol-3-yl]methyl}morpholin-4-yl]-6,6-dimethyl-6,7-dihydro[1,3]thiazolo[5,4-c]pyridin-4(5H)-one To a stirred solution of Example 26 (0.25 g, 0.51 mmol) in DCM (4 mL) and THF (1 mL) at 0° C. was added thionyl chloride (0.08 mL, 1.03 mmol) dropwise. The reaction mixture was stirred at this temperature for 1 h. DCM (20 mL) and aqueous sat. NaHCO$_3$ (5 mL) were added. The organic fraction was washed with water (2×5 mL), then brine (5 mL), dried (MgSO$_4$), filtered and concentrated in vacuo. Purification by column chromatography (SiO$_2$, 0-4% MeOH/DCM) gave the title compound (0.083 g, 35%) as a white solid. $\delta_H$ (CDCl$_3$) 8.61 (1H, s), 8.50 (1H, s), 7.90-7.87 (1H, m), 7.45-7.37 (1H, d, J 8.5 Hz), 7.15 (1H, d, J 1.8 Hz), 5.15 (1H, s), 4.54-4.47 (2H, m), 4.40-4.22 (1H, m), 4.20-4.00 (3H, m), 3.88 (1H, d, J 11.8 Hz), 3.80-3.35 (5H, m), 3.13-3.01 (1H, m), 2.96 (2H, d, 5.6 Hz), 1.41 (6H, m). LCMS (ES+) 466.3 (M+H)$^+$, RT 1.85 minutes (Method 12).

Example 203

3-{[(3S)-4-(6,6-Dimethyl-4-oxo-4,5,6,7-tetrahydro [1,3]thiazolo[5,4-c]pyridin-2-yl)morpholin-3-yl] methyl}-1-benzofuran-5-carbonitrile The title compound was prepared from Intermediate 46 and Intermediate 194 according to Method N and was isolated as a white solid (15%) after purification by preparative HPLC (Method 13). $\delta_H$ (CDCl$_3$) 8.65 (1H, s), 7.66-7.55 (3H, m), 5.27 (1H, s), 4.52-4.40 (1H, d, J 10.6 Hz), 4.11-4.08 (1H, d, J 11.3 Hz), 3.90-3.50 (4H, m), 3.43-3.30 (2H, m), 3.02 (2H, s), 3.00-2.90 (1H, d, J 13.7 Hz), 1.44 (6H, s). LCMS (ES+) 423.3 (M+H)$^+$, RT 2.32 minutes (Method 12).

Example 204

2-{(3S)-3-[(5,6-Dimethoxy-1H-indol-3-yl)methyl] morpholin-4-yl}-6,6-dimethyl-6,7-dihydro[1,3]thiazolo[5,4-c]pyridin-4(5H)-one The title compound was prepared from Intermediate 46 and Intermediate 199 according to Method N and was isolated as a white solid (57%) after trituration in DCM, then in Et$_2$O. $\delta_H$ (CDCl$_3$) 7.90 (1H, s), 7.37 (1H, s), 7.02 (1H, d, J 2.0 Hz), 6.90 (1H, s), 5.09 (1H, s), 4.15-4.08 (2H, m), 4.03 (3H, s), 3.94 (3H, s), 3.83 (1H, d, J 10.6 Hz), 3.74-3.59 (2H, m), 3.58-3.35 (3H, m), 3.02 (1H, dd, J 13.6 and 3.3 Hz), 2.84 (2H, s), 1.41 (6H, d, J 1.8 Hz). LCMS (ES+) 457.0 (M+H)$^+$, RT 2.81 minutes (Method 5).

Example 205

6,6-Dimethyl-2-{(3S)-3-[(6-methoxy-1H-indol-3-yl) methyl]morpholin-4-yl}-6,7-dihydro[1,3]thiazolo[5, 4-c]pyridin-4(5H)-one The title compound was prepared from Intermediate 201 and Intermediate 46 according to Method K, followed by Method N, and was isolated as a pale yellow solid (40%) after trituration in DCM and recrystallisation from MeOH. $\delta_H$ (CDCl$_3$) 7.97 (1H, s), 7.79 (1H, d, J 8.3 Hz), 7.03 (1H, d, J 2.0 Hz), 6.93-6.80 (2H, m), 5.13 (1H, s), 4.19-4.10 (1H, m), 4.10-4.04 (1H, m), 3.96-3.88 (1H, m), 3.87 (3H, s), 3.80 (1H, d, J 11.1 Hz), 3.74-3.58 (2H, m), 3.56-3.52 (1H, m), 3.41 (1H, dd, J 13.9 and 11.1 Hz), 3.04 (1H, dd, J 13.6 and 4.0 Hz), 2.86 (2H, s), 1.40 (6H, s). LCMS (ES+) 427.0 (M+H)$^+$, RT 2.96 minutes (Method 5).

Example 206

6,6-Dimethyl-2-[(3S)-3-{[5-(methylsulfonyl)-1H-indol-3-yl]methyl}morpholin-4-yl]-6,7-dihydro[1,3] thiazolo[5,4-c]pyridin-4(5H)-one The title compound was prepared from Intermediate 46 and Intermediate 205 according to Method N and was isolated as a pale yellow foam (66%) after purification by column chromatography (SiO$_2$, 0-100% EtOAc/hexanes). $\delta_H$ (DMSO-d$_6$) 11.48 (1H, s), 8.44 (1H, d, J 0.8 Hz), 7.67-7.50 (2H, m), 7.45 (1H, s), 7.28 (1H, s), 4.30 (1H, br. s), 4.02-3.92 (1H, m), 3.75 (1H, d, J 11.6 Hz), 3.66-3.45 (5H, m), 3.16 (3H, s), 3.03 (1H, dd, J 14.1 and 4.8 Hz), 2.77 (2H, m), 1.24 (3H, s), 1.23 (3H, s). LCMS (ES+) 475.0 (M+H)$^+$, RT 2.73 minutes (Method 5).

Example 207

6,6-Dimethyl-2-[(3S)-3-(5H-[1,3]dioxolo[4,5-f]indol-7-ylmethyl)morpholin-4-yl]-6,7-dihydro[1,3] thiazolo[5,4-c]pyridin-4(5H)-one The title compound was prepared from Intermediate 46 and Intermediate 210 according to Method N and was isolated as a white solid (46%) after trituration in DCM, and then in Et$_2$O. $\delta_H$ (DMSO-d$_6$) 10.69 (1H, d, J 1.0 Hz), 7.32 (1H, s), 7.25 (1H, s), 7.02 (1H, d, J 2.3 Hz), 6.86 (1H, s), 5.93 (2H, m), 4.14-4.03 (1H, m), 4.01-3.94 (1H, m), 3.76-3.68 (1H, m), 3.67-3.43 (4H, m), 3.21 (1H, dd, J 13.6 and 10.6 Hz), 2.81 (1H, dd, J 13.9 and 4.0 Hz), 2.74 (2H, s), 1.26 (6H, s). LCMS (ES+) 444.1 (M+H)$^+$, RT 2.98 minutes (Method 5).

Example 208

Methyl 6-chloro-3-{[(3S)-4-(6,6-dimethyl-4-oxo-4, 5,6,7-tetrahydro[1,3]thiazolo[5,4-c]pyridin-2-yl) morpholin-3-yl]methyl}-1H-indole-5-carboxylate The title compound was prepared from Intermediate 46 and Intermediate 212 according to Method N and was isolated as a white solid (47%) after trituration in DCM, and then in Et$_2$O. $\delta_H$ (CDCl$_3$) 8.62 (1H, s), 8.50 (1H, s), 7.46 (1H, s), 7.13 (1H, s), 5.21 (1H, s), 4.30-4.17 (1H, m), 4.08 (1H, d, J 10.9 Hz), 4.00 (3H, s), 3.84 (1H, d, J 11.9 Hz), 3.71-3.53 (4H, m), 3.40 (1H, m), 3.09 (1H, dd, J 13.9 and 4.0 Hz), 2.86 (2H, s), 1.41 (3H, s), 1.39 (3H, s). LCMS (ES+) 489.0 and 491.0 (M+H)$^+$, RT 3.04 minutes (Method 5).

Example 209

6,6-Dimethyl-2-[(3S)-3-[5-(1H-1,2,4-triazol-1-yl)-1H-indol-3-yl]methyl morpholin-4-yl]-6,7-dihydro [1,3]thiazolo[5,4-c]pyridin-4(5H)-one The title compound was prepared from Intermediate 46 and Intermediate 216 according to Method N and was isolated as a yellow solid (32%) after purification by column chromatography (SiO$_2$, 0-10% MeOH/DCM, followed by SiO$_2$, 0-8% MeOH/DCM). $\delta_H$ (DMSO-d$_6$) 11.19 (1H, d, J 0.8 Hz), 9.10 (1H, s), 8.24 (1H, s), 8.19 (1H, s), 7.49 (2H, s), 7.35 (1H, d, J 2.0 Hz), 7.29 (1H, s), 4.35-4.24 (1H, m), 4.06-3.99 (1H, m), 3.76 (1H, d, J 11.6 Hz), 3.65-3.42 (4H, m), 3.35-3.26 (1H, m), 2.98 (1H, dd, J 13.6 and 4.0 Hz), 2.70-2.61 (2H, m), 1.24 (3H, s), 1.23 (3H, s). LCMS (ES+) 464.0 (M+H)$^+$, RT 2.75 minutes (Method 5).

Example 210

2-(7-Bromo-6-methyl-2,3-dihydro-4H-1,4-benzoxazin-4-yl)-6,6-dimethyl-6,7-dihydro[1,3]thiazolo[5, 4-c]pyridin-4(5H)-one The title compound was prepared from Intermediate 46 and Intermediate 219 according to Method N (heating to 120°

C. under microwave irradiation in a sealed tube for 20 minutes) and was isolated as a yellow solid (83%) after purification by column chromatography (SiO$_2$, 0-100% EtOAc/heptane, followed by SiO$_2$, 15% MeOH/DCM). $\delta_H$ (DMSO-d$_6$) 8.17 (1H, s), 7.57 (1H, br. s), 7.19 (1H, s), 4.32-4.27 (2H, m), 4.04 (2H, t, J 4.9 Hz), 2.83 (2H, s), 2.30 (3H, s), 1.28 (6H, s). LCMS (ES+) 408.0 and 410.0 (M+H)$^+$, RT 3.88 minutes (Method 1).

Example 211

2-[7-(3-Aminopyrrolidin-1-yl)-6-methyl-2,3-dihydro-4H-1,4-benzoxazin-4-yl]-6,6-dimethyl-6,7-dihydro[1,3]thiazolo[5,4-c]pyridin-4(5H)-one formate The title compound was prepared from Example 210 and 3-(tert-butoxycarbonyl)-aminopyrrolidine according to Method U and was isolated as a yellow glass (19%) after purification by column chromatography (SiO$_2$, 0-100% EtOAc/heptane, followed by SiO$_2$, 15% MeOH/DCM), then by treatment with 2M HCl in Et$_2$O for 16 h, concentration in vacuo and further purification by preparative HPLC (Method 6). $\delta_H$ (CD$_3$OD) 8.49 (2H, s, formic acid), 7.64 (1H, s), 6.60 (1H, s), 4.32-4.25 (2H, dd, J 5.7 and 4.0 Hz), 4.16-4.10 (2H, m), 3.99-3.90 (1H, m), 3.78-3.71 (1H, m), 3.54-3.43 (1H, m), 3.12-2.98 (1H, m), 2.88 (2H, s), 2.54-2.40 (1H, m), 2.32 (3H, s), 2.08-1.98 (1H, m), 1.92-1.88 (1H, m), 1.39 (6H, m). Exchangeable protons were not observed. LCMS (ES+) 414.0 (M+H)$^+$, RT 1.96 minutes (Method 1).

Example 212

2-(7-{N-[3-(Dimethylamino)propyl]-N-(methyl)amino}-6-methyl-2,3-dihydro-4H-1,4-benzoxazin-4-yl)-6,6-dimethyl-6,7-dihydro[1,3]thiazolo[5,4-c]pyridin-4(5H)-one The title compound was prepared from Example 210 and N,N,N'-trimethyl-1,3-propanediamine according to Method U and was isolated as an off-white solid (6%) after purification by preparative HPLC (Method 6). $\delta_H$ (CD$_3$OD) 7.60 (1H, s), 6.63 (1H, s), 4.31-4.26 (2H, m), 4.16-4.12 (2H, m), 2.94-2.83 (4H, m), 2.62 (3H, s), 2.55-2.44 (2H, m), 2.35 (6H, s), 2.23 (3H, s), 1.98-1.55 (2H, m), 1.39 (6H, s). Exchangeable proton was not observed. LCMS (ES+) 444.1 (M+H)$^+$, RT 1.96 minutes (Method 1).

Example 213

6,6-Dimethyl-2-{6-methyl-7-[N-methyl-N-(piperidin-4-yl)amino]-2,3-dihydro-4H-1,4-benzoxazin-4-yl}-6,7-dihydro[1,3]thiazolo[5,4-c]pyridin-4(5H)-one To a stirred solution of Intermediate 221 (0.03 g, 0.06 mmol) in DCM (2 mL) was added 2M HCl in Et$_2$O (2 mL). The reaction mixture was stirred at r.t. for 16 h, then concentrated in vacuo. Purification by column chromatography (SiO$_2$, 5-15% MeOH/DCM with 2% NH$_4$OH added) gave the title compound (0.024 g, 92%) as a yellow solid. $\delta_H$ (CDCl$_3$) 7.62 (1H, s), 6.65 (1H, s), 5.24 (1H, br. s), 4.29 (2H, dd, J 5.7 and 4.0 Hz), 4.17-4.11 (2H, m), 3.12 (2H, d, J 12.2 Hz), 2.89-2.78 (3H, m), 2.62 (3H, s), 2.56 (2H, td, J 11.9 and 2.3 Hz), 2.22 (3H, s), 1.79-1.69 (2H, m), 1.66-1.51 (2H, m), 1.39 (6H, s). One exchangeable proton was not observed. LCMS (ES+) 442.1 (M+H)$^+$, RT 2.01 minutes (Method I).

Example 214

2-(7-Bromo-2,3-dihydro-4H-1,4-benzoxazin-4-yl)-6,6-dimethyl-6,7-dihydro[1,3]thiazolo[5,4-c]pyridin-4(5H)-one The title compound was prepared from Intermediate 46 and Intermediate 223 according to Method N (at 120° C. under microwave irradiation in a sealed tube for 20 minutes) and was isolated as a yellow solid (76%) after purification by column chromatography (SiO$_2$, 0-100% EtOAc/heptane, followed by SiO$_2$, 15% MeOH/DCM with 2% NH$_4$OH added). $\delta_H$ (DMSO-d$_6$) 8.21 (1H, d, J 8.7 Hz), 7.57 (1H, s), 7.20-7.13 (2H, m), 4.37-4.31 (2H, m), 4.06-4.01 (2H, m), 2.82 (2H, s), 1.28 (6H, s). LCMS (ES+) 396.1 and 394.1 (M+H)$^+$, RT 3.66 minutes (Method 1).

Example 215

Method AL 2-(7-{N-[2-(Diethylamino)ethyl]-N-(methyl)amino}-2,3-dihydro-4H-1,4-benzoxazin-4-yl)-6,6-dimethyl-6,7-dihydro[1,3]thiazolo[5,4-c]pyridin-4(5H)-one acetate A stirred solution of Example 214 (0.05 g, 0.13 mmol), N,N-diethyl-N'-methylethylenediamine (0.03 g, 0.25 mmol), sodium tert-butoxide (0.029 g, 0.305 mmol), palladium acetate (0.003 g, 0.013 mmol) and tri-tert-butylphosphonium tetrafluoroborate (0.007 g, 0.025 mmol) in DME (1 mL) was heated to 140° C. under microwave irradiation in a sealed tube for 2 h, then concentrated in vacuo. Purification by preparative HPLC (Method 7) gave the title compound (0.019 g, 30%) as a brown gum. $\delta_H$ (CDCl$_3$) 7.63 (1H, d, J 9.0 Hz), 6.31 (1H, dd, J 9.0 and 2.8 Hz), 6.27-6.23 (1H, m), 5.64 (1H, s), 4.33-4.26 (2H, m), 4.17-4.08 (2H, m), 3.56-3.46 (2H, m), 2.94 (3H, s), 2.84 (2H, s), 2.76-2.68 (2H, m), 2.79-2.65 (4H, m), 2.04 (3H, s, AcOH), 1.39 (6H, s) 1.11 (6H, t, J 7.2 Hz). LCMS (ES+) 444.0 (M+H)$^+$, RT 1.98 minutes (Method 1).

Example 216

2-(7-{N-[3-(Dimethylamino)propyl]-N-(methyl)amino}-2,3-dihydro-4H-1,4-benzoxazin-4-yl)-6,6-dimethyl-6,7-dihydro[1,3]thiazolo[5,4-c]pyridin-4(5H)-one formate The title compound was prepared from Example 214 and N,N,N'-trimethyl-1,3-propanediamine according to Method AL and was isolated as a beige solid (55%) after purification by preparative HPLC (Method 7). $\delta_H$ (CDCl$_3$) 8.43 (1H, s, formic acid), 7.64 (1H, d, J 9.0 Hz), 6.30 (1H, dd, J 9.0 and 2.8 Hz), 6.25 (1H, d, J 2.8 Hz), 5.47 (1H, s), 4.32-4.27 (2H, m), 4.15-4.10 (2H, m), 3.38 (2H, t, J 7.0 Hz), 2.94-2.80 (2H, m), 2.90 (3H, s), 2.84 (2H, s), 2.63 (6H, s), 1.98 (2H, quintet, J 7.0 Hz), 1.38 (6H, s). LCMS (ES+) 430.0 (M+H)$^+$, RT 1.92 minutes (Method 1).

Example 217

2-[7-(3-Aminopyrrolidin-1-yl)-2,3-dihydro-4H-1,4-benzoxazin-4-yl]-6,6-dimethyl-6,7-dihydro[1,3]thiazolo[5,4-c]pyridin-4(5H)-one formate The title compound was prepared from Example 214 and 3-aminopyrrolidine according to Method AL and was isolated as a yellow gum (7%) after purification by preparative HPLC (Method 7). $\delta_H$ (CD$_3$OD) 8.55 (1H, s, formic acid), 7.63 (1H, d, J 8.9 Hz), 6.32 (1H, dd, J 9.0 and 2.5 Hz), 6.23 (1H, d, J 2.5 Hz), 4.34-4.23 (2H, m), 4.18-4.12 (1H, m), 4.03-3.92 (1H, m), 3.67-3.52 (2H, m), 3.44-3.35 (2H, m), 2.85 (2H, s), 2.52-2.38 (1H, m), 2.20-2.02 (1H, m), 1.38 (6H, s). LCMS (ES+) 400.0 (M+H)$^+$, RT 1.86 minutes (Method 1).

Example 218

6,6-Dimethyl-2-{7-[N-methyl-N-(1-methylpyrrolidin-3-yl)amino]-2,3-dihydro-4H-1,4-benzoxazin-4-yl}-6,7-dihydro[1,3]thiazolo[5,4-c]pyridin-4(5H)-one formate The title compound was prepared from Example 214 and 1-methyl-3-(methylamino)pyrrolidine according to Method AL and was isolated as a yellow gum (9%) after purification by preparative HPLC (Method 7). $\delta_H$ (CDCl$_3$) 8.42 (1H, s, formic acid), 7.70 (1H, d, J 9.0 Hz), 6.46 (1H, dd, J 9.0 and 3.0 Hz), 6.41 (1H, d, J 2.9 Hz), 5.38 (1H, s), 4.61-4.47 (1H, m), 4.30 (2H, s), 4.15-4.08 (2H, m), 3.22-2.80 (4H, m) 2.85 (2H, s), 2.83 (3H, s), 2.63 (3H, s), 2.34-2.17 (1H, m), 2.15-2.00 (1H, m), 1.38 (6H, s). LCMS (ES+) 428.0 (M+H)$^+$, RT 1.90 minutes (Method 1).

Example 219

6,6-Dimethyl-2-{7-[N-methyl-N-(2-(pyridin-2-yl)ethyl)amino]-2,3-dihydro-4H-1,4-benzoxazin-4-yl}-6,7-dihydro[1,3]thiazolo[5,4-c]pyridin-4(5H)-one The title compound was prepared from Example 214 and 2-[2-(methylamino)-ethyl]pyridine according to Method AL and was isolated as a yellow gum (25%) after purification by preparative HPLC (Method 7). $\delta_H$ (CDCl$_3$) 8.57 (1H, d, J 2.0 Hz), 7.63 (1H, d, J 9.1 Hz), 7.58 (1H, dd, J 7.5 and 1.5 Hz), 7.17-7.11 (2H, m), 6.34 (1H, dd, J 8.9 and 2.9 Hz), 6.28 (1H, d, J 2.9 Hz), 5.31 (1H, s), 4.34-4.26 (2H, m), 4.17-4.10 (2H, m), 3.73 (2H, t, J 7.5 Hz), 3.03 (2H, t, J 7.5 Hz), 2.85 (5H, s), 1.39 (6H, s). LCMS (ES+) 450.0 (M+H)$^+$, RT 2.11 minutes (Method 1).

Example 220

2-(7-{N-[2-(Dimethylamino)ethyl]-N-(ethyl)amino}-2,3-dihydro-4H-1,4-benzoxazin-4-yl)-6,6-dimethyl-6,7-dihydro[1,3]thiazolo[5,4-c]pyridin-4(5H)-one formate The title compound was prepared from Example 214 and N,N-dimethyl-N'-ethyl-ethylenediamine according to Method AL and was isolated as a yellow gum (17%) after purification by preparative HPLC (Method 6). $\delta_H$ (CDCl$_3$) 8.44 (1H, s, formic acid), 7.65 (1H, d, J 9.0 Hz), 6.30 (1H, dd, J 9.0 and 2.9 Hz), 6.26 (1H, d, J 2.9 Hz), 5.39 (1H, s), 4.34-4.26 (2H, m), 4.16-4.09 (2H, m), 3.57 (2H, t, J 7.5 Hz), 3.36 (2H, q, J 7.0 Hz), 2.84 (2H, s), 2.82 (2H, t, J 7.5 Hz), 2.56 (6H, s), 1.38 (6H, s), 1.14 (3H, t, J 7.0 Hz). LCMS (ES+) 430.0 (M+H)$^+$, RT 1.98 minutes (Method 1).

Example 221

6,6-Dimethyl-2-{7-[N-methyl-N-(1-methylpiperidin-4-yl)amino]-2,3-dihydro-4H-1,4-benzoxazin-4-yl}-6,7-dihydro[1,3]thiazolo[5,4-c]pyridin-4(5H)-one formate The title compound was prepared from Example 214 and 1-methyl-4-(methylamino)piperidine according to Method AL and was isolated as a cream solid (3%) after purification by preparative HPLC (Method 6). $\delta_H$ (CDCl$_3$) 8.43 (1H, s, formic acid), 7.65 (1H, d, J 8.9 Hz), 6.40 (1H, dd, J 9.1 and 2.9 Hz), 6.34 (1H, d, J 3.0 Hz), 5.21 (1H, s), 4.34-4.26 (2H, m), 4.19-4.09 (2H, m), 3.71-3.57 (1H, m), 3.37-3.26 (2H, m), 2.84 (2H, s), 2.77 (3H, s), 2.53 (3H, s), 2.52-4.38 (2H, m), 2.20-1.76 (4H, m), 1.38 (6H, s). LCMS (ES+) 442.0 (M+H)$^+$, RT 1.86 minutes (Method 1).

Example 222

6,6-Dimethyl-2-{7-[N-methyl-N-(piperidin-4-ylmethyl)amino]-2,3-dihydro-4H-1,4-benzoxazin-4-yl}-6,7-dihydro[1,3]thiazolo[5,4-c]pyridin-4(5H)-one acetate A stirred solution of Example 214 (0.05 g, 0.13 mmol), 1-BOC-4-(aminomethyl)-piperidine (0.054 g, 0.25 mmol), potassium tert-butoxide (0.034 g, 0.305 mmol), palladium acetate (0.003 g, 0.013 mmol) and tri-tert-butylphosphonium tetrafluoroborate (0.007 g, 0.025 mmol) in DME (1 mL) was heated to 140° C. under microwave irradiation in a sealed tube for 1 h, then concentrated in vacuo. The residue was purified by column chromatography (SiO$_2$, 20-100% EtOAc/heptane), then dissolved in DMF (1 mL). Na$_2$CO$_3$ (0.05 g, 0.47 mmol) was added, followed by iodomethane (1 mL, excess). The reaction mixture was heated to 100° C. under microwave irradiation in a sealed tube for 10 minutes. Water (10 mL) and EtOAc (20 mL) were added. The organic fraction was separated, dried (Na$_2$SO$_4$), filtered, and concentrated in vacuo. The residue was purified by column chromatography (SiO$_2$, 20-100% EtOAc/heptane), then dissolved in MeOH before addition of TFA (0.5 mL). The reaction mixture was heated to 100° C. under microwave irradiation in a sealed tube for 5 minutes, then concentrated in vacuo. Purification by preparative HPLC (Method 7) gave the title compound (0.0025 g, 4%) as a cream solid. $\delta_H$ (CDCl$_3$) 7.62 (1H, d, J 9.0 Hz), 6.26 (1H, dd, J 8.9 and 2.8 Hz), 6.22-6.18 (1H, m), 5.45 (1H, s), 4.34-4.26 (2H, m), 4.16-4.10 (2H, m), 3.34-3.23 (2H, m), 3.19 (2H, d, J 7.2 Hz), 2.95 (3H, s), 2.84 (2H, s), 2.74-2.60 (2H, m), 2.02 (3H, s, AcOH), 1.99-1.85 (1H, m), 1.85-1.72 (2H, m), 1.46-1.33 (2H, m), 1.38 (6H, s). One exchangeable proton was not observed. LCMS (ES+) 442.0 (M+H)$^+$, RT 2.41 minutes (Method 2).

Example 223

Method AM 6,6-Dimethyl-2-{7-[(4-methylpiperazin-1-yl)carbonyl]-2,3-dihydro-4H-1,4-benzoxazin-4-yl}-6,7-dihydro[1,3]thiazolo[5,4-c]pyridin-4(5H)-one To a stirred suspension of Example 214 (0.12 g, 0.29 mmol) in THF (8 mL) at −78° C. was added n-butyllithium (0.3 mL, 2.5M in hexanes, 0.74 mmol). After stirring at this temperature for 1 h, CO$_2$ was bubbled through the reaction mixture, which was then allowed to warm to r.t. Aqueous NaOH (2M, 10 mL) and DCM (20 mL) were added. The aqueous fraction was washed with DCM (10 mL), then acidified with 2M aqueous HCl and extracted with a mixture of DCM/THF (4:1, 2×20 mL). The combined organic fractions were concentrated in vacuo, and the residue was dissolved in DMF (5 mL). DIPEA (0.2 mL, excess) was added, followed by 2-(1H-benzotriazol-1-yl)-1,1,3,3-tetramethyluronium hexafluorophosphate (0.08 g, 0.29 mmol). The reaction mixture was stirred at r.t. until homogeneous, then for a further 30 minutes, and separated into four equal portions. 1-Methylpiperazine (0.1 g, excess) was added to one portion, and the reaction mixture left to stand for 1 h before being filtered. Purification by preparative HPLC (Method 7) gave the title compound (0.023 g, 70%) as a yellow gum. $\delta_H$ (CDCl$_3$) 8.08 (1H, d, J 8.1 Hz), 7.04 (1H, d, J 1.9 Hz), 7.01 (1H, dd, J 8.0 and 1.9 Hz), 5.75 (1H, s), 4.41-4.30 (2H, m), 4.18-4.08 (2H, m), 3.90-3.00 (8H, m), 2.89 (2H, s), 2.33 (3H, s), 1.40 (6H, s). LCMS (ES+) 442.0 (M+H)$^+$, RT 2.17 minutes (Method 2).

Example 224

4-(6,6-Dimethyl-4-oxo-4,5,6,7-tetrahydro[1,3]thiazolo[5,4-c]pyridin-2-yl)-N-[2-(piperidin-1-yl)ethyl]-3,4-dihydro-2H-1,4-benzoxazine-7-carboxamide The title compound was prepared from Example 214 and 1-(2-aminoethyl)-piperidine according to Method AM and was isolated as a yellow gum (70%) after purification by preparative HPLC (Method 7). $\delta_H$ (CDCl$_3$) 8.13 (1H, d, J 8.7 Hz), 7.60-7.53 (1H, m), 7.47 (1H, d, J 2.1 Hz), 7.01 (1H, dd, J 8.5 and 2.1 Hz), 5.42 (1H, s), 4.40-4.33 (2H, m), 4.18-4.09 (2H, m), 3.65-3.56 (2H, m), 2.89 (2H, s), 2.77-2.62 (2H, m), 2.67-2.55 (4H, m), 1.73-1.64 (4H, m), 1.57-1.46 (2H, m), 1.40 (6H, s). LCMS (ES+) 470 (M+H)$^+$, RT 2.14 minutes (Method 2).

Example 225

6,6-Dimethyl-2-[7-(2-methylpiperazin-1-yl)-2,3-dihydro-4H-1,4-benzoxazin-4-yl]-6,7-dihydro[1,3]thiazolo[5,4-c]pyridin-4(5H)-one acetate The title compound was prepared from Example 214 and 4-(N—BOC)-2-methylpiperazine according to Method AL, followed by treatment with TFA, heating to 140° C. under microwave irradiation in a sealed tube for 5 minutes and concentration in vacuo, and was isolated as a yellow gum (4%) after purification by preparative HPLC (Method 7). $\delta_H$ (CDCl$_3$) 7.74 (1H, d, J 9.0 Hz), 6.55 (1H, dd, J 8.9 and 2.6 Hz), 6.49 (1H, d, J 2.6 Hz), 5.78 (1H, s), 4.36-4.26 (2H, m), 4.18-4.09 (2H, m), 3.80.3-69 (1H, m), 3.12-2.86 (6H, m), 2.85 (2H, s), 2.08 (3H, s, AcOH), 1.29 (3H, s), 1.24 (3H, s), 1.07 (3H, d, J 6.5 Hz). One exchangeable proton was not observed. LCMS (ES+) 414.0 (M+H)$^+$, RT 1.83 minutes (Method 1).

Example 226

6,6-Dimethyl-2-[7-(piperidin-4-ylamino)-2,3-dihydro-4H-1,4-benzoxazin-4-yl]-6,7-dihydro[1,3]thiazolo[5,4-c]pyridin-4(5H)-one acetate The title compound was prepared from Example 214 and 4-amino-1-BOC-piperidine according to Method AL, followed by treatment with TFA, heating to 140° C. under microwave irradiation in a sealed tube for 5 minutes and concentration in vacuo, and was isolated as a cream solid (30%) after purification by preparative HPLC (Method 7). $\delta_H$ (CD$_3$OD) 7.52 (1H, d, J 8.9 Hz), 6.34 (1H, dd, J 8.9 and 2.6 Hz), 6.28 (1H, d, J 2.4 Hz), 4.31-4.22 (2H, m), 4.15-4.09 (2H, m), 3.65-3.51 (1H, m), 3.47-3.35 (2H, m), 3.17-3.03 (2H, m), 2.85 (2H, s), 2.28-2.14 (2H, m), 1.92 (3H, s, AcOH), 1.75-1.55 (2H, m), 1.40 (6H, s). Exchangeable protons were not observed. LCMS (ES+) 414.0 (M+H)$^+$, RT 2.07 minutes (Method 7).

Example 227

6,6-Dimethyl-2-{7-[(4-methylpiperazin-1-yl)methyl]-2,3-dihydro-4H-1,4-benzoxazin-4-yl}-6,7-dihydro[1,3]thiazolo[5,4-c]pyridin-4(5H)-one acetate To a stirred suspension of Example 214 (0.11 g, 0.28 mmol) in THF (10 mL) at −78° C. was added n-butyllithium (0.3 mL, 2.5M in hexanes, 0.70 mmol). After stirring at this temperature for 45 minutes, DMF (0.1 mL) was added and the reaction mixture allowed to warm to r.t. Brine (20 mL) and EtOAc (50 mL) were added. The organic fraction was dried (Na$_2$SO$_4$), filtered, and concentrated in vacuo. The residue was dissolved in DCM (5 mL). 1-Methylpiperazine (0.1 mL, excess) was added, followed by triethyl orthoformate (0.3 mL, excess). The reaction mixture was stirred at r.t. for 1 h before addition of sodium triacetoxyborohydride (0.10 g, 0.47 mmol). The reaction mixture was stirred at r.t. for 30 minutes, and then left to stand at r.t. for 16 h. Aqueous sat. Na$_2$CO$_3$ (20 mL) and DCM (20 mL) were added. The organic fraction was separated, dried (Na$_2$SO$_4$), filtered and concentrated in vacuo. Purification by preparative HPLC (Method 7) gave the title compound (0.011 g, 9%) as a yellow gum. $\delta_H$ (CDCl$_3$) 7.86 (1H, d, J 8.5 Hz), 6.94-6.87 (2H, m), 5.89 (1H, s), 4.35-4.29 (2H, m), 4.17-4.11 (2H, m), 3.47 (2H, s), 2.86 (2H, s), 2.80-2.48 (8H, m), 2.38 (3H, s), 2.03 (3H, s, AcOH), 1.39 (6H, s). LCMS (ES+) 428.0 (M+H)$^+$, RT 2.18 minutes (Method 2).

Example 228

6,6-Dimethyl-2-{7-[N-methyl-N-(piperidin-4-yl)amino]-2,3-dihydro-4H-1,4-benzoxazin-4-yl}-6,7-dihydro[1,3]thiazolo[5,4-c]pyridin-4(5H)-one acetate The title compound was prepared from Example 214 and 1-BOC-4-(methylamino)piperidine according to Method AL, followed by treatment with TFA, heating to 140° C. under microwave irradiation in a sealed tube for 5 minutes and concentration in vacuo, and was isolated as a yellow gum (83%) after purification by preparative HPLC (Method 7). $\delta_H$ (CDCl$_3$) 7.66 (1H, d, J 9.0 Hz), 6.41 (1H, dd, J 9.2 and 3.0 Hz), 6.35 (1H, d, J 2.8 Hz), 5.75 (1H, s), 4.36-4.24 (2H, m), 4.17-4.09 (2H, m), 3.77-3.62 (1H, m), 3.46-3.37 (2H, m), 2.90-2.78 (2H, m), 2.84 (2H, s), 2.78 (3H, s), 2.06-1.80 (4H, m), 2.03 (3H, s, AcOH), 1.39 (6H, s). One exchangeable proton was not observed. LCMS (ES+) 428.0 (M+H)$^+$, RT 2.21 minutes (Method 2).

Example 229

6,6-Dimethyl-2-[6-(6-methyl-1-oxidopyridin-3-yl)-2,3-dihydro-4H-1,4-benzoxazin-4-yl]-6,7-dihydro[1,3]thiazolo[5,4-c]pyridin-4(5H)-one To a stirred solution of Example 48 (0.08 g, 0.19 mmol) in DCM (10 ml) was added peracetic acid (0.14 mL, 32 wt % in AcOH, 0.59 mmol). The reaction mixture was stirred at r.t. for 16 h, then concentrated in vacuo. Purification by preparative HPLC (Method 6) gave the title compound (0.014 g, 22%) as a white solid. $\delta_H$ (CD$_3$OD) 8.53 (1H, d, J 1.5 Hz), 8.40 (1H, d, J 2.1 Hz), 7.69 (1H, dd, J 8.1 and 1.7 Hz), 7.55 (1H, d, J 8.3 Hz), 7.34 (1H, dd, J 8.7 and 2.3 Hz), 7.10 (1H, d, J 8.5 Hz), 4.46-4.37 (2H, m), 4.19-4.13 (2H, m), 2.92 (2H, s), 2.58 (3H, s), 1.41 (6H, s,). LCMS (ES+) 423.0 (M+H)$^+$, RT 2.48 minutes (Method 1).

Example 230

Method AO 6,6-Dimethyl-2-{7-[N-methyl-N-(3-(pyrrolidin-1-yl)propyl)amino]-2,3-dihydro-4H-1,4-benzoxazin-4-yl}-6,7-dihydro[1,3]thiazolo[5,4-c]pyridin-4(5H)-one formate A stirred solution of Example 214 (0.2 g, 0.51 mmol), 1-(3-aminopropyl)-pyrrolidine (0.32 g, 2.54 mmol), sodium tert-butoxide (0.136 g, 1.22 mmol), palladium acetate (0.011 g, 0.051 mmol) and tri-tert-butylphosphonium tetrafluoroborate (0.029 g, 0.101 mmol) in DME (3 mL) was heated to 140° C. under microwave irradiation in a sealed tube for 1 h, then concentrated in vacuo. The residue was purified by column chromatography ($SiO_2$, 3-8% MeOH/DCM), then dissolved in MeOH (2 mL). Formaldehyde (0.164 g, 37% wt/water, 2.02 mmol) in MeOH (0.5 mL) was added. The reaction mixture was diluted with THF (2 mL) before the addition of sodium cyanoborohydride (0.044 g, 0.70 mmol). The reaction mixture was stirred at r.t. for 3 h. A solution of glacial AcOH in MeOH (1 drop diluted in 1 mL of MeOH, 0.2 mL) was then added, and the reaction mixture stirred for 4 h. Sodium cyanoborohydride (0.04 g, 0.70 mmol) was added, followed by the rest of the glacial AcOH solution (0.8 mL). The reaction mixture was stirred for 16 h at r.t. Water (3 mL) was added. The organic fraction was separated and concentrated in vacuo. DCM (10 mL) and water (7 mL) were added. The aqueous layer was separated and extracted with DCM (2×10 mL). The combined organic fractions were washed with brine (10 mL), dried ($MgSO_4$), filtered and concentrated in vacuo. Purification by preparative HPLC (Method 6) gave the title compound (0.057 g, 24%) as a yellow solid. $\delta_H$ ($CDCl_3$) 8.48 (1H, s, formic acid), 7.64 (1H, d, J 9.0 Hz), 6.29 (1H, dd, J 9.0 and J 2.8 Hz), 6.24 (1H, d, J 2.8 Hz), 5.36 (1H, s), 4.32-4.27 (2H, m), 4.16-4.10 (2H, m), 3.43-3.33 (2H, m), 3.22-3.10 (4H, m), 3.03-2.95 (2H, m), 2.90 (3H, s), 2.85 (2H, s), 2.09-1.99 (6H, m), 1.39 (6H, s). LCMS (ES+) 456.2 $(M+H)^+$, RT 2.42 min (Method 2).

Example 231

6,6-Dimethyl-2-{7-[N-methyl-N-(2-(pyrrolidin-1-yl)ethyl)amino]-2,3-dihydro-4H-1,4-benzoxazin-4-yl}-6,7-dihydro[1,3]thiazolo[5,4-c]pyridin-4(5H)-one The title compound was prepared from Example 214 and 1-(2-aminoethyl)-pyrrolidine according to Method AO and was isolated as a brown solid (24%) after purification by preparative HPLC (Method 7). $\delta_H$ ($CDCl_3$) 7.62 (1H, d, J 8.9 Hz), 6.33 (1H, dd, J 8.9 and 2.8 Hz), 6.26 (1H, d, J 2.8 Hz), 5.15 (1H, s), 4.32-4.27 (2H, m), 4.15-4.10 (2H, m), 3.50-3.43 (2H, m), 2.94 (3H, s), 2.84 (2H, s), 2.69-2.62 (2H, m), 2.62-2.54 (4H, m), 1.85-1.77 (4H, m), 1.38 (6H, s). LCMS (ES+) 442.2 $(M+H)^+$, RT 2.38 min (Method 2).

Example 232

6,6-Dimethyl-2-{6-[(6-methylpyridazin-3-yl)oxy]-2,3-dihydro-4H-1,4-benzoxazin-4-yl}-6,7-dihydro[1,3]thiazolo[5,4-c]pyridin-4(5H)-one A stirred solution of Example 57 (0.05 g, 0.15 mmol) and 3-chloro-6-methylpyridazine (0.019 g, 0.15 mmol) in DIPEA (0.1 mL, 0.3 mmol) was heated to 180° C. under microwave irradiation in a sealed tube for 4 h, then concentrated in vacuo. Purification by preparative HPLC (Method 7) gave the title compound (0.053 g, 19%) as an off-white solid. $\delta_H$ ($CDCl_3$) 7.98 (1H, d, J 2.4 Hz), 7.34 (1H, d, J 9.0 Hz), 7.08 (1H, d, J 9.0 Hz), 7.00-6.80 (2H, m), 5.45 (1H, s), 4.40-4.30 (2H, m), 4.20-4.10 (2H, m), 2.86 (2H, s), 2.64 (3H, s), 1.38 (6H, s). LCMS (ES+) 424.0 $(M+H)^+$, RT 2.92 minutes (Method 2).

Example 233

2-(7-Amino-2,3-dihydro-4H-1,4-benzoxazin-4-yl)-6,6-dimethyl-6,7-dihydro[1,3]thiazolo[5,4-c]pyridin-4(5H)-one A stirred solution of Example 214 (0.50 g, 1.28 mmol), benzophenone imine (0.003 mL, 1.90 mmol), sodium tert-butoxide (0.37 g, 3.84 mmol), tris(dibenzylideneacetone)dipalladium(0) (0.117 g, 0.13 mmol) and 2,2'-bis(diphenylphosphino)-1,1'-binaphthyl (0.082 g, 0.13 mmol) in THF (6.3 mL) was heated to 120° C. under microwave irradiation in a sealed tube for 30 minutes, then concentrated in vacuo. DCM (5 mL) and MeOH (3 mL) were added, followed by 2M HCl in $Et_2O$ (5 mL). The reaction mixture was stirred at r.t. for 16 h, then concentrated in vacuo. Purification by column chromatography ($SiO_2$, 0-100% EtOAc/heptane, followed by $SiO_2$, 10% MeOH/DCM, then by $SiO_2$, 15% MeOH/DCM with 2% $NH_4OH$ added) gave the title compound (0.458 g, quantitative) as a dark brown solid. $\delta_H$($CD_3OD$) 8.36-8.30 (1H, m), 7.06-6.99 (2H, m), 4.45-4.39 (2H, m), 4.19-4.13 (2H, m), 2.92 (2H, s), 1.40 (6H, s). Exchangeable protons were not observed. LCMS (ES+) 331.2 $(M+H)^+$, RT 1.95 minutes (Method 1).

Example 234

N-[4-(6,6-Dimethyl-4-oxo-4,5,6,7-tetrahydro[1,3]thiazolo[5,4-c]pyridin-2-yl)-3,4-dihydro-2H-1,4-benzoxazin-7-yl]-1-methylpiperidine-4-carboxamide To a stirred solution of Example 233 (0.049 g, 0.15 mmol), 2-(1H-benzotriazol-1-yl)-1,1,3,3-tetramethyluronium hexafluorophosphate (0.111 g, 0.29 mmol) and 1-methylpiperidine-4-carboxylic acid hydrochloride (0.034 g, 0.19 mmol) in DMF (0.5 mL) was added DIPEA (0.06 mL, 0.35 mmol). The reaction mixture was stirred at r.t. for 16 h. MeCN (1 mL) and water (1 mL) were added. The insoluble material was filtered, and the filtrate concentrated in vacuo. Purification by preparative HPLC (Method 6) gave the title compound (0.035 g, 51%) as a yellow solid. $\delta_H$ ($CD_3OD$) 7.91 (1H, d, J 9.0 Hz), 7.37 (1H, d, J 2.3 Hz), 7.11 (1H, dd, J 8.9 and 2.3 Hz), 4.40-4.30 (2H, m), 4.20-4.09 (2H, m), 3.62 (2H, d, J 12.6 Hz), 3.17-3.02 (2H, m), 2.92 (3H, s), 2.89 (2H, s), 2.76-2.60 (1H, m), 2.34-1.91 (4H, m), 1.39 (6H, s). Exchangeable protons were not observed. LCMS (ES+) 456.21 $(M+H)^+$, RT 1.80 minutes (Method 1).

Example 235

6,6-Dimethyl-2-[7-(2-(morpholin-4-yl)ethoxy)-2,3-dihydro-4H-1,4-benzoxazin-4-yl]-6,7-dihydro[1,3]thiazolo[5,4-c]pyridin-4(5H)-one A stirred solution of Example 214 (0.052 g, 0.13 mmol), tris(dibenzylideneacetone)dipalladium(0) (0.004 g, 0.005 mmol) and 2-(di-tert-butylphosphino)-2',4',6'-triisopropyl-1,1'-biphenyl (0.011 g, 0.025 mmol) in 1,4-dioxane (0.5 mL) and 2M aqueous NaOH (0.2 mL) was heated to 100° C. under microwave irradiation in a sealed tube for 1 h. Cetylammonium bromide (0.008 g, 0.022 mmol) and 4-(2-bromoethyl)-morpholine (0.037 g, 0.19 mmol) were added. The reaction mixture was heated to 100° C. under microwave irradiation in a sealed tube for 3 h. Water (20 mL) was added. The aqueous layer was separated and extracted with EtOAc (3×20 mL). The combined organic layers were dried (MgSO$_4$), filtered and concentrated in vacuo. Purification by column chromatography (SiO$_2$, 0-100% EtOAc/heptane, followed by SiO$_2$, 15% MeOH/DCM with 2% NH$_4$OH added), then by preparative HPLC (Method 6), gave the title compound (0.011 g, 18%) as a white oily solid. $\delta_H$ (CDCl$_3$) 7.74 (1H, d, J 9.2 Hz), 6.57-6.49 (2H, m), 5.25 (1H, s), 4.34-4.28 (2H, m), 4.16-4.06 (4H, m), 3.78-3.72 (4H, m), 2.85 (2H, s), 2.80 (2H, t, J 5.7 Hz), 2.62-2.56 (4H, m), 1.39 (6H, s). LCMS 445.19 (M+H)$^+$, RT 1.83 minutes (Method 1).

Example 236

Method AN 6,6-Dimethyl-2-[7-(2-methoxypyridin-3-yl)-6-methyl-2,3-dihydro-4H-1,4-benzoxazin-4-yl]-6,7-dihydro[1,3]thiazolo[5,4-c]pyridin-4(5H)-one A stirred solution of Example 210 (0.075 g, 0.18 mmol), 2-methoxypyridine-3-boronic acid (0.051 g, 0.33 mmol), tetrakis(triphenylphosphine)palladium(0) (0.018 g, 0.016 mmol) and potassium phosphate (0.140 g, 0.66 mmol) in DME (2 mL) and water (0.5 ml) was heated to 120° C. under microwave irradiation in a sealed tube for 1 h. Water (10 mL) was added. The aqueous fraction was separated and extracted with EtOAc (3×10 mL). The combined organic fractions were washed with brine (10 mL), dried (Na$_2$SO$_4$), filtered and concentrated in vacuo. Purification by column chromatography (SiO$_2$, 0-100% EtOAc/heptane, followed by SiO$_2$, 15% MeOH/DCM with 2% NH$_4$OH added), then by preparative HPLC (Method 6), gave the title compound (0.050 g, 57%) as an off-white solid. $\delta_H$(CDCl$_3$) 8.19 (1H, dd, J 5.1 and 1.9 Hz), 7.79 (1H, s), 7.44 (1H, dd, J 7.2 and 1.9 Hz), 6.96 (1H, dd, J 7.3 and 5.1 Hz), 6.80 (1H, s), 5.16 (1H, br. s), 4.36-4.30 (2H, m), 4.23-4.17 (2H, m), 3.94 (3H, s), 2.89 (2H, s), 2.09 (3H, s), 1.41 (6H, s). LCMS (ES+) 437.17 (M+H)$^+$, RT 3.62 minutes (Method 1).

Example 237

6,6-Dimethyl-2-[7-(2-methoxypyridin-3-yl)-2,3-dihydro-4H-1,4-benzoxazin-4-yl]-6,7-dihydro[1,3]thiazolo[5,4-c]pyridin-4(5H)-one The title compound was prepared from Example 214 and 2-methoxypyridine-3-boronic acid according to Method AN and was isolated as a white solid (15%) after purification by column chromatography (SiO$_2$, 0-100% EtOAc/heptane, followed by SiO$_2$, 15% MeOH/DCM with 2% NH$_4$OH added), then by preparative HPLC (Method 6). $\delta_H$ (CDCl$_3$) 8.16 (1H, dd, J 4.9 and 1.9 Hz), 8.02 (1H, d, J 8.5 Hz), 7.62 (1H, dd, J 7.3 and 1.9 Hz), 7.22 (1H, d, J 2.1 Hz), 7.17 (1H, dd, J 8.5 and 2.1 Hz), 6.97 (1H, dd, J 7.3 and 5.1 Hz), 5.16 (1H, br. s), 4.40-4.35 (2H, m), 4.21-4.16 (2H, m), 3.99 (3H, s), 2.89 (2H, s), 1.41 (6H, s). LCMS (ES+) 423.2 (M+H)$^+$, RT 3.56 minutes (Method 1).

Example 238

2-(7-Acetyl-2,3-dihydro-4H-1,4-benzoxazin-4-yl)-6,6-dimethyl-6,7-dihydro[1,3]thiazolo[5,4-c]pyridin-4(5H)-one To a stirred solution of Example 214 (0.52 g, 1.27 mmol), 1,3-bis(diphenylphosphino)propane (0.046 g, 0.11 mmol) and palladium acetate (0.023 g, 0.10 mmol) in DMF (4 mL) was added NEt$_3$ (0.29 mL, 2.08 mmol), followed by butyl vinyl ether (0.82 mL, 6.37 mmol). The reaction mixture was heated to 140° C. under microwave irradiation in a sealed tube for 1 h. Additional palladium acetate (0.013 g, 0.058 mmol), 1,3-bis(diphenylphosphino)propane (0.046 g, 0.11 mmol), NEt$_3$ (0.29 mL, 2.08 mmol) and butyl vinyl ether (0.82 mL, 6.37 mmol) were added. The reaction mixture was heated to 120° C. under microwave irradiation in a sealed tube for 1 h, then filtered through Celite®, washed with DCM (5 mL) and MeOH (5 mL) and concentrated in vacuo. The residue was dissolved in MeCN (10 mL) and DCM (5 mL), and 1M aqueous HCl (5 mL) was added. The reaction mixture was stirred at r.t. for 16 h, then concentrated in vacuo. Purification by column chromatography (SiO$_2$, 35%-100% EtOAc/heptane, followed by SiO$_2$, 0-15% MeOH/DCM with 2% NH$_4$OH added), then by preparative HPLC (Method 6), gave the title compound (0.183 g, 40%) as a white solid. $\delta_H$ (CDCl$_3$) 8.25-8.20 (1H, m), 7.61-7.56 (2H, m), 5.19 (1H, br. s), 4.41-4.36 (2H, m), 4.17-4.12 (2H, m), 2.92 (2H, s), 2.57 (3H, s), 1.41 (6H, s). LCMS (ES+) 358.10 (M+H)$^+$, 715.21 (2M+H)$^+$, RT 2.92 minutes (Method 1).

Example 239

6,6-Dimethyl-2-{6-[1-(2-hydroxy-2-methylpropyl)-1H-pyrazol-4-yl]-2,3-dihydro-4H-1,4-benzoxazin-4-yl}-6,7-dihydro[1,3]thiazolo[5,4-c]pyridin-4(5H)-one To a stirred solution of 4-bromopyrazole (0.5 g, 3.40 mmol) in DMF (2.5 mL) was added SiO$_2$ (0.54 g, 0.01 mmol) and isobutylene oxide (1.8 mL, 35.91 mmol). The reaction mixture was stirred at 105° C. for 16 hours, then cooled to r.t., filtered and concentrated in vacuo. DME (8 mL), water (2 mL), Example 292 (0.81 g, 1.82 mmol), tetrakis(triphenylphosphine)palladium(0) (0.214 g, 0.180 mmol), potassium phosphate (0.578 g, 2.73 mmol) and tetrabutylammonium bromide (0.293 g, 0.91 mmol) were added. The reaction mixture was heated to 140° C. under microwave irradiation in a sealed tube for 20 minutes, then concentrated in vacuo. Purification by preparative HPLC (Method 6) gave the title compound (0.045 g, 10%) as a pale orange solid. $\delta_H$ (CDCl$_3$) 8.01 (1H, d, J 2.1 Hz), 7.76 (1H, s), 7.63 (1H, s), 7.18 (1H, dd, J 8.5 and 1.9 Hz), 6.96 (1H, d, J 8.3 Hz), 5.52 (1H, s), 4.36-4.25 (2H, m), 4.27-4.15 (2H, m), 4.10 (2H, s), 2.88 (2H, s), 1.41 (6H, s), 1.21 (6H, s). One exchangeable proton was not observed. LCMS (ES+) 454.0 (M+H)$^+$, RT 2.63 minutes (Method 2).

Example 240

6,6-Dimethyl-2-[3-(3-{[3-(methylsulfonyl)phenyl]amino}benzyl)morpholin-4-yl]-6,7-dihydro[1,3]thiazolo[5,4-c]pyridin-4(5H)-one trifluoroacetate The title compound was prepared from Example 31 and 3-(methylsulfonyl)aniline according to Method P (in toluene and worked-up with EtOAc and water) and was isolated in 100% purity after purification by preparative HPLC. LCMS (ES+) 527.2 (M+H)$^+$, RT 1.77 minutes (Method 14).

Example 241

6,6-Dimethyl-2-[3-(3-{[4-(morpholin-4-ylcarbonyl)phenyl]amino}benzyl)morpholin-4-yl]-6,7-dihydro[1,3]thiazolo[5,4-c]pyridin-4(5H)-one trifluoroacetate The title compound was prepared from Example 31 and 4-(4-aminobenzoyl)-morpholine according to Method P (in toluene and worked-up with EtOAc and water) and was isolated in 98% purity after purification by preparative HPLC. LCMS (ES+) 562.2 (M+H)+, RT 1.70 minutes (Method 14).

Example 242

6,6-Dimethyl-2-[3-(3-{[3-(3-methyl-5-oxo-4,5-dihydro-1H-pyrazol-1-yl)phenyl]amino}-benzyl)morpholin-4-yl]-6,7-dihydro[1,3]thiazolo[5,4-c]pyridin-4 (5H)-one trifluoroacetate The title compound was prepared from Example 31 and 2-(3-aminophenyl)-5-methyl-2,4-dihydropyrazol-3-one according to Method P (in toluene and worked-up with EtOAc and water) and was isolated in 100% purity after purification by preparative HPLC. LCMS (ES+) 545.2 (M+H)+, RT 1.41 minutes (Method 14).

Example 243

2-{3-[3-(1,3-Benzodioxol-5-ylamino)benzyl]morpholin-4-yl}-6,6-dimethyl-6,7-dihydro[1,3]thiazolo[5,4-c]pyridin-4(5H)-one trifluoroacetate The title compound was prepared from Example 31 and 1,3-benzodioxol-5-amine according to Method P (in toluene and worked-up with EtOAc and water) and was isolated in 100% purity after purification by preparative HPLC. LCMS (ES+) 493.2 (M+H)+, RT 1.97 minutes (Method 14).

Example 244

6,6-Dimethyl-2-[3-(3-{[3-(1,3-oxazol-5-yl)phenyl] amino}benzyl)morpholin-4-yl]-6,7-dihydro[1,3] thiazolo[5,4-c]pyridin-4(5H)-one trifluoroacetate The title compound was prepared from Example 31 and 3-(1,3-oxazol-5-yl)aniline according to Method P (in toluene and worked-up with EtOAc and water) and was isolated in 100% purity after purification by preparative HPLC. LCMS (ES+) 516.2 (M+H)+, RT 1.92 minutes (Method 14).

Example 245

6,6-Dimethyl-2-(3-{3-[(2-oxo-2,3-dihydro-1,3-benzoxazol-6-yl)amino]benzyl}-morpholin-4-yl)-6,7-dihydro[1,3]thiazolo[5,4-c]pyridin-4(5H)-one trifluoroacetate The title compound was prepared from Example 31 and 6-amino-1,3-benzoxazol-2(3H)-one according to Method P (in toluene and worked-up with EtOAc and water) and was isolated in 100% purity after purification by preparative HPLC. LCMS (ES+) 506.2 (M+H)+, RT 1.69 minutes (Method 14).

Example 246

2-{3-[3-(1,3-Benzothiazol-6-ylamino)benzyl]morpholin-4-yl}-6,6-dimethyl-6,7-dihydro[1,3]thiazolo[5,4-c]pyridin-4(5H)-one trifluoroacetate The title compound was prepared from Example 31 and 1,3-benzothiazol-6-amine according to Method P (in toluene and worked-up with EtOAc and water) and was isolated in 100% purity after purification by preparative HPLC. LCMS (ES+) 506.2 (M+H)+, RT 1.85 minutes (Method 14).

Example 247

6,6-Dimethyl-2-[3-(3-{[3-(4-methyl-4H-1,2,4-triazol-3-yl)phenyl]amino}benzyl)-morpholin-4-yl]-6,7-dihydro[1,3]thiazolo[5,4-c]pyridin-4(5H)-one trifluoroacetate The title compound was prepared from Example 31 and 3-(4-methyl-4H-1,2,4-triazol-3-yl)aniline according to Method P (in toluene and worked-up with EtOAc and water) and was isolated in 100% purity after purification by preparative HPLC. LCMS (ES+) 530.2 (M+H)+, RT 1.63 minutes (Method 14).

Example 248

N-{3-[(3-{[4-(6,6-dimethyl-4-oxo-4,5,6,7-tetrahydro [1,3]thiazolo[5,4-c]pyridin-2-yl)morpholin-3-yl] methyl}phenyl)amino]phenyl}methanesulfonamide trifluoroacetate The title compound was prepared from Example 31 and N-(3-aminophenyl)-methanesulfonamide according to Method P (in toluene and worked-up with EtOAc and water) and was isolated in 100% purity after purification by preparative HPLC. LCMS (ES+) 542.2 (M+H)+, RT 1.76 minutes (Method 14).

Example 249

6,6-Dimethyl-2-[3-(3-{[3-(1H-1,2,4-triazol-1-yl) phenyl]amino}benzyl)morpholin-4-yl]-6,7-dihydro [1,3]thiazolo[5,4-c]pyridin-4(5H)-one trifluoroacetate The title compound was prepared from Example 31 and 3-(1H-1,2,4-triazol-1-yl)aniline according to Method P (in toluene and worked-up with EtOAc and water) and was isolated in 100% purity after purification by preparative HPLC. LCMS (ES+) 516.2 (M+H)+, RT 1.74 minutes (Method 14).

Example 250

6,6-Dimethyl-2-(3-{3-[(1-methyl-1H-benzimidazol-4-yl)amino]benzyl}morpholin-4-yl)-6,7-dihydro[1,3] thiazolo[5,4-c]pyridin-4(5H)-one trifluoroacetate The title compound was prepared from Example 31 and 4-amino-1-methylbenzimidazole according to Method P (in toluene and worked-up with EtOAc and water) and was isolated in 100% purity after purification by preparative HPLC. LCMS (ES+) 503.2 (M+H)+, RT 1.82 minutes (Method 14).

Example 251

6,6-Dimethyl-2-[3-(3-{[1-(methylsulfonyl)-2,3-dihydro-1H-indol-5-yl]amino}benzyl)-morpholin-4-yl]-6,7-dihydro[1,3]thiazolo[5,4-c]pyridin-4(5H)-one trifluoroacetate The title compound was prepared from Example 31 and 1-(methylsulfonyl)-indolin-5-amine according to Method P (in toluene and worked-up with EtOAc and water) and was isolated in 80% purity after purification by preparative HPLC. LCMS (ES+) 568.2 (M+H)⁺, RT 1.88 minutes (Method 14).

Example 252

6,6-Dimethyl-2-(3-{3-[(2-oxo-2,3-dihydro-1H-benzimidazol-5-yl)amino]benzyl}morpholin-4-yl)-6,7-dihydro[1,3]thiazolo[5,4-c]pyridin-4(5H)-one trifluoroacetate The title compound was prepared from Example 31 and 5-amino-2H-benzimidazol-2-one according to Method P (in toluene and worked-up with EtOAc and water) and was isolated in 98% purity after purification by preparative HPLC. LCMS (ES+) 505.2 (M+H)⁺, RT 1.59 minutes (Method 14).

Example 253

2-{3-[3-(1-Benzothien-5-ylamino)benzyl]morpholin-4-yl}-6,6-dimethyl-6,7-dihydro[1,3]thiazolo[5,4-c]pyridin-4(5H)-one trifluoroacetate The title compound was prepared from Example 31 and 1-benzothiophen-5-amine according to Method P (in toluene and worked-up with EtOAc and water) and was isolated in 100% purity after purification by preparative HPLC. LCMS (ES+) 505.2 (M+H)⁺, RT 2.16 minutes (Method 14).

Example 254

6,6-Dimethyl-2-[3-(3-{[4-(morpholin-4-ylmethyl)phenyl]amino}benzyl)morpholin-4-yl]-6,7-dihydro[1,3]thiazolo[5,4-c]pyridin-4(5H)-one trifluoroacetate The title compound was prepared from Example 31 and 4-(morpholin-4-ylmethyl)aniline according to Method P (in toluene and worked-up with EtOAc and water) and was isolated in 100% purity after purification by preparative HPLC. LCMS (ES+) 548.2 (M+H)⁺, RT 1.88 minutes (Method 14).

Example 255

6,6-Dimethyl-2-[3-(3-{[4-(1H-1,2,4-triazol-1-ylmethyl)phenyl]amino}benzyl)morpholin-4-yl]-6,7-dihydro[1,3]thiazolo[5,4-c]pyridin-4(5H)-one trifluoroacetate The title compound was prepared from Example 31 and 1-[(4-aminophenyl)-methyl]-1,2,4-triazole according to Method P (in toluene and worked-up with EtOAc and water) and was isolated in 100% purity after purification by preparative HPLC. LCMS (ES+) 530.2 (M+H)⁺, RT 1.71 minutes (Method 14).

Example 256

6,6-Dimethyl-2-(3-{3-[(3-methylcinnolin-5-yl)amino]benzyl}morpholin-4-yl)-6,7-dihydro[1,3]thiazolo[5,4-c]pyridin-4(5H)-one trifluoroacetate The title compound was prepared from Example 31 and 3-methylcinnolin-5-amine according to Method P (in toluene and worked-up with EtOAc and water) and was isolated in 100% purity after purification by preparative HPLC. LCMS (ES+) 515.2 (M+H)⁺, RT 1.76 minutes (Method 14).

Example 257

6,6-Dimethyl-2-{3-[3-(quinoxalin-6-ylamino)benzyl]morpholin-4-yl}-6,7-dihydro[1,3]thiazolo[5,4-c]pyridin-4(5H)-one trifluoroacetate The title compound was prepared from Example 31 and 6-aminoquinoxaline according to Method P (in toluene and worked-up with EtOAc and water) and was isolated in 100% purity after purification by preparative HPLC. LCMS (ES+) 501.2 (M+H)⁺, RT 1.71 minutes (Method 14).

Example 258

6,6-Dimethyl-2-(3-{3-[(2-methyl-4-oxo-4H-chromen-7-yl)amino]benzyl}morpholin-4-yl)-6,7-dihydro[1,3]thiazolo[5,4-c]pyridin-4(5H)-one trifluoroacetate The title compound was prepared from Example 31 and 7-amino-2-methylchromone according to Method P (in toluene and worked-up with EtOAc and water) and was isolated in 100% purity after purification by preparative HPLC. LCMS (ES+) 531.2 (M+H)⁺, RT 1.77 minutes (Method 14).

Example 259

6,6-Dimethyl-2-(3-{3-[(1-methyl-1H-indazol-5-yl)amino]benzyl}morpholin-4-yl)-6,7-dihydro[1,3]thiazolo[5,4-c]pyridin-4(5H)-one trifluoroacetate The title compound was prepared from Example 31 and 1-methyl-1H-indazol-5-amine according to Method P (in toluene and worked-up with EtOAc and water) and was isolated in 100% purity after purification by preparative HPLC. LCMS (ES+) 503.2 (M+H)⁺, RT 1.84 minutes (Method 14).

Example 260

2-{3-[3-(1,3-Benzoxazol-6-ylamino)benzyl]morpholin-4-yl}-6,6-dimethyl-6,7-dihydro[1,3]thiazolo[5,4-c]pyridin-4(5H)-one trifluoroacetate The title compound was prepared from Example 31 and 1,3-benzoxazol-6-amine according to Method P (in toluene and worked-up with EtOAc and water) and was isolated in 95% purity after purification by preparative HPLC. LCMS (ES+) 490.2 (M+H)⁺, RT 1.72 minutes (Method 14).

Example 261

2-{3-[3-(2,3-Dihydro-1-benzofuran-5-ylamino)benzyl]morpholin-4-yl}-6,6-dimethyl-6,7-dihydro[1,3]thiazolo[5,4-c]pyridin-4(5H)-one trifluoroacetate The title compound was prepared from Example 31 and 2,3-dihydro-1-benzofuran-5-amine according to Method P (in toluene and worked-up with EtOAc and water) and was

Example 262

6,6-Dimethyl-2-[3-(3-{[3-(2-methylpyrimidin-4-yl)
phenyl]amino}benzyl)morpholin-4-yl]-6,7-dihydro
[1,3]thiazolo[5,4-c]pyridin-4(5H)-one trifluoroacetate The title compound was prepared from Example 31 and 3-(2-methylpyrimidin-4-yl)aniline according to Method P (in toluene and worked-up with EtOAc and water) and was isolated in 100% purity after purification by preparative HPLC. LCMS (ES+) 541.2 (M+H)+, RT 1.94 minutes (Method 14).

Example 263

6,6-Dimethyl-2-[3-(3-{[3-(morpholin-4-ylsulfonyl)
phenyl]amino}benzyl)morpholin-4-yl]-6,7-dihydro
[1,3]thiazolo[5,4-c]pyridin-4(5H)-one trifluoroacetate The title compound was prepared from Example 31 and 3-(morpholin-4-ylsulfonyl)aniline according to Method P (in toluene and worked-up with EtOAc and water) and was isolated in 100% purity after purification by preparative HPLC. LCMS (ES+) 598.2 (M+H)+, RT 1.90 minutes (Method 14).

Example 264

2-[3-(3-{[4-(4,5-Dihydro-1,3-oxazol-2-yl)phenyl]
amino}benzyl)morpholin-4-yl]-6,6-dimethyl-6,7-
dihydro[1,3]thiazolo[5,4-c]pyridin-4(5H)-one trifluoroacetate The title compound was prepared from Example 31 and 4-(4,5-dihydro-1,3-oxazol-2-yl)aniline according to Method P (in toluene and worked-up with EtOAc and water) and was isolated in 87% purity after purification by preparative HPLC. LCMS (ES+) 518.2 (M+H)+, RT 1.83 minutes (Method 14).

Example 265

6,6-Dimethyl-2-(3-{3-[(1-methyl-1H-indazol-6-yl)
amino]benzyl}morpholin-4-yl)-6,7-dihydro[1,3]
thiazolo[5,4-c]pyridin-4(5H)-one trifluoroacetate The title compound was prepared from Example 31 and 1-methyl-1H-indazol-6-ylamine according to Method P (in toluene and worked-up with EtOAc and water) and was isolated in 100% purity after purification by preparative HPLC. LCMS (ES+) 503.2 (M+H)+, RT 1.84 minutes (Method 14).

Example 266

6,6-Dimethyl-2-[3-(3-{[3-(1H-pyrazol-1-ylmethyl)
phenyl]amino}benzyl)morpholin-4-yl]-6,7-dihydro
[1,3]thiazolo[5,4-c]pyridin-4(5H)-one trifluoroacetate The title compound was prepared from Example 31 and 3-(pyrazol-1-ylmethyl)-phenylamine according to Method P (in toluene and worked-up with EtOAc and water) and was isolated in 100% purity after purification by preparative HPLC. LCMS (ES+) 491.2 (M+H)+, RT 1.98 minutes (Method 14).

Example 267

2-(3-{3-[(1,3-Dimethyl-2-oxo-2,3-dihydro-1H-benz-
imidazol-5-yl)amino]benzyl}-morpholin-4-yl)-6,6-
dimethyl-6,7-dihydro[1,3]thiazolo[5,4-c]pyridin-4
(5H)-one trifluoroacetate The title compound was prepared from Example 31 and 5-amino-1,3-dimethyl-1,3-dihydrobenzimidazol-2-one according to Method P (in toluene and worked-up with EtOAc and water) and was isolated in 100% purity after purification by preparative HPLC. LCMS (ES+) 533.2 (M+H)+, RT 1.74 minutes (Method 14).

Example 268

6-[(3-{[4-(6,6-Dimethyl-4-oxo-4,5,6,7-tetrahydro[1,
3]thiazolo[5,4-c]pyridin-2-yl)-morpholin-3-yl]
methyl}phenyl)amino]-3,4-dihydroquinolin-2(1H)-
one trifluoroacetate The title compound was prepared from Example 31 and 6-amino-3,4-dihydro-1H-quinoline-2-one according to Method P (in toluene and worked-up with EtOAc and water) and was isolated in 100% purity after purification by preparative HPLC. LCMS (ES+) 518.2 (M+H)+, RT 1.69 minutes (Method 14).

Example 269

6,6-Dimethyl-2-(3-{3-[(4-(isoxazol-5-yl)phenyl)
amino]benzyl}morpholin-4-yl)-6,7-dihydro[1,3]
thiazolo[5,4-c]pyridin-4(5H)-one trifluoroacetate The title compound was prepared from Example 31 and 4-(isoxazol-5-yl)aniline according to Method P (in toluene and worked-up with EtOAc and water) and was isolated in 95% purity after purification by preparative HPLC. LCMS (ES+) 516.2 (M+H)+, RT 1.79 minutes (Method 14).

Example 270

6,6-Dimethyl-2-(3-{3-[(1,3,5-trimethyl-1H-pyrazol-
4-yl)amino]benzyl}morpholin-4-yl)-6,7-dihydro[1,3]
thiazolo[5,4-c]pyridin-4(5H)-one trifluoroacetate The title compound was prepared from Example 31 and 1,3,5-trimethyl-1H-pyrazol-4-amine according to Method P (in toluene and worked-up with EtOAc and water) and was isolated in 95% purity after purification by preparative HPLC. LCMS (ES+) 481.2 (M+H)+, RT 1.72 minutes (Method 14).

Example 271

6,6-Dimethyl-2-{3-[3-(1H-indol-5-ylamino)benzyl]-
morpholin-4-yl}-6,7-dihydro[1,3]thiazolo[5,4-c]
pyridin-4(5H)-one trifluoroacetate The title compound was prepared from Example 31 and 1H-indol-5-amine according to Method P (in toluene and worked-up with EtOAc and water) and was isolated in 95%

Example 272

5-[(3-{[4-(6,6-Dimethyl-4-oxo-4,5,6,7-tetrahydro[1,3]thiazolo[5,4-c]pyridin-2-yl)morpholin-3-yl]methyl}phenyl)amino]-1H-indole-2,3-dione trifluoroacetate The title compound was prepared from Example 31 and 5-aminoisatin according to Method P (in toluene and worked-up with EtOAc and water) and was isolated in 88% purity after purification by preparative HPLC. LCMS (ES+) 518.2 (M+H)+, RT 1.83 minutes (Method 14).

Example 273

2-(3-{3-[(4-Bromo-1-methyl-1H-pyrazol-5-yl)amino]benzyl}morpholin-4-yl)-6,6-dimethyl-6,7-dihydro[1,3]thiazolo[5,4-c]pyridin-4(5H)-one trifluoroacetate The title compound was prepared from Example 31 and 3-amino-4-bromo-2-methylpyrazole according to Method P (in toluene and worked-up with EtOAc and water) and was isolated in 100% purity after purification by preparative HPLC. LCMS (ES+) 533.2 (M+H)+, RT 1.80 minutes (Method 14).

Example 274

6,6-Dimethyl-2-(3-{3-[(3-methylisothiazol-5-yl)amino]benzyl}morpholin-4-yl)-6,7-dihydro[1,3]thiazolo[5,4-c]pyridin-4(5H)-one trifluoroacetate The title compound was prepared from Example 31 and 3-methylisothiazol-5-amine according to Method P (in toluene and worked-up with EtOAc and water) and was isolated in 100% purity after purification by preparative HPLC. LCMS (ES+) 470.2 (M+H)+, RT 1.74 minutes (Method 14).

Example 275

6,6-Dimethyl-2-(3-{3-[(5-methyl-1,3,4-oxadiazol-2-yl)amino]benzyl}morpholin-4-yl)-6,7-dihydro[1,3]thiazolo[5,4-c]pyridin-4(5H)-one trifluoroacetate The title compound was prepared from Example 31 and 2-amino-5-methyl-1,3,4-oxadiazole according to Method P (in toluene and worked-up with EtOAc and water) and was isolated in 90% purity after purification by preparative HPLC. LCMS (ES+) 455.2 (M+H)+, RT 1.53 minutes (Method 14).

Example 276

6,6-Dimethyl-2-[3-(3-{[5-(2-furyl)-1,3,4-oxadiazol-2-yl]amino}benzyl)morpholin-4-yl]-6,7-dihydro[1,3]thiazolo[5,4-c]pyridin-4(5H)-one trifluoroacetate The title compound was prepared from Example 31 and 2-amino-5-(2-furyl)-1,3,4-oxadiazole according to Method P (in toluene and worked-up with EtOAc and water) and was isolated in 90% purity after purification by preparative HPLC. LCMS (ES+) 507.2 (M+H)+, RT 1.71 minutes (Method 14).

Example 277

2-(3-{3-[(3,5-Dimethylisoxazol-4-yl)amino]benzyl}morpholin-4-yl)-6,6-dimethyl-6,7-dihydro[1,3]thiazolo[5,4-c]pyridin-4(5H)-one trifluoroacetate The title compound was prepared from Example 31 and 3,5-dimethylisoxazol-4-amine according to Method P (in toluene and worked-up with EtOAc and water) and was isolated in 100% purity after purification by preparative HPLC. LCMS (ES+) 468.2 (M+H)+, RT 1.80 minutes (Method 14).

Example 278

7-[(3-{[4-(6,6-Dimethyl-4-oxo-4,5,6,7-tetrahydro-[1,3]thiazolo[5,4-c]pyridin-2-yl)-morpholin-3-yl]methyl}phenyl)amino]-2H-1,4-benzoxazin-3(4H)-one trifluoroacetate The title compound was prepared from Example 31 and 7-amino-2H-1,4-benzoxazin-3(4H)-one according to Method P (in toluene and worked-up with EtOAc and water) and was isolated in 100% purity after purification by preparative HPLC. LCMS (ES+) 520.2 (M+H)+, RT 1.70 minutes (Method 14).

Example 279

6,6-Dimethyl-2-(3-{3-[(2-oxo-1,2-dihydropyridin-3-yl)amino]benzyl}morpholin-4-yl)-6,7-dihydro[1,3]thiazolo[5,4-c]pyridin-4(5H)-one trifluoroacetate The title compound was prepared from Example 31 and 3-aminopyridin-2(1H)-one according to Method P (in toluene and worked-up with EtOAc and water) and was isolated in 100% purity after purification by preparative HPLC. LCMS (ES+) 466.2 (M+H)+, RT 1.59 minutes (Method 14).

Example 280

6,6-Dimethyl-2-(3-{3-[(3-(isoxazol-5-yl)phenyl)amino]benzyl}morpholin-4-yl)-6,7-dihydro[1,3]thiazolo[5,4-c]pyridin-4(5H)-one trifluoroacetate The title compound was prepared from Example 31 and 3-(isoxazol-5-yl)aniline according to Method P (in toluene and worked-up with EtOAc and water) and was isolated in 90% purity after purification by preparative HPLC. LCMS (ES+) 516.2 (M+H)+, RT 1.76 minutes (Method 14).

Example 281

6,6-Dimethyl-2-(3-{3-[(2-oxo-1,2-dihydropyrimidin-4-yl)amino]benzyl}morpholin-4-yl)-6,7-dihydro[1,3]thiazolo[5,4-c]pyridin-4(5H)-one trifluoroacetate The title compound was prepared from Example 31 and 4-amino-2(1H)-pyrimidone according to Method P (in toluene and worked-up with EtOAc and water) and was isolated in 100% purity after purification by preparative HPLC. LCMS (ES+) 467.2 (M+H)+, RT 1.38 minutes (Method 14).

Example 282

6,6-Dimethyl-2-(3-{3-[(2-oxo-2H-chroman-6-yl)amino]benzyl}morpholin-4-yl)-6,7-dihydro[1,3]thiazolo[5,4-c]pyridin-4(5H)-one trifluoroacetate The title compound was prepared from Example 31 and 6-aminochroman-2-one according to Method P (in toluene

Example 283

6,6-Dimethyl-2-(3-{3-[(2-thioxo-1,2-dihydropyrimidin-4-yl)amino]benzyl}morpholin-4-yl)-6,7-dihydro[1,3]thiazolo[5,4-c]pyridin-4(5H)-one trifluoroacetate The title compound was prepared from Example 31 and 2-thiocytosine according to Method P (in toluene and worked-up with EtOAc and water) and was isolated in 62% purity after purification by preparative HPLC. LCMS (ES+) 483.2 (M+H)$^+$, RT 1.61 minutes (Method 14).

Example 284

2-(3-{3-[(6-Chloro-3-methoxypyridazin-4-yl)amino]benzyl}morpholin-4-yl)-6,6-dimethyl-6,7-dihydro[1,3]thiazolo[5,4-c]pyridin-4(5H)-one trifluoroacetate The title compound was prepared from Example 31 and 6-chloro-3-methoxypyridazin-4-amine according to Method P (in toluene and worked-up with EtOAc and water) and was isolated in 71% purity after purification by preparative HPLC. LCMS (ES+) 515.2 (M+H)$^+$, RT 1.74 minutes (Method 14).

Example 285

[Omitted]

Example 286

2-(6-{[(5-Chloro-1,3-dimethyl-1H-pyrazol-4-yl)methyl]amino}-2,3-dihydro-4H-1,4-benzoxazin-4-yl)-6,6-dimethyl-6,7-dihydro[1,3]thiazolo[5,4-d]pyridin-4(5H)-one The title compound was prepared from Example 42 and 1,3-dimethyl-5-chloropyrazole-4-carboxaldehyde according to Method V and was isolated as a yellow solid (18%) after purification by preparative HPLC (Method 6). $\delta_H$ (CDCl$_3$) 7.26 (1H, s), 6.82 (1H, d, J 8.7 Hz), 6.42 (1H, dd, J 8.9 and 2.6 Hz), 5.52 (1H, s), 4.31-4.23 (2H, m), 4.20-4.07 (2H, m), 4.03 (2H, s), 3.78 (3H, s), 2.87 (2H, m), 2.25 (3H, s), 1.39 (6H, s). LCMS (ES+) 473.3 (M+H)$^+$, RT 2.60 minutes (Method 1).

Example 287

1-[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]pyrrolidine-2,5-dione A mixture of Example 42 (50 mg, 0.15 mmol) and succinic anhydride (20 mg, 0.15 mmol) in DMF (4 mL) was stirred at 140° C. under microwave irradiation for 1 h. The reaction mixture was concentrated in vacuo, dissolved in acetic acid and stirred at 140° C. under microwave irradiation for 1 h. It was concentrated in vacuo and purified by preparative HPLC (Method 7) to give the title compound (21 mg, 34%) as an off-white solid. $\delta_H$ (CDCl$_3$) 8.05 (1H, d, J 2.1 Hz), 7.11-6.91 (2H, m), 5.45 (1H, s), 4.41-4.32 (2H, m), 4.19-4.10 (2H, m), 2.92 (4H, s), 2.88 (2H, s), 1.39 (6H, s). LCMS (ES+) 413.0 (M+H)$^+$, RT 2.58 minutes (Method 2).

Example 288

6,6-Dimethyl-2-[6-(isoquinolin-1-ylamino)-2,3-dihydro-4H-1,4-benzoxazin-4-yl]-6,7-dihydro[1,3]thiazolo[5,4-c]pyridin-4(5H)-one The title compound was prepared from Example 42 and 1-chloroisoquinoline according to Method AB (using [1,1'-bis(di-tert-butylphosphino)ferrocene]palladium(II) dichloride) and was isolated as an off-white solid (36%) after purification by preparative HPLC (Method 7). $\delta_H$ (CDCl$_3$) 8.37 (1H, d, J 2.4 Hz), 8.07 (1H, d, J 5.8 Hz), 7.97 (1H, d, J 8.3 Hz), 7.78-7.72 (1H, m), 7.68-7.53 (2H, m), 7.36-7.21 (2H, m), 7.22-7.06 (2H, m), 7.01-6.93 (1H, m), 5.35 (1H, s), 4.38-4.29 (2H, m), 4.22-4.15 (2H, m), 2.87 (2H, s), 1.39 (6H, s). LCMS (ES+) 458.0 (M+H)$^+$, RT 3.64 minutes (Method 2).

Example 289

N-[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]-N-(6-methylpyridin-3-yl)acetamide A mixture of Example 60 (17 mg, 0.04 mmol), acetyl chloride (3.2 mg, 0.4 mmol) and pyridine (0.5 mL, 0.8 mmol) in THF (10 mL) was stirred at r.t. for 2 days. It was concentrated in vacuo and purified by preparative HPLC (Method 7) to give the title compound (8.8 mg, 47%) as an off-white solid. $\delta_H$ (CDCl$_3$) 8.53-8.34 (1H, m), 8.31-8.18 (1H, m), 7.60-7.51 (1H, m), 7.24-7.11 (1H, m), 7.03-6.88 (2H, m), 5.23 (1H, br s), 4.47-4.28 (2H, m), 4.14-3.98 (2H, m), 2.94-2.80 (2H, m), 2.63-2.48 (3H, m), 2.27-2.07 (3H, m), 1.40 (6H, s). LCMS (ES+) 464 (M+H)$^+$, RT 2.70 minutes (Method 2).

Example 290

2-{6-[Bis(6-methylpyridazin-3-yl)amino]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 42 and 3-chloro-6-methylpyridazine according to Method AB (using [1,1'-bis(di-tert-butylphosphino)ferrocene]-palladium(II) dichloride) and was isolated as an off-white solid (17%) after purification by preparative HPLC (Method 7). $\delta_H$ (CDCl$_3$) 7.86 (1H, d, J 2.1 Hz), 7.38 (2H, d, J 9.0 Hz), 7.24 (2H, d, J 9.0 Hz), 7.06-6.93 (2H, m), 5.14 (1H, s), 4.41-4.31 (2H, m), 4.23-4.08 (2H, m), 2.79 (2H, s), 2.64 (6H, s), 1.36 (6H, s). LCMS (ES+) 515.0 (M+H)$^+$, RT 2.52 minutes (Method 2).

Example 291

2-(6-{Bis[5-(trifluoromethyl)pyridin-2-yl]amino}-2,3-dihydro-4H-1,4-benzoxazin-4-yl)-6,6-dimethyl-6,7-dihydro[1,3]thiazolo[5,4-c]pyridin-4(5H)-one The title compound was prepared from Example 42 and 2-bromo-5-(trifluoromethyl)pyridine according to Method AB (using [1,1'-bis(di-tert-butylphosphino)-ferrocene]palladium(II) dichloride) and was isolated as an off-white solid (40%) after purification by preparative HPLC (Method 7). $\delta_H$ (CDCl$_3$) 8.57 (2H, dd, J 1.5 and 0.8 Hz), 8.01 (1H, d, J 2.4 Hz), 7.85-7.78 (2H, m), 7.32-7.17 (2H, m), 7.07-7.01 (1H, m), 6.92 (1H, dd, J 8.7 and 2.4 Hz), 5.13 (1H, s), 4.44-4.35 (2H, m), 4.17-4.07 (2H, m), 2.73 (2H, s), 1.34 (6H, s). LCMS (ES+) 621.0 (M+H)$^+$, RT 4.42 minutes (Method 2).

Example 292

6,6-Dimethyl-2-[6-(4,4,5,5-tetramethyl-[1,3,2]dioxaborolan-2-yl)-2,3-dihydro-4H-1,4-benzoxazin-4-yl]-6,7-dihydro[1,3]thiazolo[5,4-c]pyridin-4(5H)-one To a suspension of Example 39 (1 g, 2.54 mmol) in THF (15 mL) was added potassium acetate (0.37 g, 3.81 mmol), bis(pinacolato)diboron (0.90 g, 3.81 mmol) and [1,1'-bis(di-tert-butylphosphino)ferrocene]palladium(II) dichloride (0.41 g, 0.51 mmol). The mixture was heated at 125° C. under microwave irradiation for 70 minutes, allowed to cool to r.t. and the resulting precipitate filtered off and washed with Et$_2$O (2×100 mL). The combined organic fraction was washed with water (100 mL) and brine (100 mL), dried (MgSO$_4$), filtered and concentrated in vacuo. The resulting solid was triturated with heptane (100 mL), filtered, washed with heptane (2×100 mL) and dried in vacuo to yield the title compound (0.84 g, 75%) as a beige solid. $\delta_H$ (CDCl$_3$) 8.16 (1H, d, J 1.3 Hz), 7.53 (1H, dd, J 8.3 and 1.5 Hz), 6.94 (1H, d, J 8.1 Hz), 5.29 (1H, s), 4.36-4.31 (2H, m), 4.22-4.16 (2H, m), 2.86 (2H, s), 1.40 (6H, s), 1.33 (12H, s). LCMS (ES+) 442.0 (M+H)$^+$, RT 2.91 minutes (Method 1).

Example 293

6,6-Dimethyl-2-[6-(2-methyl-1H-imidazol-4-yl)-2,3-dihydro-4H-1,4-benzoxazin-4-yl]-6,7-dihydro[1,3]thiazolo[5,4-c]pyridin-4(5H)-one, ammonium acetate salt A mixture of Example 292 (152 mg, 0.34 mmol), 4-bromo-2-methylimidazole (110 mg, 0.68 mmol), potassium phosphate (220 mg, 1.03 mmol) and tetrakis(triphenylphosphine)palladium(0) (10 mg) in DME (10 mL) and water (2 mL) was stirred at 120° C. under microwave irradiation for 1 h. It was concentrated in vacuo and purified by preparative HPLC (Method 6) to give the title compound (19.6 mg, 15%) as an off-white solid. $\delta_H$ (CDCl$_3$) 8.02 (1H, d, J 1.9 Hz), 7.39 (1H, dd, J 8.5 and 1.9 Hz), 7.02 (1H, s), 6.93 (1H, d, J 8.5 Hz), 5.71 (1H, s), 4.37-4.27 (2H, m), 4.26-4.14 (2H, m), 2.86 (2H, s), 2.47 (3H, s), 2.08 (1H, s), 1.40 (6H, s). LCMS (ES+) 396.0 (M+H)$^+$, RT 2.45 minutes (Method 1).

Example 294

6,6-Dimethyl-2-(6-methyl-2,3-dihydro-4H-1,4-benzoxazin-4-yl)-6,7-dihydro[1,3]thiazolo[5,4-c]pyridin-4(5H)-one A solution of n-butyllithium (0.5 mL, 2.5 M in hexanes, 1.25 mmol) was added to a solution of Example 210 (209 mg, 0.51 mmol) in THF (10 mL), pre-cooled in a dry-ice/acetone bath under nitrogen and the mixture stirred for 75 minutes. Anhydrous DMF (0.2 mL, 2.58 mmol) was added, and the mixture allowed to warm to r. t. It was stirred overnight, then concentrated in vacuo. DCM (30 mL) and water (30 mL) were added. The aqueous fraction was washed with DCM (2×30 mL). The organic fractions were combined, dried (Na$_2$SO$_4$), filtered and concentrated in vacuo. Purification by column chromatography (SiO$_2$, 0-100% heptane/EtOAc) gave the title compound (38.0 mg, 23%) as a white solid. $\delta_H$ (CDCl$_3$) 7.69-7.65 (1H, m), 6.88-6.83 (2H, m), 4.32-4.27 (2H, m), 4.19-4.13 (2H, m), 2.87 (2H, s), 2.30 (3H, s), 1.40 (6H, s). Exchangeable protons were not observed. LCMS (ES+) 330.1 (M+H)$^+$, RT 3.35 minutes (Method 1).

Example 295

Method AP 2-(7-{[3-(Dimethylamino)propyl]amino}-6-methyl-2,3-dihydro-4H-1,4-benzoxazin-4-yl)-6,6-dimethyl-6,7-dihydro[1,3]thiazolo[5,4-c]pyridin-4(5H)-one, formic acid salt Toluene (1.5 mL) and N,N-dimethyl-1,3-propanediamine (46.7 μL, 0.371 mmol) were added to a stirred mixture of Example 210 (75.7 mg, 0.185 mmol), sodium tert-butoxide (57.5 mg, 0.599 mmol) and [1,1'-bis(di-tert-butylphosphino)ferrocene]palladium dichloride (13.62 mg, 0.0188 mmol) under nitrogen. The mixture was degassed by evacuating and purging with nitrogen three times. It was heated to 130° C. under microwave irradiation for 3 h, then concentrated in vacuo. Purification by preparative HPLC (Method 6) gave the title compound (15.9 mg, 18.4%) as a yellow oil. $\delta_H$ (CD$_3$OD) 8.56 (1H, s, formic acid), 7.38 (1H, s), 6.21 (1H, s), 4.28-4.22 (2H, m), 4.14-4.08 (2H, m), 3.23 (2H, t, J 6.8 Hz), 2.92-2.82 (4H, m), 2.60 (6H, s), 2.11 (3H, s), 2.02-1.90 (2H, m), 1.38 (6H, s). Exchangeable protons were not observed. LCMS (ES+) 430.11 (M+H)$^+$, RT 1.95 minutes (Method 1).

Example 296

6,6-Dimethyl-2-{6-methyl-7-[(2-(pyrrolidin-1-yl)ethyl)amino]-2,3-dihydro-4H-1,4-benzoxazin-4-yl}-6,7-dihydro[1,3]thiazolo[5,4-c]pyridin-4(5H)-one, formic acid salt The title compound was prepared from Example 210 and 1-(2-aminoethyl)-pyrrolidine according to Method AP and was isolated as a yellow solid (34%) after purification by column chromatography (SiO$_2$, 0-100% heptane/EtOAc, 15% MeOH/DCM) followed by preparative HPLC (Method 6). $\delta_H$ (CD$_3$OD) 8.52 (1H, s, formic acid), 7.44 (1H, s), 6.29 (1H, s), 4.29-4.23 (2H, m), 4.15-4.07 (2H, m), 3.55 (2H, t, J 5.8 Hz), 3.48-3.36 (6H, m), 2.86 (2H, s), 2.16 (3H, s), 2.14-2.06 (4H, m), 1.38 (6H, s). Exchangeable protons were not observed. LCMS (ES+) 442.12 (M+H)$^+$, RT 1.99 minutes (Method 1).

Example 297

2-(7-{N[2-(Dimethylamino)ethyl]-N-(methyl)amino}-6-methyl-2,3-dihydro-4H-1,4-benzoxazin-4-yl)-6,6-dimethyl-6,7-dihydro[1,3]thiazolo[5,4-c]pyridin-4(5H)-one, formic acid salt The title compound was prepared from Example 210 and N,N,N'-trimethylethylenediamine according to Method AP and was isolated as a straw-coloured solid (2%) after purification by preparative HPLC (Method 6). $\delta_H$ (CD$_3$OD) 8.56 (4.73H, s, formic acid), 7.72 (1H, s), 6.77 (1H, s), 4.33-4.25 (2H, m), 4.17-4.09 (2H, m), 3.27-3.17 (2H, m), 3.07-2.98 (2H, m), 2.88 (2H, s), 2.71-2.66 (9H, m), 2.30 (3H, s), 1.39 (6H, s). Exchangeable protons were not observed. LCMS (ES+) 430.08 (M+H)$^+$, RT 2.03 minutes (Method 1).

Example 298

6,6-Dimethyl-2-[6-methyl-7-(piperidin-4-ylamino)-2,3-dihydro-4H-1,4-benzoxazin-4-yl]-6,7-dihydro[1,3]thiazolo[5,4-c]pyridin-4(5H)-one To a stirred solution of Intermediate 220 (91 mg, 0.172 mmol) in DCM (10 mL) was added 2M HCl in Et$_2$O (10 mL). The reaction mixture was stirred at r.t. overnight, then concentrated in vacuo. Purification by column chromatography (SiO$_2$, 0-15% MeOH/DCM with 2% NH$_4$OH added) gave the title compound (68.7 mg, 62%) as a yellow solid. $\delta_H$ (CD$_3$OD) 7.42 (1H, s), 6.31 (1H, s), 4.28-4.22 (2H, m), 4.15-4.09 (2H, m), 3.68-3.54 (1H, m), 3.46-3.37 (2H, m), 3.16-3.05 (2H, m), 2.86 (2H, s), 2.30-2.20 (2H, m), 2.13 (3H, s), 1.77-1.61 (2H, m), 1.38 (6H, s). Exchangeable protons were not observed. LCMS (ES+) 428.11 (M+H)$^+$, RT 1.91 minutes (Method 1).

Example 299

Method AQ

2-{6-[3,5-Dimethyl-1-(3-methylbutyl)-1H-pyrazol-4-yl]-2,3-dihydro-4H-1,4-benzoxazin-4-yl}-6,6-dimethyl-6,7-dihydro[1,3]thiazolo[5,4-c]pyridin-4(5H)-one To a stirred solution of 3,5-dimethyl-4-(4,4,5,5-tetramethyl-[1,3,2]dioxaborolan-2-yl)-1H-pyrazole (0.25 g, 1.26 mmol) in THF (3 mL) was added sodium bis(trimethylsilyl)amide (2M in THF, 0.840 mL, 1.23 mmol). The reaction mixture was stirred at r.t. for 5 minutes followed by the addition of 1-bromo-3-methylbutane (0.416 mL, 2.5 mmol). The reaction was heated at 70° C. for 16 h in a sealed tube. It was then filtered and concentrated in vacuo. To the residue (0.332 g, 1.14 mmol) and Example 39 (0.150 g, 0.38 mmol) in DME (2.5 mL) and water (0.75 mL) were added tetrakis(triphenylphosphine)palladium(0) (0.045 g, 0.038 mmol) and sodium carbonate (0.123 g, 1.14 mmol). The reaction mixture was heated to 140° C. under microwave irradiation for 15 minutes and then concentrated in vacuo. It was purified by preparative HPLC (Method 6) to give the title compound (0.047 g, 26%) as a white solid. $\delta_H$ (CDCl$_3$) 7.79 (1H, d, J 1.9 Hz), 7.02-6.92 (2H, m), 6.06 (1H, s), 4.39-4.34 (2H, m), 4.21-4.15 (2H, m), 4.08-4.00 (2H, m), 2.86 (2H, s), 2.28 (6H, d, J 2.8 Hz), 1.78-1.63 (3H, m), 1.40 (6H, s), 0.98 (6H, d, J 6.4 Hz). LCMS (ES+) 480 (M+H)$^+$, RT 3.89 minutes (Method 1).

Example 300

2-{6-[1-(Cyclopropylmethyl)-3,5-dimethyl-1H-pyrazol-4-yl]-2,3-dihydro-4H-1,4-benzoxazin-4-yl}-6,6-dimethyl-6,7-dihydro[1,3]thiazolo[5,4-c]pyridin-4(5H)-one The title compound was prepared from 3,5-dimethyl-4-(4,4,5,5-tetramethyl-[1,3,2]dioxaborolan-2-yl)-1H-pyrazole, Example 39 and (bromomethyl)cyclopropane according to Method AQ and was isolated as a white solid (26%) after purification by preparative HPLC (Method 6). $\delta_H$ (CDCl$_3$) 7.81 (1H, d, J 1.7 Hz), 7.03-6.93 (2H, m), 5.39 (1H, s), 4.39-4.34 (2H, m), 4.21-4.16 (2H, m), 3.93 (2H, d, J 6.8 Hz), 2.86 (2H, s), 2.30 (3H, s), 2.28 (3H, s), 1.39 (6H, s), 1.34-1.23 (1H, m), 0.65-0.57 (2H, m), 0.44-0.36 (2H, m). LCMS (ES+) 464 (M+H)$^+$, RT 3.40 minutes (Method 1).

Example 301

Method AR

6,6-Dimethyl-2-[6-(5-methyl-1,3,4-thiadiazol-2-yl)-2,3-dihydro-4H-1,4-benzoxazin-4-yl]-6,7-dihydro[1,3]thiazolo[5,4-c]pyridin-4(5H)-one To a stirred solution of 2-bromo-5-methyl-[1,3,4]thiadiazole (0.0062 g, 0.037 mmol) and Example 292 (0.050 g, 0.11 mmol) in DME (2 mL) and water (0.5 mL) was added tetrakis(triphenylphosphine)palladium(0) (0.013 g, 0.011 mmol) and potassium phosphate (0.023 g, 0.11 mmol). The reaction mixture was heated at 140° C. under microwave irradiation for 15 minutes, then concentrated in vacuo. It was purified by preparative HPLC (Method 6) to give the title compound (0.0068 g, 44%) as an off-white solid. $\delta_H$ (CDCl$_3$) 8.68 (1H, d, J 2.1 Hz) 7.65 (1H, dd, J 8.5 and 2.1 Hz), 7.04 (1H, d, J 8.5 Hz), 5.51 (1H, s), 4.43-4.38 (2H, m), 4.17-4.12 (2H, m), 2.91 (2H, s), 2.81 (3H, s), 1.41 (6H, s). LCMS (ES+) 414 (M+H)$^+$, RT 2.91 minutes (Method 1).

Example 302

2-[6-(3-Amino-5-methylisoxazol-4-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from 3-amino-4-bromo-5-methylisoxazole and Example 292 according to Method AR and was isolated as an off-white solid (17%) after purification by preparative HPLC (Method 6). $\delta_H$ (CDCl$_3$) 8.06 (1H, s), 7.03 (2H, s), 5.29 (1H, s), 4.42-4.36 (2H, m), 4.14-4.03 (4H, m), 2.86 (2H, s), 2.39 (3H, s), 1.40 (6H, s). LCMS (ES+) 412 (M+H)$^+$, RT 2.81 minutes (Method 1).

Example 303

6,6-Dimethyl-2-[6-(2-oxo-2,3-dihydro-1H-indol-5-yl)-2,3-dihydro-4H-1,4-benzoxazin-4-yl]-6,7-dihydro[1,3]thiazolo[5,4-c]pyridin-4(5H)-one The title compound was prepared from 5-bromo-2-oxo-2,3-dihydro-1H-indole and Example 292 according to Method AR and was isolated as an off-white solid (23%) after purification by preparative HPLC (Method 6). $\delta_H$ (CDCl$_3$) 8.56 (1H, s), 7.97 (1H, d, J 2.1 Hz), 7.46-7.39 (2H, m), 7.26-7.24 (1H, m), 6.99 (2H, dd, J 14.5 and 8.5 Hz), 5.77 (1H, s), 4.40-4.32 (2H, m), 4.29-4.22 (2H, m), 3.61 (2H, s), 2.88 (2H, s), 1.42 (6H, s). LCMS (ES+) 445 (M−H)$^+$, RT 2.92 minutes (Method 1).

Example 304

{2-[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]phenoxy}acetonitrile The title compound was prepared from 2-bromophenoxyacetonitrile and Example 292 according to Method AR and was isolated as an off-white solid (57%) after purification by preparative HPLC (Method 6). $\delta_H$ (CDCl$_3$) 8.01 (1H, s), 7.41-7.33 (2H, m), 7.24-7.16 (2H, m), 7.11 (1H, d, J 8.1 Hz), 7.02 (1H, d, J 8.5 Hz), 5.58 (1H, s), 4.79 (2H, s), 4.39-4.34 (2H, m), 4.25-4.20 (2H, m), 2.87 (2H, s), 1.40 (6H, s). LCMS (ES+) 447 (M+H)$^+$, RT 3.56 minutes (Method 1).

Example 305

2-[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]-N-methylbenzamide The title compound was prepared from 2-bromo-N-methylbenzamide and Example 292 according to Method AR and was isolated as an off-white solid (28%) after purification by preparative HPLC (Method 6). $\delta_H$ (CDCl$_3$) 8.02 (1H, d, J 2.1 Hz), 7.64 (1H, dd, J 7.3 and 1.1 Hz), 7.51-7.34 (3H, m), 7.13 (1H, dd, J 8.5 and 2.1 Hz), 6.99 (1H, d, J 8.5 Hz), 5.54-5.43 (2H, m), 4.41-4.35 (2H, m), 4.23-4.17 (2H, m), 2.90 (2H, s), 2.79 (3H, d, J 4.9 Hz), 1.40 (6H, s). LCMS (ES+) 449 (M+H)$^+$, RT 2.80 minutes (Method 1).

Example 306

2-{6-[3,5-Dimethyl-1-(tetrahydro-2H-pyran-2-ylmethyl)-1H-pyrazol-4-yl]-2,3-dihydro-4H-1,4-benzoxazin-4-yl}-6,6-dimethyl-6,7-dihydro[1,3]thiazolo[5,4-c]pyridin-4(5H)-one The title compound was prepared from 3,5-dimethyl-4-(4,4,5,5-tetramethyl-[1,3,2]dioxaborolan-2-yl)-1H-pyrazole, Example 39 and 2-(bromomethyl)tetrahydro-2H-pyran according to Method AQ and was isolated as a white solid (14%) after purification by preparative HPLC (Method 6). $\delta_H$ (CDCl$_3$) 7.82 (1H, d, J 1.5 Hz), 7.01-6.93 (2H, m), 5.73 (1H, s), 4.39-4.34 (2H, m), 4.20-4.15 (2H, m), 4.12-3.91 (2H, m), 4.12-3.91 (1H, m), 3.80-3.71 (1H, m), 3.46-3.36 (1H, m), 2.86 (2H, s), 2.29 (6H, d, J 6.2 Hz), 1.91-1.82 (1H, m), 1.70-1.47 (5H, m), 1.39 (6H, s). LCMS (ES+) 507 (M+H)$^+$, RT 3.51 minutes (Method 1).

Example 307

Method AS

2-[6-(6-Aminopyridazin-3-yl)-2,3-dihydro-4H-1,4-benzoxazin-4-yl]-6,6-dimethyl-6,7-dihydro[1,3]thiazolo[5,4-c]pyridin-4(5H)-one To a stirred solution of 6-amino-3-chloropyridazine (0.019 g, 0.15 mmol) and Example 292 (0.200 g, 0.44 mmol) in DME (3 mL) and water (1 mL) was added tetrakis(triphenylphosphine)palladium(0) (0.0179 g, 0.015 mmol), tetra-n-butyl-ammonium bromide (0.048 g, 0.15 mmol) and sodium carbonate (0.048 g, 0.45 mmol). The reaction mixture was heated at 140° C. under microwave irradiation for 15 minutes and then concentrated in vacuo. The residue was purified by column chromatography (SiO$_2$, 0-100% EtOAc/heptane) followed by trituration with MeOH/Et$_2$O to give the title compound (0.0148 g, 24%) as a white solid. $\delta_H$ (DMSO-d$_6$) 8.68 (1H, d, J 2.1 Hz), 7.74 (1H, d, J 9.2 Hz), 7.66 (1H, dd, J 8.5 and 1.9 Hz), 7.55 (1H, s), 7.05 (1H, d, J 8.5 Hz), 6.85 (1H, d, J 9.2 Hz), 6.46-6.41 (1H, m), 4.39-4.32 (2H, m), 4.18-4.12 (2H, m), 2.83 (2H, s), 1.29 (6H, s). LCMS (ES+) 409 (M+H)$^+$, RT 1.95 minutes (Method 1).

Example 308

6,6-Dimethyl-2-[6-(3-methoxypyrazin-2-yl)-2,3-dihydro-4H-1,4-benzoxazin-4-yl]-6,7-dihydro[1,3]thiazolo[5,4-c]pyridin-4(5H)-one The title compound was prepared from 2-chloro-3-methoxypyrazine and Example 292 according to Method AS and was isolated as a white solid (18%) after purification by column chromatography (SiO$_2$, 0-100% EtOAc/heptane) followed by trituration with Et$_2$O. $\delta_H$ (DMSO-d$_6$) 8.82 (1H, d, J 2.1 Hz), 8.32 (1H, d, J 2.6 Hz), 8.19 (1H, d, J 2.6 Hz), 7.81 (1H, dd, J 8.7 and 2.1 Hz), 7.56 (1H, s), 7.09 (1H, d, J 8.7 Hz), 4.41-4.35 (2H, m), 4.20-4.15 (2H, m), 4.02 (3H, s), 2.82 (2H, s), 1.29 (6H, s). LCMS (ES+) 424 (M+H)$^+$, RT 3.36 minutes (Method 1).

Example 309

6,6-Dimethyl-2-[6-(6-methoxypyridazin-3-yl)-2,3-dihydro-4H-1,4-benzoxazin-4-yl]-6,7-dihydro[1,3]thiazolo[5,4-c]pyridin-4(5H)-one The title compound was prepared from 3-chloro-6-methoxypyridazine and Example 292 according to Method AS and was isolated as a white solid (21%) after purification by column chromatography (SiO$_2$, 0-100% EtOAc/heptane) followed by trituration with MeOH/Et$_2$O. $\delta_H$ (CDCl$_3$) 8.53 (1H, d, J 2.1 Hz), 7.80 (1H, dd, J 8.5 and 2.1 Hz), 7.73 (1H, d, J 9.2 Hz), 7.06 (2H, t, J 9.0 Hz), 5.29 (1H, s), 4.42-4.36 (2H, m), 4.24-4.19 (2H, m), 4.18 (3H, s), 2.89 (2H, s), 1.40 (6H, s). LCMS (ES+) 424 (M+H)$^+$, RT 3.05 minutes (Method 1).

Example 310

2-[6-(2,4-Dimethyl-1,3-thiazol-5-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from 5-bromo-2,4-dimethyl-1,3-thiazole and Example 292 according to Method AR and was isolated as an off-white solid (24%) after purification by preparative HPLC (Method 6). $\delta_H$ (CDCl$_3$) 8.11 (1H, d, J 2.1 Hz), 7.10 (1H, dd, J 8.3 and 1.9 Hz), 6.99 (1H, d, J 8.5 Hz), 5.19 (1H, s), 4.40-4.35 (2H, m), 4.18-4.12 (2H, m), 2.88 (2H, s), 2.68 (3H, s), 2.49 (3H, s), 1.40 (6H, s). LCMS (ES+) 427 (M+H)$^+$, RT 3.26 minutes (Method 1).

Example 311

6,6-Dimethyl-2-(6-{6-[(2-hydroxyethyl)amino]pyridazin-3-yl}-2,3-dihydro-4H-1,4-benzoxazin-4-yl)-6,7-dihydro[1,3]thiazolo[5,4-c]pyridin-4(5H)-one The title compound was prepared from 2-[(6-chloropyridazin-3-yl)amino]ethanol and Example 292 according to Method AS and was isolated as a white solid (29%) after purification by preparative HPLC (Method 6) followed by trituration with MeOH/heptane. $\delta_H$ (DMSO-d$_6$) 8.69 (1H, d, J 2.1 Hz), 7.74 (1H, d, J 9.4 Hz), 7.65 (1H, dd, J 8.5 and 2.1 Hz), 7.56 (1H, s), 7.06 (1H, d, J 8.7 Hz), 6.94 (1H, d, J 9.4 Hz), 4.38-4.32 (2H, m), 4.20-4.14 (2H, m), 3.63-3.56 (2H, m), 3.51-3.45 (2H, m), 2.83 (2H, s), 1.29 (6H, s). LCMS (ES+) 453 (M+H)$^+$, RT 1.89 minutes (Method 1).

Example 312

2-[6-(3-Aminopyrazin-2-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from 2-amino-3-chloropyrazine and Example 292 according to Method AS and was isolated as a white solid (10%) after preparative HPLC (Method 6). $\delta_H$ (CDCl$_3$) 8.42 (1H, d, J 2.1 Hz), 8.02 (1H, d, J 2.8 Hz), 7.97 (1H, d, J 2.6 Hz), 7.47 (1H, dd, J 8.5 and 2.1 Hz), 7.09 (1H, d, J 8.5 Hz), 5.22 (1H, s), 4.94 (2H, s), 4.43-4.38 (2H, m), 4.17-4.11 (2H, m), 2.86 (2H, s), 1.39 (6H, s). LCMS (ES+) 409 (M+H)$^+$, RT 2.50 minutes (Method 1).

Example 313

2-{6-[6-(Dimethylamino)pyridazin-3-yl]-2,3-dihydro-4H-1,4-benzoxazin-4-yl}-6,6-dimethyl-6,7-dihydro[1,3]thiazolo[5,4-c]pyridin-4(5H)-one, formic acid salt The title compound was prepared from (6-chloropyridazin-3-yl)dimethylamine and Example 292 according to Method AS and was isolated as a white solid (36%) after purification by preparative HPLC (Method 6). $\delta_H$ (CDCl$_3$) 8.43 (1H, d, J 1.5 Hz), 8.20 (1H, s), 7.78 (1H, dd, J 8.5 and 1.3 Hz), 7.59 (1H, d, J 9.4 Hz), 7.05 (1H, d, J 8.7 Hz), 6.90 (1H, d, J 9.6 Hz), 6.26 (1H, s), 4.41-4.34 (2H, m), 4.25-4.18 (2H, m), 3.23 (6H, s), 2.89 (2H, s), 1.41 (6H, s). LCMS (ES+) 437 (M+H)$^+$, RT 1.92 minutes (Method 1).

Example 314

6,6-Dimethyl-2-[6-(6-(piperidin-1-yl)pyridazin-3-yl)-2,3-dihydro-4H-1,4-benzoxazin-4-yl]-6,7-dihydro[1,3]thiazolo[5,4-c]pyridin-4(5H)-one The title compound was prepared from 3-chloro-6-(piperidin-1-yl)pyridazine and Example 292 according to Method AS and was isolated as a white solid (5%) after purification by preparative HPLC (Method 6). $\delta_H$ (DMSO-d$_6$) 8.74 (1H, d, J 1.9 Hz), 7.84 (1H, d, J 9.8 Hz), 7.71 (1H, dd, J 8.5 and 1.9 Hz), 7.07 (1H, d, J 8.5 Hz), 7.34 (1H, d, J 9.6 Hz), 7.56 (1H, s), 4.39-4.33 (2H, m), 4.20-4.13 (2H, m), 3.71-3.63 (4H, m), 2.83 (2H, s), 1.70-1.53 (6H, m), 1.29 (6H, s). LCMS (ES+) 437 (M+H)$^+$, RT 2.28 minutes (Method 1).

Example 315

2-[6-(3,5-Dimethyl-1-ethyl-1H-pyrazol-4-yl)-2,3-dihydro-4H-1,4-benzoxazin-4-yl]-6,6-dimethyl-6,7-dihydro[1,3]thiazolo[5,4-c]pyridin-4(5H)-one To a stirred solution of 3,5-dimethyl-4-(4,4,5,5-tetramethyl-[1,3,2]dioxaborolan-2-yl)-1H-pyrazole (0.5 g, 2.25 mmol) in THF (6 mL) was added sodium bis(trimethylsilyl)amide (2M in THF, 65 mL, 2.47 mmol). The reaction was stirred at r.t. for 5 minutes before addition of ethyl iodide (0.539 mL, 6.75 mmol). It was heated at 70° C. for 16 h in a sealed tube and then was filtered and concentrated in vacuo. To the residue (0.560 g, 2.24 mmol) and Example 39 (0.294 g, 0.74 mmol) in DME (6 mL) and water (2 mL) was added tetrakis(triphenylphosphine)palladium(0) (0.088 g, 0.074 mmol), tetra-n-butyl-ammonium bromide (0.239 g, 0.74 mmol) and sodium carbonate (0.241 g, 2.24 mmol). The reaction mixture was heated at 140° C. under microwave irradiation for 15 minutes and then the solvent was evaporated in vacuo. The residue was purified by preparative HPLC (Method 6) followed by trituration with Et$_2$O to give the title compound (0.0026 g, 0.8%) as a white solid. $\delta_H$(CDCl$_3$) 7.81 (1H, d, J 1.9 Hz), 7.01-6.91 (2H, m), 5.13 (1H, d, J 1.3 Hz), 4.39-4.33 (2H, m), 4.20-4.15 (2H, m), 4.09 (2H, q, J 7.3 Hz), 2.86 (2H, s), 2.28 (6H, d, J 3.6 Hz), 1.44 (3H, t, J 7.2 Hz), 1.39 (6H, s). LCMS (ES+) 438 (M+H)$^+$, RT 3.07 minutes (Method 1).

Example 316

Diethyl (3-{4-[4-(6,6-dimethyl-4-oxo-4,5,6,7-tetrahydro[1,3]thiazolo[5,4-c]pyridin-2-yl)-3,4-dihydro-2H-1,4-benzoxazin-6-yl]-1H-pyrazol-1-yl}propyl)phosphonate The title compound was prepared from Example 39 and Intermediate 224 according to Method AD (heating at 100° C. for 22 h followed by addition of further Intermediate 224 and heating at 100° C. for a further 24 h) and was isolated as a white solid (63%) after purification by preparative HPLC (Method 6). $\delta_H$ (CDCl$_3$) 8.00 (1H, s), 7.71 (1H, s), 7.61 (1H, s), 7.20-7.13 (1H, m), 6.99-6.92 (1H, m), 5.84 (1H, s), 4.38-4.30 (2H, m), 4.28-4.02 (8H, m), 2.88 (2H, s), 2.31-2.12 (2H, m), 1.83-1.66 (2H, m), 1.40 (6H, s), 1.37-1.26 (6H, m). LCMS (ES+) 560 (M+H)$^+$, RT 3.02 minutes (Method 1).

Example 317

6,6-Dimethyl-2-{6-[1-(tetrahydro-2H-pyran-2-ylmethyl)-1H-pyrazol-4-yl]-2,3-dihydro-4H-1,4-benzoxazin-4-yl}-6,7-dihydro[1,3]thiazolo[5,4-c]pyridin-4(5H)-one The title compound was prepared from Example 39 and Intermediate 225 according to Method AD (heating at 100° C. for 22 h followed by addition of further Intermediate 225 and heating at 100° C. for a further 24 h) and was isolated as a colourless oil (quantitative) after purification by preparative HPLC (Method 6). $\delta_H$ (CDCl$_3$) 8.02 (1H, d, J 2.1 Hz), 7.71 (1H, s), 7.66 (1H, s), 7.18 (1H, dd, J 8.5 Hz and 2.1 Hz), 6.94 (1H, d, J 8.5 Hz), 5.53 (1H, s), 4.36-4.31 (2H, t, J 4.3 Hz), 4.21-4.13 (2H, m), 4.14 (2H, d, J 5.6 Hz), 4.03-3.95 (1H, m), 3.79-3.68 (1H, m), 3.47-3.36 (1H, m), 2.88 (2H, s), 1.91-1.82 (1H, m), 1.58-1.47 (4H, m), 1.40 (6H, s), 1.33-1.25 (1H, m). LCMS (ES+) 480 (M+H)$^+$, RT 3.37 minutes (Method 1).

Example 318

2-{4-[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]-1H-pyrazol-1-yl}-N,N-dimethylacetamide The title compound was prepared from Example 39 and Intermediate 226 according to Method AD (heating at 90° C. for 69 h) and was isolated as a clear colourless oil (18%) after purification by preparative HPLC (Method 6). $\delta_H$ (CDCl$_3$) 8.03 (1H, d, J 1.9 Hz), 7.74 (1H, s), 7.73 (1H, s), 7.18 (1H, dd, J 8.5 and 2.1 Hz), 6.94 (1H, d, J 8.5 Hz), 5.57 (1H, s), 5.03 (2H, s), 4.36-4.30 (2H, m), 4.21-4.15 (2H, m), 3.11 (3H, s), 3.00 (3H, s), 2.88 (2H, s), 1.40 (6H, s). LCMS (ES+) 467 (M+H)$^+$, RT 2.63 minutes (Method 1).

Example 319

6,6-Dimethyl-2-{6-[1-(3-hydroxypropyl)-1H-pyrazol-4-yl]-2,3-dihydro-4H-1,4-benzoxazin-4-yl}-6,7-dihydro[1,3]thiazolo[5,4-c]pyridin-4(5H)-one The title compound was prepared from Example 39 and Intermediate 227 according to Method AD (heating at 100° C. for 23 h followed by addition of further Intermediate 227 and heating at 100° C. for a further 6 h) and was isolated as a clear colourless oil (55%) after purification by preparative HPLC (Method 6). $\delta_H$ (CDCl$_3$) 7.99 (1H, d, J 1.9 Hz), 7.71 (1H, s), 7.62 (1H, s), 7.16 (1H, dd, J 8.3 and 1.9 Hz), 6.94 (1H, d, J 8.5 Hz), 5.63 (1H, s), 4.38-4.29 (4H, m), 4.23-4.14 (2H, m), 3.67 (2H, t, J 5.8 Hz), 2.88 (2H, s), 2.17-2.03 (2H, m), 1.40 (6H, s). LCMS (ES+) 440 (M+H)$^+$, RT 2.67 minutes (Method 1).

Example 320

6,6-Dimethyl-2-{6-[1-(2-(piperidin-1-yl)ethyl)-1H-pyrazol-4-yl]-2,3-dihydro-4H-1,4-benzoxazin-4-yl}-6,7-dihydro[1,3]thiazolo[5,4-c]pyridin-4(5H)-one The title compound was prepared from Example 39 and Intermediate 228 according to Method AD (heating at 100° C. for 17 h) and was isolated as a clear colourless oil (24%) after purification by preparative HPLC (Method 6). $\delta_H$ (CDCl$_3$) 8.02 (1H, d, J 1.9 Hz), 7.70 (1H, s), 7.69 (1H, s), 7.17 (1H, dd, J 8.3 and 1.9 Hz), 6.95 (1H, d, J 8.5 Hz), 5.43 (1H, s), 4.40-4.31 (4H, m), 4.21-4.16 (2H, m), 2.97 (2H, t, J 7.0 Hz), 2.89 (2H, s), 2.61-2.54 (4H, m), 1.72-1.59 (4H, m), 1.53-1.43 (2H, m), 1.41 (6H, s). LCMS (ES+) 493 (M+H)$^+$, RT 2.04 minutes (Method 1).

Example 321

6,6-Dimethyl-2-{6-[1-(2-(pyrrolidin-1-yl)ethyl)-1H-pyrazol-4-yl]-2,3-dihydro-4H-1,4-benzoxazin-4-yl}-6,7-dihydro[1,3]thiazolo[5,4-c]pyridin-4(5H)-one, formic acid salt The title compound was prepared from Example 39 and Intermediate 229 according to Method AD (heating at 100° C. for 17 h) and was isolated as a white solid (41%) after purification by preparative HPLC (Method 6). $\delta_H$ (CDCl$_3$) 8.48 (1H, s), 8.04 (1H, d, J 1.9 Hz), 7.81 (1H, s), 7.75 (1H, s), 7.19 (1H, dd, J 8.5 and 2.1 Hz), 6.95 (1H, d, J 8.5 Hz), 6.60 (2H, br. s), 5.68 (1H, s), 4.67-4.60 (2H, t, J 6.4 Hz), 4.37-4.31 (2H, m), 4.22-4.15 (2H, m), 3.66-3.58 (2H, m), 2.95 (4H, t, J 6.6 Hz), 2.89 (2H, s), 2.03-1.93 (4H, m), 1.41 (6H, s). LCMS (ES+) 479 (M+H)$^+$, RT 2.00 minutes (Method 1).

Example 322

2-(6-{1-[2-(Dimethylamino)ethyl]-1H-pyrazol-4-yl}-2,3-dihydro-4H-1,4-benzoxazin-4-yl)-6,6-dimethyl-6,7-dihydro[1,3]thiazolo[5,4-c]pyridin-4(5H)-one, hemi-formic acid salt The title compound was prepared from Example 39 and Intermediate 230 according to Method AD (heating at 100° C. for 17 h) and was isolated as a white solid (30%) after purification by preparative HPLC (Method 7). $\delta_H$ (CDCl$_3$) 8.37 (0.5H, s, formic acid), 8.00 (1H, d, J 2.1 Hz), 7.72 (1H, s), 7.68 (1H, s), 7.18 (1H, dd, J 8.5 and 1.9 Hz), 6.95 (1H, d, J 8.5 Hz), 5.55 (1H, s), 4.88 (2H, br. s), 4.39-4.31 (4H, m), 4.21-4.16 (2H, m), 2.99 (2H, t, J 6.8 Hz), 2.89 (2H, s), 2.39 (6H, s), 1.41 (6H, s). LCMS (ES+) 453 (M+H)$^+$, RT 1.96 minutes (Method 2).

Example 323

6,6-Dimethyl-2-{6-[1-(pyridin-3-ylmethyl)-1H-pyrazol-4-yl]-2,3-dihydro-4H-1,4-benzoxazin-4-yl}-6,7-dihydro[1,3]thiazolo[5,4-c]pyridin-4(5H)-one A stirred solution of Example 39 (0.793 g, 2.00 mmol), Intermediate 231 (0.524 g, 1.57 mmol), potassium phosphate (0.840 g, 3.96 mmol), tetra-n-butylammonium bromide (0.064 g, 0.197 mmol) and tetrakis(triphenylphosphine)palladium(0) (0.107 g, 0.092 mmol) in THF/H$_2$O (12 mL/3 mL) was heated to 100° C. in a sealed vessel under microwave irradiation for 3 h and then heated thermally at 120° C. for 16 h. Additional tetrakis(triphenylphosphine)palladium(0) (0.052 g, 0.045 mmol) was added and the reaction mixture heated to 120° C. for a further 16 h and then allowed to cool to r.t. It was diluted with EtOAc (10 mL) and washed with water (10 mL) and brine (10 mL). The organic fraction was dried (MgSO$_4$), filtered through Celite and concentrated in vacuo. Purification by column chromatography [SiO$_2$, gradient elution of EtOAc/MeOH/7M NH$_3$ in MeOH (100:10:1) in heptane] gave the title compound (0.166 g, 18%) as a beige foam. $\delta_H$ (CDCl$_3$) 8.63-8.55 (2H, m), 8.00 (1H, d, J 2.1 Hz), 7.77 (1H, d, J 0.8 Hz), 7.63 (1H, d, J 0.6 Hz), 7.62-7.57 (1H, m), 7.35-7.29 (1H, m), 7.16 (1H, dd, J 8.3 and 1.9 Hz), 6.94 (1H, d, J 8.3 Hz), 5.66 (1H, s), 5.37 (2H, s), 4.36-4.31 (2H, m), 4.21-4.16 (2H, m), 2.87 (2H, s), 1.40 (6H, s). LCMS (ES+) 473 (M+H)$^+$, RT 2.34 minutes (Method 1).

Example 324

2-(6-{1-[3-(Dimethylamino)propyl]-1H-pyrazol-4-yl}-2,3-dihydro-4H-1,4-benzoxazin-4-yl)-6,6-dimethyl-6,7-dihydro[1,3]thiazolo[5,4-c]pyridin-4(5H)-one The title compound was prepared from Example 39 and Intermediate 232 according to Method AD (heating at 100° C. for 6 days) and was isolated as a white solid (3%) after purification by preparative HPLC (Method 6). $\delta_H$ (CD$_3$OD) 8.09 (1H, d, J 1.9 Hz), 7.99 (1H, s), 7.85 (1H, s), 7.31 (1H, dd, J 8.5 and 1.9 Hz), 7.02-6.95 (1H, m), 4.38-4.30 (4H, m), 4.25-4.17 (2H, m), 2.94-2.90 (10H, m), 2.37-2.26 (2H, m), 1.40 (6H, s). Exchangeable protons were not observed. LCMS (ES+) 467 (M+H)$^+$, RT 2.08 minutes (Method 2).

Example 325

6,6-Dimethyl-2-(6-{1-[2-(1-methylpiperidin-2(RS)-yl)ethyl]-1H-pyrazol-4-yl}-2,3-dihydro-4H-1,4-benzoxazin-4-yl)-6,7-dihydro[1,3]thiazolo[5,4-c]pyridin-4(5H)-one The title compound was prepared from Example 39 and Intermediate 233 according to Method AD (heating at 100° C. for 6 days) and was isolated as a colourless residue (6%) after purification by preparative HPLC (Method 7). $\delta_H$ (CD$_3$OD) 8.10 (1H, d, J 2.1 Hz), 8.02 (1H, s), 7.85 (1H, s), 7.31 (1H, dd, 8.5 and 1.9 Hz), 6.99 (1H, d, J 8.5 Hz), 4.39-4.30 (4H, m), 4.24-4.18 (2H, m), 3.50-3.39 (1H, m), 3.18-3.05 (2H, m), 2.85 (2H, s), 2.68 (3H, s), 2.59-2.47 (1H, m), 2.21-2.04 (2H, m), 1.67-1.51 (2H, m), 1.40 (6H, s). LCMS (ES+) 507 (M+H)$^+$, RT 2.09 minutes (Method 2).

Example 326

Method AT

2-[6-(1-Benzothien-2-yl)-2,3-dihydro-4H-1,4-benzoxazin-4-yl]-6,6-dimethyl-6,7-dihydro[1,3]thiazolo[5,4-c]pyridin-4(5H)-one A stirred solution of Example 292 (0.048 g, 0.109 mmol), 2-bromobenzothiophene (0.035 g, 0.163 mmol), potassium phosphate (0.045 g, 0.212 mmol), tetra-n-butyl-ammonium bromide (0.045 g, 0.140 mmol) and tetrakis(triphenylphosphine)palladium(0) (0.008 g, 0.007 mmol) in THF (2 mL) and H$_2$O (0.5 mL) was heated to 100° C. in a sealed vessel under a nitrogen atmosphere for 1 h. The reaction mixture was diluted with DCM (10 mL) and washed with water (10 mL) and brine (10 mL). The organic fraction was dried (MgSO$_4$) and concentrated in vacuo. Purification by preparative HPLC (Method 6) gave the title compound (0.003 g, 7%) as a white solid. $\delta_H$ (CDCl$_3$) 8.35 (1H, d, J 2.1 Hz), 7.88-7.73 (2H, m), 7.46 (1H, s), 7.41 (1H, dd, J 8.5 and 2.1 Hz), 7.37-7.28 (2H, m), 7.01 (1H, d, J 8.5 Hz), 5.27 (1H, s), 4.42-4.35 (2H, m), 4.23-4.17 (2H, m), 2.91 (2H, s), 1.42 (6H, s). LCMS (ES+) 448 (M+H)$^+$, RT 4.37 minutes (Method 1).

Example 327

6,6-Dimethyl-2-(6-(pyrazolo[1,5-a]pyridin-3-yl)-2,3-dihydro-4H-1,4-benzoxazin-4-yl)-6,7-dihydro[1,3]thiazolo[5,4-c]pyridin-4(5H)-one The title compound was prepared from Example 292 and 3-bromopyrazolo[1,5-a]pyridine according to Method AT and was isolated as a beige solid (1%) after purification by preparative HPLC (Method 6). $\delta_H$ (CDCl$_3$) 8.50 (1H, d, J 7.0 Hz), 8.29 (1H, d, J 1.9 Hz), 8.11 (1H, s), 7.89 (1H, d, J 8.9 Hz), 7.32-7.28 (1H, m), 7.19 (1H, ddd, J 9.0, 7.0 and 1.1 Hz), 7.05 (1H, d, J 8.5 Hz), 6.80 (1H, dt, J 7.0 and 1.3 Hz), 5.20 (1H, s), 4.42-4.36 (2H, m), 4.20-4.14 (2H, m), 2.90 (2H, s), 1.41 (6H, s). LCMS (ES+) 432 (M+H)$^+$, RT 3.35 minutes (Method 1).

Example 328

2-[6-(1-Benzofuran-3-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 292 and 3-bromobenzofuran according to Method AT and was isolated as a white solid (4%) after purification by preparative HPLC (Method 6). $\delta_H$ (CDCl$_3$) 8.40 (1H, d, J 1.9 Hz), 7.97-7.89 (1H, m), 7.79 (1H, s), 7.55 (1H, dd, J 7.0 and 1.3 Hz), 7.38-7.29 (3H, m), 7.06 (1H, d, J 8.5 Hz), 5.22 (1H, s), 4.43-4.37 (2H, m), 4.19-4.13 (2H, m), 2.91 (2H, s), 1.41 (6H, s). LCMS (ES+) 432 (M+H)$^+$, RT 4.11 minutes (Method 1).

Example 329

2-[6-(1-Benzofuran-2-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 292 and 2-bromobenzofuran according to Method AT and was isolated as a white solid (9%) after purification by preparative HPLC (Method 6). $\delta_H$ (CDCl$_3$) 8.44 (1H, d, J 2.1 Hz), 7.61-7.49 (3H, m), 7.32-7.19 (2H, m), 7.04 (1H, d, J 8.7 Hz), 6.94 (1H, d, J 0.9 Hz), 5.28 (1H, s), 4.42-4.36 (2H, m), 4.24-4.19 (2H, m), 2.92 (2H, s), 1.42 (6H, s). LCMS (ES+) 432 (M+H)$^+$, RT 4.21 minutes (Method 1).

Example 330

6,6-Dimethyl-2-[6-(2-methylimidazo[1,2-a]pyridin-3-yl)-2,3-dihydro-4H-1,4-benzoxazin-4-yl]-6,7-dihydro[1,3]thiazolo[5,4-d]pyridin-4(5H)-one The title compound was prepared from Example 292 and 3-bromo-2-methylimidazo[1,2-a]pyridine according to Method AT and was isolated as a white solid (16%) after purification by preparative HPLC (Method 6). $\delta_H$ (CDCl$_3$) 8.23 (1H, d, J 1.7 Hz), 8.22-8.18 (1H, m), 7.60 (1H, d, J 9.0 Hz), 7.24-7.09 (3H, m), 6.78 (1H, dt, J 6.8 and 1.1 Hz), 5.32 (1H, s), 4.46-4.41 (2H, m), 4.18-4.12 (2H, m), 2.86 (2H, s), 2.53 (3H, s), 1.38 (6H, s). LCMS (ES+) 446 (M+H)$^+$, RT 1.97 minutes (Method 1).

Example 331

6,6-Dimethyl-2-(6-(imidazo[1,2-a]pyrazin-3-yl)-2,3-dihydro-4H-1,4-benzoxazin-4-yl)-6,7-dihydro[1,3]thiazolo[5,4-c]pyridin-4(5H)-one The title compound was prepared from Example 292 and 3-bromoimidazo[1,2-a]pyrazine according to Method AT and was isolated as a beige solid (5%) after purification by preparative HPLC (Method 6). $\delta_H$ (CDCl$_3$) 9.16 (1H, d, J 1.5 Hz), 8.51 (1H, d, J 2.1 Hz), 8.42 (1H, dd, J 4.9 and 1.5 Hz), 7.93 (1H, d, J 4.7 Hz), 7.88 (1H, s), 7.29-7.24 (1H, m), 7.16-7.12 (1H, m), 5.26 (1H, s), 4.48-4.42 (2H, m), 4.14-4.09 (2H, m), 2.89 (2H, s), 1.40 (6H, s). LCMS (ES+) 433 (M+H)$^+$, RT 2.55 minutes (Method 1).

Example 332

2-[6-(1-Benzothien-3-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 292 and 3-bromobenzo[b]thiophene according to Method AT and was isolated as a white solid (6%) after purification by preparative HPLC (Method 6). $\delta_H$ (CDCl$_3$) 8.22 (1H, d, J 1.9 Hz), 8.04-7.99 (1H, m), 7.95-7.89 (1H, m), 7.44-7.37 (3H, m), 7.30 (1H, dd, J 8.5 and 2.1 Hz), 7.07 (1H, d, J 8.3 Hz), 5.20 (1H, s), 4.44-4.37 (2H, m), 4.23-4.16 (2H, m), 2.88 (2H, s), 1.39 (6H, s). LCMS (ES+) 448 (M+H)$^+$, RT 4.28 minutes (Method 1).

Example 333

6,6-Dimethyl-2-(6-imidazo[1,2-a]pyridin-3-yl-2,3-dihydro-4H-1,4-benzoxazin-4-yl)-6,7-dihydro[1,3]thiazolo[5,4-c]pyridin-4(5H)-one The title compound was prepared from Example 292 and 3-bromoimidazo[1,2-a]pyridine according to Method AT and was isolated as an off-white solid (3%) after purification by preparative HPLC (Method 6). $\delta_H$ (CDCl$_3$) 8.44 (1H, d, J 7.0 Hz), 8.35 (1H, d, J 1.9 Hz), 7.75-7.65 (2H, m), 7.28-7.17 (2H, m), 7.15-7.07 (1H, m), 6.86 (1H, dt, J 6.8 and 0.9 Hz), 5.30 (1H, s), 4.48-4.38 (2H, m), 4.18-4.09 (2H, m), 2.88 (2H, s), 1.40 (6H, s). LCMS (ES+) 432 (M+H)$^+$, RT 2.00 minutes (Method 1).

Example 334

6,6-Dimethyl-2-(6-{1-[(1-oxidopyridin-3-yl)methyl]-1H-pyrazol-4-yl}-2,3-dihydro-4H-1,4-benzoxazin-4-yl)-6,7-dihydro[1,3]thiazolo[5,4-c]pyridin-4(5H)-one To a stirred solution of Example 323 (0.013 g, 0.028 mmol) in DCM (1.0 mL) was added peracetic acid (0.010 mL, 36-40 wt % in acetic acid, 0.055-0.061 mmol). The reaction mixture was stirred at r.t. for 150 minutes and then additional peracetic acid (0.040 mL, 36-40 wt % in acetic acid, 0.214-0.238 mmol) was added. After 46 h, the reaction mixture was concentrated in vacuo. Purification by preparative HPLC (Method 6) gave the title compound (0.003 g, 20%) as a white solid. $\delta_H$ (CDCl$_3$) 8.19-8.13 (2H, m), 7.98 (1H, d, J 1.9 Hz), 7.78 (1H, s), 7.66 (1H, s), 7.32-7.27 (1H, m), 7.20-7.14 (2H, m), 6.97 (1H, d, J 8.5 Hz), 5.42 (1H, s), 5.33 (2H, s), 4.37-4.31 (2H, m), 4.23-4.17 (2H, m), 2.89 (2H, s), 1.41 (6H, s). LCMS (ES+) 489 (M+H)$^+$, RT 2.48 minutes (Method 1).

Examples 335 and 336

6,6-Dimethyl-2-(6-(imidazo[1,2-a]pyrimidin-3-yl)-2, 3-dihydro-4H-1,4-benzoxazin-4-yl)-6,7-dihydro[1,3] thiazolo[5,4-c]pyridin-4(5H)-one and 6,6-Dimethyl-2-(6-(imidazo[1,2-a]pyrimidin-2-yl)-2,3-dihydro-4H-1,4-benzoxazin-4-yl)-6,7-dihydro[1,3]thiazolo[5, 4-c]pyridin-4(5H)-one The title compounds were prepared from Example 292 and 3-bromoimidazo[1,2-a]pyrimidine according to Method AT. Purification by preparative HPLC (Method 6 followed by Method 7) gave the first title compound (2%) as a pale yellow solid [$\delta_H$ (CDCl$_3$) 8.77 (1H, dd, J 7.0 and 1.9 Hz), 8.59 (1H, dd, J 4.1 and 2.1 Hz), 8.39 (1H, d, J 2.1 Hz), 7.89 (1H, s), 7.23 (1H, dd, J 8.3 and 1.9 Hz), 7.16-7.10 (1H, m), 6.93 (1H, dd, J 6.8 and 4.0 Hz), 5.43 (1H, s), 4.46-4.41 (2H, m), 4.15-4.09 (2H, m), 2.88 (2H, s), 1.40 (6H, s). LCMS (ES+) 433 (M+H)$^+$, RT 2.04 minutes (Method 1)] followed by the second title compound (2%) as a pale yellow solid [$\delta_H$ (CDCl$_3$) 8.53 (1H, dd, J 4.0 and 1.9 Hz), 8.47-8.42 (2H, m), 7.84 (1H, dd, J 8.5 and 2.1 Hz), 7.78 (1H, s), 7.05 (1H, d, J 8.5 Hz,), 6.87 (1H, dd, J 6.8 and 4.1 Hz), 5.38 (1H, s), 4.41-4.35 (2H, m), 4.26-4.20 (2H, m), 2.90 (2H, s), 1.41 (6H, s). LCMS (ES+) 433 (M+H)$^+$, RT 2.33 minutes (Method 1)].

Example 337

4-[4-(6,6-Dimethyl-4-oxo-4,5,6,7-tetrahydro[1,3] thiazolo[5,4-c]pyridin-2-yl)-3,4-dihydro-2H-1,4-benzoxazin-6-yl]-N-methyl-1-(4-methylphenyl)-1H-pyrazole-5-carboxamide The title compound was prepared from Example 292 and 4-bromo-2-(p-tolyl)-2H-pyrazole-3-carboxylic acid methylamide according to Method AT (heating to 100° C. for 2 h) and was isolated as a white solid (39%) after purification by preparative HPLC (Method 6). $\delta_H$ (CDCl$_3$) 8.10 (1H, d, J 2.1 Hz), 7.61 (1H, s), 7.52 (2H, d, J 8.5 Hz), 7.29 (2H, d, J 8.3 Hz), 7.10-6.98 (2H, m), 6.16 (1H, q, J 5.3 Hz), 5.65 (1H, s), 4.43-4.36 (2H, m), 4.20-4.12 (2H, m), 2.87 (2H, s), 2.65 (3H, d, J 5.7 Hz), 2.40 (3H, s), 1.39 (6H, s). LCMS (ES+) 529 (M+H)$^+$, RT 3.70 minutes (Method 1).

Example 338

2-{6-[3,5-Dimethyl-1-(2-oxo-2-phenylethyl)-1H-pyrazol-4-yl]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 292 and 2-(4-bromo-3,5-dimethylpyrazol-1-yl)-1-phenylethanone according to Method AT (heating to 100° C. for 2 h followed by addition of a further portion of catalyst and heating to 100° C. under microwave irradiation for 2 h) and was isolated as a white solid (13%) after purification by preparative HPLC (Method 6). $\delta_H$ (CDCl$_3$) 8.08-7.98 (2H, m), 7.90 (1H, s), 7.69-7.61 (1H, m), 7.53 (2H, t, J 7.7 Hz), 7.01 (2H, s), 5.55 (2H, s), 5.43 (1H, s), 4.40-4.34 (2H, m), 4.19-4.13 (2H, m), 2.86 (2H, s), 2.31 (3H, s), 2.23 (3H, s), 1.39 (6H, s). LCMS (ES+) 528 (M+H)$^+$, RT 3.45 minutes (Method 1).

Example 339

2-{6-[1,5-Dimethyl-3-(trifluoromethyl)-1H-pyrazol-4-yl]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 292 and 4-bromo-1,5-dimethyl-3-(trifluoromethyl)-1H-pyrazole according to Method AT (heating to 100° C. for 2 h followed by addition of a further portion of catalyst and heating to 100° C. under microwave irradiation for 2 h) and was isolated as a white solid (13%) after purification by preparative HPLC (Method 6). $\delta_H$ (CDCl$_3$) 7.87 (1H, s), 7.00 (2H, s), 5.27 (1H, s), 4.41-4.35 (2H, m), 4.22-4.15 (2H, m), 3.89 (3H, s), 2.86 (2H, s), 2.30 (3H, s), 1.39 (6H, s). LCMS (ES+) 478 (M+H)$^+$, RT 3.49 minutes (Method 1).

Examples 340 and 341

2-{4-[4-(6,6-Dimethyl-4-oxo-4,5,6,7-tetrahydro[1,3] thiazolo[5,4-c]pyridin-2-yl)-3,4-dihydro-2H-1,4-benzoxazin-6-yl]-1H-pyrazol-1-yl}acetamide and {4-[4-(6,6-Dimethyl-4-oxo-4,5,6,7-tetrahydro[1,3] thiazolo[5,4-c]pyridin-2-yl)-3,4-dihydro-2H-1,4-benzoxazin-6-yl]-1H-pyrazol-1-yl}acetonitrile The title compounds were prepared from Example 292 and (4-bromo-1H-pyrazol-1-yl)acetonitrile according to Method AT (heating to 100° C. for 22 h). Purification by preparative HPLC (Method 6) gave the first title compound (14%) as a white solid [$\delta_H$ (CD$_3$OD) 8.15 (1H, d, J 1.9 Hz), 7.96 (1H, s), 7.82 (1H, d, J 0.6 Hz), 7.29 (1H, dd, J 8.5 and 1.9 Hz), 6.97 (1H, d, J 8.5 Hz), 4.36-4.31 (2H, m), 4.21-4.15 (2H, m), 2.90 (2H, s), 1.38 (6H, s). Exchangeable protons were not observed. LCMS (ES+) 439 (M+H)$^+$, RT 3.63 minutes (Method 2)] followed by the second title compound (33%) as a white solid [$\delta_H$ (CDCl$_3$) 8.05 (1H, d, J 1.9 Hz), 7.80 (1H, d, J 0.6 Hz), 7.74 (1H, s), 7.17 (1H, dd, J 8.5 and 2.1 Hz), 6.97 (1H, d, J 8.5 Hz), 5.55 (1H, s), 5.14 (2H, s), 4.39-4.31 (2H, m), 4.22-4.15 (2H, m), 2.89 (2H, s), 1.41 (6H, s). LCMS (ES+) 421 (M+H)$^+$, RT 4.10 minutes (Method 1)].

Example 342

2-[6-(1,3-Dimethyl-1H-pyrazol-4-yl)-2,3-dihydro-4H-1,4-benzoxazin-4-yl]-6,6-dimethyl-6,7-dihydro [1,3]thiazolo[5,4-c]pyridin-4(5H)-one The title compound was prepared from Example 292 and 4-bromo-1,3-dimethyl-1H-pyrazole according to Method AT (heating to 100° C. for 22 h) and was isolated as a white solid (43%) after purification by preparative HPLC (Method 7). $\delta_H$ (CDCl$_3$) 7.95 (1H, d, J 1.9 Hz), 7.41 (H, s), 7.08 (1H, dd, J 8.5 and 2.1 Hz), 7.00-6.93 (1H, m), 5.51 (1H, s), 4.40-4.32 (2H, m), 4.24-4.14 (2H, m), 3.88 (3H, s), 2.87 (2H, s), 2.41 (3H, s), 1.40 (6H, s). LCMS (ES+) 410 (M+H)$^+$, RT 4.07 minutes (Method 2).

Example 343

6,6-Dimethyl-2-{6-[5-phenyl-3-(trifluoromethyl)-1H-pyrazol-4-yl]-2,3-dihydro-4H-1,4-benzoxazin-4-yl}-6,7-dihydro[1,3]thiazolo[5,4-c]pyridin-4(5H)-one The title compound was prepared from Example 292 and 4-bromo-5-phenyl-3-(trifluoromethyl)-1H-pyrazole according to Method AT (heating to 100° C. for 22 h) and was isolated as a white solid (23%) after purification by preparative HPLC (Method 7). $\delta_H$ (CDCl$_3$) 13.00 (1H, br s), 7.56 (1H, d, J 1.9 Hz), 7.42-7.31 (4H, m), 7.26-7.19 (1H, m), 7.12 (1H, dd, J 8.3 and 1.3 Hz), 7.02-6.97 (1H, m), 6.82 (1H, s), 4.38-4.31 (2H, m), 4.25-4.18 (2H, m), 2.79 (2H, s), 1.39 (6H, s). LCMS (ES+) 526 (M+H)$^+$, RT 4.63 minutes (Method 2).

Example 344

6,6-Dimethyl-2-(6-(pyrimidin-2-yl)-2,3-dihydro-4H-1,4-benzoxazin-4-yl)-6,7-dihydro[1,3]thiazolo[5,4-c]pyridin-4(5H)-one The title compound was prepared from Example 292 and 2-bromopyrimidine according to Method AT (heating to 100° C. for 22 h) and was isolated as a white solid (68%) after purification by preparative HPLC (Method 7). $\delta_H$ (CDCl$_3$) 9.00 (1H, d, J 2.1 Hz), 8.76 (2H, d, J 4.9 Hz), 8.18 (1H, dd, J 8.7 and 2.1 Hz), 7.15 (1H, t, J 4.9 Hz), 7.06 (1H, d, J 8.7 Hz), 5.56 (1H, s), 4.42-4.36 (2H, m), 4.27-4.22 (2H, m), 2.88 (2H, s), 1.40 (6H, s). LCMS (ES+) 394 (M+H)$^+$, RT 4.22 minutes (Method 2).

Examples 345 and 346

2-{4-[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]-3,5-dimethyl-1H-pyrazol-1-yl}acetamide and {4-[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]-3,5-dimethyl-1H-pyrazol-1-yl}acetonitrile The title compounds were prepared from Example 292 and (4-bromo-3,5-dimethyl-1H-pyrazol-1-yl)acetonitrile according to Method AT (heating to 100° C. for 22 h). Purification by preparative HPLC (Method 6) gave the first title compound (46%) as a white solid [$\delta_H$ (CD$_3$OD) 7.90 (1H, t, J 1.1 Hz), 7.00 (2H, d, J 1.1 Hz), 4.78 (2H, s), 4.38-4.32 (2H, m), 4.18-4.11 (2H, m), 2.86 (2H, s), 2.28 (3H, s), 2.24 (3H, s), 1.36 (6H, s). Exchangeable protons were not observed. LCMS (ES+) 467 (M+H)$^+$, RT 3.75 minutes (Method 2)] followed by the second title compound (18%) as a white solid [$\delta_H$ (CDCl$_3$) 7.86 (1H, d, J 1.9 Hz), 7.04-6.99 (1H, m), 6.96-6.90 (1H, m), 5.31 (1H, s), 5.00 (2H, s), 4.40-4.35 (2H, m), 4.19-4.13 (2H, m), 2.86 (2H, s), 2.37 (3H, s), 2.26 (3H, s), 1.39 (6H, s). LCMS (ES+) 449 (M+H)$^+$, RT 3.08 minutes (Method 1)].

Example 347

2-{6-[1-(2-Aminoethyl)-1H-pyrazol-4-yl]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 292 and 2-(4-bromo-1H-pyrazol-1-yl)ethanamine hydrochloride according to Method AT (heating to 100° C. for 22 h) and was isolated as a translucent solid (31%) after purification by preparative HPLC (Method 7) followed by absorption onto an Isolute PRS solid phase extraction cartridge (2 g), elution with methanolic ammonia solution (~7N, 2×5 mL) and concentration of the filtrate in vacuo. $\delta_H$ (CDCl$_3$) 7.99 (1H, d, J 1.9 Hz), 7.74 (1H, s), 7.64 (1H, s), 7.17 (1H, dd, J 8.3 and 1.9 Hz), 6.95 (1H, d, J 8.5 Hz), 5.62 (1H, s), 4.38-4.29 (4H, m), 4.23-4.15 (2H, m), 3.21 (2H, t, J 5.7 Hz), 2.87 (2H, s), 2.03 (2H, s), 1.40 (6H, s). LCMS (ES+) 425 (M+H)$^+$, RT 2.36 minutes (Method 2).

Example 348

2-{6-[1-(3-Aminopropyl)-1H-pyrazol-4-yl]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 292 and 3-(4-bromo-1H-pyrazol-1-yl)propan-1-amine according to Method AT (heating to 100° C. for 46 h) and was isolated as a white solid (39%) after purification by preparative HPLC (Method 7) followed by absorption onto an Isolute PRS solid phase extraction cartridge (2 g), elution with methanolic ammonia solution (~7N, 2×5 mL) and concentration of the filtrate in vacuo. $\delta_H$ (CDCl$_3$) 7.97 (1H, d, J 1.9 Hz), 7.70 (1H, s), 7.61 (1H, s), 7.17 (1H, dd, J 8.5 and 1.9 Hz), 6.95 (1H, d, J 8.5 Hz), 5.54 (1H, s), 4.38-4.31 (2H, m), 4.26 (2H, t, J 6.8 Hz), 4.23-4.17 (2H, m), 2.88 (2H, s), 2.77 (2H, t, J 6.8 Hz), 2.48 (2H, s), 2.12-2.00 (2H, m), 1.40 (6H, s). LCMS (ES+) 439 (M+H)$^+$, RT 2.37 minutes (Method 2).

Example 349

2-{6-[1-(3-Aminopropyl)-3-methyl-1H-pyrazol-4-yl]-2,3-dihydro-4H-1,4-benzoxazin-4-yl}-6,6-dimethyl-6,7-dihydro[1,3]thiazolo[5,4-c]pyridin-4-(5H)-one The title compound was prepared from Example 292 and 3-(4-bromo-3-methyl-1H-pyrazol-1-yl)propan-1-amine according to Method AT (heating to 100° C. for 22 h) and was isolated as a translucent solid (28%) after purification by preparative HPLC (Method 7) followed by absorption onto an Isolute PRS solid phase extraction cartridge (2 g), elution with methanolic ammonia solution (~7N, 2×5 mL) and concentration of the filtrate in vacuo. $\delta_H$ (CDCl$_3$) 7.94 (1H, d, J 2.1 Hz), 7.45 (1H, s), 7.08 (1H, dd, J 8.5 and 2.1 Hz), 6.99-6.94 (1H, m), 5.56 (1H, s), 4.39-4.31 (2H, m), 4.23-4.13 (4H, m), 2.87 (2H, s), 2.77 (2H, t, J 6.8 Hz), 2.41 (3H, s), 2.12 (2H, s), 2.08-1.97 (3H, m), 1.40 (6H, s). LCMS (ES+) 453 (M+H)$^+$, RT 2.43 minutes (Method 2).

Example 350

2-{6-[1-(3-Aminopropyl)-3,5-dimethyl-1H-pyrazol-4-yl]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 292 and 3-(4-bromo-3,5-dimethyl-1H-pyrazol-1-yl)propan-1-amine according to Method AT (heating to 100° C. for 22 h) and was isolated as a translucent solid (26%) after purification by preparative HPLC (Method 7) followed by absorption onto an Isolute PRS solid phase extraction cartridge (2 g), elution with methanolic ammonia solution (~7N, 2×5 mL) and concentration of the filtrate in vacuo. $\delta_H$ (CDCl$_3$) 7.80 (1H, d, J 1.7 Hz), 7.05-6.89 (2H, m), 5.57 (1H, s), 4.39-4.33 (2H, m), 4.21-4.14 (2H, m), 4.13 (2H, t, J 7.2 Hz), 2.86 (2H, s), 2.80 (2H, t, J 6.8 Hz), 2.26 (3H, s), 2.29 (3H, s), 1.98 (2H, quint, J 6.8 Hz), 1.39 (6H, s). LCMS (ES+) 467 (M+H)$^+$, RT 2.42 minutes (Method 2).

Example 351

6,6-Dimethyl-2-{6-[1-ethyl-3-(piperazin-1-ylcarbonyl)-1H-pyrazol-4-yl]-2,3-dihydro-4H-1,4-benzoxazin-4-yl}-6,7-dihydro[1,3]thiazolo[5,4-c]pyridin-4(5H)-one The title compound was prepared from Example 292 and 1-[(4-bromo-1-ethyl-1H-pyrazol-3-yl)carbonyl]piperazine hydrochloride according to Method AT (heating to 100° C. for 22 h) and was isolated as a translucent solid (16%) after purification by preparative HPLC (Method 7) followed by absorption onto an Isolute PRS solid phase extraction cartridge (2 g), elution with methanolic ammonia solution (~7N, 2×5 mL) and concentration of the filtrate in vacuo. $\delta_H$ (CDCl$_3$) 8.12 (1H, d, J 1.9 Hz), 7.58 (1H, s), 7.10-7.02 (1H, m), 6.99-6.93 (1H, m), 5.59 (1H, s), 4.41-4.05 (6H, m), 3.82-3.67 (2H, m), 3.26-3.01 (2H, m), 2.92 (2H, s), 2.83 (2H, br s), 2.44 (2H, d, J 0.6 Hz), 2.28 (1H, s), 1.47 (3H, t, J 7.3 Hz), 1.40 (6H, s). LCMS (ES+) 522 (M+H)$^+$, RT 2.35 minutes (Method 2).

Example 352

6,6-Dimethyl-2-{6-[1-(3-hydroxypropyl)-3,5-dimethyl-1H-pyrazol-4-yl]-2,3-dihydro-4H-1,4-benzoxazin-4-yl}-6,7-dihydro[1,3]thiazolo[5,4-c]pyridin-4(5H)-one The title compound was prepared from Example 292 and 3-(4-bromo-3,5-dimethyl-1H-pyrazol-1-yl)propan-1-ol according to Method AT (heating to 100° C. for 22 h) and was isolated as a white solid (30%) after purification by preparative HPLC (Method 6) followed by absorption onto an Isolute PRS solid phase extraction cartridge (2 g), elution with methanolic ammonia solution (~7N, 2×5 mL) and concentration of the filtrate in vacuo. $\delta_H$ (CDCl$_3$) 7.81 (1H, d, J 1.9 Hz), 7.02-6.97 (1H, m), 6.96-6.90 (1H, m), 5.58 (1H, s), 4.40-4.32 (2H, m), 4.26-4.14 (4H, m), 3.69 (2H, t, J 5.5 Hz), 2.86 (2H, s), 2.30 (3H, s), 2.26 (3H, s), 2.09-1.97 (2H, m), 1.39 (6H, s). LCMS (ES+) 468 (M+H)$^+$, RT 2.69 minutes (Method 1).

Example 353

2-{6-[1-(3-Aminobenzyl)-1H-pyrazol-4-yl]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 292 and 3-[(4-bromo-1H-pyrazol-1-yl)methyl]aniline hydrochloride according to Method AT (heating to 100° C. for 22 h) and was isolated as a white solid (7%) after purification by preparative HPLC (Method 7) followed by absorption onto an Isolute PRS solid phase extraction cartridge (2 g), elution with methanolic ammonia solution (~7N, 2×5 mL) and concentration of the filtrate in vacuo. $\delta_H$ (CDCl$_3$) 8.01 (1H, d, J 1.9 Hz), 7.74 (1H, d, J 0.6 Hz), 7.57 (1H, d, J 0.6 Hz), 7.21-7.09 (2H, m), 6.94 (1H, d, J 8.5 Hz), 6.71-6.65 (1H, m), 6.62 (1H, dd, J 8.1 and 1.7 Hz), 6.56 (1H, d, J 1.7 Hz), 5.33 (1H, s), 5.24 (2H, s), 4.36-4.31 (2H, m), 4.20-4.14 (2H, m), 2.87 (2H, s), 1.40 (6H, s). LCMS (ES+) 487 (M+H)$^+$, RT 2.61 minutes (Method 1).

Example 354

2-(7-{N[2-(Dimethylamino)ethyl]-N-(methyl)amino}-2,3-dihydro-4H-1,4-benzoxazin-4-yl)-6,6-dimethyl-6,7-dihydro[1,3]thiazolo[5,4-c]pyridin-4(5H)-one, formic acid salt The title compound was prepared from Example 214 and N,N,N'-trimethylethylenediamine according to Method AL and was isolated as a beige solid (5%) after purification by preparative HPLC (Method 6). $\delta_H$ (CDCl$_3$) 8.41 (1H, s, formic acid), 7.67 (1H, d, J 9.0 Hz), 6.32 (1H, dd, J 9.0 and 2.5 Hz), 6.28 (1H, d, J 2.5 Hz), 5.39 (1H, s), 4.33-4.27 (2H, m), 4.15-4.09 (2H, m), 3.68-3.58 (2H, m), 3.14-2.79 (2H, m), 2.95 (3H, s), 2.84 (2H, s), 2.58 (6H, s), 1.38 (6H, s). LCMS (ES+) 416 (M+H)$^+$, RT 1.90 minutes (Method 1).

Example 355

6,6-Dimethyl-2-(7-(piperazin-1-yl)-2,3-dihydro-4H-1,4-benzoxazin-4-yl)-6,7-dihydro[1,3]thiazolo[5,4-c]pyridin-4(5H)-one, acetic acid salt The title compound was prepared from Example 214 and piperazine according to Method AL and was isolated as a cream-yellow solid (19%) after purification by preparative HPLC (Method 7). $\delta_H$ (CDCl$_3$) 7.72 (1H, d, J 8.9 Hz), 6.54 (1H, dd, J 8.9 and 2.5 Hz), 6.48 (1H, d, J 2.5 Hz), 5.58 (1H, s), 4.33-4.28 (2H, m), 4.15-4.11 (2H, m), 3.21-3.13 (4H, m), 3.12-3.04 (4H, m), 2.85 (2H, s), 2.06 (3H, s, acetic acid), 1.38 (6H, s). LCMS (ES+) 400 (M+H)$^+$, RT 1.73 minutes (Method 1).

Example 356

2-[7-(1,4-Diazepan-1-yl)-2,3-dihydro-4H-1,4-benzoxazin-4-yl]-6,6-dimethyl-6,7-dihydro[1,3]thiazolo[5,4-c]pyridin-4(5H)-one, acetic acid salt The title compound was prepared from Example 214 and homopiperazine according to Method AL and was isolated as a cream-yellow solid (52%) after purification by preparative HPLC (Method 7). $\delta_H$ (CDCl$_3$) 7.63 (1H, d, J 8.9 Hz), 6.29 (1H, dd, J 8.9 and 3.0 Hz), 6.24 (1H, d, J 3.0 Hz), 5.93 (1H, s), 4.32-4.26 (2H, m), 4.16-4.10 (2H, m), 3.66-3.60 (2H, m) 3.59-3.53 (2H, m), 3.18-3.11 (2H, m), 3.01-2.95 (2H, m), 2.83 (2H, s), 2.12-2.03 (2H, m), 2.00 (3H, s, acetic acid), 1.39 (6H, s). LCMS (ES+) 414 (M+H)$^+$, RT 1.83 minutes (Method 1).

Example 357

6,6-Dimethyl-2-[7-(4-methylpiperazin-1-yl)-2,3-dihydro-4H-1,4-benzoxazin-4-yl]-6,7-dihydro[1,3]thiazolo[5,4-c]pyridin-4(5H)-one, formic acid salt The title compound was prepared from Example 214 and 1-methylpiperazine according to Method AL and was isolated as a cream-yellow solid (15%) after purification by preparative HPLC (Method 6). $\delta_H$ (CDCl$_3$) 8.30 (1H, s, formic acid), 7.75 (1H, d, J 8.9 Hz), 6.54 (1H, dd, J 8.9 and 3.0 Hz), 6.48 (1H, d, J 3.0 Hz), 5.41 (1H, s), 4.33-4.28 (2H, m), 4.15-4.10 (2H, m), 3.31-3.25 (4H, m), 2.85 (2H, s), 2.84-2.78 (4H, m), 2.48 (3H, s), 1.38 (6H, s). LCMS (ES+) 414 (M+H)+, RT 1.79 minutes (Method 1).

Example 358

6,6-Dimethyl-2-[7-(4-methyl-1,4-diazepan-1-yl)-2,3-dihydro-4H-1,4-benzoxazin-4-yl]-6,7-dihydro[1,3]thiazolo[5,4-c]pyridin-4(5H)-one, formic acid salt The title compound was prepared from Example 214 and 1-methylhomopiperazine according to Method AL and was isolated as a mid-brown solid (20%) after purification by preparative HPLC (Method 6). $\delta_H$ (CDCl$_3$) 8.43 (1H, s, formic acid), 7.67 (1H, d, J 8.9 Hz), 6.29 (1H, dd, J 9.0 and 3.0 Hz), 6.24 (1H, d, J 3.0 Hz), 5.39 (1H, s), 4.33-4.28 (2H, m), 4.16-4.11 (2H, m), 3.76-3.70 (2H, m) 3.52-3.45 (2H, m), 3.16-3.10 (2H, m), 3.06-3.00 (2H, m), 2.84 (2H, s), 2.66 (3H, s), 2.34-2.25 (2H, m), 1.39 (6H, s). LCMS (ES+) 428 (M+H)+, RT 1.88 minutes (Method 1).

Example 359

2-(7-{N-Benzyl-N-[2-(dimethylamino)ethyl]amino}-2,3-dihydro-4H-1,4-benzoxazin-4-yl)-6,6-dimethyl-6,7-dihydro[1,3]thiazolo[5,4-c]pyridin-4(5H)-one, formic acid salt The title compound was prepared from Example 214 and N'-benzyl-N,N-dimethylethylenediamine according to Method AL and was isolated as a cream solid (12%) after purification by preparative HPLC (Method 6). $\delta_H$ (CDCl$_3$) 8.34 (1H, s, formic acid), 7.67 (1H, d, J 9.0 Hz), 7.36-7.18 (5H, m), 6.36 (1H, dd, J 9.0 and 2.5 Hz), 6.32 (1H, d, J 2.5 Hz), 5.39 (1H, s), 4.53 (2H, s), 4.30-4.25 (2H, m), 4.13-4.07 (2H, m), 3.72 (2H, t, J 7.5 Hz), 2.89 (2H, s), 2.84 (2H, t, J 7.5 Hz), 2.55 (6H, s), 1.38 (6H, s). LCMS (ES+) 492 (M+H)+, RT 2.28 minutes (Method 1).

Example 360

Method AU 2-(7-{[3-(Dimethylamino)propyl]amino}-2,3-dihydro-4H-1,4-benzoxazin-4-yl)-6,6-dimethyl-6,7-dihydro[1,3]thiazolo[5,4-c]pyridin-4(5H)-one, formic acid salt DME (1 mL) was added to a mixture of Example 214 (0.05 g, 0.127 mmol), potassium tert-butoxide (0.034 g, 0.305 mmol), palladium(II) acetate (0.003 g, 0.013 mmol) and tri-tert-butylphosphonium tetrafluoroborate (0.007 g, 0.025 mmol). N,N-Dimethyl-1,3-propanediamine (0.026 g, 0.254 mmol) was added, and the mixture was degassed by evacuating and purging with nitrogen three times over a period of 5 minutes. The mixture was heated at 140° C. under microwave irradiation for 2 h, then filtered and concentrated in vacuo. The residue was purified by preparative HPLC (Method 6) to give the title compound (0.023 g, 39%) as a yellow-brown gum. $\delta_H$ (CDCl$_3$) 8.47 (1H, s, formic acid), 7.55 (1H, d, J 9.0 Hz), 6.24 (1H, dd, J 9.0 and 2.5 Hz), 6.17 (1H, d, J 2.5 Hz), 5.51 (1H, s), 4.30-4.25 (2H, m), 4.14-4.09 (2H, m), 3.22 (1H, t, J 7.0 Hz), 2.99 (2H, t, J 7.0 Hz), 2.84 (2H, s), 2.66 (6H, s), 2.01 (2H, quintet, J 7.0 Hz), 1.38 (6H, s). LCMS (ES+) 416 (M+H)+, RT 1.75 minutes (Method 1).

Example 361

4-(6,6-Dimethyl-4-oxo-4,5,6,7-tetrahydro[1,3]thiazolo[5,4-d]pyridin-2-yl)-N-(1-methylpiperidin-4-yl)-3,4-dihydro-2H-1,4-benzoxazine-7-carboxamide, acetic acid salt The title compound was prepared from Example 214 and 4-amino-1-methylpiperidine according to Method AM and was isolated as a colourless gum (21%) after purification by preparative HPLC (Method 7). $\delta_H$ (CDCl$_3$) 8.13 (1H, d, J 8.5 Hz), 7.44 (1H, d, J 2.1 Hz), 7.37 (1H, dd, J 8.5 and 2.1 Hz), 5.76 (1H, s), 4.50-4.33 (3H, m), 4.17-4.03 (3H, m), 3.16 (2H, br. s), 2.89 (2H, s), 2.51-2.37 (5H, m), 2.10-2.01 (5H, m), 1.90 (2H, m), 1.40 (6H, s). LCMS (ES+) 456 (M+H)+, RT 2.07 minutes (Method 2).

Example 362

4-(6,6-Dimethyl-4-oxo-4,5,6,7-tetrahydro[1,3]thiazolo[5,4-c]pyridin-2-yl)-N-methyl-N-(1-methylpiperidin-4-yl)-3,4-dihydro-2H-1,4-benzoxazine-7-carboxamide, acetic acid salt The title compound was prepared from Example 214 and 1-methyl-4-(methylamino)piperidine according to Method AM and was isolated as a colourless gum (6%) after purification by preparative HPLC (Method 7). $\delta_H$ (CDCl$_3$) 8.08 (1H, d, J 8.5 Hz), 7.03-6.93 (2H, m), 5.70 (1H, s), 4.40-4.34 (2H, m), 4.17-4.11 (2H, m), 3.60 (1H, br), 3.20-2.92 (3H, m), 2.89 (2H, s), 2.42-1.58 (11H, m), 2.04 (3H, s, acetic acid), 1.40 (6H, s). LCMS (ES+) 456 (M+H)+, RT 2.11 minutes (Method 2).

Example 363

6,6-Dimethyl-2-{7-[(1-methylpiperidin-4-yl)amino]-2,3-dihydro-4H-1,4-benzoxazin-4-yl}-6,7-dihydro[1,3]thiazolo[5,4-c]pyridin-4(5H)-one, acetic acid salt The title compound was prepared from Example 214 and 4-amino-1-methylpiperidine according to Method AU and was isolated as a pale yellow-brown gum (0.012 g, 19%) after purification by preparative HPLC (Method 7). $\delta_H$ (CDCl$_3$) 7.57 (1H, d, J 8.5 Hz), 6.21 (1H, dd, J 8.5 and 2.5 Hz), 6.16 (1H, d, J 2.5 Hz), 5.82 (1H, s), 4.31-4.26 (2H, m), 4.14-4.09 (2H, m), 3.32 (1H, tt, J 10.0 and 4.0 Hz), 3.15-3.04 (2H, m), 2.83 (2H, s), 2.47-2.33 (2H, m), 2.44 (3H, s), 2.16-2.01 (2H, m), 2.05 (3H, s, acetic acid), 1.75-1.60 (2H, m), 1.38 (6H, s). LCMS (ES+) 428 (M+H)+, RT 2.16 minutes (Method 2).

Example 364

2-{7-[N-Cyclohexyl-N-(methyl)amino]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 214 and N-cyclohexyl-N-methylamine according to Method AU and was isolated as a pale yellow-brown gum (13%) after purification by preparative HPLC (Method 7). $\delta_H$ (CDCl$_3$) 7.62 (1H, d, J 9.2 Hz), 6.39 (1H, dd, J 9.0 and 2.8 Hz), 6.31 (1H, d, J 3.0 Hz), 5.16 (1H, s), 4.32-4.27 (2H, m), 4.16-4.11 (2H, m), 3.57-3.45 (1H, m), 2.84 (2H, s), 2.75 (3H, s), 1.90-1.08 (10H, s), 1.38 (6H, s). LCMS (ES+) 427 (M+H)+, RT 2.73 minutes (Method 1).

Example 365

2-{7-[N-Benzyl-N-(methyl)amino]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 214 and N-benzyl-N-methylamine according to Method AU and was isolated as a beige solid (36%) after purification by preparative HPLC (Method 7). $\delta_H$ (CDCl$_3$) 7.60 (1H, d, J 9.0 Hz), 7.37-7.18 (5H, m), 6.36 (1H, dd, J 9.0 and 2.8 Hz), 6.29 (1H, d, J 2.8 Hz), 5.29 (1H, s), 4.51 (2H, s), 4.30-4.25 (2H, m), 4.15-4.09 (2H, m), 3.00 (3H, s), 2.83 (2H, s), 1.37 (6H, s). LCMS (ES+) 435 (M+H)$^+$, RT 3.87 minutes (Method 1).

Example 366

Method AV

6,6-Dimethyl-2-[6-(2-methoxy-6-methylpyridin-3-yl)-2,3-dihydro-4H-1,4-benzoxazin-4-yl]-6,7-dihydro[1,3]thiazolo[5,4-c]pyridin-4(5H)-one To a suspension of Example 39 (100 mg, 0.254 mmol) in THF (3 mL) and water (1 mL) was added tetra-n-butylammonium bromide (164 mg, 0.509 mmol), sodium carbonate (54 mg, 0.509 mmol), 2-methoxy-6-methylpyridine-3-boronic acid (85 mg, 0.509 mmol) and tetrakis(triphenylphosphine)palladium(0) (catalytic amount). The reaction was heated at 120° C. under microwave irradiation for 20 minutes. The resulting mixture was partitioned between DCM (50 mL) and water (50 mL); the organic fraction was washed with brine (50 mL), dried (MgSO$_4$), and concentrated in vacuo. The residue was purified by preparative HPLC (Method 6) to yield the title compound (28 mg, 25%) as a beige solid. $\delta_H$ (CDCl$_3$) 8.06 (1H, d, J 1.9 Hz), 7.50 (1H, d, J 7.3 Hz), 7.26 (1H, dd, J 8.5 and 2.1 Hz), 6.99 (1H, d, J 8.5 Hz), 6.81 (1H, d, J 7.5 Hz), 5.22 (1H, br. s), 4.39-4.31 (2H, m), 4.26-4.19 (2H, m), 4.00 (3H, s), 2.87 (2H, s), 2.49 (3H, s), 1.39 (6H, s). LCMS (ES+) 437.0 (M+H)$^+$, RT 3.99 minutes (Method 1).

Example 367

6,6-Dimethyl-2-[6-(2-fluoro-6-methylpyridin-3-yl)-2,3-dihydro-4H-1,4-benzoxazin-4-yl]-6,7-dihydro[1,3]thiazolo[5,4-c]pyridin-4(5H)-one The title compound was prepared from Example 39 and 2-fluoro-6-methylpyridine-3-boronic acid according to Method AV and was isolated as an off-white solid (17%) after trituration with acetone then Et$_2$O. $\delta_H$ (CDCl$_3$) 8.17 (1H, d, J 0.9 Hz), 7.76 (1H, dd, J 10.2 and 7.7 Hz), 7.33-7.25 (1H, m), 7.13 (1H, dd, J 7.5 and 1.3 Hz), 7.04 (1H, d, J 8.7 Hz), 5.23 (1H, br. s), 4.41-4.35 (2H, m), 4.22-4.15 (2H, m), 2.88 (2H, s), 2.55 (3H, s), 1.39 (6H, s). LCMS (ES+) 425.0 (M+H)$^+$, RT 3.52 minutes (Method 1).

Example 368

6,6-Dimethyl-2-(6-(pyrazin-2-yl)-2,3-dihydro-4H-1,4-benzoxazin-4-yl)-6,7-dihydro[1,3]thiazolo[5,4-c]pyridin-4(5H)-one To a solution of Example 292 (60 mg, 0.167 mol) in THF (3 mL) and water (1 mL) was added tetra-n-butylammonium bromide (107 mg, 0.334 mmol), sodium carbonate (36 mg, 0.334 mmol), iodopyrazine (69 mg, 0.509 mmol) and tetrakis-(triphenylphosphine)palladium(0) (19 mg, 0.017 mmol). The reaction was heated at 120° C. under microwave irradiation for 20 minutes. The resulting mixture was partitioned between DCM (50 mL) and water (50 mL); the organic phase was washed with brine (50 mL), dried (MgSO$_4$), and concentrated in vacuo. The residue was purified by preparative HPLC (Method 6) to yield the title compound (15 mg, 23%) as an off-white solid. $\delta_H$ (CDCl$_3$) 9.00 (1H, s), 8.75 (1H, d, J 2.1 Hz), 8.60 (1H, dd, J 2.4 and 1.7 Hz), 8.48 (1H, d, J 2.4 Hz), 7.74 (1H, dd, J 8.5 and 2.1 Hz), 7.09 (1H, d, J 8.7 Hz), 5.34 (1H, s), 4.43-4.39 (2H, m), 4.22-4.18 (2H, m), 2.90 (2H, s), 1.41 (6H, s). LCMS (ES+) 394.0 (M+H)$^+$, RT 2.93 minutes (Method 1).

Example 369

Method AW

2-[6-(1,2-Dimethyl-1H-imidazol-4-yl)-2,3-dihydro-4H-1,4-benzoxazin-4-yl]-6,6-dimethyl-6,7-dihydro[1,3]thiazolo[5,4-c]pyridin-4(5H)-one To a solution of Example 292 (75 mg, 0.17 mmol) in THF (3 mL) and water (1 mL) was added tetra-n-butylammonium bromide (107 mg, 0.34 mmol), sodium carbonate (36 mg, 0.34 mmol), 4-bromo-1,2-dimethyl-1H-imidazole (60 mg, 0.34 mmol) and tetrakis(triphenylphosphine)palladium(0) (20 mg, 0.017 mmol). The reaction was heated at 140° C. under microwave irradiation for 25 minutes. The resulting mixture was partitioned between DCM (50 mL) and water (50 mL); the organic fraction was washed with brine (50 mL), dried (MgSO$_4$), and concentrated in vacuo. The residue was purified by preparative HPLC (Method 6) to yield the title compound (10 mg, 14%) as an off-white solid. $\delta_H$ (CDCl$_3$) 8.09 (1H, d, J 2.1 Hz), 7.48 (1H, dd, J 8.5 and 2.1 Hz), 7.02 (1H, s), 6.95 (1H, d, J 8.5 Hz), 5.22 (1H, br. s), 4.36-4.29 (2H, m), 4.24-4.19 (2H, m), 3.60 (3H, s), 2.88 (2H, s), 2.42 (3H, s), 1.40 (6H, s). LCMS (ES+) 410.0 (M+H)$^+$, RT 1.86 minutes (Method 1).

Example 370

6,6-Dimethyl-2-{6-[6-(hydroxymethyl)pyridin-3-yl]-2,3-dihydro-4H-1,4-benzoxazin-4-yl}-6,7-dihydro[1,3]thiazolo[5,4-c]pyridin-4(5H)-one To a solution of Intermediate 234 (50 mg, 0.119 mmol) in 4:1 THF/MeOH (10 mL) was added sodium borohydride (14 mg, 0.357 mmol) and the reaction was stirred for 1 h. The resulting mixture was partitioned between DCM (50 mL) and water (50 mL). The organic phase was washed with brine (50 mL), dried (MgSO$_4$), filtered and concentrated in vacuo. The residue was purified by preparative HPLC (Method 6) to yield the title compound (4.5 mg, 9%) as a white solid. $\delta_H$ (CD$_3$OD) 8.69 (1H, dd, J 2.1 and 0.6 Hz), 8.28 (1H, d, J 2.1 Hz), 8.02 (1H, dd, J 8.3 and 2.4 Hz), 7.63 (1H, d, J 8.1 Hz), 7.36 (1H, dd, J 8.5 and 2.1 Hz), 7.09 (1H, d, J 8.5 Hz), 4.80 (2H, m), 4.48-4.38 (2H, m), 4.25-4.13 (2H, m), 2.91 (2H, s), 1.41 (6H, s). LCMS (ES+) 423.0 (M+H)$^+$, RT 2.08 minutes (Method 1).

Example 371

2-[6-(6-Aminopyridin-3-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 292 and 2-amino-5-bromopyridine according to Method AW and was

Example 372

6,6-Dimethyl-2-[6-(5-fluoropyridin-2-yl)-2,3-dihydro-4H-1,4-benzoxazin-4-yl]-6,7-dihydro[1,3]thiazolo[5,4-c]pyridin-4(5H)-one The title compound was prepared from Example 292 and 2-bromo-5-fluoropyridine according to Method AW and was isolated as an off-white solid (29%) after purification by preparative HPLC (Method 6). $\delta_H$ (CDCl$_3$) 8.50 (1H, d, J 2.8 Hz), 8.49 (1H, d, J 2.1 Hz), 7.71-7.62 (2H, m), 7.46 (1H, td, J 8.3 and 2.8 Hz), 7.05 (1H, d, J 8.7 Hz), 5.42 (1H, s), 4.40-4.36 (2H, m), 4.25-4.20 (2H, m), 2.89 (2H, s), 1.40 (6H, s). LCMS (ES+) 411.0 (M+H)$^+$, RT 3.42 minutes (Method 1).

Example 373

6,6-Dimethyl-2-[6-(6-oxo-1,6-dihydropyridin-3-yl)-2,3-dihydro-4H-1,4-benzoxazin-4-yl]-6,7-dihydro[1,3]thiazolo[5,4-d]pyridin-4(5H)-one The title compound was prepared from Example 292 and 5-bromo-2-hydroxypyridine according to Method AW and was isolated as an off-white solid (1%) after purification by preparative HPLC (Method 6). $\delta_H$ (CDCl$_3$) 9.07 (1H, br. s), 7.71 (1H, d, J 2.1 Hz), 7.68 (1H, dd, J 9.4 and 2.6 Hz), 7.62-7.57 (1H, m), 7.12 (1H, dd, J 8.5 and 1.9 Hz), 7.03 (1H, d, J 8.5 Hz), 6.67 (1H, d, J 9.4 Hz), 5.30 (1H, s), 4.39-4.30 (4H, m), 2.88 (2H, s), 1.47 (6H, s). LCMS (ES+) 409.0 (M+H)$^+$, RT 2.47 minutes (Method 1).

Example 374

Method AX

2-[6-(1,2-Dimethyl-1H-imidazol-5-yl)-2,3-dihydro-4H-1,4-benzoxazin-4-yl]-6,6-dimethyl-6,7-dihydro[1,3]thiazolo[5,4-c]pyridin-4(5H)-one To a solution of Example 292 (75 mg, 0.17 mmol) in THF (3 mL) and water (1 mL) was added tetra-n-butylammonium bromide (107 mg, 0.34 mmol), potassium phosphate (72 mg, 0.34 mmol), 5-bromo-1,2-dimethyl-1H-imidazole (60 mg, 0.34 mmol) and tetrakis(triphenylphosphine)palladium(0) (20 mg, 0.017 mmol). The reaction was heated at 140° C. under microwave irradiation for 25 minutes. The resulting mixture was partitioned between DCM (50 mL) and water (50 mL); the organic fraction was washed with brine (50 mL), dried (MgSO$_4$), and concentrated in vacuo. The residue was purified by preparative HPLC (Method 7) to yield the title compound (20 mg, 28%) as a white solid. $\delta_H$ (CDCl$_3$) 7.99 (1H, d, J 1.9 Hz), 7.06 (1H, dd, J 8.5 and 1.9 Hz), 7.01 (1H, d, J 8.5 Hz), 6.93 (1H, s), 5.34 (1H, s), 4.40-4.35 (2H, m), 4.19-4.13 (2H, m), 3.57 (3H, s), 2.87 (2H, s), 2.46 (3H, s), 1.40 (6H, s). LCMS (ES+) 410.0 (M+H)$^+$, RT 1.95 minutes (Method 1).

Example 375

2-[6-(2,6-Dimethylpyridin-3-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 292 and 3-bromo-2,6-dimethylpyridine according to Method AX and was isolated as a white solid (30%) after purification by preparative HPLC (Method 6). $\delta_H$ (CDCl$_3$) 7.93 (1H, d, J 1.1 Hz), 7.43 (1H, d, J 7.7 Hz), 7.05 (1H, d, J 7.9 Hz), 7.01 (2H, d, J 1.1 Hz), 5.33 (1H, s), 4.42-4.34 (2H, m), 4.21-4.15 (2H, m), 2.86 (2H, s), 2.57 (3H, s), 2.55 (3H, s), 1.38 (6H, s). LCMS (ES+) 421.0 (M+H)$^+$, RT 2.04 minutes (Method 1).

Example 376

5-[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]pyrimidine-2-carboxylic acid To a solution of Example 292 (100 mg, 0.227 mmol) in THF (3 mL) and water (1 mL) was added tetra-n-butylammonium bromide (146 mg, 0.454 mmol), potassium phosphate (144 mg, 0.681 mmol), 5-bromopyrimidine-2-carboxylic acid (70 mg, 0.34 mmol) and tetrakis(triphenylphosphine)palladium(0) (20 mg, 0.017 mmol). The reaction was heated at 120° C. under microwave irradiation for 30 minutes then cooled to r.t. The mixture was partitioned between DCM (50 mL) and water (50 mL). The aqueous phase was acidified with 1M HCl and the resulting precipitate was collected, washed with water (2×10 mL), Et$_2$O (3×10 mL) and dried in vacuo to yield the title compound (16 mg, 16%) as an off-white solid. $\delta_H$ (CD$_3$OD) 9.06 (2H, br s), 8.57 (1H, br. s), 7.32 (1H, s), 7.31 (1H, d, J 8.5 Hz), 7.07 (1H, d, J 8.5 Hz), 4.41-4.34 (2H, m), 4.07-4.01 (2H, m), 2.83 (2H, s), 1.34 (6H, s). LCMS (ES+) 875.0 (2M+H)$^+$, RT 2.43 minutes (Method 1).

Example 377

6,6-Dimethyl-2-[6-(6-fluoropyridin-3-yl)-2,3-dihydro-4H-1,4-benzoxazin-4-yl]-6,7-dihydro[1,3]thiazolo[5,4-c]pyridin-4(5H)-one The title compound was prepared from Example 292 and 5-bromo-2-fluoropyridine according to Method AX and was isolated as an off-white solid (23%) after purification by preparative HPLC (Method 6). $\delta_H$ (CD$_3$OD) 8.36 (1H, d, J 2.4 Hz), 8.21 (1H, d, J 2.1 Hz), 8.06 (1H, ddd, J 8.5, 7.5 and 2.6 Hz), 7.58 (1H, s), 7.29 (1H, dd, J 8.5 and 2.3 Hz), 7.13-7.03 (2H, m), 4.47-4.34 (2H, m), 4.21-4.14 (2H, m), 2.89 (2H, s), 1.40 (6H, s). LCMS (ES+) 411.0 (M+H)$^+$, RT 3.39 minutes (Method 1).

Example 378

6-{[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]oxy}pyridine-2-carboxylic acid To a solution of Example 57 (50 mg, 0.151 mmol) in THF (4 mL) was added 2-fluoro-6-pyridinecarboxylic acid (53 mg, 0.378 mmol) and sodium tert-butoxide (73 mg, 0.755 mmol). The mixture was heated to 140° C. under microwave irradiation for 90 minutes, cooled to r.t. and concentrated in vacuo. The residue was purified by preparative HPLC (Method 6) to give the title compound (15 mg, 22%) as an off-white solid. $\delta_H$ (CDCl$_3$) 8.07 (1H, d, J 2.4 Hz), 7.94-7.91 (2H, m), 7.24-7.16 (1H, m), 7.00 (1H, d, J 8.9 Hz), 6.85 (1H, dd, J 8.9 and 2.6 Hz), 5.45 (1H, s), 4.52-4.20 (2H, m), 4.20-4.01 (2H, m), 2.84 (2H, s), 1.38 (6H, s). LCMS (ES+) 453.0 (M+H)$^+$, RT 2.94 minutes (Method 1).

Example 379

Method AY

5-[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]pyrimidine-2-carboxamide To a solution of Example 292 (100 mg, 0.227 mmol) in THF (3 mL) and water (1 mL) was added tetrabutylammonium bromide (146 mg, 0.454 mmol), potassium phosphate (144 mg, 0.681 mmol), Intermediate 235 (92 mg, 0.454 mmol) and tetrakis(triphenylphosphine)palladium(0) (20 mg, 0.017 mmol). The reaction was heated at 140° C. under microwave irradiation for 30 minutes then cooled to r.t. The mixture was partitioned between DCM (50 mL) and water (50 mL) and the resulting precipitate was collected, washed with water (2×10 mL), Et$_2$O (3×10 mL) and dried in vacuo to yield the title compound (21 mg, 21%) as a grey solid. $\delta_H$ (DMSO-d$_6$) 9.20 (2H, s), 8.73 (1H, d, J 1.7 Hz), 8.25 (1H, br. s), 7.82 (1H, br. s), 7.62 (1H, dd, J 8.5 and 1.9 Hz), 7.58 (1H, s), 7.16 (1H, d, J 8.5 Hz), 4.45-4.33 (2H, m), 4.18-4.07 (2H, m), 2.85 (2H, s), 1.29 (6H, s). LCMS (ES+) 437.0 (M+H)$^+$, RT 2.41 minutes (Method 1).

Example 380

6,6-Dimethyl-2-{6-[6-(methoxymethyl)pyridin-3-yl]-2,3-dihydro-4H-1,4-benzoxazin-4-yl}-6,7-dihydro[1,3]thiazolo[5,4-c]pyridin-4(5H)-one The title compound was prepared from Example 292 and Intermediate 236 according to Method AX and was isolated as an off-white solid (1%) after purification by preparative HPLC (Method 6). $\delta_H$ (CDCl$_3$) 8.78 (1H, d, J 1.7 Hz), 8.27 (1H, d, J 2.1 Hz), 7.87 (1H, dd, J 8.1 and 2.4 Hz), 7.48 (1H, d, J 7.9 Hz), 7.29 (1H, dd, J 8.5 and 2.3 Hz), 7.06 (1H, d, J 8.5 Hz), 5.22 (1H, s), 4.64 (2H, s), 4.52-4.29 (2H, m), 4.28-4.08 (2H, m), 3.50 (3H, s), 2.89 (2H, s), 1.40 (6H, s). LCMS (ES+) 437.0 (M+H)$^+$, RT 2.66 minutes (Method 1).

Example 381

6,6-Dimethyl-2-[6-(6-vinylpyridin-3-yl)-2,3-dihydro-4H-1,4-benzoxazin-4-yl]-6,7-dihydro[1,3]thiazolo[5,4-c]pyridin-4(5H)-one A solution of methyltriphenylphosphonium bromide (294 mg, 0.821 mmol) in THF (10 mL) was cooled to 0° C. under an atmosphere of nitrogen and a solution of sodium bis(trimethylsilyl)amide in THF (1M, 0.82 ml, 0.821 mmol) was added dropwise. The resulting mixture was stirred at 0° C. for 30 minutes then cooled to −70° C. and a solution of Intermediate 234 in THF (5 mL) was added. This solution was kept at −70° C. for 15 minutes then allowed to warm to r.t. and stirred for a further 30 minutes. The mixture was quenched with water (2 mL), concentrated in vacuo, and partitioned between DCM (50 mL) and water (50 mL). The organic layer was dried (MgSO$_4$), filtered, concentrated in vacuo and the residue purified by preparative HPLC (Method 6) to give the title compound (1.2 mg, 1%). $\delta_H$ (CDCl$_3$) 8.80 (1H, d, J 1.9 Hz), 8.27 (1H, d, J 2.1 Hz), 7.82 (1H, dd, J 8.1 and 2.4 Hz), 7.42 (1H, d, J 8.3 Hz), 7.30 (1H, dd, J 8.3 and 2.1 Hz), 7.06 (1H, d, J 8.5 Hz), 6.87 (1H, dd, J 17.5 and 10.7 Hz), 6.23 (1H, dd, J 17.3 and 1.1 Hz), 5.51 (1H, dd, J 10.9 and 1.1 Hz), 4.42-4.35 (2H, m), 5.21 (1H, s), 4.21-4.14 (2H, m), 2.90 (2H, s), 1.40 (5H, s). LCMS (ES+) 419.0 (M+H)$^+$, RT 2.82 minutes (Method 1).

Example 382

2-{6-[(6-Bromopyridin-2-yl)oxy]-2,3-dihydro-4H-1,4-benzoxazin-4-yl}-6,6-dimethyl-6,7-dihydro[1,3]thiazolo[5,4-c]pyridin-4(5H)-one To a solution of Example 57 (50 mg, 0.151 mmol) in THF (4 mL) was added 2-bromo-6-fluoropyridine (53 mg, 0.302 mmol) and sodium tert-butoxide (58 mg, 0.604 mmol). The mixture was heated to 150° C. under microwave irradiation for 30 minutes then cooled to r.t. The resulting mixture was partitioned between DCM (50 mL) and water (50 mL); the organic phase was washed with brine (50 mL), dried (MgSO$_4$), and concentrated in vacuo. The residue was triturated with Et$_2$O to yield the title compound (10 mg, 14%) as an off-white solid. $\delta_H$ (CDCl$_3$) 7.95 (1H, d, J 2.6 Hz), 7.52 (1H, t, J 7.9 Hz), 7.19 (1H, d, J 7.5 Hz), 6.97 (1H, d, J 8.9 Hz), 6.85 (1H, dd, J 8.9 and 2.6 Hz), 6.80 (1H, d, J 8.1 Hz), 5.32 (1H, s), 4.39-4.32 (2H, m), 4.16-4.10 (2H, m), 2.86 (2H, s), 1.38 (6H, s). LCMS (ES+) 487.0 (M+H)$^+$, RT 3.73 minutes (Method 1).

Example 383

6,6-Dimethyl-2-(6-{[6-(1-methyl-1H-pyrazol-4-yl)pyridin-2-yl]oxy}-2,3-dihydro-4H-1,4-benzoxazin-4-yl)-6,7-dihydro[1,3]thiazolo[5,4-c]pyridin-4(5H)-one To a suspension of Example 382 (40 mg, 0.082 mmol) in THF (3 mL) and water (1 mL) was added tetra-n-butylammonium bromide (53 mg, 0.164 mmol), potassium phosphate (35 mg, 0.164 mmol), 1-methylpyrazole-4-boronic acid pinacol ester (34 mg, 0.164 mmol) and tetrakis(triphenylphosphine)palladium(0) (9 mg, 0.008 mmol). The reaction was heated at 130° C. under microwave irradiation for 20 minutes then cooled to r.t. The resulting mixture was partitioned between DCM (50 mL) and water (50 mL); the organic phase was washed with brine (50 mL), dried (MgSO$_4$), and concentrated in vacuo. The residue was purified by preparative HPLC (Method 6) to yield the title compound (16 mg, 40%) as a white solid. $\delta_H$ (CDCl$_3$) 8.00 (1H, d, J 2.6 Hz), 7.88 (1H, s), 7.83 (1H, s), 7.63 (1H, t, J 8.1 Hz), 7.16 (1H, d, J 7.5 Hz), 6.98 (1H, d, J 8.9 Hz), 6.90 (1H, dd, J 8.7 and 2.4 Hz), 6.61 (1H, d, J 8.3 Hz), 5.28 (1H, s), 4.40-4.34 (2H, m), 4.15-4.08 (2H, m), 3.91 (3H, s), 2.82 (2H, s), 1.36 (6H, s). LCMS (ES+) 487.0 (M+H)$^+$, RT 3.25 minutes (Method 1).

Example 384

6,6-Dimethyl-2-[6-(2-methoxypyrimidin-5-yl)-2,3-dihydro-4H-1,4-benzoxazin-4-yl]-6,7-dihydro[1,3]thiazolo[5,4-c]pyridin-4(5H)-one The title compound was prepared from Example 292 and 5-bromo-2-methoxypyrimidine according to Method AX and was isolated as a white solid (13%) after trituration with EtOAc (2×10 mL) and MeOH (2×10 mL) and drying in vacuo. δ$_H$ (CDCl$_3$) 8.70 (2H, s), 8.28 (1H, d, J 2.1 Hz), 7.21 (1H, dd, J 8.5 and 2.1 Hz), 7.07 (1H, d, J 8.5 Hz), 5.22 (1H, s), 4.45-4.34 (2H, m), 4.22-4.11 (2H, m), 4.07 (3H, s), 2.90 (2H, s), 1.40 (6H, s). LCMS (ES+) 424.0 (M+H)$^+$, RT 3.19 minutes (Method 2).

Example 385

6,6-Dimethyl-2-[6-(2-hydroxypyrimidin-5-yl)-2,3-dihydro-4H-1,4-benzoxazin-4-yl]-6,7-dihydro[1,3]thiazolo[5,4-c]pyridin-4(5H)-one The title compound was prepared from Example 292 and 5-bromo-2-hydroxypyrimidine according to Method AX and was isolated as a white solid (6%) after purification by preparative HPLC (Method 7). δ$_H$ (CD$_3$OD) 8.41 (2H, s), 8.05 (1H, d, J 1.9 Hz), 7.17 (1H, dd, J 8.5 and 2.3 Hz), 7.07 (1H, dd, J 8.3 and 1.9 Hz), 4.46-4.36 (2H, m), 4.23-4.17 (2H, m), 2.91 (2H, s), 1.42 (6H, s). LCMS (ES+) 410.0 (M+H)$^+$, RT 2.34 minutes (Method 2).

Example 386

2-[6-(2-Aminopyrimidin-5-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 292 and 2-amino-5-bromopyrimidine according to Method AX and was isolated as a white solid (10%) after purification by preparative HPLC (Method 7). δ$_H$ (CD$_3$OD) 8.39 (2H, s), 8.06 (1H, d, J 2.1 Hz), 7.12 (1H, dd, J 8.5 and 2.1 Hz), 6.97 (1H, d, J 8.5 Hz), 4.36-4.26 (2H, m), 4.09-4.05 (2H, m), 2.81 (2H, s), 1.32 (6H, s). LCMS (ES+) 409.0 (M+H)$^+$, RT 2.69 minutes (Method 2).

Example 387

6,6-Dimethyl-2-[6-(2-(pyrrolidin-1-yl)pyrimidin-5-yl)-2,3-dihydro-4H-1,4-benzoxazin-4-yl]-6,7-dihydro[1,3]thiazolo[5,4-c]pyridin-4(5H)-one The title compound was prepared from Example 292 and 5-bromo-2-(pyrrolidin-1-yl)pyrimidine according to Method AY and was isolated as an off-white solid (6%). δ$_H$ (CDCl$_3$) 8.55 (2H, s), 8.18 (1H, d, J 1.9 Hz), 7.16 (1H, dd, J 8.3 and 1.7 Hz), 7.02 (1H, d, J 8.5 Hz), 5.20 (1H, s), 4.46-4.29 (2H, m), 4.23-4.10 (2H, m), 3.63 (4H, t, J 6.6 Hz), 2.89 (2H, s), 2.19-1.94 (4H, m), 1.40 (6H, s). LCMS (ES+) 463.0 (M+H)$^+$, RT 3.28 minutes (Method 1).

Example 388

6,6-Dimethyl-2-[6-(4-hydroxy-2-methylpyrimidin-5-yl)-2,3-dihydro-4H-1,4-benzoxazin-4-yl]-6,7-dihydro[1,3]thiazolo[5,4-c]pyridin-4(5H)-one The title compound was prepared from Example 292 and 5-bromo-4-hydroxy-2-methylpyrimidine according to Method AX and was isolated as a white solid (16%) after purification by preparative HPLC (Method 6). δ$_H$ (CD$_3$OD) 8.27 (1H, d, J 1.5 Hz), 8.00 (1H, s), 7.40 (1H, dd, J 8.5 and 1.9 Hz), 7.02 (1H, d, J 8.5 Hz), 5.37 (1H, s), 4.45-4.32 (2H, m), 4.27-4.12 (2H, m), 2.89 (2H, s), 2.45 (3H, s), 1.41 (6H, s). LCMS (ES+) 424.0 (M+H)$^+$, RT 2.33 minutes (Method 1).

Example 389

6-{[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]oxy}pyridine-2-carboxamide To a solution of Example 57 (75 mg, 0.227 mmol) in THF (4 mL) was added 2-fluoro-6-pyridinecarboxamide (64 mg, 0.453 mmol) and sodium tert-butoxide (87 mg, 0.906 mmol). The reaction was heated to 145° C. under microwave irradiation for 50 minutes then cooled to r.t. The mixture was partitioned between DCM (50 mL) and water (50 mL); the organic phase was washed with brine (50 mL), dried (MgSO$_4$), and concentrated in vacuo. The residue was purified by preparative HPLC (Method 6) to give the title compound (12 mg, 12%) as a white solid. δ$_H$ (CDCl$_3$) 8.02 (1H, d, J 2.6 Hz), 7.91 (1H, dd, J 7.2 and 0.9 Hz), 7.85 (1H, t, J 7.9 Hz), 7.08 (1H, dd, J 7.9 and 0.9 Hz), 6.98 (1H, d, J 8.9 Hz), 6.85 (1H, dd, J 8.9 and 2.6 Hz), 4.27-4.43 (2H, m), 4.05-4.17 (2H, m), 2.83 (2H, s), 1.37 (6H, s). LCMS (ES+) 452.0 (M+H)$^+$, RT 2.85 minutes (Method 1).

Example 390

Method AZ 6,6-Dimethyl-2-{6-[(6-(pyrrolidin-1-yl)pyridin-2-yl)oxy]-2,3-dihydro-4H-1,4-benzoxazin-4-yl}-6,7-dihydro[1,3]thiazolo[5,4-c]pyridin-4(5H)-one To a suspension of Example 382 (50 mg, 0.103 mmol) in toluene (4 mL) was added pyrrolidine (0.025 ml, 0.308 mmol), sodium tert-butoxide (20 mg, 0.206 mmol) and [1,1'-bis(di-tert-butylphosphino)ferrocene]palladium(II) dichloride (10 mg, 20% wt). The reaction was heated to 140° C. under microwave irradiation for 90 minutes then cooled to room temperature. The mixture was partitioned between DCM (50 mL) and water (50 mL); the organic phase was washed with brine (50 mL), dried (MgSO$_4$), and concentrated in vacuo. The residue was purified by preparative HPLC (Method 6) to give the title compound (17 mg, 35%) as an off-white solid. δ$_H$ (CDCl$_3$) 7.91 (1H, d, J 2.4 Hz), 7.39 (1H, t, J 7.9 Hz), 6.93 (1H, d, J 8.9 Hz), 6.88 (1H, dd, J 8.9 and 2.4 Hz), 6.02 (1H, d, J 8.1 Hz), 5.91 (1H, d, J 7.7 Hz), 5.29 (1H, s), 4.38-4.29 (2H, m), 4.15-4.06 (2H, m), 3.45-3.37 (4H, m), 2.85 (2H, s), 2.01-1.92 (4H, m), 1.37 (6H, s). LCMS (ES+) 478.0 (M+H)$^+$, RT 3.96 minutes (Method 1).

Example 391

6,6-Dimethyl-2-(6-{[6-(isopropylamino)pyridin-2-yl]oxy}-2,3-dihydro-4H-1,4-benzoxazin-4-yl)-6,7-dihydro[1,3]thiazolo[5,4-c]pyridin-4(5H)-one The title compound was prepared from Example 382 and isopropylamine according to Method AZ and was isolated as an off-white solid (35%) after purification by preparative HPLC (Method 7). δ$_H$ (CDCl$_3$) 7.89 (1H, d, J 2.4 Hz), 7.39 (1H, t, J 7.9 Hz), 6.93 (1H, d, J 8.9 Hz), 6.84 (1H, dd, J 8.9 and 2.6 Hz), 6.03 (1H, d, J 7.9 Hz), 5.99 (1H, dd, J 7.7 and 0.4 Hz), 5.26 (1H, s), 4.39-4.28 (2H, m), 4.18-4.07 (2H, m), 3.87-3.72 (1H, m), 2.86 (2H, s), 1.38 (6H, s), 1.19 (6H, d, J 6.4 Hz). LCMS (ES+) 466.0 (M+H)$^+$, RT 3.97 minutes (Method 2).

Example 392

6,6-Dimethyl-2-[6-(pyrazin-2-yloxy)-2,3-dihydro-4H-1,4-benzoxazin-4-yl]-6,7-dihydro[1,3]thiazolo[5,4-c]pyridin-4(5H)-one To a solution of Example 57 (70 mg, 0.211 mmol) in THF (4 mL) was added 2-fluoropyrazine (41 mg, 0.423 mmol) and sodium tert-butoxide (81 mg, 0.846 mmol). The reaction was heated to 150° C. under microwave irradiation for 50 minutes then cooled to r.t. The resulting precipitate was collected, washed with water (4×10 mL), Et$_2$O (3×10 mL) and dried in vacuo to yield the title compound (35 mg, 41%) as an off-white solid. $\delta_H$ (CDCl$_3$) 8.44 (1H, d, J 1.3 Hz), 8.26 (1H, d, J 2.6 Hz), 8.12 (1H, dd, J 2.8 and 1.5 Hz), 8.02 (1H, d, J 2.6 Hz), 7.01 (1H, d, J 8.9 Hz), 6.86 (1H, dd, J 8.9 and 2.6 Hz), 5.26 (1H, s), 4.42-4.30 (2H, m), 4.15-4.10 (2H, m), 2.86 (2H, s), 1.38 (6H, s). LCMS (ES+) 410.0 (M+H)$^+$, RT 3.04 minutes (Method 2).

Example 393

6,6-Dimethyl-2-(6-{[6-(4-methylpiperazin-1-yl)pyridin-2-yl]oxy}-2,3-dihydro-4H-1,4-benzoxazin-4-yl)-6,7-dihydro[1,3]thiazolo[5,4-c]pyridin-4(5H)-one The title compound was prepared from Example 382 and 1-methylpiperazine according to Method AZ and was isolated as an off-white solid (36%) after purification by preparative HPLC (Method 6). $\delta_H$ (CDCl$_3$) 7.90 (1H, d, J 2.6 Hz), 7.45 (1H, t, J 7.9 Hz), 6.94 (1H, d, J 8.7 Hz), 6.86 (1H, dd, J 8.9 and 2.6 Hz), 6.29 (1H, d, J 8.3 Hz), 6.05 (1H, d, J 7.9 Hz), 5.22 (1H, s), 4.43-4.28 (2H, m), 4.18-4.06 (2H, m), 3.59-3.41 (4H, m), 2.86 (2H, s), 2.56-2.44 (4H, m), 2.33 (3H, s), 1.38 (6H, s). LCMS (ES+) 507.0 (M+H)$^+$, RT 2.33 minutes (Method 1).

Example 394

2-{6-[(6-Chloro-2-methylpyrimidin-4-yl)oxy]-2,3-dihydro-4H-1,4-benzoxazin-4-yl}-6,6-dimethyl-6,7-dihydro[1,3]thiazolo[5,4-c]pyridin-4(5H)-one To a suspension of Example 57 (70 mg, 0.211 mmol) in THF (4 mL) was added 4,6-dichloro-2-methylpyrimidine (86 mg, 0.529 mmol) and sodium tert-butoxide (81 mg, 0.846 mmol). The reaction was heated to 155° C. under microwave irradiation for 30 minutes then cooled to room temperature. The mixture was partitioned between DCM (50 mL) and water (50 mL); the organic phase was washed with brine (50 mL), dried (MgSO$_4$), and concentrated in vacuo. The residue was purified by preparative HPLC (Method 6) to give the title compound (32 mg, 35%) as an off-white solid. $\delta_H$ (CDCl$_3$) 8.02 (1H, d, J 2.8 Hz), 6.99 (1H, d, J 8.9 Hz), 6.82 (1H, dd, J 8.9 and 2.6 Hz), 6.66 (1H, s), 5.50 (1H, s), 4.47-4.26 (2H, m), 4.19-4.04 (2H, m), 2.86 (2H, s), 2.61 (3H, s), 1.38 (6H, s). LCMS (ES+) 458.0 (M+H)$^+$, RT 3.50 minutes (Method 1).

Example 395

6,6-Dimethyl-2-{6-[(2-methylpyrimidin-4-yl)oxy]-2,3-dihydro-4H-1,4-benzoxazin-4-yl}-6,7-dihydro[1,3]thiazolo[5,4-c]pyridin-4(5H)-one To a suspension of Example 394 (40 mg, 0.088 mmol) in MeOH (15 mL) was added triethylamine (0.040 mL, 0.263 mmol) and 5% Pd/C (10 mg, 25% wt). The reaction mixture was stirred under an atmosphere of hydrogen for 24 h, then the catalyst was filtered off and the filtrate was concentrated in vacuo. The residue was partitioned between DCM (50 mL) and water (50 mL); the organic phase was washed with brine (50 mL), dried (MgSO$_4$), and concentrated in vacuo to give the title compound (24 mg, 65%) as an off-white solid. $\delta_H$ (CDCl$_3$) 8.45 (1H, d, J 5.8 Hz), 7.97 (1H, d, J 2.6 Hz), 6.98 (1H, d, J 8.9 Hz), 6.84 (1H, dd, J 8.9 and 2.6 Hz), 6.63 (1H, d, J 5.8 Hz), 5.58 (1H, s), 4.41-4.26 (2H, m), 4.16-4.05 (2H, m), 2.84 (2H, s), 2.62 (3H, s), 1.37 (6H, s). LCMS (ES+) 424.0 (M+H)$^+$, RT 2.75 minutes (Method 1).

Example 396

6,6-Dimethyl-2-[6-(6-methoxypyridin-3-yl)-2,3-dihydro-4H-1,4-benzoxazin-4-yl]-6,7-dihydro[1,3]thiazolo[5,4-c]pyridin-4(5H)-one A mixture of 5-bromo-2-methoxypyridine (0.135 g, 0.72 mmol), potassium phosphate (0.232 g, 1.92 mmol) and Example 292 (0.212 g, 0.48 mmol) in water (2 mL) was degassed; THF (10 mL) was added and the mixture was degassed again. Tetrakis-(triphenylphosphine)palladium(0) (0.040 g, 0.035 mmol) was added and the mixture was degassed. The reaction mixture was stirred at 100° C. for 0.5 h, then cooled to room temperature. 5-Bromo-2-methoxypyridine (0.135 g, 0.72 mmol) and tetrakis(triphenylphosphine)palladium(0) (0.040 g, 0.035 mmol) were added and the mixture was degassed and heated at 110° C. for 0.5 h. The THF was evaporated in vacuo and DCM (25 mL) was added. The organic fraction was separated, dried (MgSO$_4$), filtered and concentrated in vacuo. The residue was purified by column chromatography (SiO$_2$, 0-10% MeOH/DCM elution) to give the title compound (0.194 g, 96%) as an off-white solid. A sample (0.023 g) was further purified by preparative HPLC (Method 6) to give the title compound (0.012 g, 52%) as a white solid. $\delta_H$ (CDCl$_3$) 8.36 (1H, d, J 2.6 Hz), 8.1 (1H, d, J 2.1 Hz), 7.26 (1H, dd, J 8.5 and 2.6 Hz), 7.23 (1H, dd, J 8.5 and 2.1 Hz), 7.03 (1H, d, J 8.3 Hz), 6.82 (1H, d, J 8.5 Hz), 5.25 (1H, s), 4.41-4.34 (2H, m), 4.23-4.17 (2H, m), 3.98 (3H, s), 2.89 (2H, s), 1.40 (6H, s). LCMS (ES+) 423.08 (M+H)$^+$, RT 3.52 minutes (Method 1).

Example 397

2-(6-Cyclopropyl-2,3-dihydro-4H-1,4-benzoxazin-4-yl)-6,6-dimethyl-6,7-dihydro[1,3]thiazolo[5,4-c]pyridin-4(5H)-one A mixture of cyclopropylboronic acid pinacol ester (0.091 mL, 0.5 mmol), potassium phosphate (0.212 g, 1.0 mmol) and Example 39 (0.10 g, 0.25 mmol) in water (1 mL) was degassed, THF (3.5 mL) was added and the mixture degassed again. Tetrakis(triphenylphosphine)palladium(0) (0.040 g. 0.035 mmol) was added and the mixture was degassed. The reaction mixture was stirred at 120° C. for 0.5 h, then cooled to r.t. Cyclopropylboronic acid pinacol ester (0.091 mL, 0.5 mmol) and tetrakis(triphenylphosphine)palladium(0) (0.040 g. 0.035 mmol) were added and the mixture was degassed and heated at 120° C. for 0.5 h then cooled to room temperature. The organic fraction was separated and concentrated in vacuo and DCM (10 mL) and water (10 mL) were then added. The organic fraction was dried (MgSO$_4$), filtered and concentrated in vacuo. The residue was purified by preparative HPLC (Method 6) to give the title compound (0.023 g, 26%) as a white solid. $\delta_H$ (CDCl$_3$) 7.58 (1H, d, J 2.1 Hz), 6.88-6.77 (2H, m), 5.21 (1H, s), 4.31-4.27 (2H, m), 4.19-4.14 (2H, m), 2.87 (2H, s), 1.91-1.81 (1H, m), 1.40 (6H, s), 0.97-0.89 (2H, m), 0.68-0.61 (2H, m). LCMS (ES+) 356.15 (M+H)$^+$, RT 3.64 minutes (Method 1).

Example 398

2-(6-Benzyl-2,3-dihydro-4H-1,4-benzoxazin-4-yl)-6,6-dimethyl-6,7-dihydro[1,3]thiazolo[5,4-c]pyridin-4(5H)-one A mixture of benzylboronic acid pinacol ester (0.111 mL, 0.5 mmol), potassium phosphate (0.212 g, 1 mmol) and Example 39 (0.1 g, 0.25 mmol) in water (1 mL) was degassed; THF (3.5 mL) was added and the mixture was degassed again. Tetrakis-(triphenylphosphine)palladium(0) (0.040 g. 0.035 mmol) was added and the mixture was degassed. The reaction mixture was stirred at 120° C. for 0.5 h, then cooled to room temperature. The organic layer was evaporated in vacuo and DCM (10 mL) and water (10 mL) were added. The organic layer was dried (MgSO$_4$), filtered and the solvent removed in vacuo. The residue was purified by preparative HPLC (Method 6) to give the title compound (0.017 g, 17%) as a white solid. $\delta_H$ (CDCl$_3$) 7.72 (1H, s), 7.34-7.27 (2H, m), 7.24-7.17 (3H, m), 6.89-6.86 (2H, m), 5.24 (1H, s), 4.32-4.28 (2H, m), 4.16-4.12 (2H, m), 3.93 (2H, s), 2.84 (2H, s), 1.38 (6H, s). LCMS (ES+) 406.3 (M+H)$^+$, RT 4.02 minutes (Method 1).

Example 399

Method BA 6,6-Dimethyl-2-{7-[(3-(pyrrolidin-1-yl)propyl)amino]-2,3-dihydro-4H-1,4-benzoxazin-4-yl}-6,7-dihydro[1,3]thiazolo[5,4-c]pyridin-4(5H)-one DME (2 mL) was added to a mixture of Example 214 (0.1 g, 0.254 mmol), potassium tert-butoxide (0.068 g, 0.609 mmol), palladium(II) acetate (0.006 g, 0.025 mmol) and tri-tert-butylphosphonium tetrafluoroborate (0.015 g, 0.051 mmol). 1-(3-Aminopropyl)pyrrolidine (0.065 g, 0.507 mmol) was added and the mixture was degassed by evacuating and purging with nitrogen four times over a period of 5 minutes. The mixture was heated at 140° C. under microwave irradiation for 1 h. The mixture was filtered and the solvent was evaporated in vacuo. The residue was purified by preparative HPLC (Method 7) to give the title compound (0.0237 g, 21%) as a brown solid. $\delta_H$ (CDCl$_3$) 7.54 (1H, d, J 8.7 Hz), 6.20 (1H, dd, J 8.7 and 2.4 Hz), 6.15 (1H, d, J 2.4 Hz), 5.18 (1H, s), 4.30-4.25 (2H, m), 4.15-4.10 (2H, m), 3.17 (2H, t, J 6.6 Hz), 2.83 (2H, s), 2.68-2.55 (6H, m), 1.90-1.78 (6H, m), 1.38 (6H, s). LCMS (ES+) 442.2 (M+H)$^+$, RT 2.20 minutes (Method 2).

Example 400

6,6-Dimethyl-2-{7-[(2-(pyrrolidin-1-yl)ethyl)amino]-2,3-dihydro-4H-1,4-benzoxazin-4-yl}-6,7-dihydro[1,3]thiazolo[5,4-c]pyridin-4(5H)-one The title compound was prepared from Example 214 and 1-(2-aminoethyl)-pyrrolidine according to Method BA and was isolated as a brown solid (17%) after purification by preparative HPLC (Method 7). $\delta_H$ (CDCl$_3$) 7.56 (1H, d, J 8.7 Hz), 6.25 (1H, dd, J 8.7 and 2.6 Hz), 6.19 (1H, d, J 2.6 Hz), 5.14 (1H, s), 4.37-4.25 (3H, m), 4.14-4.10 (2H, m), 3.20-3.12 (2H, m), 2.84 (2H, s), 2.75-2.70 (2H, m), 2.57-2.49 (4H, m), 1.83-1.75 (4H, m), 1.38 (6H, s). LCMS (ES+) 428.2 (M+H)$^+$, RT 2.25 minutes (Method 2).

Example 401

6,6-Dimethyl-2-{7-[N-(3-methoxypropyl)-N-(methyl)amino]-2,3-dihydro-4H-1,4-benzoxazin-4-yl}-6,7-dihydro[1,3]thiazolo[5,4-c]pyridin-4(5H)-one DME (3 mL) was added to a mixture of Example 214 (0.2 g, 0.507 mmol), potassium tert-butoxide (0.136 g, 1.22 mmol), palladium(II) acetate (0.0114 g, 0.051 mmol) and tri-tert-butylphosphonium tetrafluoroborate (0.0293 g, 0.101 mmol). 3-Methoxypropylamine (0.259 mL, 2.54 mmol) was added and the mixture was degassed by evacuating and purging with nitrogen four times over a period of 5 minutes. The mixture was heated at 140° C. under microwave irradiation for 1 h. The mixture was filtered and the solvent was evaporated in vacuo. The residue was purified by column chromatography (SiO$_2$, 2-5% MeOH/DCM). To a solution of the purified material in MeOH (3 mL) was added 37% wt/water formaldehyde (0.115 g, 1.417 mmol) in MeOH (0.5 mL) followed by sodium cyanoborohydride (0.0619 g, 0.986 mmol) and then 1 drop of glacial acetic acid. The reaction was stirred for 18 h. Water (1 mL) was added and the organic fraction was separated and concentrated in vacuo. DCM (10 mL) and water (7 mL) were added and the aqueous layer was extracted with DCM (2×10 mL). The combined organic fractions were washed with brine (10 mL), dried (MgSO$_4$), filtered and concentrated in vacuo. The residue was purified by preparative HPLC (Method 7) to give the title compound (0.036 g, 17%) as a yellow solid. $\delta_H$ (CDCl$_3$) 7.62 (1H, d, J 8.9 Hz), 6.33 (1H, dd, J 8.9 and 2.8 Hz), 6.26 (1H, d, J 2.8 Hz), 5.39 (1H, s), 4.32-4.26 (2H, m), 4.16-4.10 (2H, m), 3.45-3.37 (4H, m), 3.35 (3H, s), 2.91 (3H, s), 2.84 (2H, s), 1.89-1.76 (2H, m), 1.38 (6H, s). LCMS (ES+) 417.1 (M+H)$^+$, RT 3.58 minutes (Method 2).

Example 402

6,6-Dimethyl-2-{7-[(3-methoxypropyl)amino]-2,3-dihydro-4H-1,4-benzoxazin-4-yl}-6,7-dihydro[1,3]thiazolo[5,4-c]pyridin-4(5H)-one The title compound was prepared from Example 214 and 3-methoxypropylamine according to Method BA and was isolated as a light brown solid (10%) after purification by preparative HPLC (Method 7). $\delta_H$ (CDCl$_3$) 7.55 (1H, d, J 8.7 Hz), 6.22 (1H, dd, J 8.7 and 2.6 Hz), 6.18 (1H, d, J 2.6 Hz), 5.21 (1H, s), 4.30-4.26 (2H, m), 4.15-4.10 (2H, m), 4.01 (1H, s), 3.51 (2H, t, J 5.8 Hz), 3.36 (3H, s), 3.24-3.16 (2H, m), 2.84 (2H, s), 1.88 (2H, quint), 1.38 (6H, s). LCMS (ES+) 403.1 (M+H)$^+$, RT 3.18 minutes (Method 2).

Example 403

2-{7-[N-(Cyclopropylmethyl)-N-(piperidin-4-yl)amino]-2,3-dihydro-4H-1,4-benzoxazin-4-yl}-6,6-dimethyl-6,7-dihydro[1,3]thiazolo[5,4-c]pyridin-4(5H)-one, acetate salt DME (12 mL) was added to a mixture of Example 214 (0.6 g, 1.52 mmol), potassium tert-butoxide (0.409 g, 3.65 mmol), palladium(II) acetate (0.0341 g, 0.152 mmol) and tri-tert-butylphosphonium tetrafluoroborate (0.088 g, 0.304 mmol). 4-Amino-1-(tert-butoxycarbonyl)piperidine (0.609 g, 3.04 mmol) was added, and the mixture was degassed by evacuating and purging with nitrogen four times over a period of 5 minutes. The mixture was heated at 140° C. under microwave irradiation for 1 h. The solvent was evaporated in vacuo and the residue purified by column chromatography (SiO$_2$, 1-3% MeOH/DCM). To a portion of the purified material (0.085 g, 0.165 mmol) in DMF (10 mL) was added sodium carbonate (0.035 g, 0.331 mmol) followed by (bromomethyl)-cyclopropane (0.160 mL, 1.65 mmol). The mixture was heated at 120° C. under microwave irradiation for 3 h. A further portion of (bromomethyl)cyclopropane (0.160 mL, 1.65 mmol) was added and the mixture was heated at 120° C. under microwave irradiation for a further 3 h. The solvent was evaporated in vacuo. To a solution of the residue in MeOH (1.3 mL) was added TFA (0.216 mL, 2.81 mmol). The mixture was heated at 100° C. under microwave irradiation for 1 h. The solvent was evaporated in vacuo and the residue was purified by preparative HPLC (Method 7) to give the title compound (0.0181 g, 19%) as a brown solid. $\delta_H$ (CDCl$_3$) 7.68 (1H, d, J 9.0 Hz), 6.96-6.76 (5H, m), 6.49 (1H, dd, J 9.0 and 2.8 Hz), 6.44 (1H, d, J 2.8 Hz), 6.09 (1H, s), 4.33-4.28 (2H, m), 4.16-4.11 (2H, m), 3.77-3.62 (1H, m), 3.50-3.41 (2H, m), 3.06 (2H, d, J 5.7 Hz), 2.96-2.80 (4H, m), 2.03 (6H, s), 2.02-1.89 (4H, m), 1.39 (6H, s), 1.03-0.89 (1H, m), 0.59-0.51 (2H, m), 0.27-0.20 (2H, m). LCMS (ES+) 468.2 (M+H)$^+$, RT 2.55 minutes (Method 2).

Example 404

2-{7-[N-Ethyl-N-(piperidin-4-yl)amino]-2,3-dihydro-4H-1,4-benzoxazin-4-yl}-6,6-dimethyl-6,7-dihydro[1,3]thiazolo[5,4-c]pyridin-4(5H)-one DME (12 mL) was added to a mixture of Example 214 (0.6 g, 1.52 mmol), potassium tert-butoxide (0.409 g, 3.65 mmol), palladium(II) acetate (0.0341 g, 0.152 mmol) and tri-tert-butylphosphonium tetrafluoroborate (0.088 g, 0.304 mmol). 4-Amino-1-(tert-butoxycarbonyl)piperidine (0.609 g, 3.04 mmol) was added, and the mixture was degassed by evacuating and purging with nitrogen four times over a period of 5 minutes. The mixture was heated at 140° C. under microwave irradiation for 1 h. The solvent was evaporated in vacuo and the residue was purified by column chromatography (SiO$_2$, 1-3% MeOH/DCM). To a portion of the purified material (0.074 g, 0.144 mmol) in DMF (10 mL) was added sodium carbonate (0.030 g, 0.288 mmol) followed by iodoethane (0.115 mL, 1.44 mmol). The mixture was heated at 100° C. under microwave irradiation for 3 h. A further portion of iodoethane (0.115 mL, 1.44 mmol) was added and the mixture heated at 100° C. under microwave irradiation for a further 3 h. The solvent was evaporated in vacuo and the residue was partitioned between EtOAc (10 mL) and water (10 mL). The aqueous phase was extracted with EtOAc (2×10 mL). The combined organic fractions were washed with brine (10 mL), dried (MgSO$_4$), filtered and the solvent evaporated in vacuo. The residue was purified by column chromatography (SiO$_2$, 50-100% EtOAc/heptane). The resulting brown solid was suspended in MeOH (0.5 mL). TFA (0.079 mL, 1.02 mmol) was added and the mixture was heated at 100° C. under microwave irradiation for 1 h. A further portion of TFA (0.079 mL, 1.02 mmol) was added and the mixture heated at 100° C. under microwave irradiation for a further 20 minutes. The solvent was evaporated in vacuo and the residue was purified by preparative HPLC (Method 7) to give the title compound (0.010 g, 16%) as a brown solid. $\delta_H$ (CDCl$_3$) 7.62 (1H, d, J 9.0 Hz), 6.36 (1H, dd, J 9.0 and 2.8 Hz), 6.29 (1H, d, J 2.8 Hz), 5.19-5.15 (1H, s), 4.31-4.27 (2H, m), 4.15-4.10 (2H, m), 3.66-3.53 (1H, m), 3.28 (2H, q, J 7.0 Hz), 3.23-3.14 (2H, m), 2.84 (2H, s), 2.78-2.61 (2H, m), 1.71-1.55 (2H, m), 1.86-1.76 (2H, m), 1.38 (6H, s), 1.16 (3H, t, J 7.0 Hz). LCMS (ES+) 442.1 (M+H)$^+$, RT 2.38 minutes (Method 2).

Example 405

Method BB 6,6-Dimethyl-2-{6-[(6-(piperidin-1-yl)pyridazin-3-yl)amino]-2,3-dihydro-4H-1,4-benzoxazin-4-yl}-6,7-dihydro[1,3]thiazolo[5,4-c]pyridin-4(5H)-one To a stirred solution of 3-chloro-6-(piperidin-1-yl)pyridazine (15 mg, 0.075 mmol) and Example 42 (31 mg, 0.094 mmol) in toluene (5 mL) was added sodium tert-butoxide (27 mg, 0.28 mmol) and [1,1'-bis(di-tert-butylphosphino)ferrocene]-palladium(II) dichloride (10 mg). The reaction mixture was stirred at 140° C. under microwave irradiation for 3 h, then cooled to room temperature and the solvent evaporated in vacuo. The residue was purified by preparative HPLC (Method 7) to give the title compound (22 mg, 60%) as an off-white solid. $\delta_H$ (CDCl$_3$) 7.94 (1H, d, J 2.4 Hz), 7.08 (1H, dd, J 8.7 and 2.4 Hz), 7.00 (2H, d, J 0.8 Hz), 6.88-6.92 (1H, m), 6.45-6.35 (1H, m), 5.19 (1H, dd, J 0.9 and 0.4 Hz), 4.35-4.27 (2H, m), 4.15-4.08 (2H, m), 3.52-3.45 (4H, m), 2.88 (2H, s), 1.74-1.52 (6H, m), 1.40 (6H, s). LCMS (ES+) 492 (M+H)$^+$, RT 3.38 minutes (Method 2).

Example 406

2-{6-[N-Benzyl-N-(6-methylpyridazin-3-yl)amino]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 39 and Intermediate 237 according to Method BB and was isolated as an off-white solid (44%) after purification by preparative HPLC (Method 7). $\delta_H$ (CDCl$_3$) 7.90 (1H, d, J 2.4 Hz), 7.41-7.30 (2H, m), 7.26-7.09 (3H, m), 7.05-6.89 (2H, m), 6.82 (1H, dd, J 8.7 and 2.4 Hz), 6.68 (1H, d, J 9.2 Hz), 5.32 (2H, s), 5.20 (1H, s), 4.39-4.29 (2H, m), 4.12-4.07 (2H, m), 2.80 (2H, s), 2.55 (3H, s), 1.37 (6H, s). LCMS (ES+) 513 (M+H)$^+$, RT 3.55 minutes (Method 2).

Example 407

6,6-Dimethyl-2-{6-[(5-methyl-1,3,4-thiadiazol-2-yl)amino]-2,3-dihydro-4H-1,4-benzoxazin-4-yl}-6,7-dihydro[1,3]thiazolo[5,4-c]pyridin-4(5H)-one A solution of 2-bromo-5-methyl-1,3,4-thiadiazole (20 mg, 0.11 mmol) and Example 42 (70 mg, 0.21 mmol) in DIPEA (0.074 mL, 0.43 mmol) was stirred at 180° C. under microwave irradiation for 4 h. The reaction mixture was cooled to r.t. and concentrated in vacuo. The residue was purified by preparative HPLC (Method 7) to give the title compound (10.5 mg, 22%) as an off-white solid. $\delta_H$(CDCl$_3$/CD$_3$OD) 8.13 (1H, d, J 2.6 Hz), 7.24 (H, dd, J 8.9 and 2.6 Hz), 6.95 (1H, d, J 8.9 Hz), 4.38-4.32 (2H, m), 4.20-4.10 (2H, m), 2.90 (2H, s), 2.61 (3H, s), 1.42 (6H, s). LCMS (ES+) 429 (M+H)$^+$, RT 2.85 minutes (Method 2).

Example 408

2-(7-{N-[3-(Dimethylamino)propyl]-N-(ethyl)amino}-6-methyl-2,3-dihydro-4H-1,4-benzoxazin-4-yl)-6,6-dimethyl-6,7-dihydro[1,3]thiazolo[5,4-c]pyridin-4(5H)-one, formic acid salt To a stirred solution of Example 295 (13 mg, 0.031 mmol) in 1,2-dichloroethane (2 mL) and MeOH (0.1 mL) was added acetaldehyde [140 μL of a solution of acetaldehyde (250 mg) in 1,2-dichloroethane (2 mL) containing 18 mg, 0.40 mmol] and the reaction mixture was stirred at r.t. for 90 minutes. Sodium triacetoxyborohydride (13 mg, 0.062 mmol) was added and the mixture was stirred for 72 h. Additional acetaldehyde (10 drops, ±250 mg) was added and the reaction mixture was stirred at r.t. for 1 h. Further sodium triacetoxyborohydride (12 mg, 0.059 mmol) was added and the mixture was stirred overnight. Additional acetaldehyde (10 drops, ~250 mg) was added and the reaction mixture was stirred at r.t. for 2 h. Sodium triacetoxyborohydride (16 mg, 0.075 mmol) was added and the mixture was stirred overnight and saturated aqueous sodium hydrogencarbonate solution (30 mL) was added. The aqueous layer was extracted with EtOAc (3×25 mL) and the combined organic fractions were dried ($Na_2SO_4$), filtered and concentrated in vacuo. The residue was purified by preparative HPLC (Method 6) to give the title compound (7.8 mg, 51%) as a yellow oil. $\delta_H$ ($CDCl_3$) 8.52 (1H, s), 7.64 (1H, s), 6.65 (1H, s), 5.27 (1H, br s), 4.32-4.27 (2H, m), 4.15 (2H, dd, J 4.9 and 3.4 Hz), 3.00 (2H, t, J 6.6 Hz), 2.95-2.87 (2H, m), 2.87 (2H, s), 2.76-2.68 (2H, m), 2.49 (6H, s), 2.21 (3H, s), 1.82-1.69 (2H, m), 1.40 (6H, s), 0.99 (3H, t, J 7.0 Hz). LCMS (ES+) 458.28 $(M+H)^+$, RT 1.83 minutes (Method 1).

Example 409

Method BC 6,6-Dimethyl-2-{6-methyl-7-[N-methyl-N-(2-(pyrrolidin-1-yl)ethyl)amino]-2,3-dihydro-4H-1,4-benzoxazin-4-yl}-6,7-dihydro[1,3]thiazolo[5,4-c]pyridin-4 (5H)-one, formic acid salt To a stirred solution of Example 296 (24 mg, 0.054 mmol) in 1,2-dichloroethane (2 mL) was added formaldehyde (37 wt % in water, 279 μL, 3.44 mmol) and the reaction mixture was stirred at r.t. for 3 h. Sodium triacetoxyborohydride (19 mg, 0.089 mmol) was added and the mixture was stirred for 72 h. Additional formaldehyde (37 wt % in water, 279 μL, 3.44 mmol) was added and the reaction mixture was stirred at r.t. for a further 1 h. Sodium triacetoxyborohydride (33 mg, 0.16 mmol) was added; the mixture was stirred for 18 h, and saturated aqueous sodium hydrogencarbonate solution (30 mL) was added. The aqueous layer was extracted with EtOAc (3×25 mL) and the combined organic fractions were dried ($Na_2SO_4$), filtered and concentrated in vacuo. The residue was purified by preparative HPLC (Method 6) to yield the title compound (11 mg, 41%) as a colourless oil. $\delta_H$ ($CDCl_3$) 8.55 (1H, s), 7.65 (1H, s), 6.64 (1H, s), 5.35 (1H, br s), 4.32-4.26 (2H, m), 4.17-4.10 (2H, m), 3.28 (2H, t, J 6.8 Hz), 3.13-3.04 (4H, m), 3.04-2.97 (2H, m), 2.91-2.85 (2H, m), 2.66 (3H, s), 2.23 (3H, s), 2.02-1.94 (4H, m), 1.50 (1H, s), 1.40 (5H, s). LCMS (ES+) 456.25 $(M+H)^+$, RT 2.08 minutes (Method 1).

Example 410

2-(7-Amino-6-methyl-2,3-dihydro-4H-1,4-benzoxazin-4-yl)-6,6-dimethyl-6,7-dihydro[1,3]thiazolo[5, 4-c]pyridin-4(5H)-one THF (2.5 mL) and benzophenone imine (123 μL, 0.74 mmol) were added to a stirred mixture of Example 210 (202 mg, 0.50 mmol), sodium tert-butoxide (145 mg, 1.51 mmol), BINAP (30 mg, 0.050 mmol) and $Pd_2$ $dba_3$ (44 mg, 0.048 mmol) under nitrogen and the mixture was degassed by evacuating and purging with nitrogen three times. The mixture was heated at 120° C. under microwave irradiation for 30 minutes. The reaction mixture was filtered through celite, the solvent was evaporated in vacuo and the residue was dissolved in DCM (8 mL) and MeOH (3 mL). To the solution was added HCl in $Et_2O$ (2M, 4 mL) and the reaction mixture was stirred overnight and the solvent was evaporated in vacuo. The residue was purified by column chromatography ($SiO_2$, 0-100% EtOAc/heptane, 10% MeOH/DCM, 15% MeOH/DCM+2% $NH_4OH$) to give the title compound as a dark brown solid (155 mg, 91%). $\delta_H$ (DMSO-$d_6$) 8.00-7.90 (1H, m), 7.55 (1H, s), 6.96-6.84 (1H, m), 4.32-4.24 (2H, m), 4.09-4.01 (2H, m), 2.81 (2H, s), 2.24 (3H, s), 1.27 (6H, s). LCMS (ES+) 345.2 $(M+H)^+$, 711.0 $(2M+Na)^+$, RT 2.16 minutes (Method 1).

Example 411

6,6-Dimethyl-2-{6-methyl-7-[N-methyl-N-(1-methylpiperidin-4-yl)amino]-2,3-dihydro-4H-1,4-benzoxazin-4-yl}-6,7-dihydro[1,3]thiazolo[5,4-c]pyridin-4 (5H)-one, formic acid salt The title compound was prepared from Example 298 and formaldehyde according to Method BC and was isolated as a colourless oil (27%) after purification by preparative HPLC (Method 6). $\delta_H$ ($CDCl_3$) 8.55 (1H, s), 7.65 (1H, s), 6.66 (1H, s), 5.23 (1H, br. s), 4.29 (2H, dd, J 5.7 and 4.0 Hz), 4.14 (2H, dd, J 5.1 and 3.4 Hz), 3.11 (2H, br. d, J 11.7 Hz), 2.97-2.84 (3H, m), 2.59 (3H, s), 2.48 (3H, s), 2.46-2.29 (2H, m), 2.23 (3H, s), 2.04-1.79 (4H, m), 1.40 (6H, s). LCMS (ES+) 456.28 $(M+H)^+$, RT 2.02 minutes (Method 1).

Example 412

Method BD

N-[4-(6,6-Dimethyl-4-oxo-4,5,6,7-tetrahydro[1,3] thiazolo[5,4-c]pyridin-2-yl)-3,4-dihydro-2H-1,4-benzoxazin-7-yl]-N',N'-dimethyl-beta-alaninamide, formic acid salt To a stirred solution of Example 233 (49 mg, 0.15 mmol), HBTU (74 mg, 0.20 mmol) and 3-(dimethylamino)propionic acid hydrochloride (31 mg, 0.20 mmol) in DMF (0.5 mL) was added DIPEA (0.06 mL, 0.35 mmol). The reaction mixture was stirred at r.t. overnight, diluted with MeCN/water and filtered. The resulting mixture was purified by preparative HPLC (Method 6) to give the title compound (24 mg, 34%) as an off-white solid. $\delta_H$ ($CD_3OD$) 8.50 (1H, s), 7.91 (1H, d, J 9.0 Hz), 7.39 (1H, d, J 2.3 Hz), 7.12 (1H, dd, J 9.0 and 2.3 Hz), 4.37-4.30 (2H, m), 4.19-4.11 (2H, m), 3.43-3.35 (2H, m), 2.92-2.84 (10H, m), 1.39 (6H, s). LCMS (ES+) 430.17 $(M+H)^+$, RT 1.79 minutes (Method 1).

Example 413

N-[4-(6,6-Dimethyl-4-oxo-4,5,6,7-tetrahydro[1,3] thiazolo[5,4-c]pyridin-2-yl)-3,4-dihydro-2H-1,4-benzoxazin-7-yl]cyclohexanecarboxamide, formic acid salt The title compound was prepared from Example 233 and cyclohexylcarboxylic acid according to Method BD and was isolated as a colourless oil (45%) after purification by preparative HPLC (Method 6). $\delta_H$ ($CD_3OD$) 7.88 (1H, d, J 9.0 Hz), 7.37 (1H, d, J 2.3 Hz), 7.09 (1H, dd, J 9.0 and 2.4 Hz), 4.38-4.28 (2H, m), 4.18-4.08 (2H, m), 2.87 (2H, s), 2.43-2.30

(1H, m), 1.95-1.80 (4H, br. m), 1.74 (1H, d, J 8.7 Hz), 1.63-1.46 (2H, m), 1.46-1.22 (9H, m). LCMS (ES+) 441.20 (M+H)+, RT 3.37 minutes (Method 1).

Example 414

6,6-Dimethyl-2-[6-methyl-7-(1-methyl-1H-pyrazol-4-yl)-2,3-dihydro-4H-1,4-benzoxazin-4-yl]-6,7-dihydro[1,3]thiazolo[5,4-c]pyridin-4(5H)-one The title compound was prepared from Example 210 and 1-methyl-4-(4,4,5,5-tetramethyl-[1,3,2]dioxaborolan-2-yl)-1H-pyrazole according to Method AN and was isolated as a pale orange solid (56%) after purification by column chromatography (SiO$_2$, 0-100% EtOAc/heptane, 15% MeOH/DCM). $\delta_H$ (DMSO-d$_6$) 7.96 (1H, s), 7.92 (1H, s), 7.67 (1H, s), 7.53 (1H, s), 6.97 (1H, s), 4.28 (2H, t, J 4.1 Hz), 4.11-4.04 (2H, m), 3.88 (3H, s), 2.82 (2H, s), 2.33 (3H, s), 1.28 (6H, s). LCMS (ES+) 410.16 (M+H)+, 819.36 (2M+H)+, RT 2.92 minutes (Method 1).

Example 415

2-[7-(3,5-Dimethyl-1H-pyrazol-4-yl)-6-methyl-2,3-dihydro-4H-1,4-benzoxazin-4-yl]-6,6-dimethyl-6,7-dihydro[1,3]thiazolo[5,4-c]pyridin-4(5H)-one The title compound was prepared from Example 210 and 3,5-dimethyl-4-(4,4,5,5-tetramethyl-[1,3,2]dioxaborolan-2-yl)-1H-pyrazole according to Method AN and was isolated as a pale orange solid (22%) after purification by column chromatography (SiO$_2$, 0-100% EtOAc/heptane, 15% MeOH/DCM). $\delta_H$ (DMSO-d$_6$) 7.99 (1H, s), 7.53 (1H, s), 6.65 (1H, s), 4.33-4.26 (2H, m), 4.13-4.06 (2H, m), 2.82 (2H, s), 2.02 (3H, s), 1.99 (6H, br. s), 1.28 (6H, s). LCMS (ES+) 424.16 (M+H)+, 847.39 (2M+H)+, RT 2.55 minutes (Method 1).

Example 416

6,6-Dimethyl-2-[6-methyl-7-(6-methylpyridin-3-yl)-2,3-dihydro-4H-1,4-benzoxazin-4-yl]-6,7-dihydro[1,3]thiazolo[5,4-c]pyridin-4(5H)-one The title compound was prepared from Example 210 and 2-picoline-5-boronic acid pinacol ester according to Method AN and was isolated as a pale orange solid (59%) after purification by column chromatography (SiO$_2$, 0-100% EtOAc/heptane, 15% MeOH/DCM). $\delta_H$ (DMSO-d$_6$) 8.43 (1H, d, J 2.3 Hz), 8.04 (1H, s), 7.69 (1H, dd, J 8.1 and 2.4 Hz), 7.55 (1H, s), 7.32 (1H, d, J 8.1 Hz), 6.84 (1H, s), 4.34-4.28 (2H, m), 4.13-4.07 (2H, m), 3.31 (3H, s, obscured by MeOH peak), 2.83 (2H, s), 2.20 (3H, s), 1.29 (6H, s). LCMS (ES+) 421.16 (M+H)+, 841.37 (2M+H)+, RT 2.11 minutes (Method 1).

Example 417

6,6-Dimethyl-2-(6-methyl-7-(pyridin-4-yl)-2,3-dihydro-4H-1,4-benzoxazin-4-yl)-6,7-dihydro[1,3]thiazolo[5,4-c]pyridin-4(5H)-one The title compound was prepared from Example 210 and 4-pyridineboronic acid according to Method AN and was isolated as a pale orange solid (23%) after purification by column chromatography (SiO$_2$, 0-100% EtOAc/heptane, 15% MeOH/DCM). $\delta_H$ (DMSO-d$_6$) 8.63 (2H, d, J 6.0 Hz), 8.10 (1H, s), 7.57 (1H, s), 7.41 (2H, d, J 6.0 Hz), 6.88 (1H, s), 4.36-4.29 (2H, m), 4.14-4.07 (2H, m), 2.84 (2H, s), 2.23 (3H, s), 1.29 (6H, s). LCMS (ES+) 407.13 (M+H)+, RT 2.09 minutes (Method 1).

Example 418

6,6-Dimethyl-2-(6-methyl-7-(pyridin-3-yl)-2,3-dihydro-4H-1,4-benzoxazin-4-yl)-6,7-dihydro[1,3]thiazolo[5,4-c]pyridin-4(5H)-one The title compound was prepared from Example 210 and 3-pyridineboronic acid according to Method AN and was isolated as a pale orange solid (57%) after purification by column chromatography (SiO$_2$, 0-100% EtOAc/heptane, 15% MeOH/DCM). $\delta_H$ (DMSO-d$_6$) 8.61-8.55 (2H, m), 8.08 (1H, s), 7.82 (1H, dt, J 7.9 and 2.3 Hz), 7.56 (1H, s), 7.47 (1H, dd, J 7.7 and 4.7 Hz), 6.88 (1H, s), 4.36-4.29 (2H, m), 4.14-4.07 (2H, m), 2.84 (2H, s), 2.20 (3H, s), 1.29 (6H, s). LCMS (ES+) 407.15 (M+H)+, 813.34 (2M+H)+, RT 2.30 minutes (Method 1).

Example 419

6,6-Dimethyl-2-(6-methyl-7-(pyrimidin-5-yl)-2,3-dihydro-4H-1,4-benzoxazin-4-yl)-6,7-dihydro[1,3]thiazolo[5,4-c]pyridin-4(5H)-one DME (2 mL) and water (0.5 mL) were added to a stirred mixture of Example 210 (100 mg, 0.25 mmol), 5-pyrimidineboronic acid (36 mg, 0.29 mmol), tetrakis(triphenylphosphine)palladium(0) (22 mg, 0.019 mmol) and potassium phosphate (174 mg, 0.82 mmol) under nitrogen and the mixture was degassed by evacuating and purging with nitrogen three times. The mixture was heated at 120° C. under microwave irradiation for 30 minutes followed by 140° C. for 60 minutes. Water (10 mL) was added, the aqueous layer was extracted with EtOAc (3×10 mL) and the combined organic layers were washed with brine (10 mL). The organic fraction was dried (Na$_2$SO$_4$), filtered and the solvent was evaporated in vacuo. The residue was purified by column chromatography (SiO$_2$, 0-100% EtOAc/heptane, 15% MeOH/DCM) to give the title compound (20 mg, 20%) as a pale orange solid. $\delta_H$ (DMSO-d$_6$) 9.20 (1H, s), 8.87 (2H, s), 8.13 (1H, s), 7.57 (1H, s), 6.99 (1H, s), 4.36-4.30 (2H, m), 4.13-4.08 (2H, m), 2.84 (2H, s), 2.24 (3H, s), 1.29 (6H, s). LCMS (ES+) 408.14 (M+H)+, 815.31 (2M+H)+, RT 2.80 minutes (Method 1).

Example 420

6,6-Dimethyl-2-(7-hydroxy-2,3-dihydro-4H-1,4-benzoxazin-4-yl)-6,7-dihydro[1,3]thiazolo[5,4-c]pyridin-4(5H)-one 1,4-Dioxane (0.5 mL) and an aqueous solution of potassium hydroxide (0.21 mL containing 22 mg of potassium hydroxide, 0.41 mmol) were added to a stirred mixture of Example 214 (51 mg, 0.13 mmol), Pd$_2$dba$_3$ (6.3 mg, 0.007 mmol) and 2-di-tert-butylphosphino-2',4',6'-triisopropyl-1,1'-biphenyl (11 mg, 0.027 mmol) under nitrogen and the mixture was degassed by evacuating and purging with nitrogen three times. The reaction mixture was heated at 100° C. under microwave irradiation for 1 h. Aqueous hydrochloric acid (1M, 10 mL) was added, and the aqueous layer was extracted with EtOAc (3×10 mL). The combined organic layers were dried (Na$_2$SO$_4$), filtered and concentrated in vacuo. The residue was purified by column chromatography (SiO$_2$, 0-100% EtOAc/heptane, 15% MeOH/DCM) to yield the title compound (34 mg, 79%) as a pale yellow solid. $\delta_H$ (DMSO-$d_6$) 9.51 (1H, s), 7.72 (1H, d, J 8.9 Hz), 6.40 (1H, dd, J 8.7 and 2.4 Hz), 6.34 (1H, d, J 2.4 Hz), 4.27-4.19 (2H, m), 4.06-3.98 (2H, m), 2.77 (2H, s), 1.26 (6H, s). LCMS (ES+) 332.12 (M+H)$^+$, 685.20 (2M+Na)$^+$, RT 2.48 minutes (Method 1).

Example 421

6,6-Dimethyl-2-(7-propyl-2,3-dihydro-4H-1,4-benzoxazin-4-yl)-6,7-dihydro[1,3]thiazolo[5,4-c]pyridin-4(5H)-one To a stirred solution of Example 214 (201 mg, 0.51 mmol) in THF (10 mL) cooled to −78° C. under nitrogen was added n-butyllithium (2.5M in hexanes, 0.51 mL, 1.27 mmol). The reaction mixture was stirred at −78° C. for 1.25 h prior to the addition of 1-iodopropane (102 μL, 1.01 mmol). The reaction mixture was allowed to warm slowly to r.t. overnight and was left to stand for 2 days. It was concentrated in vacuo and partitioned between DCM (20 mL) and water (20 mL). The aqueous layer was extracted with DCM (2×20 mL), the organic fractions were combined, dried ($Na_2SO_4$), filtered and concentrated in vacuo. The residue was purified by column chromatography ($SiO_2$, 0-100% EtOAc/heptane, followed by $SiO_2$, 15% MeOH/DCM+2% $NH_4OH$) followed by preparative HPLC (Method 6) to give the title compound (5.5 mg, 2.9%) as a brown oil. $\delta_H$ (CDCl$_3$) 7.78 (1H, d, J 8.9 Hz), 6.81-6.74 (2H, m), 5.16 (1H, s), 4.34-4.29 (2H, m), 4.17-4.11 (2H, m), 2.86 (2H, s), 2.56 (2H, t, J 7.3 Hz), 1.68-1.51 (2H, m, obscured by water peak), 1.42-1.24 (8H, m), 0.93 (3H, t, J 7.2 Hz). LCMS (ES+) 372.18 (M+H)$^+$, 765.36 (2M+Na)$^+$, RT 4.23 minutes (Method 1).

Example 422

Benzyl 4-{[4-(6,6-dimethyl-4-oxo-4,5,6,7-tetrahydro [1,3]thiazolo[5,4-c]pyridin-2-yl)-3,4-dihydro-2H-1,4-benzoxazin-7-yl]oxy}piperidine-1-carboxylate 1,4-Dioxane (0.5 mL) and an aqueous solution of potassium hydroxide (0.21 mL containing 22 mg of potassium hydroxide, 0.41 mmol) were added to a stirred mixture of Example 214 (51 mg, 0.13 mmol), Pd$_2$ dba$_3$ (6.3 mg, 0.007 mmol) and 2-di-tert-butylphosphino-2',4',6'-triisopropyl-1,1'-biphenyl (11 mg, 0.026 mmol) under nitrogen and the mixture was degassed by evacuating and purging with nitrogen three times. The mixture was heated at 100° C. under microwave irradiation for 1 h. To the reaction mixture was added cetylammonium bromide (12 mg, 0.034 mmol) and 4-bromo-1-(benzyloxycarbonyl)piperidine (55 μL, 0.25 mmol) and the reaction mixture was heated at 100° C. under microwave irradiation for 1 h. Further 4-bromo-1-(benzyloxycarbonyl)piperidine (55 μL, 76 mg, 0.25 mmol) was added and the mixture was heated at 100° C. under microwave irradiation for a further 4 h. Water (20 mL) was added, and the aqueous layer was extracted with EtOAc (3×20 mL). The combined organic fractions were dried (MgSO$_4$), filtered and concentrated in vacuo. The residue was purified by column chromatography ($SiO_2$, 0-100% EtOAc/heptane, 15% MeOH/DCM+2% $NH_4OH$) followed by preparative HPLC (Method 6) to give the title compound (21 mg, 30%) as a white oily solid. $\delta_H$ (CDCl$_3$) 7.76 (1H, d, J 9.0 Hz), 7.42-7.28 (5H, m), 6.56-6.48 (2H, m), 5.24 (1H, s), 5.15 (2H, s), 4.49-4.39 (1H, m), 4.35-4.28 (2H, m), 4.16-4.09 (2H, m), 3.80-3.68 (2H, m), 3.53-3.41 (2H, m), 2.85 (2H, s), 2.00-1.85 (2H, m), 1.85-1.71 (2H, m), 1.39 (6H, s). LCMS (ES+) 549.21 (M+H)$^+$, RT 3.96 minutes (Method 1).

Example 423

6,6-Dimethyl-2-(7-isopropoxy-2,3-dihydro-4H-1,4-benzoxazin-4-yl)-6,7-dihydro[1,3]thiazolo[5,4-c]pyridin-4(5H)-one 1,4-Dioxane (0.5 mL) and an aqueous solution of potassium hydroxide (0.21 mL containing 22 mg of potassium hydroxide, 0.41 mmol) were added to a stirred mixture of Example 214 (50 mg, 0.13 mmol), Pd$_2$ dba$_3$ (3.2 mg, 0.0035 mmol) and 2-di-tert-butylphosphino-2',4',6'-triisopropyl-1, 1'-biphenyl (10 mg, 0.024 mmol) under nitrogen and the mixture was degassed by evacuating and purging with nitrogen three times. The mixture was heated at 100° C. under microwave irradiation for 60 minutes. To the reaction mixture was added cetylammonium bromide (6.5 mg, 0.018 mmol) and 2-bromopropane (24 μL, 31 mg, 0.25 mmol) and the reaction mixture was heated at 100° C. under microwave irradiation for 1 h. Water (20 mL) was added and the aqueous layer was extracted with EtOAc (3×20 mL). The combined organic fractions were dried (MgSO$_4$), filtered and concentrated in vacuo. The residue was purified by preparative HPLC (Method 6) to give the title compound (14 mg, 29%) as a white solid. $\delta_H$ (CDCl$_3$) 7.75-7.70 (1H, m), 6.53-6.47 (2H, m), 5.26 (1H, s), 4.46 (1H, septet, J 6.0 Hz), 4.31 (2H, dd, J 5.7 and 4.1 Hz), 4.15-4.10 (2H, m), 2.85 (2H, s), 1.39 (6H, s), 1.33 (6H, d, J 6.0 Hz). LCMS (ES+) 374.16 (M+H)$^+$, 747.34 (2M+H)$^+$, RT 3.59 minutes (Method 1).

Example 424

6,6-Dimethyl-2-(7-(pyridin-3-yl)-2,3-dihydro-4H-1,4-benzoxazin-4-yl)-6,7-dihydro[1,3]thiazolo[5,4-c]pyridin-4(5H)-one The title compound was prepared from Example 214 and 3-pyridineboronic acid according to Method AN and was isolated as a cream solid (49%) after purification by column chromatography ($SiO_2$, 0-100% EtOAc/heptane, 15% MeOH/DCM+2% $NH_4OH$) followed by preparative HPLC (Method 6). $\delta_H$ (CDCl$_3$) 8.84 (1H, d, J 1.9 Hz), 8.59 (1H, dd, J 4.9 and 1.5 Hz), 8.13 (1H, d, J 9.2 Hz), 7.88-7.83 (1H, m), 7.39-7.34 (1H, m), 7.22-7.18 (2H, m), 5.19 (1H, br s), 4.42-4.37 (2H, m), 4.20-4.15 (2H, m), 2.90 (2H, s), 1.41 (6H, s). LCMS (ES+) 393.15 (M+H)$^+$, 807.33 (2M+Na)$^+$, RT 2.18 minutes (Method 1).

Example 425

6,6-Dimethyl-2-[7-(1-hydroxy-1-methylethyl)-2,3-dihydro-4H-1,4-benzoxazin-4-yl]-6,7-dihydro[1,3]thiazolo[5,4-c]pyridin-4(5H)-one To a stirred solution of Example 214 (100 mg, 0.25 mmol) in THF (5 mL) cooled to −78° C. under nitrogen was added n-butyllithium (2.5M in hexanes, 0.41 mL, 1.03 mmol). The reaction mixture was stirred at −78° C. for 1 h prior to the addition of acetone (75 μL, 1.01 mmol) dissolved in THF (1 mL). The reaction mixture was allowed to warm slowly to r.t. overnight and was left to stand for 4 days. The reaction mixture was quenched with sat. aqueous ammonium chloride solution (10 mL) and the aqueous layer was extracted with DCM (3×10 mL). The combined organic fractions were dried ($Na_2SO_4$), filtered and concentrated in vacuo. The residue was purified by preparative HPLC (Method 6) to give the title compound (18 mg, 19%) as a pale cream solid. $\delta_H$ (CDCl$_3$/CD$_3$OD) 7.87 (1H, d, J 8.5 Hz), 7.11-7.04 (2H, m), 4.36-4.31 (2H, m), 4.17-4.11 (2H, m), 2.87 (2H, s), 1.56 (6H, s), 1.40 (6H, s). LCMS (ES+) 374.18 (M+H)$^+$, 747.37 (2M+H)$^+$, RT 2.74 minutes (Method 1).

Example 426

6,6-Dimethyl-2-[6-methyl-7-(4-methylpyridin-3-yl)-2,3-dihydro-4H-1,4-benzoxazin-4-yl]-6,7-dihydro[1,3]thiazolo[5,4-c]pyridin-4(5H)-one The title compound was prepared from Example 210 and 4-picoline-3-boronic acid according to Method AN and was isolated as a cream solid (1%) after purification by preparative HPLC (Method 6). $\delta_H$ (CDCl$_3$) 8.47 (1H, d, J 5.1 Hz), 8.33 (1H, s), 7.85 (1H, s), 7.20 (1H, d, J 5.1 Hz), 6.73 (1H, s), 5.18 (1H, br. s), 4.38-4.32 (2H, m), 4.32-4.23 (1H, m), 4.17-4.09 (1H, m), 2.90 (2H, s), 2.13 (3H, s), 2.00 (3H, s), 1.41 (6H, s). LCMS (ES+) 421.18 (M+H)$^+$, 841.42 (2M+H)$^+$, RT 2.11 minutes (Method 1).

Example 427

6,6-Dimethyl-2-[7-(4-methylpyridin-3-yl)-2,3-dihydro-4H-1,4-benzoxazin-4-yl]-6,7-dihydro[1,3]thiazolo[5,4-c]pyridin-4(5H)-one The title compound was prepared from Example 214 and 4-picoline-3-boronic acid according to Method AN and was isolated as a cream solid (1.5%) after purification by preparative HPLC (Method 6). $\delta_H$ (CDCl$_3$) 8.48-8.42 (2H, m), 8.12-8.06 (1H, m), 7.19 (1H, br. d, J 4.7 Hz), 6.96-6.90 (2H, m), 5.18 (1H, br. s), 4.43-4.37 (2H, m), 4.21-4.16 (2H, m), 2.91 (2H, s), 2.33 (3H, s), 1.41 (6H, s). LCMS (ES+) 407.17 (M+H)$^+$, 813.37 (2M+H)$^+$, RT 2.05 minutes (Method 1).

Example 428

2-{7-[3-(Dimethylamino)pyrrolidin-1-yl]-6-methyl-2,3-dihydro-4H-1,4-benzoxazin-4-yl}-6,6-dimethyl-6,7-dihydro[1,3]thiazolo[5,4-c]pyridin-4(5H)-one, formic acid salt The title compound was prepared from Example 211 according to Method BC and was isolated as a yellow oil (44%) after purification by preparative HPLC (Method 6). $\delta_H$ (CDCl$_3$) 7.52 (1H, s), 6.45 (1H, s), 5.20 (1H, br. s), 4.31-4.02 (4H, m), 3.32 (1H, td, J 8.9 and 7.0 Hz), 3.23 (2H, d, J 7.2 Hz), 3.16 (1H, td, J 8.7 and 3.4 Hz), 2.95 (1H, t, J 7.3 Hz), 2.85 (2H, s), 2.36 (6H, s), 2.25 (3H, s), 2.22-2.10 (1H, m), 1.98-1.84 (1H, m), 1.39 (6H, s). LCMS (ES+) 442.26 (M+H)$^+$, RT 1.98 minutes (Method 1).

Example 429

6,6-Dimethyl-2-[7-(1-methyl-1H-pyrazol-4-yl)-2,3-dihydro-4H-1,4-benzoxazin-4-yl]-6,7-dihydro[1,3]thiazolo[5,4-c]pyridin-4(5H)-one The title compound was prepared from Example 214 and 1-methyl-4-(4,4,5,5-tetramethyl-[1,3,2]dioxaborolan-2-yl)-1H-pyrazole according to Method AN and was isolated as a pale yellow solid (81%) after purification by column chromatography (SiO$_2$, 40-100% EtOAc/heptane, 30% MeOH/DCM+4% NH$_4$OH). $\delta_H$ (CDCl$_3$) 7.92 (1H, d, J 9.0 Hz), 7.73 (1H, s), 7.58 (1H, s), 7.09-7.04 (2H, m), 5.17 (1H, br. s), 4.38-4.33 (2H, m), 4.19-4.13 (2H, m), 3.95 (3H, s), 2.88 (2H, s), 1.40 (6H, s). LCMS (ES+) 396.15 (M+H)$^+$, 791.33 (2M+H)$^+$, RT 2.87 minutes (Method 1).

Example 430

6,6-Dimethyl-2-(7-isopropyl-2,3-dihydro-4H-1,4-benzoxazin-4-yl)-6,7-dihydro[1,3]thiazolo[5,4-c]pyridin-4(5H)-one THF (2 mL) was added to a mixture of Example 214 (79 mg, 0.20 mmol), [1,1'-bis(diphenylphosphino)ferrocene]palladium(II) dichloride complex with DCM (13 mg, 0.015 mmol) and copper(I) iodide (33 mg, 0.17 mmol) under nitrogen and the mixture was degassed by evacuating and purging with nitrogen three times. To this was added isopropylzinc bromide (0.5M solution in THF, 0.76 mL, 0.38 mmol) and the reaction mixture was stirred under nitrogen at r.t. for 1 h. To the stirred solution was added further isopropylzinc bromide (0.5M solution in THF, 0.76 mL, 0.38 mmol) and the reaction mixture was stirred at r.t. overnight. The resulting solution was washed with sat. aqueous ammonium chloride solution (20 mL). The organic fraction was separated, dried (Na$_2$SO$_4$), filtered and concentrated in vacuo. The residue was purified by preparative HPLC (Method 6) to give the title compound (35 mg, 48%) as a pale brown solid. $\delta_H$ (CDCl$_3$) 7.81 (1H, d, J 8.9 Hz), 6.86-6.80 (2H, m), 5.38-5.20 (1H, br. m), 4.35-4.29 (2H, m), 4.17-4.11 (2H, m), 2.93-2.78 (3H, m), 1.39 (6H, s), 1.23 (6H, d, J 7.0 Hz). LCMS (ES+) 358.14 (M+H), 715.31 (2M+H)$^+$, RT 3.89 minutes (Method 1).

Example 431

6,6-Dimethyl-2-[6-(5-methyl-1-phenyl-1H-pyrazol-4-yl)-2,3-dihydro-4H-1,4-benzoxazin-4-yl]-6,7-dihydro[1,3]thiazolo[5,4-c]pyridin-4(5H)-one The title compound was prepared from Example 39 and 5-methyl-1-phenyl-4-(4,4,5,5-tetramethyl-[1,3,2]dioxaborolan-2-yl)-1H-pyrazole according to Method AD (heating at 125° C. for 72 h) and was isolated as a white solid (6%) after purification by column chromatography [SiO$_2$, EtOAc/MeOH (9:1) in heptane], trituration with Et$_2$O and preparative HPLC (Method 6). $\delta_H$ (CDCl$_3$) 8.04 (1H, d, J 1.9 Hz), 7.76 (1H, s), 7.54-7.48 (5H, m), 7.16 (1H, dd, J 8.5 and 2.1 Hz), 7.03 (1H, d, J 8.5 Hz), 5.24 (1H, br. s), 4.40-4.34 (2H, m), 4.22-4.16 (2H, m), 3.50 (3H, s), 2.88 (2H, s), 1.41 (6H, s). LCMS (ES+) 472.3 (M+H)$^+$, RT 3.64 minutes (Method 1).

Example 432

6,6-Dimethyl-2-[6-(1-ethyl-1H-pyrazol-4-yl)-2,3-dihydro-4H-1,4-benzoxazin-4-yl]-6,7-dihydro[1,3]thiazolo[5,4-c]pyridin-4(5H)-one The title compound was prepared from Example 39 and 1-ethyl-4-(4,4,5,5-tetramethyl-[1,3,2]dioxaborolan-2-yl)-1H-pyrazole according to Method AD (heating at 85° C. for 24 h) and was isolated as a white solid (32%) after purification by column chromatography [SiO$_2$, EtOAc/MeOH (9:1) in heptane]. $\delta_H$ (CDCl$_3$) 7.99 (1H, d, J 1.9 Hz), 7.72 (1H, s), 7.60 (1H, s), 7.19 (1H, d, J 8.5 and 2.1 Hz), 6.96 (1H, d, J 8.5 Hz), 5.53 (1H, br. s), 4.38-4.32 (2H, m), 4.27-4.17 (4H, m), 2.89 (2H, s), 1.54 (3H, t, J 7.3 Hz), 1.41 (6H, s). LCMS (ES+) 410.4 (M+H)$^+$, RT 3.07 minutes (Method 1).

Example 433

6,6-Dimethyl-2-{6-[1-(3-methylbutyl)-1H-pyrazol-4-yl]-2,3-dihydro-4H-1,4-benzoxazin-4-yl}-6,7-dihydro[1,3]thiazolo[5,4-c]pyridin-4(5H)-one

The title compound was prepared from Example 39 and 1-(3-methylbutyl)-4-(4,4,5,5-tetramethyl[1,3,2]dioxaborolan-2-yl)-1H-pyrazole according to Method AD (heating at 120° C. for 1 h) and was isolated as a white solid (55%) after purification by column chromatography [SiO$_2$, EtOAc/MeOH (9:1) in heptane] and trituration with Et$_2$O. $\delta_H$ (CDCl$_3$) 8.00 (1H, d, J 1.9 Hz), 7.71 (1H, s), 7.59 (1H, s), 7.20 (1H, dd, J 8.5 and 1.9 Hz), 6.97 (1H, d, J 8.5 Hz), 5.26 (1H, br. s), 4.40-4.31 (2H, m), 4.25-4.13 (4H, m), 2.90 (2H, s), 1.88-1.78 (2H, m), 1.65 (1H, m, obscured by HOD), 1.42 (6H, s), 0.99 (6H, d, J 6.6 Hz). LCMS (ES+) 452.4 (M+H)$^+$, RT 3.75 minutes (Method 1).

Example 434

6,6-Dimethyl-2-[6-(5-fluoro-3-methylpyridin-2-yl)-2,3-dihydro-4H-1,4-benzoxazin-4-yl]-6,7-dihydro[1,3]thiazolo[5,4-c]pyridin-4(5H)-one

The title compound was prepared from Example 292 and 2-chloro-5-fluoro-3-methylpyridine according to Method AT (heated to 100° C. for 27 h) and was isolated as a white solid (56%) after purification by preparative HPLC (Method 7). $\delta_H$ (CDCl$_3$) 8.30 (1H, d, J 2.8 Hz), 8.18 (1H, d, J 2.1 Hz), 7.56 (1H, dd, J 9.2 and 2.8 Hz), 7.20 (1H, dd, J 8.5 and 2.1 Hz), 7.09-7.04 (1H, m), 5.46 (1H, br. s), 4.44-4.35 (2H, m), 4.21-4.11 (2H, m), 2.86 (3H, s), 1.37 (6H, s). LCMS (ES+) 425 (M+H)$^+$, RT 3.55 minutes (Method 2).

Example 435

2-{6-[4-(Dimethylamino)-5-fluoropyrimidin-2-yl]-2,3-dihydro-4H-1,4-benzoxazin-4-yl}-6,6-dimethyl-6,7-dihydro[1,3]thiazolo[5,4-c]pyridin-4(5H)-one

The title compound was prepared from Example 292 and 2-chloro-4-(dimethylamino)-5-fluoropyrimidine according to Method AT (heated to 100° C. for 27 h) and was isolated as a beige solid (23%) after purification by preparative HPLC (Method 7). $\delta_H$ (CDCl$_3$) 8.92 (1H, d, J 1.7 Hz), 8.08-8.01 (2H, m), 7.02-6.98 (1H, m), 5.34 (1H, br. s), 4.41-4.33 (2H, m), 4.27-4.19 (2H, m), 3.30 (6H, s), 2.87 (2H, s), 1.40 (6H, s). LCMS (ES+) 455 (M+H)$^+$, RT 3.84 minutes (Method 2).

Example 436

2-{6-[5-(Dimethylamino)pyrimidin-2-yl]-2,3-dihydro-4H-1,4-benzoxazin-4-yl}-6,6-dimethyl-6,7-dihydro[1,3]thiazolo[5,4-c]pyridin-4(5H)-one

The title compound was prepared from Example 292 and 2-bromo-5-(dimethylamino)pyrimidine according to Method AT (heated to 100° C. for 27 h) and was isolated as a beige solid (12%) after purification by preparative HPLC (Method 7). $\delta_H$ (CDCl$_3$) 8.54 (2H, s), 8.15 (1H, d, J 2.1 Hz), 7.16 (1H, dd, J 8.5 and 2.1 Hz), 7.02 (1H, d, J 8.5 Hz), 5.30 (1H, br. s), 4.40-4.33 (2H, m), 4.18-4.12 (2H, m), 3.24 (6H, s), 2.89 (2H, s), 1.40 (6H, s). LCMS (ES+) 437 (M+H)$^+$, RT 3.52 minutes (Method 2).

Example 437

6,6-Dimethyl-2-{6-[6-(4-methylpiperazin-1-yl)pyridin-3-yl]-2,3-dihydro-4H-1,4-benzoxazin-4-yl}-6,7-dihydro[1,3]thiazolo[5,4-c]pyridin-4(5H)-one

The title compound was prepared from Example 292 and 1-(5-bromopyridin-2-yl)-4-methylpiperazine according to Method AT (heated to 100° C. for 27 h) and was isolated as a white solid (34%) after purification by preparative HPLC (Method 7) followed by partitioning between CDCl$_3$ and aqueous sodium bicarbonate, then drying the organic fraction (MgSO$_4$) and concentration in vacuo. $\delta_H$ (CDCl$_3$) 8.41 (1H, d, J 2.4 Hz), 8.07 (1H, d, J 2.1 Hz), 7.68 (1H, dd, J 8.9 and 2.4 Hz), 7.21 (1H, dd, J 8.5 and 2.3 Hz), 7.01 (1H, d, J 8.5 Hz), 6.72 (1H, d, J 8.9 Hz), 5.48 (1H, br. s), 4.39-4.32 (2H, m), 4.23-4.16 (2H, m), 3.66-3.58 (4H, m), 2.88 (2H, s), 2.60-2.51 (4H, m), 2.36 (3H, s), 1.40 (6H, s). LCMS (ES+) 491 (M+H)$^+$, RT 2.62 minutes (Method 2).

Example 438 tert-Butyl 4-{5-[4-(6,6-dimethyl-4-oxo-4,5,6,7-tetrahydro[1,3]thiazolo[5,4-c]pyridin-2-yl)-3,4-dihydro-2H-1,4-benzoxazin-6-yl]-3-methylpyridin-2-yl}piperazine-1-carboxylate

The title compound was prepared from Example 292 and 5-bromo-2-(4-tertbutoxycarbonylpiperazin-1-yl)-3-methylpyridine according to Method AT (heated to 100° C. for 27 h) and was isolated as a white solid (19%) after purification by preparative HPLC (Method 7). $\delta_H$ (CDCl$_3$) 8.04 (1H, s), 7.85 (1H, s), 6.99 (1H, s), 6.55 (1H, s), 5.25 (1H, br. s), 4.40-4.34 (2H, m), 4.22-4.16 (2H, m), 3.56 (8H, br. s), 2.85 (2H, s), 2.30 (3H, s), 1.49 (9H, s), 1.38 (6H, s). LCMS (ES+) 591 (M+H)$^+$, RT 4.38 minutes (Method 2).

Example 439

6,6-Dimethyl-2-[6-(5-methyl-6-(piperazin-1-yl)pyridin-3-yl)-2,3-dihydro-4H-1,4-benzoxazin-4-yl]-6,7-dihydro[1,3]thiazolo[5,4-d]pyridin-4(5H)-one

Example 438 (15 mg, 0.025 mmol) was dissolved in CDCl$_3$ (1 mL) and methanol (1 mL). A solution of HCl in diethyl ether (500 µL of a 2.0M solution, 1 mmol) was added, and the mixture was heated to 100° C. for 1 h then stirred at r.t. overnight. It was concentrated in vacuo and partitioned between CDCl$_3$ (3 mL) and saturated aqueous sodium bicarbonate (2 mL). The organic fraction was dried (MgSO$_4$) and concentrated in vacuo to give the title compound as a white solid (12 mg, quantitative). $\delta_H$ (CDCl$_3$) 8.04 (1H, s), 7.85 (1H, s), 6.99 (1H, s), 6.55 (1H, s), 5.39 (1H, br. s), 4.41-4.33 (2H, m), 4.23-4.16 (2H, m), 3.64-3.55 (4H, m), 3.10-3.02 (4H, m), 2.85 (3H, br. s), 2.30 (3H, s), 1.39 (6H, s). LCMS (ES+) 491 (M+H)$^+$, RT 2.55 minutes (Method 2).

Example 440

6,6-Dimethyl-2-{6-[2-(4-methylpiperazin-1-yl)pyrimidin-5-yl]-2,3-dihydro-4H-1,4-benzoxazin-4-yl}-6,7-dihydro[1,3]thiazolo[5,4-c]pyridin-4(5H)-one

The title compound was prepared from Example 292 and 5-bromo-2-(4-methylpiperazin-1-yl)pyrimidine according to Method AT (heated to 100° C. for 27 h) and was isolated as a white solid (19%) after purification by preparative HPLC (Method 7) followed by absorption onto an Isolute PRS solid phase extraction cartridge (2 g) and elution with water, filtration of the resulting precipitate from the filtrate and drying in vacuo. $\delta_H$ (CDCl$_3$) 8.52 (2H, s), 8.15 (1H, d, J 1.9 Hz), 7.16 (1H, dd, J 8.3 and 2.1 Hz), 7.06-7.00 (1H, m), 5.18 (1H, br.s), 4.41-4.33 (2H, m), 4.19-4.12 (2H, m), 3.94-3.86 (4H, m), 2.89 (2H, s), 2.54-2.46 (4H, m), 2.37 (3H, s), 1.40 (6H, s). LCMS (ES+) 492 (M+H)$^+$, RT 2.80 minutes (Method 2).

Example 441

6,6-Dimethyl-2-[6-({6-[(E)-2-methoxyvinyl]pyridin-2-yl}amino)-2,3-dihydro-4H-1,4-benzoxazin-4-yl]-6,7-dihydro[1,3]thiazolo[5,4-c]pyridin-4(5H)-one A mixture of Example 42 (50 mg, 0.15 mmol), Intermediate 238 (32 mg, 0.15 mmol), [1,1'-bis(di-tert-butylphosphino) ferrocene]palladium(II) dichloride (5 mg) and sodium tert-butoxide (29 mg, 0.3 mmol) in toluene (2 mL) was heated at 120° C. under microwave irradiation for 30 minutes; additional [1,1'-bis(di-tert-butylphosphino)-ferrocene]palladium (II) dichloride (5 mg) and sodium tert-butoxide (30 mg, 0.3 mmol) were added and the reaction mixture was heated for a further 30 minutes at 120° C. The reaction mixture was filtered through celite and concentrated in vacuo. The crude material was purified by preparative HPLC (Method 6) to give the title compound (15 mg, 21%) as a yellow solid. $\delta_H$ (CDCl$_3$) 8.10 (1H, d, J 2.4 Hz), 7.56 (1H, d, J 12.4 Hz), 7.38 (1H, t, J 7.9 Hz), 7.05 (1H, dd, J 8.7 and 2.4 Hz), 6.51 (1H, d, J 7.3 Hz), 6.42 (1H, br. s), 5.57 (1H, d, J 12.5 Hz), 5.17 (1H, br. s), 4.39-4.29 (2H, m), 4.17-4.06 (2H, m), 3.70 (3H, s), 2.87 (2H, s), 1.39 (6H, s). LCMS (ES+) 464.0 (M+H)$^+$, RT 2.33 minutes (Method 1).

Example 442

6,6-Dimethyl-2-(6-{[6-(2-methoxyethyl)pyridin-2-yl]amino}-2,3-dihydro-4H-1,4-benzoxazin-4-yl)-6,7-dihydro[1,3]thiazolo[5,4-c]pyridin-4(5H)-one To a solution of Example 441 (100 mg, 0.2 mmol) in EtOH (4 mL) was added cyclohexene (1 mL) and palladium on carbon (120 mg, 10% wt). The reaction mixture was heated at 120° C. under microwave irradiation for 1 h. Additional palladium on carbon (40 mg, 10% wt) was added and the reaction mixture heated at 130° C. under microwave irradiation for 5 h. The reaction mixture was filtered through celite and concentrated in vacuo. Purification by preparative HPLC (Method 6) gave the title compound (12.5 mg, 12.5%) as a brown solid. $\delta_H$ (CDCl$_3$) 8.11 (1H, d, J 2.4 Hz), 7.42 (1H, dd, J 8.1 and 7.3 Hz), 7.01 (1H, dd, J 8.9 and 2.4 Hz), 6.92 (1H, d, J 8.7 Hz), 6.68 (1H, d, J 7.9 Hz), 6.64 (1H, d, J 7.3 Hz), 6.42 (1H, br. s), 5.15 (1H, br. s), 4.26-4.38 (2H, m), 4.18-4.08 (2H, m), 3.76 (2H, t, J 6.8 Hz), 3.36 (3H, s), 2.94 (2H, t, J 6.8 Hz), 2.87 (2H, s), 1.39 (6H, s). LCMS (ES+) 466.18 (M+H)$^+$, RT 2.17 minutes (Method 1).

Example 443

6,6-Dimethyl-2-[7-(isopropylamino)-2,3-dihydro-4H-1,4-benzoxazin-4-yl]-6,7-dihydro[1,3]thiazolo[5,4-c]pyridin-4(5H)-one The title compound was prepared from Example 214 and isopropylamine according to Method AU and was isolated as a pale yellow-brown gum (5%) after purification by preparative HPLC (Method 7). $\delta_H$ (CDCl$_3$) 7.55 (1H, d, J 8.5 Hz), 6.23-6.12 (2H, m), 5.30 (1H, s), 4.31-4.24 (2H, m), 4.16-4.08 (2H, m), 3.63-3.52 (1H, m), 2.83 (2H, s), 1.38 (6H, s), 1.21 (6H, d, J 6.2 Hz). LCMS (ES+) 373 (M+H)$^+$, RT 3.46 minutes (Method 2).

Example 444

6,6-Dimethyl-2-{7-[(2-methoxyethyl)amino]-2,3-dihydro-4H-1,4-benzoxazin-4-yl}-6,7-dihydro[1,3] thiazolo[5,4-c]pyridin-4(5H)-one The title compound was prepared from Example 214 and 2-methoxyethylamine according to Method AU and was isolated as a pale yellow gum (6%) after purification by preparative HPLC (Method 7). $\delta_H$ (CDCl$_3$) 7.58 (1H, d, J 8.5 Hz), 6.25 (1H, dd, J 8.5 and 2.5 Hz), 6.20 (1H, d, J 2.5 Hz), 5.23 (1H, s), 4.32-4.26 (2H, m), 4.15-4.09 (2H, m), 3.60 (2H, t, J 4.9 Hz), 3.39 (3H, s), 3.25 (2H, t, J 4.9 Hz), 2.83 (2H, s), 1.38 (6H, s). LCMS (ES+) 389 (M+H)$^+$, RT 3.02 minutes (Method 2).

Example 445

6,6-Dimethyl-2-{7-[N-(2-methoxyethyl)-N-(methyl) amino]-2,3-dihydro-4H-1,4-benzoxazin-4-yl}-6,7-dihydro[1,3]thiazolo[5,4-c]pyridin-4(5H)-one The title compound was prepared from Example 214 and N-(2-methoxyethyl)-methylamine according to Method AU and was isolated as a yellow gum (37%) after purification by preparative HPLC (Method 7). $\delta_H$ (CDCl$_3$) 7.62 (1H, d, J 9.0 Hz), 6.33 (1H, dd, J 9.0 and 2.8 Hz), 6.27 (1H, d, J 2.8 Hz), 5.44 (1H, s), 4.33-4.26 (2H, m), 4.17-4.10 (2H, m), 3.58-3.46 (4H, m), 3.36 (3H, s), 2.96 (3H, s), 2.83 (2H, s), 1.38 (6H, s). LCMS (ES+) 403 (M+H)$^+$, RT 3.39 minutes (Method 2).

Example 446

2-(7-{[2-(Dimethylamino)ethyl]amino}-2,3-dihydro-4H-1,4-benzoxazin-4-yl)-6,6-dimethyl-6,7-dihydro [1,3]thiazolo[5,4-c]pyridin-4(5H)-one, acetic acid salt The title compound was prepared from Example 214 and N,N-dimethylethylenediamine according to Method AU and was isolated as a yellow gum (38%) after purification by preparative HPLC (Method 7). $\delta_H$ (CDCl$_3$) 7.56 (1H, d, J 9.0 Hz), 6.37 (1H, s), 6.23 (1H, dd, J 9.0 and 2.5 Hz), 6.17 (1H, d, J 2.5 Hz), 4.31-4.25 (2H, m), 4.15-4.09 (2H, m), 3.36-3.29 (2H, m), 2.93-2.87 (2H, m), 2.83 (2H, s), 2.51 (6H, s), 2.05 (3H, s), 1.38 (6H, s). LCMS (ES+) 402 (M+H)$^+$, RT 2.19 minutes (Method 2).

Example 447

6,6-Dimethyl-2-(8-methyl-2,3-dihydro-4H-1,4-benzoxazin-4-yl)-6,7-dihydro[1,3]thiazolo[5,4-c]pyridin-4(5H)-one A mixture of Intermediate 240 (0.064 g, 0.31 mmol), Intermediate 46 (0.115 g, 0.52 mmol) and DIPEA (0.11 mL, 0.62 mmol) in THF (3 mL) was heated at 120° C. under microwave irradiation for 20 minutes. The mixture was partitioned between water/brine (1:1, 10 mL) and EtOAc (20 mL). The organic fraction was concentrated and purified by preparative HPLC (Method 6) to give the title compound (0.051 g, 50%) as a pale cream solid. $\delta_H$ (CDCl$_3$) 7.70 (1H, dd, J 8.1 and 0.9

Hz), 6.98-6.93 (1H, m), 6.89-6.82 (1H, m), 5.34 (1H, s), 4.40-4.33 (2H, m), 4.19-4.14 (2H, m), 2.86 (2H, s), 2.22 (3H, s), 1.39 (6H, s). LCMS (ES+) 330 (M+H)$^+$, RT 3.46 minutes (Method 1).

Example 448

2-(6-Allyl-2,3-dihydro-4H-1,4-benzoxazin-4-yl)-6,6-dimethyl-6,7-dihydro[1,3]thiazolo[5,4-c]pyridin-4(5H)-one The title compound was prepared from Example 39 and allylboronic acid pinacol ester according to Method Z (heating to 90° C. for 3.5 h followed by addition of further tetrakis(triphenylphosphine)palladium(0) and allylboronic acid pinacol ester and heating to 90° C. for a further 1.5 h) and was isolated as a white solid (5%) after purification by preparative HPLC (Method 6). $\delta_H$ (CDCl$_3$) 7.69 (1H, s), 6.90-6.87 (2H, m), 6.03-5.87 (1H, m), 5.35 (1H, br. s), 5.14-5.05 (2H, m), 4.34-4.27 (2H, m), 4.20-4.14 (2H, m), 3.34 (2H, d, J 6.6 Hz), 2.87 (2H, s), 1.40 (6H, s). LCMS (ES+) 356.14 (M+H)$^+$, RT 3.7 minutes (Method 1).

Example 449

Method BE 6,6-Dimethyl-2-[6-(4-fluorophenoxy)-2,3-dihydro-4H-1,4-benzoxazin-4-yl]-6,7-dihydro[1,3]thiazolo[5,4-c]pyridin-4(5H)-one A mixture of 4-fluorophenol (0.154 g, 1.4 mmol) and cesium carbonate (0.446 g, 1.4 mmol) in 1-methyl-2-pyrrolidinone (3 mL) was degassed, copper(I) chloride (0.035 g, 0.35 mmol), 2,2,6,6-tetramethyl-3,5-heptanedione (0.013 g, 0.07 mmol) and Example 39 (0.27 g, 0.7 mmol) were added and the mixture degassed again before heating to 125° C. for 21 h. After cooling to r.t., DMSO (5 mL) was added. The mixture was filtered and purified by preparative HPLC (Method 6) to give the title compound (0.038 g, 34%) as a tan solid. $\delta_H$ (CDCl$_3$) 7.82 (1H, d, J 2.8 Hz), 6.95-7.05 (4H, m), 6.91, (1H, d, J 8.9 Hz), 6.69 (1H, dd, J 8.9 and 2.6 Hz), 5.36 (1H, s), 4.32 (2H, m), 4.08 (2H, m), 2.83 (2H, s), 1.38 (6H, s). LCMS (ES+) 426.13 (M+H)$^+$, RT 3.94 minutes (Method 1).

Example 450

6,6-Dimethyl-2-(6-phenoxy-2,3-dihydro-4H-1,4-benzoxazin-4-yl)-6,7-dihydro[1,3]thiazolo[5,4-c]pyridin-4(5H)-one The title compound was prepared from Example 39 and phenol according to Method BE and was isolated as a white solid (29%) after purification by preparative HPLC (Method 6). $\delta_H$ (CDCl$_3$) 7.83 (1H, d, J 2.8 Hz), 7.38-7.29 (2H, m), 7.12-6.98 (3H, m), 6.96-6.89 (1H, m), 6.73 (1H, dd, J 8.9 and 2.6 Hz), 5.27 (1H, s), 4.36-4.30 (2H, m), 4.13-4.07 (2H, m), 2.83 (2H, s), 1.37 (6H, s). LCMS (ES+) 408.11 (M+H)$^+$, RT 3.92 minutes (Method 1).

Example 451

6,6-Dimethyl-2-{6-[(4-fluorophenyl)amino]-2,3-dihydro-4H-1,4-benzoxazin-4-yl}-6,7-dihydro[1,3]thiazolo[5,4-c]pyridin-4(5H)-one The title compound was prepared from Example 39 and 4-fluoroaniline according to Method AP (heating to 120° C. under microwave irradiation for 1 h) and was isolated as a tan solid (61%) after purification by column chromatography (SiO$_2$, 0-5% MeOH/DCM). $\delta_H$ (CDCl$_3$/CD$_3$OD) 7.68 (1H, d, J 2.6 Hz), 6.94-7.02 (4H, m), 6.90-6.84 (1H, m), 6.75 (1H, dd, J 8.9 and 2.6 Hz), 4.33-4.27 (2H, m), 4.15-4.09 (2H, m), 2.86 (2H, s), 1.39 (6H, s). Exchangeable protons were not observed. LCMS (ES+) 425.14 (M+H)$^+$, RT 3.70 minutes (Method 1).

Example 452

6,6-Dimethyl-2-{6-[N-(4-fluorophenyl)-N-(methyl)amino]-2,3-dihydro-4H-1,4-benzoxazin-4-yl}-6,7-dihydro[1,3]thiazolo[5,4-c]pyridin-4(5H)-one The title compound was prepared from Example 39 and 4-fluoro-N-methylaniline according to Method AP (heating to 120° C. under microwave irradiation for 1 h) and was isolated as a white solid (20%) after purification by column chromatography (SiO$_2$, 1-5% MeOH/DCM). $\delta_H$ (CDCl$_3$) 7.58 (1H, d, J 2.6 Hz), 7.01-6.92 (4H, m), 6.90-6.84 (1H, m), 6.70 (1H, dd, J 8.9 and 2.6 Hz), 5.34 (1H, s), 4.33-4.27 (2H, m), 4.16-4.11 (2H, m), 3.26 (3H, s), 2.82 (2H, s), 1.38 (6H, s). LCMS (ES+) 439.16 (M+H)$^+$, RT 4.04 minutes (Method 1).

Example 453

2-[6-(2,3-Dihydroxypropyl)-2,3-dihydro-4H-1,4-benzoxazin-4-yl]-6,6-dimethyl-6,7-dihydro[1,3]thiazolo[5,4-c]pyridin-4(5H)-one A mixture of Example 448 (0.136 g, 0.38 mmol), 4-methylmorpholine N-oxide (0.067 g, 0.57 mmol) and polymer-supported osmium tetroxide (0.027 g, 0.006 mmol) in acetone (4 mL) and water (0.14 mL) was stirred at r.t. for 25 h. Further portions of 4-methylmorpholine N-oxide (0.091 g, 0.77 mmol) and polymer-supported osmium tetroxide (0.020 g, 0.004 mmol) were added and the reaction stirred for a further 3 days. It was filtered, concentrated in vacuo and purified by preparative HPLC (Method 6) to give the title compound (0.029 g, 20%) as a white solid. $\delta_H$ (DMSO-d$_6$) 7.70 (1H, d, J 1.9 Hz), 7.30 (2H, s), 6.97-6.92 (1H, m), 6.90-6.87 (1H, m), 5.82 (1H, br. s), 4.34-4.27 (2H, m), 4.22-4.14 (2H, m), 3.97-3.82 (2H, m), 3.73-3.60 (2H, m), 3.56-3.44 (1H, m), 2.87 (2H, s), 1.40 (6H, m). LCMS (ES+) 390.16 (M+H)$^+$, RT 2.37 minutes (Method 1).

Example 454

2-{6-[N-Methyl-N-(6-methylpyridazin-3-yl)amino]-2,3-dihydro-4H-1,4-benzoxazin-4-yl}-5,6,6-trimethyl-6,7-dihydro[1,3]thiazolo[5,4-c]pyridin-4(5H)-one To Example 173 (0.2 g, 0.48 mmol) in THF (20 mL) was added sodium tert-butoxide (0.145 g, 1.5 mmol). After stirring for 10 minutes, iodomethane (0.06 mL, 0.96 mmol) was added and the mixture was stirred at r.t. for 48 h. It was concentrated in vacuo and purified by preparative HPLC (Method 6), then dissolved in DCM (15 mL), washed with aqueous potassium carbonate solution (0.7M) and concentrated in vacuo to give the title compound (0.067 g, 31%) as a pale yellow solid. $\delta_H$ (CDCl$_3$) 7.96 (1H, d, J 2.4 Hz), 7.00-6.88 (3H, m), 6.74 (1H, d, J 9.2 Hz), 4.37-4.33 (2H, m), 4.14-4.09 (2H, m), 3.56 (3H, s), 2.98 (3H, s), 2.86 (2H, s), 2.54 (3H, s), 1.36 (6H, s). LCMS (ES+) 451.18 (M+H)$^+$, RT 2.12 minutes (Method 1).

Example 455

2-{6-[(4,6-Dimethylpyridazin-3-yl)amino]-2,3-dihydro-4H-1,4-benzoxazin-4-yl}-6,6-dimethyl-6,7-dihydro[1,3]thiazolo[5,4-c]pyridin-4(5H)-one Example 42 (0.227 g, 0.69 mmol) and Intermediate 241 (0.108 g, 0.76 mmol) were suspended in n-propanol (1.5 mL) and heated to reflux for 48 h. The reaction mixture was then heated to 150° C. under microwave irradiation for 3.5 h. It was concentrated in vacuo, purified by preparative HPLC (Method 6), then dissolved in DCM (15 mL), washed with saturated aqueous sodium bicarbonate solution and concentrated in vacuo to give the title compound (0.128 g, 43%) as a yellow solid. $\delta_H$ (CDCl$_3$) 8.17 (1H, d, J 2.4 Hz), 7.36 (1H, dd, J 8.7 and 2.4 Hz), 7.01 (1H, s), 6.92 (1H, d, J 8.9 Hz), 6.02 (1H, s), 5.19 (1H, s), 4.34-4.29 (2H, m), 4.20-4.15 (2H, m), 2.87 (2H, s), 2.55-2.51 (3H, m), 2.26 (3H, d, J 0.8 Hz), 1.39 (6H, s). LCMS (ES+) 437.2 (M+H)$^+$, RT 1.98 minutes (Method 1).

Example 456

2-[6-(6-Chloro-2-methylpyrimidin-4-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 292 and 4,6-dichloro-2-methylpyrimidine according to Method AX (heating to 120° C. under microwave irradiation for 20 minutes) and was isolated as an off-white solid [77%, 92% pure by LCMS (Method 1)] after trituration with Et$_2$O (3×30 mL). A sample of this solid (25 mg) was purified by preparative HPLC (Method 6) to yield the title compound (20 mg, 10%) as an off-white solid. $\delta_H$ (CDCl$_3$) 8.76 (1H, d, J 2.1 Hz), 7.79 (1H, dd, J 8.5 and 2.1 Hz), 7.47 (1H, s), 7.07 (1H, d, J 8.7 Hz), 5.43 (1H, br s), 4.46-4.35 (2H, m), 4.23-4.13 (2H, m), 2.90 (2H, s), 2.76 (3H, s), 1.41 (6H, s). LCMS (ES+) 442.0 (M+H)$^+$, RT 3.69 minutes (Method 1).

Example 457

6,6-Dimethyl-2-[6-(2-methylpyrimidin-4-yl)-2,3-dihydro-4H-1,4-benzoxazin-4-yl]-6,7-dihydro[1,3]thiazolo[5,4-c]pyridin-4(5H)-one To a solution of Example 456 (100 mg, 0.227 mmol) in DMF (4 mL) was added vinyl acetate (0.11 mL, 1.13 mmol), triethylamine (0.06 mL, 0.454 mmol), 1,3-bis-(diphenylphosphino)propane (10 mg, 0.023 mmol) and palladium acetate (2.5 mg, 0.011 mmol). The mixture was heated to 140° C. under microwave irradiation for 1 h. The resulting suspension was partitioned between DCM (50 mL) and water (50 mL); the organic fraction was washed with brine (50 mL), dried (MgSO$_4$) and concentrated in vacuo. The residue was purified by preparative HPLC (Method 6) to yield the title compound (34 mg, 35%) as an off-white solid. $\delta_H$ (CDCl$_3$) 8.72 (1H, d, J 2.1 Hz), 8.65 (1H, d, J 5.4 Hz), 7.84 (1H, dd, J 8.6 and 2.1 Hz), 7.44 (1H, d, J 5.4 Hz), 7.07 (1H, d, J 8.6 Hz), 5.24 (1H, br. s), 4.47-4.28 (2H, m), 4.30-4.11 (2H, m), 2.90 (2H, s), 2.78 (3H, s), 1.41 (6H, s). LCMS (ES+) 408.0 (M+H)$^+$, RT 2.83 minutes (Method 1).

Example 458 tert-Butyl 4-{6-[4-(6,6-dimethyl-4-oxo-4,5,6,7-tetrahydro[1,3]thiazolo[5,4-c]pyridin-2-yl)-3,4-dihydro-2H-1,4-benzoxazin-6-yl]-2-methylpyrimidin-4-yl}piperazine-1-carboxylate The title compound was prepared from Example 456 and tert-butyl piperazine-1-carboxylate according to Method BB (heating to 130° C. under microwave irradiation for 60 minutes) and was isolated as an off-white solid (20%) after purification by preparative HPLC (Method 7). $\delta_H$ (CDCl$_3$) 8.54 (1H, d, J 2.0 Hz), 7.68 (1H, dd, J 8.6 and 2.0 Hz), 1.40 (6H, s), 7.03 (1H, d, J 8.6 Hz), 6.61 (1H, s), 5.22 (1H, br. s), 4.45-4.32 (2H, m), 4.27-4.14 (2H, m), 3.81-3.66 (4H, m), 3.60-3.48 (4H, m), 2.88 (2H, s), 2.57 (3H, s), 1.49 (9H, s). LCMS (ES+) 592.0 (M+H)$^+$, RT 2.48 minutes (Method 1).

Example 459

{6-[4-(6,6-Dimethyl-4-oxo-4,5,6,7-tetrahydro[1,3]thiazolo[5,4-c]pyridin-2-yl)-3,4-dihydro-2H-1,4-benzoxazin-6-yl]pyridin-3-yl}acetic acid The title compound was prepared from Example 292 and 2-chloropyridine-5-acetic acid according to Method AX (heating to 120° C. under microwave irradiation for 30 minutes) and was isolated as a white solid (2%) after purification by preparative HPLC (Method 6). $\delta_H$ (CDCl$_3$) 8.81 (1H, d, J 1.9 Hz), 8.51 (1H, d, J 1.7 Hz), 7.88-7.71 (3H, m), 7.56 (1H, s), 7.07 (1H, d, J 8.5 Hz), 4.43-4.31 (2H, m), 4.23-4.10 (2H, m), 3.64 (2H, s), 2.84 (2H, s), 1.29 (6H, s). Exchangeable protons were not observed. LCMS (ES+) 451.2 (M+H)$^+$, RT 2.33 minutes (Method 1).

Example 460

6,6-Dimethyl-2-{6-[5-(2-hydroxyethyl)pyridin-2-yl]-2,3-dihydro-4H-1,4-benzoxazin-4-yl}-6,7-dihydro[1,3]thiazolo[5,4-c]pyridin-4(5H)-one The title compound was prepared from Example 292 and Intermediate 242 according to Method AX (heating to 125° C. under microwave irradiation for 80 minutes) and was isolated as an off-white solid (5%) after purification by preparative HPLC (Method 6). $\delta_H$ (CDCl$_3$) 8.53 (1H, s), 8.50 (1H, d, J 2.0 Hz), 7.71 (1H, dd, J 8.7 and 2.0 Hz), 7.63-7.60 (2H, m), 7.05 (1H, d, J 8.7 Hz), 5.22 (1H, br. s), 4.47-4.32 (2H, m), 4.30-4.13 (2H, m), 3.91 (2H, t, J 6.4 Hz), 2.96-2.85 (4H, m), 1.40 (6H, s). Exchangeable protons were not observed. LCMS (ES+) 437.0 (M+H)$^+$, RT 2.06 minutes (Method 1).

Example 461

6,6-Dimethyl-2-{6-[6-(3-hydroxyprop-1-yn-1-yl)-2-methylpyrimidin-4-yl]-2,3-dihydro-4H-1,4-benzoxazin-4-yl}-6,7-dihydro[1,3]thiazolo[5,4-c]pyridin-4(5H)-one To Example 456 (100 mg, 0.227 mmol) in DMF (4 mL) was added triethylamine (0.08 mL, 0.554 mmol), propargyl alcohol (0.02 mL, 0.345 mmol), copper(I) iodide (4 mg, 0.023 mmol) and tetrakis(triphenylphosphine)palladium(0) (13 mg, 0.011 mmol). The reaction mixture was heated to 100° C. under microwave irradiation for 15 minutes. The resulting mixture was partitioned between DCM (50 mL) and water (50 mL); the organic fraction was washed with brine (50 mL), dried (MgSO$_4$) and concentrated in vacuo. The solid was purified by preparative HPLC (Method 6) to yield the title compound (30 mg, 24%) as a pale yellow solid. $\delta_H$ (CD$_3$OD) 8.73 (1H, d, J 2.1 Hz), 7.83 (1H, dd, J 8.7 and 2.1 Hz), 7.61 (1H, s), 7.50 (1H, s), 7.11 (1H, d, J 8.7 Hz), 4.48 (2H, s), 4.45-4.41 (2H, m), 4.29-4.17 (2H, m), 2.92 (2H, s), 2.74 (3H, s), 1.43 (6H, s). Exchangeable protons were not observed. LCMS (ES+) 462.0 (M+H)$^+$, RT 2.89 minutes (Method 1).

Example 462

6,6-Dimethyl-2-{6-[6-(3-hydroxypropyl)-2-methylpyrimidin-4-yl]-2,3-dihydro-4H-1,4-benzoxazin-4-yl}-6,7-dihydro[1,3]thiazolo[5,4-c]pyridin-4(5H)-one To Example 461 (25 mg, 0.054 mmol) in MeOH (15 mL) and DCM (3 mL) was added 5% Pd/C (5 mg, 20% wt) and the reaction was stirred under an atmosphere of hydrogen for 2 h. The resulting mixture was filtered through celite and the filtrate was concentrated in vacuo to give the title compound (22 mg, 89%) as an off-white solid. $\delta_H$ (CD$_3$OD) 8.61 (1H, d, J 2.0 Hz), 7.72 (1H, dd, J 8.7 and 2.0 Hz), 7.34 (1H, s), 7.00 (1H, d, J 8.7 Hz), 4.41-4.27 (2H, m), 4.25-4.03 (2H, m), 3.59 (2H, t, J 6.0 Hz), 2.82 (2H, s), 2.82-2.76 (2H, m), 2.65 (3H, s), 1.97-1.85 (2H, m), 1.33 (6H, s). Exchangeable protons were not observed. LCMS (ES+) 466.0 (M+H)$^+$, RT 2.28 minutes (Method 1).

Example 463

6,6-Dimethyl-2-[6-(2-methyl-6-(piperazin-1-yl)pyrimidin-4-yl)-2,3-dihydro-4H-1,4-benzoxazin-4-yl]-6,7-dihydro[1,3]thiazolo[5,4-c]pyridin-4(5H)-one The title compound was prepared from Example 292 and Intermediate 244 according to Method AX (heating to 125° C. under microwave irradiation for 30 minutes) and was isolated as an off-white solid (11%) after purification by preparative HPLC (Method 6). $\delta_H$ (CDCl$_3$) 8.54 (1H, d, J 2.0 Hz), 7.68 (1H, dd, J 8.7 and 2.0 Hz), 7.02 (1H, d, J 8.7 Hz), 6.61 (1H, s), 5.32 (1H, br. s), 4.43-4.28 (2H, m), 4.24-4.13 (2H, m), 3.76-3.64 (4H, m), 3.06-2.91 (4H, m), 2.88 (2H, s), 2.57 (3H, s), 1.40 (6H, s). LCMS (ES+) 492.0 (M+H)$^+$, RT 1.42 minutes (Method 1).

Example 464

Method BF

Methyl {6-[4-(6,6-dimethyl-4-oxo-4,5,6,7-tetrahydro[1,3]thiazolo[5,4-c]pyridin-2-yl)-3,4-dihydro-2H-1,4-benzoxazin-6-yl]-2-methylpyrimidin-4-yl}acetate To a solution of Example 292 (427 mg, 0.968 mmol) in THF (3 mL) and water (1 mL) were added potassium phosphate (514 mg, 2.42 mmol), Intermediate 245 (300 mg, 1.16 mmol) and tetrakis(triphenylphosphine)palladium(0) (55 mg, 0.48 mmol). The reaction was heated at 120° C. under microwave irradiation for 15 minutes. The resulting mixture was partitioned between DCM (50 mL) and water (50 mL); the organic fraction was washed with brine (50 mL), dried (MgSO$_4$) and concentrated in vacuo. The residue was purified by preparative HPLC (Method 6) to yield the title compound (50 mg, 11%) as a yellow solid. $\delta_H$ (CDCl$_3$) 8.72 (1H, d, J 1.7 Hz), 7.81 (1H, dd, J 8.5 and 1.7 Hz), 7.48 (1H, s), 7.07 (1H, d, J 8.5 Hz), 4.54-4.33 (2H, m), 4.29-4.14 (2H, m), 3.85 (2H, s), 3.76 (3H, s), 2.91 (2H, s), 2.76 (3H, s), 1.41 (6H, s). LCMS (ES+) 480.0 (M+H)$^+$, RT 3.13 minutes (Method 1).

Example 465

6,6-Dimethyl-2-{6-[4-(4-methylpiperazin-1-yl)pyridin-2-yl]-2,3-dihydro-4H-1,4-benzoxazin-4-yl}-6,7-dihydro[1,3]thiazolo[5,4-c]pyridin-4(5H)-one The title compound was prepared from Example 292 and Intermediate 246 according to Method BF (heating to 130° C. under microwave irradiation for 30 minutes) and was isolated as an off-white solid (26%) after purification by preparative HPLC (Method 6). $\delta_H$ (CDCl$_3$) 8.50 (1H, d, J 2.0 Hz), 8.33 (1H, d, J 6.0 Hz), 7.65 (1H, dd, J 8.5 and 2.0 Hz), 7.03 (1H, s), 7.02 (1H, d, J 6.6 Hz), 6.62 (1H, dd, J 6.0 and 2.4 Hz), 5.41 (1H, br. s), 4.49-4.29 (2H, m), 4.32-4.10 (2H, m), 3.60-3.31 (4H, m), 2.87 (2H, s), 2.65-2.49 (4H, m), 2.36 (3H, s), 1.39 (6H, s). LCMS (ES+) 491.0 (M+H)$^+$, RT 1.46 minutes (Method 1).

Example 466

6,6-Dimethyl-2-{6-[5-(4-methylpiperazin-1-yl)pyridin-2-yl]-2,3-dihydro-4H-1,4-benzoxazin-4-yl}-6,7-dihydro[1,3]thiazolo[5,4-c]pyridin-4(5H)-one The title compound was prepared from Example 292 and Intermediate 247 according to Method BF (heating to 125° C. under microwave irradiation for 15 minutes) and was isolated as an off-white solid (10%) after purification by preparative HPLC (Method 6). $\delta_H$ (CDCl$_3$) 8.43 (1H, d, J 2.1 Hz), 8.35 (1H, d, J 2.7 Hz), 7.66 (1H, dd, J 8.5 and 2.1 Hz), 7.55 (1H, d, J 8.9 Hz), 7.25 (1H, dd, J 8.5 and 2.7 Hz), 7.02 (1H, d, J 8.7 Hz), 5.23 (1H, br. s), 4.46-4.29 (2H, m), 4.29-4.17 (2H, m), 3.43-3.19 (4H, m), 2.88 (2H, s), 2.68-2.52 (4H, m), 2.37 (3H, s), 1.40 (6H, s). LCMS (ES+) 491.0 (M+H)$^+$, RT 1.79 minutes (Method 1).

Example 467

6,6-Dimethyl-2-{6-[6-(2-hydroxyethyl)-2-methylpyrimidin-4-yl]-2,3-dihydro-4H-1,4-benzoxazin-4-yl}-6,7-dihydro[1,3]thiazolo[5,4-c]pyridin-4(5H)-one To a suspension of Example 464 (140 mg, 0.294 mmol) in THF (10 mL) was added lithium borohydride (12 mg, 0.588 mmol) and the reaction was heated to reflux for 2 h. The resulting mixture was cooled to r.t. and partitioned between DCM (50 mL) and water (50 mL). The organic phase was washed with brine (50 mL), dried (MgSO$_4$) and concentrated in vacuo. The residue was purified by preparative HPLC (Method 6) to yield the title compound (16 mg, 12%) as an off-white solid. $\delta_H$ (CDCl$_3$) 8.65 (1H, d, J 2.0 Hz), 7.81 (1H, dd, J 8.7 and 2.0 Hz), 7.31 (1H, s), 7.06 (1H, d, J 8.7 Hz), 5.33 (1H, br. s), 4.45-4.33 (2H, m), 4.25-4.18 (2H, m), 4.06 (2H, t, J 5.3 Hz), 3.02 (2H, t, J 5.3 Hz), 2.89 (2H, s), 2.74 (3H, s), 1.41 (6H, s). LCMS (ES+) 452.0 (M+H)$^+$, RT 2.45 minutes (Method 1).

Example 468

6,6-Dimethyl-2-[6-(6-methoxy-4-methylpyridin-3-yl)-2,3-dihydro-4H-1,4-benzoxazin-4-yl]-6,7-dihydro[1,3]thiazolo[5,4-c]pyridin-4(5H)-one The title compound was prepared from Example 292 and 5-bromo-2-methoxy-4-methylpyridine according to Method BF (heating to 100° C. under microwave irradiation for 30 minutes) and was isolated as a white solid (53%) after purification by preparative HPLC (Method 6) then dissolving the product in DCM (15 mL), washing with aqueous potassium carbonate solution (0.7 M) and concentration in vacuo. $\delta_H$ (CD$_3$OD) 7.96 (2H, d, J 10.4 Hz), 7.05 (2H, d, J 1.1 Hz), 6.75 (1H, s), 4.41-4.36 (2H, m), 4.21-4.16 (2H, m), 3.93 (3H, s), 2.88 (2H, s), 2.34 (3H, s), 1.38 (6H, s). LCMS (ES+) 437.13 (M+H)$^+$, RT 3.59 minutes (Method 1).

Example 469

6,6-Dimethyl-2-[6-(6-methoxy-2-methylpyridin-3-yl)-2,3-dihydro-4H-1,4-benzoxazin-4-yl]-6,7-dihydro[1,3]thiazolo[5,4-c]pyridin-4(5H)-one

The title compound was prepared from Example 292 and 3-bromo-6-methoxy-2-methylpyridine according to Method BF (heating to 100° C. under microwave irradiation for 30 minutes) and was isolated as a cream solid (62%) after purification by preparative HPLC (Method 6) then dissolving the product in DCM (15 mL), washing with aqueous potassium carbonate solution (0.7 M) and concentration in vacuo. $\delta_H$ (CDCl$_3$) 7.88 (1H, t, J 1.1 Hz), 7.43 (1H, d, J 8.3 Hz), 7.00 (2H, d, J 1.1 Hz), 6.63 (1H, d, J 8.3 Hz), 5.21 (1H, s), 4.39-4.35 (2H, m), 4.20-4.16 (2H, m), 3.96 (3H, s), 2.86 (2H, s), 2.48 (3H, s), 1.38 (6H, s). LCMS (ES+) 437.16 (M+H)$^+$, RT 3.64 minutes (Method 1).

Example 470

2-[6-(2,4-Dimethyl-6-methoxypyridin-3-yl)-2,3-dihydro-4H-1,4-benzoxazin-4-yl]-6,6-dimethyl-6,7-dihydro[1,3]thiazolo[5,4-c]pyridin-4(5H)-one

The title compound was prepared from Example 292 and Intermediate 249 according to Method BF (heating to 100° C. under microwave irradiation for 30 minutes) and was isolated as a cream solid (69%) after purification by preparative HPLC (Method 6). $\delta_H$ (CDCl$_3$) 7.67 (1H, d, J 1.9 Hz), 7.02-6.98 (1H, m), 6.85-6.80 (1H, m), 6.48 (1H, s), 5.18 (1H, s), 4.40-4.35 (2H, m), 4.30-4.12 (2H, m), 3.93 (3H, s), 2.84 (2H, s), 2.25 (3H, s), 2.06 (3H, s), 1.37 (6H, s). LCMS (ES+) 451.14 (M+H)$^+$, RT 3.21 minutes (Method 1).

Example 471

Method BH

2-[6-(3,5-Dimethyl-1-isopropyl-1H-pyrazol-4-yl)-2,3-dihydro-4H-1,4-benzoxazin-4-yl]-6,6-dimethyl-6,7-dihydro[1,3]thiazolo[5,4-c]pyridin-4(5H)-one

To a stirred solution of 4-bromo-3,5-dimethyl-1H-pyrazole (0.10 g, 0.57 mmol) in EtOH (2 mL) was added KOH (0.096 mg, 1.71 mmol) and 2-bromopropane (0.159 mL, 1.71 mmol). The reaction was heated at 80° C. for 16 h in a sealed tube, then diluted with DCM (10 mL), filtered and concentrated in vacuo. To the residue (0.04 g, 0.18 mmol) and Example 292 (0.162 g, 0.36 mmol) in DME (2 mL) and water (0.5 mL) was added tetrakis(triphenylphosphine)palladium (0) (0.044 g, 0.036 mmol), tetra-n-butylammonium bromide (0.058 g, 0.18 mmol) and potassium phosphate (0.115 g, 0.54 mmol). The reaction mixture was heated at 140° C. under microwave irradiation for 15 minutes and then concentrated in vacuo. The residue was purified by preparative HPLC (Method 6) to give the title compound (0.024 g, 29%) as an ivory foam. $\delta_H$ (CDCl$_3$) 7.79 (1H, d, J 1.7 Hz), 6.99 (1H, d, J 8.3 Hz), 6.95 (1H, dd, J 8.5 and 1.7 Hz), 5.65 (1H, s), 4.48-4.40 (1H, m), 4.39-4.34 (2H, m), 4.22-4.16 (2H, m), 2.86 (2H, s), 2.28 (6H, s), 1.51 (6H, d, J 6.6 Hz), 1.39 (6H, s). LCMS (ES+) 452/453 (M+H)$^+$, RT 3.34 minutes (Method 1).

Example 472

2-[6-(3,5-Dimethyl-1-isobutyl-1H-pyrazol-4-yl)-2,3-dihydro-4H-1,4-benzoxazin-4-yl]-6,6-dimethyl-6,7-dihydro[1,3]thiazolo[5,4-c]pyridin-4(5H)-one

The title compound was prepared from 4-bromo-3,5-dimethyl-1H-pyrazole, 1-bromo-2-methylpropane and Example 292 according to Method BH and was isolated as a pale orange solid (9%) after purification by preparative HPLC (Method 6). $\delta_H$ (CDCl$_3$) 7.80 (1H, d, J 1.7 Hz), 6.99 (1H, d, J 8.3 Hz), 6.95 (1H, dd, J 8.3 and 1.7 Hz), 5.62 (1H, s), 4.40-4.33 (2H, m), 4.21-4.15 (2H, m), 3.82 (2H, d, J 7.3 Hz), 2.86 (2H, s), 2.28 (6H, s), 1.39 (6H, s), 0.95 (6H, d, J 6.6 Hz). LCMS (ES+) 466/467 (M+H)$^+$, RT 3.59 minutes (Method 1).

Example 473

2-{6-[(1,3-Dimethyl-1H-pyrazol-5-yl)amino]-2,3-dihydro-4H-1,4-benzoxazin-4-yl}-6,6-dimethyl-6,7-dihydro[1,3]thiazolo[5,4-c]pyridin-4(5H)-one

The title compound was prepared from Example 42 and 5-chloro-1,3-dimethyl-1H-pyrazole according to Method U and was isolated as a dark brown glass (5%) after purification by preparative HPLC (Method 6). $\delta_H$ (CDCl$_3$) 7.60 (1H, d, J 2.4 Hz), 6.84 (1H, d, J 8.9 Hz), 6.50 (1H, dd, J 8.7 and 2.4 Hz), 5.82 (1H, s), 5.47 (1H, s), 5.36 (1H, s), 4.35-4.22 (2H, m), 4.16-3.97 (2H, m), 3.68 (3H, s), 2.87 (3H, s), 2.62 (2H, s), 1.39 (6H, s). LCMS (ES+) 425.3 (M+H)$^+$, RT 2.40 minutes (Method 1).

Example 474

6,6-Dimethyl-2-{6-[(1-methyl-1H-pyrazol-5-yl)amino]-2,3-dihydro-4H-1,4-benzoxazin-4-yl}-6,7-dihydro[1,3]thiazolo[5,4-d]pyridin-4(5H)-one

The title compound was prepared from Example 39 and 5-amino-1-methyl-1H-pyrazole according to Method AP and was isolated as a dark brown glass (21%) after purification by preparative HPLC (Method 6). $\delta_H$ (CDCl$_3$) 7.58 (1H, d, J 1.9 Hz), 7.44 (1H, s), 6.84 (1H, d, J 8.7 Hz), 6.53-6.46 (1H, m), 6.02 (1H, s), 5.52 (1H, s), 5.38 (1H, s), 4.38-4.21 (2H, m), 4.17-3.96 (2H, m), 3.76 (3H, s), 2.86 (2H, s), 1.39 (6H, s). LCMS (ES+) 411.2 (M+H)$^+$, RT 2.63 minutes (Method 1).

Example 475

6,6-Dimethyl-2-{6-[(1,3,5-trimethyl-1H-pyrazol-4-yl)amino]-2,3-dihydro-4H-1,4-benzoxazin-4-yl}-6,7-dihydro[1,3]thiazolo[5,4-c]pyridin-4(5H)-one

The title compound was prepared from Example 39 and 4-amino-1,3,5-trimethyl-1H-pyrazole according to Method AP and was isolated as a dark brown glass (18%) after purification by preparative HPLC (Method 6). $\delta_H$ (CDCl$_3$) 7.13 (1H, d, J 2.6 Hz), 6.76 (1H, d, J 8.7 Hz), 6.28 (1H, dd, J 8.7 and 2.6 Hz), 5.49 (1H, s), 4.89-4.64 (1H, m), 4.31-4.19 (2H, m), 4.16-4.05 (2H, m), 3.75 (3H, s), 2.84 (2H, s), 2.14 (3H, s), 2.11 (3H, s), 1.39 (6H, s). LCMS (ES+) 439.3 (M+H)$^+$, RT 2.70 minutes (Method 1).

Example 476

6,6-Dimethyl-2-{6-[(1-methyl-1H-pyrazol-3-yl)amino]-2,3-dihydro-4H-1,4-benzoxazin-4-yl}-6,7-dihydro[1,3]thiazolo[5,4-c]pyridin-4(5H)-one The title compound was prepared from Example 39 and 3-amino-1-methyl-1H-pyrazole according to Method AP and was isolated as a dark brown glass (10%) after purification by preparative HPLC (Method 6). $\delta_H$ (CDCl$_3$) 7.90 (1H, d, J 2.4 Hz), 7.21 (1H, d, J 2.3 Hz), 6.87-6.83 (1H, m), 6.81-6.76 (1H, m), 6.00-5.83 (2H, m), 5.33 (1H, s), 4.33-4.25 (2H, m), 4.22-4.08 (2H, m), 3.80 (3H, s), 2.87 (2H, s), 1.39 (6H, s). LCMS (ES+) 411.1 (M+H)$^+$, RT 2.86 minutes (Method 1).

Example 477

2-{6-[3,5-Dimethyl-1-(2-hydroxyethyl)-1H-pyrazol-4-yl]-2,3-dihydro-4H-1,4-benzoxazin-4-yl}-6,6-dimethyl-6,7-dihydro[1,3]thiazolo[5,4-c]pyridin-4(5H)-one To a stirred solution of 4-bromo-3,5-dimethyl-1H-pyrazole (0.5 g, 2.84 mmol) in DMF (5 mL) was added ethylene carbonate (0.500 mg, 5.68 mmol) and NaOH (4 mg). The reaction was heated at 150° C. for 5 hours and then the reaction was filtered and concentrated in vacuo. To the residue (0.066 g, 0.3 mmol) and Example 292 (0.400 g, 0.95 mmol) in DME (3 mL) and water (1.5 mL) were added tetrakis(triphenylphosphine)-palladium(0) (0.072 g, 0.060 mmol) and potassium phosphate (0.190 g, 0.90 mmol). The reaction mixture was heated at 140° C. under microwave irradiation for 15 minutes and then concentrated in vacuo. The residue was purified by preparative HPLC (Method 6) to give the title compound (0.053 g, 39%) as an ivory solid. $\delta_H$ (CDCl$_3$) 7.82 (1H, d, J 1.9 Hz), 7.00 (1H, d, J 8.5 Hz), 6.94 (1H, dd, J 8.3 and 1.9 Hz), 6.30 (1H, s), 5.73 (2H, d, J 0.9 Hz), 4.39-4.34 (2H, m), 4.20-4.12 (4H, m), 4.06-4.01 (2H, m), 2.86 (2H, s), 2.29 (6H, s), 1.39 (6H, s). LCMS (ES+) 454/455 (M+H)$^+$, RT 2.67 minutes (Method 1).

Example 478

6,6-Dimethyl-2-[6-(1H-imidazol-2-ylamino)-2,3-dihydro-4H-1,4-benzoxazin-4-yl]-6,7-dihydro[1,3]thiazolo[5,4-c]pyridin-4(5H)-one To a flask charged with Example 39 (0.05 g, 0.126 mmol), copper(I) iodide (0.005 g, 0.025 mmol), potassium carbonate (0.052 g, 0.37 mmol), (±)-proline (0.006 g, 0.05 mmol) and 2-aminoimidazole (0.02 g, 0.24 mmol) was added DMSO (1 mL), and the reaction mixture was heated to 120° C. for 15 h. It was filtered and purified by preparative HPLC (Method 6) to give the title compound (0.017 g, 34%) as a yellow solid. $\delta_H$ (CDCl$_3$) 8.53 (1H, d, J 2.4 Hz), 7.14-7.10 (1H, m), 7.02 (1H, d, J 2.4 Hz), 6.80 (1H, d, J 2.3 Hz), 6.63 (1H, d, J 2.3 Hz), 5.57 (1H, s), 4.50-4.40 (2H, m), 4.10-3.98 (2H, m), 2.91 (2H, s), 1.41 (6H, s). Exchangeable protons were not observed. LCMS (ES+) 397.3 (M+H)$^+$, RT 1.72 minutes (Method 1).

Example 479

6,6-Dimethyl-2-[6-(1,3-thiazol-2-ylamino)-2,3-dihydro-4H-1,4-benzoxazin-4-yl]-6,7-dihydro[1,3]thiazolo[5,4-c]pyridin-4(5H)-one The title compound was prepared from Example 42 and 2-bromothiazole according to Method BB and was isolated as a dark brown glass (5%) after purification by preparative HPLC (Method 6). $\delta_H$ (CDCl$_3$) 8.16 (1H, d, J 2.4 Hz), 7.25-7.21 (1H, m), 7.07 (1H, dd, J 8.9 and 2.6 Hz), 6.98-6.92 (1H, m), 6.59 (1H, d, J 3.4 Hz), 5.68 (1H, s), 4.41-4.28 (2H, m), 4.19-4.07 (2H, m), 2.89 (2H, s), 1.41 (6H, s). Exchangeable protons not observed. LCMS (ES+) 414.1 (M+H)$^+$, RT 2.50 minutes (Method 1).

Example 480

6,6-Dimethyl-2-{6-[N-ethyl-N-(1-methyl-1H-pyrazol-5-yl)amino]-2,3-dihydro-4H-1,4-benzoxazin-4-yl}-6,7-dihydro[1,3]thiazolo[5,4-d]pyridin-4(5H)-one The title compound was prepared from Example 474 and acetaldehyde according to Method AA (heating to 120° C. under microwave irradiation for 1 h) and was isolated as a dark yellow glass (28%) after purification by preparative HPLC (Method 6). $\delta_H$ (CDCl$_3$) 7.50 (1H, d, J 1.9 Hz), 7.41 (1H, d, J 2.6 Hz), 6.81 (1H, d, J 8.9 Hz), 6.30 (1H, dd, J 8.9 and 2.8 Hz), 6.05 (1H, d, J 2.1 Hz), 5.47 (1H, s), 4.31-4.24 (2H, m), 4.11-4.05 (2H, m), 3.65-3.55 (2H, m), 2.85 (2H, s), 1.39 (6H, s), 1.23 (3H, t, J 7.2 Hz). LCMS (ES+) 439/440 (M+H)$^+$, RT 3.33 minutes (Method 1).

Example 481

6,6-Dimethyl-2-[6-(2-methylphenyl)-2,3-dihydro-4H-1,4-benzoxazin-4-yl]-6,7-dihydro[1,3]thiazolo[5,4-c]pyridin-4(5H)-one The title compound was prepared from Example 39 and o-tolylboronic acid according to Method Z and was isolated as a dark orange solid (40%) after purification by preparative HPLC (Method 6). $\delta_H$ (CDCl$_3$) 7.86 (1H, d, J 1.7 Hz), 7.35-7.16 (4H, m), 7.10-6.92 (2H, m), 5.60 (1H, s), 4.43-4.30 (2H, m), 4.27-4.14 (2H, m), 2.85 (2H, s), 2.34 (3H, s), 1.38 (6H, s). LCMS (ES+) 406.3 (M+H)$^+$, RT 4.14 minutes (Method 1).

Example 482

2-[6-(2,6-Dimethylphenyl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 39 and 2,6-dimethylphenylboronic acid according to Method Z and was isolated as a dark orange solid (18%) after purification by preparative HPLC (Method 6). $\delta_H$ (CDCl$_3$) 7.63 (1H, d, J 1.9 Hz), 7.19-7.07 (3H, m), 7.04-7.00 (1H, m), 6.85 (1H, dd, J 8.3 and 1.9 Hz), 5.87 (1H, s), 4.31-4.45 (2H, m), 4.16-4.29 (2H, m), 2.84 (2H, s), 2.10 (6H, s), 1.37 (6H, s). LCMS (ES+) 420.3 (M+H)$^+$, RT 4.32 minutes (Method 1).

Example 483

2-{6-[(1,3-Dimethyl-1H-pyrazol-5-yl)oxy]-2,3-dihydro-4H-1,4-benzoxazin-4-yl}-6,6-dimethyl-6,7-dihydro[1,3]thiazolo[5,4-c]pyridin-4(5H)-one A mixture of ethyl-2-oxocyclohexane carboxylate (0.017 g, 0.1 mmol), copper(I) bromide (0.0072 g, 0.05 mmol) and cesium carbonate (0.342 mg, 1.05 mmol) in DMSO (0.5 mL) was degassed and stirred under nitrogen at r.t. for 30 minutes in a sealed tube. Example 39 (0.200 g, 0.5 mmol) and 1,3-dimethyl-5-hydroxypyrazole (0.068 g, 0.6 mmol) were added followed by DMSO (0.5 mL) and the reaction mixture was heated to 80° C. for 16 h. Additional Example 39 (0.400 g, 1 mmol), copper(I) bromide (0.070 g, 0.5 mmol) and cesium carbonate (0.494 g, 1.5 mmol) in DMSO (1 mL) were added and heating was continued for a further 16 h at 80° C. The reaction mixture was cooled to r.t. and purified by preparative HPLC (Method 7) to give the title compound (0.019 g, 7%) as a light brown solid. $\delta_H$ (CDCl$_3$) 8.17 (1H, d, J 2.3 Hz), 7.04 (1H, d, J 8.7 Hz), 6.87 (1H, dd, J 8.7 and 2.4 Hz), 5.98 (1H, s), 5.47 (1H, s), 4.54-4.30 (2H, m), 4.18-4.00 (2H, m), 3.20 (3H, s), 2.89 (2H, s), 2.05 (3H, s), 1.41 (6H, s). LCMS (ES+) 426/427 (M+H)$^+$, RT 2.38 min (Method 1).

Example 484

Ethyl 4-{[4-(6,6-dimethyl-4-oxo-4,5,6,7-tetrahydro[1,3]thiazolo[5,4-c]pyridin-2-yl)-3,4-dihydro-2H-1,4-benzoxazin-6-yl]amino}-1-methyl-1H-imidazole-2-carboxylate A mixture of Example 39 (0.4 g, 1.015 mmol), copper(I) iodide (0.038 g, 0.203 mmol), potassium carbonate (0.420 g, 3.04 mmol), proline (0.045 g, 0.406 mmol) and 4-amino-1-methylimidazole-2-carboxylic acid ethyl ester hydrochloride (0.417 g, 2.03 mmol) in DMSO (3 mL) was heated to 120° C. for 16 h in a sealed tube. It was concentrated in vacuo and purified by preparative HPLC (Method 6) to give the title compound (0.007 g, 1.6%) as a yellow solid. $\delta_H$ (DMSO-d$_6$) 8.39 (1H, s), 7.99 (1H, d, J 2.1 Hz), 7.52 (1H, s), 7.06 (1H, s), 6.83-6.76 (2H, m), 4.32-4.18 (4H, m), 4.10-4.01 (2H, m), 3.92 (3H, s), 2.83 (2H, s), 1.32-1.22 (9H, m). LCMS (ES+) 483/484 (M+H)$^+$, RT 2.94 minutes (Method 1).

Example 485

2-[6-(2,6-Dimethylpyrimidin-4-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 292 and 4-chloro-2,6-dimethylpyrimidine (73 mg, 0.51 mmol) according to Method AX (heating at 120° C. under microwave irradiation for 20 minutes) and was isolated as a yellow solid (53%) after purification by preparative HPLC (Method 6). $\delta_H$ (CDCl$_3$) 8.64 (1H, d, J 2.1 Hz), 7.82 (1H, dd, J 8.5 and 2.1 Hz), 7.30 (1H, s), 7.06 (1H, d, J 8.5 Hz), 5.45 (1H, br. s), 4.46-4.35 (2H, m), 4.28-4.16 (2H, m), 2.90 (2H, s), 2.75 (3H, s), 2.56 (3H, s), 1.41 (6H, s). LCMS (ES+) 422.10 (M+H)$^+$, RT 2.67 minutes (Method 1).

Example 486

Ethyl {6-[4-(6,6-dimethyl-4-oxo-4,5,6,7-tetrahydro[1,3]thiazolo[5,4-c]pyridin-2-yl)-3,4-dihydro-2H-1,4-benzoxazin-6-yl]pyridin-2-yl}acetate The title compound was prepared from Example 292 and Intermediate 250 (73 mg, 0.51 mmol) according to Method AX (heating at 120° C. under microwave irradiation for 20 minutes) and was isolated as a beige solid (33%) after purification by preparative HPLC (Method 6). $\delta_H$ (CDCl$_3$) 8.52 (1H, d, J 1.9 Hz), 7.81-7.67 (3H, m), 7.56 (2H, d, J 7.3 Hz), 7.22 (1H, d, J 7.7 Hz), 7.04 (1H, d, J 8.7 Hz), 5.18 (1H, s), 4.46-4.31 (2H, m), 4.29-4.13 (4H, m), 3.91 (2H, s), 2.89 (2H, s), 1.40 (6H, s), 1.27 (3H, t, J 7.0 Hz). LCMS (ES+) 479.17 (M+H)$^+$, RT 3.46 minutes (Method 1).

Example 487

6,6-Dimethyl-2-{6-[6-(2-hydroxyethyl)pyridin-2-yl]-2,3-dihydro-4H-1,4-benzoxazin-4-yl}-6,7-dihydro[1,3]thiazolo[5,4-d]pyridin-4(5H)-one To a solution of Example 486 (47.6 mg, 0.1 mmol) in THF (5 mL) was added lithium borohydride (4 mg, 0.2 mmol) and the reaction mixture was heated under reflux for 4 h. An additional equivalent of lithium borohydride (2 mg, 0.1 mmol) was added and the reaction mixture was heated under reflux for a further 1 h. The resulting solution was cooled to r.t. and MeOH (1 mL) was added followed by 1N NaOH (few drops), water (10 mL) and EtOAc (20 mL). The aqueous layer was neutralised with 2M HCl and extracted with EtOAc (3×20 mL). The combined organic fractions were washed with brine (20 mL), dried (MgSO$_4$) and concentrated in vacuo. Purification by preparative HPLC (Method 6) gave the title compound (43 mg, 62%) as a colourless solid. $\delta_H$ (CDCl$_3$) 8.58 (1H, d, J 1.9 Hz), 7.72-7.64 (2H, m), 7.54 (1H, d, J 7.7 Hz), 7.14-7.00 (2H, m), 5.21 (1H, s), 4.42-4.35 (2H, m), 4.24-4.18 (2H, m), 4.11 (2H, t, J 5.5 Hz), 3.08 (2H, t, J 5.5 Hz), 2.92 (2H, s), 1.41 (6H, s). LCMS (ES+) 439.13 (M+H)$^+$, RT 2.93 minutes (Method 1).

Example 488

2-[7-(2,3-Dihydro-1H-indol-1-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 214 and indoline according to Method AP and was isolated as a brown solid (33%) after purification by preparative HPLC (Method 6). $\delta_H$ (DMSO-d$_6$) 8.02 (1H, dd, J 8.9 and 0.9 Hz), 7.49 (1H, s), 7.18 (1H, d, J 7.0 Hz), 7.12-7.01 (2H, m), 6.91 (1H, dd, J 9.2 and 2.6 Hz), 6.79-6.69 (2H, m), 4.32 (2H, t, J 4.3 Hz), 4.07 (2H, t, J 4.3 Hz), 3.91 (2H, t, J 8.7 Hz), 3.08 (2H, t, J 8.5 Hz), 2.80 (2H, s), 1.28 (6H, s). LCMS (ES+) 433.3 (MH$^+$), RT 4.09 minutes (Method 1).

Example 489

6,6-Dimethyl-2-(7-methoxy-2,3-dihydro-4H-1,4-benzoxazin-4-yl)-6,7-dihydro[1,3]thiazolo[5,4-c]pyridin-4(5H)-one To a stirred suspension of Intermediate 46 (2.453 g, 11.15 mmol) in THF (12.5 mL) was added 2,6-lutidine (1.298 mL, 11.15 mmol). A suspension of Intermediate 253 (2.5 g, 11.15 mmol) in THF (12.5 mL) was added and the reaction mixture was stirred at r.t. for 1.5 h. Further Intermediate 46 (0.245 g, 1.11 mmol) was added and the mixture was stirred at r.t. overnight. The reaction mixture was filtered and the solid washed with THF (2×5 mL). The solid was suspended in water (30 mL) and stirred for 0.5 h. The solid was collected by filtration, washed with water (2×10 mL) and dried in vacuo. The THF filtrate was concentrated in vacuo. EtOAc (10 mL) was added to the residue and the solid was collected by filtration, washed with water (2×10 mL) and dried in vacuo to yield a second crop. The two batches were combined to give the title compound (3.219 g, 83%) as a light brown solid. $\delta_H$ (CDCl$_3$) 7.75 (1H, d, J 8.7 Hz), 6.56-6.48 (2H, m), 5.18 (1H, s), 4.34-4.28 (2H, m), 4.16-4.10 (2H, m), 3.79 (3H, s), 2.85 (2H, s), 1.39 (6H, s). LCMS (ES+) 346.1 (M+H)$^+$, RT 3.13 minutes (Method 1).

Example 490

2-(6-Bromo-7-methoxy-2,3-dihydro-4H-1,4-benzoxazin-4-yl)-6,6-dimethyl-6,7-dihydro[1,3]thiazolo[5,4-c]pyridin-4(5H)-one To a stirred solution of Example 489 (0.05 g, 0.145 mmol) in MeCN (1 mL) and THF (1 mL) was added N-bromosuccinimide (0.026 g, 0.145 mmol). The mixture was stirred at r.t. overnight and then concentrated in vacuo. EtOAc (10 mL) and 1% aqueous sodium sulfite (5 mL) were added and the mixture was rapidly stirred for 10 minutes. The aqueous layer was extracted with EtOAc (10 mL) and then DCM (2×10 mL). The EtOAc extracts were concentrated in vacuo and the residue was dissolved in DCM (5 mL). The combined organic fractions were washed with brine (10 mL), dried (MgSO$_4$), filtered and the solvent was evaporated in vacuo to give the title compound (0.062 g, 100%) as a light brown solid. $\delta_H$ (CDCl$_3$) 8.17 (1H, s), 6.52 (1H, s), 5.22 (1H, s), 4.35-4.30 (2H, m), 4.10-4.05 (2H, m), 3.86 (3H, s), 2.88 (2H, s), 1.39 (6H, s). LCMS (ES+) 424.1, 426.0 (M+H)$^+$, RT 3.47 minutes (Method 1).

Example 491

Method BI 6,6-Dimethyl-2-{7-[N-(1-isobutylpiperidin-4-yl)-N-(methyl)amino]-2,3-dihydro-4H-1,4-benzoxazin-4-yl}-6,7-dihydro[1,3]thiazolo[5,4-c]pyridin-4(5H)-one To Example 228 [free base formed by partitioning between saturated aqueous NaHCO$_3$ solution and DCM, followed by drying the organic phase (MgSO$_4$) and concentration in vacuo] (0.0425 g, 0.099 mmol) in anhydrous DCM (1.5 mL) was added isobutyraldehyde (0.009 mL, 0.099 mmol) and the mixture was stirred for 30 minutes at r.t., then cooled to 0° C. in an ice bath and treated with sodium triacetoxyborohydride (0.0316 g, 0.149 mmol). The reaction was allowed to warm to r.t. and stirred overnight. Water (0.2 mL) was added and the DCM was removed in vacuo. The residue was purified by preparative HPLC (Method 7) to give the title compound (0.0242 g, 50%) as a yellow solid. $\delta_H$ (CDCl$_3$) 7.63 (1H, d, J 9.0 Hz), 6.40 (1H, dd, J 9.0 and 2.8 Hz), 6.33 (1H, d, J 2.8 Hz), 5.22 (1H, s), 4.32-4.26 (2H, m), 4.17-4.10 (2H, m), 3.58-3.45 (1H, m), 3.01-2.91 (2H, m), 2.84 (2H, s), 2.77 (3H, s), 2.08 (2H, d), 2.04-1.91 (2H, m), 1.89-1.63 (5H, m), 1.38 (6H, s), 0.90 (6H, d, J 6.6 Hz). LCMS (ES+) 484.2 (M+H)$^+$, RT 2.07 minutes (Method 1).

Example 492

6,6-Dimethyl-2-{7-methoxy-6-[3-(piperidin-1-ylmethyl)phenyl]-2,3-dihydro-4H-1,4-benzoxazin-4-yl}-6,7-dihydro[1,3]thiazolo[5,4-c]pyridin-4(5H)-one A mixture of Example 490 (0.05 g, 0.118 mmol), 3-(piperidin-1-ylmethyl)-phenylboronic acid pinacol ester hydrochloride (0.0478 g, 0.141 mmol), potassium phosphate (0.1 g, 0.471 mmol) and tetrakis(triphenylphosphine)palladium(0) (0.0082 g, 0.0071 mmol) was degassed under 3 cycles of nitrogen and vacuum. DME (1.2 mL) and water (0.3 ml) were added and the mixture was degassed as before. The mixture was heated to 120° C. under microwave irradiation in a sealed tube for 1 h. Water (15 mL) and DCM (15 mL) were added. The aqueous fraction was separated and extracted with DCM (2×10 mL). The combined organic fractions were filtered through a Whatman 1µ PTFE tube and concentrated in vacuo. The residue was purified by preparative HPLC (Method 6) to give the title compound (0.0243 g, 40%) as a colourless solid. $\delta_H$ (CDCl$_3$) 7.76 (1H, s), 7.45 (1H, s), 7.41-7.31 (2H, m), 7.30-7.25 (1H, m), 6.57 (1H, s), 5.28 (1H, s), 4.37-4.32 (2H, m), 4.21-4.16 (2H, m), 3.78 (3H, s), 3.54 (2H, s), 2.84 (2H, s), 2.49-2.37 (4H, m), 1.64-1.54 (4H, m), 1.48-1.35 (8H, m). LCMS (ES+) 519.3 (M+H)$^+$, RT 2.32 minutes (Method 1).

Example 493

2-{7-[N-(1-Cyclopentylpiperidin-4-yl)-N-(methyl)amino]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 228 and cyclopentanone according to Method BI and was isolated as a yellow solid (56%) after purification by preparative HPLC (Method 7). $\delta_H$ (CDCl$_3$) 7.63 (1H, d, J 9.2 Hz), 6.40 (1H, dd, J 9.2 and 2.8 Hz), 6.33 (1H, d, J 2.8 Hz), 5.18 (1H, s), 4.32-4.27 (2H, m), 4.16-4.10 (2H, m), 3.60-3.48 (1H, m), 3.19-3.10 (2H, m), 2.84 (2H, s), 2.77 (3H, s), 2.57-2.44 (1H, m), 2.08-1.97 (2H, m), 1.95-1.50 (10H, m), 1.49-1.34 (8H, m). LCMS (ES+) 496.3 (M+H)$^+$, RT 2.10 minutes (Method 1).

Example 494

2-{7-[N-(1-Acetylpiperidin-4-yl)-N-(methyl)amino]-2,3-dihydro-4H-1,4-benzoxazin-4-yl}-6,6-dimethyl-6,7-dihydro[1,3]thiazolo[5,4-c]pyridin-4(5H)-one To Example 228 (0.0491 g, 0.115 mmol) in pyridine (1 mL) was added acetic anhydride (0.108 mL, 1.15 mmol) dropwise. The reaction was stirred at r.t. overnight. The pyridine was removed in vacuo and DCM (1 mL) and water (0.2 mL) were added. The mixture was stirred rapidly for 1 h. The DCM was removed in vacuo and the residue was purified by preparative HPLC (Method 7) to give the title compound (0.0356 g, 66%) as a yellow solid. $\delta_H$ (CDCl$_3$) 7.66 (1H, d, J 9.0 Hz), 6.43 (1H, dd, J 9.0 and 2.8 Hz), 6.36 (1H, d, J 2.8 Hz), 5.29 (1H, s), 4.83-4.74 (1H, m), 4.33-4.28 (2H, m), 4.16-4.10 (2H, m), 3.98-3.87 (1H, m), 3.82-3.69 (1H, m), 3.20-3.08 (1H, m), 2.84 (2H, s), 2.73 (3H, s), 2.64-2.53 (1H, m), 2.13 (3H, s), 1.87-1.56 (4H, m), 1.39 (6H, s). LCMS (ES+) 470.2 (M+H)$^+$, RT 2.23 minutes (Method 1).

Example 495

6,6-Dimethyl-2-[7-methoxy-6-(1-methyl-1H-pyrazol-4-yl)-2,3-dihydro-4H-1,4-benzoxazin-4-yl]-6,7-dihydro[1,3]thiazolo[5,4-c]pyridin-4(5H)-one To Example 490 (0.1 g, 0.236 mmol) was added 1-methyl-4-(4,4,5,5-tetramethyl-[1,3,2]dioxaborolan-2-yl)-1H-pyrazole (0.0589 g, 0.283 mmol) and tetrakis(triphenylphosphine)palladium(0) (0.0163 g, 0.0141 mmol). The mixture was degassed under 3 cycles of nitrogen and vacuum. DME (2.4 mL) and 1.57M aqueous potassium phosphate (0.6 mL, 0.943 mmol) were added and the mixture was degassed as before. The mixture was heated to 120° C. under microwave irradiation in a sealed tube for 1 h. Water (15 mL) and DCM (15 mL) were added. The aqueous fraction was separated and extracted with DCM (2×10 mL). The combined organic fractions were filtered through a Whatman 1µ PTFE tube and concentrated in vacuo. The residue was purified by preparative HPLC (Method 7) to give the title compound (0.0764 g, 76%) as an off-white solid. $\delta_H$ (DMSO-d$_6$) 8.14 (1H, s), 8.01 (1H, s), 7.75 (1H, s), 7.50 (1H, s), 6.68 (1H, s), 4.32-4.27 (2H, m), 4.11-4.06 (2H, m), 3.86 (3H, s), 3.84 (3H, s), 2.81 (2H, s), 1.28 (6H, s). LCMS (ES+) 426.1 (M+H)$^+$, RT 2.95 minutes (Method 1).

Example 496

6,6-Dimethyl-2-{6-[6-(piperidin-1-ylmethyl)pyridin-2-yl]-2,3-dihydro-4H-1,4-benzoxazin-4-yl}-6,7-dihydro[1,3]thiazolo[5,4-c]pyridin-4(5H)-one To Example 292 (0.1 g, 0.227 mmol) was added 6-bromo-2-pyridinecarboxaldehyde (0.0421 g, 0.227 mmol) and tetrakis(triphenylphosphine)palladium(0) (0.0157 g, 0.0136 mmol). The mixture was degassed under 3 cycles of nitrogen and vacuum. DME (2.32 mL) and 1.57M aqueous potassium phosphate (0.58 mL, 0.906 mmol) were added and the mixture was degassed as before. The mixture was heated to 120° C. under microwave irradiation in a sealed tube for 1 h. The mixture was filtered. Water (15 mL) and DCM (15 mL) were added to the filtrate. The aqueous fraction was separated and extracted with DCM (2×10 mL). The combined organic fractions were washed with brine (10 mL), dried (MgSO$_4$), filtered and concentrated in vacuo. To a stirred suspension of the crude material in anhydrous DCM (2.8 mL) was added piperidine (0.0172 mL, 0.174 mmol). The reaction was stirred for 30 minutes, then cooled to 0° C. in an ice bath and treated with sodium triacetoxyborohydride (0.0552 g, 0.260 mmol). The reaction was allowed to warm to r.t. and stirred overnight. Water (0.2 mL) was added and the DCM was removed in vacuo. The residue was purified by preparative HPLC (Method 6) to give the title compound (0.0443 g, 52%) as a pale yellow solid. $\delta_H$ (DMSO-d$_6$) 8.87 (1H, s), 7.87-7.71 (3H, m), 7.56 (1H, s), 7.34 (1H, d, J 7.5 Hz), 7.07 (1H, d, J 8.5 Hz), 4.40-4.34 (2H, m), 4.18-4.11 (2H, m), 3.61 (2H, s), 2.83 (2H, s), 2.47-2.38 (4H, m), 1.57-1.46 (4H, m), 1.45-1.35 (2H, m), 1.29 (6H, s). LCMS (ES+) 490.1 (M+H)$^+$, RT 2.20 minutes (Method 1).

Example 497

6,6-Dimethyl-2-[7-(isopropylthio)-2,3-dihydro-4H-1,4-benzoxazin-4-yl]-6,7-dihydro[1,3]thiazolo[5,4-c]pyridin-4(5H)-one To a stirred solution of Example 214 (206 mg, 0.52 mmol) in THF (25 mL) cooled to −78° C. under nitrogen was added n-butyllithium (2.5M in hexanes, 0.81 mL, 2.03 mmol). The reaction mixture was stirred at −78° C. for 1 h prior to the addition of isopropyl disulfide (0.323 mL, 2.03 mmol). It was warmed slowly to r.t. overnight, diluted with MeOH/DCM and concentrated in vacuo. To the residue was added water (10 mL) and the aqueous layer was washed with DCM (3×10 mL). The organic fractions were combined, dried (Na$_2$SO$_4$), filtered and concentrated in vacuo. The residue was purified by preparative HPLC (Method 6) to give the title compound (46 mg, 23%) as a cream solid. $\delta_H$ (CDCl$_3$) 7.92 (1H, d, J 8.9 Hz), 7.03-6.96 (2H, m), 5.18 (1H, br. s), 4.36-4.31 (2H, m), 4.15-4.10 (2H, m), 3.35 (1H, m), 2.88 (2H, s), 1.40 (6H, s), 1.30 (6H, d, J 6.6 Hz). LCMS (ES+) 390.13 (M+H)$^+$, RT 3.97 minutes (Method 1).

Examples 498 & 499

6,6-Dimethyl-2-[7-(isopropylsulfonyl)-2,3-dihydro-4H-1,4-benzoxazin-4-yl]-6,7-dihydro[1,3]thiazolo[5,4-c]pyridin-4(5H)-one and 6,6-Dimethyl-2-[7-(isopropylsulfinyl)-2,3-dihydro-4H-1,4-benzoxazin-4-yl]-6,7-dihydro[1,3]thiazolo[5,4-c]pyridin-4(5H)-one To a stirred solution of Example 497 (31 mg, 0.079 mmol) in DCM (5 mL) was added meta-chloroperbenzoic acid (70-75% purity, 30 mg, 0.12 mmol) dissolved in DCM (1 mL) and the reaction mixture was stirred at r.t. overnight. Sat. sodium hydrogen-carbonate solution (10 mL) was added and the reaction mixture was stirred for 2 h. The aqueous layer was extracted with DCM (2×10 mL) and the combined organic layers were washed with water (10 mL) and brine (10 mL). The organic fraction was dried (Na$_2$SO$_4$), filtered and concentrated in vacuo. The residue was purified by preparative HPLC (Method 6) to give Example 498 (19 mg, 56%) as a white solid [$\delta_H$ (CD$_3$OD/CDCl$_3$) 8.49-8.43 (1H, m), 7.49-7.42 (2H, m), 4.46-4.40 (2H, m), 4.16-4.09 (2H, m), 3.27-3.16 (1H, m), 2.93 (2H, s), 1.42 (6H, s), 1.32 (6H, d, J 7.0 Hz). LCMS (ES+) 422.11 (M+H)$^+$, 463.14 (M+MeCN+H)$^+$, RT 2.98 minutes (Method 1)] and Example 499 (5.0 mg, 15%) as a white solid [$\delta_H$ (MeOD/CDCl$_3$) 8.58 (0.27H, s, formate), 8.34 (1H, d, J 8.7 Hz), 7.23 (1H, d, J 2.1 Hz), 7.18 (1H, dd, J 8.5 and 2.1 Hz), 4.47-4.40 (2H, m), 4.20-4.12 (2H, m), 2.99-2.87 (3H, m), 1.42 (6H, s), 1.25 (3H, d, J 6.8 Hz), 1.21 (3H, d, J 6.8 Hz). LCMS (ES+) 406.11 (M+H)$^+$, 811.26 (2M+H)$^+$, RT 2.64 minutes (Method 1)].

Example 500

6,6-Dimethyl-2-[7-(2-Methoxyphenyl)-2,3-dihydro-4H-1,4-benzoxazin-4-yl]-6,7-dihydro[1,3]thiazolo[5,4-c]pyridin-4(5H)-one The title compound was prepared from Example 214 and 2-methoxyphenylboronic acid according to Method AN and was isolated as a cream solid (64%) after purification by column chromatography (SiO$_2$, 30-100% EtOAc/heptane) followed by preparative HPLC (Method 6). $\delta_H$ (CDCl$_3$) 7.97 (1H, d, J 8.5 Hz), 7.36-7.29 (2H, m), 7.18 (1H, d, J 1.9 Hz), 7.14 (1H, dd, J 8.5 and 2.1 Hz), 7.06-6.96 (2H, m), 5.15 (1H, br. s), 4.39-4.34 (2H, m), 4.22-4.16 (2H, m), 3.84 (3H, s), 2.89 (2H, s), 1.40 (6H, s). LCMS (ES+) 422.18 (M+H)$^+$, RT 3.84 minutes (Method 1).

Example 501

2-(7-{2-[(Dimethylamino)methyl]phenyl}-2,3-dihydro-4H-1,4-benzoxazin-4-yl)-6,6-dimethyl-6,7-dihydro[1,3]thiazolo[5,4-c]pyridin-4(5H)-one The title compound was prepared from Example 214 and 2-(N,N-dimethylaminomethyl)phenylboronic acid according to Method AN and was isolated as a brown oil (69%) after purification by column chromatography (SiO$_2$, 0-100% EtOAc/heptane followed by 10% MeOH/DCM). $\delta_H$ (CDCl$_3$) 8.00 (1H, d, J 8.3 Hz), 7.56 (1H, d, J 7.3 Hz), 7.40-7.22 (3H, m), 7.02 (1H, d, J 1.9 Hz), 6.97 (1H, dd, J 8.5 and 2.1 Hz), 5.27 (1H, br. s), 4.42-4.35 (2H, m), 4.24-4.16 (2H, m), 3.43 (2H, br. s), 2.90 (2H, s), 2.20 (6H, s), 1.41 (6H, s). LCMS (ES+) 449.20 (M+H)$^+$, RT 2.17 minutes (Method 1).

Example 502

6,6-Dimethyl-2-{7-[1-(4-methylpiperazin-1-yl) ethyl]-2,3-dihydro-4H-1,4-benzoxazin-4-yl}-6,7-dihydro[1,3]thiazolo[5,4-c]pyridin-4(5H)-one, acetic acid salt To a stirred solution of Example 238 (83% purity, 30 mg, 0.069 mmol) dissolved in 1,2-dichloroethane (4 mL) was added acetic acid (0.032 mL, 0.56 mmol) and 1-methylpiperazine (0.079 mL, 0.71 mmol) and the reaction mixture was stirred at r.t. for 1 h. Sodium triacetoxyborohydride (76 mg, 0.36 mmol) was added and the reaction mixture was stirred at r.t. overnight and the solvent was evaporated in vacuo. To a stirred solution of the residue in 1,2-dichloroethane (4 mL) was added acetic acid (0.032 mL, 0.56 mmol) and 1-methylpiperazine (0.079 mL, 0.71 mmol) and the reaction was stirred under nitrogen at room temperature for 1 h before heating to reflux. Sodium triacetoxyborohydride (81 mg, 0.38 mmol) was added and the reaction mixture was heated. Additional 1-methylpiperazine (0.237 mL, 2.13 mmol) and sodium triacetoxyborohydride (152 mg, 0.72 mmol) were added and the reaction mixture was heated at reflux overnight. Additional 1-methylpiperazine (0.237 mL, 2.13 mmol) and sodium triacetoxyborohydride (150 mg, 0.71 mmol) were added and the reaction mixture was heated at reflux for 5 h, then cooled to r.t. and sat. sodium hydrogencarbonate solution (15 mL) was added. The aqueous layer was extracted with DCM (3×15 mL) and the combined organic fractions were dried (Na$_2$SO$_4$), filtered and the solvent was evaporated in vacuo. The residue was purified by preparative HPLC (Method 7) to give the title compound (6.0 mg, 15%) as a brown oil. $\delta_H$ (CDCl$_3$) 7.89-7.85 (1H, m), 6.95-6.87 (2H, m), 5.93 (1H, br. s), 4.33 (2H, t, J 4.7 Hz), 4.17-4.11 (2H, m), 3.65-3.13 (1H obscured by water, m), 2.87 (2H, s), 2.85-2.52 (8H, m), 2.47 (3H, s), 2.06 (7.02H, s, acetate), 1.40 (6H, s), 1.34 (3H, d, J 6.8 Hz). LCMS (ES+) 442.23 (M+H)$^+$, RT 2.40 minutes (Method 1).

Example 503

Method BJ 6,6-Dimethyl-2-{6-[3-(piperazin-1-ylmethyl)phenyl]-2,3-dihydro-4H-1,4-benzoxazin-4-yl}-6,7-dihydro[1,3]thiazolo[5,4-c]pyridin-4(5H)-one, acetic acid salt A solution of sodium carbonate (0.124 g, 1.17 mmol) in water (1.2 mL) and DME (2.3 mL) was added to a mixture of Example 39 (0.21 g, 0.53 mmol), 3-formylphenylboronic acid (0.23 g, 0.53 mmol) and tetrakis(triphenylphosphine)palladium(0) (0.018 g, 0.016 mmol). The mixture was heated at 120° C. under microwave irradiation for 20 minutes. The organic phase was adsorbed onto silica and purified by column chromatography (SiO$_2$, 20-100% EtOAc/heptane) to give the intermediate aldehyde (0.25 g, 60%) as a cream solid (purity ca. 80%). LCMS (ES+) 420 (M+H)$^+$, RT 3.58 minutes (Method 1). 1-(tert-Butoxycarbonyl)piperazine (0.056 g, 0.3 mmol) was added to a solution of the aldehyde (125 mg, 0.3 mmol) in DCM (5 mL) and THF (5 mL). Trimethyl orthoformate (0.5 mL) was added and the mixture was left to stand. After 1 h, sodium triacetoxyborohydride (79 mg, 0.37 mmol) was added and the mixture stirred for 2 h at r.t. The mixture was concentrated in vacuo and dissolved in DCM (2 mL). TFA (0.5 mL) was added, and the resulting mixture heated at 100° C. under microwave irradiation for 5 minutes. The mixture was concentrated in vacuo and purified by preparative HPLC (Method 7) to give the title compound (0.039 g, 24%) as a cream solid. $\delta_H$ (CDCl$_3$) 8.04 (1H, d, J 2.1 Hz), 7.56 (1H, s), 7.49-7.42 (1H, m), 7.37 (1H, t, J 7.5 Hz), 7.30 (1H, dd, J 8.5 and 2.1 Hz), 7.26-7.21 (1H, m), 7.03 (1H, d, J 8.5 Hz), 6.03 (1H, s), 4.42-4.32 (2H, m), 4.30-4.20 (2H, m), 3.62 (2H, s), 3.22-3.06 (4H, m), 2.87 (2H, s), 2.76-2.58 (4H, br. m), 2.00 (3H, s), 1.40 (6H, s). LCMS (ES+) 490 (M+H)$^+$, RT 2.07 minutes (Method 1).

Example 504

6,6-Dimethyl-2-(6-{3-[(4-methylpiperazin-1-yl)methyl]phenyl}-2,3-dihydro-4H-1,4-benzoxazin-4-yl)-6,7-dihydro[1,3]thiazolo[5,4-c]pyridin-4(5H)-one, formic acid salt The title compound was prepared from Example 39, 3-formylphenylboronic acid and 1-methylpiperazine according to Method BJ and was isolated as a colourless gum (30%) after purification by preparative HPLC (Method 6). $\delta_H$ (CDCl$_3$) 8.46 (1H, s), 8.02 (1H, d, J 2.1 Hz), 7.55 (1H, s), 7.50-7.44 (1H, m), 7.38 (1H, t, J 7.5 Hz), 7.31 (1H, dd, J 8.5 and 2.1 Hz), 7.23 (1H, d, J 7.5 Hz), 7.03 (1H, d, J 8.5 Hz), 5.55 (1H, s), 4.41-4.32 (2H, m), 4.31-4.22 (2H, m), 3.65 (2H, s), 3.15-2.93 (4H, br. m), 2.89 (2H, s), 2.84-2.68 (4H, br. m), 2.63 (3H, s), 1.41 (6H, s). LCMS (ES+) 504 (M+H)$^+$, RT 2.18 minutes (Method 1).

Example 505

6,6-Dimethyl-2-{6-[3-(morpholin-4-ylmethyl)phenyl]-2,3-dihydro-4H-1,4-benzoxazin-4-yl}-6,7-dihydro[1,3]thiazolo[5,4-c]pyridin-4(5H)-one, formic acid salt A solution of sodium carbonate (0.065 g, 0.61 mmol) in water (0.3 mL) and DME (0.6 mL) was added to a mixture of Example 39, (0.11 g, 0.28 mmol), 3-(morpholin-4-ylmethyl)phenylboronic acid pinacol ester hydrochloride (0.095 g, 0.28 mmol) and tetrakis(triphenylphosphine)palladium(0) (0.0097 g, 0.008 mmol). The mixture was heated at 120° C. under microwave irradiation for 20 minutes. The organic phase was concentrated in vacuo and the resulting residue was purified by preparative HPLC (Method 6) to give the title compound (0.023 g, 17%) as a colourless gum. $\delta_H$ (CDCl$_3$) 8.08 (1H, d, J 2.1 Hz), 7.54-7.45 (2H, m), 7.40 (1H, t, J 7.5 Hz), 7.34-7.28 (2H, m), 7.03 (1H, d, J 8.5 Hz), 5.70 (1H, s), 4.43-4.32 (2H, m), 4.29-4.19 (2H, m), 3.84-3.71 (2H, m), 3.67 (2H, s), 2.88 (2H, s), 2.68-2.51 (4H, br. m), 1.40 (6H, s). LCMS (ES+) 491 (M+H)$^+$, RT 2.19 minutes (Method 1).

Example 506

6,6-Dimethyl-2-[6-(3-phenylpiperidin-1-yl)-2,3-dihydro-4H-1,4-benzoxazin-4-yl]-6,7-dihydro[1,3]thiazolo[5,4-c]pyridin-4(5H)-one The title compound was prepared from Example 39 and 3-phenylpiperidine according to Method AP (heating at 130° C. under microwave irradiation for 1 h) and was isolated as a beige solid (30%) after purification by preparative HPLC (Method 6). $\delta_H$ (CDCl$_3$) 7.50 (1H, d, J 2.5 Hz), 7.37-7.20 (5H, m), 6.85 (1H, d, J 9.0 Hz), 6.73 (1H, dd, J 9.0 and 2.5 Hz), 5.25 (1H, s), 4.30-4.24 (2H, m), 4.18-4.12 (2H, m), 3.68-3.55 (2H, m), 3.03-2.90 (1H, m), 2.83 (2H, s), 2.78-2.68 (2H, m), 2.10-

1.99 (1H, m), 1.97-1.75 (2H, m), 1.72-1.54 (1H, m), 1.39 (6H, s). LCMS (ES+) 475 (M+H)$^+$, RT 3.15 minutes (Method 1).

Example 507

N,N-Diethyl-1-[4-(6,6-dimethyl-4-oxo-4,5,6,7-tetrahydro[1,3]thiazolo[5,4-c]pyridin-2-yl)-3,4-dihydro-2H-1,4-benzoxazin-6-yl]piperidine-3-carboxamide The title compound was prepared from Example 39 and N,N-diethylnipecotamide according to Method AP (heating at 130° C. under microwave irradiation for 1 h) and was isolated as a pale brown gum (52%) after purification by preparative HPLC (Method 6). $\delta_H$ (CDCl$_3$) 7.46 (1H, d, J 2.5 Hz), 6.86 (1H, d, J 9.0 Hz), 6.71 (1H, dd, J 9.0 and 2.5 Hz), 5.36 (1H, s), 4.32-4.07 (4H, m), 3.59-3.46 (2H, m), 3.38 (4H, q, J 7.0 Hz), 2.98-2.77 (2H, m), 2.86 (2H, s), 2.77-2.64 (1H, m), 1.94-1.64 (4H, m), 1.39 (6H, s), 1.22 (3H, t, J 7.0 Hz), 1.12 (3H, t, J 7.0 Hz). LCMS (ES+) 498 (M+H)$^+$, RT 2.39 minutes (Method 1).

Example 508

2-{6-[3-(4-Chlorophenyl)pyrrolidin-1-yl]-2,3-dihydro-4H-1,4-benzoxazin-4-yl}-6,6-dimethyl-6,7-dihydro[1,3]thiazolo[5,4-c]pyridin-4(5H)-one Toluene (2 mL) was added to a mixture of Example 39 (0.05 g, 0.127 mmol), sodium tert-butoxide (0.043 g, 0.444 mmol) and [1,1'-bis(di-tert-butylphosphino)-ferrocene]palladium(II) dichloride (0.009 g, 0.013 mmol). 3-(4-Chlorophenyl)pyrrolidine (0.025 g, 0.254 mmol) was added, and the mixture was degassed by evacuating and purging with nitrogen three times over a period of around 5 minutes. The mixture was heated at 130° C. under microwave irradiation for 1 h. The mixture was filtered and the solvent was evaporated in vacuo. The residue was purified by preparative HPLC (Method 6) to give the title compound (0.0054 g, 9%) as a mid-brown solid. $\delta_H$ (CDCl$_3$) 7.33-7.19 (4H, m), 7.02 (1H, d, J 2.5 Hz), 6.87 (1H, d, J 9 Hz), 6.34 (1H, dd, J 9.0 and 2.5 Hz), 5.18 (1H, s), 4.35-4.07 (4H, m), 3.71-3.63 (1H, m), 3.56-3.36 (3H, m), 3.33-3.26 (1H, m), 2.86 (2H, s), 2.48-2.35 (1H, m), 2.18-2.02 (1H, m), 1.39 (6H, s). LCMS (ES+) 495 (M+H)$^+$, RT 4.53 minutes (Method 1).

Example 509

2-{6-[4-(3-Chlorophenyl)piperazin-1-yl]-2,3-dihydro-4H-1,4-benzoxazin-4-yl}-6,6-dimethyl-6,7-dihydro[1,3]thiazolo[5,4-c]pyridin-4(5H)-one The title compound was prepared from Example 39 and 1-(3-chlorophenyl)-piperazine according to Method AP (heating at 130° C. under microwave irradiation for 1 h) and was isolated as a beige solid (17%) after purification by preparative HPLC (Method 6). $\delta_H$ (CDCl$_3$) 7.50 (1H, d, J 2.5 Hz), 7.20 (1H, t, J 8.5 Hz), 6.95-6.81 (4H, m), 6.74 (1H, dd, J 9.0 and 2.5 Hz), 5.17 (1H, s), 4.32-4.25 (2H, m), 4.23-4.15 (2H, m), 3.39-3.30 (4H, m), 3.29-3.20 (4H, m), 2.87 (2H, s), 1.40 (6H, s). LCMS (ES+) 510 (M+H)$^+$, RT 4.24 minutes (Method 1).

Example 510

6,6-Dimethyl-2-[6-(4-(pyridin-2-yl)piperazin-1-yl)-2,3-dihydro-4H-1,4-benzoxazin-4-yl]-6,7-dihydro[1,3]thiazolo[5,4-c]pyridin-4(5H)-one The title compound was prepared from Example 39 and 1-(pyridin-2-yl)piperazine according to Method AP (heating at 130° C. under microwave irradiation for 1 h) and was isolated as a pale brown solid (26%) after purification by preparative HPLC (Method 6). $\delta_H$ (CDCl$_3$) 8.22 (1H, dd, J 5.0 and 1.5 Hz), 7.56-7.48 (2H, m), 6.90 (1H, d, J 7.5 Hz), 6.79-6.63 (3H, m), 5.82 (1H, s), 4.33-4.24 (2H, m), 4.22-4.13 (2H, m), 3.76-3.65 (4H, m), 3.28-3.16 (4H, m), 2.88 (2H, s), 1.41 (6H, s). LCMS (ES+) 477 (M+H)$^+$, RT 2.17 minutes (Method 1).

Example 511

6,6-Dimethyl-2-{6-[4-(2-furoyl)piperazin-1-yl]-2,3-dihydro-4H-1,4-benzoxazin-4-yl}-6,7-dihydro[1,3]thiazolo[5,4-c]pyridin-4(5H)-one The title compound was prepared from Example 39 and 1-(2-furoyl)piperazine according to Method AP (heating at 130° C. under microwave irradiation for 1 h) and was isolated as a beige solid (7%) after purification by preparative HPLC (Method 6). $\delta_H$ (CDCl$_3$) 7.53-7.50 (1H, m), 7.48 (1H, d, J 2.5 Hz), 7.07-7.04 (1H, m), 6.90 (1H, d, J 9 Hz), 6.71 (1H, dd, J 9.0 and 2.5 Hz), 6.50 (1H, dd, J 3.5 and 1.5 Hz), 5.16 (1H, s), 4.34-4.24 (2H, m), 4.23-4.15 (2H, m), 4.05-3.90 (4H, m), 3.20-3.11 (4H, m), 2.87 (2H, s), 1.40 (6H, s). LCMS (ES+) 494 (M+H)$^+$, RT 3.02 minutes (Method 1).

Example 512

2-[6-(4-Benzoylpiperidin-1-yl)-2,3-dihydro-4H-1,4-benzoxazin-4-yl]-6,6-dimethyl-6,7-dihydro[1,3]thiazolo[5,4-c]pyridin-4(5H)-one The title compound was prepared from Example 39 and 4-(benzoyl)piperidine according to Method AP (heating at 130° C. under microwave irradiation for 1 h) and was isolated as a beige solid (8%) after purification by preparative HPLC (Method 6). $\delta_H$ (CDCl$_3$) 8.02-7.95 (2H, m), 7.62-7.55 (1H, m), 7.54-7.46 (2H, m), 7.45 (1H, d, J 2.5 Hz), 6.88 (1H, d, J 9 Hz), 6.75 (1H, dd, J 9.0 and 2.5 Hz), 5.20 (1H, s), 4.33-4.24 (2H, m), 4.24-4.14 (2H, m), 3.68-3.57 (2H, m), 3.45-3.31 (1H, m), 2.91-2.76 (2H, s), 2.87 (2H, s), 2.08-1.93 (4H, m), 1.40 (6H, s). LCMS (ES+) 503 (M+H)$^+$, RT 2.93 minutes (Method 1).

Example 513

6,6-Dimethyl-2-[6-(1H-pyrazol-4-yl)-2,3-dihydro-4H-1,4-benzoxazin-4-yl]-6,7-dihydro[1,3]thiazolo[5,4-c]pyridin-4(5H)-one The title compound was prepared from Example 39 and 4-(4,4,5,5-tetramethyl-[1,3,2]dioxaborolan-2-yl)-1H-pyrazole according to Method AT (heating to 90° C. for 5 h) and was isolated as a white solid (25%) after purification by column chromatography (SiO$_2$, 0-10% MeOH/DCM). $\delta_H$ (CDCl$_3$) 8.04 (1H, d, J 2.1 Hz), 7.78 (2H, s), 7.22 (1H, dd, J 8.5 and 2.1 Hz), 6.97 (1H, d, J 8.5 Hz), 4.38-4.32 (2H, m), 4.23-4.17 (2H, m), 2.89 (2H, s), 1.41 (6H, s). LCMS (ES+) 382 (M+H)$^+$, RT 2.67 minutes (Method 1).

Example 514

6,6-Dimethyl-2-[6-(1-(piperidin-4-yl)-1H-pyrazol-4-yl)-2,3-dihydro-4H-1,4-benzoxazin-4-yl]-6,7-dihydro[1,3]thiazolo[5,4-c]pyridin-4(5H)-one A solution of Intermediate 254 (0.033 g, 0.06 mmol) in CDCl$_3$ (2 mL) and 0.8N HCl in MeOH (2 mL) was stirred at r.t for 16 h then heated to 55° C. for a further 2.5 h. It was concentrated in vacuo and partitioned between a mixture of 10% w/v aqueous $K_2CO_3$ and $CDCl_3$. The organic fraction was dried ($MgSO_4$) and concentrated in vacuo to give the title compound (0.021 g, 77%) as a white solid. $\delta_H$ ($CDCl_3$) 7.97 (1H, d, J 1.9 Hz), 7.71 (1H, s), 7.67 (1H, s), 7.19 (1H, dd, J 8.5 and 2.1 Hz), 6.96 (1H, d, J 8.5 Hz). 5.86 (1H, s), 4.38-4.32 (2H, m), 4.31-4.24 (2H, m), 4.23-4.17 (2H, m), 3.32-3.21 (2H, m), 2.89 (2H, s), 2.85-2.73 (2H, m), 2.25-2.13 (2H, m), 2.04-1.87 (2H, m), 1.41 (6H, s). LCMS (ES+) 465.17 (M+H)+, RT 1.99 minutes (Method 1).

Example 515

6,6-Dimethyl-2-(6-{1-[(2R)-2-hydroxy-3-methoxypropyl]-1H-pyrazol-4-yl}-2,3-dihydro-4H-1,4-benzoxazin-4-yl)-6,7-dihydro[1,3]thiazolo[5,4-c]pyridin-4(5H)-one A mixture of S-(−)-4-(methoxymethyl)-1,3-dioxolan-2-one (0.015 g, 0.11 mmol), sodium hydroxide (0.001 g, 0.025 mmol) and Example 513 (0.039 g, 0.1 mmol) in DMF (0.5 mL) was stirred at 155° C. for 4 h. A further portion of S-(−)-4-(methoxymethyl)-1,3-dioxolan-2-one (0.124 g, 0.94 mmol) was added and heating continued for a further 2 h. The reaction was cooled to r.t. and purified by preparative HPLC (Method 6) to give the title compound (0.023 g, 49%) as a white solid. $\delta_H$ ($CDCl_3$) 8.03 (1H, d, J 1.9 Hz), 7.73 (1H, d, J 0.8 Hz), 7.64 (1H, d, J 0.6 Hz), 7.17 (1H, dd, J 8.5 and 2.1 Hz), 6.96 (1H, d, J 8.5 Hz), 5.33 (1H, s), 4.15-4.35 (7H, m), 3.59-3.54 (1H, m), 3.32-3.42 (5H, m), 2.88 (2H, s), 1.40 (6H, s). LCMS (ES+) 470.05 (M+H)+, RT 2.73 minutes (Method 1).

Example 516

N-(2-Aminoethyl)-4-[4-(6,6-dimethyl-4-oxo-4,5,6,7-tetrahydro[1,3]thiazolo[5,4-c]pyridin-2-yl)-3,4-dihydro-2H-1,4-benzoxazin-6-yl]-1-methyl-1H-pyrazole-3-carboxamide The title compound was prepared from Example 292 and 4-bromo-1-methyl-1H-pyrazole-3-carboxylic acid (2-aminoethyl)amide according to Method AT (heating to 100° C. for 2.5 days) and was isolated as a colourless residue (9%) after purification by preparative HPLC (Method 6). $\delta_H$ ($CDCl_3$) 7.93 (1H, d, J 1.9 Hz), 7.45 (1H, s), 7.40 (1H, dd, J 8.5 and 1.9 Hz), 7.23-7.13 (1H, m), 6.96 (1H, d, J 8.5 Hz), 5.22 (1H, s), 4.35-4.30 (2H, m), 4.26-4.20 (2H, m), 3.96 (3H, s), 3.44 (2H, q, J 6.0 Hz), 2.89 (2H, t, J 6.0 Hz), 2.86 (2H, s), 1.39 (6H, s). Exchangeable protons were not observed. LCMS (ES+) 482 (M+H)+, RT 1.91 minutes (Method 1).

The invention claimed is:
1. A compound of formula (I), or a pharmaceutically acceptable salt thereof:

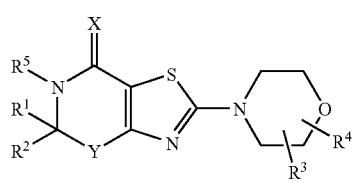

(I)

wherein
X represents oxygen or sulphur;
Y represents a group of formula $CR^6R^7$ or $NR^8$;
$R^1$ represents hydrogen or $C_{1-6}$ alkyl; and
$R^2$ represents hydrogen; or $C_{1-6}$ alkyl, $C_{1-6}$ alkoxy, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or
$R^1$ and $R^2$, when taken together with the carbon atom to which they are both attached, represent $C_{3-7}$ cycloalkyl or $C_{3-7}$ heterocycloalkyl, either of which groups may be optionally substituted by one or more substituents;
$R^3$ and $R^4$ independently represent hydrogen; or $C_{1-6}$ alkyl, $C_{2-6}$ alkynyl, $C_{3-7}$ cycloalkyl, $C_{3-7}$ cycloalkyl($C_{1-6}$) alkyl, aryl, aryl($C_{1-6}$)alkyl, aryl($C_{2-6}$)alkenyl, aryl ($C_{2-6}$)-alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroarylaryl($C_{1-6}$)alkyl or arylheteroaryl($C_{1-6}$)alkyl, any of which groups may be optionally substituted by one or more substituents; or
$R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or
$R^3$ and $R^4$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;
$R^5$ represents hydrogen or $C_{1-6}$ alkyl;
$R^6$ represents hydrogen; or $C_{1-6}$ alkyl, $C_{1-6}$ alkoxy, $C_{3-7}$ cycloalkyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl ($C_{1-6}$)alkyl, heteroaryl or heteroaryl($C_{1-6}$)alkyl, any of which groups may be optionally substituted by one or more substituents; and
$R^7$ represents hydrogen or $C_{1-6}$ alkyl; or
$R^6$ and $R^7$, when taken together with the carbon atom to which they are both attached, represent $C_{3-7}$ cycloalkyl or $C_{3-7}$ heterocycloalkyl, either of which groups may be optionally substituted by one or more substituents; or
$R^2$ and $R^6$, when taken together with the carbon atoms to which they are attached, represent $C_{5-7}$ cycloalkyl, phenyl or heteroaryl, any of which groups may be optionally benzo-fused and/or substituted by one or more substituents; and
$R^8$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; or
$R^2$ and $R^8$, when taken together with the carbon and nitrogen atoms to which they are respectively attached, represent $C_{5-7}$ heterocycloalkyl or heteroaryl, either of which groups may be optionally benzo-fused and/or substituted by one or more substituents.

2. A compound as claimed in claim 1 represented by formula (IIA), or a pharmaceutically acceptable salt thereof:

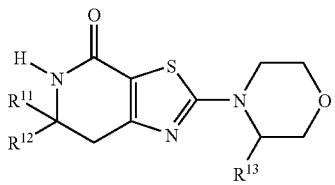

(IIA)

wherein
- $R^{11}$ represents hydrogen or $C_{1-6}$ alkyl; and
- $R^{12}$ represents hydrogen; or $C_{1-6}$ alkyl, $C_{1-6}$ alkoxy, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or
- $R^{11}$ and $R^{12}$, when taken together with the carbon atom to which they are both attached, represent $C_{3-7}$ cycloalkyl or $C_{3-7}$ heterocycloalkyl, either of which groups may be optionally substituted by one or more substituents; and
- $R^{13}$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$) alkyl, heteroaryl-aryl($C_{1-6}$)alkyl or aryl-heteroaryl ($C_{1-6}$)alkyl, any of which groups may be optionally substituted by one or more substituents.

3. A compound as claimed in claim 2 represented by formula (IIB), or a pharmaceutically acceptable salt thereof:

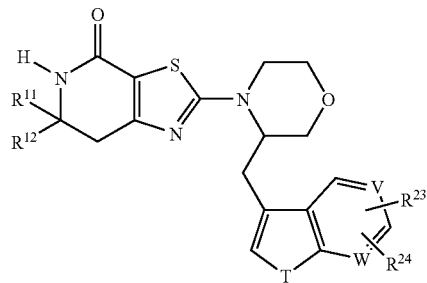

(IIB)

wherein
- $R^{11}$ represents hydrogen or $C_{1-6}$ alkyl; and
- $R^{12}$ represents hydrogen; or $C_{1-6}$ alkyl, $C_{1-6}$ alkoxy, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or
- $R^{11}$ and $R^{12}$, when taken together with the carbon atom to which they are both attached, represent $C_{3-7}$ cycloalkyl or $C_{3-7}$ heterocycloalkyl, either of which groups may be optionally substituted by one or more substituents; and
- T represents N—$R^{25}$;
- V represents carbon or nitrogen;
- W represents carbon or nitrogen;
- $R^{23}$ represents hydrogen, halogen, cyano, nitro, $C_{1-6}$ alkyl, hydroxy($C_{1-6}$)alkyl, trifluoromethyl, aryl($C_{1-6}$)alkyl, oxazolinyl, triazolyl, hydroxy, $C_{1-6}$ alkoxy, difluoromethoxy, trifluoromethoxy, $C_{3-7}$ cycloalkoxy, $C_{3-7}$ cycloalkyl($C_{1-6}$)alkoxy, morpholinyl($C_{1-6}$)alkoxy, aryloxy, aryl($C_{1-6}$)alkoxy, $C_{1-6}$ alkylthio, $C_{1-6}$ alkylsulphinyl, arylsulphinyl, arylsulphonyl, $C_{1-6}$ alkylsulphonyloxy, amino, azetidinyl, morpholinyl, $C_{2-6}$ alkylcarbonylamino, $C_{2-6}$ alkylcarbonylaminomethyl, $C_{2-6}$ alkoxycarbonylamino, [($C_{2-6}$)alkoxycarbonyl][($C_{1-6}$)alkyl]amino, $C_{1-6}$ alkylsulphonylamino, $C_{2-6}$ alkylcarbonyl, $C_{2-6}$ alkylcarbonyl oxime, $C_{2-6}$ alkylcarbonyl O-(methyl)oxime, trifluoromethylcarbonyl, carboxy, $C_{2-6}$ alkoxycarbonyl, aminocarbonyl, $C_{1-6}$ alkylaminocarbonyl, [hydroxy($C_{1-6}$)alkyl]aminocarbonyl, [di($C_{1-6}$)alkylamino($C_{1-6}$)alkyl]aminocarbonyl, di($C_{1-6}$)alkylaminocarbonyl, [($C_{1-6}$)alkyl][cyano($C_{1-6}$)alkyl]aminocarbonyl, [($C_{1-6}$)alkyl][hydroxy($C_{1-6}$)alkyl]aminocarbonyl, [($C_{1-6}$)alkoxy($C_{1-6}$)alkyl][($C_{1-6}$)alkyl]aminocarbonyl, [di($C_{1-6}$)alkylamino($C_{1-6}$)alkyl][($C_{1-6}$)alkyl]aminocarbonyl, $C_{3-7}$ cycloalkyl($C_{1-6}$)alkylaminocarbonyl, aryl($C_{1-6}$)alkylaminocarbonyl, heteroarylaminocarbonyl, heteroaryl($C_{1-6}$)alkylaminocarbonyl, azetidinylcarbonyl, hydroxyazetidinylcarbonyl, aminoazetidinylcarbonyl, $C_{2-6}$ alkoxycarbonylaminoazetidinylcarbonyl, pyrrolidinylcarbonyl, ($C_{1-6}$)alkylpyrrolidinylcarbonyl, $C_{1-6}$ alkoxy($C_{1-6}$)alkylpyrrolidinylcarbonyl, di($C_{1-6}$)alkylaminopyrrolidinyl-carbonyl, thiazolidinylcarbonyl, oxothiazolidinylcarbonyl, piperidinylcarbonyl, ($C_{1-6}$)alkylpiperazinylcarbonyl, morpholinylcarbonyl, $C_{1-6}$ alkylsulphonyl, $C_{1-6}$ alkylsulphonylmethyl or di($C_{1-6}$)alkylaminosulphonyl; and
- $R^{24}$ represents hydrogen, halogen, $C_{1-6}$ alkoxy or di($C_{1-6}$)alkylaminocarbonyl; or
- $R^{23}$ and $R^{24}$, when situated on adjacent carbon atoms, together represent methylenedioxy or difluoromethylenedioxy; and
- $R^{25}$ represents hydrogen.

4. A compound as claimed in claim 2 represented by formula (IIC), or a pharmaceutically acceptable salt thereof:

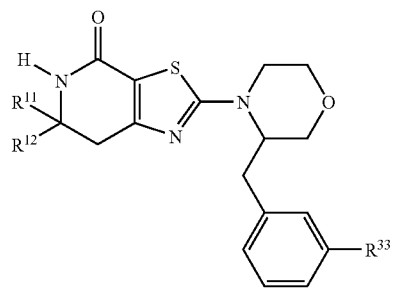

(IIC)

wherein
- $R^{11}$ represents hydrogen or $C_{1-6}$ alkyl; and
- $R^{12}$ represents hydrogen; or $C_{1-6}$ alkyl, $C_{1-6}$ alkoxy, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; or
- $R^{11}$ and $R^{12}$, when taken together with the carbon atom to which they are both attached, represent $C_{3-7}$ cycloalkyl or $C_{3-7}$ heterocycloalkyl, either of which groups may be optionally substituted by one or more substituents; and
- $R^{33}$ represents halogen or —$NHR^{34}$; or aryl or heteroaryl, either of which groups may be optionally substituted by one or more substituents; and $R^{34}$ represents methylenedioxyphenyl, morpholinyl($C_{1-6}$) alkylphenyl, oxazolinylphenyl, [($C_{1-6}$)alkyl](oxo)pyrazolylphenyl, oxazolylphenyl, isoxazolylphenyl, triazolyl-phenyl, ($C_{1-6}$)alkyltriazolylphenyl, ($C_{1-6}$) alkylpyrimidinylphenyl, pyrazolyl($C_{1-6}$)alkyl-phenyl, triazolyl($C_{1-6}$)alkylphenyl, $C_{1-6}$ alkylsulphonylaminophenyl, morpholinylcarbonyl-phenyl, $C_{1-6}$ alkylsulphonylphenyl, morpholinylsulphonylphenyl, dihydrobenzofuranyl, $C_{1-6}$ alkylsulphonylindolinyl, chromanonyl, dihydroquinolinonyl, benzoxazinonyl, benzothienyl, indolyl, dioxoindolyl, [($C_{1-6}$)alkyl](halo) pyrazolyl, tri($C_{1-6}$)alkylpyrazolyl, ($C_{1-6}$)alkylindazolyl, benzoxazolyl, benzoxazolonyl, di($C_{1-6}$)alkylisoxazolyl, benzothiazolyl, ($C_{1-6}$)alkylisothiazolyl, ($C_{1-6}$)alkylbenzimidazolyl, benzimidazolonyl, di($C_{1-6}$)alkylbenzimidazolonyl, ($C_{1-6}$)alkyloxadiazolyl, furyloxadiazolyl, pyridinyl, halopyridinyl, ($C_{1-6}$)alkylpyridinyl, di($C_{1-6}$) alkylpyridinyl, ($C_{1-6}$)alkoxypyridinyl, oxopyridinyl, oxopyrimidinyl, thioxopyrimidinyl, [($C_{1-6}$)alkoxy] (halo)pyridazinyl, ($C_{1-6}$)alkylcinnolinyl, quinoxalinyl or ($C_{1-6}$)alkylchromenyl.

5. A compound as claimed in claim 1 represented by formula (IID-1) or (IID-2), or a pharmaceutically acceptable salt thereof:

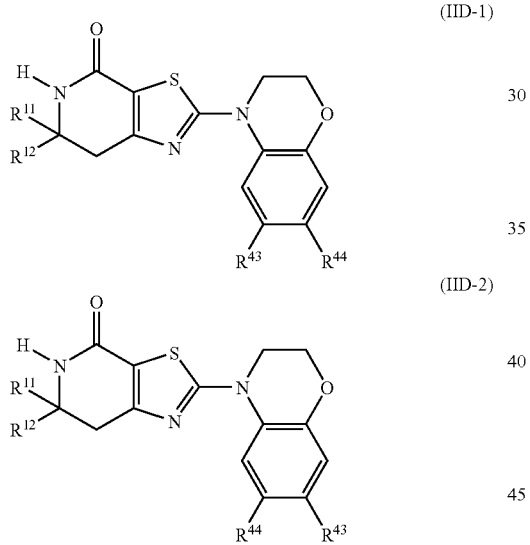

wherein
- $R^{11}$ represents hydrogen or $C_{1-6}$ alkyl; and
- $R^{12}$ represents hydrogen; or $C_{1-6}$ alkyl, $C_{1-6}$ alkoxy, $C_{3-7}$ cycloalkyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl ($C_{1-6}$)alkyl, heteroaryl or heteroaryl[($C_{1-6}$)alkyl, any of which groups may be optionally substituted by one or more substituents; or
- $R^{11}$ and $R^{12}$, when taken together with the carbon atom to which they are both attached, represent $C_{3-7}$ cycloalkyl or $C_{3-7}$ heterocycloalkyl, either of which groups may be optionally substituted by one or more substituents; and
- $R^{43}$ represents hydrogen, halogen, nitro, $C_{1-6}$ alkyl, $C_{2-6}$ alkenyl, $C_{3-7}$ cycloalkyl, ($C_{1-6}$)alkylaryl, di($C_{1-6}$)alkylaryl, piperidinyl($C_{1-6}$)alkylaryl, piperazinyl($C_{1-6}$)alkylaryl, ($C_{1-6}$)alkylpiperazinyl($C_{1-6}$)alkylaryl, morpholinyl($C_{1-6}$)alkylaryl, ($C_{1-6}$)alkoxyaryl, cyano($C_{1-6}$) alkoxyaryl, di($C_{1-6}$)alkylamino($C_{1-6}$)alkylaryl, ($C_{1-6}$) alkylaminocarbonylaryl, aryl($C_{1-6}$)alkyl, haloarylpyrrolidinyl, dioxopyrrolidinyl, aminopyrrolidinyl, di($C_{1-6}$)alkylaminopyrrolidinyl, indolinyl, oxoindolinyl, arylpiperidinyl, arylcarbonylpiperidinyl, di($C_{1-6}$)alkylaminocarbonylpiperidinyl, piperazinyl, ($C_{1-6}$)alkylpiperazinyl, haloaryl-piperazinyl, pyridinylpiperazinyl, furoylpiperazinyl, homopiperazinyl, ($C_{1-6}$)alkyl-homopiperazinyl, ($C_{1-6}$)alkylpiperazinyl ($C_{1-6}$)alkyl, morpholinyl($C_{1-6}$)alkyl, benzofuryl, benzothienyl, pyrazolyl, ($C_{1-6}$)alkylpyrazolyl, di($C_{1-6}$)alkylpyrazolyl, tri($C_{1-6}$)alkyl-pyrazolyl, [di($C_{1-6}$)alkyl] (trifluoromethyl)pyrazolyl, cyano($C_{1-6}$)alkylpyrazolyl, [cyano($C_{1-6}$)alkyl][di($C_{1-6}$)alkyl]pyrazolyl, hydroxy ($C_{1-6}$)alkylpyrazolyl, [hydroxy($C_{1-6}$)alkyl][di($C_{1-6}$) alkyl]pyrazolyl, methoxy($C_{1-6}$)alkylpyrazolyl, [(hydroxy)(methoxy)($C_{1-6}$)alkyl]pyrazolyl, amino($C_{1-6}$) alkylpyrazolyl, [($C_{1-6}$)alkyl][amino($C_{1-6}$)alkyl] pyrazolyl, [amino($C_{1-6}$)alkyl][di($C_{1-6}$)alkyl]pyrazolyl, di($C_{1-6}$)alkylamino($C_{1-6}$)alkylpyrazolyl, di($C_{1-6}$) alkoxyphosphono($C_{1-6}$)alkylpyrazolyl, ($C_{2-6}$)alkenylpyrazolyl, ($C_{3-7}$)cycloalkyl($C_{1-6}$)alkylpyrazolyl, [($C_{3-7}$)cycloalkyl($C_{1-6}$)alkyl][di($C_{1-6}$)alkyl]pyrazolyl, [($C_{1-6}$)alkyl]-(aryl)pyrazolyl, (aryl)(trifluoromethyl) pyrazolyl, aryl($C_{1-6}$)alkylpyrazolyl, aminoaryl($C_{1-6}$) alkylpyrazolyl, piperidinylpyrazolyl, tetrahydropyranyl ($C_{1-6}$)alkylpyrazolyl, [di($C_{1-6}$)alkyl][tetrahydropyranyl ($C_{1-6}$)alkyl]pyrazolyl, pyrrolidinyl($C_{1-6}$)alkylpyrazolyl, piperidinyl($C_{1-6}$)alkylpyrazolyl, ($C_{1-6}$)alkylpiperidinyl ($C_{1-6}$)alkylpyrazolyl, morpholinyl($C_{1-6}$)alkylpyrazolyl, pyridinyl($C_{1-6}$)alkylpyrazolyl, oxypyridinyl($C_{1-6}$)alkylpyrazolyl, [arylcarbonyl($C_{1-6}$)alkyl][di($C_{1-6}$)alkyl] pyrazolyl, [($C_{1-6}$)alkyl](piperazinylcarbonyl)pyrazolyl, [($C_{1-6}$)alkylaminocarbonyl][($C_{1-6}$)alkylaryl]pyrazolyl, [($C_{1-6}$)alkyl]-[amino($C_{1-6}$)alkylaminocarbonyl]pyrazolyl, aminocarbonyl($C_{1-6}$)alkylpyrazolyl, [aminocarbonyl($C_{1-6}$)alkyl][di($C_{1-6}$)alkyl]pyrazolyl, di($C_{1-6}$) alkylaminocarbonyl($C_{1-6}$)alkylpyrazolyl, pyrazolo[1,5-c]pyridinyl, di($C_{1-6}$)alkylisoxazolyl, (amino)[($C_{1-6}$) alkyl]-isoxazolyl, thiazolyl, di($C_{1-6}$)alkylthiazolyl, imidazolyl, ($C_{1-6}$)alkylimidazolyl, di($C_{1-6}$)-alkylimidazolyl, imidazo[1,2-c]pyridinyl, ($C_{1-6}$)alkylimidazo[1,2-c]pyridinyl, ($C_{1-6}$)-alkylimidazo[4,5-b]pyridinyl, imidazo[1,2-c]pyrimidinyl, imidazo[1,2-c]pyrazinyl, ($C_{1-6}$)-alkylthiadiazolyl, pyridinyl, halopyridinyl, ($C_{1-6}$) alkyl-pyridinyl, [($C_{1-6}$)alkyl](halo)-pyridinyl, di($C_{1-6}$) alkylpyridinyl, ($C_{2-6}$)alkenylpyridinyl, ($C_{1-6}$)alkylpiperazinylpyridinyl, [($C_{1-6}$)alkyl](piperazinyl)pyridinyl, [($C_{1-6}$)alkoxycarbonylpiperazinyl][($C_{1-6}$)alkyl]-pyridinyl, piperidinyl($C_{1-6}$)alkylpyridinyl, [($C_{1-6}$)alkyl](oxy)pyridinyl, hydroxypyridinyl, hydroxy ($C_{1-6}$)alkylpyridinyl, ($C_{1-6}$)alkoxypyridinyl, [($C_{1-6}$) alkoxy][($C_{1-6}$)alkyl]pyridinyl, [($C_{1-6}$)alkoxy][di($C_{1-6}$) alkyl]pyridinyl, ($C_{1-6}$)alkoxy($C_{1-6}$)alkylpyridinyl, aminopyridinyl, carboxy($C_{1-6}$)alkylpyridinyl, ($C_{1-6}$) alkoxycarbonyl($C_{1-6}$)alkylpyridinyl, pyridazinyl, ($C_{1-6}$) alkylpyridazinyl, piperidinylpyridazinyl, oxypyridazinyl, ($C_{1-6}$)alkoxypyridazinyl, aminopyridazinyl, hydroxy($C_{1-6}$)alkylaminopyridazinyl, di($C_{1-6}$)alkylaminopyridazinyl, pyrimidinyl, ($C_{1-6}$)alkylpyrimidinyl, [($C_{1-6}$)alkyl](halo)pyrimidinyl, di($C_{1-6}$)alkyl-pyrimidinyl, pyrrolidinylpyrimidinyl, ($C_{1-6}$) alkylpiperazinylpyrimidinyl, [($C_{1-6}$)alkyl](piperazinyl) pyrimidinyl, [($C_{1-6}$)alkoxycarbonyl][($C_{1-6}$)alkyl] piperazinylpyrimidinyl, hydroxypyrimidinyl, [($C_{1-6}$) alkyl](hydroxy)pyrimidinyl, [($C_{1-6}$)alkyl]-[hydroxy ($C_{1-6}$)alkyl]pyrimidinyl, [($C_{1-6}$)alkyl][hydroxy($C_{2-6}$) alkynyl]pyrimidinyl, ($C_{1-6}$)alkoxypyrimidinyl, aminopyrimidinyl, di($C_{1-6}$)alkylaminopyrimidinyl, [di (C₁₋₆)alkylamino](halo)pyrimidinyl, carboxypyrimidinyl, [(C₁₋₆)alkoxycarbonyl(C₁₋₆)alkyl][(C₁₋₆)alkyl]pyrimidinyl, aminocarbonylpyrimidinyl, pyrazinyl, (C₁₋₆)alkoxypyrazinyl, aminopyrazinyl, hydroxy, (C₁₋₆)alkoxy, aryl(C₁₋₆)alkoxycarbonylpiperidinyloxy, morpholinyl(C₁₋₆)alkoxy, aryloxy, haloaryloxy, di(C₁₋₆)alkylpyrazolyloxy, halopyridinyloxy, pyrrolidinylpyridinyloxy, (C₁₋₆)alkylpiperazinylpyridinyloxy, (C₁₋₆)alkylpyrazolylpyridinyloxy, (C₁₋₆)alkylaminopyridinyloxy, carboxypyridinyloxy, aminocarbonylpyridinyloxy, (C₁₋₆)alkylpyridazinyloxy, pyrimidinyloxy, (C₁₋₆)alkylpyrimidinyloxy, [(C₁₋₆)alkyl](halo)pyrimidinyloxy, hydroxy(C₁₋₆)alkyl, dihydroxy(C₁₋₆)alkyl, pyridinyloxy(C₁₋₆)alkyl, amino, (C₁₋₆)alkylamino, dihydroxy(C₁₋₆)alkylamino, (C₁₋₆)alkoxy(C₁₋₆)alkylamino, N—[(C₁₋₆)alkoxy(C₁₋₆)alkyl]-N—[(C₁₋₆)alkyl]amino, di(C₁₋₆)alkylamino(C₁₋₆)alkylamino, N—[(C₁₋₆)alkyl]-N-[di(C₁₋₆)alkylamino(C₁₋₆)alkyl]amino, N—[(C₁₋₆)alkyl]-N—[(C₃₋₇)cycloalkyl]amino, haloarylamino, N—[(C₁₋₆)alkyl]-N-(haloaryl)amino, N—[(C₁₋₆)alkyl]-N—[aryl(C₁₋₆)alkyl]amino, N-[di(C₁₋₆)alkylamino(C₁₋₆)alkyl]-N—[aryl(C₁₋₆)alkyl]amino, cyanoaryl(C₁₋₆)alkylamino, (cyano)(halo)aryl(C₁₋₆)alkylamino, methylenedioxyaryl(C₁₋₆)alkylamino, N—[(C₁₋₆)alkyl]-N—[(C₁₋₆)alkylpyrrolidinyl]amino, piperidinylamino, N—[(C₁₋₆)alkyl]-N-(piperidinyl)amino, N—[(C₃₋₇)cycloalkyl(C₁₋₆)alkyl]-N(piperidinyl)amino, (C₁₋₆)alkylpiperidinylamino, N—[(C₁₋₆)alkyl]-N—[(C₁₋₆)alkylpiperidinyl]amino, N—[(C₁₋₆)alkyl]-N—[(C₃₋₇)cycloalkylpiperidinyl]amino, N—[(C₁₋₆)alkyl]-N—[(C₂₋₆)alkylcarbonylpiperidinyl]amino, pyrrolidinyl(C₁₋₆)alkylamino, N—[(C₁₋₆)alkyl]-N—[pyrrolidinyl(C₁₋₆)alkyl]amino, N—[(C₁₋₆)alkyl]-N-[piperidinyl(C₁₋₆)alkyl]amino, (C₁₋₆)alkylpyrazolylamino, di(C₁₋₆)alkylpyrazolylamino, tri(C₁₋₆)alkylpyrazolylamino, N—[(C₁₋₆)alkyl]-N—[(C₁₋₆)alkylpyrazolyl]amino, thiazolylamino, imidazolylamino, [(C₁₋₆)alkoxycarbonyl][(C₁₋₆)alkyl]imidazolylamino, (C₁₋₆)alkylthiadiazolylamino, pyridinylamino, halopyridinylamino, (C₁₋₆)alkylpyridinylamino, di(C₁₋₆)alkylpyridinylamino, trifluoromethylpyridinylamino, hydroxypyridinylamino, hydroxy(C₁₋₆)alkylpyridinylamino, dihydroxy(C₁₋₆)alkylpyridinylamino, (C₁₋₆)alkoxypyridinylamino, dihydroxy(C₁₋₆)alkoxypyridinylamino, di(C₁₋₆)alkyldioxolanyl(C₁₋₆)alkoxypyridinylamino, (C₁₋₆)alkoxy(C₁₋₆)alkylpyridinylamino, (C₁₋₆)alkoxy(C₂₋₆)alkenylpyridinylamino, dihydroxy(C₁₋₆)alkylaminopyridinylamino, di(C₁₋₆)alkylaminopyridinylamino, (C₁₋₆)alkylamino(C₁₋₆)alkylpyridinylamino, di(C₁₋₆)alkylamino(C₁₋₆)alkylpyridinylamino, carboxypyridinylamino, N—[(C₁₋₆)alkyl]-N—[(C₁₋₆)alkylpyridinyl]amino, bis[(C₁₋₆)alkylpyridinyl]amino, bis(trifluoromethylpyridinyl)amino, isoquinolinylamino, (C₁₋₆)alkylpyridazinylamino, N—[(C₁₋₆)alkyl]-N—[(C₁₋₆)alkylpyridazinyl]amino, N-[aryl(C₁₋₆)alkyl]-N—[(C₁₋₆)alkylpyridazinyl]amino, di(C₁₋₆)alkylpyridazinylamino, arylpyridazinylamino, piperidinylpyridazinylamino, (C₁₋₆)alkoxypyridazinylamino, di(C₁₋₆)alkylaminopyridazinylamino, bis[(C₁₋₆)alkylpyridazinyl]-amino, benzofuryl(C₁₋₆)alkylamino, thienyl(C₁₋₆)alkylamino, indolyl(C₁₋₆)alkylamino, (C₁₋₆)alkylpyrazolyl(C₁₋₆)alkylamino, [di(C₁₋₆)alkyl](halo)pyrazolyl(C₁₋₆)alkylamino, di(C₁₋₆)alkylisoxazolyl(C₁₋₆)alkylamino, thiazolyl(C₁₋₆)alkylamino, imidazolyl(C₁₋₆)alkylamino, (C₁₋₆)alkylimidazolyl(C₁₋₆)alkylamino, pyridinyl(C₁₋₆)alkylamino, (C₁₋₆)alkylpyridinyl(C₁₋₆)alkylamino, N—[(C₁₋₆)alkyl]-N-[pyridinyl(C₁₋₆)alkyl]amino, N-[dihydroxy(C₁₋₆)alkyl]-N-[pyridinyl(C₁₋₆)alkyl]amino, N—[(C₁₋₆)alkylpyridinyl(C₁₋₆)alkyl]-N-[dihydroxy(C₁₋₆)alkyl]amino, amino(C₁₋₆)alkyl, (C₁₋₆)alkylamino(C₁₋₆)alkyl, di(C₁₋₆)alkylamino(C₁₋₆)alkyl, pyridinylamino(C₁₋₆)alkyl, N—[(C₂₋₆)alkylcarbonyl]-N—[(C₁₋₆)alkylpyridinyl(C₁₋₆)alkyl]amino, di(C₁₋₆)alkylamino(C₁₋₆)alkylcarbonylamino, (C₃₋₇)cycloalkylcarbonylamino, (C₁₋₆)alkylpiperidinylcarbonylamino, (C₁₋₆)alkylimidazolylcarbonylamino, formyl, C₂₋₆ alkylcarbonyl, (C₁₋₆)alkylpiperidinylaminocarbonyl, N—[(C₁₋₆)alkyl]-N—[(C₁₋₆)alkylpiperidinyl]aminocarbonyl, piperidinyl(C₁₋₆)alkylaminocarbonyl, (C₁₋₆)alkylpiperazinylcarbonyl, C₁₋₆ alkylthio, C₁₋₆ alkylsulphinyl, C₁₋₆ alkylsulphonyl, C₂₋₆ alkoxycarbonyloxy or tetra(C₁₋₆)alkyldioxaborolanyl; and R⁴⁴ represents hydrogen, halogen, C₁₋₆ alkyl or C₁₋₆ alkoxy.

6. A compound as claimed in claim 1 represented by formula (IIE), or a pharmaceutically acceptable salt thereof:

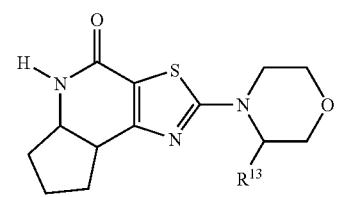

(IIE)

wherein

R¹³ represents hydrogen; or C₁₋₆ alkyl, C₃₋₇ cycloalkyl, C₃₋₇ cycloalkyl(C₁₋₆)alkyl, aryl, aryl(C₁₋₆)alkyl, aryl(C₂₋₆)alkenyl, aryl(C₂₋₆)alkynyl, biaryl(C₁₋₆)alkyl, C₃₋₇ heterocycloalkyl, C₃₋₇ heterocycloalkyl(C₁₋₆)alkyl, C₃₋₇ heterocycloalkylcarbonyl, heteroaryl, heteroaryl(C₁₋₆)alkyl, heteroaryl-aryl(C₁₋₆)alkyl or aryl-heteroaryl(C₁₋₆)alkyl, any of which groups may be optionally substituted by one or more substituents.

7. A pharmaceutical composition comprising a compound of formula (I) as defined in claim 1, or a pharmaceutically acceptable salt thereof, in association with a pharmaceutically acceptable carrier.

* * * * *